(12) United States Patent
Albrecht et al.

(10) Patent No.: US 10,308,614 B2
(45) Date of Patent: Jun. 4, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Alexandre Cote, Cambridge, MA (US); Terry Crawford, South San Francisco, CA (US); Martin Duplessis, Cambridge, MA (US); Andrew Charles Good, Cambridge, MA (US); Yves LeBlanc, Cambridge, MA (US); Steven R. Magnuson, South San Francisco, CA (US); Christopher G. Nasveschuk, Cambridge, MA (US); F. Anthony Romero, South San Francisco, CA (US); Yong Tang, Cambridge, MA (US); Alexander M. Taylor, Cambridge, MA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/686,028

(22) Filed: Aug. 24, 2017

(65) Prior Publication Data
US 2018/0086720 A1   Mar. 29, 2018

Related U.S. Application Data

(63) Continuation of application No. PCT/US2016/019328, filed on Feb. 24, 2016.
(Continued)

(51) Int. Cl.
| | | |
|---|---|---|
| C07D 237/20 | (2006.01) | |
| C07D 401/04 | (2006.01) | |
| C07D 403/04 | (2006.01) | |
| C07D 403/12 | (2006.01) | |
| C07D 403/14 | (2006.01) | |
| C07D 405/04 | (2006.01) | |
| C07D 405/14 | (2006.01) | |
| C07D 413/04 | (2006.01) | |
| C07D 413/14 | (2006.01) | |
| C07D 471/04 | (2006.01) | |
| C07D 471/10 | (2006.01) | |
| C07D 487/08 | (2006.01) | |
| C07D 498/10 | (2006.01) | |
| A61K 31/50 | (2006.01) | |
| A61K 31/51 | (2006.01) | |
| C07D 401/12 | (2006.01) | |
| C07D 237/22 | (2006.01) | |

(Continued)

(52) U.S. Cl.
CPC .......... *C07D 237/20* (2013.01); *A61K 31/337* (2013.01); *A61K 31/437* (2013.01); *A61K 31/501* (2013.01); *A61K 45/06* (2013.01); *C07D 237/22* (2013.01); *C07D 401/04* (2013.01); *C07D 401/12* (2013.01); *C07D 403/04* (2013.01); *C07D 403/12* (2013.01); *C07D 403/14* (2013.01); *C07D 405/04* (2013.01); *C07D 405/14* (2013.01); *C07D 413/04* (2013.01); *C07D 413/12* (2013.01); *C07D 413/14* (2013.01); *C07D 417/14* (2013.01); *C07D 451/02* (2013.01); *C07D 471/10* (2013.01); *C07D 487/04* (2013.01); *C07D 487/08* (2013.01); *C07D 498/10* (2013.01)

(58) Field of Classification Search
CPC .. C07D 237/20; C07D 401/04; C07D 403/04; C07D 403/12; C07D 403/14
See application file for complete search history.

(56) References Cited

U.S. PATENT DOCUMENTS 4,677,106 A    6/1987   Wermuth et al.

OTHER PUBLICATIONS

Aurora Fine Chemicals Product Guide.1 page, retrieved from the Internet at http://www.aurorafinechemicals.com/abouthtml on Apr. 28, 2015.*

(Continued)

*Primary Examiner* — Emily A Bernhardt
(74) *Attorney, Agent, or Firm* — Viksnins Harris Padys Malen LLP

(57) ABSTRACT

The present invention relates to compounds of formula (I):

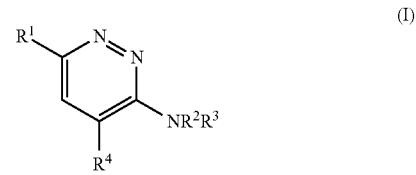

and salts thereof, wherein: $R^1$-$R^4$ have any of the values defined in the specification, and compositions and uses thereof. The compounds are useful as inhibitors of BRG1, BRM and/or PB1. Also included are pharmaceutical compositions comprising a compound of formula (I) or a pharmaceutically acceptable salt thereof, and methods of using such compounds and salts in the treatment of various BRG1-mediated disorders, BRM-mediated disorders and/or PB1-mediated disorders.

21 Claims, No Drawings
Specification includes a Sequence Listing.

Related U.S. Application Data

(60) Provisional application No. 62/120,732, filed on Feb. 25, 2015.

(51) Int. Cl.

| | | |
|---|---|---|
| *C07D 417/14* | (2006.01) | |
| *C07D 413/12* | (2006.01) | |
| *C07D 451/02* | (2006.01) | |
| *C07D 487/04* | (2006.01) | |
| *A61K 45/06* | (2006.01) | |
| *A61K 31/337* | (2006.01) | |
| *A61K 31/437* | (2006.01) | |
| *A61K 31/501* | (2006.01) | |

(56) References Cited

OTHER PUBLICATIONS

Ukrorgsyntez Product Guide,1 page, retrieved from the internet at http://ukrorgsyntez.lookchem.com/About.html on Mar. 16, 2018.*
Iqbal et al. Bioorganic & Medicinal Chemistry Letters 21 (2011) 4252-4254.*
CA Registry No. 1271631-67-4, entered into CA Registry File on Mar. 29, 2011, supplied by FCH Group. (Year: 2011).*
FCH Group Product Guide, 1 page, retrieved from the Internet at http://fchgroup.net/products.php on Apr. 5, 2014. (Year: 2014).*
Caldwell, et al., "Structure-Based Design of Potent and Selective 2-(Quinazolin-2-yl)phenol Inhibitors of Checkpoint Kinase 2", J Med Chem 54, 580-590 (2011).
Database Registry, Chemical Abstracts Service, Database accession No. 1339378-93-6, 1 page (Nov. 2, 2011).
Database Registry, Chemical Abstracts Service, Database accession No. 1342352-89-9, 1 page, (Nov. 8, 2011).
Database Registry, Chemical Abstracts Service, Database accession No. 1344358-47-9 and 1344266-02-9, 1 page (Nov. 11, 2011).
Database Registry, Chemical Abstracts Service, Database accession No. 1405741-65-2, 1 page (Nov. 25, 2012).
Database Registry, Chemical Abstracts Service, Database accession No. 1491575-81-5, 1 page (Dec. 10, 2013).
Database Registry, Chemical Abstracts Service, Database accession No. 766463-61-0, 1 page (Oct. 20, 2004).
Hoffman, et al., "Functional epigenetics approach identifies BRM/SMARCA2 as a critical synthetic lethal target in BRG1-deficient cancers", PNAS 111(8), 3128-3133 (2014).
Hohmann, et al., "A rationale to target the SWI/SNF complex for cancer therapy", Trends Genet 30(8), 356-363 (2014).
Jeanmougin, "The bromodomain revisited", Trends Biochem Sci 22(5), 151-153 (1997).
Muller, et al., "Bromodomains as therapeutic targets", Expert Rev Mol Med 13 (29), 1-21 (2011).
Oike, et al., "A Synthetic Lethality—Based Strategy to Treat Cancers Harboring a Genetic Deficiency in the Chromatin Remodeling Factor BRG1", Cancer Res 73(17), 5508-5518 (2013).
Patent Cooperation Treaty, International Searching Authority, Search Report and Written Opinion for PCT/US2016/019328, 14 pages, dated Jul. 8, 2016.
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila* homeotic genes structurally related to the yeast transcriptional activator SNF2/SWI2", Cell 68, 561-572 (1992).

* cited by examiner

THERAPEUTIC COMPOUNDS AND USES THEREOF

CROSS-REFERENCE TO RELATED APPLICATION(S)

This patent application is a continuation of International Application No. PCT/US2016/019328, filed Feb. 24, 2016, which claims the benefit of priority of U.S. provisional application Ser. No. 62/120,732, filed Feb. 25, 2015, which applications are herein incorporated by reference.

SEQUENCE LISTING

The instant application contains a Sequence Listing which has been submitted electronically in ASCII format and is hereby incorporated by reference in its entirety. Said ASCII copy, created on Oct. 24, 2017, is named 01075_027US1_SL.txt and is 4,545 bytes in size.

TECHNICAL FIELD OF THE INVENTION

The present invention relates to compounds useful as inhibitors of BRG1, BRM and/or PB1.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. An example of such a complex is the SWI/SNF chromatin-remodeling complex, which has been reported to be involved in gene regulation, cell lineage specification and development, and comprises a number of bromodomain containing subunits, including BRG1 (also known as SMARCA4), BRM (also known as SMARCA2) and PB1 (also known as PBRM1) (see, Hohmann et al., Trends in Genetics, 30(8):356-363 (2014)). Inactivating mutations in SWI/SNF subunits have been reported to be found in nearly 20% of human cancers and recent studies have revealed synthetic lethal interactions between certain subunits (Id.). For example, BRM has been identified as a synthetic lethal target in BRG1-deficient cancers (Hoffman et al., PNAS, 111(8):3128-3133 (2014); Oike et al., Cancer Research, 73(17):5508-5518 (2013)). Additionally, other studies have shown that certain cancers lacking SWI/SNF mutations are sensitive to BRG1 inhibition. Hence, the selective inhibition of certain SWI/SNF subunits, including BRG1, BRM and PB1, creates varied opportunities for the development of novel therapeutic agents for the treatment of human dysfunction, including cancer.

Accordingly, there is a need for compounds that inhibit BRG1, BRM and/or PB1 for treating diseases such as cancer, as well as for use as tools for studying the pharmacology of these bromodomain containing subunits.

SUMMARY OF THE INVENTION

One aspect includes compound of formula (I):

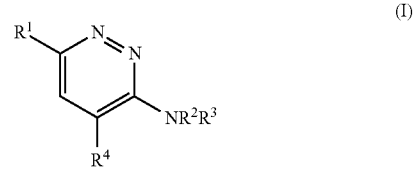

(I)

or a salt thereof, wherein:

$R^1$ is phenyl that is substituted with hydroxy and that is optionally substituted with one or more groups independently selected from the group consisting of halo, cyano, trifluoromethyl, trifluoromethoxy, $C_{1-3}$alkyl, and $C_{1-3}$alkoxy;

$R^2$ is H, $C_{1-6}$alkyl, or —C(=O)—$C_{1-6}$alkyl;

$R^3$ is H or $C_{1-6}$alkyl;

$R^4$ is selected from the group consisting of —$R^b$, —O—$R^b$, —S(O)$_2R^b$, and —C(O)—N($R^b$)$_2$;

each $R^b$ is independently selected from the group consisting of hydrogen, $C_{1-6}$alkyl, $C_{2-6}$alkenyl, $C_{2-6}$alkynyl, 3-15 membered carbocyclyl, and 3-15 membered heterocyclyl, wherein each $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —$NO_2$, —$N(R^c)_2$, —CN, —C(O)—$N(R^c)_2$, —S(O)—N$(R^c)_2$, —$S(O)_2$—$N(R^c)_2$, —O—$R^c$, —S—$R^c$, —O—C(O)—$R^c$, —C(O)—$R^c$, —C(O)—$OR^c$, —S(O)—$R^c$, —S$(O)_2$—$R^c$, —$N(R^c)$—C(O)—$R^c$, —$N(R^c)$—S(O)—$R^c$, —$N(R^c)$—C(O)—$N(R^c)_2$, and —$N(R^c)$—$S(O)_2$—$R^c$;

each $R^c$ is independently selected from the group consisting of hydrogen, $C_{1-6}$alkyl, $C_{2-6}$alkenyl, $C_{2-6}$alkynyl, $C_{1-6}$alkoxy, 3-15 membered carbocyclyl, and 3-15 membered heterocyclyl, wherein each $C_{1-6}$alkyl, $C_{2-6}$alkenyl, $C_{2-6}$alkynyl, $C_{1-6}$alkoxy, 3-15 membered carbocyclyl, and 3-15 membered heterocyclyl is optionally substituted with one or more groups independently selected from $R^d$; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^d$ is independently selected from the group consisting of oxo, halo, —$NO_2$, —$N(R^e)_2$, —CN, —C(O)—N$(R^e)_2$, —S(O)—$N(R^e)_2$, —$S(O)_2$—$N(R^e)_2$, —S—$R^e$, —O—C(O)—$R^e$, —C(O)—$R^e$, —C(O)—$OR^e$, —S(O)—$R^e$, —$S(O)_2$—$R^e$, —$N(R^e)$—C(O)—$R^e$, —$N(R^e)$—S(O)—$R^e$, —$N(R^e)$—C(O)—$N(R^e)_2$, —$N(R^e)$—$S(O)_2$—$R^e$, $C_{1-6}$alkyl, $C_{2-6}$alkenyl, $C_{2-6}$alkynyl, 3-15 membered carbocyclyl, and 3-15 membered heterocyclyl, wherein any $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^e$, oxo, halo, —$NO_2$, —N$(R^e)_2$, —CN, —C(O)—$N(R^e)_2$, —S(O)—$N(R^e)_2$, —S$(O)_2$—$N(R^e)_2$, —O—$R^e$, —S—$R^e$, —O—C(O)—$R^e$, —C(O)—$R^e$, —C(O)—$OR^e$, —S(O)—$R^e$, —$S(O)_2$—$R^e$, —$N(R^e)$—C(O)—$R^e$, —$N(R^e)$—S(O)—$R^e$, —$N(R^e)$—C(O)—$N(R^e)_2$, and —$N(R^e)$—$S(O)_2$—$R^e$; and each $R^e$ is independently selected from the group consisting of hydrogen, $C_{1-6}$alkyl, $C_{2-6}$alkenyl, $C_{2-6}$alkynyl, carbocyclyl, and carbocyclyl($C_{1-3}$alkyl)-.

Another aspect includes a composition comprising a compound of formula (I) or a pharmaceutically acceptable salt thereof, and a pharmaceutically acceptable adjuvant, carrier, or vehicle.

Another aspect includes a method for treating a BRG1-mediated disorder, a BRM-mediated disorder and/or a PB1-mediated disorder in an animal comprising administering a compound of formula (I) or a pharmaceutically acceptable salt thereof to the animal.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a BRG1-mediated disorder, a BRM-mediated disorder and/or a PB1-mediated disorder.

Another aspect includes the use of a compound of formula (I) or a pharmaceutically acceptable salt thereof to prepare a medicament for treating a BRG1-mediated disorder, a BRM-mediated disorder and/or a PB1-mediated disorder in an animal (e.g. a mammal such as a human).

Another aspect includes compounds for the study of BRG1, BRM and/or PB1.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O or (=O)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and Spiro carbocyclyls include spiro[2.2]pentane, spiro[2.3] hexane, spiro[2.4]heptane, spiro[2.5]octane and spiro[4.5] decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain monovalent hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, heptyl, octyl, nonyl, decyl, undecyl and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. The term heterocyclyl also includes $C_3$-$C_8$heterocycloalkyl, which is a saturated or partially unsaturated mono-, bi-, or spiro-ring system comprising 3-8 carbons and one or more (1, 2, 3, or 4) heteroatoms.

In one example, heterocyclyl includes 3-12 ring atoms and includes monocycles, bicycles, tricycles and Spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, SO$_2$), and any nitrogen heteroatom may optionally be quaternized (e.g. [NR$_4$]$^+$Cl$^-$, [NR$_4$]$^+$OH$^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "polycycle" refers to a ring system with two or more (e.g. 2, 3, 4, or 5) rings that may be fused, bridged, or in a spiro relationship.

As used herein, the term "inhibitor" refers to a compound that binds to and inhibits a BRG1, BRM and/or PB1 bromodomain with measurable affinity and activity. In certain embodiments, an inhibitor has an IC$_{50}$ or binding constant of less about 50 µM, less than about 1 µM, less than about 500 nM, less than about 100 nM, or less than about 10 nM.

The terms "measurable affinity" and "measurably inhibit," as used herein, refer to a measurable reduction in activity of a BRG1, BRM and/or PB1 bromodomain between: (i) a sample comprising a compound of formula I or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

As used herein, "a" or "an" means one or more, unless clearly indicated otherwise. As used herein, "another" means at least a second or more.

Exemplary Values

In one embodiment $R^1$ is 2-hydroxy phenyl that is optionally substituted with one or more groups independently selected from the group consisting of halo.

In one embodiment $R^1$ is 2-hydroxy phenyl that is optionally substituted with one or more fluoro.

In one embodiment $R^1$ is 2-hydroxyphenyl, 3-fluoro2-hydroxyphenyl, 4-fluoro2-hydroxyphenyl, 5-fluoro2-hydroxyphenyl, or 3,5-difluoro-2-hydroxyphenyl.

In one embodiment $R^2$ is H, methyl, or acetyl; and $R^3$ is H.

In one embodiment $R^2$ is H; and $R^3$ is H.

In one embodiment the compound is a compound of formula (Ia):

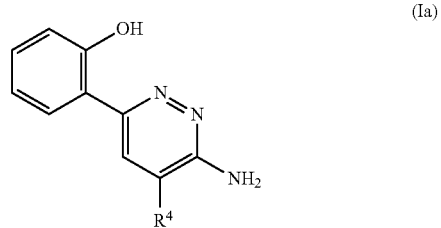

(Ia)

wherein the 2-hydroxy phenyl group shown is is optionally substituted with one or more fluoro.

In one embodiment $R^4$ is a 3-15 membered heterocyclyl that is optionally substituted with one or more groups independently selected from the group consisting of $R^c$, oxo, halo, —$NO_2$, —$N(R^c)_2$, —CN, —C(O)—$N(R^c)_2$, —S(O)—$N(R^c)_2$, —$S(O)_2$—$N(R^c)_2$, —O—$R^c$, —S—$R^c$, —O—C(O)—$R^c$, —C(O)—$R^c$, —C(O)—$OR^c$, —S(O)—$R^c$, —$S(O)_2$—$R^c$, —$N(R^c)$—C(O)—$R^c$, —$N(R^c)$—S(O)—$R^c$, —$N(R^c)$—C(O)—$N(R^c)_2$, and —$N(R^c)$—$S(O)_2$—$R^c$.

In one embodiment $R^4$ is selected from the group consisting of: H,

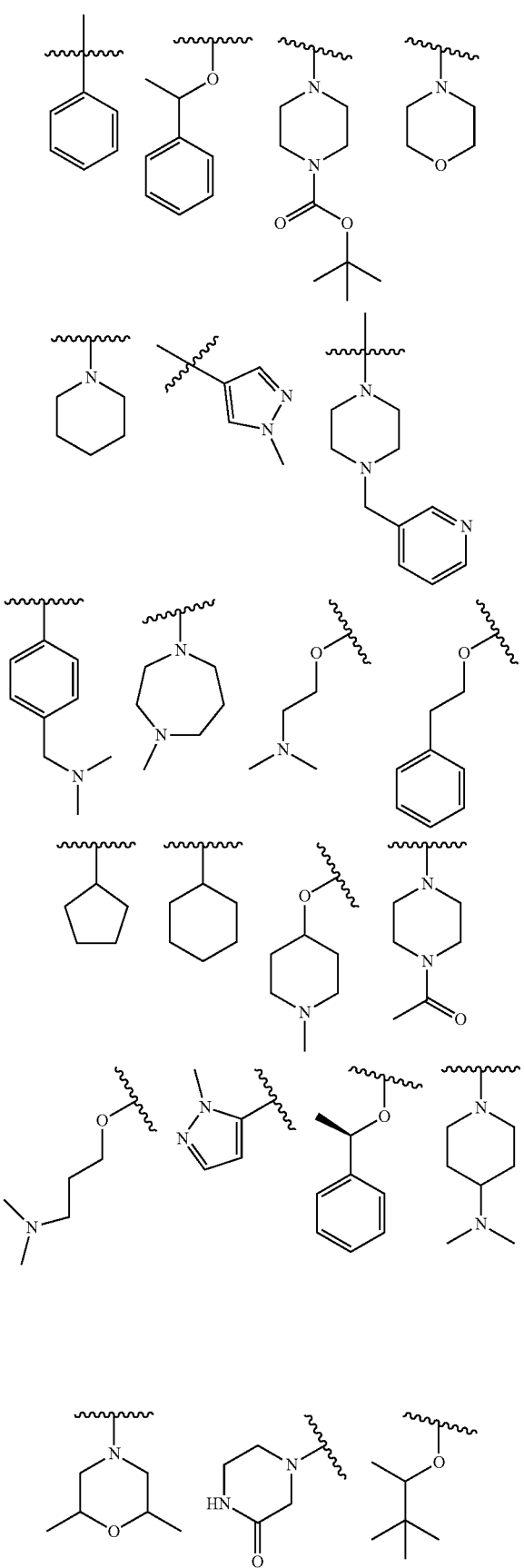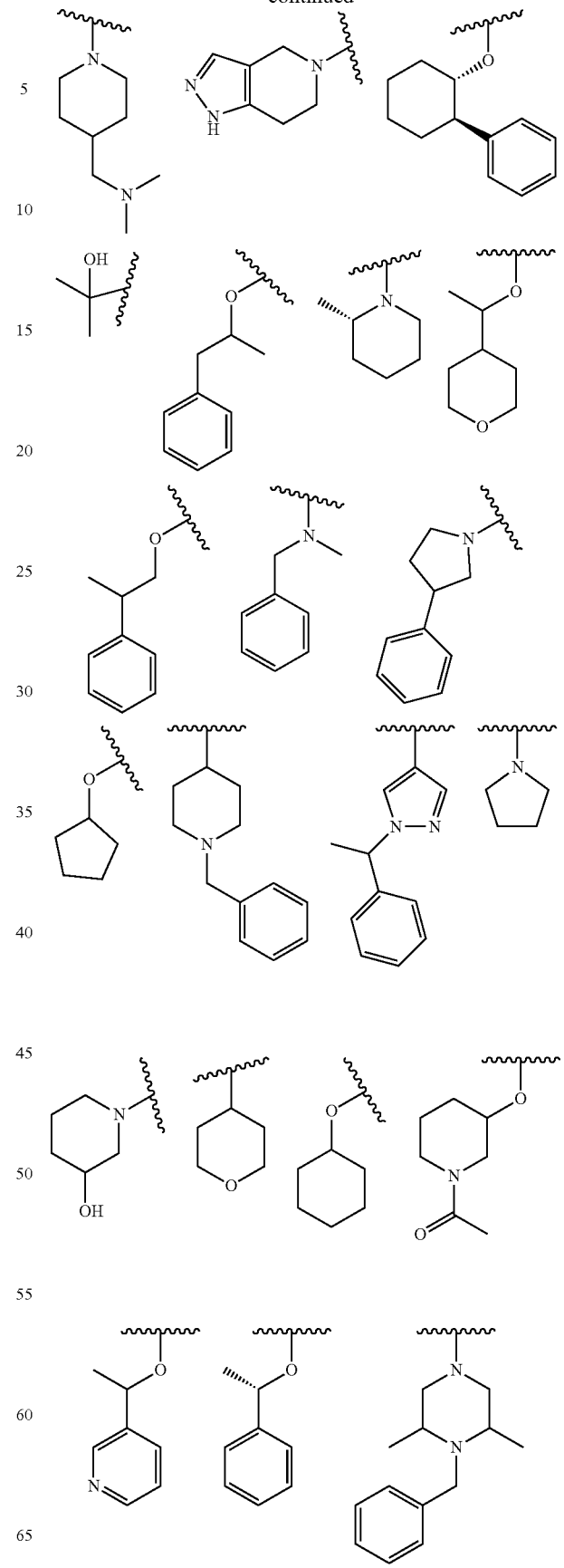

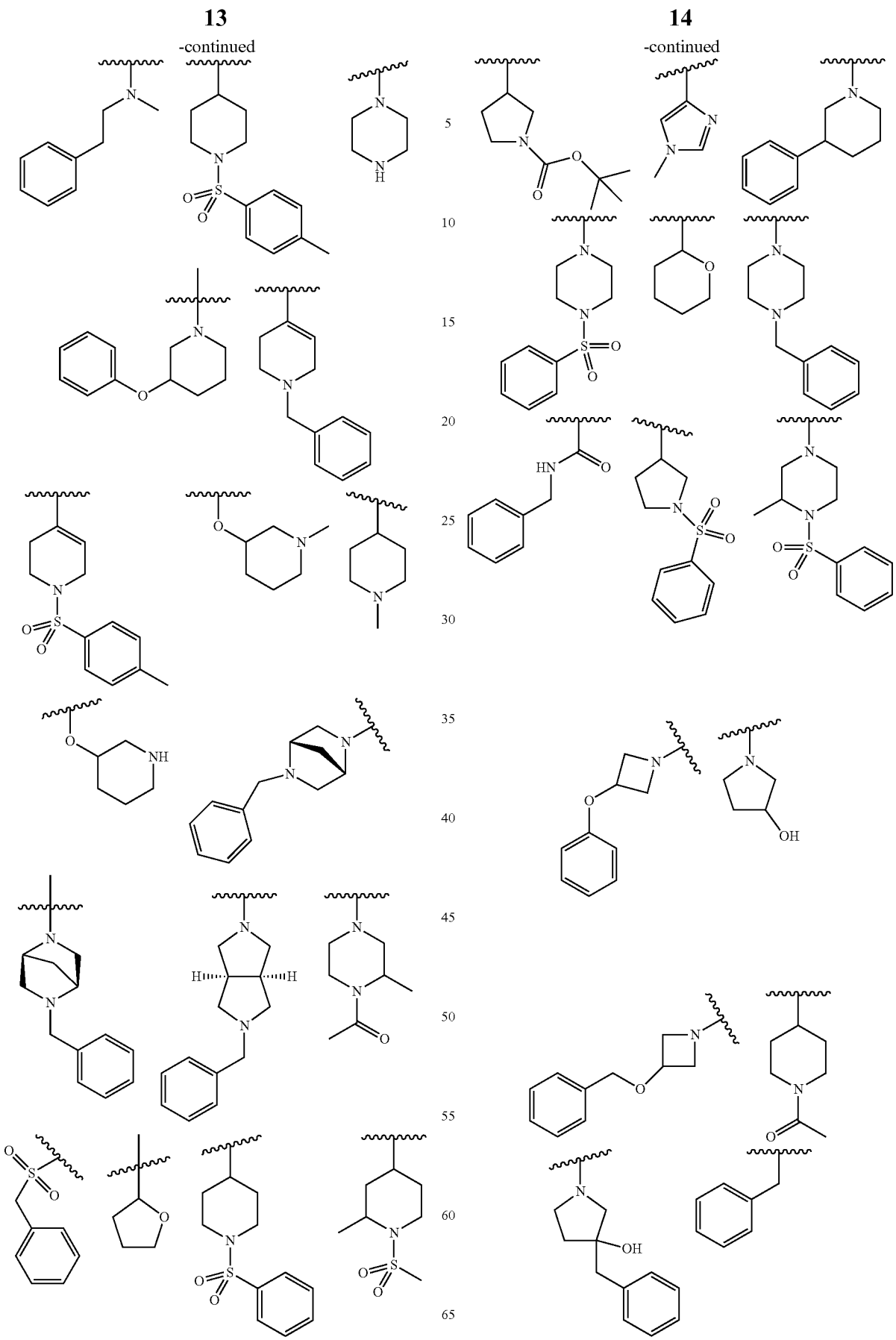

-continued
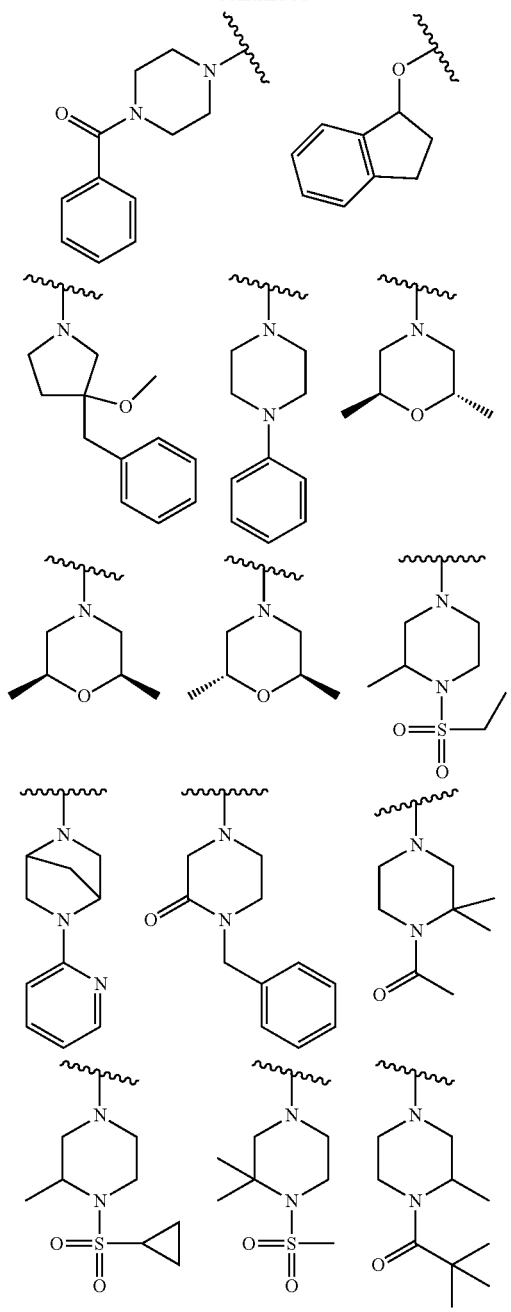
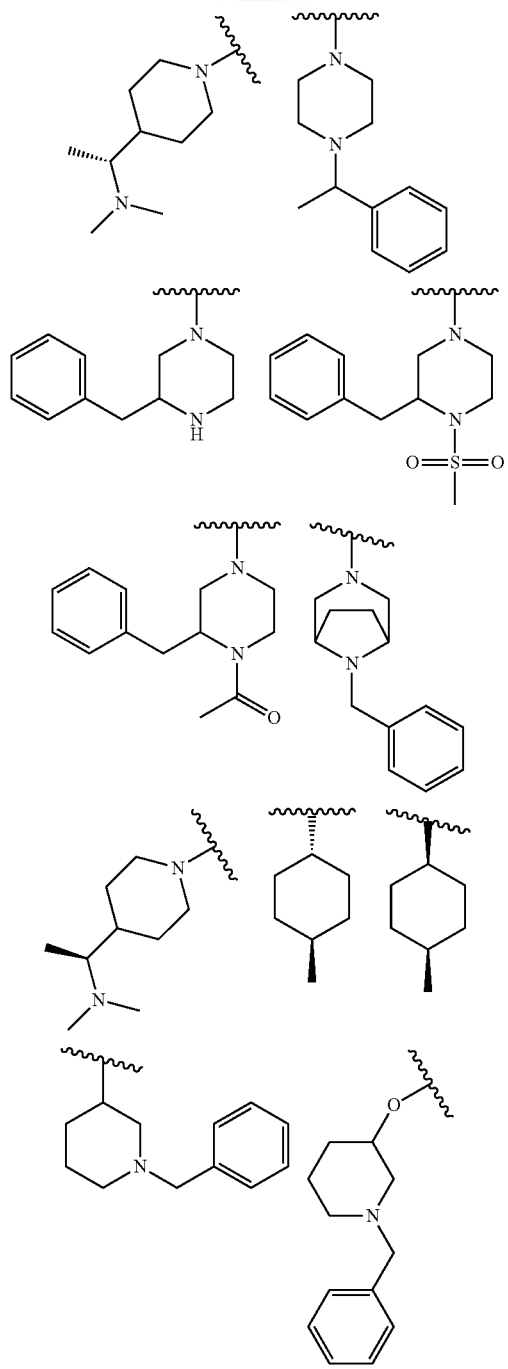
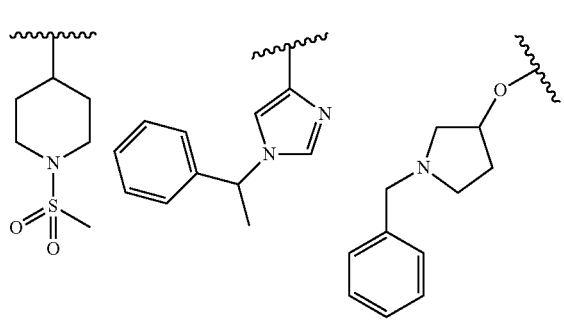
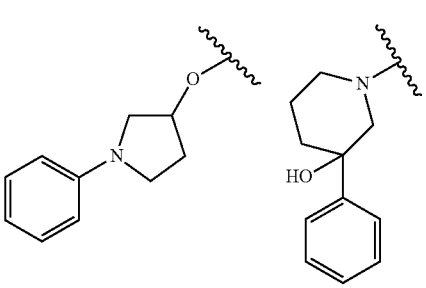

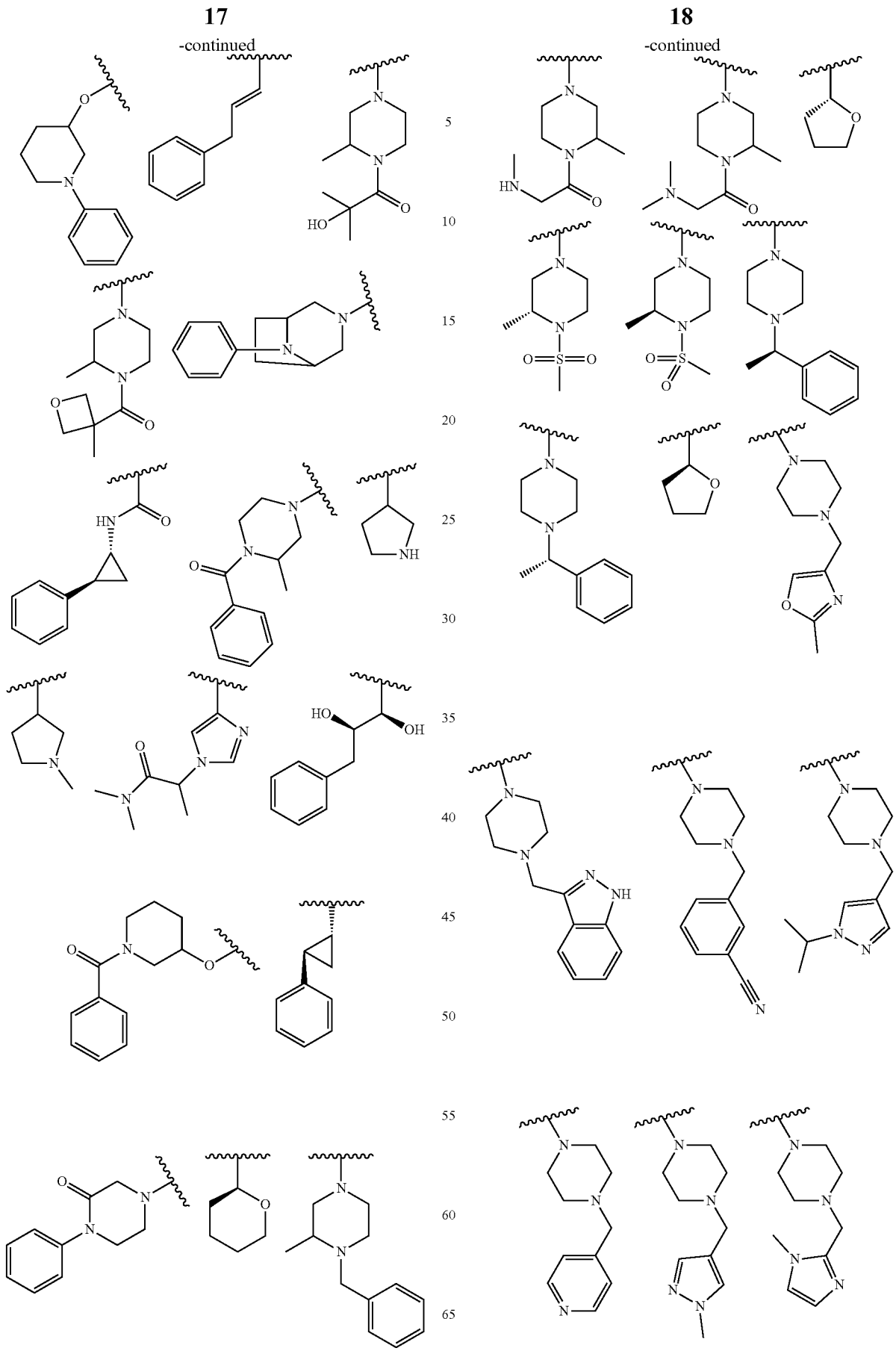

-continued
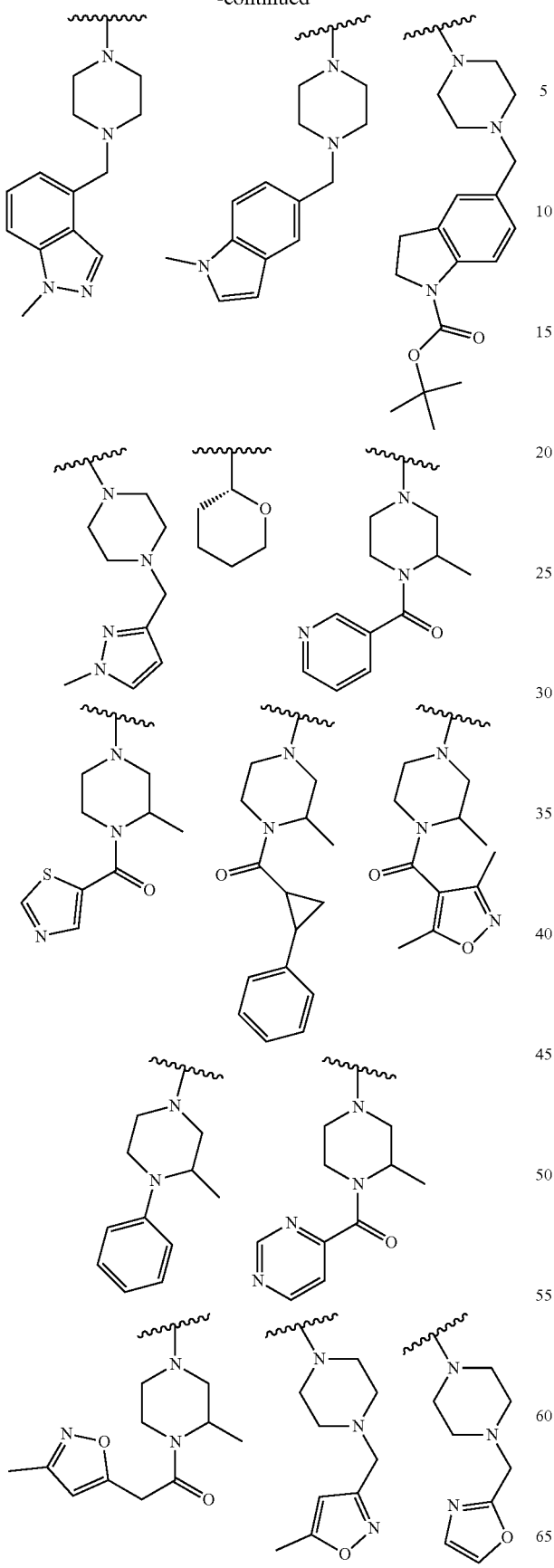
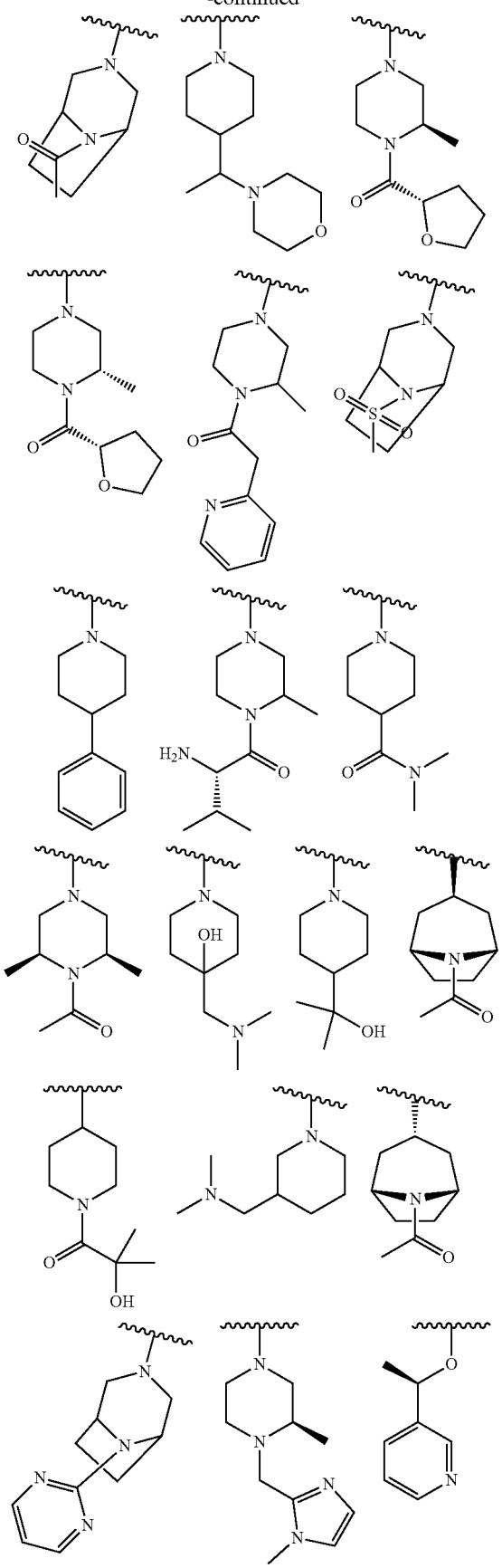

-continued
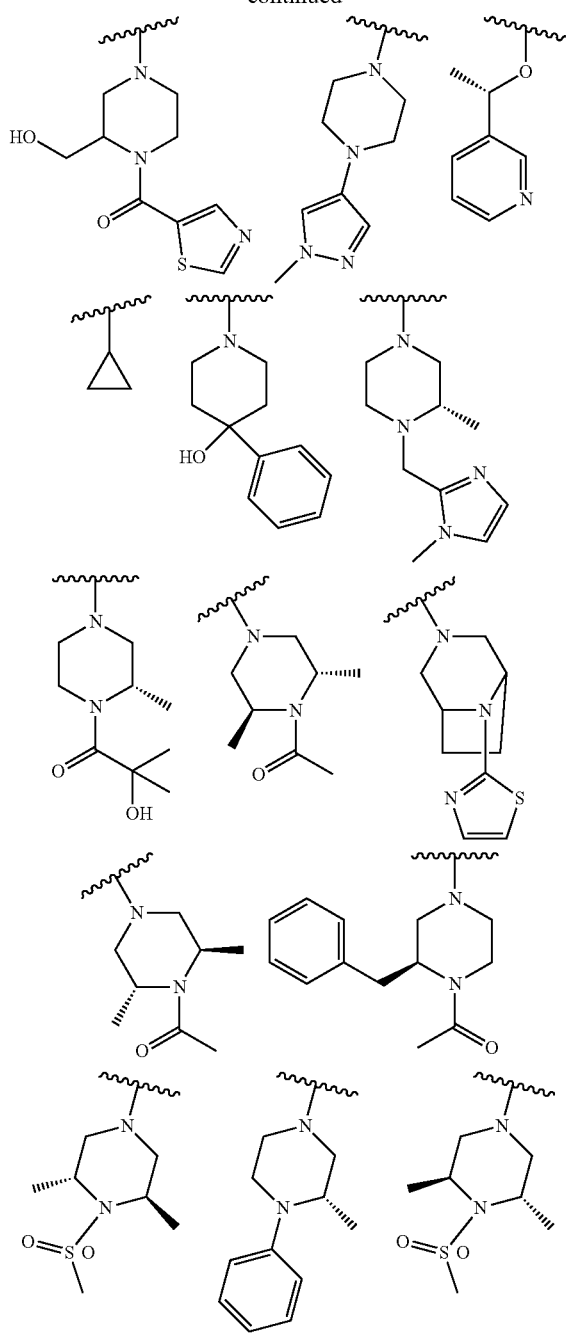
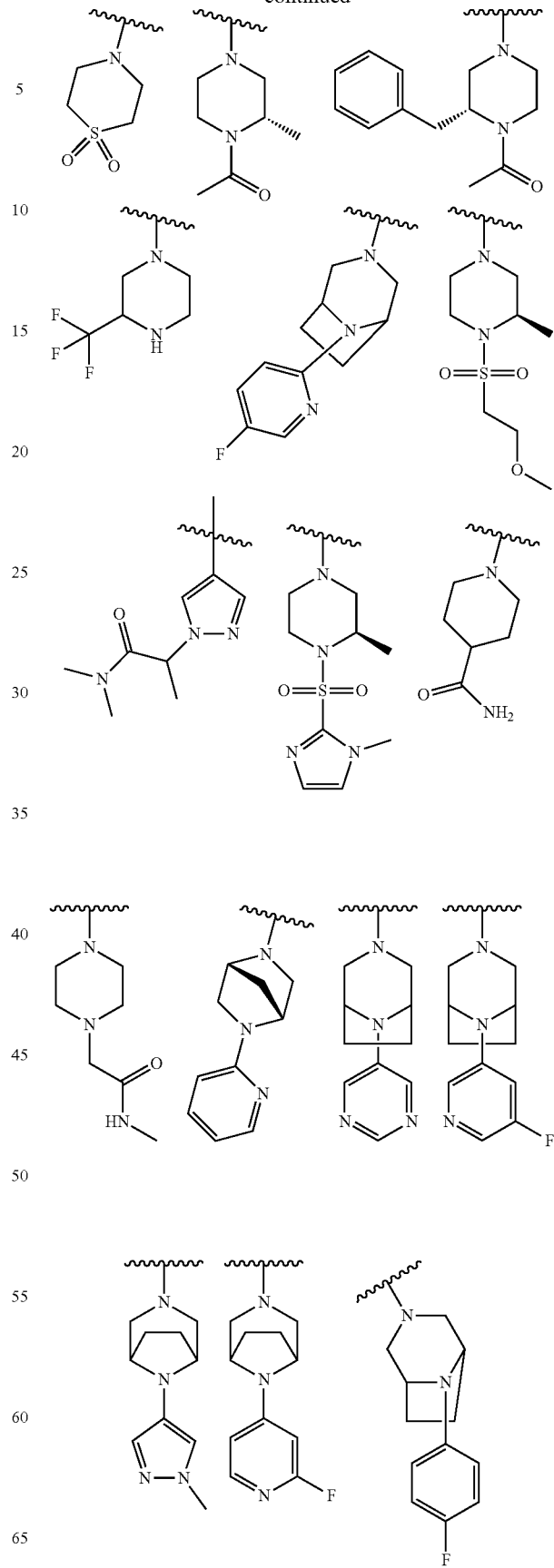

-continued
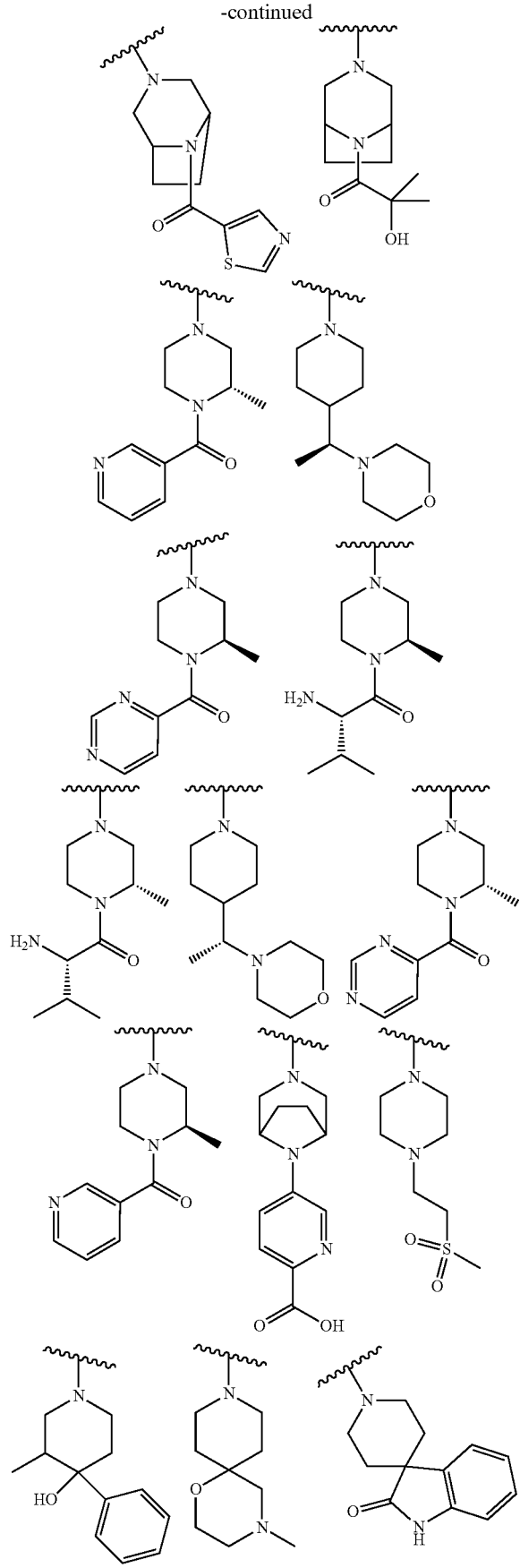
-continued
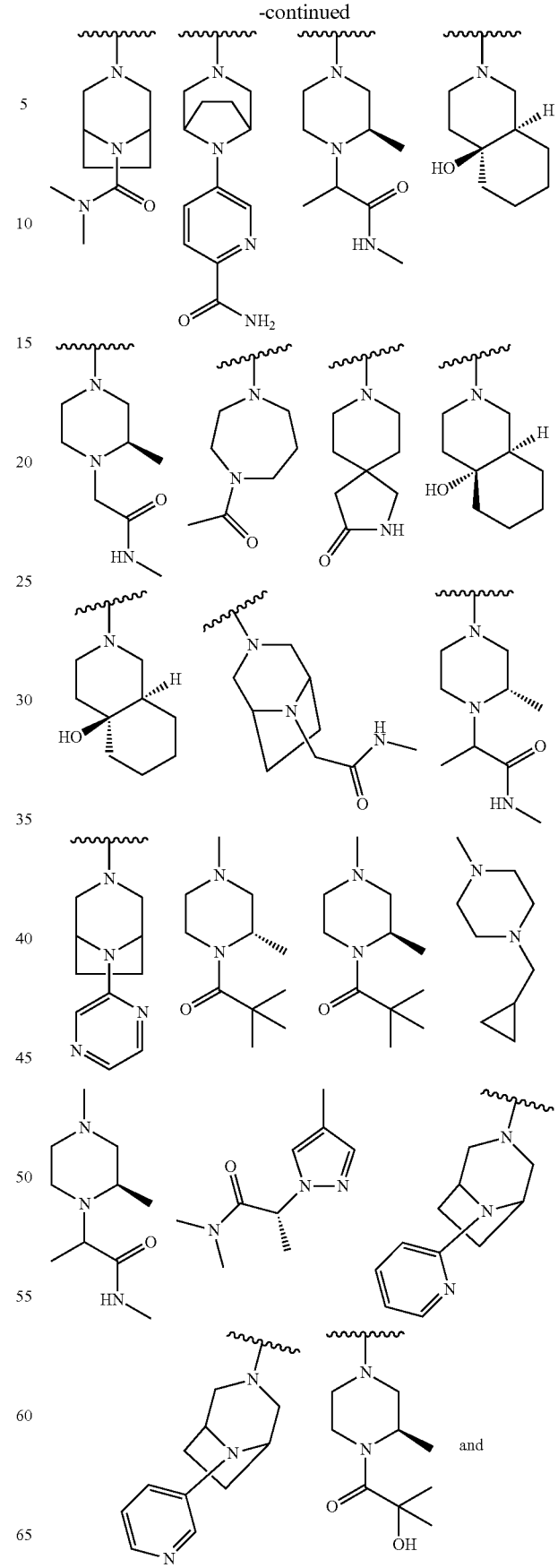

-continued

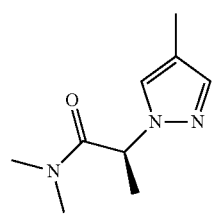

In one embodiment $R^4$ is a 3-15 membered N-linked heterocyclyl that is optionally substituted with one or more groups independently selected from the group consisting of $R^c$, oxo, halo, $-NO_2$, $-N(R^c)_2$, $-CN$, $-C(O)-N(R^c)_2$, $-S(O)-N(R^c)_2$, $-S(O)_2-N(R^c)_2$, $-O-R^c$, $-S-R^c$, $-O-C(O)-R^c$, $-C(O)-R^c$, $-C(O)-OR^c$, $-S(O)-R^c$, $-S(O)_2-R^c$, $-N(R^c)-C(O)-R^c$, $-N(R^c)-S(O)-R^c$, $-N(R^c)-C(O)-N(R^c)_2$, and $-N(R^c)-S(O)_2-R^c$.

In one embodiment $R^4$ is selected from the group consisting of:

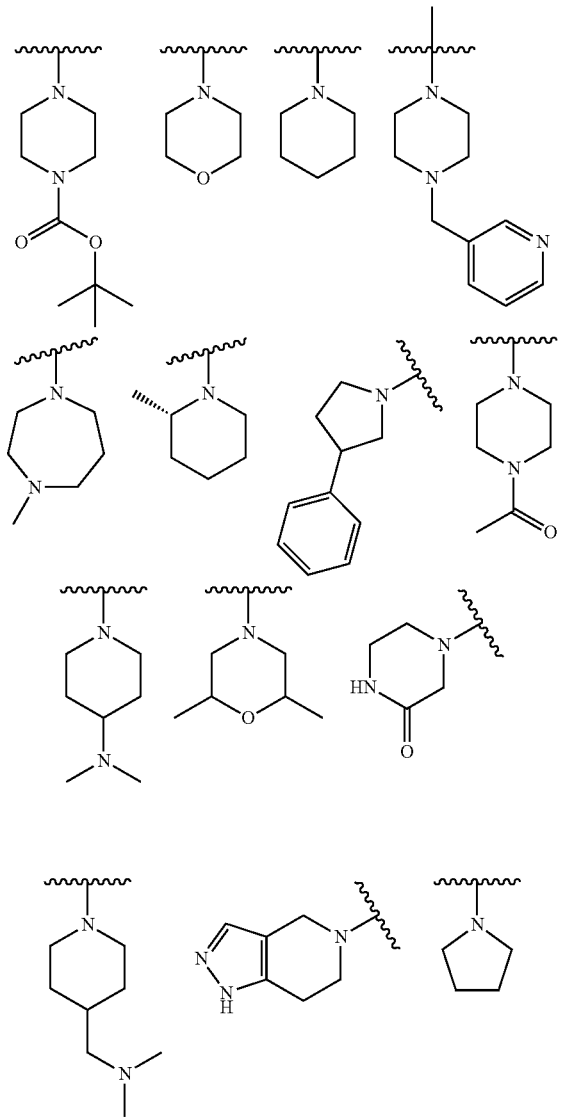

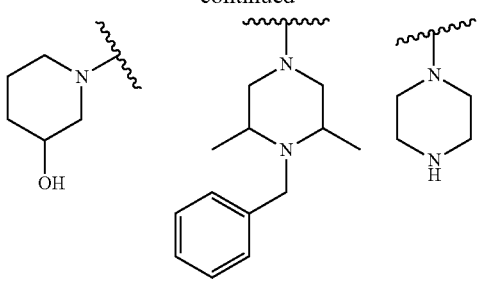

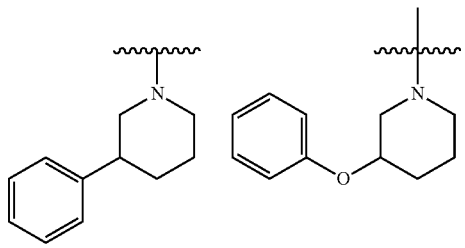

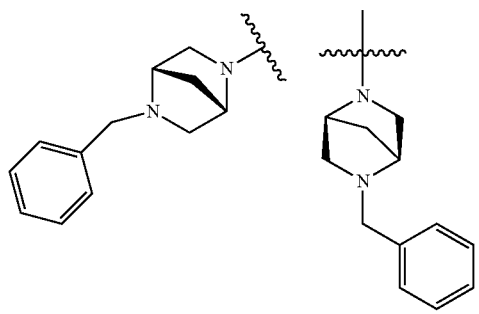

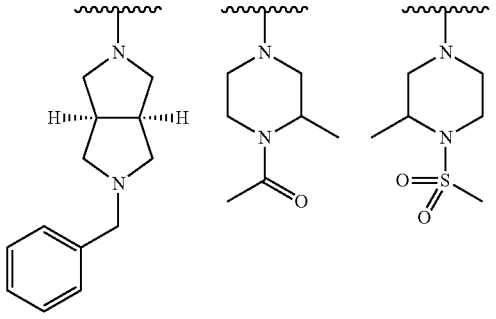

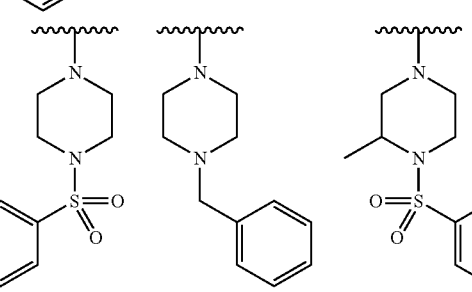

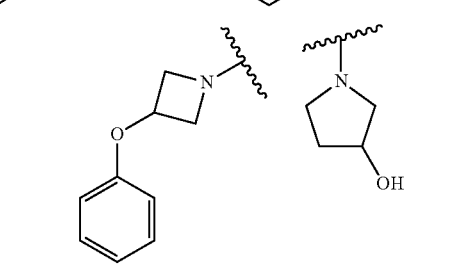

-continued
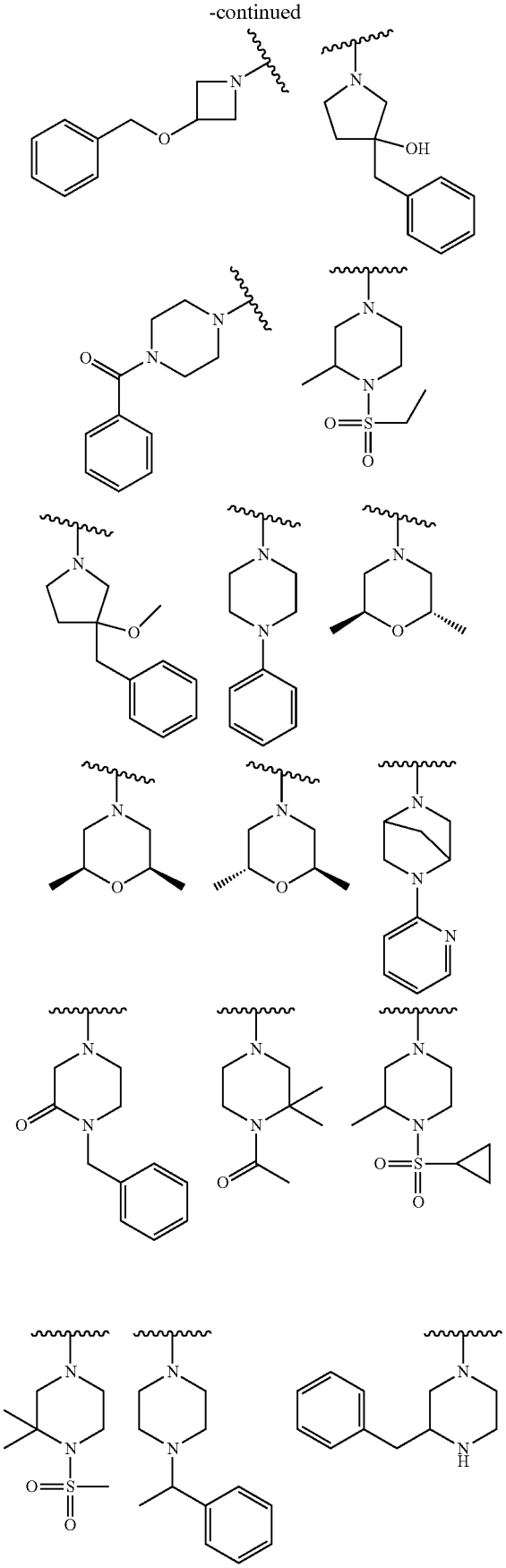
-continued
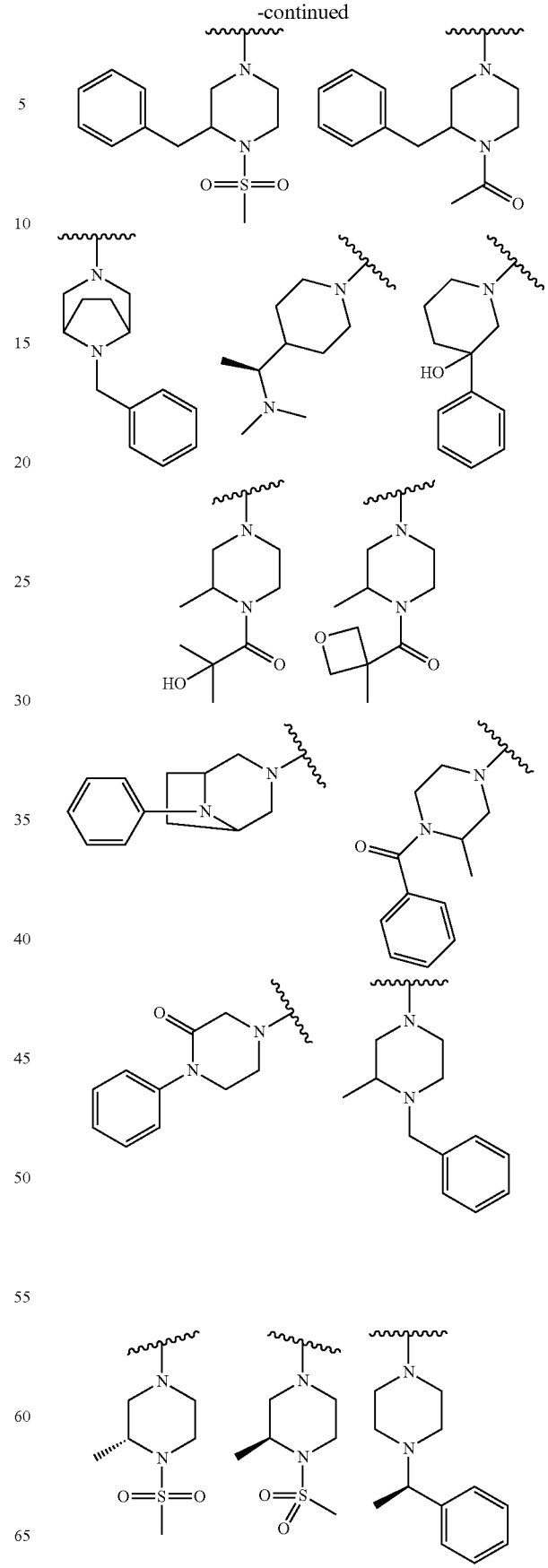

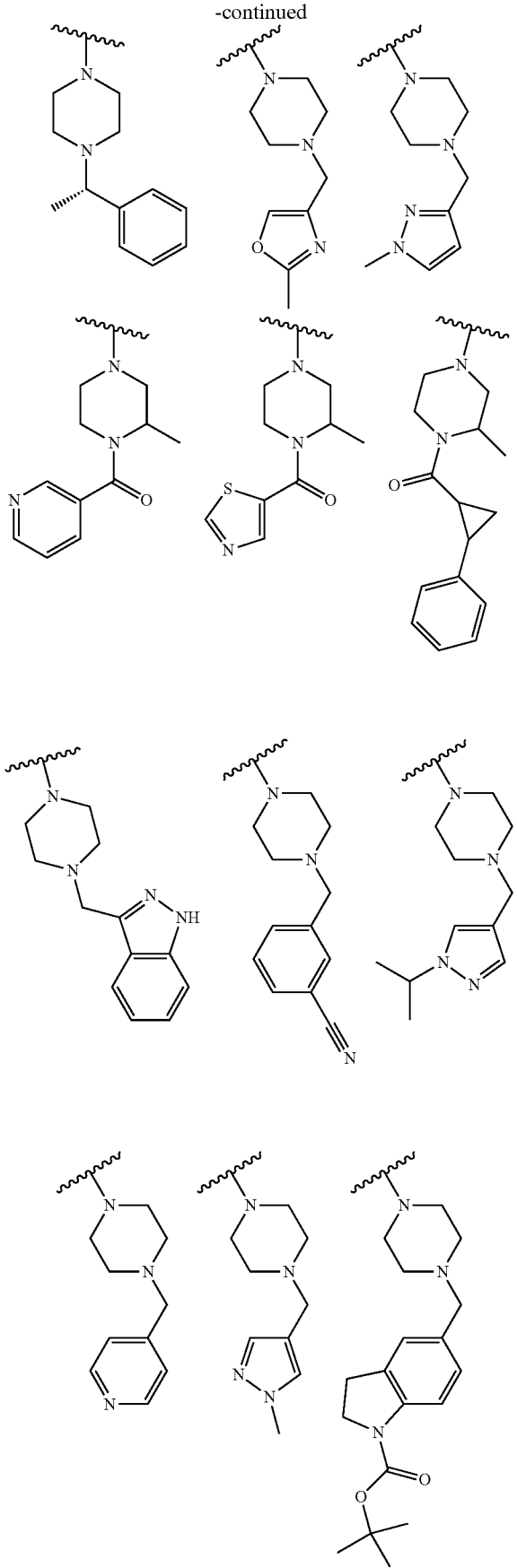
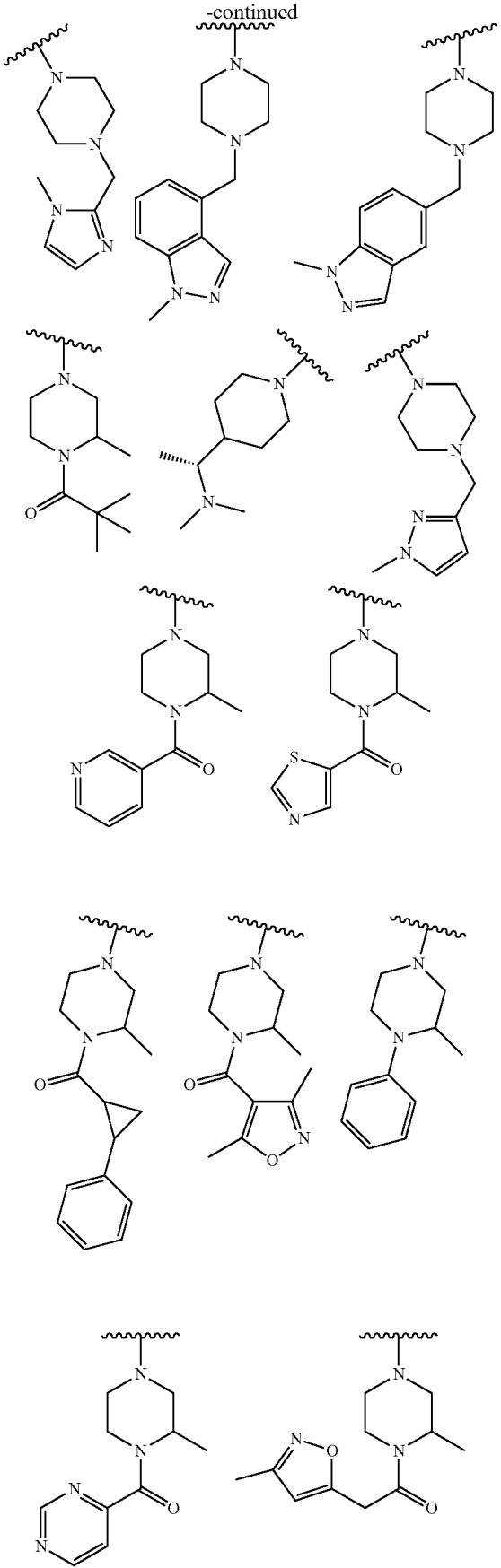

31
-continued
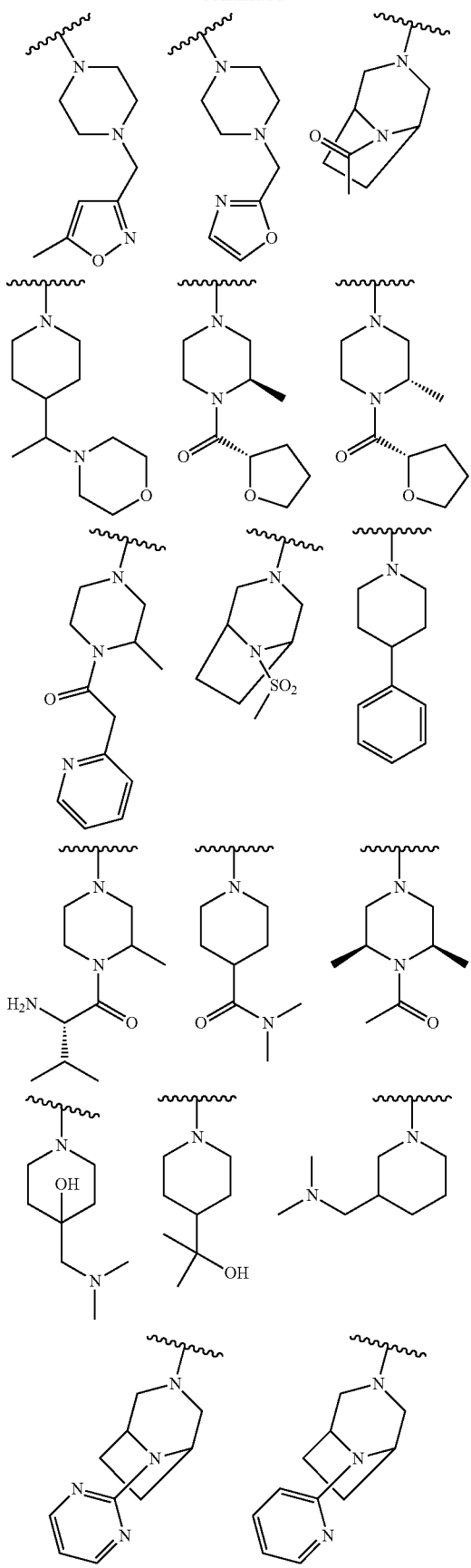
32
-continued
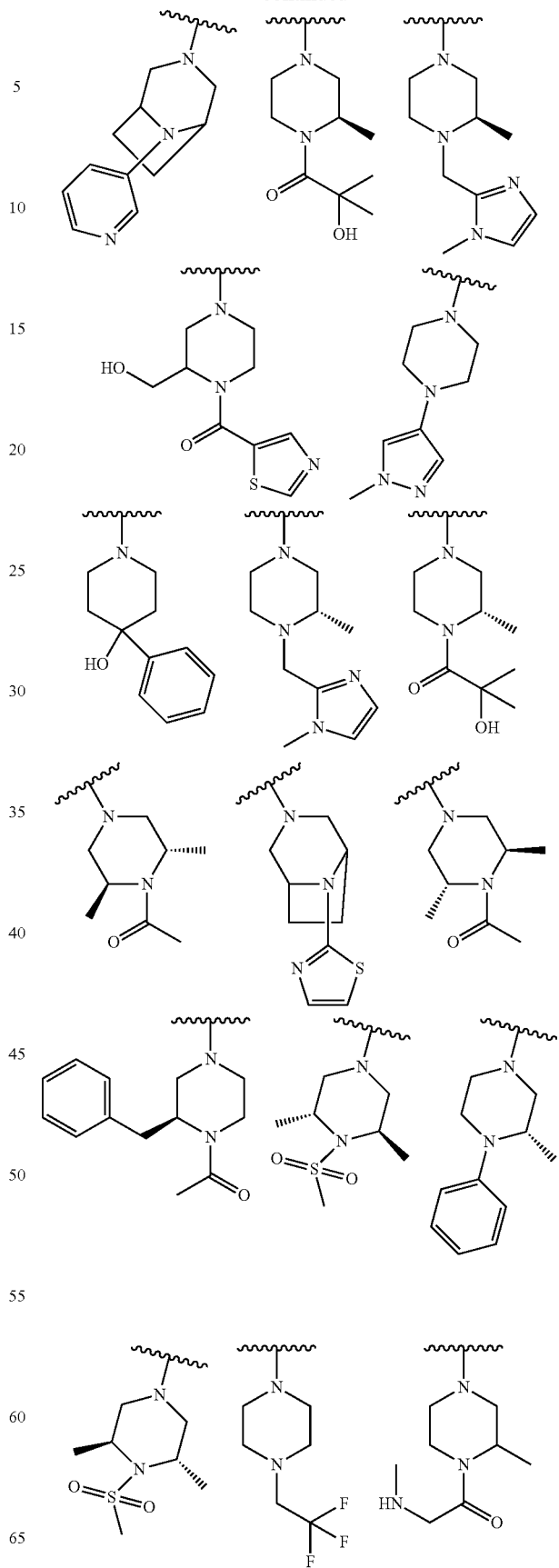

33
-continued
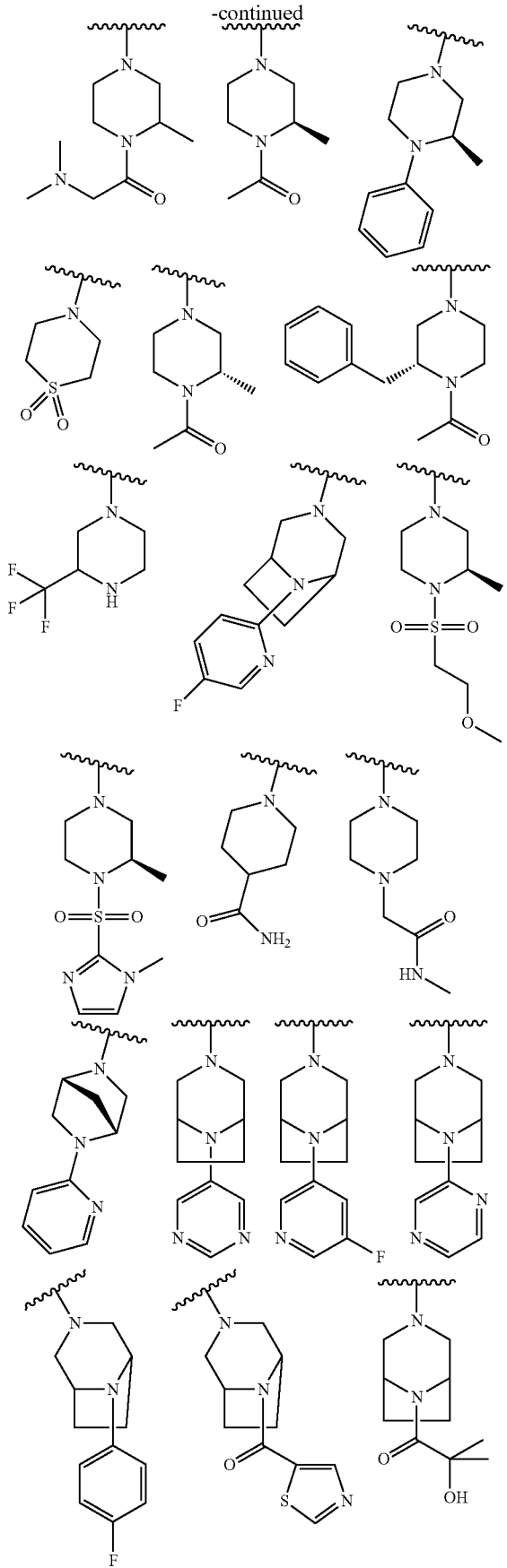
34
-continued
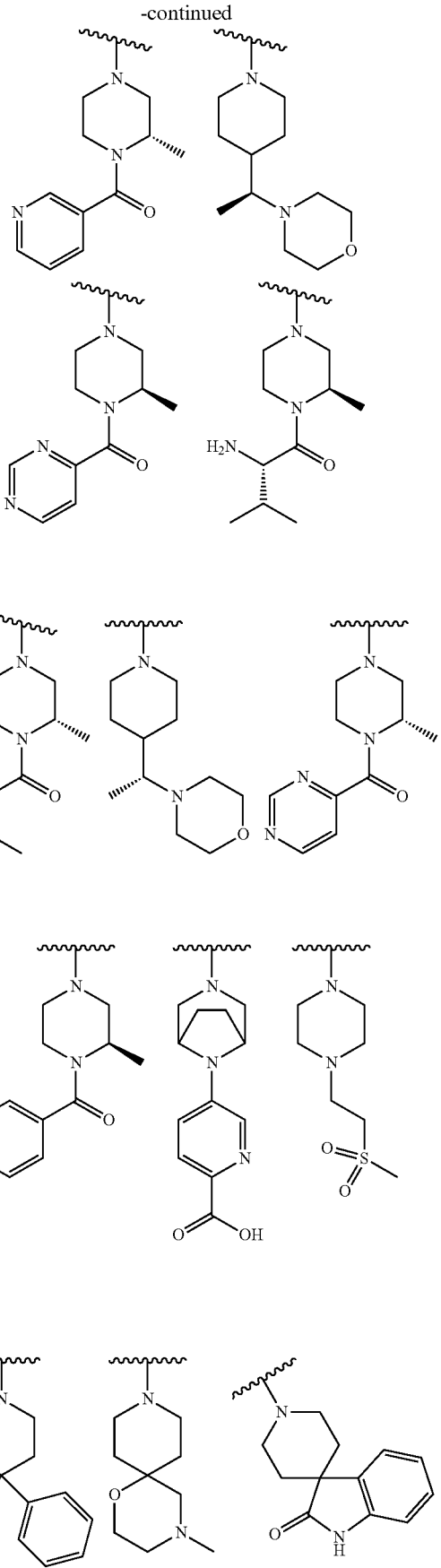

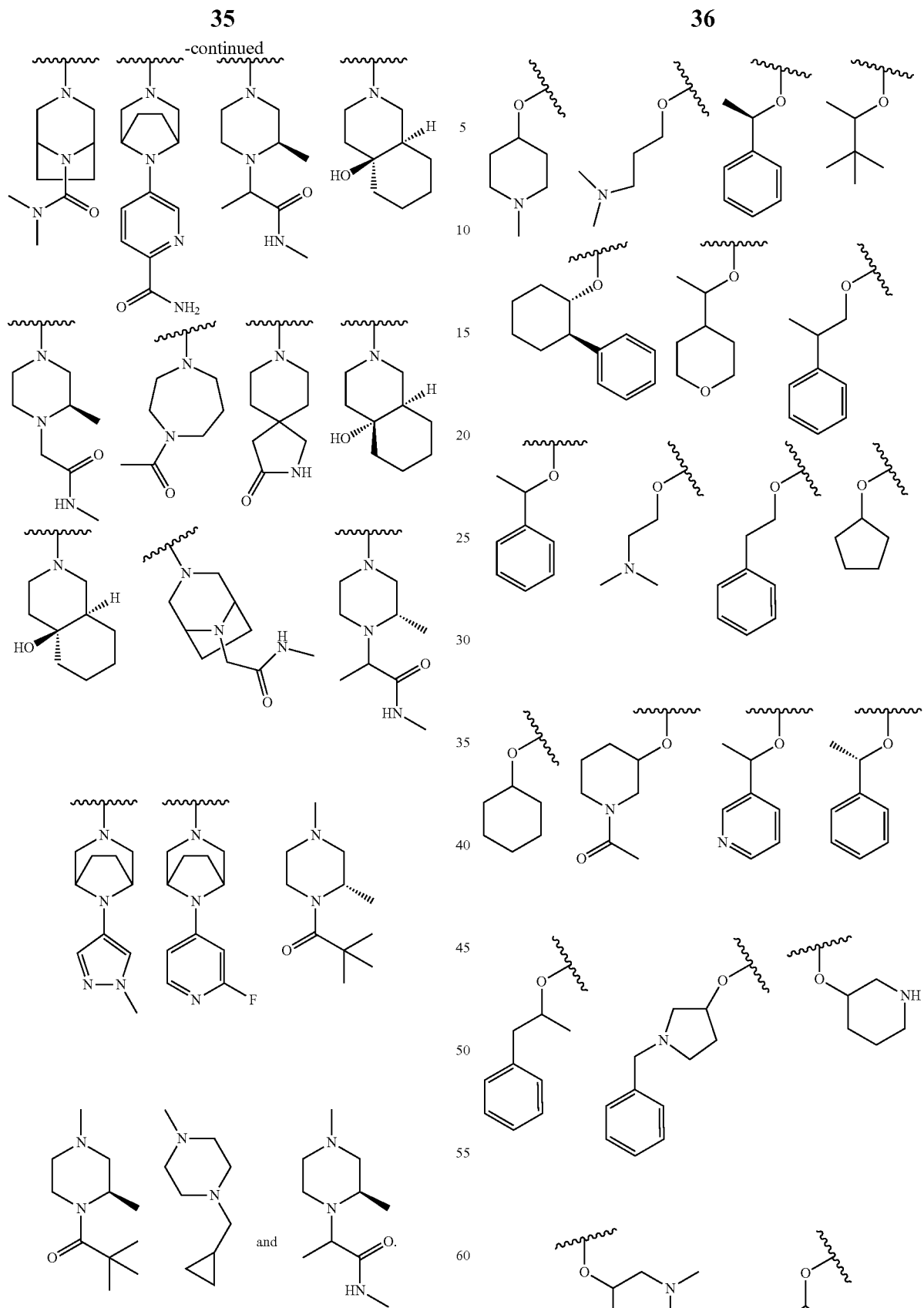
In one embodiment $R^4$ is —O—$R^b$.
In one embodiment $R^4$ is selected from the group consisting of:

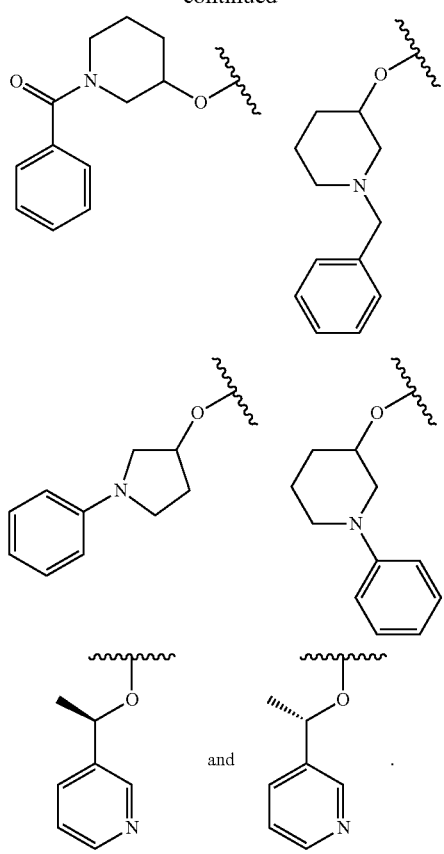
In one embodiment R$^4$ is —N(R$^b$)$_2$.
In one embodiment R$^4$ is selected from the group consisting of:
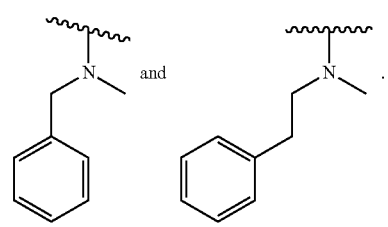
In one embodiment R$^4$ is selected from the group consisting of —R$^b$ and —C(O)—N(R$^b$)$_2$.
In one embodiment R$^4$ is selected from the group consisting of:
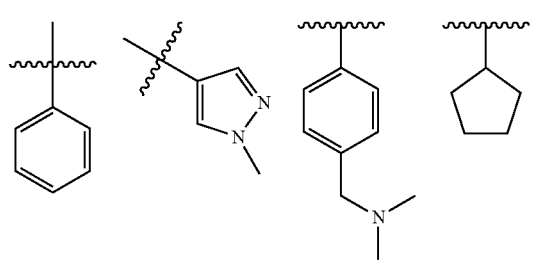
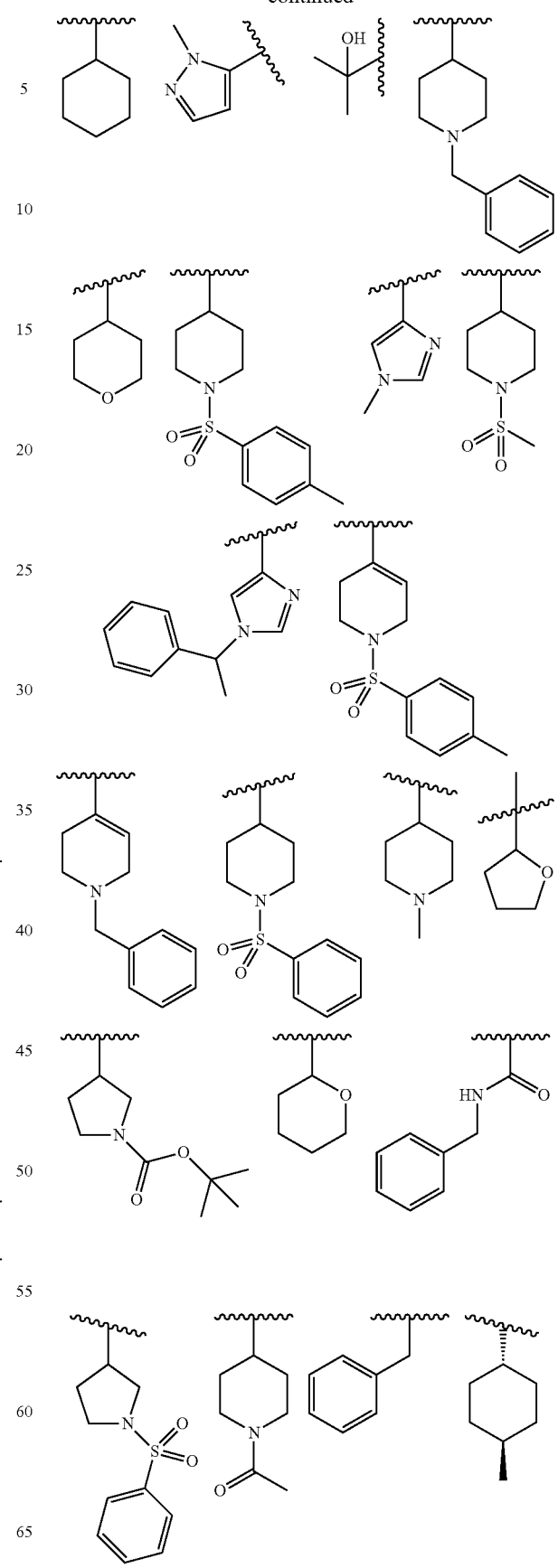

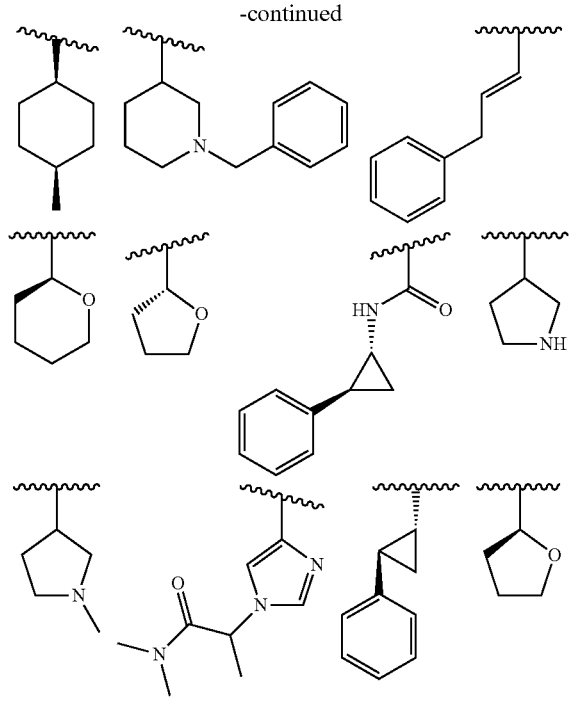
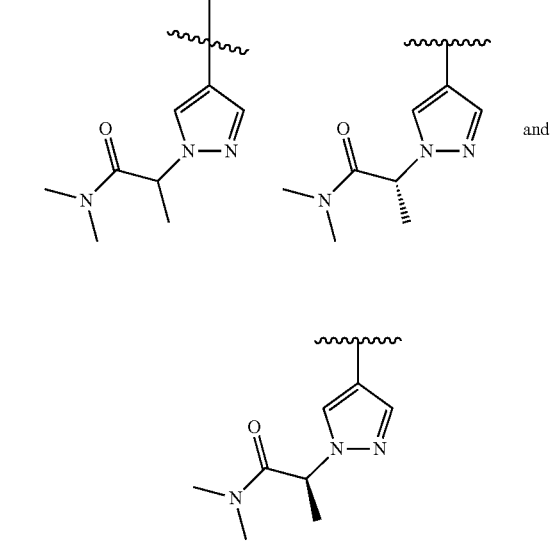
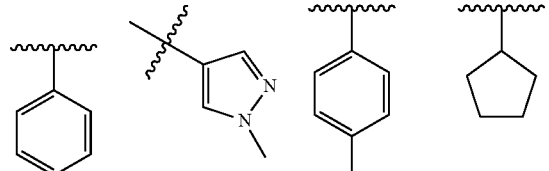
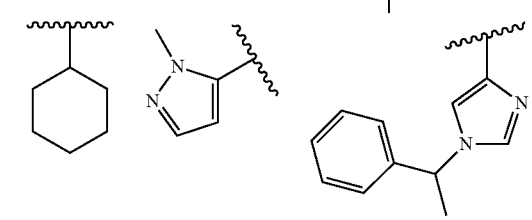
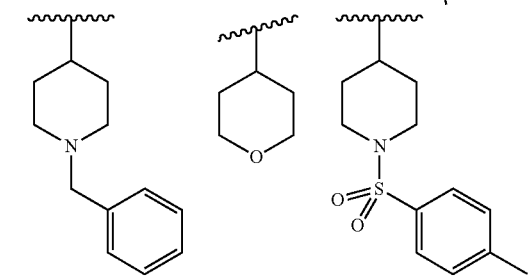
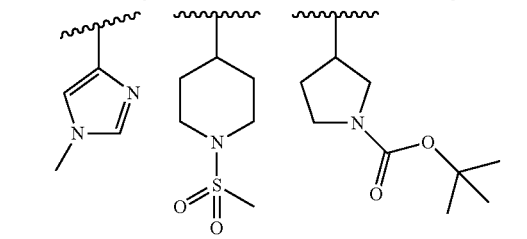
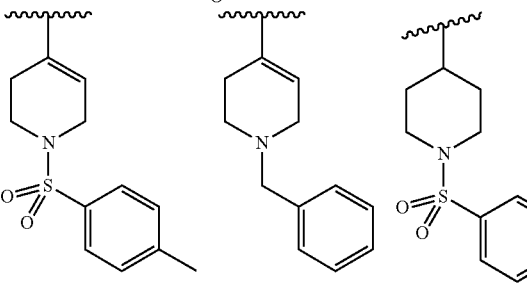
In one embodiment R⁴ is selected from the group consisting of:

-continued
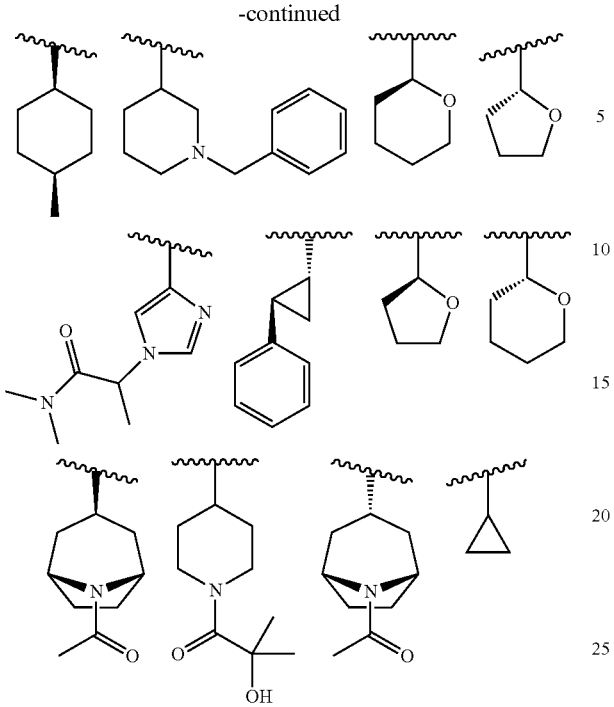
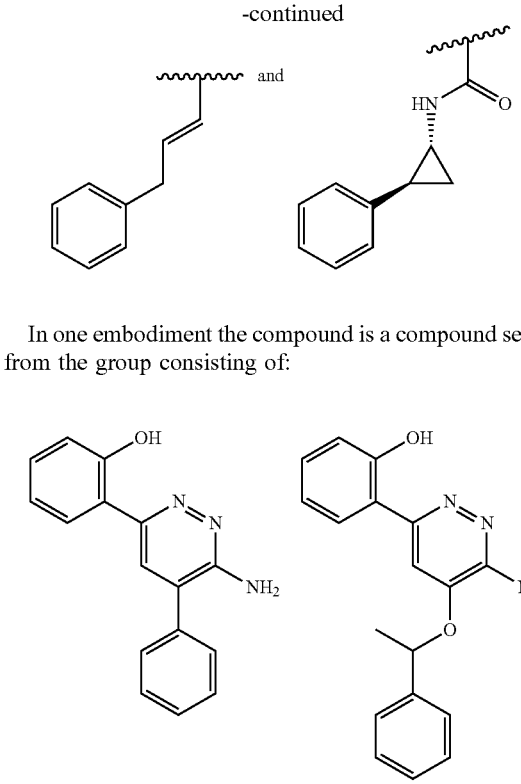
In one embodiment the compound is a compound selected from the group consisting of:
In one embodiment $R^4$ is selected from the group consisting of:
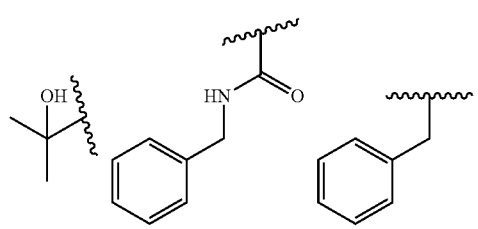
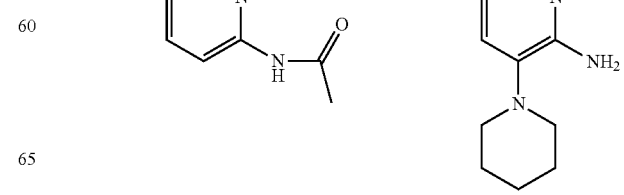

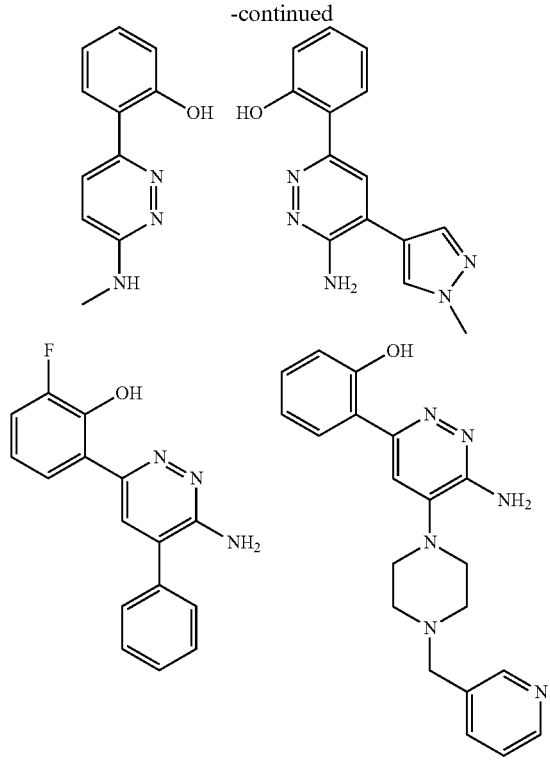
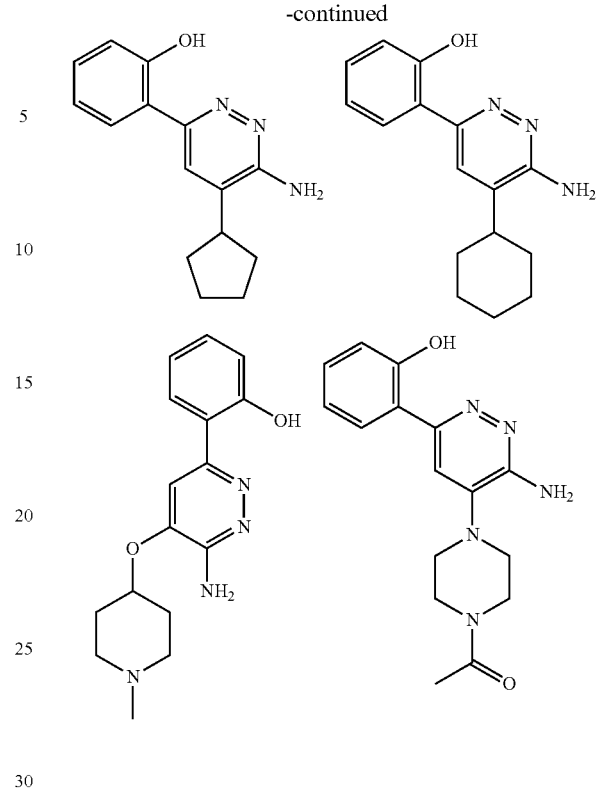
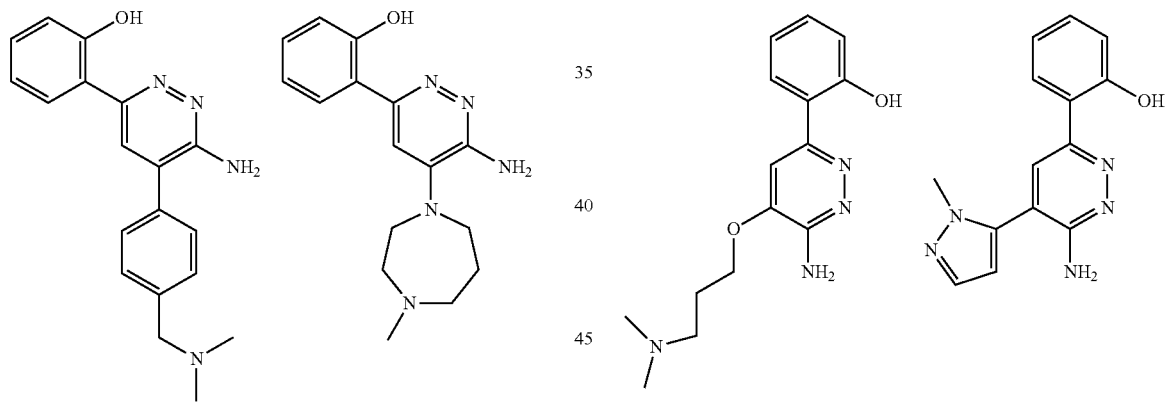
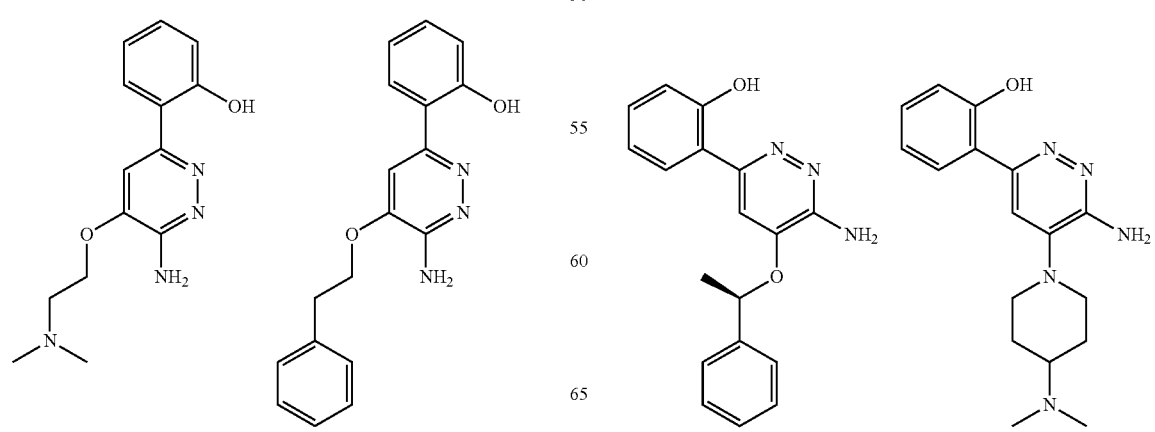

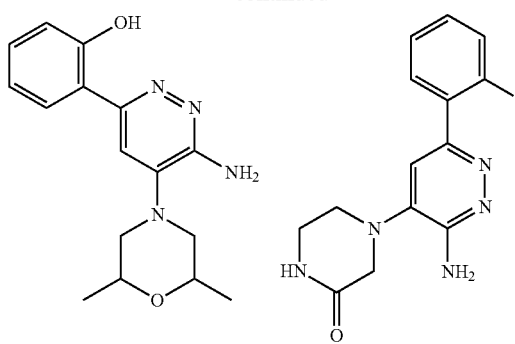
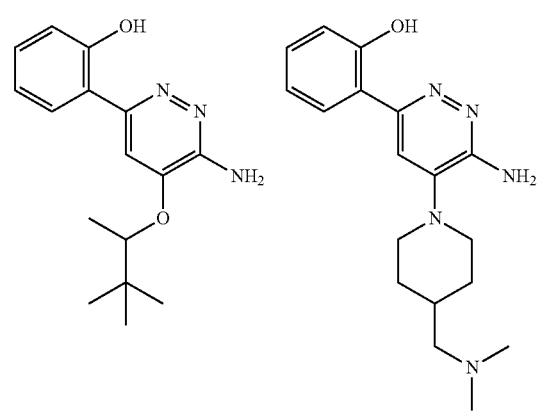
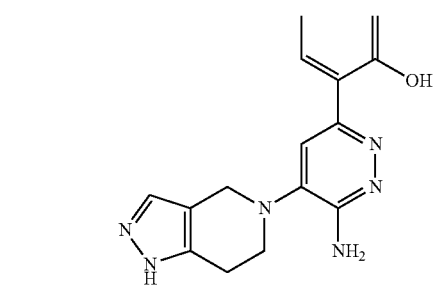
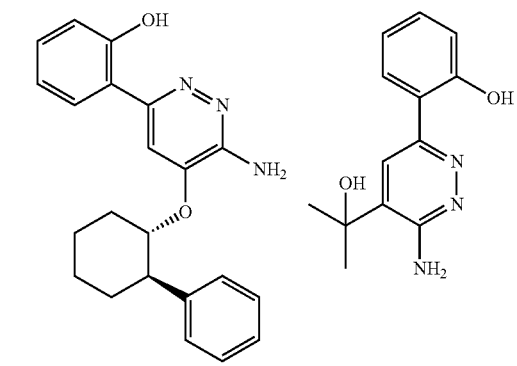
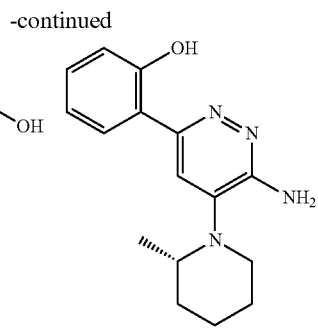
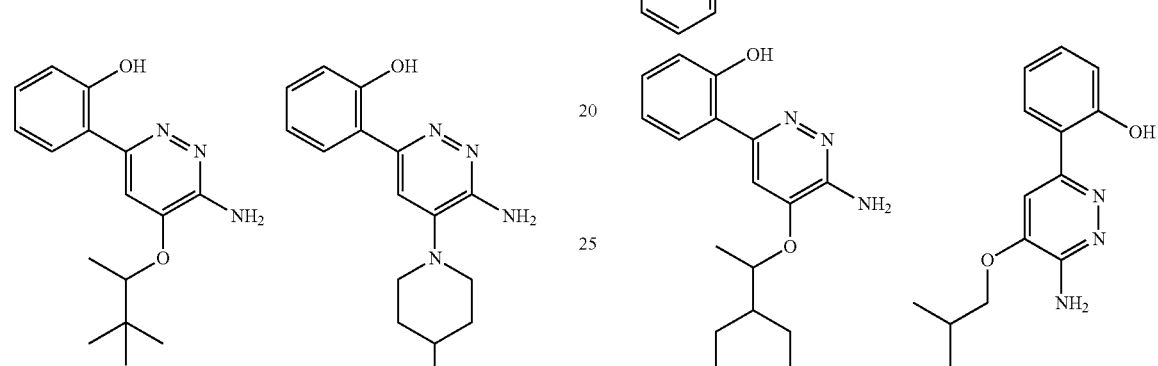
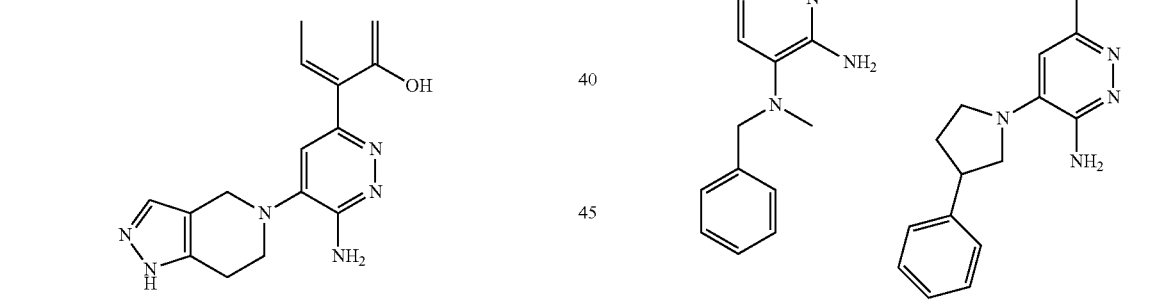
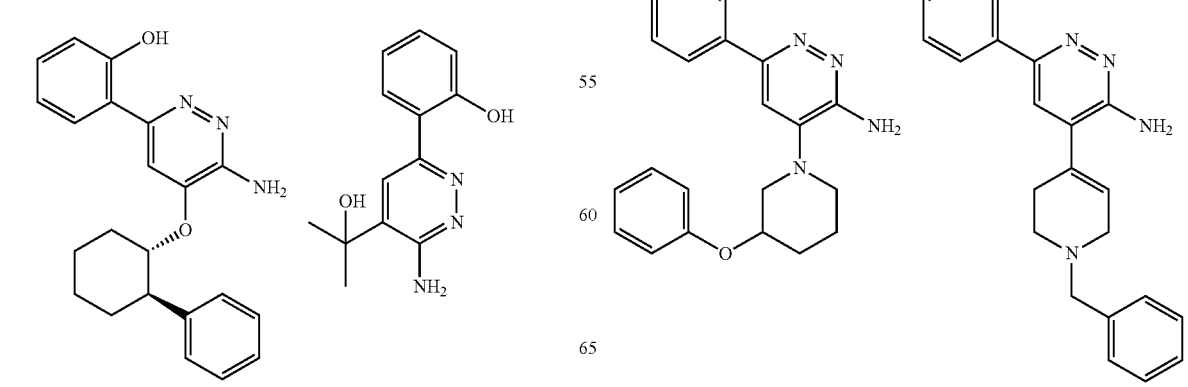

-continued
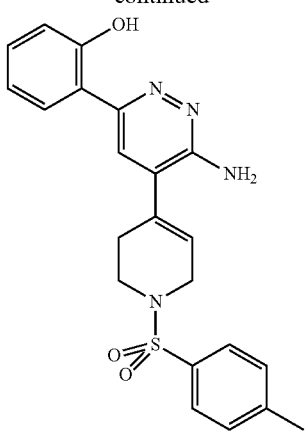
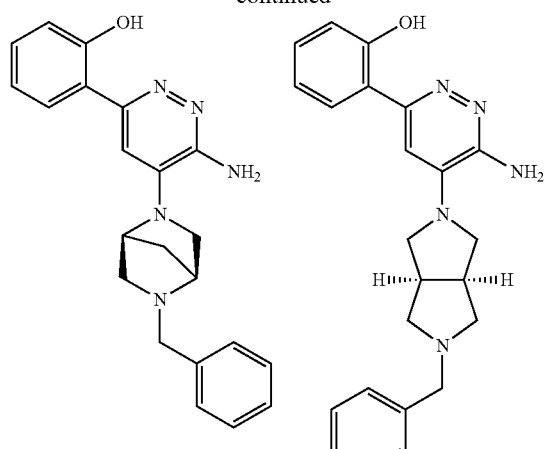
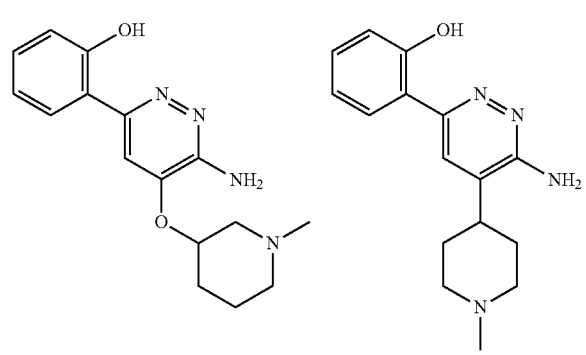
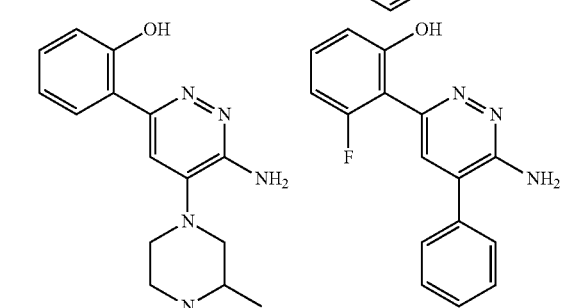
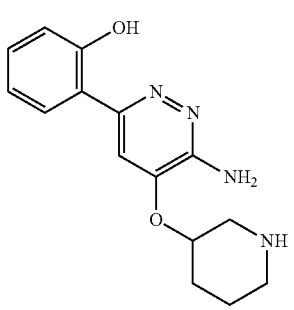
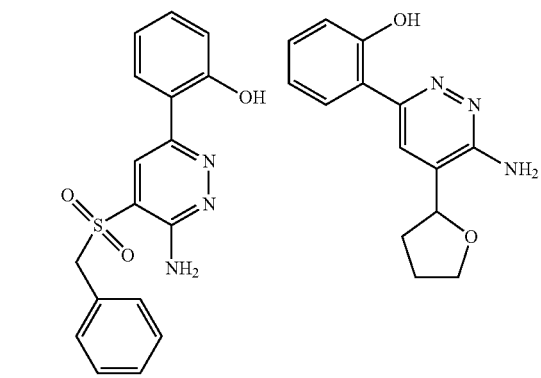
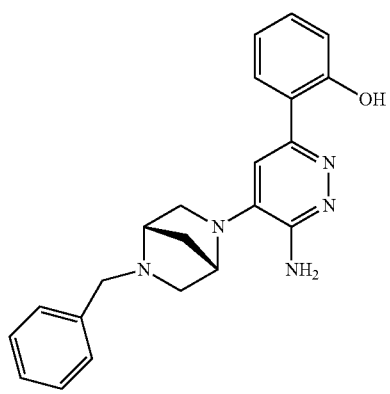
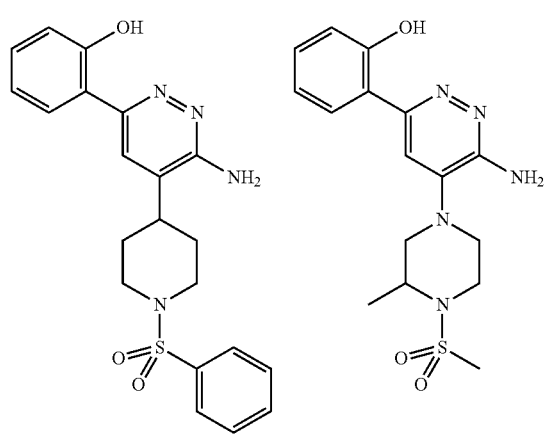

49
-continued
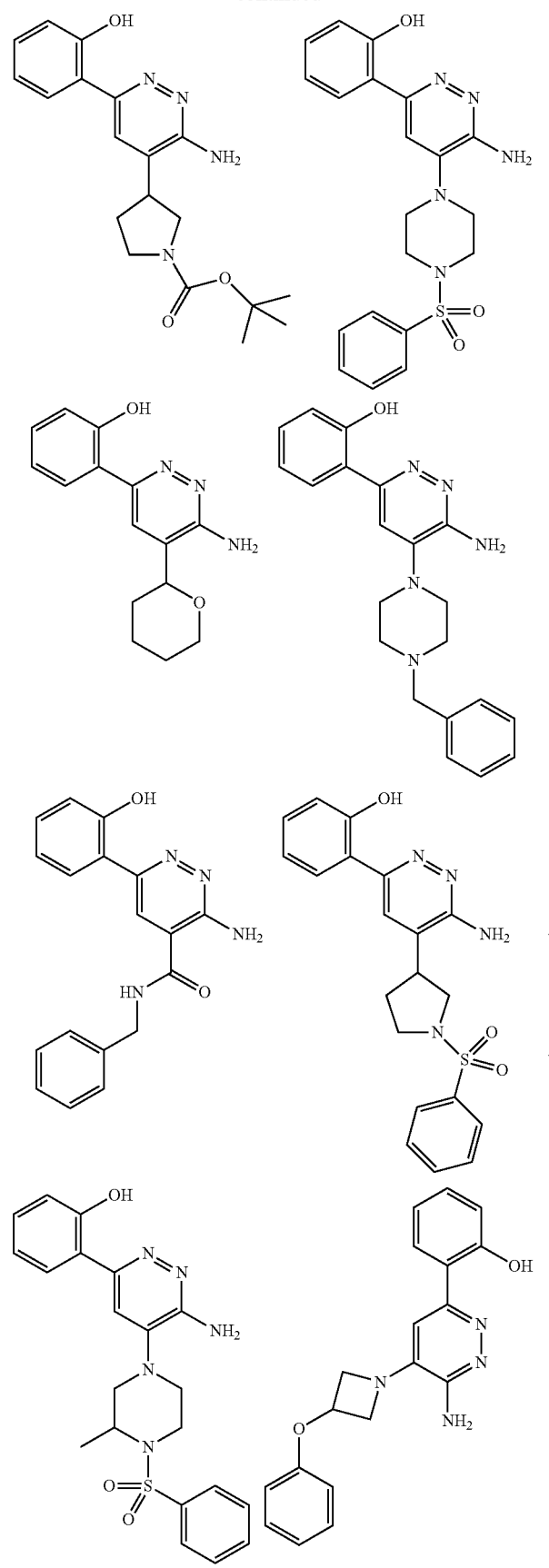
50
-continued
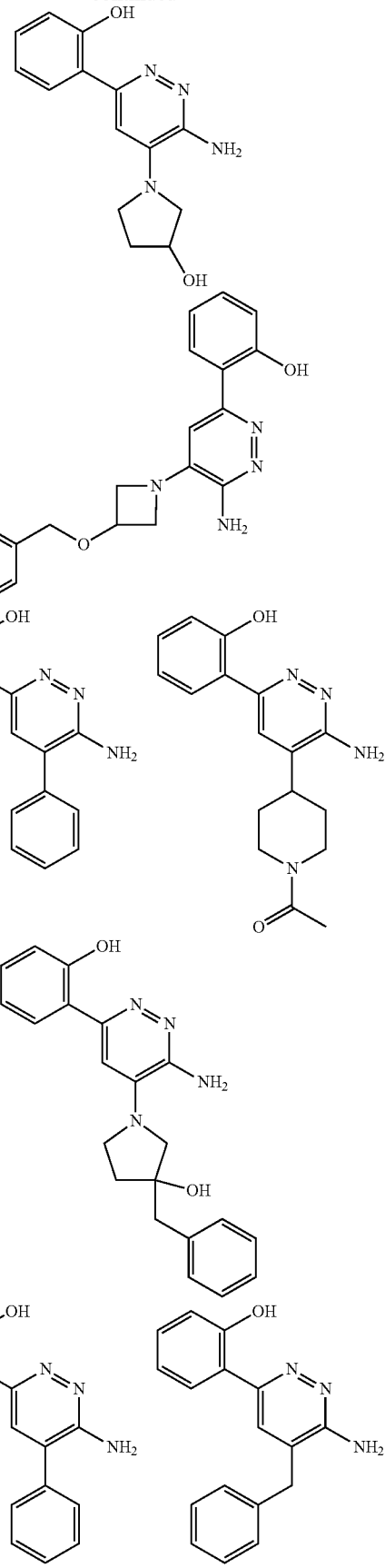

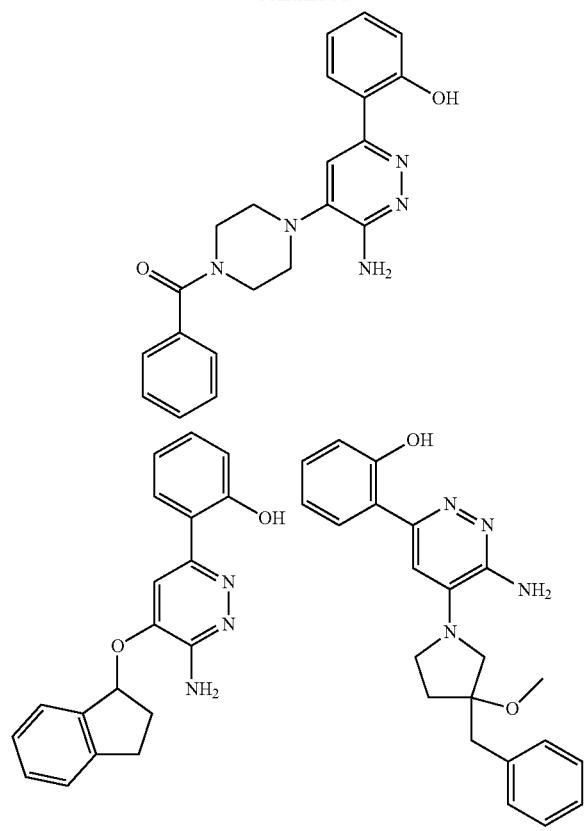
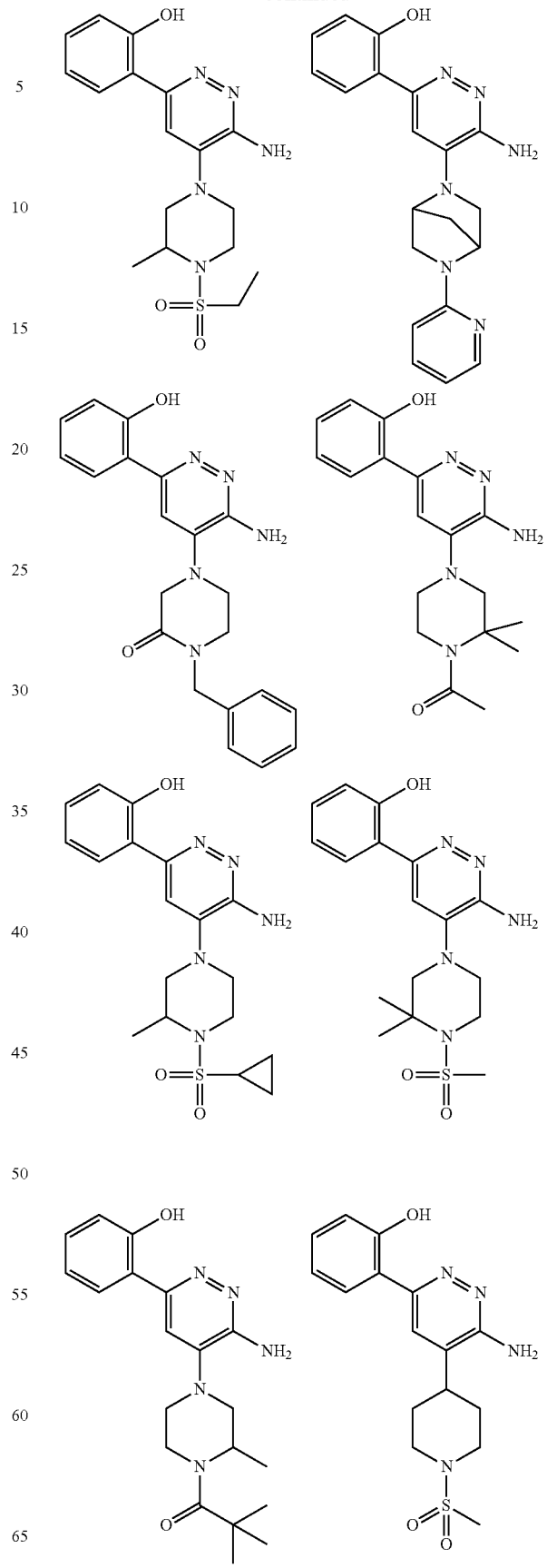

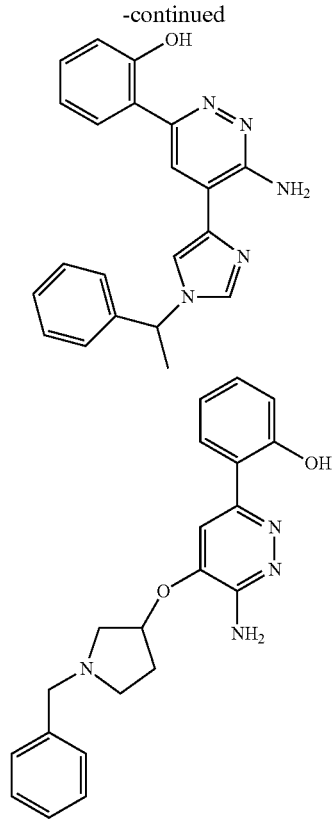
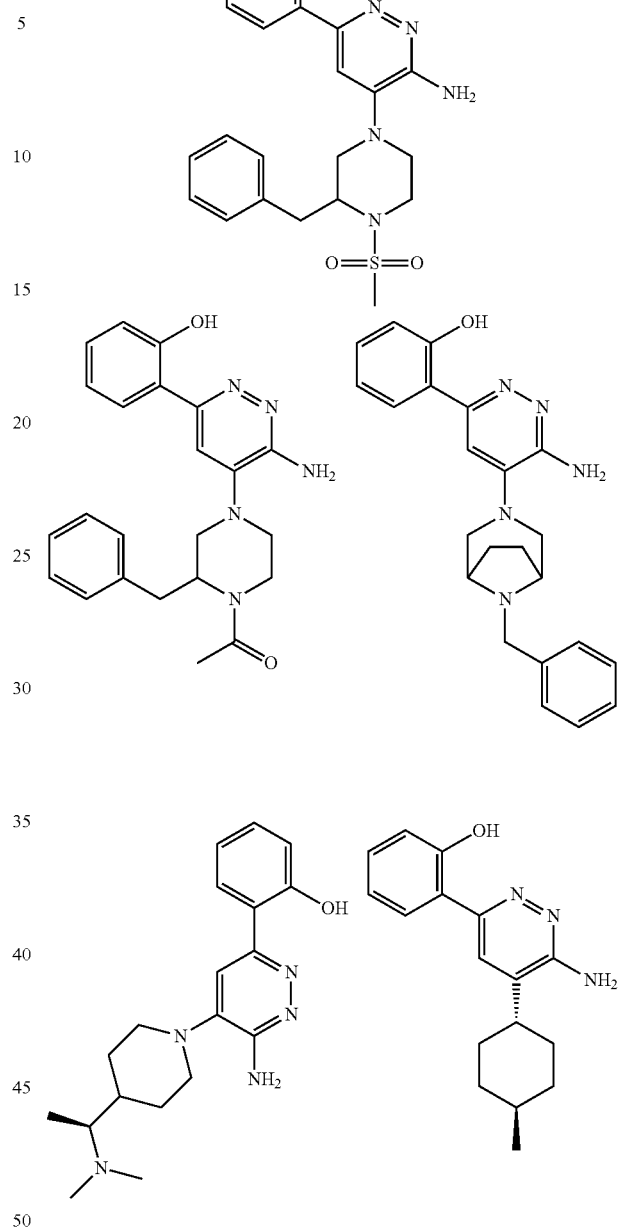
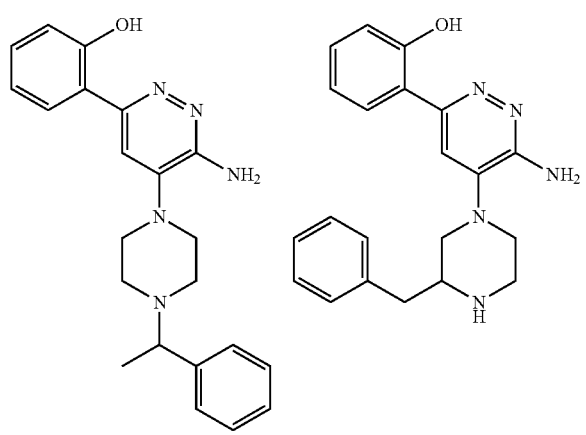
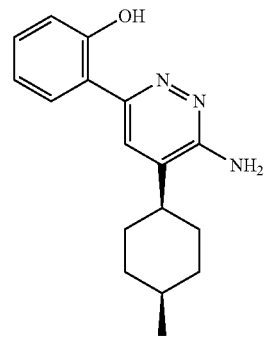

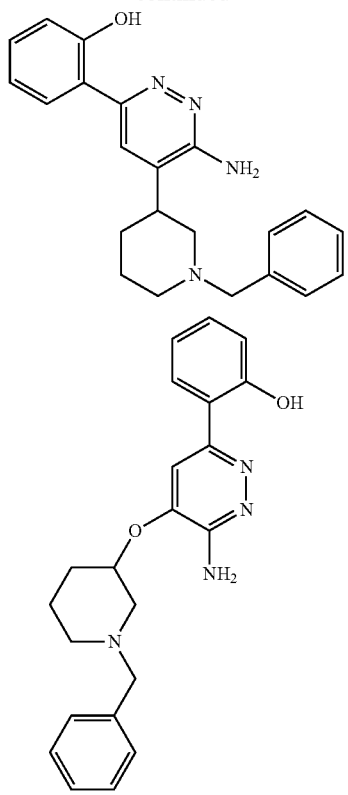
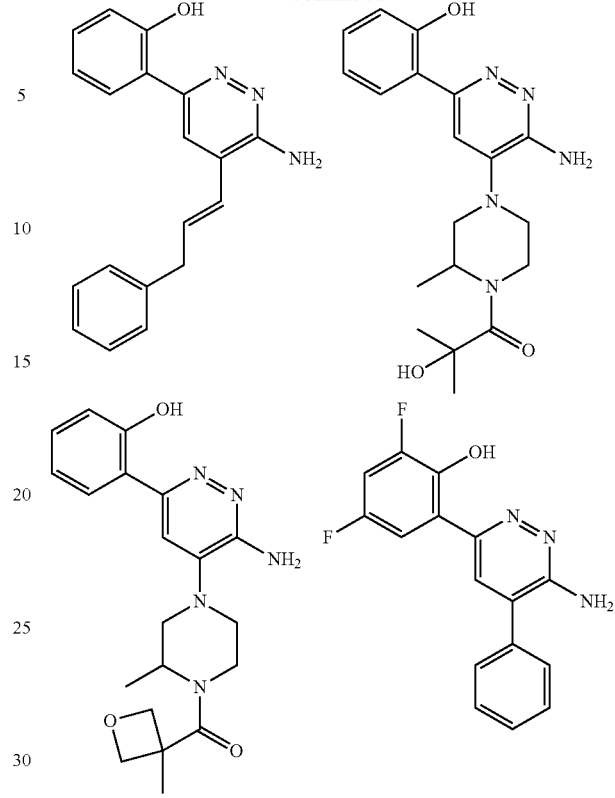
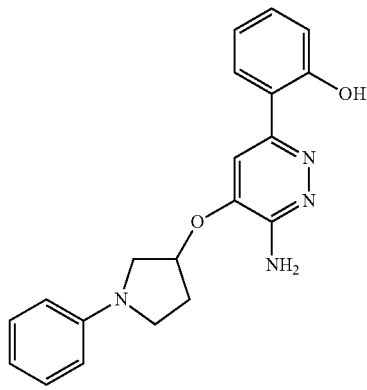
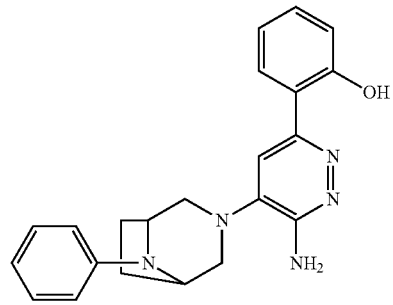
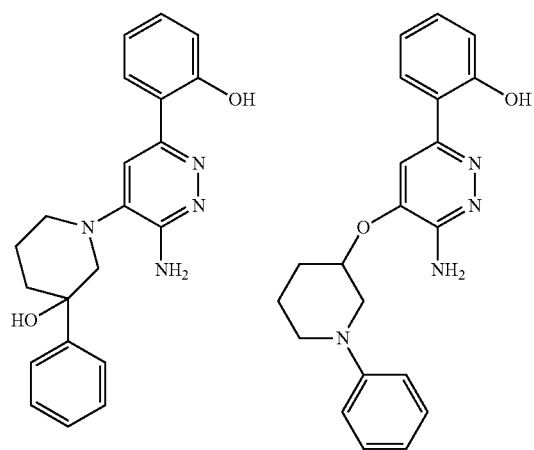
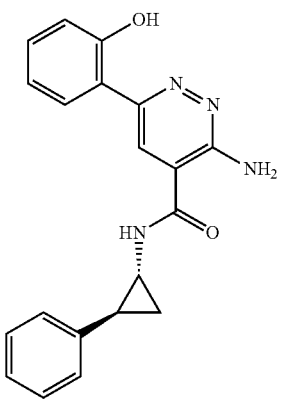

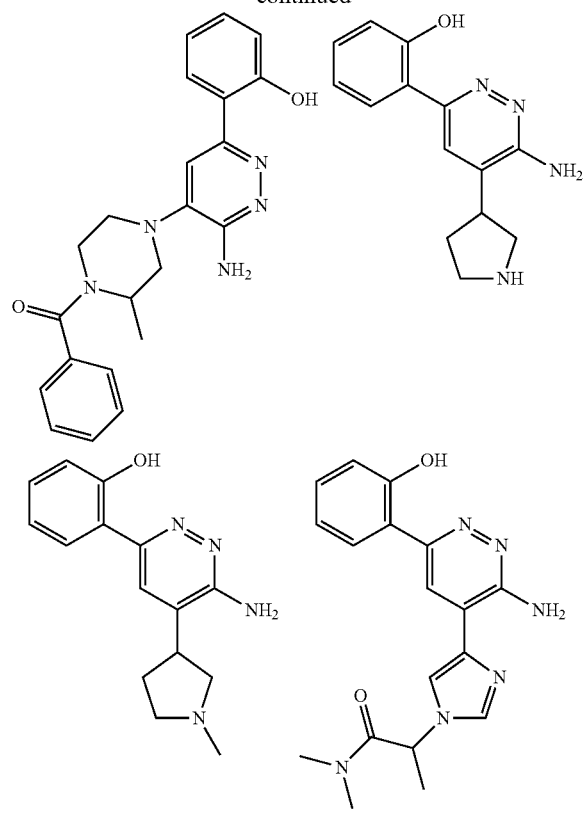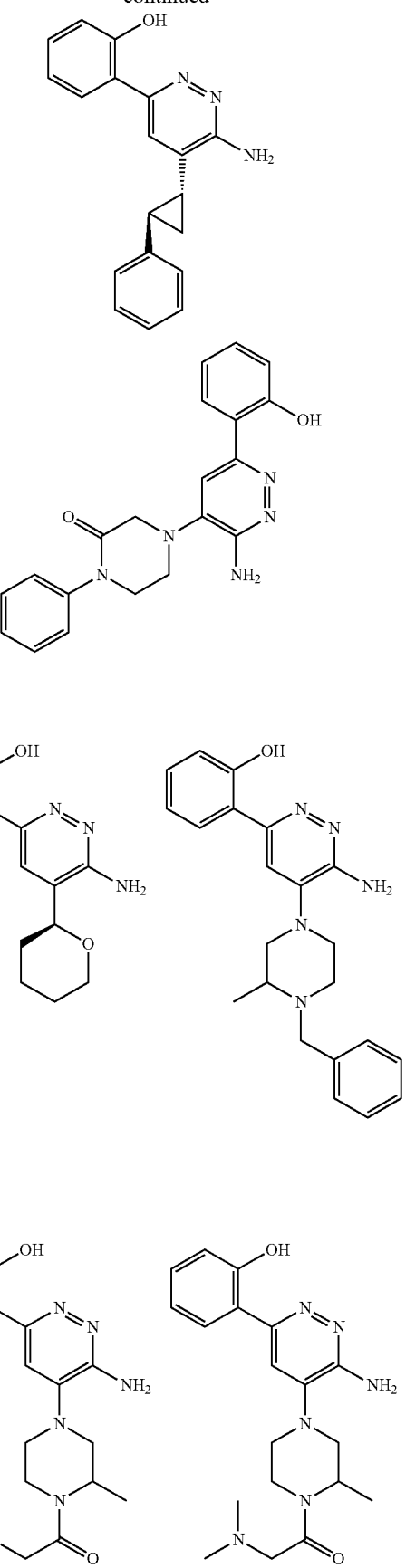

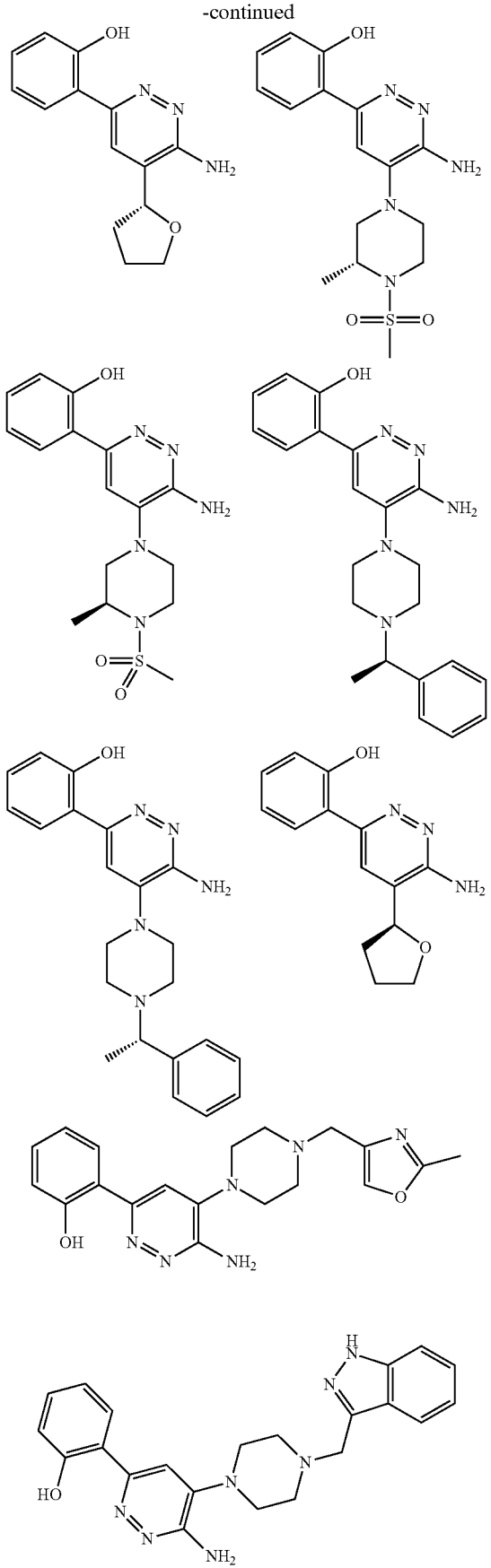
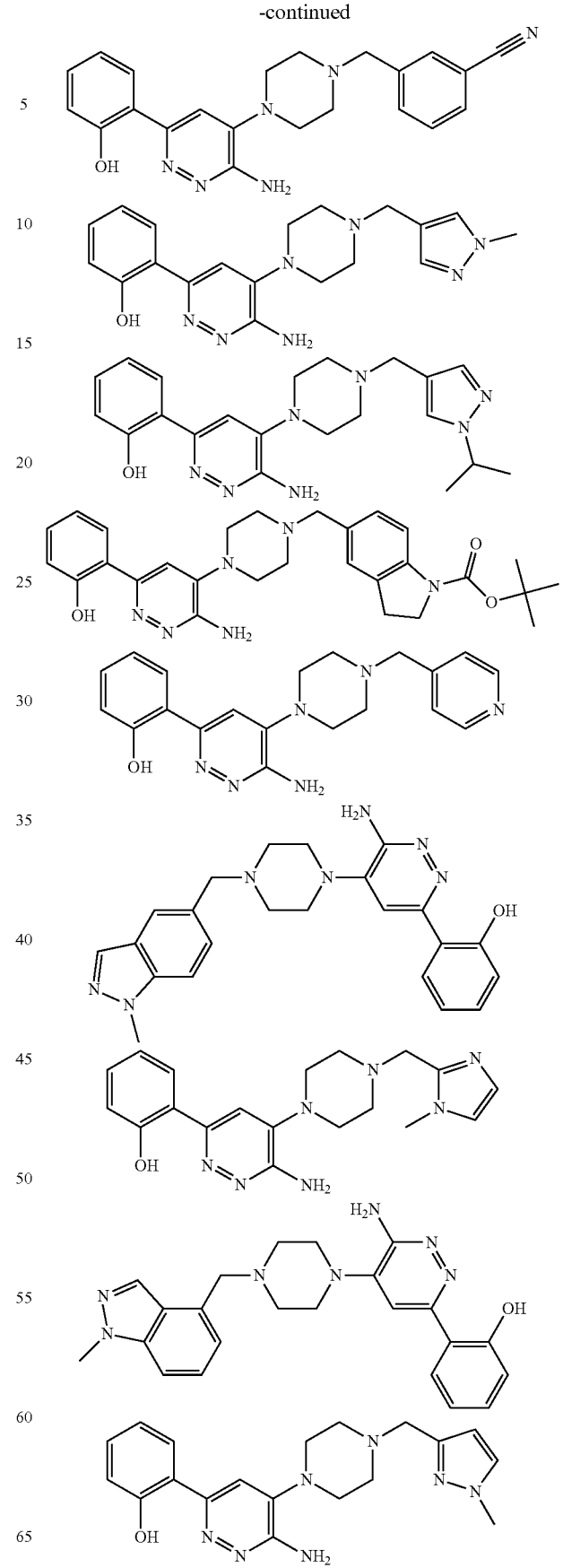

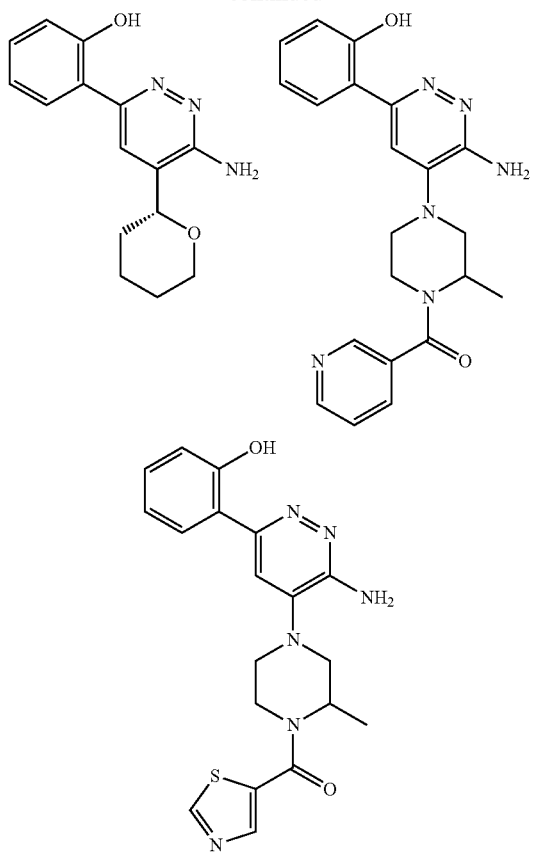
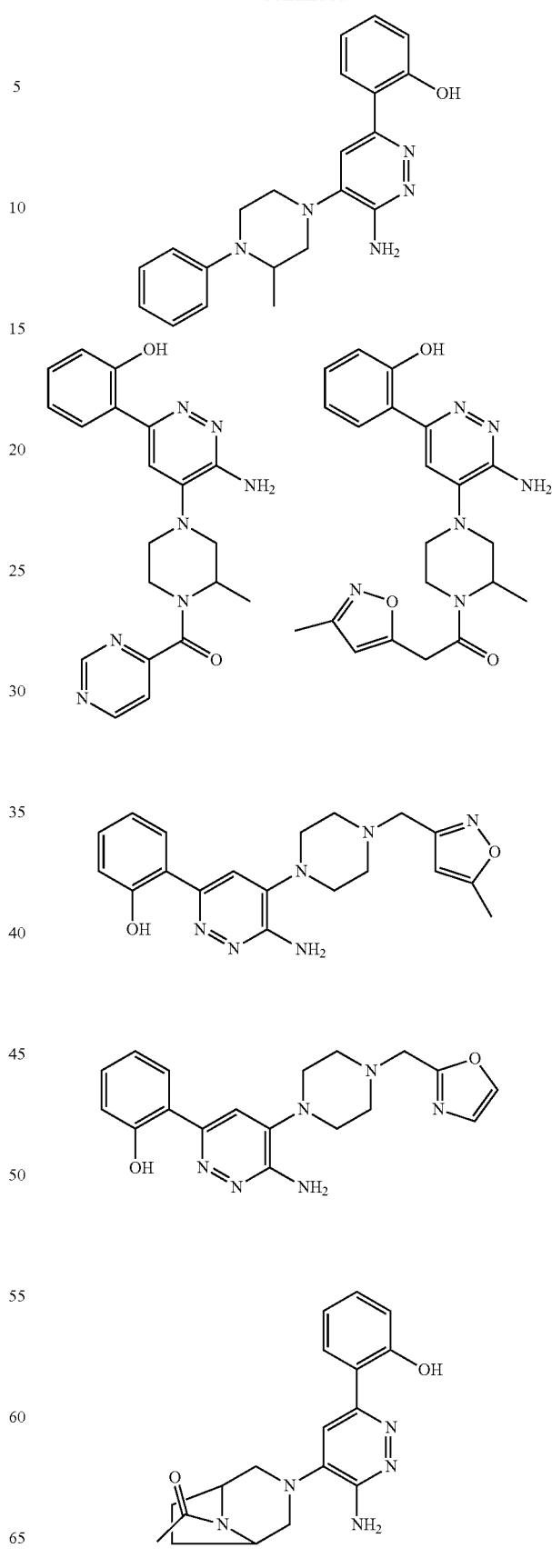

-continued
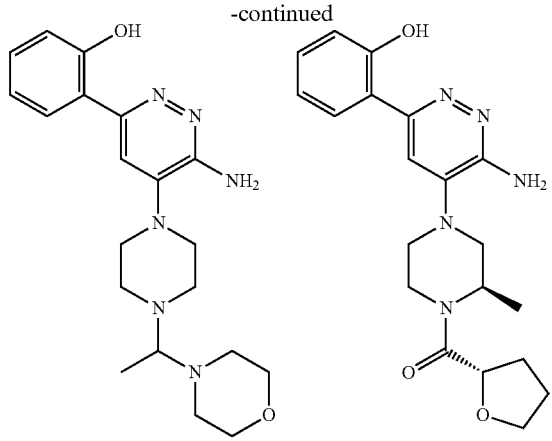
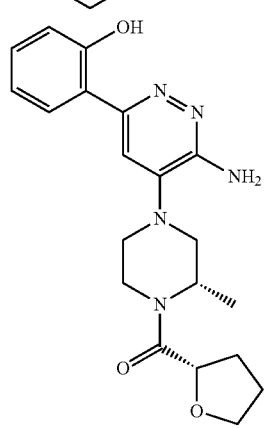
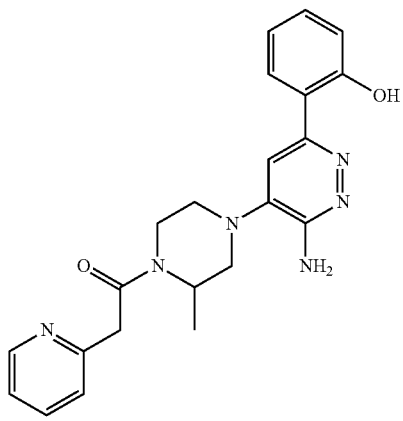
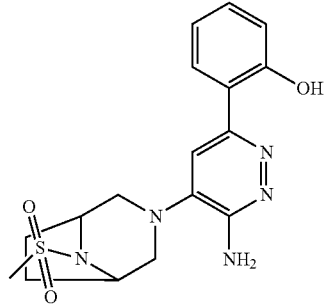
-continued
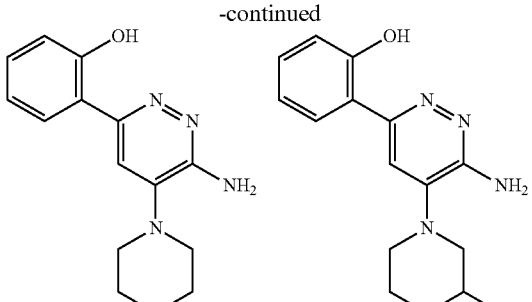
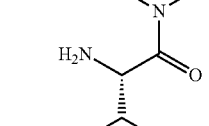
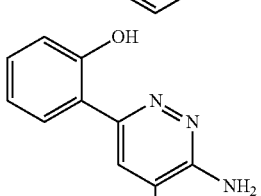
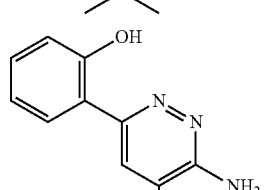
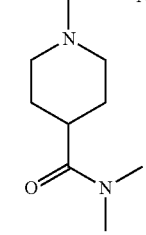
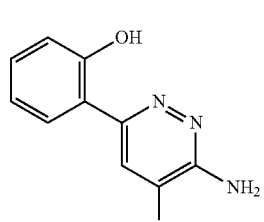
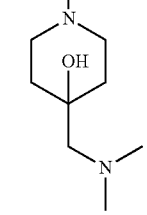
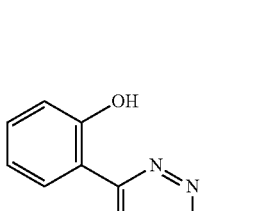
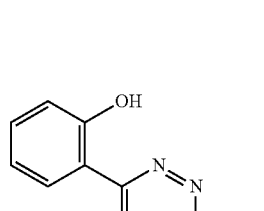
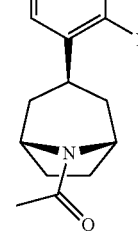
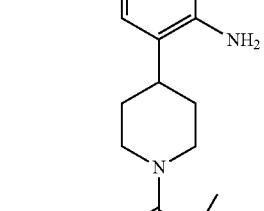

-continued
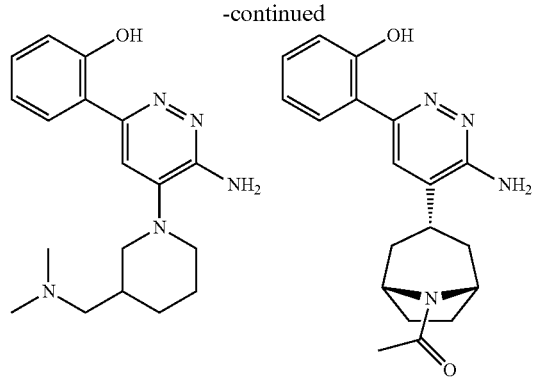
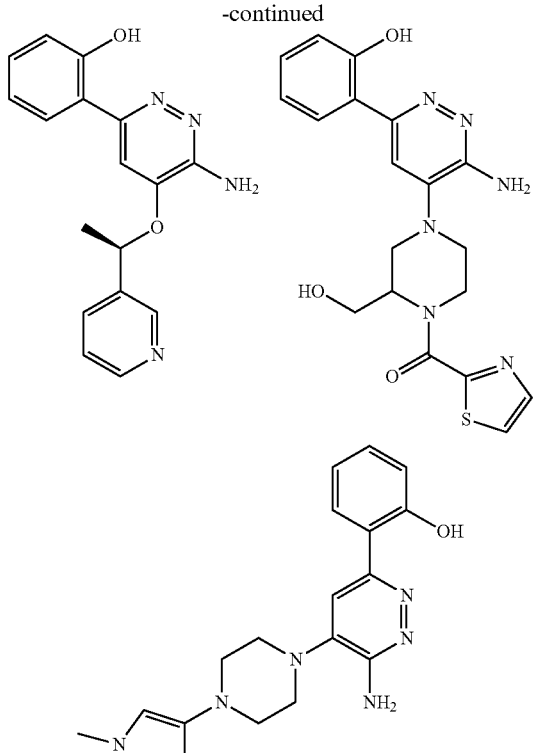
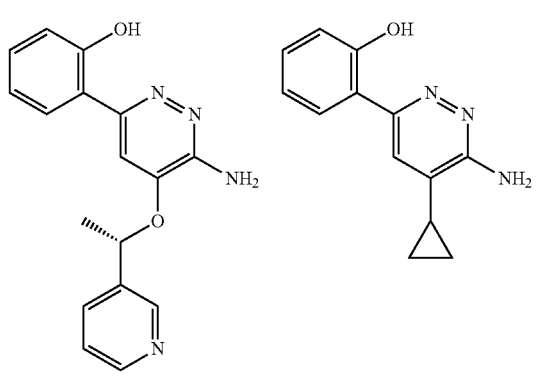
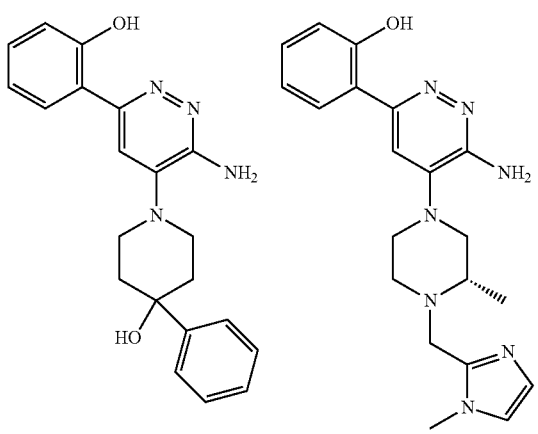

-continued
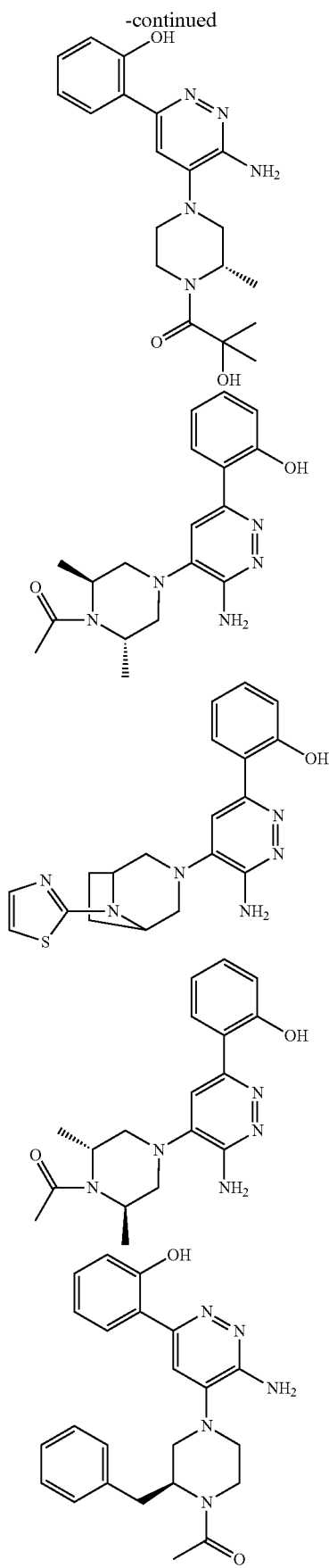
-continued
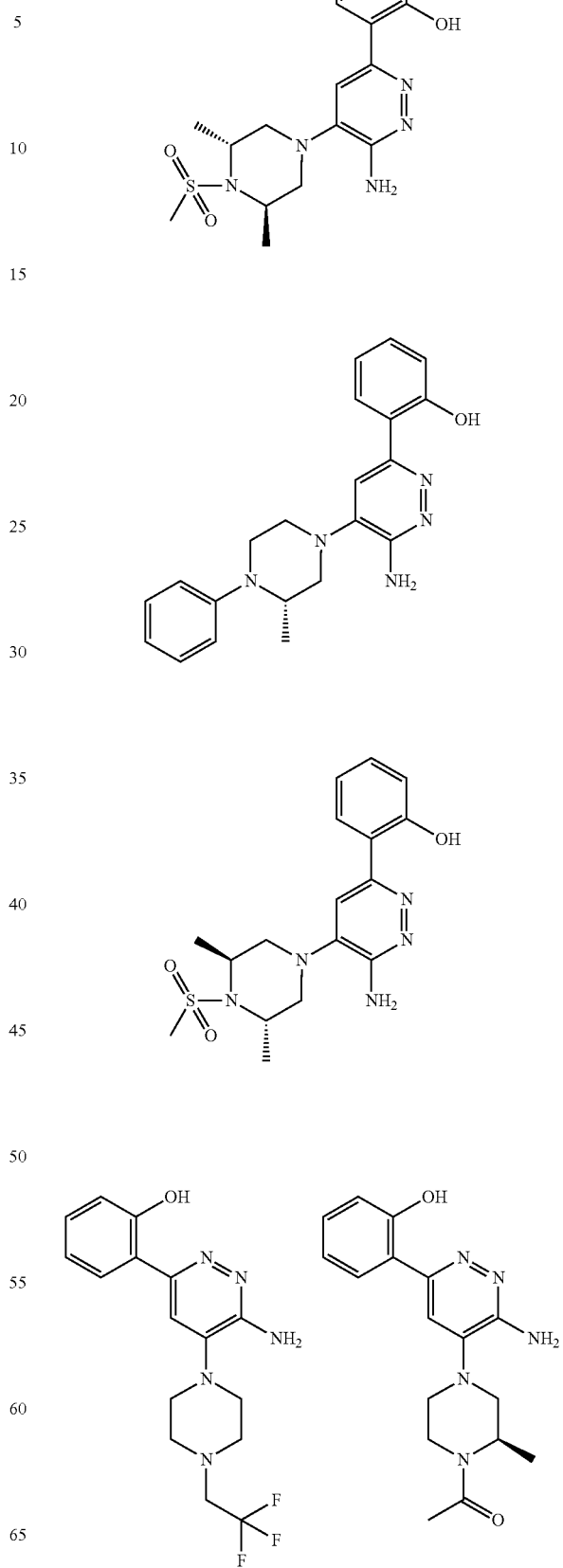

-continued
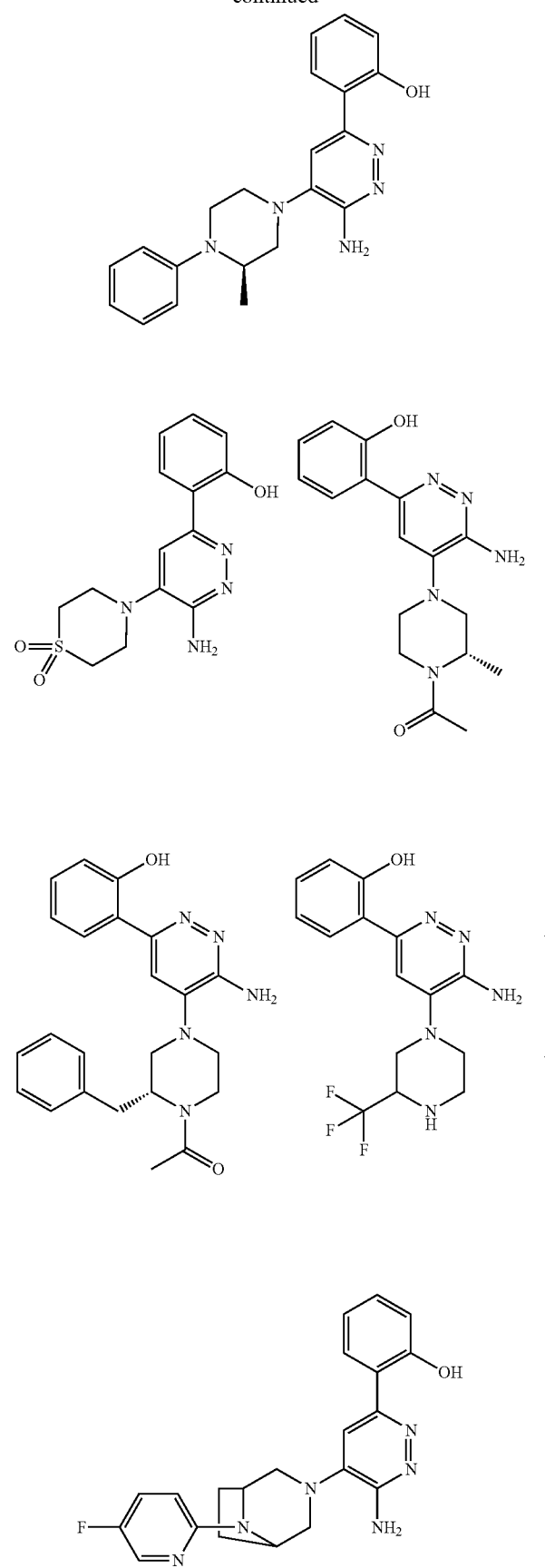
-continued
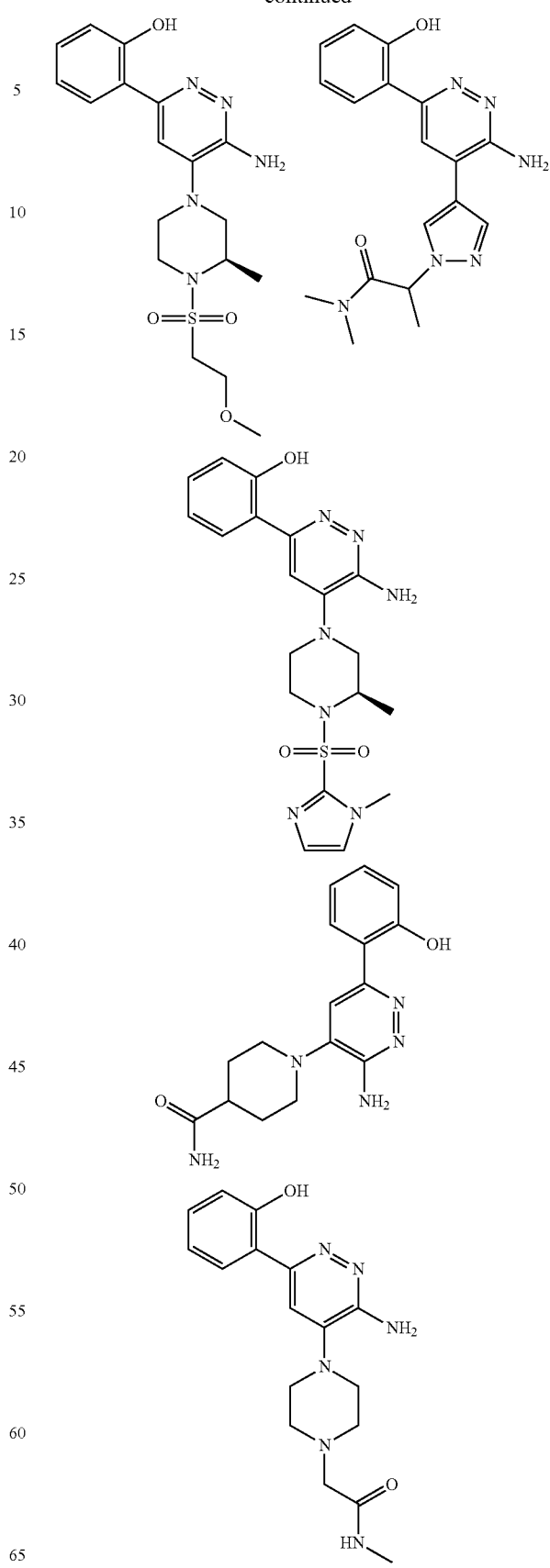

-continued
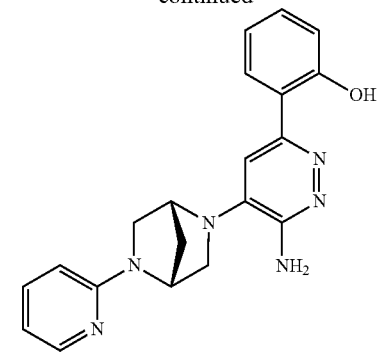
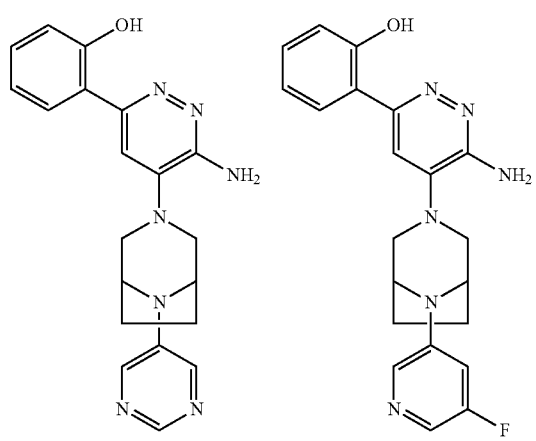
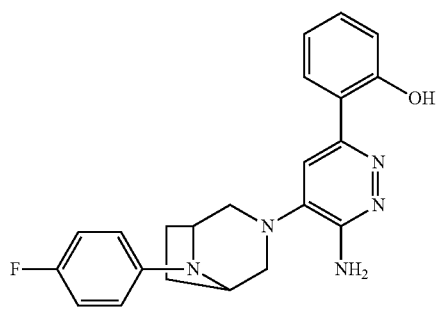
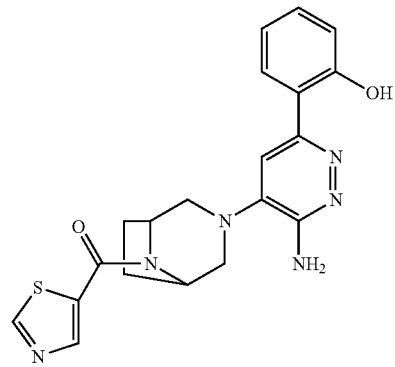
-continued
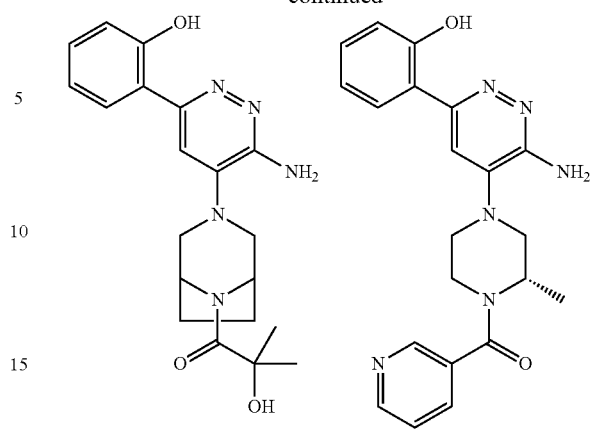
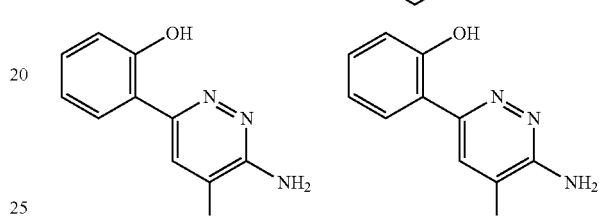
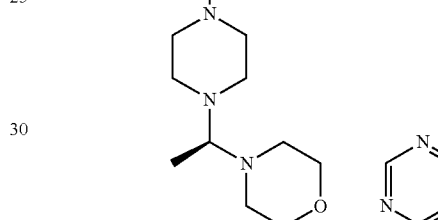
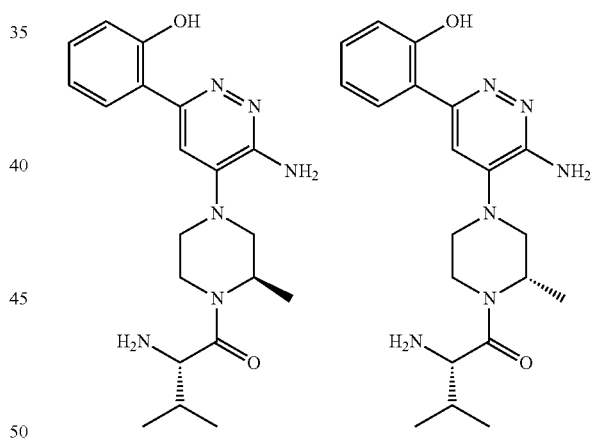
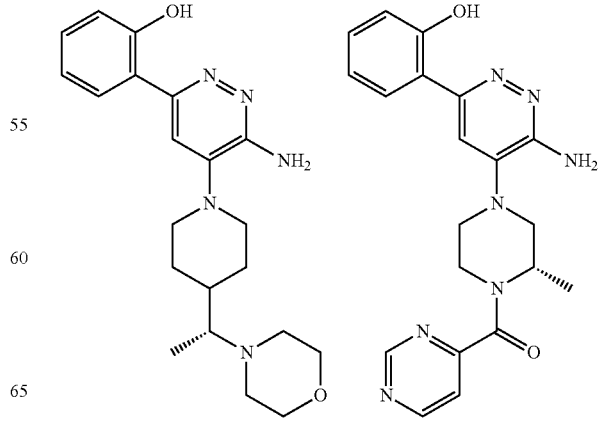

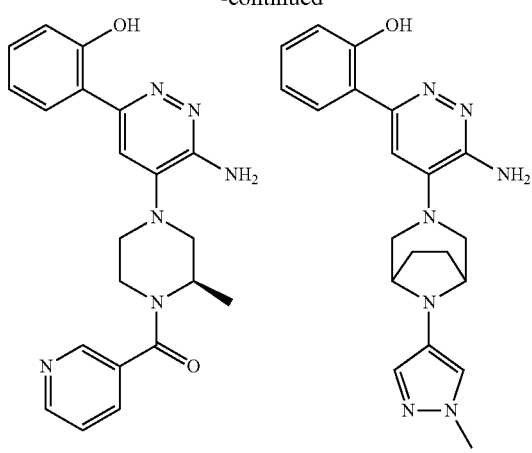
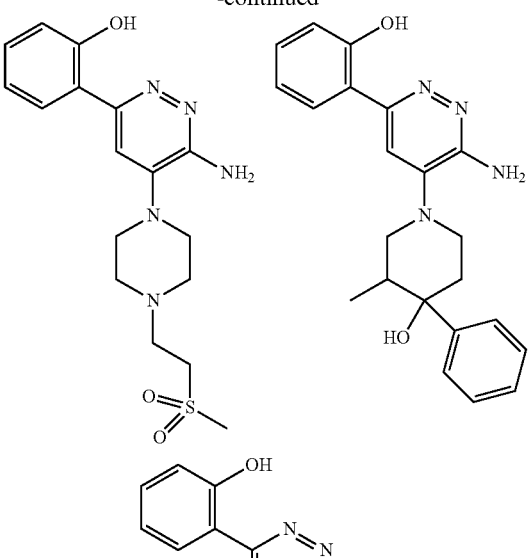
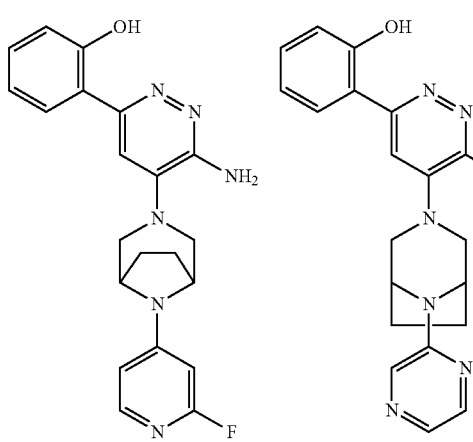
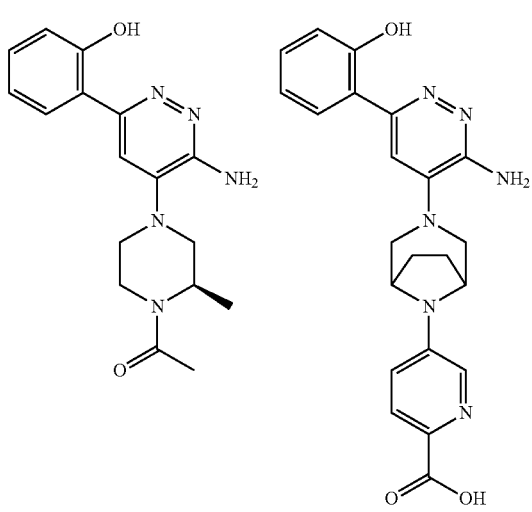
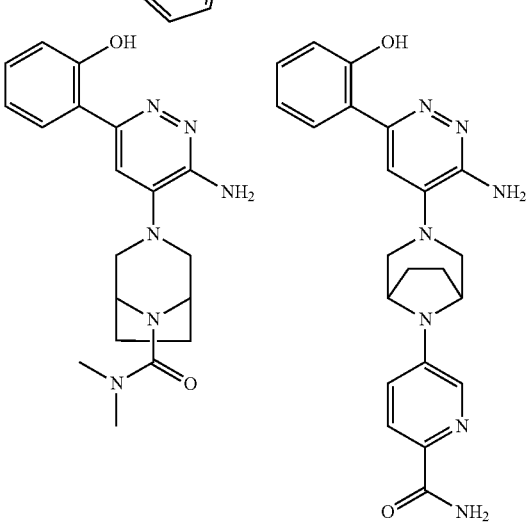

75
-continued
76
-continued
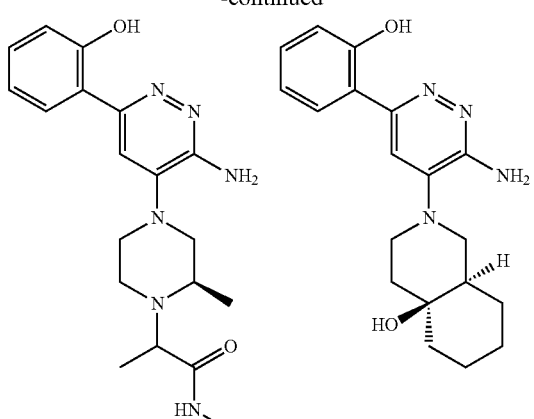
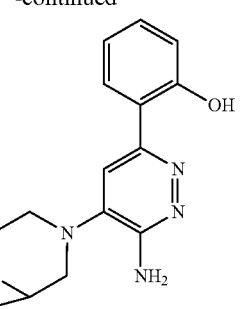
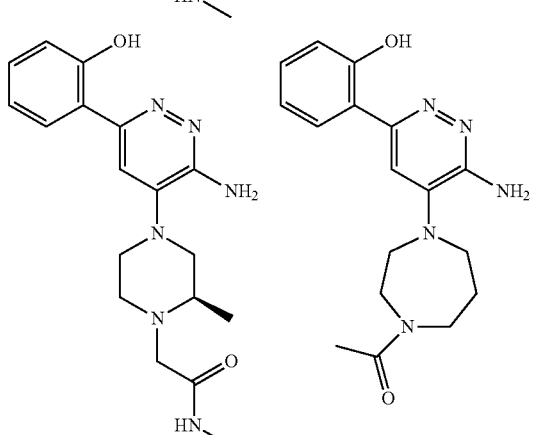
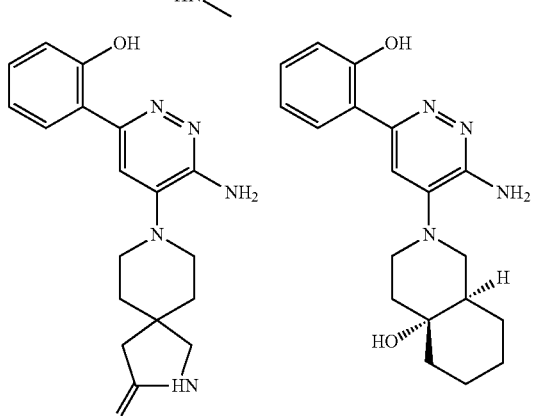
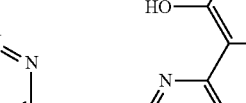
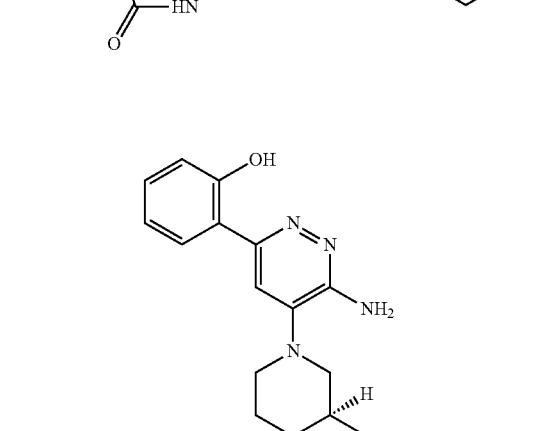

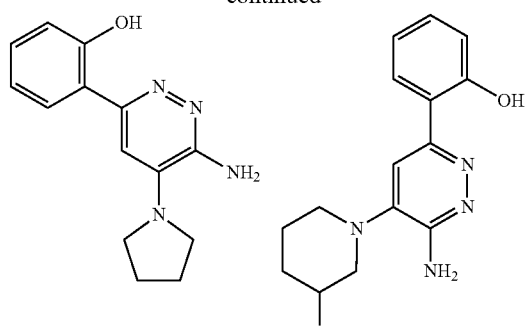
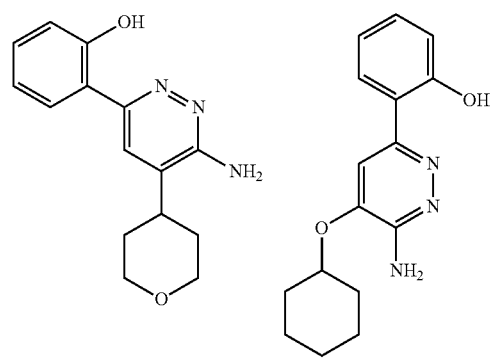
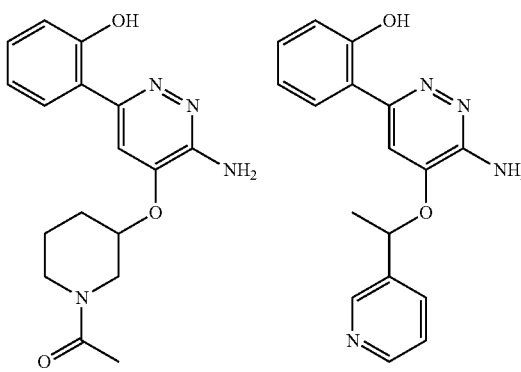
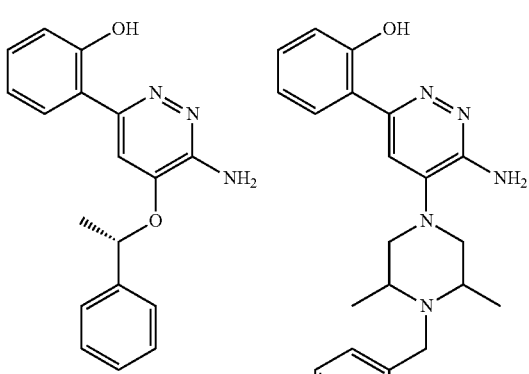
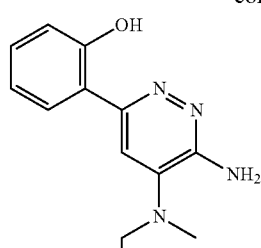
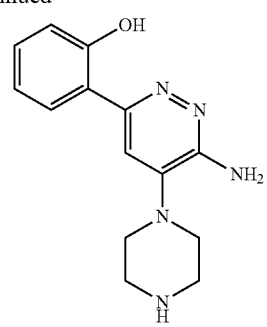
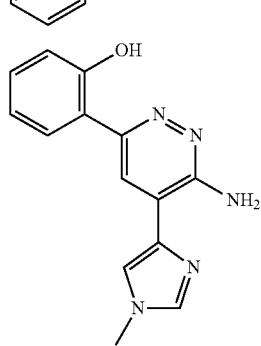
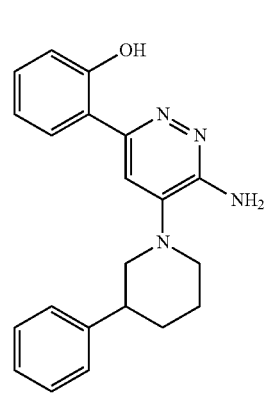
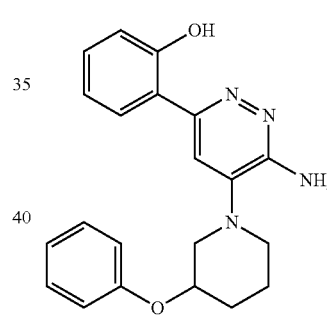
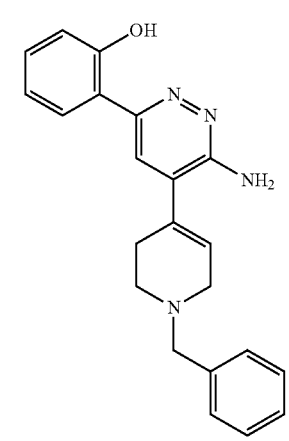

79
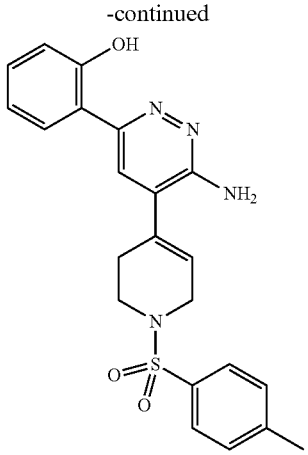
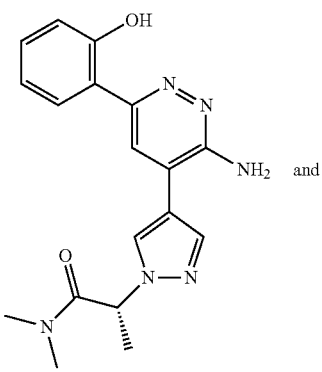
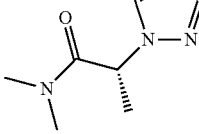
and
80
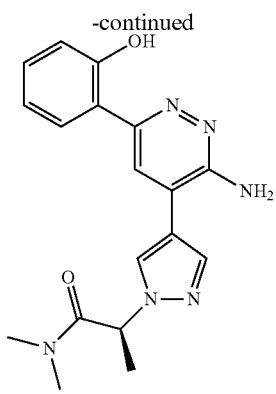
and salts thereof.
In one embodiment the compound is:
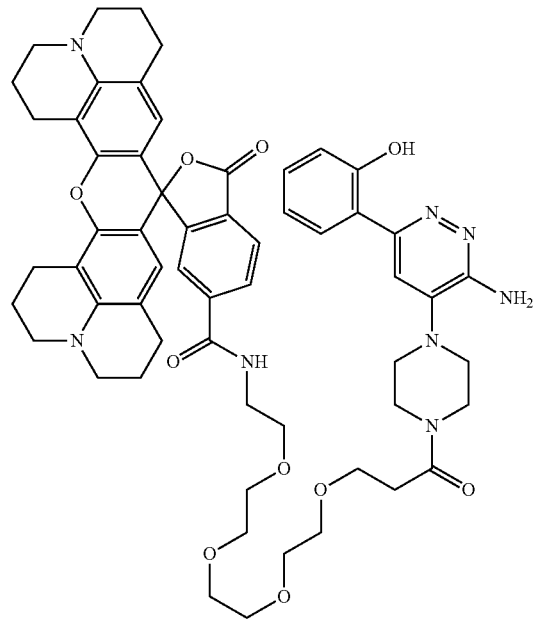 [SMILES: Nc1nnc(-c2ccccc2O)cc1N1CCN(C(=O)CCOCCOCCOCCOCCNC(=O)c2ccc3c(c2)C2(OC3=O)c3cc4c5c(c3Oc3c2cc2c6c3CCCN6CCC2)CCCN5CCC4)CC1]
or a salt thereof.
In one embodiment the compound is:
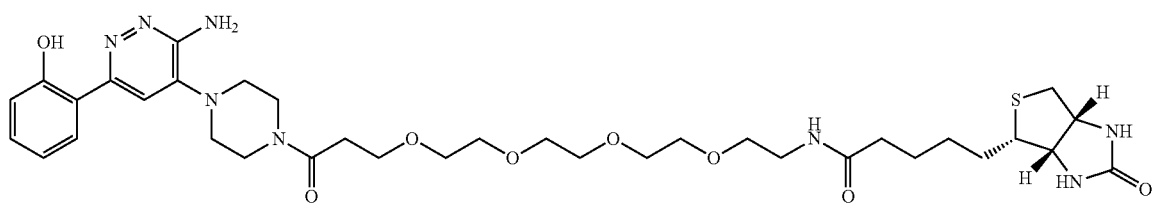 [SMILES: Nc1nnc(-c2ccccc2O)cc1N1CCN(C(=O)CCOCCOCCOCCOCCNC(=O)CCCC[C@@H]2SC[C@@H]3NC(=O)N[C@@H]32)CC1]
or a salt thereof.

In one embodiment the compound of formula (I) is not 2-(6-aminopyridazin-3-yl)phenol or 2-(6-(methylamino) pyridazin-3-yl)phenol.

In one embodiment one of $R^2$ and $R^3$ is other than H.

In one embodiment $R^4$ is not hydrogen or $C_{1-2}$alkyl.

In one embodiment $R^4$ is not hydrogen or $C_{1-6}$alkyl.

In one embodiment $R^2$ and $R^3$ are not each H when $R^4$ is hydrogen.

In one embodiment $R^2$ and $R^3$ are not each H when $R^4$ is hydrogen or $C_{1-2}$alkyl.

In one embodiment when $R^2$ is hydrogen and $R^3$ is methyl, then $R^4$ is not hydrogen.

In one embodiment when $R^2$ is hydrogen and $R^3$ is methyl, then $R^4$ is not hydrogen or $C_{1-2}$alkyl.

In one embodiment when $R^2$ is hydrogen and $R^3$ is $C_{1-2}$alkyl, then $R^4$ is not hydrogen.

In one embodiment when $R^2$ is hydrogen and $R^3$ is $C_{1-2}$alkyl, then $R^4$ is not hydrogen or $C_{1-2}$alkyl.

Uses, Formulation and Administration

Pharmaceutically Acceptable Compositions

Another aspect includes a pharmaceutical composition comprising a compound of formula (I) or a pharmaceutically acceptable salt thereof or a compound disclosed herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a BRG1, a BRM and/or a PB1 bromodomain. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof or a compound disclosed herein or a pharmaceutically acceptable salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further or a compound disclosed herein or a pharmaceutically acceptable salt thereof comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof or a compound disclosed herein or a pharmaceutically acceptable salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula (I) or salt thereof or a compound disclosed herein or a salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I) or a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof or a compound disclosed herein or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I) or the compound disclosed herein.

Example dosage forms for topical or transdermal administration of a compound of formula (I) or a compound disclosed herein include ointments, pastes, creams, lotions, gels, powders, solutions, sprays, inhalants or patches. The compound of formula (I) or a salt thereof or the compound disclosed herein or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof or a compound disclosed herein or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof or a compound disclosed herein or a salt thereof for the inhibition of BRG1, BRM and/or PB1 (in vitro or in vivo).

Another embodiment includes a method for treating a BRG1-mediated disorder, a BRM-mediated disorder and/or a PB1-mediated disorder in an animal comprising administering a compound of formula (I), or a pharmaceutically acceptable salt thereof or a compound disclosed herein or a pharmaceutically acceptable salt thereof to the animal. BRG1-mediated disorders, BRM-mediated disorders and PB1-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or a pharmaceutically acceptable salt thereof or a compound disclosed herein or a pharmaceutically acceptable salt thereof.

Another embodiment includes a method of delaying or preventing development of cancer resistance to a cytotoxic agent in an animal, comprising administering to the animal a compound of formula (I) or a pharmaceutically acceptable salt thereof or a compound disclosed herein or a pharmaceutically acceptable salt thereof.

Another embodiment includes a method of extending the duration of response to a cancer therapy in an animal, comprising administering to an animal undergoing the cancer therapy a compound of formula (I) or a pharmaceutically acceptable salt thereof or a compound disclosed herein or a pharmaceutically acceptable salt thereof, wherein the duration of response to the cancer therapy when the compound of formula (I) or the pharmaceutically acceptable salt or a compound disclosed herein or a pharmaceutically acceptable salt thereof is administered is extended over the duration of response to the cancer therapy in the absence of the administration of the compound of formula (I) or the pharmaceutically acceptable salt thereof or a compound disclosed herein or a pharmaceutically acceptable salt thereof.

Another embodiment includes a method of treating cancer in an individual comprising administering to the individual (a) a compound of formula (I) or a pharmaceutically acceptable salt thereof or a compound disclosed herein or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

BRG1-Mediated Disorders, BRM-Mediated Disorders, and PB1-Mediated Disorders

A "BRG1-mediated disorder" is characterized by the participation BRG1 in the inception, manifestation of one or more symptoms or disease markers, severity, or progression of a disorder.

A "BRM-mediated disorder" is characterized by the participation BRM in the inception, manifestation of one or more symptoms or disease markers, severity, or progression of a disorder.

A "PB1-mediated disorder" is characterized by the participation PB1 in the inception, manifestation of one or more symptoms or disease markers, severity, or progression of a disorder.

BRG1-mediated disorders, BRM-mediated disorders and PB1-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, liver cancer, lung cancer, lymphagibendotheliosarcoma, lymphangiosarcoma, lymphoblastic leukemia, lymphoma (Hodgkin's and non-Hodgkin's; Burkitt's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

BRM has recently been reported as a synthetic lethal target in BRG1-deficient cancers (e.g., cancers comprising BRG1 loss of function mutations and/or cancers having reduced or absent expression, e.g., due to epigenetic alterations) (Hoffman et al., PNAS, 111(8):3128-3133 (2014); Oike et al., Cancer Res, 73(17):5508-5518 (2013). Specifically, BRM depletion has been shown to selectively inhibit the growth of BRG1-mutant cancer cells (Id.).

Accordingly, in certain embodiments, a compound described herein, or a salt thereof, is a BRM inhibitor (e.g., inhibits a BRM bromodomain) and the cancer is a BRG1-deficient cancer (e.g, a cancer harboring a loss of function mutation and/or having reduced or absent BRG1 expression). In certain embodiments, the cancer is lung cancer (e.g., nonsmall cell lung cancer, such as lung adenocarcinoma or squamous carcinoma), ovarian cancer, liver cancer, endometrial cancer, pancreatic cancer, skin cancer, Burkitt's lymphoma or brain cancer (e.g., medulloblastoma).

Conversely, it has also been shown that certain cancers are dependent on BRG1 for disease progression and are vulnerable to BRG1 inhibition, including certain acute leukemias and small cell lung cancers (Hohmann et al., Trends in Genetics, 30(8):356-363 (2014)). In certain embodiments, the cancer is leukemia (e.g., acute leukemia, e.g., acute myeloid leukemia), breast cancer, small cell lung cancer, or malignant rhabdoid tumor (MRT) (e.g., a SNF5-deficient malignant rhabdoid tumor).

BRG1-mediated disorders, BRM-mediated disorders and PB1-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

BRG1-mediated disorders, BRM-mediated disorders and PB1-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

Co Administration of Compounds and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methylpiperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal antiinflammatory drugs with analgesic, antipyretic and antiinflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; antiinflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RIL siL-6R), an antiinflammatory cytokine (e.g. IL-4, IL-1 0, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SC10-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RIL siL-6R), and an antiinflammatory cytokine (e.g. IL-4, IL-1 0, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, a n adensosine agonist, an antithrombotic agent, a complement inhibitor, a n adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-1 0, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, a n anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/ chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/ castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); a n inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with UP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, a n HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof or a compound disclosed herein or a salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) or the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 μg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof or a compound disclosed herein or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof or a compound disclosed herein or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

EXEMPLIFICATION

As depicted in the Examples below, in certain exemplary embodiments, compounds can be prepared according to the general procedures illustrated in Scheme 1. It will be appreciated that, although the general methods depict the synthesis of certain compounds of the present invention, the following general methods, and other methods known to one of ordinary skill in the art, can be applied to all compounds and subclasses and species of each of these compounds, as described herein.

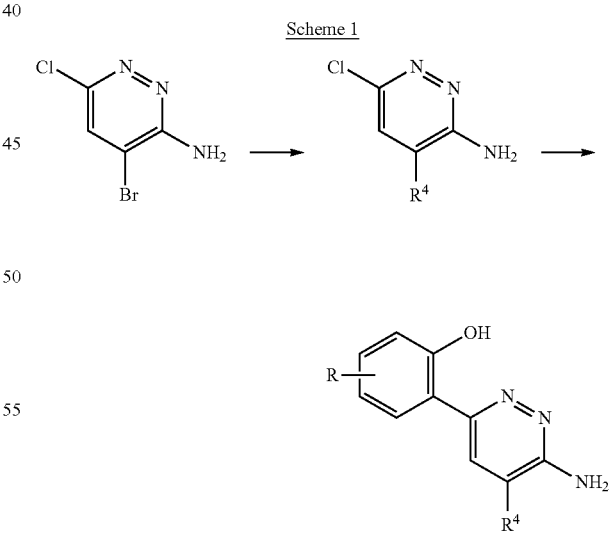

Scheme 1

In general, compounds can be prepared from 4-bromo-6-chloropyridazin-3-amine. Substituents can be introduced at C-4 via palladium-catalyzed cross coupling or nucleophilic aromatic substitution, followed by palladium-catalyzed cross coupling of appropriately-substituted ortho phenol boronic acids at C-6.

Example 1 tert-butyl 4-(3-amino-6-(2-hydroxyphenyl)pyridazin-4-yl)piperazine-1-carboxylate

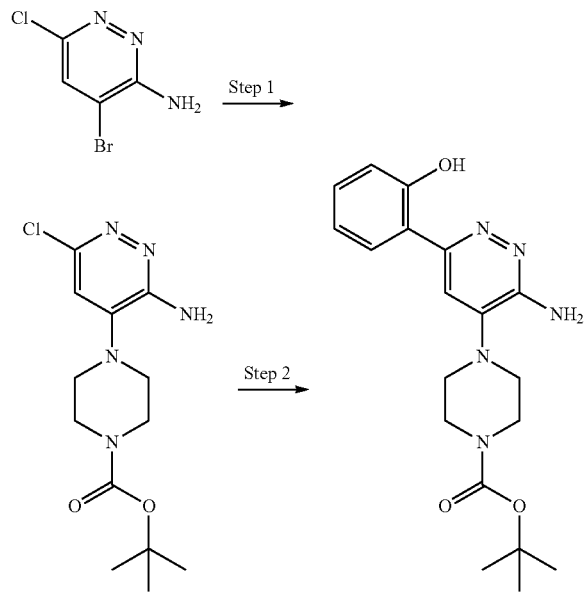

Step 1: tert-butyl 4-(3-amino-6-chloropyridazin-4-yl)piperazine-1-carboxylate

In a pyrex vial 4-bromo-6-chloropyridazin-3-amine (100 mg, 0.48 mmol) was dissolved in tetrahydrofuran (1 mL). tert-butyl piperazine-1-carboxylate (447 mg, 2.4 mmol) was added and the reaction was stirred at 80° C. overnight. The crude reaction was concentrated to dryness, deposited onto silica gel and purified by silica gel chromatography (eluting with ethyl acetate) to provide tert-butyl 4-(3-amino-6-chloropyridazin-4-yl)piperazine-1-carboxylate (97.6 mg, 65%) as a yellow solid. LCMS M/Z (M+H) 314.

Step 2: tert-butyl 4-(3-amino-6-(2-hydroxyphenyl)pyridazin-4-yl)piperazine-1-carboxylate A microwave vial was charged with tert-butyl 4-(3-amino-6-chloropyridazin-4-yl)piperazine-1-carboxylate (97.6 mg, 0.31 mmol), 1,1 bis(di-tert-butylphosphino)ferrocene palladium dichloride (20 mg, 0.03 mmol), (2-hydroxyphenyl)boronic acid (86 mg, 0.62 mmol), and potassium carbonate (86 mg, 0.62 mmol). The vial was sealed 1:1, acetonitrile:water was added (1.5 mL), the reaction was evacuated and purged with nitrogen (g) (3×) then heated in the microwave at 120° C. for 0.5 h. The reaction was cooled to ambient temperature, concentrated to dryness, loaded onto silica gel and purified by silica gel chromatography (eluting with hexanes/ethyl acetate) to provide tert-butyl 4-(3-amino-6-(2-hydroxyphenyl)pyridazin-4-yl)piperazine-1-carboxylate (8 mg, 7%). $^1$H NMR (400 MHz, DMSO-$d_6$) δ 14.21-14.11 (m, 1H), 7.93 (dd, J=1.3, 8.3 Hz, 1H), 7.55 (s, 1H), 7.29-7.19 (m, 1H), 6.93-6.84 (m, 2H), 6.38 (s, 2H), 3.55 (br. s., 4H), 3.08-2.99 (m, 4H), 1.50-1.34 (m, 9H). LCMS M/Z (M+H) 372.

Examples 2-79 were prepared in a similar fashion (sometimes using acetonitrile in place of tetrahydrofuran in step 1 and sometimes using methanesulfonato(2-dicyclohexylphosphino-2',4',6'-tri-i-propyl-1,1'-biphenyl)(2'-amino-1,1'-biphenyl-2-yl)palladium(II) in place of 1,1 bis(di-tert-butylphosphino)ferrocene palladium dichloride in step 2) to Example 1. The syntheses of non-commercially available intermediates used in the preparation of these examples are described below the table.

| Example | Compound Name | NMR | m/z |
|---|---|---|---|
| 2 | 2-(6-amino-5-(4-methyl-1,4-diazepan-1-yl)pyridazin-3-yl)phenol | | 300 |
| 3 | 2-(6-amino-5-(4-(pyridin-3-ylmethyl)piperazin-1-yl)pyridazin-3-yl)phenol | | 363 |
| 4 | 1-(4-(3-amino-6-(2-hydroxyphenyl)pyridazin-4-yl)piperazin-1-yl)ethan-1-one | | 314 |
| 5 | 2-(6-amino-5-(4-((dimethylamino)methyl)piperidin-1-yl)pyridazin-3-yl)phenol | $^1$H NMR (400 MHz, DMSO-$d_6$) δ 13.50-13.84 (m, 1H), 7.80 (d, J = 7.81 Hz, 1H), 7.45 (s, 1H), 7.17-7.28 (m, 1H), 6.82-6.96 (m, 2H), 5.67 (br. s., 2H), 3.48 (d, J = 12.21 Hz, 2H), 2.80 (t, J = 11.84 Hz, 2H), 2.14-2.24 (m, 8H), 1.87 (d, J = 12.70 Hz, 2H), 1.62-1.77 (m, 1H), 1.35-1.50 (m, 2H) | 328 |
| 6 | (S)-2-(6-amino-5-(2-methylpiperidin-1-yl)pyridazin-3-yl)phenol | | 285 |
| 7 | 2-(6-amino-5-(piperazin-1-yl)pyridazin-3-yl)phenol | $^1$H NMR (400 MHz, DMSO-$d_6$) δ 7.82 (dd, J = 1.34, 7.69 Hz, 1H), 7.46 (s, 1H), 7.20-7.28 (m, 1H), 6.82-6.94 (m, 2H), 5.77 (br. s., 3H), 3.14-3.20 (m, 4H), 3.05-3.10 (m, 4H) | 272 |
| 8 | 2-(6-amino-5-(3-phenoxypiperidin-1-yl)pyridazin-3-yl)phenol | $^1$H NMR (400 MHz, DMSO-$d_6$) δ 14.21 (br. s., 1H), 7.91 (d, J = 7.57 Hz, 1H), 7.56 (s, 1H), 7.29 (t, J = 7.69 Hz, 2H), 7.24 (t, J = 7.69 Hz, 1H), 7.02 (d, J = 8.55 Hz, 2H), 6.91-6.98 (m, 1H), 6.85-6.91 (m, 2H), 6.28 (s, 2H), 4.73 (td, J = 4.03, 7.57 Hz, 1H), 3.54 (br. s., 1H), 3.28 (d, J = 4.88 Hz, 1H), 2.87-3.03 (m, 2H), 2.09 (d, J = 6.84 Hz, 1H), 1.91 (dd, J = 4.03, 9.16 | 363 |

-continued

| Example | Compound Name | NMR | m/z |
|---|---|---|---|
| | | Hz, 1H), 1.78 (td, J = 9.37, 13.25 Hz, 1H), 1.58-1.71 (m, 1H) | |
| 9 | 2-(6-amino-5-((3aR,6aS)-5-benzylhexahydropyrrolo[3,4-c]pyrrol-2(1H)-yl)pyridazin-3-yl)phenol | $^1$H NMR (400 MHz, DMSO-$d_6$) δ 14.46 (br. s., 1H), 7.93 (d, J = 7.81 Hz, 1H), 7.27-7.36 (m, 5H), 7.19-7.26 (m, 2H), 6.84-6.91 (m, 2H), 6.15 (s, 2H), 3.58-3.69 (m, 4H), 2.96 (d, J = 9.52 Hz, 2H), 2.87 (br. s., 2H), 2.58 (d, J = 8.79 Hz, 2H), 2.50 (br. s., 2H) | 388 |
| 10 | 2-(6-amino-5-(3-phenylpiperidin-1-yl)pyridazin-3-yl)phenol | $^1$H NMR (400 MHz, DMSO-$d_6$) δ 14.26 (s, 1H), 7.88-7.96 (m, 1H), 7.53 (s, 1H), 7.30-7.38 (m, 4H), 7.19-7.26 (m, 2H), 6.83-6.91 (m, 2H), 6.27 (s, 2H), 3.52 (d, J = 6.84 Hz, 2H), 3.07 (br. s., 1H), 2.64-2.82 (m, 2H), 1.80-2.02 (m, 3H), 1.57-1.73 (m, 1H) | 347 |
| 11 | 2-(6-amino-5-(4-(phenylsulfonyl)piperazin-1-yl)pyridazin-3-yl)phenol | | 412 |
| 12 | 2-(6-amino-5-(4-benzylpiperazin-1-yl)pyridazin-3-yl)phenol | $^1$H NMR (400 MHz, DMSO-$d_6$) δ 14.23 (br. s., 1H), 7.91 (d, J = 7.57 Hz, 1H), 7.51 (s, 1H), 7.32-7.40 (m, 4H), 7.20-7.31 (m, 2H), 6.85-6.99 (m, 2H), 6.25 (s, 2H), 2.89-3.46 (m, 6H), 2.60 (br. s., 4H) | 362 |
| 13 | 2-(6-amino-5-(4-phenylpiperazin-1-yl)pyridazin-3-yl)phenol | $^1$H NMR (400 MHz, DMSO-$d_6$) δ 14.21 (br. s., 1H), 7.95 (d, J = 7.81 Hz, 1H), 7.58 (br. s., 1H), 7.25 (br. s., 3H), 7.02 (d, J = 8.06 Hz, 2H), 6.86-6.95 (m, 2H), 6.77-6.85 (m, 1H), 6.35 (br. s., 2H), 3.38 (br. s., 4H), 3.25 (br. s., 4H) | 348 |
| 14 | 4-(3-amino-6-(2-hydroxyphenyl)pyridazin-4-yl)-1-benzylpiperazin-2-one | $^1$H NMR (400 MHz, DMSO-$d_6$) δ 14.10 (s, 1H), 7.93 (dd, J = 1.59, 8.42 Hz, 1H), 7.54 (s, 1H), 7.22-7.37 (m, 6H), 6.88-6.94 (m, 2H), 6.46 (s, 2H), 4.60 (s, 2H), 3.90 (s, 2H), 3.43 (d, J = 3.66 Hz, 4H) | 376 |
| 15 | 2-(6-amino-5-(4-(1-phenylethyl)piperazin-1-yl)pyridazin-3-yl)phenol | $^1$H NMR (400 MHz, DMSO-$d_6$) δ 14.23 (s, 1H), 7.91 (dd, J = 1.46, 8.30 Hz, 1H), 7.49 (s, 1H), 7.31-7.38 (m, 4H), 7.20-7.29 (m, 2H), 6.85-6.91 (m, 2H), 6.21 (s, 2H), 3.50 (q, J = 6.51 Hz, 1H), 3.09 (br. s., 4H), 2.52-2.71 (m, 4H), 1.34 (d, J = 6.84 Hz, 3H) | 376 |
| 16 | 2-(6-amino-5-(8-benzyl-3,8-diazabicyclo[3.2.1]octan-3-yl)pyridazin-3-yl)phenol | | 388 |
| 17 | 2-(6-amino-5-((1S,4S)-5-benzyl-2,5-diazabicyclo[2.2.1]heptan-2-yl)pyridazin-3-yl)phenol | $^1$H NMR (400 MHz, DMSO-$d_6$) δ 14.71 (br. s., 1H), 7.90 (dd, J = 1.46, 7.81 Hz, 2H), 7.25-7.34 (m, 5H), 7.16-7.24 (m, 2H), 7.10 (s, 1H), 6.81-6.88 (m, 2H), 5.90 (s, 1H), 4.58 (s, 1H), 3.68-3.77 (m, 1H), 3.47-3.55 (m, 3H), 2.84 (dd, J = 2.20, 10.01 Hz, 1H), 2.71 (d, J = 10.01 Hz, 1H), 1.96 (d, J = 9.28 Hz, 1H), 1.77 (d, J = 9.28 Hz, 1H) | 374 |
| 18 | 2-(6-amino-5-(4-phenylpiperidin-1-yl)pyridazin-3-yl)phenol | $^1$H NMR (400 MHz, DMSO-$d_6$) δ 14.29 (s, 1H), 7.94 (dd, J = 1.34, 8.18 Hz, 1H), 7.55 (s, 1H), 7.30-7.36 (m, 4H), 7.18-7.27 (m, 2H), 6.85-6.93 (m, 2H), 6.29 (s, 2H), 3.60 (d, J = 12.21 Hz, 2H), 2.68-2.87 (m, 3H), 2.01 (dq, J = 3.42, 12.37 Hz, 2H), 1.83-1.92 (m, 2H) | 347 |
| 19 | 1-(3-amino-6-(2-hydroxyphenyl)pyridazin-4-yl)-N,N-dimethylpiperidine-4-carboxamide | $^1$H NMR (400 MHz, DMSO-$d_6$) δ 14.24 (s, 1H), 7.90 (dd, J = 1.6, 8.2 Hz, 1H), 7.48 (s, 1H), 7.28-7.15 (m, 1H), 6.91-6.82 (m, 2H), 6.23 (s, 2H), 3.56 (d, J = 0.7 Hz, 1H), 3.51 (d, J = 12.5 Hz, 2H), 3.05 (s, 3H), 2.83 (s, 3H), 2.78-2.67 (m, 2H), 1.96-1.81 (m, 2H), 1.74 (d, J = 10.7 Hz, 2H) | 342 |
| 20 | 2-(6-amino-5-(4-(2-hydroxypropan-2-yl)piperidin-1-yl)pyridazin-3-yl)phenol | $^1$H NMR (400 MHz, DMSO-$d_6$) δ 14.29 (s, 1H), 7.90 (dd, J = 1.59, 8.18 Hz, 1H), 7.48 (s, 1H), 7.23 (dt, J = 1.71, 7.69 Hz, 1H), 6.85-6.92 (m, 2H), 6.18 (s, 2H), 4.17 (s, 1H), 3.50-3.60 (m, 2H), 2.59 (t, J = 11.47 Hz, 2H), 1.79 (d, J = 11.47 Hz, 2H), 1.54 (dd, J = 3.42, 12.45 Hz, 2H), 1.38 (d, J = 12.21 Hz, 1H), 1.06-1.13 (m, 6H) | 329 |
| 21 | 2-(6-amino-5-(3-((dimethylamino)methyl)piperidin-1-yl)pyridazin-3-yl)phenol | $^1$H NMR (400 MHz, DMSO-$d_6$) δ 14.25-14.41 (m, 1H), 7.89 (dd, J = 1.34, 8.18 Hz, 1H), 7.43 (s, 1H), 7.22 (s, 2H), 6.85-6.91 (m, 2H), 6.82 (br. s., 2H), 3.11-3.23 (m, 1H), 3.01 (br. s., 2H), 2.86-2.94 (m, 1H), 2.57-2.70 (m, 1H), | 328 |

| Example | Compound Name | NMR | m/z |
|---|---|---|---|
| | | 2.15-2.21 (m, 5H), 1.95-2.08 (m, 2H), 1.73 (br. s., 4H), 1.25-1.37 (m, 1H) | |
| 22 | 2-(6-amino-5-(4-benzyl-3-methylpiperazin-1-yl)pyridazin-3-yl)phenol | $^1$H NMR (400 MHz, DMSO-$d_6$) δ 14.23 (s, 1H), 7.84-8.00 (m, 1H), 7.49 (s, 1H), 7.31-7.37 (m, 4H), 7.20-7.28 (m, 2H), 6.85-6.92 (m, 2H), 6.23 (s, 2H), 3.99-4.10 (m, 1H), 3.36 (d, J = 11.23 Hz, 1H), 3.24 (d, J = 13.43 Hz, 2H), 2.85 (t, J = 9.89 Hz, 1H), 2.69-2.79 (m, 2H), 2.60-2.68 (m, 1H), 2.38 (t, J = 9.52 Hz, 1H), 1.14-1.22 (m, 3H) | 376 |
| 23 | 2-(6-amino-5-(3-(trifluoromethyl)piperazin-1-yl)pyridazin-3-yl)phenol | $^1$H NMR (400 MHz, DMSO-$d_6$) δ 14.15 (br. s., 1H), 7.96 (dd, J = 1.46, 8.30 Hz, 1H), 7.59 (s, 1H), 7.20-7.28 (m, 1H), 6.85-6.94 (m, 2H), 6.37 (s, 2H), 3.72-3.84 (m, 1H), 3.52-3.60 (m, 1H), 3.28 (d, J = 11.23 Hz, 1H), 2.88-3.08 (m, 3H), 2.79 (dt, J = 3.30, 10.93 Hz, 1H), 2.65 (t, J = 10.74 Hz, 1H) | 340 |
| 24 | 2-(4-(3-amino-6-(2-hydroxyphenyl)pyridazin-4-yl)piperazin-1-yl)-N-methylacetamide | $^1$H NMR (400 MHz, DMSO-$d_6$) δ 14.21 (br. s., 1H), 7.91 (d, J = 8.30 Hz, 1H), 7.73 (d, J = 4.39 Hz, 1H), 7.48 (s, 1H), 7.23 (t, J = 7.69 Hz, 1H), 6.83-6.93 (m, 2H), 6.25 (s, 2H), 3.14 (br. s., 4H), 2.98 (s, 2H), 2.64 (t, J = 4.88 Hz, 7H) | 343 |
| 25 | 2-(6-amino-5-(4-methyl-1-oxa-4,9-diazaspiro[5.5]undecan-9-yl)pyridazin-3-yl)phenol | $^1$H NMR (400 MHz, DMSO-$d_6$) δ 14.24-14.37 (m, 1H), 7.88-8.03 (m, 1H), 7.53 (s, 1H), 7.23 (s, 1H), 6.88 (d, J = 7.57 Hz, 2H), 6.23 (s, 2H), 3.66 (br. s., 2H), 3.11-3.20 (m, 2H), 2.94-3.05 (m, 2H), 2.12-2.30 (m, 7H), 1.93-2.03 (m, 2H), 1.71-1.83 (m, 2H) | 356 |
| 26 | 2-(6-amino-5-(4-(2-(methylsulfonyl)ethyl)piperazin-1-yl)pyridazin-3-yl)phenol | $^1$H NMR (400 MHz, DMSO-$d_6$) δ 14.22 (s, 1H), 7.93 (dd, J = 1.34, 8.18 Hz, 1H), 7.52 (s, 1H), 7.20-7.27 (m, 1H), 6.85-6.92 (m, 2H), 6.26 (s, 2H), 3.35 (t, J = 6.71 Hz, 2H), 3.11 (br. s., 4H), 3.07 (s, 3H), 2.79 (t, J = 6.71 Hz, 2H), 2.67 (br. s., 4H) | 378 |
| 27 | 2-(6-amino-5-(4-(2,2,2-trifluoroethyl)piperazin-1-yl)pyridazin-3-yl)phenol | | 354 |
| 28 | (trans-4a,8a)-2-(3-amino-6-(2-hydroxyphenyl)pyridazin-4-yl)octahydroisoquinolin-4a(2H)-ol | $^1$H NMR (400 MHz, DMSO-$d_6$) δ 14.25-14.38 (m, 1H), 7.90-7.97 (m, 1H), 7.51 (s, 1H), 7.19-7.28 (m, 1H), 6.84-6.91 (m, 2H), 6.12 (s, 2H), 4.31 (s, 1H), 3.37-3.44 (m, 1H), 3.14-3.29 (m, 1H), 2.83-3.08 (m, 2H), 1.13-1.91 (m, 11H) | 341 |
| 29 | 8-(3-amino-6-(2-hydroxyphenyl)pyridazin-4-yl)-2,8-diazaspiro[4.5]decan-3-one | $^1$H NMR (400 MHz, DMSO-$d_6$) d 14.26 (br. s., 1H), 7.91 (d, J = 7.81 Hz, 1H), 7.56 (d, J = 13.67 Hz, 2H), 7.24 (t, J = 7.45 Hz, 1H), 6.89 (d, J = 7.08 Hz, 2H), 6.24 (br. s., 2H), 2.97-3.18 (m, 6H), 2.13 (s, 2H), 1.78 (br. s., 4H) | 340 |
| 30 | 1-(4-(3-amino-6-(2-hydroxyphenyl)pyridazin-4-yl)-1,4-diazepan-1-yl)ethan-1-one | $^1$H NMR (400 MHz, DMSO-$d_6$) δ 14.25 (br. s., 1H), 7.85-7.94 (m, 1H), 7.51 (s, 1H), 7.19-7.27 (m, 1H), 6.84-6.92 (m, 2H), 6.15 (d, J = 10.25 Hz, 2H), 3.70 (t, J = 5.37 Hz, 1H), 3.61-3.66 (m, 1H), 3.54-3.61 (m, 2H), 3.44-3.49 (m, 1H), 3.34-3.39 (m, 2H), 3.28-3.33 (m, 1H), 1.89-2.06 (m, 5H) | 329 |
| 31 | 1-(3-amino-6-(2-hydroxyphenyl)pyridazin-4-yl)-4-((dimethylamino)methyl)piperidin-4-ol | | 344 |
| 32 | 2-(6-amino-5-(4-(1-morpholinoethyl)piperidin-1-yl)pyridazin-3-yl)phenol | $^1$H NMR (400 MHz, DMSO-$d_6$) δ 14.29 (s, 1 H), 7.89 (dd, J = 1.5, 8.3 Hz, 1 H), 7.47 (s, 1 H), 7.34-7.07 (m, 1 H), 6.97-6.71 (m, 2 H), 6.19 (s, 2 H), 3.46-3.63 (m, 6H), 2.57-2.69 (m, 2H), 2.52-2.56 (m, 2H), 2.20-2.37 (m, 3H), 2.07 (d, J = 13.18 Hz, 1H), 1.75 (d, J = 12.21 Hz, 1H), 1.34-1.58 (m, 3H), 0.93 (d, J = 6.59 Hz, 3H) | 384 |
| 33 | 2-(6-amino-5-(2,6-dimethylmorpholino)pyridazin-3-yl)phenol (racemic mixture of diasteromers) | $^1$H NMR (400 MHz, DMSO-$d_6$) δ 14.22 (s, 1 H), 7.97-7.90 (m, 1 H), 7.49 (s, 1 H), 7.28-7.22 (m, 1 H), 6.93-6.85 (m, 2 H), 6.35 (s, 2 H), 3.94-3.81 (m, 2 H), 3.38 (d, J = 11.5 Hz, 2 H), 2.38 (dd, J = 10.5, 12.0 Hz, 2 H), 1.17-1.08 (m, 6 H) | 301 |

| Example | Compound Name | NMR | m/z |
|---|---|---|---|
| 34 | 2-(6-amino-5-(benzyl(methyl)amino)pyridazin-3-yl)phenol | $^1$H NMR (400 MHz, DMSO-d$_6$) δ 14.32 (s, 1H), 7.83 (d, J = 7.32 Hz, 1H), 7.39 (s, 1H), 7.27-7.36 (m, 4H), 7.19-7.27 (m, 2H), 6.82-6.91 (m, 2H), 6.37 (s, 2H), 4.44 (s, 2H), 2.76 (s, 3H) | 307 |
| 35 | 2-(6-amino-5-(pyrrolidin-1-yl)pyridazin-3-yl)phenol | | 257 |
| 36 | 2-(6-amino-5-(methyl(phenethyl)amino)pyridazin-3-yl)phenol | $^1$H NMR (400 MHz, DMSO-d$_6$) δ 14.33 (br. s., 1 H), 7.89 (dd, J = 1.5, 8.3 Hz, 1 H), 7.44 (s, 1 H), 7.30-7.13 (m, 6 H), 6.93-6.84 (m, 2 H), 6.09 (s, 2 H), 3.46-3.36 (m, 2 H), 2.94 (s, 3 H), 2.86-2.76 (m, 2 H) | 321 |
| 37 | 2-(6-amino-5-(4-benzyl-3,5-dimethylpiperazin-1-yl)pyridazin-3-yl)phenol | $^1$H NMR (400 MHz, DMSO-d$_6$) δ 14.24 (s, 1 H), 7.94 (dd, J = 1.5, 8.3 Hz, 1 H), 7.49 (s, 1 H), 7.45-7.37 (m, 2 H), 7.35-7.16 (m, 4 H), 6.94-6.84 (m, 2 H), 6.25 (s, 2 H), 3.82 (s, 2 H), 3.39 (d, J = 11.5 Hz, 2 H), 2.95-2.84 (m, 2 H), 2.59-2.52 (m, 2 H), 1.03 (d, J = 5.9 Hz, 6 H) | 390 |
| 38 | 1-(3-amino-6-(2-hydroxyphenyl)pyridazin-4-yl)pyrrolidin-3-ol | | 273 |
| 38 | 1-(3-amino-6-(2-hydroxyphenyl)pyridazin-4-yl)-3-benzylpyrrolidin-3-ol | | 363 |
| 40 | 2-(6-amino-5-(3-benzyl-3-methoxypyrrolidin-1-yl)pyridazin-3-yl)phenol | | 377 |
| 41 | 2-(6-amino-5-(5-(pyridin-2-yl)-2,5-diazabicyclo[2.2.1]heptan-2-yl)pyridazin-3-yl)phenol | $^1$H NMR (400 MHz, DMSO-d$_6$) δ 14.59 (s, 1 H), 8.04-7.99 (m, 1 H), 7.96 (dd, J = 1.5, 7.8 Hz, 1 H), 7.48-7.40 (m, 1 H), 7.28-7.16 (m, 2 H), 6.95-6.79 (m, 2 H), 6.62-6.49 (m, 2 H), 5.89 (s, 2 H), 4.88 (s, 2 H), 4.00 (dd, J = 1.7, 9.3 Hz, 1 H), 3.57 (s, 1 H), 3.28 (d, J = 9.0 Hz, 1 H), 2.12-1.99 (m, 2 H) | 361 |
| 42 | 1-(3-amino-6-(2-hydroxyphenyl)pyridazin-4-yl)-4-phenylpiperidin-4-ol | $^1$H NMR (400 MHz, DMSO-d$_6$) δ 14.34 (br. s., 1 H), 7.97 (dd, J = 1.5, 8.3 Hz, 1 H), 7.61-7.52 (m, 3 H), 7.36 (t, J = 7.7 Hz, 2 H), 7.28-7.19 (m, 2 H), 6.93-6.83 (m, 2 H), 6.31 (s, 2 H), 5.05 (s, 1 H), 3.35 (d, J = 11.7 Hz, 2 H), 3.16 (t, J = 11.4 Hz, 2 H), 2.31 (dt, J = 4.0, 12.8 Hz, 2 H), 1.72 (d, J = 12.7 Hz, 2 H) | 363 |
| 43 | 2-(6-amino-5-(8-(pyrimidin-5-yl)-3,8-diazabicyclo[3.2.1]octan-3-yl)pyridazin-3-yl)phenol | $^1$H NMR (400 MHz, DMSO-d$_6$) δ 14.13 (s, 1 H), 8.54-8.46 (m, 3 H), 7.89 (dd, J = 1.3, 7.9 Hz, 1 H), 7.51 (s, 1 H), 7.22 (ddd, J = 1.5, 7.1, 8.3 Hz, 1 H), 6.90-6.80 (m, 2 H), 5.99 (s, 2 H), 4.59 (br. s., 2 H), 3.24 (d, J = 10.5 Hz, 2 H), 3.10 (d, J = 11.5 Hz, 2 H), 2.21 (d, J = 7.3 Hz, 2 H), 2.04-1.92 (m, 2 H) | 376 |
| 44 | 1-(3-amino-6-(2-hydroxyphenyl)pyridazin-4-yl)-3-methyl-4-phenylpiperidin-4-ol | $^1$H NMR (400 MHz, DMSO-d$_6$) δ 14.36 (s, 1 H), 7.97 (dd, J = 1.5, 8.3 Hz, 1 H), 7.58-7.50 (m, 3 H), 7.35 (t, J = 7.7 Hz, 2 H), 7.28-7.17 (m, 2 H), 6.94-6.84 (m, 2 H), 6.32 (s, 2 H), 4.90 (s, 1 H), 3.41-3.33 (m, 1 H), 3.27-3.18 (m, 1 H), 3.09 (s, 1 H), 2.96-2.85 (m, 1 H), 2.38 (d, J = 3.9 Hz, 2 H), 1.68 (d, J = 13.4 Hz, 1 H), 0.57 (d, J = 6.6 Hz, 3 H) | 377 |
| 45 | 2-(6-amino-5-morpholinopyridazin-3-yl)phenol | $^1$H NMR (400 MHz, DMSO-d$_6$) δ 14.20 (s, 1 H), 7.93 (dd, J = 1.4, 8.4 Hz, 1 H), 7.52 (s, 1 H), 7.28-7.18 (m, 1 H), 6.95-6.83 (m, 2 H), 6.36 (s, 2 H), 3.87-3.76 (m, 4 H), 3.14-3.04 (m, 4 H) | 273 |
| 46 | 4-(3-amino-6-(2-hydroxyphenyl)pyridazin-4-yl)thiomorpholine1,1-dioxide | $^1$H NMR (400 MHz, DMSO-d$_6$) δ 14.05 (s, 1H), 7.96 (dd, J = 1.59, 8.18 Hz, 1H), 7.74 (s, 1H), 7.25 (dt, J = 1.71, 7.69 Hz, 1H), 6.85-6.93 (m, 2H), 6.51 (br. s, 2H), 3.49-3.55 (m, 4H), 3.38-3.45 (m, 4H) | 321 |
| 47 | 2-(6-amino-5-(8-(2-fluoropyridin-4-yl)-3,8-diazabicyclo[3.2.1]octan-3-yl)pyridazin-3-yl)phenol | $^1$H NMR (400 MHz, DMSO-d$_6$) δ 14.11 (s, 1H), 7.90 (dd, J = 1.47, 8.06 Hz, 1H), 7.82 (d, J = 6.10 Hz, 1H), 7.52 (s, 1H), 7.23 (ddd, J = 1.50, 7.20, 8.20 Hz, 1H), 6.82-6.89 (m, 2H), 6.79 (td, J = 1.60, 5.86 Hz, 1H), 6.51 (d, J = 1.71 Hz, 1H), 6.00 (br. s, 2H), 4.58 (br. s., 2H), 3.27 (d, J = 10.01 Hz, 2H), 3.02 (d, J = 11.48 | 393 |

-continued

| Example | Compound Name | NMR | m/z |
|---|---|---|---|
| | | Hz, 2H), 2.21 (q, J = 6.80 Hz, 2H), 1.93-2.04 (m, 2H) | |
| 48 | 2-(6-amino-5-(8-(1-methyl-1H-pyrazol-4-yl)-3,8-diazabicyclo[3.2.1]octan-3-yl)pyridazin-3-yl)phenol | | 378 |
| 49 | 2-(6-amino-5-(3-benzylpiperazin-1-yl)pyridazin-3-yl)phenol | ¹H NMR (400 MHz, DMSO-d₆) δ (s, 1H), 7.81-7.91 (m, 1H), 7.45 (s, 1H), 7.13-7.34 (m, 5H), 6.78-6.95 (m, 2H), 6.19 (s, 2H), 3.32 (s, 3H), 3.20-3.38 (m, 1H), 3.06-3.15 (m, 1H), 2.82-3.01 (m, 2H), 2.54-2.78 (m, 3H), 2.36-2.48 (m, 1H) | 362 |
| 50 | 2-(6-amino-5-(8-(pyrazin-2-yl)-3,8-diazabicyclo[3.2.1]octan-3-yl)pyridazin-3-yl)phenol | ¹H NMR (400 MHz, DMSO-d₆) δ 14.14 (s, 1H), 8.33 (d, J = 1.22 Hz, 1H), 8.11 (dd, J = 1.46, 2.69 Hz, 1H), 7.91 (dd, J = 1.46, 8.06 Hz, 1H), 7.84 (d, J = 2.69 Hz, 1H), 7.52 (s, 1H), 7.17-7.26 (m, 1H), 6.81-6.90 (m, 2H), 6.00 (s, 2H), 4.79 (br. s, 2H), 3.35 (d, J = 11.48 Hz, 2H), 3.06 (d, J = 11.48 Hz, 2H), 2.21 (d, J = 7.32 Hz, 2H), 1.97 (m, 2H) | 376 |
| 51 | 2-(6-amino-5-(8-(5-fluoropyridin-3-yl)-3,8-diazabicyclo[3.2.1]octan-3-yl)pyridazin-3-yl)phenol | ¹H NMR (400 MHz, DMSO-d₆) δ 14.14 (s, 1H), 8.17 (t, J = 1.95 Hz, 1H), 7.90 (dd, J = 1.34, 7.93 Hz, 1H), 7.84 (d, J = 2.44 Hz, 1H), 7.50 (s, 1H), 7.16-7.30 (m, 2H), 6.77-6.93 (m, 2H), 5.98 (s, 2H), 4.55 (br. s., 2H), 3.24 (d, J = 10.50 Hz, 2H), 3.09 (d, J = 11.48 Hz, 2H), 2.11-2.27 (m, 2H), 1.86-2.09 (m, 2H) | 393 |
| 52 | 2-(6-amino-5-(1,4,6,7-tetrahydro-5H-pyrazolo[4,3-c]pyridin-5-yl)pyridazin-3-yl)phenol | | 309 |
| 53 | 4-(3-amino-6-(2-hydroxyphenyl)pyridazin-4-yl)piperazin-2-one | | 286 |
| 54 | 1-(3-amino-6-(2-hydroxyphenyl)pyridazin-4-yl)piperidin-3-ol | | 287 |
| 55 | 2-(6-amino-5-(3-phenylpyrrolidin-1-yl)pyridazin-3-yl)phenol | | 333 |
| 56 | 2-(6-amino-5-(5-benzyl-2,5-diazabicyclo[2.2.1]heptan-2-yl)pyridazin-3-yl)phenol | ¹H NMR (400 MHz, DMSO-d₆) δ 14.70 (br. s., 1H), 7.89 (d, J = 8.06 Hz, 1H), 7.25-7.37 (m, 4H), 7.15-7.24 (m, 2H), 7.09 (s, 1H), 6.77-6.90 (m, 2H), 5.90 (s, 2H), 3.66-3.80 (m, 2H), 3.43-3.59 (m, 2H), 2.84 (d, J = 10.25 Hz, 1H), 2.71 (d, J = 10.25 Hz, 1H), 1.95 (br. s., 1H), 1.77 (d, J = 9.28 Hz, 1H) | 374 |
| 57 | 2-(6-amino-5-(3-phenoxyazetidin-1-yl)pyridazin-3-yl)phenol | ¹H NMR (400 MHz, DMSO-d₆) δ 9.31 (s, 1H), 8.11 (d, J = 8.06 Hz, 1H), 7.18-7.78 (m, 3H), 7.11 (s, 1H), 6.93-7.04 (m, 2H), 6.77-6.90 (m, 2H), 6.57-6.70 (m, 1H), 6.12 (br. s., 2H), 5.12 (br. s., 1H), 4.84 (d, J = 8.30 Hz, 2H), 4.42 (br. s., 2H) | 335 |
| 58 | 2-(6-amino-5-(3-(benzyloxy)azetidin-1-yl)pyridazin-3-yl)phenol | ¹H NMR (400 MHz, DMSO-d₆) δ 14.51-14.85 (m, 1H), 7.80-8.01 (m, 1H), 7.37 (d, J = 4.15 Hz, 5H), 7.14-7.25 (m, 1H), 6.95 (s, 1H), 6.78-6.90 (m, 2H), 5.91 (s, 2H), 4.55-4.64 (m, 1H), 4.50 (s, 2H), 4.40 (d, J = 8.79 Hz, 2H), 3.95-4.09 (m, 2H) | 349 |
| 59 | 1-(3-amino-6-(2-hydroxyphenyl)pyridazin-4-yl)-3-phenylpiperidin-3-ol | ¹H NMR (400 MHz, DMSO-d₆) δ 14.32 (s, 1H), 7.90 (d, J = 7.57 Hz, 1H), 7.59 (dd, J = 1.34, 8.42 Hz, 2H), 7.52 (s, 1H), 7.32-7.40 (m, 2H), 7.27 (d, J = 7.32 Hz, 1H), 7.20 (dd, J = 1.46, 7.08 Hz, 1H), 6.79-6.90 (m, 2H), 6.39 (s, 2H), 5.46 (s, 1H), 3.56 (s, 1H), 3.19-3.29 (m, 1H), 3.05 (d, J = 12.45 Hz, 1H), 2.76-2.89 (m, 1H), 2.14-2.28 (m, 1H), 1.95-2.10 (m, 1H), 1 62-1.84 (m, 2H) | 363 |
| 60 | (S)-2-(6-amino-5-(4-(1-(dimethylamino)ethyl)piperidin-1-yl)pyridazin-3-yl)phenol | ¹H NMR (400 MHz, DMSO-d₆) δ 14.28 (s, 1H), 7.89 (dd, J = 1.71, 8.30 Hz, 1H), 7.47 (s, 1H), 7.22 (dt, J = 1.71, 7.69 Hz, 1H), 6.69-6.99 (m, 2H), 6.17 (s, 2H), 3.49 (t, J = 12.57 Hz, 2H), 2.57-2.68 (m, 2H), 2.19-2.27 (m, 1H), 2.09-2.16 (m, 6H), 2.00 (d, J = 13.18 Hz, 1H), 1.74 (d, J = 10.99 Hz, 1H), 1.33-1.49 (m, 3H), 0.75-0.94 (m, 3H) | 342 |

| Example | Compound Name | NMR | m/z |
|---|---|---|---|
| 61 | (4-(3-amino-6-(2-hydroxyphenyl)pyridazin-4-yl)piperazin-1-yl)(phenyl)methanone | $^1$H NMR (400 MHz, DMSO-$d_6$) δ 14.16 (s, 1H), 7.92 (dd, J = 1.46, 8.30 Hz, 1H), 7.56 (s, 1H), 7.36-7.51 (m, 5H), 7.15-7.30 (m, 1H), 6.78-6.98 (m, 2H), 6.43 (s, 2H), 3.87 (br. s., 2H), 3.56 (br. s., 2H), 2.99-3.22 (m, 4H) | 376 |
| 62 | (4-(3-amino-6-(2-hydroxyphenyl)pyridazin-4-yl)-2-methylpiperazin-1-yl)(phenyl)methanone | $^1$H NMR (400 MHz, DMSO-$d_6$) δ 14.13 (s, 1H), 7.90 (dd, J = 1.59, 8.18 Hz, 1H), 7.54 (s, 1H), 7.44-7.50 (m, 3H), 7.37-7.44 (m, 2H), 7.18-7.28 (m, 1H), 6.81-6.94 (m, 2H), 6.37 (br. s., 2H), 3.50-3.75 (m, 4H), 3.10-3.16 (m, 3H), 1.37 (d, J = 6.84 Hz, 3H) | 390 |
| 63 | 2-(6-amino-5-(8-phenyl-3,8-diazabicyclo[3.2.1]octan-3-yl)pyridazin-3-yl)phenol | $^1$H NMR (400 MHz, DMSO-$d_6$) δ 14.15 (s, 1H), 7.85-7.93 (m, 1H), 7.45 (s, 1H), 7.13-7.25 (m, 3H), 6.90 (d, J = 7.81 Hz, 1H), 6.86 (s, 3H), 6.62-6.70 (m, 1H), 5.94 (s, 2H), 4.42 (br. s., 2H), 3.24 (s, 2H), 3.10 (s, 2H), 2.14 (s, 2H), 1.82-2.01 (m, 2H) | 374 |
| 64 | 4-(3-amino-6-(2-hydroxyphenyl)pyridazin-4-yl)-1-phenylpiperazin-2-one | $^1$H NMR (400 MHz, DMSO-$d_6$) δ 14.12 (s, 1H), 7.88-8.05 (m, 1H), 7.61 (s, 1H), 7.35-7.47 (m, 4H), 7.29 (s, 2H), 6.85-6.94 (m, 2H), 6.51 (s, 2H), 3.96 (s, 2H), 3.90 (s, 2H), 3.55 (d, J = 2.69 Hz, 2H) | 362 |
| 65 | (R)-2-(6-amino-5-(4-(1-(dimethylamino)ethyl)piperidin-1-yl)pyridazin-3-yl)phenol | $^1$H NMR (400 MHz, DMSO-$d_6$) δ 14.15-14.47 (m, 1H), 7.74-8.02 (m, 1H), 7.37-7.56 (m, 1H), 7.08-7.31 (m, 1H), 6.62-6.94 (m, 2H), 6.03-6.30 (m, 2H), 3.42-3.55 (m, 2H), 2.56-2.70 (m, 2H), 2.19-2.26 (m, 1H), 2.12 (s, 6H), 1.91-2.04 (m, 1H), 1.69-1.80 (m, 2H), 1.33-1.49 (m, 2H), 0.87 (d, J = 6.59 Hz, 3H) | 342 |
| 66 | 1-(3-(3-amino-6-(2-hydroxyphenyl)pyridazin-4-yl)-3,8-diazabicyclo[3.2.1]octan-8-yl)ethan-1-one | $^1$H NMR (400 MHz, DMSO-$d_6$) δ 14.11 (s, 1H), 7.93 (dd, J = 1.59, 8.42 Hz, 1H), 7.58 (s, 1H), 7.15-7.28 (m, 1H), 6.76-6.94 (m, 2H), 6.02 (s, 2H), 4.58 (d, J = 7.08 Hz, 1H), 4.35 (d, J = 6.10 Hz, 1H), 3.24-3.42 (m, 3H), 2.97 (d, J = 10.25 Hz, 1H), 2.86 (d, J = 10.25 Hz, 1H), 2.07-2.20 (m, 2H), 1.99-2.05 (m, 3H), 1.89-1.98 (m, 1H), 1.70-1.84 (m, 1H) | 340 |
| 67 | 2-(6-amino-5-(8-(methylsulfonyl)-3,8-diazabicyclo[3.2.1]octan-3-yl)pyridazin-3-yl)phenol | $^1$H NMR (400 MHz, DMSO-$d_6$) δ 14.10 (s, 1H), 7.95 (dd, J = 1.59, 8.42 Hz, 1H), 7.59 (s, 1H), 7.24 (dt, J = 1.46, 7.69 Hz, 1H), 6.77-6.99 (m, 2H), 6.01 (s, 2H), 4.26 (br. s., 2H), 3.41 (dd, J = 2.44, 11.72 Hz, 2H), 3.01-3.06 (m, 3H), 2.97 (d, J = 10.99 Hz, 2H), 2.05-2.13 (m, 2H), 1.93-2.00 (m, 2H) | 376 |
| 68 | 2-(6-amino-5-(4-(1-methyl-1H-pyrazol-4-yl)piperazin-1-yl)pyridazin-3-yl)phenol | $^1$H NMR (400 MHz, DMSO-$d_6$) δ 14.08-14.31 (m, 1H), 7.87-7.98 (m, 1H), 7.55 (s, 1H), 7.31 (d, J = 0.98 Hz, 1H), 7.21-7.27 (m, 1H), 7.20 (d, J = 0.73 Hz, 1H), 6.86-6.92 (m, 2H), 6.30 (s, 2H), 3.56 (s, 3H), 3.13-3.25 (m, 4H), 3.00-3.12 (m, 4H) | 352 |
| 69 | 2-(6-amino-5-(8-(pyridin-2-yl)-3,8-diazabicyclo[3.2.1]octan-3-yl)pyridazin-3-yl)phenol | $^1$H NMR (400 MHz, DMSO-$d_6$) δ 14.15 (s, 1H), 8.07-8.18 (m, 1H), 7.91 (dd, J = 1.46, 8.06 Hz, 1H), 7.53 (ddd, J = 1.95, 7.02, 8.61 Hz, 1H), 7.47 (s, 1H), 7.21 (dt, J = 1.71, 7.69 Hz, 1H), 6.78-6.88 (m, 3H), 6.58-6.65 (m, 1H), 5.96 (s, 2H), 4.70 (br. s., 2H), 3.31-3.35 (m, 2H), 3.02 (d, J = 11.23 Hz, 2H), 2.13-2.18 (m, 2H), 1.88-1.97 (m, 2H) | 375 |
| 70 | 2-(6-amino-5-(8-(pyridin-3-yl)-3,8-diazabicyclo[3.2.1]octan-3-yl)pyridazin-3-yl)phenol | $^1$H NMR (400 MHz, DMSO-$d_6$) δ 14.14 (s, 1H), 8.29 (d, J = 2.69 Hz, 1H), 7.81-7.97 (m, 2H), 7.47 (s, 1H), 7.29 (ddd, J = 1.34, 2.93, 8.42 Hz, 1H), 7.15-7.24 (m, 2H), 6.78-6.88 (m, 2H), 5.96 (s, 2H), 4.51 (br. s., 2H), 3.25 (d, J = 10.01 Hz, 2H), 3.08 (d, J = 11.48 Hz, 2H), 2.18 (d, J = 7.32 Hz, 2H), 1.89-2.01 (m, 2H) | 375 |
| 71 | 2-(6-amino-5-(8-(pyrimidin-2-yl)-3,8-diazabicyclo[3.2.1]octan-3-yl)pyridazin-3-yl)phenol | $^1$H NMR (400 MHz, DMSO-$d_6$) δ 14.14 (s, 1H), 8.39 (d, J = 4.88 Hz, 2H), 7.93 (dd, J = 1.34, 7.93 Hz, 1H), 7.52 (s, 1H), 7.08-7.29 (m, 1H), 6.79-6.93 (m, 2H), 6.67 (t, J = 4.76 Hz, 1H), 5.99 (s, 2H), 4.83 (br. s., 2H), 3.38 (dd, J = 2.20, 11.72 Hz, 2H), 3.00 (d, J = 10.74 Hz, 2H), 2.17 (d, J = 7.32 Hz, 2H), 1.85-2.08 (m, 2H) | 376 |
| 72 | 2-(6-amino-5-(3-methyl-4-phenylpiperazin-1-yl)pyridazin-3-yl)phenol | $^1$H NMR (400 MHz, DMSO-$d_6$) δ 14.17 (s, 1H), 7.94 (d, J = 6.84 Hz, 1H), 7.56 (s, 1H), 7.17-7.34 (m, 3H), 6.96 (d, J = 8.06 Hz, 2H), 6.86-6.92 (m, 2H), 6.78 (s, 1H), 6.27 (s, 2H), 4.08-4.22 (m, 1H), 3.58-3.65 (m, 1H), 3.37 | 376 |

| Example | Compound Name | NMR | m/z |
|---|---|---|---|
| | | (br. s., 2H), 3.26 (d, J = 2.93 Hz, 2H), 2.70-2.84 (m, 1H), 1.11 (d, J = 6.59 Hz, 3H) | |
| 73 | 1-(3-amino-6-(2-hydroxyphenyl)pyridazin-4-yl)piperidine-4-carboxamide | $^1$H NMR (400 MHz, DMSO-$d_6$) δ 14.14-14.41 (m, 1H), 7.86-7.95 (m, 1H), 7.49 (s, 1H), 7.28-7.33 (m, 1H), 7.18-7.27 (m, 1H), 6.83-6.93 (m, 2H), 6.75-6.81 (m, 1H), 6.21 (s, 2H), 3.42-3.52 (m, 2H), 2.60-2.72 (m, 2H), 2.19-2.35 (m, 1H), 1.82 (d, J = 4.64 Hz, 4H) | 314 |
| 74 | 2-(6-amino-5-((1R,4R)-5-(pyridin-2-yl)-2,5-diazabicyclo[2.2.1]heptan-2-yl)pyridazin-3-yl)phenol | $^1$H NMR (400 MHz, DMSO-$d_6$) δ 14.31-14.78 (m, 1H), 7.98-8.04 (m, 1H), 7.92-7.97 (m, 1H), 7.43 (m, 1H), 7.22 (m, 1H), 7.18 (s, 1H), 6.80-6.90 (m, 2H), 6.38-6.62 (m, 2H), 5.88 (s, 2H), 3.90-4.03 (m, 2H), 3.21-3.29 (m, 2H), 1.95-2.18 (m, 2H), 1.49-1.70 (m, 1H), 0.99-1.12 (m, 1H) | 361 |
| 75 | 2-(6-amino-5-(8-(5-fluoropyridin-2-yl)-3,8-diazabicyclo[3.2.1]octan-3-yl)pyridazin-3-yl)phenol | $^1$H NMR (400 MHz, DMSO-$d_6$) δ 14.14 (s, 1H), 8.12 (dd, J = 5.62, 9.77 Hz, 1H), 7.91 (dd, J = 1.46, 8.06 Hz, 1H), 7.49 (s, 1H), 7.21 (ddd, J = 1.46, 7.02, 8.36 Hz, 1H), 6.80-6.88 (m, 2H), 6.72 (dd, J = 2.08, 12.82 Hz, 1H), 6.52 (ddd, J = 2.20, 5.98, 8.42 Hz, 1H), 5.97 (s, 2H), 4.70 (br. s., 2H), 3.29 (m, 2H), 3.02 (d, J = 11.23 Hz, 2H), 2.16 (d, J = 7.08 Hz, 2H), 1.87-1.99 (m, 2H) | 393 |
| 76 | 2-(6-amino-5-(8-(4-fluorophenyl)-3,8-diazabicyclo[3.2.1]octan-3-yl)pyridazin-3-yl)phenol | $^1$H NMR (400 MHz, DMSO-$d_6$) δ 14.14 (s, 1H), 7.89 (dd, J = 1.34, 7.93 Hz, 1H), 7.45 (s, 1H), 7.15-7.28 (m, 1H), 6.98-7.06 (m, 2H), 6.79-6.94 (m, 4H), 5.94 (s, 2H), 4.36 (br. s., 2H), 3.24 (d, J = 10.25 Hz, 2H), 3.07 (d, J = 11.47 Hz, 2H), 2.07-2.19 (m, 2H), 1.85-1.99 (m, 2H) | 392 |
| 77 | 2-(6-amino-5-(8-(thiazol-2-yl)-3,8-diazabicyclo[3.2.1]octan-3-yl)pyridazin-3-yl)phenol | $^1$H NMR (400 MHz, DMSO-$d_6$) δ 14.11 (br. s., 1H), 7.93 (d, J = 7.81 Hz, 1H), 7.53 (br. s., 1H), 7.11-7.36 (m, 2H), 6.57-6.97 (m, 3H), 5.99 (br. s., 2H), 4.37 (br. s., 2H), 3.37 (d, J = 11.72 Hz, 2H), 3.12 (d, J = 11.47 Hz, 2H), 2.16 (d, J = 7.32 Hz, 2H), 1.97 (br. s., 2H) | 381 |
| 78 | 1'-(3-amino-6-(2-hydroxyphenyl)pyridazin-4-yl)spiro[indoline-3,4'-piperidin]-2-one | $^1$H NMR (400 MHz, DMSO-$d_6$) δ 14.04-14.44 (m, 1H), 10.30-10.54 (m, 1H), 7.91-8.04 (m, 1H), 7.61-7.68 (m, 1H), 7.50-7.57 (m, 1H), 7.16-7.28 (m, 2H), 6.95-7.04 (m, 1H), 6.82-6.91 (m, 3H), 6.19-6.36 (m, 2H), 3.46-3.55 (m, 2H), 3.32-3.39 (m, 2H), 1.83-2.08 (m, 4H) | 388 |
| 79 | 2-(3-(3-amino-6-(2-hydroxyphenyl)pyridazin-4-yl)-3,8-diazabicyclo[3.2.1]octan-8-yl)-N-methylacetamide | $^1$H NMR (400 MHz, DMSO-$d_6$) δ 14.10-14.31 (m, 1H), 7.88-7.96 (m, 1H), 7.80-7.87 (m, 1H), 7.50 (s, 1H), 7.13-7.31 (m, 1H), 6.76-6.98 (m, 2H), 5.82-5.98 (m, 2H), 3.24 (s, 4H), 3.00-3.10 (m, 2H), 2.94 (s, 2H), 2.66 (d, J = 4.88 Hz, 3H), 1.90 (s, 4H) | 369 |

Synthesis of Intermediates Used to Prepare Compounds in the Previous Table
3-benzylpyrrolidin-3-ol Hydrochloride

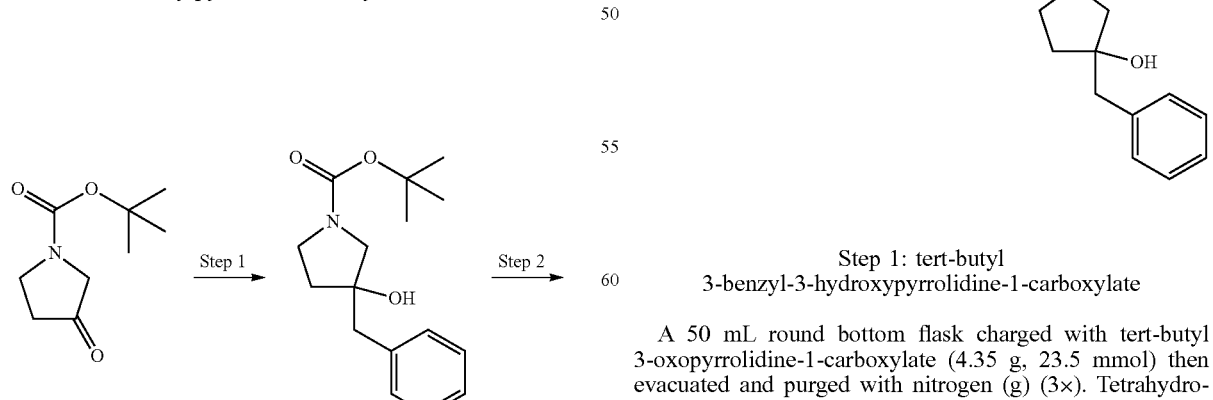

Step 1: tert-butyl 3-benzyl-3-hydroxypyrrolidine-1-carboxylate

A 50 mL round bottom flask charged with tert-butyl 3-oxopyrrolidine-1-carboxylate (4.35 g, 23.5 mmol) then evacuated and purged with nitrogen (g) (3×). Tetrahydrofuran (70 mL) was added and the solution cooled to 0° C. in an ice bath. Benzylmagnesium chloride (2 M in tetrahydrofuran, 15.29 mL, 30.5 mmol) was added and the reaction mixed at 0° C. for 10 min then warmed to ambient temperature. The reaction was then heated at 40° C. for 12 h. The reaction was cooled to ambient temperature and quenched with 1:1:1 (150 mL) of 1 N hydrochloric acid, brine, water then extracted ethyl acetate (3×). The combined organic layers were dried over sodium sulfate, filtered and concentrated. The residue was purified by silica gel chromatography (eluting with hexanes/ethyl acetate) to provide the product tert-butyl 3-benzyl-3-hydroxypyrrolidine-1-carboxylate (1.841 g, 28%) as a pale yellow oil. LCMS M/Z (M+Na) 300.

Step 2: 3-benzylpyrrolidin-3-ol Hydrochloride

In a 100 mL round bottom flask tert-butyl 3-benzyl-3-hydroxypyrrolidine-1-carboxylate (1.84 g, 6.64 mmol) was dissolved in Methanol (16 mL). Hydrochloric acid (4 M in dioxane, 16.6 mL, 66.4 mmol) was then added and the reaction was mixed ambient temperature for 12 h. The reaction was concentrated to dryness with benzene (3×). A solid was formed by concentrating with methylene chloride (2×). The residual solvent was removed under high vacuum over 1 h to provide 3-benzylpyrrolidin-3-ol hydrochloride (1.161 g, 82%) as a brown solid, which was used crude in the following reaction. LCMS M/Z (M+H) 178.

3-benzyl-3-methoxypyrrolidine Hydrochloride

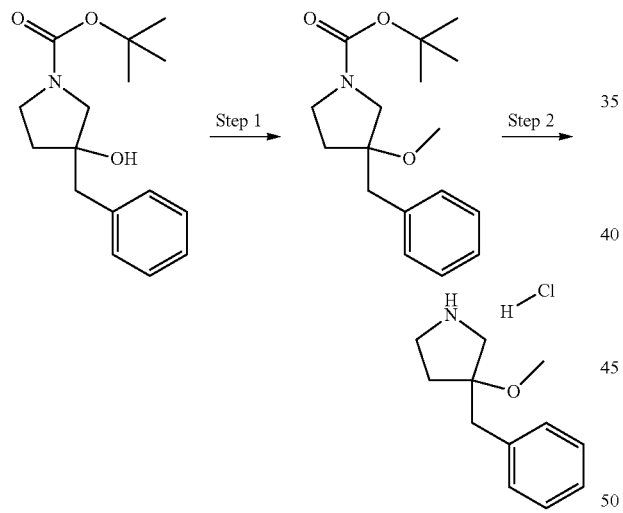

Step 1: tert-butyl 3-benzyl-3-methoxypyrrolidine-1-carboxylate

In a 250 mL round bottom flask tert-butyl 3-benzyl-3-hydroxypyrrolidine-1-carboxylate (1.598 g, 5.76 mmol) was dissolved in anhydrous dimethylformamide (15 mL). Sodium hydride (60% in mineral oil, 345 mg, 8.6 mmol) was added and the reaction was heated at 50° C. for 1 h then cooled to 0° C. Iodomethane (0.43 mL, 6.9 mmol) was then added and the reaction was mixed at ambient temperature for 12 h. The reaction was quenched with water (140 mL) and brine (10 mL) then extracted with Ethyl acetate (3×). The combined organic extracts were washed with brine, dried over sodium sulfate, and concentrated to provide tert-butyl 3-benzyl-3-methoxypyrrolidine-1-carboxylate (1.68 g, 100%) as an oil, which was used directly in the following reaction.

Step 2: tert-butyl 3-benzyl-3-methoxypyrrolidine-1-carboxylate

In a 100 mL round bottom flask tert-butyl 3-benzyl-3-methoxypyrrolidine-1-carboxylate (1.70 g, 5.83 mmol) was dissolved in Methanol (14 mL). Hydrochloric acid (4 M in dioxane, 14.6 mL, 58.3 mmol) was then added and the reaction was mixed at ambient temperature for 12 h. The reaction was concentrated to dryness with benzene (2×) and triturated by rotary evaporation with methylene chloride. A solid was formed by concentrating with methylene chloride (2×). The residual solvent was removed under high vacuum over 1 h to provide 3-benzyl-3-methoxypyrrolidine hydrochloride (500 mg, 38%) as a brown solid, which was used crude. LCMS M/Z (M+H) 192.

2-(pyridin-2-yl)-2,5-diazabicyclo[2.2.1]heptane Hydrochloride

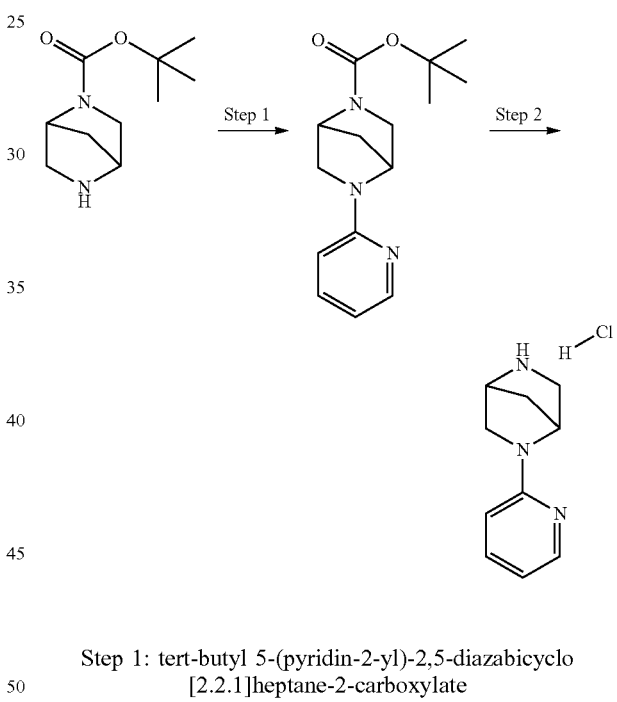

Step 1: tert-butyl 5-(pyridin-2-yl)-2,5-diazabicyclo[2.2.1]heptane-2-carboxylate In a pyrex vial tert-butyl 2,5-diazabicyclo[2.2.1]heptane-2-carboxylate (500 mg, 2.5 mmol), 2-chloropyridine (0.29 mL, 3.0 mmol), sodium tert-butoxide (364 mg, 3.8 mmol) and methanesulfonato(2-dicyclohexylphosphino-2',6'-di-i-propoxy-1,1'-biphenyl)(2'-amino-1,1'-biphenyl-2-yl)palladium(II) (105 mg, 0.13 mmol) were added. The vial was sealed, evacuated and purged with nitrogen (g) (3×). Anhydrous dioxane (6 mL) was added and the reaction was heated at 100° C. for 12 h. The reaction was cooled to ambient temperature, diluted with Ethyl acetate, filtered through a pad of celite then concentrated to dryness and deposited on to silica gel with aid of methylene chloride. The crude residue was purified by silica gel chromatography (eluting with hexanes/ethyl acetate) to provide tert-butyl 5-(pyridin-2-yl)-2,5-diazabicyclo[2.2.1]heptane-2-carboxylate (603 mg, 87%) as a white solid. LCMS M/Z (M+H) 276.

Step 2: 2-(pyridin-2-yl)-2,5-diazabicyclo[2.2.1]heptane Hydrochloride

A 50 mL round bottom flask was charged with tert-butyl 5-(pyridin-2-yl)-2,5-diazabicyclo[2.2.1]heptane-2-carboxylate (603 mg, 2.19 mmol) and diluted with Methanol (5.5 mL). Hydrochloric acid (4 M in dioxane, 5.48 mL, 21.9 mmol) was added and the solution was mixed at ambient temperature for 12 h. The reaction was concentrated to dryness then residual solvent was removed under high vacuum to provide 2-(pyridin-2-yl)-2,5-diazabicyclo[2.2.1] heptane hydrochloride (421 mg, 91%) as a solid that was used without further purification. LCMS M/Z (M+H) 176.

8-(pyrimidin-5-yl)-3,8-diazabicyclo[3.2.1]octane Hydrochloride

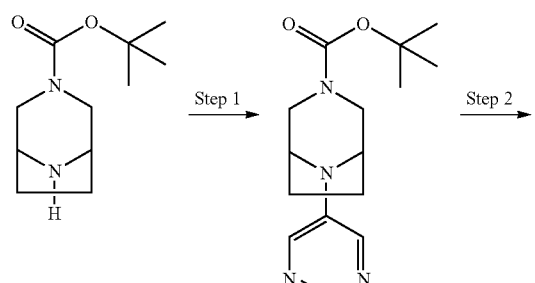

Step 1: tert-butyl 8-(pyrimidin-5-yl)-3,8-diazabicyclo[3.2.1]octane-3-carboxylate In a pyrex vial tert-butyl 3,8-diazabicyclo[3.2.1]octane-3-carboxylate (300 mg, 1.41 mmol), 5-bromopyrimidine (270 mg, 1.70 mmol), sodium tert-butoxide (204 mg, 2.12 mmol) and methanesulfonato(2-dicyclohexylphosphino-2',6'-di-i-propoxy-1,1'-biphenyl)(2'-amino-1,1'-biphenyl-2-yl)palladium(II) (59 mg, 0.07 mmol) were added. The vial was sealed, evacuated and purged with nitrogen (g) (3x). Anhydrous dioxane (4 mL) was added and the reaction was heated at 100° C. for 12 h. The reaction was cooled to ambient temperature, diluted with ethyl acetate, filtered through a pad of celite then concentrated to dryness and deposited on to silica gel with aid of methylene chloride. The crude residue was purified by silica gel chromatography (eluting with hexanes/ethyl acetate) to provide tert-butyl 8-(pyrimidin-5-yl)-3,8-diazabicyclo[3.2.1]octane-3-carboxylate (100 mg, 24%) as a yellow oil. LCMS M/Z (M+H) 291.

Step 2: 8-(pyrimidin-5-yl)-3,8-diazabicyclo[3.2.1] octane Hydrochloride

A 50 mL round bottom flask was charged with tert-butyl 8-(pyrimidin-5-yl)-3,8-diazabicyclo[3.2.1]octane-3-carboxylate (100 mg, 0.34 mmol) and diluted with Methanol (1 mL). Hydrochloric acid (4 M in dioxane, 0.85 mL, 3.4 mmol) was added and the solution was mixed at ambient temperature for 12 h. The reaction was concentrated to dryness then residual solvent was removed under high vacuum to provide 8-(pyrimidin-5-yl)-3,8-diazabicyclo [3.2.1]octane hydrochloride (80 mg, 100%) as a solid that was used without further purification. LCMS M/Z (M+H) 191.

(1R,5S)-8-(5-fluoropyridin-3-yl)-3,8-diazabicyclo [3.2.1]octane Dihydrochloride

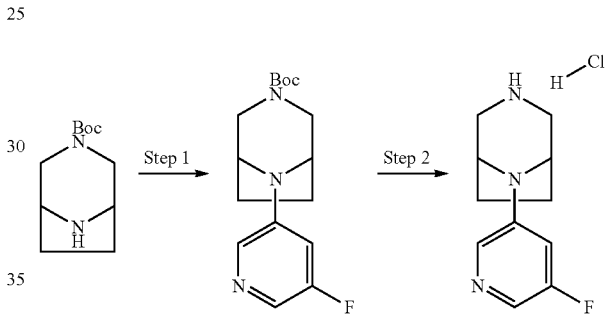

Step 1: (1R,5S)-tert-butyl 8-(5-fluoropyridin-3-yl)-3,8-diazabicyclo[3.2.1]octane-3-carboxylate A round bottomed flask was charged with (1R,5S)-tert-butyl 3,8-diazabicyclo[3.2.1]octane-3-carboxylate (250 mg, 1.1776 mmol), 3-bromo-5-fluoropyridine (0.2176 g, 1.2365 mmol), sodium 2-methylpropan-2-olate (0.1698 g, 1.7664 mmol), and a stirbar. Methanesulfonato(2-dicyclohexylphosphino-2',6'-di-i-propoxy-1,1'-biphenyl)(2'-amino-1,1'-biphenyl-2-yl)palladium(II) (0.0985 g, 0.1178 mmol) was added, followed by dioxane (5 mL), and the mixture was stirred at 90° C. 18 h. The mixture was diluted with ethyl acetate, concentrated in vacuo with celite, and purified by silica gel chromatography (eluting with hexanes and ethyl acetate) to afford the title compound (0.32 g, 1.0411 mmol). LCMS M/Z (M+H) 308.

Step 2: (1R,5S)-8-(5-fluoropyridin-3-yl)-3,8-diazabicyclo[3.2.1]octane Dihydrochloride (1R,5S)-tert-butyl 8-(5-fluoropyridin-3-yl)-3,8-diazabicyclo[3.2.1]octane-3-carboxylate (320 mg, 1.04 mmol) was dissolved in 1,4-dioxane for the addition of hydrochloric acid (4 M in dioxane) (1.04 mL, 4.16 mmol), and the mixture was stirred 16 h. The reaction mixture was concentrated in vacuo and dried under high vacuum to provide the title compound (0.28 g, 1 mmol), which was used crude.

119

8-(pyrazin-2-yl)-3,8-diazabicyclo[3.2.1]octane Hydrochloride

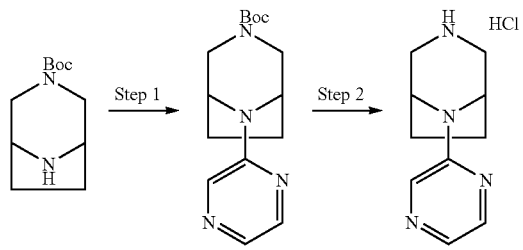 [SMILES: Cl ; CC(C)(C)OC(=O)N1CC2CCC(C1)N2 ; CC(C)(C)OC(=O)N1CC2CCC(C1)N2c1cnccn1 ; c1cnc(N2C3CCC2CNC3)cn1]

Step 1: (1R,5S)-tert-butyl 8-(pyrazin-2-yl)-3,8-diazabicyclo[3.2.1]octane-3-carboxylate A round bottomed flask was charged with (1R,5S)-tert-butyl 3,8-diazabicyclo[3.2.1]octane-3-carboxylate (250 mg, 1.1776 mmol), 2-bromopyrazine (0.1872 g, 1.1776 mmol), sodium 2-methylpropan-2-olate (0.1698 g, 1.7664 mmol), and a stirbar. Methanesulfonato(2-dicyclohexylphosphino-2',6'-di-i-propoxy-1,1'-biphenyl)(2'-amino-1,1'-biphenyl-2-yl)palladium(II) (0.0985 g, 0.1178 mmol) was added, followed by dioxane (5 mL), and the mixture was stirred at 90° C. 18 h. The mixture was diluted with ethyl acetate, filtered, concentrated with celite, and purified by silica gel chromatography (eluting with hexanes and ethyl acetaete) to afford the title compound (0.21 g, 0.7232 mmol, 61%). LCMS M/Z (M+H) 291.

Step 2: 8-(pyrazin-2-yl)-3,8-diazabicyclo[3.2.1]octane Hydrochloride

To (1R,5S)-tert-butyl 8-(pyrazin-2-yl)-3,8-diazabicyclo[3.2.1]octane-3-carboxylate (0.24 g, 0.83 mmol) dissolved in dioxane (1 ml) was added hydrochloric acid (4 M in dioxane, 0.83 ml, 3.32 mmol), and the solution was stirred for 12 h. The reaction was concentrated in vacuo to afford the title compound (180 mg, 0.7 mmol) and used crude. LCMS M/Z (M+H) 191.

3-methyl-4-phenylpiperidin-4-ol Hydrochloride

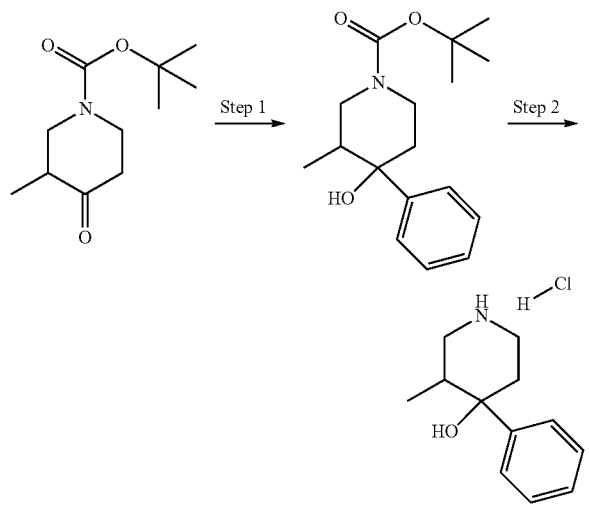

120

Step 1: tert-butyl 4-hydroxy-3-methyl-4-phenylpiperidine-1-carboxylate

In a 100 mL round bottom flask tert-butyl 3-methyl-4-oxopiperidine-1-carboxylate (988 mg, 4.63 mmol) was dissolved in tetrahydrofuran (20 mL) and cooled to 0° C. Phenylmagnesium bromide (7.72 mL, 23.17 mmol) was added and the solution was warmed to ambient temperature and mixed for 24 h. The reaction was cooled to 0° C. then 1 N hydrochloric acid was added (75 mL) and the aq. solution was extracted with ethyl acetate (3×). The combined organic phase was dried over sodium sulfate, concentrated and purified by silica gel chromatography (eluting with hexane/ethyl acetate) to provide tert-butyl 4-hydroxy-3-methyl-4-phenylpiperidine-1-carboxylate (1.133 g, 84%) as a white solid. LCMS M/Z (M-OH, t-Bu) 218.

Step 2: 3-methyl-4-phenylpiperidin-4-ol Hydrochloride

To a 100 mL round bottom flask containing tert-butyl 4-hydroxy-3-methyl-4-phenylpiperidine-1-carboxylate (1.133 g, 3.89 mmol) was added hydrochloric acid (4 M in dioxane, 9.72 mL, 38.88 mmol). The reaction was mixed at ambient temperature for 12 h. The reaction was concentrated to dryness to provide 3-methyl-4-phenylpiperidin-4-ol hydrochloride (200 mg, 26%) as a solid that was used directly in the following reaction. LCMS M/Z (M+H) 192.

8-(1-methyl-1H-pyrazol-4-yl)-3,8-diazabicyclo[3.2.1]octane Hydrochloride

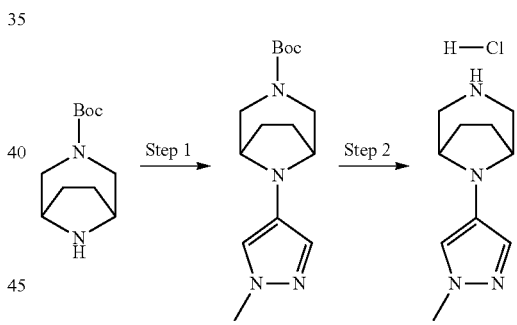

Step 1: tert-butyl 8-(1-methyl-1H-pyrazol-4-yl)-3,8-diazabicyclo[3.2.1]octane-3-carboxylate tert-butyl 3,8-diazabicyclo[3.2.1]octane-3-carboxylate (250 mg, 1.18 mmol), 4-iodo-1-methyl-1H-pyrazole (0.32 g, 1.5 mmol), sodium 2-methylpropan-2-olate (0.17 g, 1.8 mmol), methanesulfonato(2-dicyclohexylphosphino-2',6'-di-i-propoxy-1,1'-biphenyl)(2'-amino-1,1'-biphenyl-2-yl)palladium(II) (0.10 g, 0.12 mmol) and toluene (4 mL) were charged in a vial. The headspace was flushed with nitrogen and the reaction mixture was degassed using 4 cycles of vacuum and nitrogen refilling. The reaction was heated at 110° C. for 24 h then cooled to room temperature. Silica gel was added and the solvent was removed under vacuum. The desired product was purified by silica gel chromatography (eluting with hexanes/ethyl acetate/methanol). The title compound was obtained as a solid (350 mg). LCMS M/Z (M+H) 293.

Step 2: 8-(1-methyl-1H-pyrazol-4-yl)-3,8-diazabicyclo[3.2.1]octane Hydrochloride To a solution of tert-butyl 8-(1-methyl-1H-pyrazol-4-yl)-3,8-diazabicyclo[3.2.1]octane-3-carboxylate (350 mg, 1.2 mmol) in methanol (6 mL) was added hydrogen chloride (4 M in 1,4-dioxane) (0.9 g, 24.6 mmol) at room temperature. After 2 h, the reaction was concentrated to dryness. The product was neutralized with aq. sodium bicarbonate and extracted with ethyl acetate (repeated 3 times). The combined organic layers were dried with sodium sulfate, filtered and concentrated to dryness under vacuum. The title compound was used without purification. LCMS M/Z (M+H) 193.

8-(2-fluoropyridin-4-yl)-3,8-diazabicyclo[3.2.1]octane

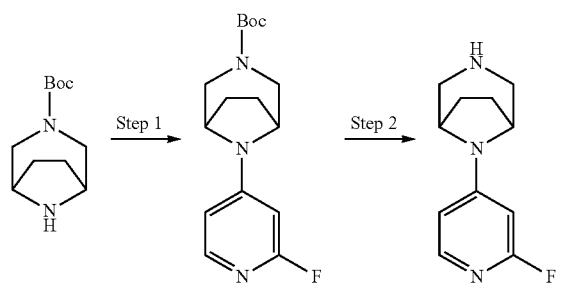 [SMILES: CC(C)(C)OC(=O)N1CC2CCC(C1)N2 ; CC(C)(C)OC(=O)N1CC2CCC(C1)N2c1ccnc(F)c1 ; Fc1cc(N2C3CCC2CNC3)ccn1]

Step 1: tert-butyl (1R,5S)-8-(2-fluoropyridin-4-yl)-3,8-diazabicyclo[3.2.1]octane-3-carboxylate tert-butyl 3,8-diazabicyclo[3.2.1]octane-3-carboxylate (250 mg, 1.178 mmol), 4-bromo-2-fluoropyridine (0.2694 g, 1.5309 mmol), sodium 2-methylpropan-2-olate (0.170 g, 1.77 mmol), methanesulfonato(2-dicyclohexylphosphino-2',6'-di-i-propoxy-1,1'-biphenyl)(2'-amino-1,1'-biphenyl-2-yl)palladium(II) (0.049 g, 0.059 mmol), and 1,4-dioxane (4 mL) were charged in a vial. The headspace was flushed with nitrogen and the reaction mixture was degassed using 4 cycles of vacuum and nitrogen refilling. The reaction was heated at 110° C. for 5 h then cooled to room temperature. Silica gel was added and the solvent was removed under vacuum. The desired product was purified by silica gel chromatography (eluting with hexane/ethyl acetate). The title compound was obtained as a solid (137 mg; 38% yield). LCMS M/Z (M+H) 308.

Step 2: 8-(2-fluoropyridin-4-yl)-3,8-diazabicyclo[3.2.1]octane

To a solution of tert-butyl 8-(2-fluoropyridin-4-yl)-3,8-diazabicyclo[3.2.1]octane-3-carboxylate (688.5 mg, 2.24 mmol) in methanol (5 mL) was added hydrogen chloride (4 M in 1,4-dioxane) (5.6 mL, 22.4 mmol) at room temperature. After 1 h the reaction is concentrated to dryness under vacuum. The product was neutralized with aq. sodium bicarbonate and extracted with ethyl acetate (repeated 3 times). The combined organic layers were dried with sodium sulfate, filtered and concentrated to dryness under vacuum. The title compound was used in the next step without purification. LCMS M/Z (M+H) 208.

2-(6-Amino-5-(4-(1-phenylethyl)piperazin-1-yl)pyridazin-3-yl)phenol was Separated into its Individual Enantiomers, Examples 80 and 81

Enantiomer 1 and Enantiomer 2 of 2-(6-amino-5-(4-(1-phenylethyl)piperazin-1-yl)pyridazin-3-yl)phenol

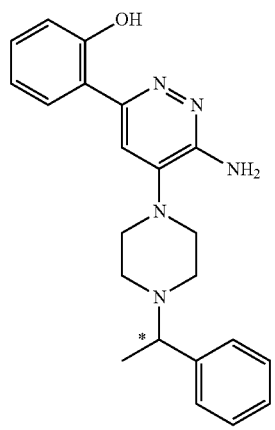 [SMILES: CC(c1ccccc1)N1CCN(c2cc(-c3ccccc3O)nnc2N)CC1]

Separated by SFC chromatography (eluting with carbon dioxide and methanol, 0.1% ammonium hydroxide) using a Chiralpak AD column.

Example 80

$^1$H NMR (400 MHz, DMSO-$d_6$) δ 14.22 (s, 1H), 7.91 (dd, J=8.3, 1.6 Hz, 1H), 7.49 (s, 1H), 7.42-7.31 (m, 3H), 7.23 (ddd, J=8.2, 7.4, 1.8 Hz, 2H), 6.95-6.64 (m, 2H), 6.20 (s, 2H), 3.50 (d, J=6.7 Hz, 1H), 3.09 (s, 3H), 2.73-2.54 (m, 3H), 1.34 (d, J=6.6 Hz, 3H). LCMS M/Z (M+H) 376.

Example 81

$^1$H NMR (400 MHz, DMSO-$d_6$) δ 14.22 (s, 1H), 7.91 (dd, J=8.4, 1.6 Hz, 1H), 7.49 (s, 1H), 7.41-7.29 (m, 4H), 7.29-7.18 (m, 2H), 6.93-6.75 (m, 2H), 6.20 (s, 2H), 3.50 (d, J=6.7 Hz, 1H), 3.08 (d, J=10.1 Hz, 4H), 2.59 (dd, J=31.5, 6.4 Hz, 4H), 1.34 (d, J=6.7 Hz, 3H). LCMS M/Z (M+H) 376.

2-(6-Amino-5-(3-methyl-4-phenylpiperazin-1-yl)pyridazin-3-yl)phenol was Separated into its Individual Enantiomers, Examples 82 and 83

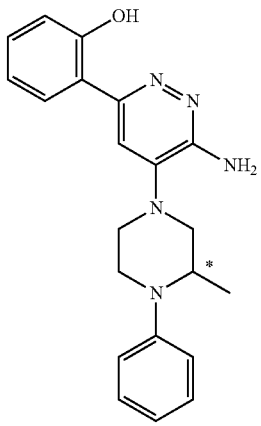

Separated by SFC chromatography (eluting with carbon dioxide and methanol, 0.1% ammonium hydroxide) using a Chiralpak AS column.

Example 82

$^1$H NMR (400 MHz, DMSO-$d_6$) δ 14.18 (s, 1H), 7.94 (dd, J=8.4, 1.6 Hz, 1H), 7.57 (s, 1H), 7.25 (ddd, J=8.4, 7.2, 1.4 Hz, 3H), 7.02-6.94 (m, 2H), 6.94-6.85 (m, 2H), 6.85-6.71 (m, 1H), 6.28 (s, 2H), 4.16 (d, J=6.6 Hz, 1H), 3.62 (d, J=12.2 Hz, 1H), 3.44-3.32 (m, 2H), 2.79 (ddd, J=11.7, 9.4, 4.4 Hz, 1H), 1.12 (d, J=6.4 Hz, 3H). LCMS M/Z (M+H) 362.

Example 83

$^1$H NMR (400 MHz, DMSO-$d_6$) δ 14.18 (s, 1H), 7.94 (dd, J=8.3, 1.6 Hz, 1H), 7.57 (s, 1H), 7.32-7.19 (m, 3H), 7.00-6.94 (m, 2H), 6.93-6.87 (m, 2H), 6.83-6.75 (m, 1H), 6.28 (s, 2H), 4.23-4.08 (m, 1H), 3.62 (d, J=12.2 Hz, 1H), 3.42-3.36 (m, 2H), 3.27 (d, J=3.1 Hz, 2H), 2.85-2.72 (m, 1H), 1.12 (d, J=6.4 Hz, 3H). LCMS M/Z (M+H) 362.

(trans-4a,8a)-2-(3-Amino-6-(2-hydroxyphenyl)pyridazin-4-yl)decahydroisoquinolin-4a-ol was Separated into its Individual Enantiomers, Examples 84 and 85

Enantiomer 1 and Enantiomer 2 of (trans-4a,8a)-2-(3-amino-6-(2-hydroxyphenyl)pyridazin-4-yl)decahydroisoquinolin-4a-ol

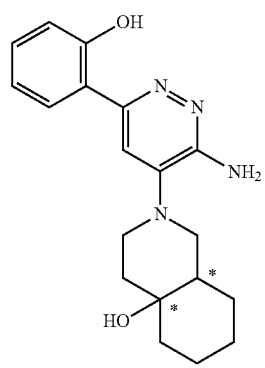 [SMILES: Nc1nnc(-c2ccccc2O)cc1N1CCC2(O)CCCCC2C1]

Separated by SFC chromatography (eluting with carbon dioxide and methanol, 0.1% ammonium hydroxide) using a Chiralpak IA column.

Example 84

$^1$H NMR (400 MHz, DMSO-$d_6$) δ 14.31 (s, 1H), 7.93 (dd, J=8.4, 1.6 Hz, 1H), 7.51 (s, 1H), 7.23 (ddd, J=8.2, 7.3, 1.6 Hz, 1H), 6.95-6.79 (m, 2H), 6.11 (s, 2H), 4.31 (s, 1H), 3.39 (s, 1H), 2.91 (dd, J=12.1, 3.7 Hz, 2H), 1.64 (d, J=24.6 Hz, 6H), 1.39 (d, J=10.6 Hz, 5H). LCMS M/Z (M+H) 341.

Example 85

$^1$H NMR (400 MHz, DMSO-$d_6$) δ 14.31 (s, 1H), 7.93 (dd, J=8.4, 1.6 Hz, 1H), 7.51 (s, 1H), 7.32-7.15 (m, 1H), 6.94-6.81 (m, 2H), 6.11 (s, 2H), 4.31 (s, 1H), 3.37 (s, 1H), 3.04-2.85 (m, 2H), 1.63 (d, J=25.5 Hz, 6H), 1.33 (d, J=52.9 Hz, 5H). LCMS M/Z (M+H) 341.

125

2-(6-Amino-5-(4-(1-morpholinoethyl)piperidin-1-yl)pyridazin-3-yl)phenol was Separated into its Individual Enantiomers, Examples 86 and 87

Enantiomer 1 and enantiomer 2 of 2-(6-amino-5-(4-(1-morpholinoethyl)piperidin-1-yl)pyridazin-3-yl)phenol

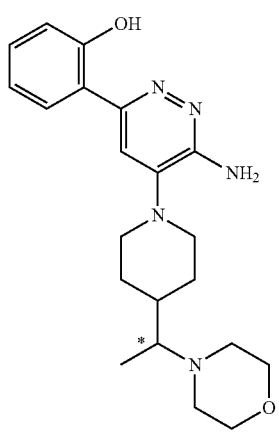 [SMILES: CC(C1CCN(c2cc(-c3ccccc3O)nnc2N)CC1)N1CCOCC1]

Separated by SFC chromatography (eluting with carbon dioxide and methanol, 0.1% ammonium hydroxide) using a Cel-1 column.

Example 86

$^1$H NMR (400 MHz, DMSO-$d_6$) δ 14.28 (s, 1H), 7.90 (dd, J=8.4, 1.6 Hz, 1H), 7.47 (s, 1H), 7.23 (ddd, J=8.2, 7.2, 1.6 Hz, 1H), 6.98-6.74 (m, 2H), 6.17 (s, 2H), 3.66-3.44 (m, 6H), 2.69-2.56 (m, 3H), 2.37-2.18 (m, 3H), 2.15-1.96 (m, 1H), 1.84-1.71 (m, 1H), 1.62-1.31 (m, 3H), 0.93 (d, J=6.5 Hz, 31). LCMS M/Z (M+H) 384.

Example 87

$^1$H NMR (400 MHz, DMSO-$d_6$) δ 14.28 (s, 1H), 7.90 (dd, J=8.4, 1.6 Hz, 1H), 7.47 (s, 1H), 7.23 (ddd, J=8.2, 7.2, 1.6 Hz, 1H), 6.96-6.71 (m, 2H), 6.17 (s, 2H), 3.69-3.44 (m, 6H), 2.70-2.59 (m, 3H), 2.39-2.17 (m, 3H), 2.12-2.01 (m, 1H), 1.76 (d, J=12.5 Hz, 1H), 1.43 (dd, J=10.0, 2.3 Hz, 3H), 0.93 (d, J=6.5 Hz, 3H). LCMS M/Z (M+H) 384.

126

Example 88

5-(3-(3-amino-6-(2-hydroxyphenyl)pyridazin-4-yl)-3,8-diazabicyclo[3.2.1]octan-8-yl)picolinic Acid

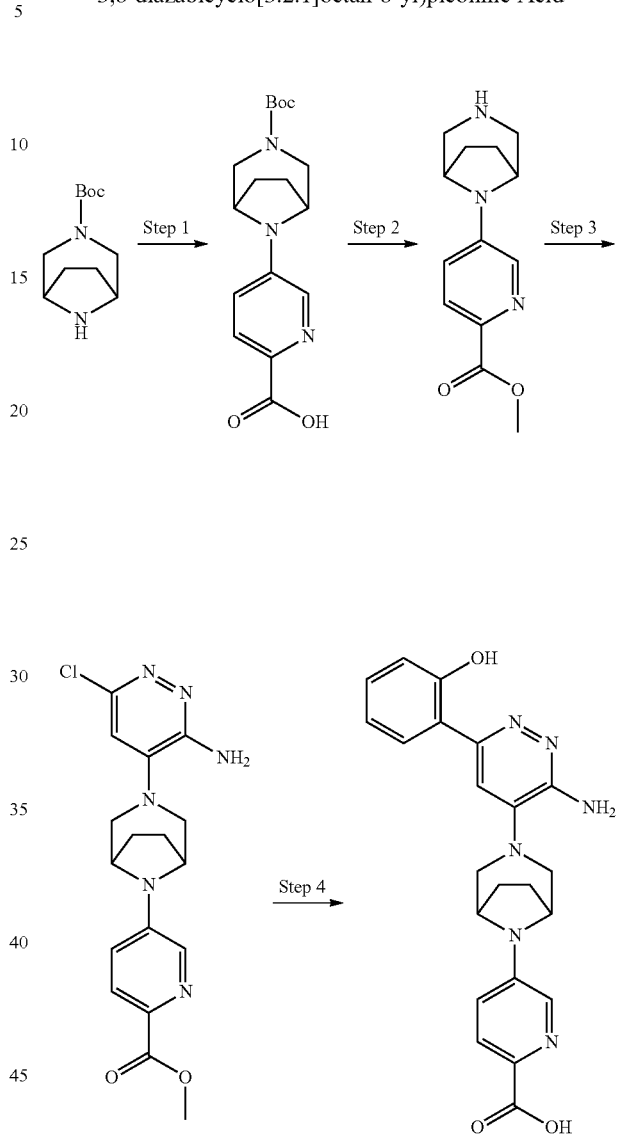

Step 1: 5-(3-(tert-butoxycarbonyl)-3,8-diazabicyclo[3.2.1]octan-8-yl)picolinic Acid Tert-butyl 3,8-diazabicyclo[3.2.1]octane-3-carboxylate (250 mg, 1.18 mmol), 5-bromopicolinic acid (0.309 g, 1.53 mmol), sodium 2-methylpropan-2-olate (0.283 g, 2.94 mmol), methanesulfonato(2-dicyclohexylphosphino-2',6'-di-i-propoxy-1,1'-biphenyl)(2'-amino-1,1'-biphenyl-2-yl)palladium(II) (0.049 g, 0.059 mmol) and 1,4-dioxane (4 mL) were charged in a vial. The headspace was flushed with nitrogen and the reaction mixture was degassed using 4 cycles of vacuum and nitrogen refilling. The reaction was heated at 110° C. for 36 h then cooled to room temperature. Silica gel was added and the solvent was removed under vacuum. The desired product was purified by silica gel chromatography (eluting with hexane/ethyl acetate/methanol). LCMS M/Z (M+H) 334.

Step 2: methyl 5-(3,8-diazabicyclo[3.2.1]octan-8-yl)picolinate

To a solution of 5-(3-(tert-butoxycarbonyl)-3,8-diazabicyclo[3.2.1]octan-8-yl)picolinic acid (666 mg, 2.00 mmol) in methanol (6 mL) was added hydrogen chloride (4 M in 1,4-dioxane) (12.5 mL, 50.0 mmol). The reaction was stirred at room temperature for 1 h then concentrated to dryness under vacuum. The product was neutralized with aq. sodium bicarbonate and extracted with ethyl acetate (repeated 3 times). The combined organic layers were dried with sodium sulfate, filtered, and concentrated to dryness under vacuum. The title compound was used in the next step without purification. LCMS M/Z (M+H) 248.

Step 3: methyl 5-((1R,5S)-3-(3-amino-6-chloropyridazin-4-yl)-3,8-diazabicyclo[3.2.1]octan-8-yl)picolinate Methyl 5-(3,8-diazabicyclo[3.2.1]octan-8-yl)picolinate (230 mg, 0.986 mmol), 4-bromo-6-chloropyridazin-3-amine (0.247 g, 1.183 mmol), N-ethyl-N-isopropylpropan-2-amine (0.765 g, 5.92 mmol), and acetonitrile (3 mL) were charged in a sealed vial and heated to 100° C. After 24 h, silica gel was added and the solvent was removed under vacuum. The desired product was purified by silica gel chromatography (eluting with hexanes/ethyl acetate). The title compound was used in the next step despite being contaminated with impurities. LCMS M/Z (M+H) 375.

Step 4: 5-(3-(3-amino-6-(2-hydroxyphenyl)pyridazin-4-yl)-3,8-diazabicyclo[3.2.1]octan-8-yl)picolinic Acid Methyl 5-(3-(3-amino-6-chloropyridazin-4-yl)-3,8-diazabicyclo[3.2.1]octan-8-yl)picolinate (75 mg, 0.20 mmol), (2-hydroxyphenyl)boronic acid (0.036 g, 0.26 mmol), potassium carbonate (0.055 g, 0.40 mmol), methanesulfonato(2-dicyclohexylphosphino-2',4',6'-tri-i-propyl-1,1'-biphenyl)(2'-amino-1,1'-biphenyl-2-yl)palladium(II) (0.017 g, 0.020 mmol), 1,4-dioxane (4 mL) and water (0.2 mL) were charged in a vial. The headspace was flushed with nitrogen and the reaction mixture was degassed using 4 cycles of vacuum and nitrogen refilling. The reaction was heated at 90° C. for 3 h, then aq. sodium hydroxide (2 M; 1 mL, 2 mmol) was added. After an additional 2 h at 90° C., acetic acid (0.5 mL) and silica gel were added at room temperature and the solvent was removed under vacuum. The desired product was purified by silica gel chromatography (eluting with methylene chloride/methanol) and by reverse phase preparative HPLC (eluting with water/acetonitrile/0.1% trifluoroacetic acid) to give the title compound as an off-white solid (58 mg; 54% yield). LCMS M/Z (M+H) 419.

Example 89

5-(3-(3-amino-6-(2-hydroxyphenyl)pyridazin-4-yl)-3,8-diazabicyclo[3.2.1]octan-8-yl)picolinamide

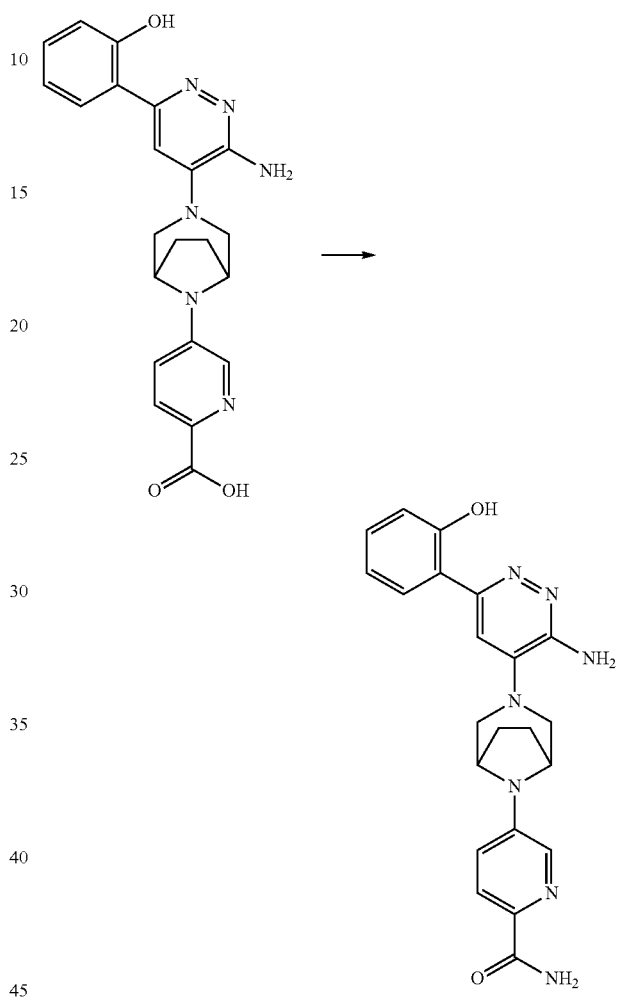

5-((1R,5S)-3-(3-amino-6-(2-hydroxyphenyl)pyridazin-4-yl)-3,8-diazabicyclo[3.2.1]octan-8-yl)picolinic acid (50 mg, 0.12 mmol) (prepared as in example G02944759), N-ethyl-N-isopropylpropan-2-amine (0.15 g, 1.2 mmol), ammonium chloride (0.064 g, 1.2 mmol) and dimethylformamide (5 mL) were charged in a vial, then COMU (0.077 g, 0.18 mmol) was added at room temperature. After 6 h, extra COMU (0.102 g, 0.239 mmol) and ammonium chloride (0.064 g, 1.2 mmol) were added and the reaction was stirred overnight. Next morning, the reaction was quenched with aq. ammonium chloride and the desired product was extracted with methylene chloride (repeated twice). The combined organic layers were washed with water, dried with sodium sulfate, filtered and concentrated to dryness under vacuum. The desired product was purified by silica gel chromatography (eluting with methylene chloride/methanol) and by reverse phase preparative HPLC (eluting with water/acetonitrile/0.1% trifluoroacetic acid) to give the title compound as an off-white solid (2 mg; 3% yield). LCMS M/Z (M+H) 418.

Example 90

2-(6-amino-5-(piperidin-1-yl)pyridazin-3-yl)phenol

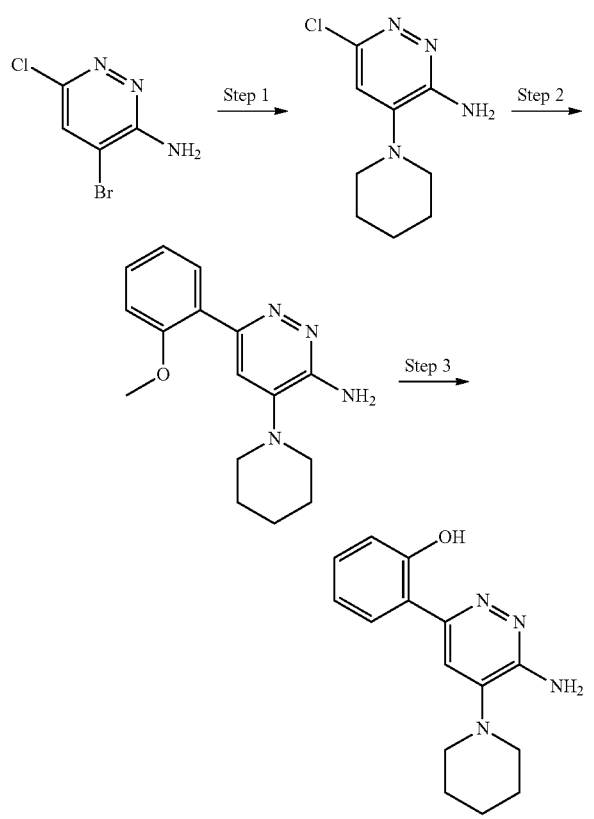

Step 1: 6-chloro-4-(piperidin-1-yl)pyridazin-3-amine

To a solution of 4-bromo-6-chloropyridazin-3-amine (500 mg, 2.4 mmol) in dioxane (30 mL) was added piperidine (410 mg, 4.8 mmol). The resulting mixture was heated to 100° C. for 16 h. The solvent was removed under reduced pressure, and the residue was purified by silica gel chromatography (eluting with ethyl acetate and petroleum ether) to give the title compound (400 mg, 78% yield) as a yellow solid.

Step 2: 6-(2-methoxyphenyl)-4-(piperidin-1-yl)pyridazin-3-amine

A mixture of 6-chloro-4-(piperidin-1-yl)pyridazin-3-amine (200 mg, 0.94 mmol), (2-methoxyphenyl)boronic acid (215 mg, 1.41 mmol), tetrakis(triphenylphosphine) palladium(0) (100 mg, 0.09 mmol) and cesium carbonate (613 mg, 1.88 mmol) in dioxane/water (30 mL/5 mL) was heated at 110° C. for 5 h. The solvent was evaporated under reduced pressure, and the residue was purified by silica gel chromatography (eluting with ethyl acetate and petroleum ether) to give the title compound (150 mg, 56%) as a yellow solid.

Step 3: 2-(6-amino-5-(piperidin-1-yl)pyridazin-3-yl)phenol

To a solution of 6-(2-methoxyphenyl)-4-(piperidin-1-yl)pyridazin-3-amine (150 mg, 0.53 mmol) in dichloromethane (20 mL) was added boron tribromide (0.2 mL) at −78° C. After addition, the resulting mixture was allowed to warm to room temperature and stirred for 16 h. The mixture was then cooled to 0° C. and quenched by addition of methanol (1.0 mL). The solvent was evaporated under reduced pressure. The residue was purified by reverse phase chromatography (eluting with acetonitrile/water/0.1% hydrochloric acid) to give the title compound (35 mg, 25% yield) as a white solid. $^1$H NMR (400 MHz, CD$_3$OD) δ 7.56 (d, J=6.8 Hz, 1H), 7.44-7.39 (m, 2H), 7.04-7.01 (m, 2H), 3.41-3.33 (m, 4H), 1.85-1.76 (m, 4H), 1.75-1.68 (m, 2H). LCMS M/Z (M+H) 271.

The following compound was prepared in a similar fashion to Example 90.

| Example | Compound Name | NMR | m/z |
| --- | --- | --- | --- |
| 91 | 2-(6-amino-5-(4-(dimethylamino)piperidin-1-yl)pyridazin-3-yl)phenol | $^1$H NMR (400 MHz, CD$_3$OD) δ 7.79-7.77 (m, 1H), 7.49 (s, 1H), 7.25-7.23 (m, 1H), 6.94-6.90 (m, 2H), 3.61-3.54 (m, 2H), 2.75-2.67 (m, 2H), 2.43-2.39 (m, 1H), 2.35 (s, 6H), 2.04-1.96 (m, 2H), 1.76-1.72 (m, 2H) | 314 |

Example 92

(S)-2-(6-amino-5-(3-methyl-4-((1-methyl-1H-imidazol-2-yl)methyl)piperazin-1-yl)pyridazin-3-yl)phenol

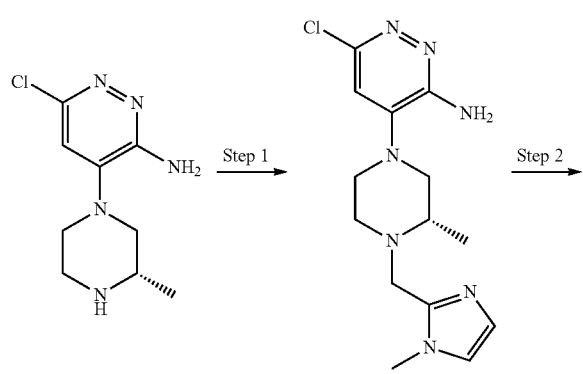

Step 1: (S)-6-chloro-4-(3-methyl-4-((1-methyl-1H-imidazol-2-yl)methyl)piperazin-1-yl)pyridazin-3-amine To a solution of (S)-6-chloro-4-(3-methylpiperazin-1-yl)pyrazin-3-amine (145 mg, 0.61 mmol) (prepared as described in example G02939250, below) in tetrahydrofuran (3 mL) were added 1-methyl-1H-imidazole-2-carbaldehyde (90 mg, 0.82 mmol) and acetic acid (180 mg, 3.05 mmol) at room temperature. After 20 min, sodium triacetoxyborohydride (260 mg, 1.22 mmol) was added and the reaction was heated to 40° C. After 2 h, the reaction is concentrated under vacuum and purified by silica gel chromatography (eluting with hexanes/ethyl acetate). The title compound was obtained as an off-white solid (115 mg, 56%).

Step 2: (S)-2-(6-amino-5-(3-methyl-4-((1-methyl-1H-imidazol-2-yl)methyl)piperazin-1-yl)pyridazin-3-yl)phenol

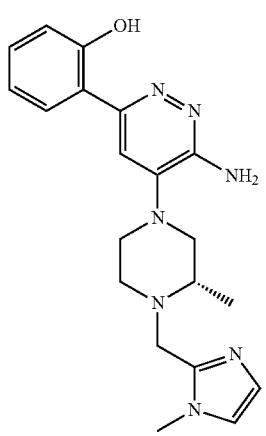

The Suzuki coupling with (2-hydroxyphenyl)boronic acid was conducted as in Step 2 of example G02861551, using methanesulfonato(2-dicyclohexylphosphino-2',4',6'-tri-i-propyl-1,1'-biphenyl)(2'-amino-1,1'-biphenyl-2-yl)palladium(II) at 90° C. for 5 h. The title compound was obtained as an off-white solid (97 mg; 72% yield). $^1$H NMR (400 MHz, DMSO-$d_6$) δ 14.18 (br. s., 1H), 7.91 (d, J=7.32 Hz, 1H), 7.48 (s, 1H), 7.23 (t, J=5.00 Hz, 1H), 7.09 (s, 1H), 6.88 (d, J=8.06 Hz, 2H), 6.77 (s, 1H), 6.24 (br. s., 2H), 4.08 (d, J=13.67 Hz, 1H), 3.68 (s, 3H), 3.57 (s, 2H), 3.23 (d, J=11.48 Hz, 1H), 2.80 (t, J=9.89 Hz, 1H), 2.55-2.74 (m, 3H), 2.41 (t, J=9.40 Hz, 1H), 1.20 (d, J=5.62 Hz, 3H). LCMS M/Z (M+H) 380.

The following compound was prepared in a similar fashion as Example 92, starting from (R)-2-methylpiperazine.

| 93 | (R)-2-(6-amino-5-(3-methyl-4-((1-methyl-1H-imidazol-2-yl)methyl)piperazin-1-yl)pyridazin-3-yl)phenol | $^1$H NMR (400 MHz, DMSO-$d_6$) δ 14.23 (br. s., 1H), 7.91 (d, J = 8.06 Hz, 1H), 7.48 (s, 1H), 7.23 (t, J = 7.57 Hz, 1H), 7.03-7.11 (m, 1H), 6.88 (d, J = 7.08 Hz, 1H), 6.72-6.80 (m, 1H), 6.24 (br. s., 2H), 5.23 (br. s., 1H), 4.45 (d, J = 2.20 Hz, 2H), 4.08 (d, J = 13.67 Hz, 1H), 3.64 (s, 2H), 3.30 (br. s., 2H), 3.23 (d, J = 10.99 Hz, 1H), 2.80 (t, J = 10.38 Hz, 1H), 2.56-2.74 (m, 3H), 2.35-2.47 (m, 1H), 1.20 (d, J = 5.37 Hz, 3H) | 380 |

Example 94

2-[6-amino-5-[4-[(1-isopropylpyrazol-4-yl)methyl]piperazin-1-yl]pyridazin-3-yl]phenol

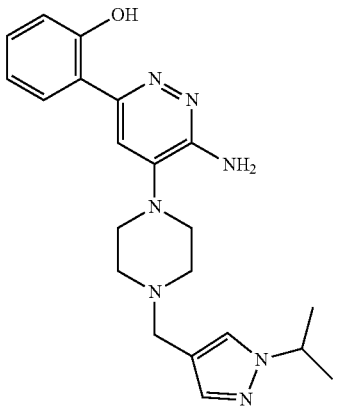 [SMILES: CC(C)n1cc(CN2CCN(c3cc(-c4ccccc4O)nnc3N)CC2)cn1]

To 2-(6-amino-5-piperazin-1-yl-pyridazin-3-yl)phenol (65 mg, 0.24 mmol) (prepared as described above for example G02938881) in a 4 mL vial was added dichloromethane (1.5 mL) followed by 1-isopropylpyrazole-4-carbaldehyde (33 mg, 0.24 mmol). The reaction was capped and shaken at 50° C. for 2 h, then sodium triacetoxyborohydride (152 mg, 0.72 mmol) was added and the reaction was capped and shaken at 50° C. overnight. The following morning the reaction was cooled to room temperature and diluted with 2 mL of dichloromethane. The organic was washed with saturated sodium carbonate, then extracted and dried under reduced pressure. The crude residue was purified by HPLC (eluting with acetonitrile/water/0.1% ammonium hydroxide) yielding title compound (17 mg, 18 $^1$H NMR (400 MHz, DMSO-$d_6$) δ 14.22 (s, 1H), 7.90 (dd, J=8.3, 1.4 Hz, 1H), 7.66 (s, 1H), 7.49 (s, 1H), 7.34 (s, 1H), 7.28-7.19 (m, 1H), 6.93-6.84 (m, 2H), 6.21 (s, 2H), 4.45 (p, J=6.7 Hz, 1H), 3.42 (s, 2H), 3.10 (s, 4H), 2.58 (s, 4H), 1.40 (d, J=6.7 Hz, 6H). LCMS M/Z (M+H) 394.

The following compounds were prepared in a similar fashion as Example 94.

Examples 95-107

| Example Number | IUPAC Name | NMR | M/Z |
|---|---|---|---|
| 95 | 2-[6-amino-5-[4-(cyclopropylmethyl)piperazin-1-yl]pyridazin-3-yl]phenol | | 326 |
| 96 | 3-[[4-[3-amino-6-(2-hydroxyphenyl)pyridazin-4-yl]piperazin-1-yl]methyl]benzonitrile | $^1$H NMR (400 MHz, DMSO-$d_6$) δ 14.22 (s, 1H), 7.91 (dd, J = 8.2, 1.3 Hz, 1H), 7.83-7.68 (m, 3H), 7.62-7.49 (m, 2H), 7.28-7.19 (m, 1H), 6.93-6.84 (m, 2H), 6.25 (s, 2H), 3.65 (s, 2H), 3.16-3.03 (m, 3H), 2.72-2.59 (m, 4H) | 387 |
| 97 | 2-[6-amino-5-[4-(oxazol-2-ylmethyl)piperazin-1-yl]pyridazin-3-yl]phenol | $^1$H NMR (400 MHz, DMSO-$d_6$) δ 8.10 (d, J = 0.8 Hz, 1H), 7.91 (dd, J = 8.3, 1.5 Hz, 1H), 7.50 (s, 1H), 7.28-7.17 (m, 2H), 6.95-6.84 (m, 2H), 6.24 (s, 2H), 3.76 (s, 2H), 3.14-3.09 (m, 4H), 2.73-2.65 (m, 4H) | 353 |
| 98 | 2-[6-amino-5-[4-(4-pyridylmethyl)piperazin-1-yl]pyridazin-3-yl]phenol | | 363 |
| 99 | 2-[6-amino-5-[4-[(1-methylimidazol-2-yl)methyl]piperazin-1-yl]pyridazin-3-yl]phenol | $^1$H NMR (400 MHz, DMSO-$d_6$) δ 14.22 (s, 1H), 7.90 (dd, J = 8.4, 1.6 Hz, 1H), 7.50 (s, 1H), 7.32-7.20 (m, 1H), 7.10 (d, J = 1.2 Hz, 1H), 6.92-6.85 (m, 2H), 6.77 (d, J = 1.2 Hz, 1H), 6.24 (s, 2H), 3.69 (s, 3H), 3.61 (s, 2H), 3.25-2.98 (m, 4H), 2.69-2.56 (m, 6H) | 366 |
| 100 | 2-[6-amino-5-[4-[(1-methylpyrazol-3-yl)methyl]piperazin-1-yl]pyridazin-3-yl]phenol | $^1$H NMR (400 MHz, DMSO-$d_6$) δ 14.22 (s, 1H), 7.90 (dd, J = 8.3, 1.5 Hz, 1H), 7.61 (d, J = 2.1 Hz, 1H), 7.49 (s, 1H), 7.28-7.19 (m, 1H), 6.93-6.84 (m, 2H), 6.21 (s, 2H), 6.15 (d, J = 2.2 Hz, 1H), 3.79 (s, 3H), 3.50 (s, 2H), 3.10 (s, 0H), 2.64-2.59 (m, 4H) | 366 |
| 101 | 2-[6-amino-5-[4-[(5-methylisoxazol-3-yl)methyl]piperazin-1-yl]pyridazin-3-yl]phenol | $^1$H NMR (400 MHz, DMSO-$d_6$) δ 14.21 (s, 1H), 7.91 (dd, J = 8.3, 1.5 Hz, 1H), 7.50 (s, 1H), 7.28-7.19 (m, 1H), 6.93-6.84 (m, 2H), 6.27-6.18 (m, 3H), 3.59 (d, J = 3.0 Hz, 2H), 3.13-3.01 (m, 0H), 2.71-2.59 (m, 4H), 2.40 (s, 3H) | 367 |
| 102 | 2-[6-amino-5-[4-(1H-indazol-3-ylmethyl)piperazin-1-yl]pyridazin-3-yl]phenol | $^1$H NMR (400 MHz, DMSO-$d_6$) δ 14.23 (s, 1H), 12.84 (s, 1H), 7.91 (d, J = 8.4 Hz, 2H), 7.49 (d, J = 7.7 Hz, 2H), 7.34 (t, J = 7.2 Hz, 1H), 7.27-7.18 (m, 1H), 7.10 (t, J = 7.2 Hz, 1H), 6.91-6.83 (m, 2H), 6.22 (s, 0H), 3.93 (s, 2H), 3.11 (s, 4H), 2.81-2.61 (m, 4H) | 402 |
| 103 | 2-[6-amino-5-[4-[(1-methylindazol-4-yl)methyl]piperazin-1-yl]pyridazin-3-yl]phenol | $^1$H NMR (400 MHz, DMSO-$d_6$) δ 14.23 (s, 1H), 8.25 (d, J = 0.9 Hz, 1H), 7.91 (dd, J = 8.4, 1.5 Hz, 1H), 7.57-7.49 (m, 2H), 7.35 (dd, J = 8.4, 7.0 Hz, 1H), 7.23 (td, J = 7.5, 1.5 Hz, 1H), 7.09 (d, J = 6.9 Hz, 1H), 6.92-6.83 (m, 2H), 6.23 (s, | 416 |

-continued

| Example Number | IUPAC Name | NMR | M/Z |
|---|---|---|---|
| | | 2H), 4.05 (s, 3H), 3.88 (s, 2H), 3.36 (s, 2H), 3.12 (s, 3H), 2.65 (s, 4H) | |
| 104 | 2-[6-amino-5-[4-[(2-methyloxazol-4-yl)methyl]piperazin-1-yl]pyridazin-3-yl]phenol | $^1$H NMR (400 MHz, DMSO-$d_6$) δ 14.21 (s, 1H), 7.90 (dd, J = 8.3, 1.6 Hz, 1H), 7.84 (s, 0H), 7.50 (d, J = 12.8 Hz, 1H), 7.28-7.19 (m, 1H), 6.93-6.84 (m, 2H), 6.22 (s, 1H), 3.43 (s, 2H), 3.20-3.00 (m, 4H), 2.74-2.57 (m, 4H), 2.38 (s, 3H) | 367 |
| 105 | 2-[6-amino-5-[4-[(1-methylindazol-5-yl)methyl]piperazin-1-yl]pyridazin-3-yl]phenol | $^1$H NMR (400 MHz, DMSO-$d_6$) δ 14.22 (s, 1H), 8.00 (d, J = 0.8 Hz, 1H), 7.91 (dd, J = 8.3, 1.5 Hz, 1H), 7.67 (s, 1H), 7.60 (d, J = 8.6 Hz, 1H), 7.50 (s, 1H), 7.41 (dd, J = 8.7, 1.4 Hz, 1H), 7.28-7.19 (m, 1H), 6.94-6.84 (m, 2H), 6.22 (s, 2H), 4.04 (s, 3H), 3.67 (s, 2H), 3.12 (s, 3H), 2.65-2.60 (m, 4H) | 416 |
| 106 | tert-butyl 5-[[4-[3-amino-6-(2-hydroxyphenyl)pyridazin-4-yl]piperazin-1-yl]methyl]indoline-1-carboxylate | $^1$H NMR (400 MHz, DMSO-$d_6$) δ 14.22 (s, 1H), 7.91 (dd, J = 8.3, 1.4 Hz, 1H), 7.50 (s, 1H), 7.28-7.14 (m, 2H), 7.09 (d, J = 8.2 Hz, 1H), 6.93-6.84 (m, 2H), 6.22 (s, 2H), 3.91 (t, J = 8.7 Hz, 2H), 3.49 (s, 2H), 3.13-3.01 (m, 6H), 2.61-2.56 (m, 4H), 1.51 (s, 9H) | 503 |
| 107 | 2-[6-amino-5-[4-[(1-methylpyrazol-4-yl)methyl]piperazin-1-yl]pyridazin-3-yl]phenol | $^1$H NMR (400 MHz, DMSO-$d_6$) δ 14.21 (s, 1H), 7.90 (dd, J = 8.3, 1.5 Hz, 1H), 7.59 (s, 1H), 7.48 (s, 1H), 7.35-7.30 (m, 1H), 7.24 (td, J = 7.7, 7.2, 1.5 Hz, 1H), 6.93-6.84 (m, 2H), 6.21 (s, 2H), 3.80 (s, 3H), 3.42 (s, 2H), 3.13-3.00 (m, 0H), 2.60-2.55 (m, 4H) | 366 |

Example 108

2-(6-amino-5-(3-methyl-4-(methylsulfonyl)piperazin-1-yl)pyridazin-3-yl)phenol

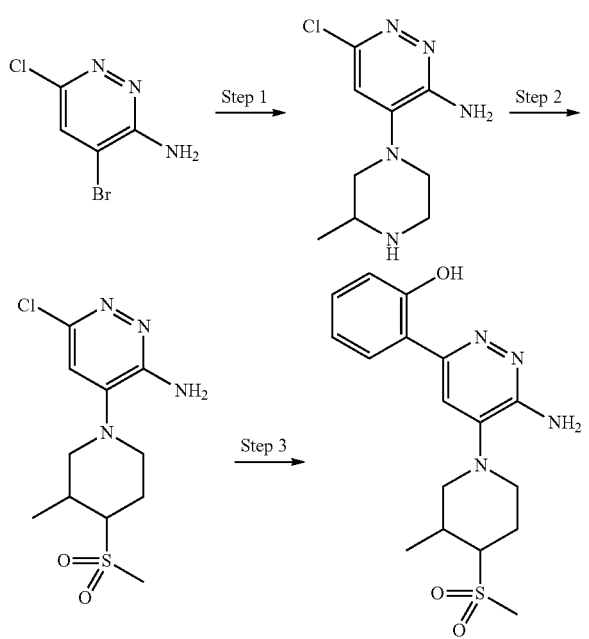

Step 1: 6-chloro-4-(3-methylpiperazin-1-yl)pyridazin-3-amine

In a pyrex vial 4-bromo-6-chloropyridazin-3-amine (1 g, 4.80 mmol) was dissolved in acetonitrile (5 mL, 5 volumes). 2-methylpiperazine (1.2 mL, 12.0 mmol) was added and the reaction was heated at 90° C. for 12 h. The crude reaction was concentrated to dryness, deposited onto silica gel and purified by silica gel chromatography (eluting with methylene chloride/methanol/ammonium hydroxide) to provide 6-chloro-4-(3-methylpiperazin-1-yl)pyridazin-3-amine (733.1 mg, 67%) as a yellow solid. LCMS M/Z (M+H) 292.

Step 2: 6-chloro-4-(3-methyl-4-(methylsulfonyl)piperazin-1-yl)pyridazin-3-amine

In a 50 mL round bottom flask 6-chloro-4-(3-methylpiperazin-1-yl)pyridazin-3-amine (207 mg, 0.91 mmol) was dissolved in methylene chloride (10 mL) and diisopropylethylamine (0.237 mL, 1.36 mmol) was added. The solution was cooled to 0° C. and methanesulfonyl chloride (78 µL, 1 mmol) was added dropwise. The reaction was mixed at 0° C. for 1 h. The crude reaction was deposited onto silica gel and purified by silica gel chromatography (eluting with ethyl acetate) to provide 6-chloro-4-(3-methyl-4-(methylsulfonyl)piperazin-1-yl)pyridazin-3-amine (236.2 mg, 85%) as a yellow solid. LCMS M/Z (M+H) 306.

Step 3: 2-(6-amino-5-(3-methyl-4-(methylsulfonyl)piperazin-1-yl)pyridazin-3-yl)phenol In a pyrex vial 6-chloro-4-(3-methyl-4-(methylsulfonyl)piperazin-1-yl)pyridazin-3-amine (236.2 mg, 0.77 mmol), (2-hydroxyphenyl)boronic acid (138 mg, 1.0 mmol), methanesulfonato(2-dicyclohexylphosphino-2',6'-dimethoxy-1,1'-biphenyl)(2'-amino-1,1'-biphenyl-2-yl)palladium(II) (60 mg, 0.08 mmol) and potassium carbonate (213 mg, 1.4 mmol) were added. The vial was sealed and the atmosphere was evacuated and purged nitrogen (g) (3×). Dioxane (4 mL) and water (0.2 mL, 20:1 ratio dioxane:water) were added, the vial was evacuated and purged with nitrogen (g) (3×), then heated at 90° C. for 12 h. The reaction was cooled to ambient temperature, quenched with 2 equiv. of aq. hydrochloric acid, stirred for 15 min, then concentrated in vacuo to dryness. The residue was then deposited onto celite and purified by silica gel chromatography (eluting with ethyl acetate). The product fractions were pooled, concentrated and lyophilized to provide 2-(6-amino-5-(3-methyl-4-(methylsulfonyl)piperazin-1-yl)pyridazin-3-yl)phenol (169 mg, 60%) as an yellow solid. $^1$H NMR (400 MHz, DMSO-d$_6$) δ 14.11 (br. s., 1H), 7.91 (d, J=7.6 Hz, 1H), 7.54 (br. s., 1H), 7.29-7.19 (m, 1H), 6.90 (br. s., 2H), 6.36 (br. s., 2H), 4.11 (br. s., 1H), 3.73-3.60 (m, 1H), 3.52 (d, J=11.0 Hz, 2H), 3.18 (br. s., 2H), 3.01 (br. s., 3H), 2.63-2.53 (m, 1H), 1.39 (d, J=5.6 Hz, 3H). LCMS M/Z (M+H) 364.

The following compounds were prepared in a similar fashion to Example 108.

Examples 109-119

| Example | Compound Name | NMR | m/z |
|---|---|---|---|
| 109 | 2-(6-amino-5-(3-methyl-4-(phenylsulfonyl)piperazin-1-yl)pyridazin-3-yl)phenol | $^1$H NMR (400 MHz, DMSO-d$_6$) δ 14.08 (s, 1 H), 7.93-7.80 (m, 3 H), 7.75-7.59 (m, 3 H), 7.47 (s, 1 H), 7.29-7.19 (m, 1 H), 6.93-6.83 (m, 2 H), 6.33 (s, 2 H), 4.16 (dd, J = 2.8, 6.2 Hz, 1 H), 3.62 (d, J = 6.8 Hz, 2 H), 3.55 (d, J = 12.2 Hz, 1 H), 3.16-3.01 (m, 2 H), 2.42 (td, J = 7.3, 12.2 Hz, 1 H), 1.16-1.09 (m, 3 H) | 426 |
| 110 | 2-(6-amino-5-(4-(ethylsulfonyl)-3-methylpiperazin-1-yl)pyridazin-3-yl)phenol | $^1$H NMR (400 MHz, DMSO-d$_6$) δ 14.12 (s, 1 H), 7.92 (dd, J = 1.3, 8.2 Hz, 1 H), 7.55 (s, 1 H), 7.28-7.21 (m, 1 H), 6.93-6.85 (m, 2 H), 6.36 (s, 2 H), 4.14-4.04 (m, 1 H), 3.73-3.63 (m, 1 H), 3.52 (t, J = 11.8 Hz, 2 H), 3.21-3.04 (m, 4 H), 2.56-2.51 (m, 1 H), 1.40 (d, J = 6.8 Hz, 3 H), 1.23 (t, J = 7.3 Hz, 3 H) | 378 |
| 111 | 2-(6-amino-5-(4-(cyclopropylsulfonyl)-3-methylpiperazin-1-yl)pyridazin-3-yl)phenol | $^1$H NMR (400 MHz, DMSO-d$_6$) δ 14.11 (s, 1 H), 7.91 (dd, J = 1.5, 8.3 Hz, 1 H), 7.54 (s, 1 H), 7.30-7.19 (m, 1 H), 6.94-6.84 (m, 2 H), 6.37 (s, 2 H), 4.18-4.07 (m, 1 H), 3.80-3.66 (m, 1 H), 3.60-3.47 (m, 2 H), 3.26-3.13 (m, 2 H), 2.69-2.52 (m, 2 H), 1.42 (d, J = 6.6 Hz, 3 H), 1.09-0.92 (m, 4 H) | 390 |
| 112 | 2-(6-amino-5-(3,3-dimethyl-4-(methylsulfonyl)piperazin-1-yl)pyridazin-3-yl)phenol | $^1$H NMR (400 MHz, DMSO-d$_6$) δ 14.15 (s, 1 H), 7.94 (dd, J = 1.6, 8.4 Hz, 1 H), 7.52 (s, 1 H), 7.29-7.20 (m, 1 H), 6.94-6.85 (m, 2 H), 6.35 (s, 2 H), 3.66-3.57 (m, 2 H), 3.11 (br. s., 2 H), 3.05-2.97 (m, 5 H), 1.52 (s, 6 H) | 378 |
| 113 | 2-(6-amino-5-((3S,5S)-3,5-dimethyl-4-(methylsulfonyl)piperazin-1-yl)pyridazin-3-yl)phenol | 1H NMR (400 MHz, DMSO-d$_6$) δ 14.00-14.26 (m, 1H), 7.84-8.02 (m, 1H), 7.49 (s, 1H), 6.80-6.96 (m, 2H), 6.57-6.75 (m, 1H), 6.32 (s, 2H), 4.02-4.17 (m, 2H), 3.37-3.47 (m, 2H), 3.04 (s, 3H), 2.76-2.87 (m, 2H), 1.32-1.41 (m, 6H) | 378 |
| 114 | 2-(6-amino-5-((3R,5R)-3,5-dimethyl-4-(methylsulfonyl)piperazin-1-yl)pyridazin-3-yl)phenol | 1H NMR (400 MHz, DMSO-d$_6$) δ 14.15 (s, 1H), 7.91 (d, J = 6.84 Hz, 1H), 7.49 (s, 1H), 7.23 (s, 1H), 6.64-6.96 (m, 2H), 6.32 (s, 2H), 3.97-4.17 (m, 2H), 3.42 (dd, J = 3.17, 11.96 Hz, 2H), 3.04 (s, 3H), 2.85 (d, J = 6.10 Hz, 2H), 1.36 (d, J = 6.59 Hz, 6H) | 378 |
| 115 | (S)-2-(6-amino-5-(3-methyl-4-(methylsulfonyl)piperazin-1-yl)pyridazin-3-yl)phenol | 1H NMR (400 MHz, DMSO-d$_6$) δ 14.10 (s, 1H), 7.89 (dd, J = 1.59, 8.42 Hz, 1H), 7.53 (s, 1H), 7.24 (ddd, J = 1.46, 7.08, 8.30 Hz, 1H), 6.79-6.99 (m, 2H), 6.35 (s, 2H), 4.02-4.17 (m, 1H), 3.59-3.71 (m, 1H), 3.51 (d, J = 9.52 Hz, 2H), 3.17 (d, J = 3.17 Hz, 2H), 3.00 (s, 3H), 2.56 (br. s., 1H), 1.37 (d, J = 6.84 Hz, 3H) | 354 |
| 116 | (R)-2-(6-amino-5-(3-methyl-4-(methylsulfonyl)piperazin-1-yl)pyridazin-3-yl)phenol | 1H NMR (400 MHz, DMSO-d$_6$) δ 14.10 (s, 1H), 7.89 (d, J = 6.84 Hz, 1H), 7.53 (s, 1H), 7.16-7.33 (m, 1H), 6.72-6.93 (m, 2H), 6.35 (s, 2H), 4.04-4.17 (m, 1H), 3.61-3.71 (m, 1H), 3.44-3.54 (m, 2H), 3.17 (d, J = 2.93 Hz, 2H), 3.00 (s, 3H), 2.52-2.62 (m, 1H), 1.37 (d, J = 6.84 Hz, 3H) | 354 |
| 117 | (R)-2-(6-amino-5-(4-((2-methoxyethyl)sulfonyl)-3-methylpiperazin-1-yl)pyridazin-3-yl)phenol | $^1$H NMR (400 MHz, DMSO-d$_6$) δ 14.11 (s, 1 H), 7.91 (d, J = 8.1 Hz, 1 H), 7.54 (s, 1 H), 7.28-7.20 (m, 1 H), 6.95-6.84 (m, 2 H), 6.35 (s, 2 H), 4.15-4.07 (m, 1 H), 3.73-3.63 (m, 3 H), 3.56-3.48 (m, 2 H), 3.41 (d, J = 7.8 Hz, 2 H), 3.31-3.23 (m, 3 H), 3.17 (m, 2 H), 2.58-2.51 (m, 1 H), 1.39 (d, J = 6.8 Hz, 3 H) | 408 |
| 118 | (R)-2-(6-amino-5-(3-methyl-4-((1-methyl-1H-imidazol-2-yl)sulfonyl)piperazin-1-yl)pyridazin-3-yl)phenol | $^1$H NMR (400 MHz, DMSO-d$_6$) δ 14.10 (s, 1 H), 7.91 (dd, J = 1.2, 8.3 Hz, 1 H), 7.50 (s, 1 H), 7.47 (d, J = 0.7 Hz, 1 H), 7.27-7.19 (m, 1 H), 7.09 (d, J = 1.0 Hz, 1 H), 6.95-6.82 (m, 2 H), 6.35 (s, 2 H), 4.23-4.12 (m, 1 H), 3.87 (s, 3 H), 3.86-3.74 (m, 1 H), 3.68-3.47 (m, 2 H), 3.25-3.10 (m, 2 H), 2.55 (dt, J = 2.9, 11.8 Hz, 1 H), 1.31-1.18 (m, 3 H) | 430 |
| 119 | 2-(6-amino-5-(3-benzyl-4- | $^1$H NMR (400 MHz, DMSO-d$_6$) δ 14.13 (s, 1H), 7.88 (dd, J = 1.46, 7.81 Hz, 1H), 7.53 (s, | 440 |

| Example | Compound Name | NMR | m/z |
|---|---|---|---|
| | (methylsulfonyl)piperazin-1-yl)pyridazin-3-yl)phenol | 1H), 7.10-7.34 (m, 6H), 6.76-6.93 (m, 2H), 6.56 (s, 2H), 4.15-4.31 (m, 1H), 3.78-3.92 (m, 1H), 3.50-3.69 (m, 2H), 3.31 (s, 3H), 3.12-3.28 (m, 3H), 3.02-3.12 (m, 1H), 2.44 (m, 1H) | |

Example 120

1-(3-(3-amino-6-(2-hydroxyphenyl)pyridazin-4-yl)-3,8-diazabicyclo[3.2.1]octan-8-yl)-2-hydroxy-2-methylpropan-1-one

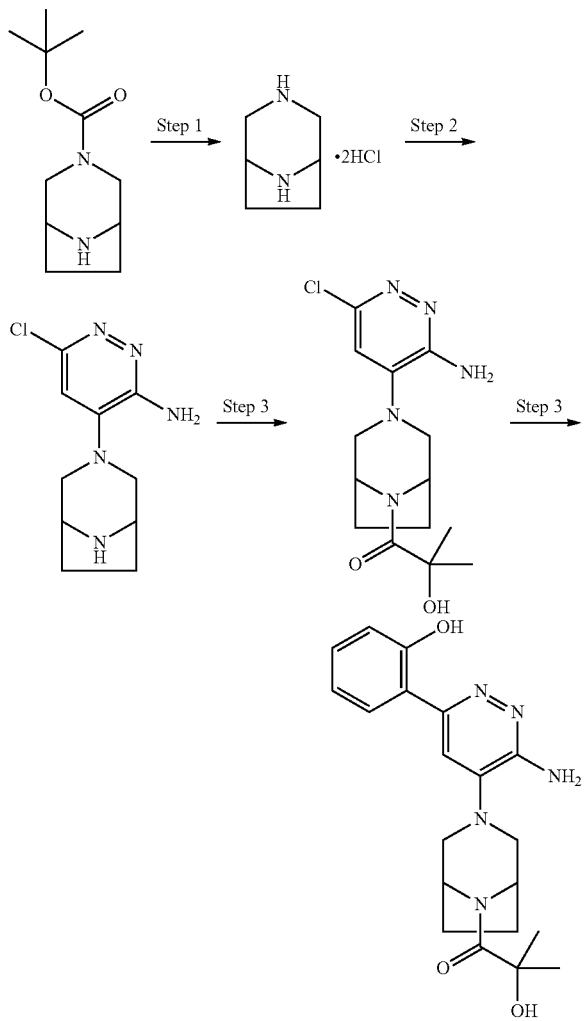

Step 1: 3,8-diazabicyclo[3.2.1]octane Dihydrochloride tert-butyl 3,8-diazabicyclo[3.2.1]octane-3-carboxylate (500 mg, 2.36 mmol) was dissolved in methanol (9 ml) for the addition of hydrochloric acid (4 M in dioxane, 2.95 mL, 11.8 mmol). The reaction mixture was stirred 16 h, then concentrated in vacuo and dried under high vacuum to afford the title compound (0.44 g, 2.38 mmol) in quantitative yield. LCMS M/Z (M+H) 113.

Step 2: 4-(3,8-diazabicyclo[3.2.1]octan-3-yl)-6-chloropyridazin-3-amine 4-bromo-6-chloropyridazin-3-amine (0.45 g, 2.16 mmol) and 3,8-diazabicyclo[3.2.1]octane dihydrochloride (400 mg, 2.16 mmol) were dissolved/suspended in acetonitrile. Diisopropylethylamine (1.54 mL, 8.64 mmol) was added, and the reaction mixture was stirred at 85° C. for 24 h. Dimethylformamide (2 mL) was added to increase solubility, and reaction was stirred for 100 h at 85° C. After removal of volatiles under reduced pressure, the reaction mixture was deposited on silica, and purified by silica gel chromatography (eluting with methylene chloride, methanol, and ammonium hydroxide). Pure fractions were pooled and concentrated in vacuo to afford the title compound (0.36 g, 1.49 mmol, 69%). LCMS M/Z (M+H, Cl pattern) 240/242.

Step 3: 1-(3-(3-amino-6-chloropyridazin-4-yl)-3,8-diazabicyclo[3.2.1]octan-8-yl)-2-hydroxy-2-methyl-propan-1-one 4-(3,8-diazabicyclo[3.2.1]octan-3-yl)-6-chloropyridazin-3-amine (199 mg, 0.83 mmol) was dissolved in dimethylformamide (3 mL) for the addition of 2-hydroxy-2-methylpropanoic acid (0.12 g, 1.15 mmol) and diisopropylethylamine (0.28 mL, 1.66 mmol). The reaction mixture was cooled to 0° C. for the addition of O-(7-Azabenzotriazol-1-yl)-N,N,N',N'-tetramethyluronium hexafluorophosphate (0.38 g, 1 mmol). The reaction was stirred for 15 min and then partitioned between ethyl acetate and aqueous, saturated sodium bicarbonate. The organic phase was concentrate in vacuo to afford the title compound (0.15 g, 0.46 mmol, 55%). LCMS M/Z (M+H, Cl pattern) 326/328

Step 4: 1-(3-(3-amino-6-(2-hydroxyphenyl)pyridazin-4-yl)-3,8-diazabicyclo[3.2.1]octan-8-yl)-2-hydroxy-2-methylpropan-1-one 1-(3-(3-amino-6-chloropyridazin-4-yl)-3,8-diazabicyclo[3.2.1]octan-8-yl)-2-hydroxy-2-methylpropan-1-one (150 mg, 0.4604 mmol), potassium carbonate (0.1273 g, 0.9208 mmol), (2-hydroxyphenyl)boronic acid (0.0794 g, 0.5755 mmol), and methanesulfonato(2-dicyclohexylphosphino-2',4',6'-tri-i-propyl-1,1'-biphenyl)(2'-amino-1,1'-biphenyl-2-yl)palladium(II) (0.0311 g, 0.0368 mmol) were placed in a sealable tube which was purged with nitrogen. Dioxane (2 ml) and water (0.7 ml) were added. The reaction mixture was degassed with a stream of nitrogen, and the mixture was stirred at 95° C. for 16 h. The reaction mixture was impregnated on silica and purified by silica gel chromatography (eluting with ethyl acetate and methanol). Pure fractions were concentrated in vacuo, and the residue was lyophilized from acetonitrile and water to afford the title compound (0.055 g, 0.1434 mmol, 31%). $^1$H NMR (400 MHz, DMSO-$d_6$) δ 14.05-14.22 (m, 1H), 7.88-7.99 (m, 1H), 7.54 (s, 1H), 7.16-7.31 (m, 1H), 6.82-6.97 (m, 2H), 6.00 (s, 2H), 5.34 (s, 1H), 5.12-5.28 (m, 1H), 4.59-4.71 (m, 1H), 3.33-3.42 (m, 2H), 2.95-3.03 (m, 1H), 2.82-2.94 (m, 1H), 2.00-2.14 (m, 2H), 1.86-1.97 (m, 1H), 1.68-1.80 (m, 1H), 1.32 (br. s., 6H). LCMS M/Z (M+H) 384.

Example 121

3-(3-amino-6-(2-hydroxyphenyl)pyridazin-4-yl)-N,N-dimethyl-3,8-diazabicyclo[3.2.1]octane-8-carboxamide

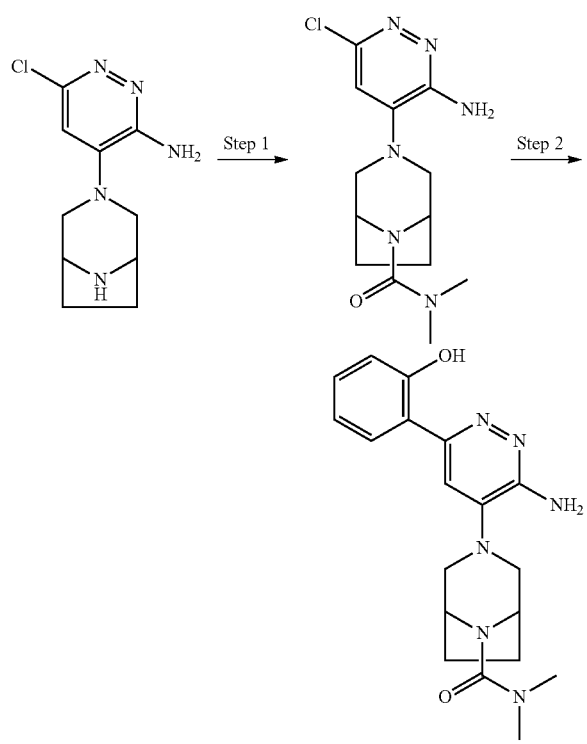

Step 1: 3-(3-amino-6-chloropyridazin-4-yl)-N,N-dimethyl-3,8-diazabicyclo[3.2.1]octane-8-carboxamide 4-(3,8-diazabicyclo[3.2.1]octan-3-yl)-6-chloropyridazin-3-amine (145 mg, 0.58 mmol) (prepared as described in example G02943766) was dissolved in tetrahydrofuran (3 mL) for the addition of diisopropylethylamine (0.11 mL, 0.61 mmol), followed by dimethylcarbamic chloride (0.06 g, 0.58 mmol). The reaction mixture was stirred at 25° C. for 30 min, then heated to 50° C. for 16 h. Volatiles were removed under reduced pressure, and the crude residue was purified by silica gel chromatography (eluting with ethyl acetate and methanol). Pure fractions were pooled and concentrated in vacuo to afford the title compound (0.17 g, 0.56 mmol, 96%). LCMS M/Z (M+H, Cl pattern) 311/313.

Step 2: 3-(3-amino-6-(2-hydroxyphenyl)pyridazin-4-yl)-N,N-dimethyl-3,8-diazabicyclo[3.2.1]octane-8-carboxamide 3-(3-amino-6-chloropyridazin-4-yl)-N,N-dimethyl-3,8-diazabicyclo[3.2.1]octane-8-carboxamide (173 mg, 0.55 mmol), (2-hydroxyphenyl)boronic acid (0.08 g, 0.58 mmol), potassium carbonate (0.15 g, 1.1 mmol), and methanesulfonato(2-dicyclohexylphosphino-2',4',6'-tri-i-propyl-1,1'-biphenyl)(2'-amino-1,1'-biphenyl-2-yl)palladium(II) (0.03 g, 0.04 mmol were placed in a sealable tube which was purged with nitrogen. Dioxane (2 ml) and water (0.7 ml) added, the reaction mixture was degassed with a stream of nitrogen, and the mixture was stirred at 95° C. for 16 h. The reaction mixture was impregnated on silica and purified by silica gel chromatography (eluting with ethyl acetate and methanol) to afford the title compound (0.04 g, 0.12 mmol, 22%). $^1$H NMR (400 MHz, DMSO-$d_6$) δ 14.15 (s, 1H), 7.94 (dd, J=1.34, 8.42 Hz, 1H), 7.56 (s, 1H), 7.24 (dt, J=1.71, 7.69 Hz, 1H), 6.83-6.93 (m, 2H), 5.97 (s, 2H), 4.09 (br. s., 2H), 3.36 (dd, J=2.56, 11.60 Hz, 2H), 3.00 (d, J=11.23 Hz, 2H), 2.86 (s, 6H), 1.92-2.04 (m, 2H), 1.66-1.87 (m, 2H). LCMS M/Z (M+H) 369.

Example 122

1-(4-(3-amino-6-(2-hydroxyphenyl)pyridazin-4-yl)-2-methylpiperazin-1-yl)ethanone

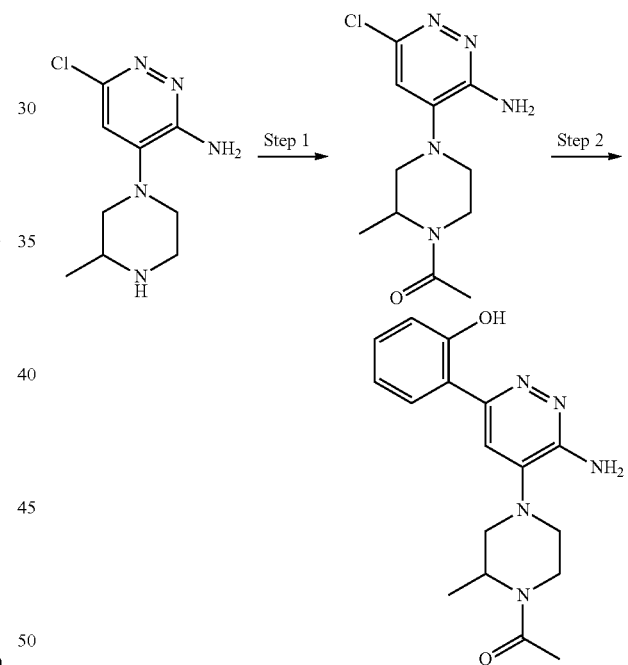

Step 2: 1-(4-(3-amino-6-chloropyridazin-4-yl)-2-methylpiperazin-1-yl)ethanone 6-chloro-4-(3-methylpiperazin-1-yl)pyridazin-3-amine (96 mg, 0.44 mmol) (prepared from 2-methylipiperazine as described in example G02861551) was dissolved in tetrahydrofuran (4.4 mL) for the addition of diisopropylethylamine (0.32 mL, 1.76 mmol) followed by acetic anhydride (0.04 g, 0.44 mmol). The reaction mixture was stirred at 25° C. for 30 min. The reaction mixture was evaporated under reduced pressure, and the crude residue was purified by silica gel chromatography (eluting with hexanes and ethyl acetate) to afford the title compound (0.07 g, 0.26 mmol, 59%). LCMS M/Z (M+H, Cl pattern) 270/272.

Step 3: 1-(4-(3-amino-6-(2-hydroxyphenyl)pyridazin-4-yl)-2-methylpiperazin-1-yl)ethanone 1-(4-(3-amino-6-chloropyridazin-4-yl)-2-methylpiperazin-1-yl)ethanone (81 mg, 0.3003 mmol), (2-hydroxyphenyl)boronic acid (0.0497 g, 0.3604 mmol), potassium carbonate (0.0913 g, 0.6607 mmol), and methanesulfonato(2-dicyclohexylphosphino-2',6'-dimethoxy-1,1'-biphenyl)(2'-amino-1,1'-biphenyl-2-yl)palladium(II) (0.0234 g, 0.03 mmol) were placed in a sealable tube. The reaction vessel was purged with nitrogen. Dioxane (2 ml) and water (0.7 ml) were added, and the reaction mixture was degassed with a stream of nitrogen. The reaction vessel was stirred at 95° C. for 16 h. The crude reaction mixture was deposited on a silica gel column and purified by silica gel chromatography (eluting with ethyl acetate and methanol). The pure fractions were pooled and concentrated in vacuo. The solid residue was lyophilized from acetonitrile and water to afford the title compound (0.025 g, 0.0764 mmol, 25%). $^1$H NMR (400 MHZ, DMSO-$d_6$) δ 14.12 (s, 1H), 7.89 (d, J=8.5 Hz, 1H), 7.50 (s, 1H), 7.22-7.25 (m, 1H), 6.87-6.90 (m, 2H), 6.33 (s, 2H), 4.72-4.77 (m, 1H), 4.22-4.25 (m, 1H), 3.70-3.79 (m, 2H), 3.59-3.59 (m, 1H), 3.21-3.25 (m, 1H), 3.07-3.17 (m, 1H), 2.01-2.06 (m, 3H), 1.23-1.37 (m, 3H). LCMS M/Z (M+H) 328.

The following compounds were prepared in a similar fashion to Example 122 (using the appropriately substituted piperidines and in some cases using the appropriate acid chlorides as acylating agents or using HATU and the appropriate carboxylic acids to effect amide bond formation).

Examples 123-146

| Example | Compound Name | NMR | m/z |
|---|---|---|---|
| 123 | (4-(3-amino-6-(2-hydroxyphenyl)pyridazin-4-yl)-2-methylpiperazin-1-yl)(3,5-dimethylisoxazol-4-yl)methanone | $^1$H NMR (400 MHz, DMSO-$d_6$) δ 14.11 (s, 1H), 7.90 (dd, J = 1.59, 8.18 Hz, 1H), 7.55 (s, 1H), 7.07-7.32 (m, 1H), 6.72-7.00 (m, 2H), 6.38 (s, 2H), 3.65-3.80 (m, 2H), 3.57-3.64 (m, 2H), 3.07-3.28 (m, 3H), 2.37-2.44 (m, 3H), 2.16-2.25 (m, 3H), 1.36 (d, J = 6.84 Hz, 3H) | 409 |
| 124 | (4-(3-amino-6-(2-hydroxyphenyl)pyridazin-4-yl)-2-methylpiperazin-1-yl)(2-phenylcyclopropyl)methanone | $^1$H NMR (400 MHz, DMSO-$d_6$) δ 14.12 (d, J = 3.91 Hz, 1H), 7.89 (dd, J = 1.59, 8.18 Hz, 1H), 7.51 (s, 1H), 7.11-7.34 (m, 6H), 6.88 (d, J = 8.06 Hz, 2H), 6.34 (d, J = 4.15 Hz, 2H), 4.70-4.86 (m, 1H), 4.50-4.67 (m, 1H), 4.17-4.31 (m, 1H), 4.09-4.16 (m, 1H), 3.71-3.88 (m, 1H), 3.59 (m, 1H), 3.34-3.43 (m, 1H), 3.21 (m, 1H), 2.98-3.15 (m, 1H), 2.33 (m, 1H), 1.42 (br. s., 1H), 1.29 (br. s., 3H) | 430 |
| 125 | 1-(4-(3-amino-6-(2-hydroxyphenyl)pyridazin-4-yl)-2-methylpiperazin-1-yl)-2-(pyridin-2-yl)ethan-1-one | $^1$H NMR (400 MHz, DMSO-$d_6$) δ 13.88-14.27 (m, 1H), 8.41-8.66 (m, 1H), 7.83-7.96 (m, 1H), 7.67-7.79 (m, 1H), 7.41-7.53 (m, 1H), 7.11-7.37 (m, 3H), 6.78-6.96 (m, 2H), 6.24-6.43 (m, 2H), 4.66-4.88 (m, 1H), 4.43-4.59 (m, 1H), 4.17-4.36 (m, 1H), 3.95-4.07 (m, 1H), 3.79-3.94 (m, 2H), 3.11-3.25 (m, 1H), 2.93-3.09 (m, 1H), 2.21-2.42 (m, 1H), 1.13-1.36 (m, 3H) | 405 |
| 126 | (3-(3-amino-6-(2-hydroxyphenyl)pyridazin-4-yl)-3,8-diazabicyclo[3.2.1]octan-8-yl)(thiazol-5-yl)methanone | $^1$H NMR (400 MHz, DMSO-$d_6$) δ 13.93-14.21 (m, 1H), 9.11-9.37 (m, 1H), 8.39 (d, J = 0.73 Hz, 1H), 7.84-8.04 (m, 1H), 7.64 (s, 1H), 7.13-7.29 (m, 1H), 6.89 (d, J = 8.06 Hz, 2H), 6.05 (s, 2H), 4.50-4.91 (m, 2H), 3.37-3.52 (m, 2H), 2.91-3.22 (m, 2H), 2.07-2.24 (m, 2H), 1.77-2.04 (m, 2H) | 409 |
| 127 | 1-((2S,6S)-4-(3-amino-6-(2-hydroxyphenyl)pyridazin-4-yl)-2,6-dimethylpiperazin-1-yl)ethan-1-one | | 342 |
| 128 | 1-((2R,6R)-4-(3-amino-6-(2-hydroxyphenyl)pyridazin-4-yl)-2,6-dimethylpiperazin-1-yl)ethan-1-one | | 342 |
| 129 | 1-(4-(3-amino-6-(2-hydroxyphenyl)pyridazin-4-yl)-2-methylpiperazin-1-yl)-2,2-dimethylpropan-1-one | $^1$H NMR (400 MHz, DMSO-$d_6$) δ 14.16 (br. s., 1 H), 7.92 (dd, J = 1.5, 8.3 Hz, 1 H), 7.53 (s, 1 H), 7.24 (dt, J = 1.7, 7.7 Hz, 1 H), 7.01-6.74 (m, 2H), 6.35 (s, 2 H), 4.69 (br. s., 1 H), 4.15 (d, J = 13.2 Hz, 1 H), 3.58 (d, J = 12.2 Hz, 2 H), 3.19 (d, J = 11.7 Hz, 1 H), 3.11-2.95 (m, 1 H), 2.40 (t, J = 10.9 Hz, 1 H), 1.33 (d, J = 6.1 Hz, 3 H), 1.23 (s, 9 H) | 370 |
| 130 | 1-(4-(3-amino-6-(2-hydroxyphenyl)pyridazin-4-yl)-2,2-dimethylpiperazin-1- | $^1$H NMR (400 MHz, DMSO-$d_6$) δ 14.32 (s, 1 H), 7.94 (dd, J = 1.3, 8.4 Hz, 1 H), 7.43 (s, 1 H), 7.32-7.09 (m, 1 H), 7.00-6.67 (m, 2 H), 6.22 (s, 2H), 3.76-3.54 (m, 2 H), | 342 |

| Example | Compound Name | NMR | m/z |
|---|---|---|---|
| | yl)ethanone | 3.43-3.33 (m, 2 H), 3.19 (s, 2 H), 2.02 (s, 3 H), 1.49 (s, 6 H) | |
| 131 | (R)-1-(4-(3-amino-6-(2-hydroxyphenyl)pyridazin-4-yl)-2-methylpiperazin-1-yl)ethanone | $^1$H NMR (400 MHz, DMSO-d$_6$) δ 14.11 (br. s., 1 H), 7.89 (d, J = 7.8 Hz, 1 H), 7.50 (s, 1 H), 7.33-7.10 (m, 1 H), 7.00-6.75 (m, 2 H), 6.33 (s, 2 H), 4.73 (br. s., 1 H), 4.37-4.09 (m, 1 H), 3.87-3.63 (m, 1 H), 3.57 (d, J = 11.5 Hz, 1 H), 3.28-3.12 (m, 1 H), 3.11-2.90 (m, 1 H), 2.46-2.24 (m, 1 H), 2.04 (d, J = 19.0 Hz, 3 H), 1.48-1.18 (m, 3 H) | 328 |
| 132 | (S)-1-(4-(3-amino-6-(2-hydroxyphenyl)pyridazin-4-yl)-2-methylpiperazin-1-yl)ethanone | $^1$H NMR (400 MHz, DMSO-d$_6$) δ 14.12 (br. s., 1 H), 7.90 (d, J = 7.8 Hz, 1 H), 7.51 (s, 1 H), 7.31-7.10 (m, 1 H), 7.02-6.76 (m, 2 H), 6.34 (br. s., 2 H), 4.74 (br. s., 1 H), 4.37-4.05 (m, 1 H), 3.73 (s, 1 H), 3.58 (d, J = 11.7 Hz, 1H), 3.21 (t, J = 12.5 Hz, 1 H), 3.12-2.90 (m, 1 H), 2.47-2.28 (m, 1 H), 2.17-1.79 (m, 3 H), 1.47-1.10 (m, 3 H) | 328 |
| 133 | (4-(3-amino-6-(2-hydroxyphenyl)pyridazin-4-yl)-2-methylpiperazin-1-yl)(3-methyloxetan-3-yl)methanone | | 384 |
| 134 | 1-(4-(3-amino-6-(2-hydroxyphenyl)pyridazin-4-yl)-2-methylpiperazin-1-yl)-2-hydroxy-2-methylpropan-1-one | | 372 |
| 135 | (4-(3-amino-6-(2-hydroxyphenyl)pyridazin-4-yl)-2-methylpiperazin-1-yl)(pyridin-3-yl)methanone | | 391 |
| 136 | 1-(4-(3-amino-6-(2-hydroxyphenyl)pyridazin-4-yl)-2-methylpiperazin-1-yl)-2-(3-methylisoxazol-5-yl)ethan-1-one | | 409 |
| 137 | (4-(3-amino-6-(2-hydroxyphenyl)pyridazin-4-yl)-2-methylpiperazin-1-yl)(pyrimidin-4-yl)methanone | | 362 |
| 138 | (4-(3-amino-6-(2-hydroxyphenyl)pyridazin-4-yl)-2-methylpiperazin-1-yl)(thiazol-5-yl)methanone | $^1$H NMR (400 MHz, DMSO-d$_6$) δ 14.11 (s, 1 H), 9.27 (d, J = 0.5 Hz, 1 H), 8.22 (d, J = 0.7 Hz, 1 H), 7.90 (dd, J = 1.6, 8.4 Hz, 1 H), 7.54 (s, 1 H), 7.24 (dt, J = 1.5, 7.7 Hz, 1 H), 7.02-6.72 (m, 2 H), 6.41 (s, 2 H), 4.62 (br. s., 1 H), 4.27-3.96 (m, 1 H), 3.89-3.71 (m, 1 H), 3.63 (d, J = 10.7 Hz, 1 H), 3.29-3.03 (m, 2 H), 2.60-2.51 (m, 1 H), 1.44 (d, J = 6.8 Hz, 3 H) | 397 |
| 139 | 1-((2S,6R)-4-(3-amino-6-(2-hydroxyphenyl)pyridazin-4-yl)-2,6-dimethylpiperazin-1-yl)ethan-1-one | $^1$H NMR (400 MHz, DMSO-d$_6$) δ 13.99 (s, 1 H), 7.93 (dd, J = 1.5, 8.3 Hz, 1 H), 7.60 (s, 1 H), 7.26 (dt, J = 1.5, 7.7 Hz, 1 H), 7.03-6.78 (m, 2 H), 5.99 (s, 2 H), 4.61-4.01 (m, 2 H), 3.37 (d, J = 12.0 Hz, 2 H), 2.82 (dd, J = 4.0, 11.8 Hz, 2 H), 2.08 (s, 3 H), 1.40 (d, J = 4.4 Hz, 6 H) | 342 |
| 140 | (2S)-2-amino-1-(4-(3-amino-6-(2-hydroxyphenyl)pyridazin-4-yl)-2-methylpiperazin-1-yl)-3-methylbutan-1-one | | 385 |
| 141 | ((R)-4-(3-amino-6-(2-hydroxyphenyl)pyridazin-4-yl)-2-methylpiperazin-1-yl)((S)-tetrahydrofuran-2-yl)methanone | $^1$H NMR (400 MHz, DMSO-d$_6$) δ 13.98-14.19 (m, 1H), 7.83-7.96 (m, 1H), 7.46-7.55 (m, 1H), 7.23 (m, 1H), 6.80-6.93 (m, 2H), 6.33 (br. s., 2H), 4.55-4.81 (m, 1H), 4.30-4.41 (m, 0.5H), 4.15-4.26 (m, 0.5H), 3.86-3.94 (m, 0.5H), 3.62-3.84 (m, 2.5H), 3.49-3.61 (m, 1H), 3.34-3.39 (m, 0.5H), 3.15-3.26 (m, 1H), 2.91-3.14 (m, 1H), 2.28-2.40 (m, 0.5H), 2.03-2.11 (m, 1H), 1.98 (s, 1H), 1.72-1.89 (m, 2H), 1.35-1.45 (m, 1.4H), 1.25 (d, J = 6.84 Hz, 1.8H) | 384 |

-continued

| Example | Compound Name | NMR | m/z |
|---|---|---|---|
| 142 | ((S)-4-(3-amino-6-(2-hydroxyphenyl)pyridazin-4-yl)-2-methylpiperazin-1-yl)((S)-tetrahydrofuran-2-yl)methanone | $^1$H NMR (400 MHz, DMSO-d$_6$) δ 14.13 (s, 1 H), 7.91 (br. s., 1 H), 7.52 (br. s., 1 H), 7.30-7.09 (m, 1 H), 7.02-6.72 (m, 2 H), 6.35 (m, 2 H), 4.70 (m, 0.5 H), 4.65 (t, J = 6.5 Hz, 1 H), 4.54 (m, 0.5 H), 4.20 (m, 1 H), 3.85-3.81 (m, 0.5H), 3.78-3.74 (m, 2 H), 3.58 (d, J = 11.5 Hz, 1 H), 3.37 (m, 0.5 H), 3.20 (d, J = 11.7 Hz, 1 H), 3.16-2.83 (m, 1 H), 2.44-2.24 (m, 1 H), 2.24-1.92 (m, 2 H), 1.93-1.71 (m, 2 H), 1.56-1.00 (m, 3 H) | 384 |
| 143 | (4-(3-amino-6-(2-hydroxyphenyl)pyridazin-4-yl)-2-(hydroxymethyl)piperazin-1-yl)(thiazol-5-yl)methanone | $^1$H NMR (400 MHz, DMSO-d$_6$) δ 14.14 (br. s., 1 H), 9.27 (s, 1 H), 8.26 (s, 1 H), 7.91 (dd, J = 1.6, 8.4 Hz, 1 H), 7.55 (s, 1 H), 7.24 (dt, J = 1.5, 7.7 Hz, 1 H), 7.03-6.72 (m, 2 H), 6.52 (s, 2 H), 5.29 (br. s., 1 H), 4.40-4.05 (m, 2 H), 3.96-3.79 (m, 2 H), 3.75-3.41 (m, 3 H), 3.08-2.87 (m, 1 H), 2.71-2.75 (m, 1 H) | 413 |
| 144 | 1-(4-(3-amino-6-(2-hydroxyphenyl)pyridazin-4-yl)-2-benzylpiperazin-1-yl)ethan-1-one | | 404 |
| 145 | (R)-1-(4-(3-amino-6-(2-hydroxyphenyl)pyridazin-4-yl)-2-methylpiperazin-1-yl)-2-hydroxy-2-methylpropan-1-one | | 372 |
| 146 | (S)-1-(4-(3-amino-6-(2-hydroxyphenyl)pyridazin-4-yl)-2-methylpiperazin-1-yl)-2-hydroxy-2-methylpropan-1-one | | 372 |

Example 147

2-((R)-4-(3-amino-6-(2-hydroxyphenyl)pyridazin-4-yl)-2-methylpiperazin-1-yl)-N-methylpropanamide

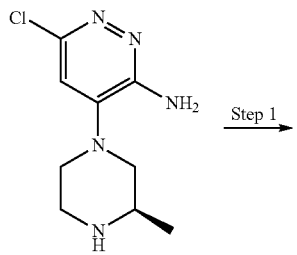

Step 1

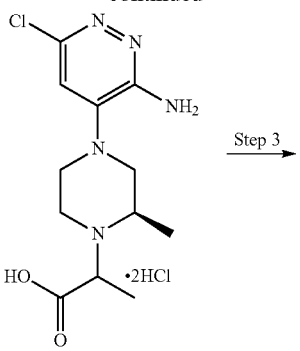

Step 3

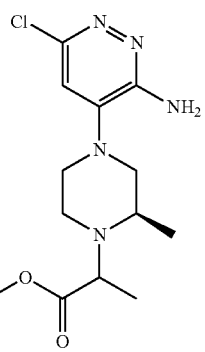

Step 2

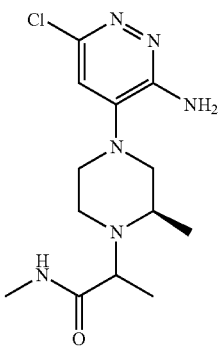

Step 4

-continued

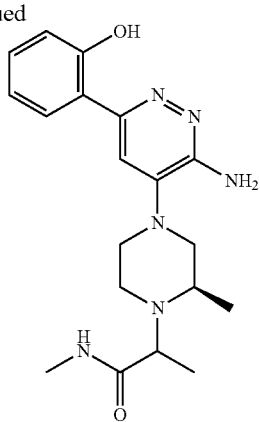

Step 1: tert-butyl 2-((R)-4-(3-amino-6-chloro-pyridazin-4-yl)-2-methylpiperazin-1-yl)propanoate (R)-6-chloro-4-(3-methylpiperazin-1-yl)pyridazin-3-amine (370 mg, 1.62 mmol) (prepared as in example G02939250) was dissolved in dimethylformamide (8 mL) for the addition of tert-butyl 2-bromopropanoate (0.44 g, 2.11 mmol), followed by potassium carbonate (0.45 g, 3.24 mmol). The solution was heated to 60° C. for 72 h. The reaction mixture was partitioned between ethyl acetate and sodium bicarbonate (aq., sat.). The organic layer was washed with brine, dried with sodium sulfate, filtered and concentrated in vacuo. The crude residue was purified by silica gel chromatography (eluting with hexanes and ethyl acetate) to afford the title compound (0.42 g, 1.19 mmol, 73%). LCMS M/Z (M+H) 356.

Step 2: 2-((R)-4-(3-amino-6-chloropyridazin-4-yl)-2-methylpiperazin-1-yl)propanoic Acid Dihydrochloride tert-butyl 2-((R)-4-(3-amino-6-chloropyridazin-4-yl)-2-methylpiperazin-1-yl)propanoate (360 mg, 1.01 mmol) was dissolved in dioxane for the addition of hydrochloric acid (4 M in dioxane, 1.01 mL, 4.04 mmol), and the reaction mixture was stirred for 4 h. Volatiles were evaporated under reduced pressure to afford the title compound (380 mg, 1.01 mmol) in quantitative yield. LCMS M/Z (M+H, Cl pattern) 300/302.

Step 3: 2-((R)-4-(3-amino-6-chloropyridazin-4-yl)-2-methylpiperazin-1-yl)-N-methylpropanamide 2-((R)-4-(3-amino-6-chloropyridazin-4-yl)-2-methylpiperazin-1-yl)propanoic acid dihydrochloride (380 mg, 1.02 mmol) was dissolved in dimethylformamide (4 mL) for the addition of diisopropylethylamine (0.89 mL, 5.1 mmol). The reaction mixture was cooled to 0° C. for the addition of HATU (430 mg, 1.12 mmol), and the mixture was stirred 10 min. Methanamine (2 M in tetrahydrofuran, 1.02 mL, 2.04 mmol) was added, and the reaction was allowed to warm to 25° C. for 1 h. The reaction mixture was partitioned between ethyl acetate and sodium bicarbonate, and the organic layer was isolated and evaporated under reduced pressure. The crude residue was purified by silica gel chromatography (eluting with ethyl acetate and methanol), and the pure fractions were concentrated in vacuo to afford the title compound (121 mg, 386 µmol) as a mixture of diastereomers in 38% yield. LCMS M/Z (M+H) 313.0/315.0.

Step 4: 2-((R)-4-(3-amino-6-(2-hydroxyphenyl)pyridazin-4-yl)-2-methylpiperazin-1-yl)-N-methylpropanamide 2-((R)-4-(3-amino-6-chloropyridazin-4-yl)-2-methylpiperazin-1-yl)-N-methylpropanamide (0.12 g, 0.38 mmol), (2-hydroxyphenyl)boronic acid (0.06 g, 0.46 mmol), potassium carbonate (0.11 g, 0.76 mmol), and methanesulfonato (2-dicyclohexylphosphino-2',4',6'-tri-i-propyl-1,1'-biphenyl)(2'-amino-1,1'-biphenyl-2-yl)palladium(II) (0.03 g, 0.03 mmol) were placed in a sealable tube which was purged with nitrogen. Dioxane (3 ml) and water (1 ml) were added, and the reaction mixture was stirred at 95° C. for 16 h. The organic supernatant was concentrated in vacuo and purified by silica gel chromatography (eluting with ethyl acetate and methanol). After evaporation of volatiles, the recovered material was lyophilized from acetonitrile and water to afford the title compound (0.04 g, 0.1 mmol) as a mixture of diastereomers in 26% yield. LCMS M/Z (M+H) 371.

Example 148

(R)-2-(4-(3-amino-6-(2-hydroxyphenyl)pyridazin-4-yl)-2-methylpiperazin-1-yl)-N-methylacetamide

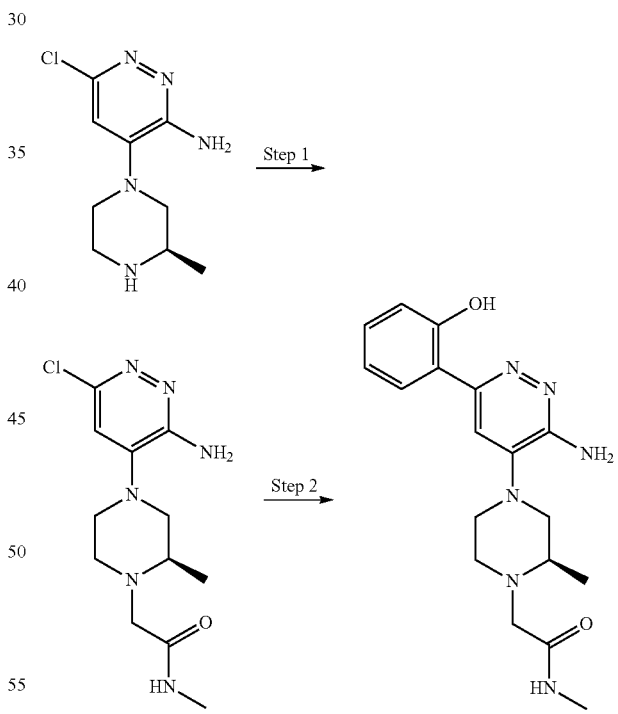

Step 1: (R)-2-(4-(3-amino-6-chloropyridazin-4-yl)-2-methylpiperazin-1-yl)-N-methylacetamide (R)-6-chloro-4-(3-methylpiperazin-1-yl)pyridazin-3-amine (270 mg, 1.19 mmol) (prepared as in example G02939250) was dissolved in acetonitrile (5 mL) for the addition of 2-chloro-N-methylacetamide (0.16 g, 1.49 mmol), followed by potassium carbonate (0.33 g, 2.38 mmol). The reaction mixture was stirred at 60° C. for 16 h.

Volatiles were removed under reduced pressure, and the residue was purified by silica gel chromatography (eluting with methylene chloride and ethyl acetate) to afford the title compound (387 mg, 1.31 mmol).

Step 2: (R)-2-(4-(3-amino-6-(2-hydroxyphenyl) pyridazin-4-yl)-2-methylpiperazin-1-yl)-N-methyl-acetamide (R)-2-(4-(3-amino-6-chloropyridazin-4-yl)-2-methylpiperazin-1-yl)-N-methylacetamide (387 mg, 1.31 mmol), (2-hydroxyphenyl)boronic acid (0.19 g, 1.38 mmol), potassium carbonate (0.36 g, 2.62 mmol), and methanesulfonato (2-dicyclohexylphosphino-2',4',6'-tri-i-propyl-1,1'-biphenyl)(2'-amino-1,1'-biphenyl-2-yl)palladium(II) (0.08 g, 0.09 mmol) were placed in a 50 mL flask equipped with a magnetic stirrer. The flask was purged with nitrogen. Dioxane (6 ml) and water (2 ml) were added, and the reaction mixture was degassed with nitrogen. The reaction vessel was fitted with a condenser and stirred at 95° C. for 16 h. The reaction mixture was impregnated on silica and purified by silica gel chromatography (eluting with ethyl acetate and methanol). The residue was lyophilized from acetonitrile and water to afford the title compound (0.12 g, 0.35 mmol, 29% over 2 steps). $^1$H NMR (400 MHz, DMSO-$d_6$) δ 14.21 (br. s., 1H), 7.92 (dd, J=1.59, 8.42 Hz, 1H), 7.74 (s, 1H), 7.47 (s, 1H), 7.23 (dt, J=1.46, 7.69 Hz, 1H), 6.70-6.98 (m, 2H), 6.23 (s, 2H), 3.32-3.37 (m, 1H), 3.23 (d, J=16.11 Hz, 1H), 2.93 (t, J=10.13 Hz, 1H), 2.79-2.89 (m, 2H), 2.74 (s, 1H), 2.52-2.70 (m, 6H), 1.04 (d, J=6.10 Hz, 3H). LCMS M/Z (M+H) 357.

1-(4-(3-Amino-6-(2-hydroxyphenyl)pyridazin-4-yl)-2-benzylpiperazin-1-yl)ethanone was Separated into its Individual Enantiomers, Examples 149 and 150

Enantiomer 1 and enantiomer 2 of 1-(4-(3-amino-6-(2-hydroxyphenyl)pyridazin-4-yl)-2-benzylpiperazin-1-yl)ethanone

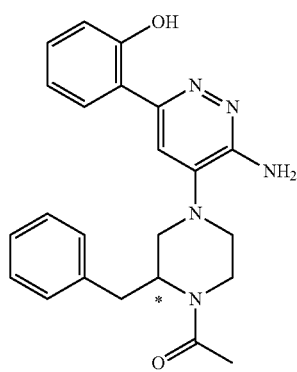 [SMILES: CC(=O)N1CCN(c2cc(-c3ccccc3O)nnc2N)CC1Cc1ccccc1]

Separated by SFC chromatography (eluting with carbon dioxide and ethanol, 0.1% ammonium hydroxide) using a Whelko-1 (S,S) column.

Example 149

$^1$H NMR (400 MHz, DMSO-$d_6$) δ 14.14 (d, J=22.6 Hz, 1H), 7.88 (d, J=7.8 Hz, 1H), 7.50 (d, J=5.9 Hz, 1H), 7.35-7.12 (m, 6H), 6.94-6.75 (m, 2H), 6.53 (d, J=9.4 Hz, 2H), 4.87 (s, OH), 4.35 (d, J=13.2 Hz, 1H), 4.23 (s, 1H), 4.00-3.87 (m, OH), 3.79-3.62 (m, 1H), 3.62-3.48 (m, 1H), 3.47-3.37 (m, 1H), 3.26-3.12 (m, 1H), 3.10-2.85 (m, 2H), 2.42-2.28 (m, 1H), 1.98 (s, 1H), 1.59 (s, 2H). LCMS M/Z (M+H) 404.

Example 150

$^1$H NMR (400 MHz, DMSO-$d_6$) δ 14.14 (d, J=22.5 Hz, 1H), 7.88 (d, J=7.9 Hz, 1H), 7.50 (d, J=5.9 Hz, 1H), 7.39-7.02 (m, 5H), 6.95-6.76 (m, 2H), 6.53 (d, J=9.2 Hz, 2H), 5.01-4.25 (m, 2H), 4.08 (d, J=115.6 Hz, 1H), 3.84-3.55 (m, 2H), 3.62-3.48 (m, 1H), 3.49-3.40 (m, OH), 3.23-3.11 (m, 1H), 3.07-2.88 (m, 2H), 2.45-2.22 (m, 1H), 1.98 (s, 1H), 1.59 (s, 1H). LCMS M/Z (M+H) 404.

1-(4-(3-Amino-6-(2-hydroxyphenyl)pyridazin-4-yl)-2-methylpiperazin-1-yl)-2,2-dimethyl-propan-1-one was Separated into its Individual Enantiomers, Examples 151 and 152

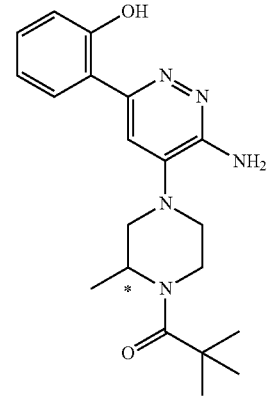 [SMILES: CC1CN(c2cc(-c3ccccc3O)nnc2N)CCN1C(=O)C(C)(C)C]

Separated by SFC chromatography (eluting with carbon dioxide and methanol, 0.1% ammonium hydroxide) using a Chiralpak AS column.

Example 151

LCMS M/Z (M+H) 370.

Example 152

LCMS M/Z (M+H) 370.

153

(4-(3-Amino-6-(2-hydroxyphenyl)pyridazin-4-yl)-2-methylpiperazin-1-yl)(pyrimidin-4-yl)methanone was Separated into its Individual Enantiomers, Examples 153 and 154

Enantiomer 1 and enantiomer 2 of (4-(3-amino-6-(2-hydroxyphenyl)pyridazin-4-yl)-2-methylpiperazin-1-yl)(pyrimidin-4-yl)methanone

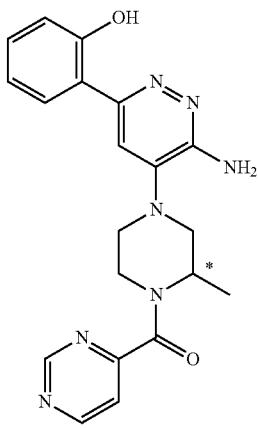

Separated by SFC chromatography (eluting with carbon dioxide and methanol, 0.1% ammonium hydroxide) using a Chiralpak AS column.

Example 153

$^1$H NMR (400 MHz, DMSO-$d_6$) δ 14.10 (s, 1H), 9.40-9.12 (m, 1H), 9.00 (dd, J=9.2, 5.1 Hz, 1H), 7.91 (t, J=8.0 Hz, 1H), 7.81-7.67 (m, 1H), 7.55 (d, J=10.8 Hz, 1H), 7.24 (t, J=7.8 Hz, 1H), 6.89 (d, J=7.9 Hz, 2H), 6.39 (d, J=28.5 Hz, 2H), 4.89 (s, 1H), 4.37 (d, J=13.1 Hz, 1H), 3.91 (d, J=49.5 Hz, 1H), 3.76-3.57 (m, 1H), 3.57-3.42 (m, 1H), 3.25-3.08 (m, 2H), 1.42 (dd, J=9.6, 6.7 Hz, 3H). LCMS M/Z (M+H) 392.

Example 154

$^1$H NMR (400 MHz, DMSO-$d_6$) δ 14.10 (s, 1H), 9.36-9.16 (m, 1H), 9.00 (dd, J=9.2, 5.1 Hz, 1H), 7.91 (t, J=8.0 Hz, 1H), 7.79-7.65 (m, 1H), 7.55 (d, J=10.8 Hz, 1H), 7.24 (t, J=7.7 Hz, 1H), 6.89 (d, J=8.0 Hz, 2H), 6.39 (d, J=28.5 Hz, 2H), 4.89 (s, 1H), 4.37 (d, J=13.2 Hz, 1H), 3.91 (d, J=49.5 Hz, 1H), 3.79-3.59 (m, 1H), 3.49 (t, J=11.3 Hz, 1H), 3.24-3.06 (m, 2H), 1.42 (dd, J=9.6, 6.7 Hz, 3H). LCMS M/Z (M+H) 392.

154

4-(3-Amino-6-(2-hydroxyphenyl)pyridazin-4-yl)-2-methylpiperazin-1-yl)(pyridin-3-yl)methanone was Separated into its Individual Enantiomers, Examples 155 and 156

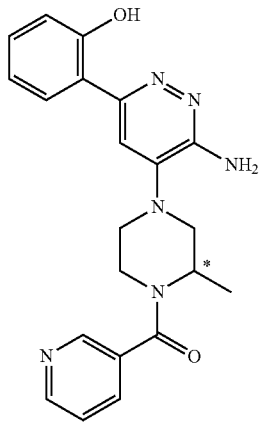

Separated by SFC chromatography (eluting with carbon dioxide and methanol, 0.1% ammonium hydroxide) using a Chiralpak AS column.

Example 155

$^1$H NMR (400 MHz, DMSO-$d_6$) δ 14.11 (s, 1H), 8.74-8.57 (m, 2H), 7.96-7.80 (m, 2H), 7.60-7.44 (m, 2H), 7.24 (ddd, J=8.2, 7.2, 1.5 Hz, 1H), 6.95-6.81 (m, 2H), 6.38 (s, 2H), 3.60 (s, 2H), 3.27-3.04 (m, 2H), 2.59-2.52 (m, 2H), 1.41 (d, J=6.8 Hz, 3H). LCMS M/Z (M+H) 391.

Example 156

$^1$H NMR (400 MHz, DMSO-$d_6$) δ 14.11 (s, 1H), 8.75-8.49 (m, 2H), 7.98-7.75 (m, 2H), 7.63-7.43 (m, 2H), 7.24 (ddd, J=8.2, 7.3, 1.6 Hz, 1H), 7.01-6.72 (m, 2H), 6.38 (s, 2H), 3.60 (s, 2H), 3.19 (s, 2H), 2.53 (d, J=8.5 Hz, 2H), 1.41 (d, J=6.8 Hz, 3H). LCMS M/Z (M+H) 391.

2-Amino-1-((R)-4-(3-amino-6-(2-hydroxyphenyl)pyridazin-4-yl)-2-methylpiperazin-1-yl)-3-methylbutan-1-one was Separated into its Individual Enantiomers, Examples 157 and 158

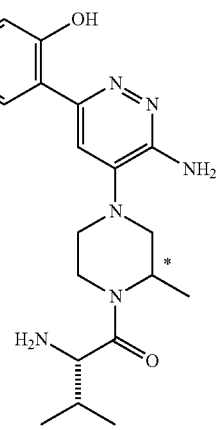

Separated by SFC chromatography (eluting with carbon dioxide and methanol, 0.1% ammonium hydroxide) using a Cel-1 column.

Example 157

LCMS M/Z (M+H) 385.

Example 158

LCMS M/Z (M+H) 385.

2-((R)-4-(3-Amino-6-(2-hydroxyphenyl)pyridazin-4-yl)-2-methylpiperazin-1-yl)-N-methylpropanamide was Separated into its Individual Diastereomer, Examples 159 and 160

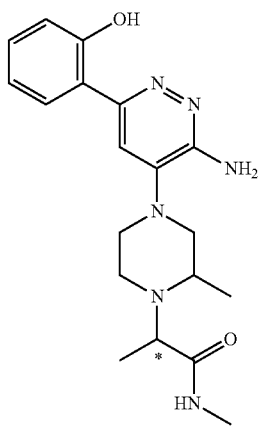 [SMILES: CNC(=O)C(C)N1CCN(c2cc(-c3ccccc3O)nnc2N)CC1C]

Separated by SFC chromatography (eluting with carbon dioxide and methanol, 0.1% ammonium hydroxide) using a Chiralpak IA column.

Example 159

$^1$H NMR (400 MHz, DMSO-d$_6$) δ 14.22 (s, 1H), 7.93 (dd, J=8.4, 1.6 Hz, 1H), 7.73 (d, J=4.8 Hz, 1H), 7.48 (s, 1H), 7.24 (ddd, J=8.2, 7.2, 1.6 Hz, 1H), 6.94-6.82 (m, 2H), 6.24 (s, 2H), 3.57 (d, J=6.9 Hz, 1H), 3.37 (d, J=1.1 Hz, 3H), 3.00-2.85 (m, 2H), 2.64 (d, J=4.6 Hz, 3H), 2.62-2.55 (m, 2H), 1.07 (dd, J=9.2, 6.5 Hz, 6H). LCMS M/Z (M+H) 371.

Example 160

$^1$H NMR (400 MHz, DMSO-d$_6$) δ 14.22 (s, 1H), 7.91 (dd, J=8.4, 1.6 Hz, 1H), 7.75 (d, J=4.9 Hz, 1H), 7.46 (s, 1H), 7.24 (ddd, J=8.2, 7.2, 1.6 Hz, 1H), 6.97-6.80 (m, 2H), 6.21 (s, 2H), 3.46-3.38 (m, 2H), 2.99-2.79 (m, 4H), 2.61 (d, J=4.7 Hz, 3H), 2.60-2.54 (m, 2H), 1.18 (d, J=7.0 Hz, 3H), 1.04 (d, J=6.3 Hz, 3H). LCMS M/Z (M+H) 371.

Examples 161 and 162

1-(4-(3-amino-6-(2-hydroxyphenyl)pyridazin-4-yl)-2-methylpiperazin-1-yl)-2-(methylamino)ethanone and 1-(4-(3-amino-6-(2-hydroxyphenyl)pyridazin-4-yl)-2-methylpiperazin-1-yl)-2-(dimethylamino)ethanone

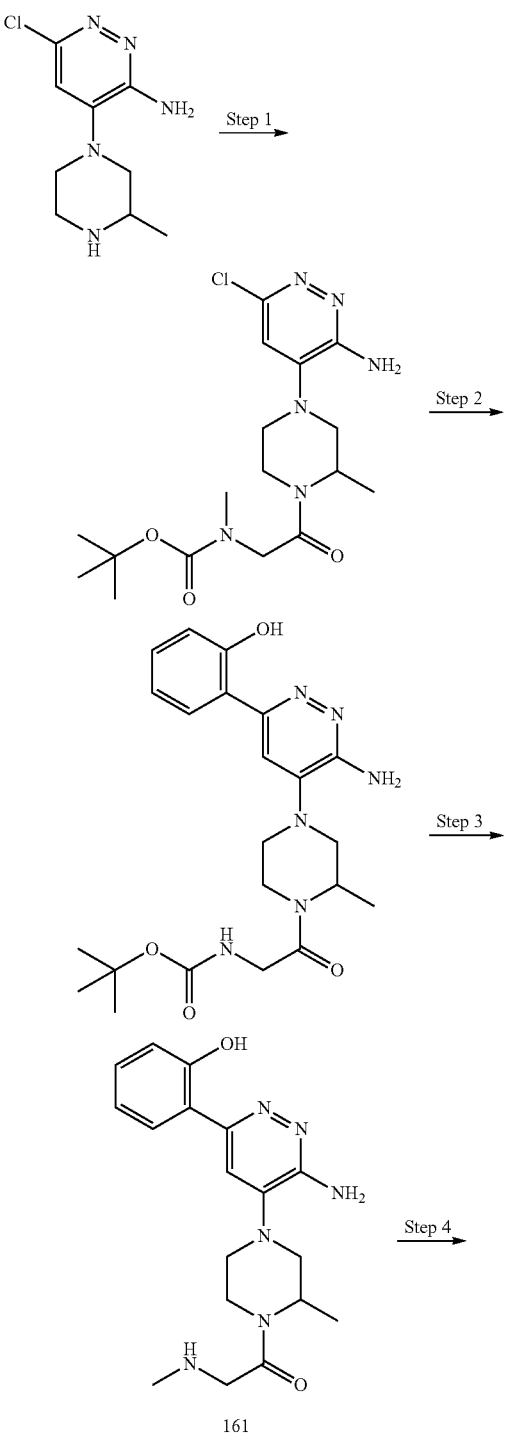

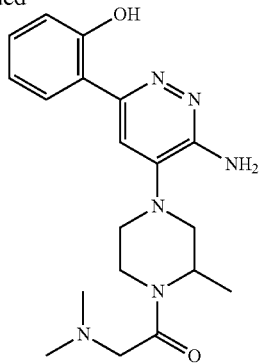

162

Step 1: tert-butyl (2-(4-(3-amino-6-chloropyridazin-4-yl)-2-methylpiperazin-1-yl)-2-oxoethyl)(methyl)carbamate To 6-chloro-4-(3-methylpiperazin-1-yl)pyridazin-3-amine (360 mg, 1.58 mmol) (prepared as in example G02939250) dissolved in dimethylformamide, was added 2-((tert-butoxycarbonyl)(methyl)amino)acetic acid (0.4 g, 2.13 mmol), followed by diisopropylethylamine (0.55 mL, 3.16 mmol). The reaction mixture was cooled to 0° C., and HATU (0.81 g, 2.13 mmol) was added. The reaction was stirred 15 min before being partitioned between ethyl acetate and sodium bicarbonate (aq., sat.). The organic phase was washed with brine, dried with sodium sulfate, filtered, and evaporated under reduced pressure. The residue was purified by silica gel chromatography (eluting with ethyl acetate and methanol) to afford the title compound (0.51 g, 1.28 mmol, 81%). LCMS M/Z (M+H, Cl pattern) 399/401.

Step 2: tert-butyl (2-(4-(3-amino-6-(2-hydroxyphenyl)pyridazin-4-yl)-2-methylpiperazin-1-yl)-2-oxoethyl)(methyl)carbamate tert-butyl (2-(4-(3-amino-6-chloropyridazin-4-yl)-2-methylpiperazin-1-yl)-2-oxoethyl)(methyl)carbamate (510 mg, 1.2786 mmol), (2-hydroxyphenyl)boronic acid (0.194 g, 1.4065 mmol), potassium carbonate (0.4418 g, 3.1965 mmol) and methanesulfonato(2-dicyclohexylphosphino-2',4',6'-tri-i-propyl-1,1'-biphenyl)(2'-amino-1,1'-biphenyl-2-yl)palladium(II) (0.0813 g, 0.1023 mmol) were placed in a sealable tube which was purged with nitrogen. Dioxane (6 ml) and water (2 ml) were added. The reaction mixture was degassed with a stream of nitrogen, and heated at 95° C. for 16 h. The reaction mixture was impregnated on silica, and purified by silica gel chromatography (eluting with ethyl acetate and methanol) to afford the title compound (0.401 g, 0.8783 mmol, 69%). LCMS M/Z (M+H) 457

Step 3: 1-(4-(3-amino-6-(2-hydroxyphenyl)pyridazin-4-yl)-2-methylpiperazin-1-yl)-2-(methylamino)ethanone tert-Butyl (2-(4-(3-amino-6-(2-hydroxyphenyl)pyridazin-4-yl)-2-methylpiperazin-1-yl)-2-oxoethyl)(methyl)carbamate (401 mg, 0.878 mmol) was dissolved in methanol (5 mL) for the addition of hydrochloric acid in dioxane (4 M, 1 mL, 4 mmol). The mixture was stirred 45 min. A portion of the material was purified by silica gel chromatography (eluting with methylene chloride, methanol, and ammonium hydroxide). Pure fractions were collected and concentrated in vacuo. The residue was lyophilized from acetonitrile and water to afford the title compound (example 161) (50 mg, 0.14 mmol) was obtained. $^1$H NMR (400 MHz, DMSO-$d_6$) δ 14.12 (br. s., 1H), 7.78-7.95 (m, 1H), 7.50 (s, 1H), 7.15-7.30 (m, 1H), 6.76-6.95 (m, 2H), 6.34 (s, 2H), 4.61-4.82 (m, 1H), 4.27 (m, 1H), 3.70 (m, 1H), 3.57 (d, J=11.96 Hz, 1H), 3.24-3.50 (m, 2H), 3.20 (d, J=11.72 Hz, 1H), 3.04 (m, 1H), 2.44 (m, 1H), 2.28 (s, 3H), 1.85-2.20 (m, 1H), 1.12-1.47 (m, 3H). LCMS M/Z (M+H) 357.

Step 4: 1-(4-(3-amino-6-(2-hydroxyphenyl)pyridazin-4-yl)-2-methylpiperazin-1-yl)-2-(dimethylamino)ethanone 1-(4-(3-amino-6-(2-hydroxyphenyl)pyridazin-4-yl)-2-methylpiperazin-1-yl)-2-(methylamino)ethanone dihydrochloride (100 mg, 0.23 mmol) (from the previous reaction) was dissolved in methanol. Formaldehyde (0.01 g, 0.46 mmol) was added and the mixture was stirred 5 min before the addition of sodium cyanoborohydride (0.01 g, 0.23 mmol). The reaction mixture was stirred for 2 h before being concentrated in vacuo and purified by silica gel chromatography (eluting with methylene chloride, methanol, and ammonium hydroxide). The pure fractions were collected and concentrated in vacuo and lyophilized from acetonitrile and water to afford the title compound (example 162) (0.07 g, 0.19 mmol, 83%). $^1$H NMR (400 MHz, DMSO-$d_6$) δ 14.15 (s, 1H), 7.93 (dd, J=1.47, 8.30 Hz, 1H), 7.52 (s, 1H), 7.24 (ddd, J=1.46, 7.20, 8.18 Hz, 1H), 6.81-6.94 (m, 2H), 6.33 (br. s., 2H), 4.65-4.75 (m, 1H), 4.14-4.29 (m, 1H), 3.87-4.03 (m, 1H), 3.64-3.76 (m, 1H), 3.58 (br. s., 1H), 2.89-3.26 (m, 4H), 2.19 (br. s., 6H), 1.16-1.49 (m, 3H). LCMS M/Z (M+H) 371.

Example 163

2-(6-amino-5-(1-phenylethoxy)pyridazin-3-yl)phenol

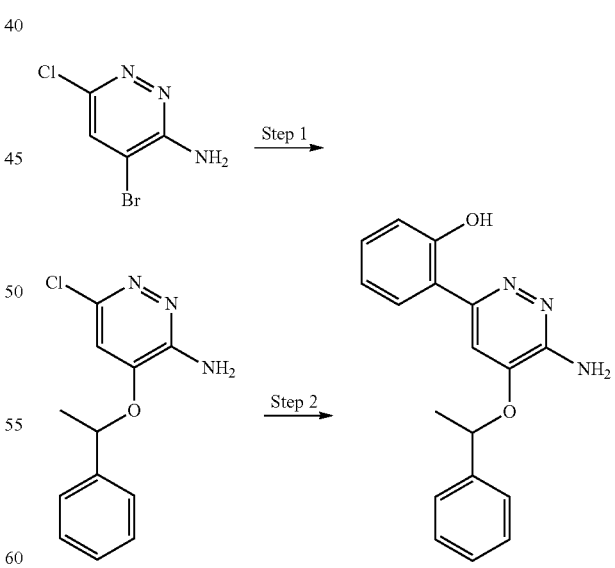

Step 1: 6-chloro-4-(1-phenylethoxy)pyridazin-3-amine

In a pyrex vial sodium hydride (60% wt in mineral oil, 28 mg, 0.72 mmol) was dissolved in tetrahydrofuran (3 mL).

1-Phenylethanol (87 µL, 0.72 mmol) and was added and the reaction was heated at 50° C. for 0.5 h. 4-bromo-6-chloropyridazin-3-amine (100 mg, 0.48 mmol) was added, and the reaction stirred at 70° C. for 12 h. The crude reaction was concentrated to dryness, deposited onto silica gel, and purified by silica gel chromatography (eluting with ethyl acetate) to provide 6-chloro-4-(1-phenylethoxy)pyridazin-3-amine (60.8 mg, 51%) as a clear colorless oil. LCMS M/Z (M+H) 250.

Step 2: 2-(6-amino-5-(1-phenylethoxy)pyridazin-3-yl)phenol

A microwave vial was charged with 6-chloro-4-(1-phenylethoxy)pyridazin-3-amine (60.8 mg, 0.24 mmol), 1,1 bis(di-tert-butylphosphino)ferrocene palladium dichloride (16 mg, 0.024 mmol), (2-hydroxyphenyl)boronic acid (67 mg, 0.49 mmol), and potassium carbonate (67 mg, 0.49 mmol). The vial was sealed and 1:1, acetonitrile:water was added (1.5 mL). The reaction was evacuated and purged with nitrogen (g) (3×) before being heated in the microwave at 120° C. for 0.5 h. The reaction was poured into brine and extracted with ethyl acetate three times. The combined organic layer was dried over sodium sulfate, concentrated, and purified by silica gel chromatography (eluting with ethyl acetate/hexanes) to provide 2-(6-amino-5-(1-phenylethoxy)pyridazin-3-yl)phenol (13.1 mg, 17%) as a tan solid. $^1$H NMR (400 MHz, DMSO-$d_6$) δ 14.24 (s, 1H), 7.74 (dd, J=1.4, 7.9 Hz, 1H), 7.61-7.47 (m, 3H), 7.43-7.34 (m, 2H), 7.32-7.17 (m, 2H), 6.92-6.82 (m, 2H), 6.67 (s, 2H), 6.03 (q, J=6.2 Hz, 1H), 1.66 (d, J=6.2 Hz, 3H). LCMS M/Z (M+H) 308.

The following compounds were prepared in a similar fashion (in some cases, methanesulfonato(2-dicyclohexylphosphino-2',4',6'-tri-i-propyl-1,1'-biphenyl)(2'-amino-1,1'-biphenyl-2-yl)palladium(II) was used in step 2 in place of 1,1 bis(di-tert-butylphosphino)ferrocene palladium dichloride).

Examples 164-185

| Example | Compound Name | NMR | m/z |
|---|---|---|---|
| 164 | 2-(6-amino-5-((3,3-dimethylbutan-2-yl)oxy)pyridazin-3-yl)phenol | $^1$H NMR (400 MHz, DMSO-$d_6$) δ 9.22 (d, J = 13.7 Hz, 1 H), 8.25 (t, J = 8.1 Hz, 1 H), 7.90 (d, J = 2.7 Hz, 1 H), 7.74 (ddd, J = 1.8, 4.3, 7.3 Hz, 1 H), 7.47 (t, J = 7.8 Hz, 1 H), 7.34-7.27 (m, 1 H), 7.24-7.17 (m, 1 H), 6.70-6.63 (m, 1 H), 4.94-4.85 (m, 1 H), 1.31-1.22 (m, 3 H), 1.00 (d, J = 4.4 Hz, 9 H) | 288 |
| 165 | 2-(6-amino-5-(((1,2-trans)-2-phenylcyclohexyl)oxy)pyridazin-3-yl)phenol | $^1$H NMR (400 MHz, DMSO-$d_6$) δ 14.35 (br. s., 1H), 7.91 (d, J = 7.32 Hz, 1H), 7.50 (s, 1H), 7.38 (d, J = 7.32 Hz, 2H), 7.03-7.27 (m, 4H), 6.78-6.95 (m, 2H), 6.26 (br. s., 2H), 5.08 (dt, J = 4.03, 10.32 Hz, 1H), 2.89 (t, J = 9.64 Hz, 1H), 2.23 (d, J = 10.01 Hz, 1H), 1.57-1.95 (m, 5H), 1.32-1.55 (m, 2H) | 362 |
| 166 | (R)-2-(6-amino-5-(1-(pyridin-3-yl)ethoxy)pyridazin-3-yl)phenol | $^1$H NMR (400 MHz, DMSO-$d_6$) δ 14.21 (s, 1H), 8.79-8.87 (m, 1H), 8.51 (dd, J = 1.46, 4.64 Hz, 1H), 7.96-8.04 (m, 1H), 7.83 (d, J = 8.06 Hz, 1H), 7.61 (s, 1H), 7.41 (dd, J = 4.88, 7.57 Hz, 1H), 7.18-7.28 (m, 1H), 6.84-6.95 (m, 2H), 6.72 (br. s., 2H), 6.14 (q, J = 6.10 Hz, 1H), 1.68 (d, J = 6.10 Hz, 3H) | 309 |
| 167 | (S)-2-(6-amino-5-(1-(pyridin-3-yl)ethoxy)pyridazin-3-yl)phenol | $^1$H NMR (400 MHz, DMSO-$d_6$) δ 14.21 (s, 1H), 8.82 (s, 1H), 8.48-8.54 (m, 1H), 8.00 (d, J = 7.81 Hz, 1H), 7.83 (d, J = 7.81 Hz, 1H), 7.61 (s, 1H), 7.41 (dd, J = 4.88, 7.57 Hz, 1H), 7.23 (t, J = 7.69 Hz, 1H), 6.84-6.95 (m, 2H), 6.72 (br. s., 2H), 6.14 (q, J = 5.94 Hz, 1H), 1.68 (d, J = 6.10 Hz, 3H) | 309 |
| 168 | 2-(6-amino-5-(1-(tetrahydro-2H-pyran-4-yl)ethoxy)pyridazin-3-yl)phenol | | 316 |
| 169 | (R)-2-(6-amino-5-(1-phenylethoxy)pyridazin-3-yl)phenol | $^1$H NMR (400 MHz, CD$_3$OD) δ 7.54-7.51 (m, 2H), 7.49-7.46 (m, 1H), 7.44-7.39 (m, 2H), 7.35-7.32 (m, 1H), 7.28 (s, 1H), 7.22-7.18 (m, 1H), 6.90-6.87 (m, 2H), 5.85-5.79 (m, 1H), 1.78 (d, J = 6.4 Hz, 3H) | 308 |
| 170 | (S)-2-(6-amino-5-(1-phenylethoxy)pyridazin-3-yl)phenol | $^1$H NMR (400 MHz, CD$_3$OD) δ 7.54-7.51 (m, 2H), 7.49-7.46 (m, 1H), 7.44-7.39 (m, 2H), 7.35-7.32 (m, 1H), 7.28 (s, 1H), 7.23-7.18 (m, 1H), 6.90-6.87 (m, 2H), 5.85-5.79 (m, 1H), 1.78 (d, J = 6.4 Hz, 3H) | 308 |
| 171 | 2-(6-amino-5-(1-(pyridin-3-yl)ethoxy)pyridazin-3-yl)phenol | $^1$H NMR (400 MHz, CD$_3$OD) δ 8.76 (d, J = 2.4 Hz, 1H), 8.54-8.51 (m, 1H), 8.04 (d, J = 7.6 Hz, 1H), 7.63-7.60 (m, 1H), 7.52-7.50 (m, 1H), 7.41 (s, 1H), 7.25-7.22 (m, 1H), 6.92-6.89 (m, 2H), 6.03-5.98 (m, 1H), 1.82 (d, J = 7.0 Hz, 3H) | 309 |
| 172 | 2-(6-amino-5-((1-methylpiperidin-4-yl)oxy)pyridazin-3-yl)phenol | $^1$H NMR (400 MHz, DMSO-$d_6$) δ 14.35 (s, 1H), 7.91-8.01 (m, 1H), 7.60 (s, 1H), 7.18-7.29 (m, 1H), 6.80-6.94 (m, 2H), 6.42 (br. s., 2H), 4.88 (td, J = 3.94, 8.00 Hz, 1H), | 301 |

| Example | Compound Name | NMR | m/z |
|---|---|---|---|
| | | 2.56-2.72 (m, 2H), 2.25 (t, J = 8.79 Hz, 2H), 2.18 (s, 3H), 1.97 (d, J = 4.88 Hz, 2H), 1.67-1.82 (m, 2H) | |
| 173 | 2-(6-amino-5-(2-(dimethylamino)ethoxy)pyridazin-3-yl)phenol | ¹H NMR (400 MHz, DMSO-d₆) δ 14.36 (br. s., 1H), 7.95 (d, J = 7.32 Hz, 1H), 7.62 (s, 1H), 7.17-7.32 (m, 1H), 6.82-6.93 (m, 2H), 6.54 (br. s., 2H), 4.37 (br. s., 2H), 2.88 (br. s., 2H), 2.36 (br. s., 6H) | 275 |
| 174 | 2-(6-amino-5-phenethoxypyridazin-3-yl)phenol | ¹H NMR (400 MHz, DMSO-d₆) δ 14.37 (s, 1H), 7.94 (d, J = 7.32 Hz, 1H), 7.60 (s, 1H), 7.37-7.43 (m, 2H), 7.32 (t, J = 7.57 Hz, 2H), 7.16-7.27 (m, 2H), 6.78-6.91 (m, 2H), 6.49 (s, 2H), 4.37-4.52 (m, 2H), 3.07-3.20 (m, 2H) | 308 |
| 175 | 2-(6-amino-5-(3-(dimethylamino)propoxy)pyridazin-3-yl)phenol | ¹H NMR (400 MHz, DMSO-d₆) δ 14.38 (br. s., 1H), 7.94 (d, J = 8.06 Hz, 1H), 7.57 (s, 1H), 7.23 (t, J = 7.57 Hz, 1H), 6.76-6.96 (m, 2H), 6.51 (br. s., 2H), 4.27 (t, J = 6.23 Hz, 2H), 2.41 (t, J = 7.08 Hz, 2H), 2.16 (s, 6H), 1.85-1.98 (m, 2H) | 289 |
| 176 | 2-(6-amino-5-(cyclopentyloxy)pyridazin-3-yl)phenol | ¹H NMR (400 MHz, DMSO-d₆) δ 14.41 (s, 1H), 7.93 (d, J = 7.57 Hz, 1H), 7.49 (s, 1H), 7.23 (t, J = 7.57 Hz, 1H), 6.71-6.97 (m, 2H), 6.48 (s, 2H), 5.20 (br. s., 1H), 2.01 (d, J = 5.62 Hz, 2H), 1.71-1.87 (m, 4H), 1.61 (br. s., 2H) | 272 |
| 177 | 2-(6-amino-5-((1-phenylpropan-2-yl)oxy)pyridazin-3-yl)phenol | ¹H NMR (400 MHz, DMSO-d₆) δ 14.36 (s, 1H), 7.90 (d, J = 8.06 Hz, 1H), 7.54 (s, 1H), 7.31-7.39 (m, 2H), 7.13-7.30 (m, 4H), 6.81-6.94 (m, 2H), 6.46 (s, 2H), 5.09-5.24 (m, 1H), 3.09 (dd, J = 7.32, 13.43 Hz, 1H), 2.88-3.03 (m, 1H), 1.24-1.54 (m, 3H) | 322 |
| 178 | 2-(6-amino-5-(2-phenylpropoxy)pyridazin-3-yl)phenol | ¹H NMR (400 MHz, DMSO-d₆) δ 14.36 (s, 1H), 7.94 (d, J = 8.06 Hz, 1H), 7.59 (s, 1H), 7.38-7.47 (m, 2H), 7.33 (t, J = 7.45 Hz, 2H), 7.12-7.25 (m, 2H), 6.77-6.96 (m, 2H), 6.45 (br. s., 2H), 4.12-4.43 (m, 3H), 1.41 (d, J = 7.08 Hz, 3H) | 322 |
| 179 | 2-(6-amino-5-(cyclohexyloxy)pyridazin-3-yl)phenol | ¹H NMR (400 MHz, DMSO-d₆) δ 14.41 (s, 1H), 7.96 (d, J = 7.81 Hz, 1H), 7.58 (s, 1H), 7.23 (t, J = 7.57 Hz, 1H), 6.75-6.97 (m, 2H), 6.44 (br. s., 2H), 4.87 (br. s., 1H), 1.93 (br. s., 2H), 1.76 (br. s., 2H), 1.55 (d, J = 9.03 Hz, 3H), 1.37-1.50 (m, 2H), 1.21-1.36 (m, 2H) | 286 |
| 180 | 2-(6-amino-5-((1-benzylpyrrolidin-3-yl)oxy)pyridazin-3-yl)phenol | ¹H NMR (400 MHz, DMSO-d₆) δ 14.36 (br. s., 1H), 8.03 (d, J = 7.08 Hz, 1H), 7.88 (br. s., 1H), 7.42-7.54 (m, 1H), 7.36 (br. s., 2H), 7.26 (br. s., 2H), 6.91 (d, J = 7.81 Hz, 2H), 6.41 (br. s., 2H), 6.33 (br. s., 1H), 3.56 (s, 1H), 3.08-3.24 (m, 2H), 2.84-2.99 (m, 2H), 2.69 (d, J = 6.10 Hz, 2H), 2.15 (br. s., 2H) | 363 |
| 181 | 2-(6-amino-5-((1-benzylpiperidin-3-yl)oxy)pyridazin-3-yl)phenol | | 377 |
| 182 | 2-(6-amino-5-((2,3-dihydro-1H-inden-1-yl)oxy)pyridazin-3-yl)phenol | ¹H NMR (400 MHz, DMSO-d₆) δ 14.36 (br. s., 1H), 8.03 (d, J = 7.08 Hz, 1H), 7.88 (br. s., 1H), 7.42-7.54 (m, 1H), 7.36 (br. s., 2H), 7.26 (br. s., 2H), 6.91 (d, J = 7.81 Hz, 2H), 6.41 (br. s., 2H), 3.56 (s, 1H), 3.07-3.25 (m, 1H), 2.84-3.00 (m, 1H), 2.69 (d, J = 6.10 Hz, 1H), 2.15 (br. s., 1H) | 320 |
| 183 | 2-(6-amino-5-((1-phenylpiperidin-3-yl)oxy)pyridazin-3-yl)phenol | ¹H NMR (400 MHz, DMSO-d₆) δ 14.37 (s, 1H), 7.98 (dd, J = 1.46, 8.30 Hz, 1H), 7.71 (s, 1H), 7.08-7.33 (m, 3H), 6.95 (d, J = 7.81 Hz, 2H), 6.83-6.91 (m, 2H), 6.75 (t, J = 7.32 Hz, 1H), 6.36 (s, 2H), 5.02 (br. s., 1H), 3.69 (d, J = 3.91 Hz, 1H), 3.38-3.51 (m, 1H), 3.19 (dd, J = 7.81, 12.45 Hz, 1H), 2.93-3.06 (m, 1H), 2.08-2.20 (m, 1H), 1.84-1.99 (m, 1H), 1.69 (br. s., 2H) | 363 |
| 184 | 2-(6-amino-5-((1-phenylpyrrolidin-3-yl)oxy)pyridazin-3-yl)phenol | ¹H NMR (400 MHz, DMSO-d₆) δ 14.35 (s, 1H), 7.84-8.10 (m, 1H), 7.62 (s, 1H), 7.21-7.30 (m, 1H), 7.16 (dd, J = 7.20, 8.67 Hz, 2H), 6.85-6.96 (m, 2H), 6.57-6.65 (m, 3H), 6.56 (s, 2H), 3.69-3.83 (m, 1H), 3.45-3.50 (m, 3H), 3.38-3.41 (m, 1H), 2.37-2.46 (m, 1H), 2.25-2.35 (m, 1H) | 349 |

| Example | Compound Name | NMR | m/z |
|---|---|---|---|
| 185 | (3-((3-amino-6-(2-hydroxyphenyl)pyridazin-4-yl)oxy)piperidin-1-yl)(phenyl)methanone | | 391 |

Example 186

2-(6-amino-5-phenylpyridazin-3-yl)phenol

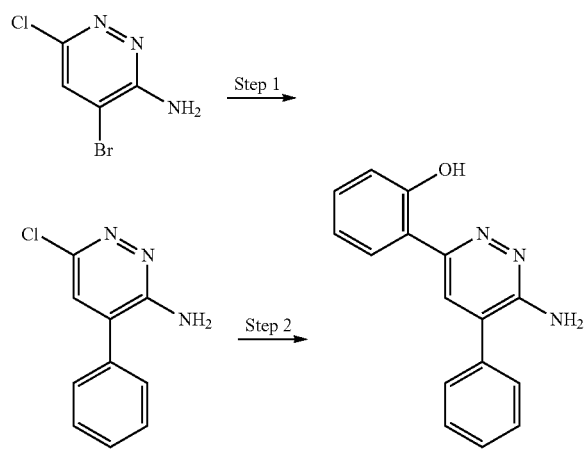

Step 1: 6-chloro-4-phenylpyridazin-3-amine phenylboronic acid (380 mg, 3.1 mmol), 4-bromo-6-chloropyridazin-3-amine (500 mg, 2.4 mmol), tetrakis(triphenylphosphine)-palladium(0) (140 mg, 0.12 mmol), potassium carbonate (660 mg, 4.8 mmol), 1,4-dioxane (9.5 mL) and water (0.5 mL) were charged in a disposable reaction tube. The headspace was flushed with nitrogen and the reaction mixture was degassed using 4 cycles of vacuum and nitrogen refilling. The reaction was heated at 100° C. for 5 hours, then cooled to room temperature. The crude mixture was purified by silica gel chromatography (eluting with hexanes/ethyl acetate) to obtain the title compound as a beige solid (355 mg; 72% yield). LCMS M/Z (M+H) 206.

Step 2: 2-(6-amino-5-phenylpyridazin-3-yl)phenol

A microwave vial was charged with 6-chloro-4-phenylpyridazin-3-amine (150 mg, 0.7294 mmol), (2-hydroxyphenyl)boronic acid (0.2012 g, 1.4588 mmol), (0.0475 g, 0.0729 mmol), potassium carbonate (0.2016 g, 1.4588 mmol) and a stirbar. 1:1 acetonitrile:water (2 mL) was added, and the mixture was heated to 120° C. in the microwave 20 min. The reaction mixture was diluted with ethyl acetate, washed with brine, and extracted twice with ethyl acetate. The organic layers were concentrated in vacuo with celite and purified by silica gel chromatography (eluting with hexanes, ethyl acetate, and methanol) to afford the title compound as a yellow amorphous solid. $^1$H NMR (400 MHz, DMSO-$d_6$) δ 13.59 (s, 1H), 8.01 (s, 1H), 7.95 (dd, J=1.56, 8.04 Hz, 1H), 7.61-7.66 (m, 2H), 7.51-7.59 (m, 3H), 7.23-7.29 (m, 1H), 6.86-6.96 (m, 2H), 6.45 (s, 2H). LCMS M/Z (M+H) 264.

The following compounds were prepared in a similar fashion to Example 186 using the appropriate boronic acid or tri-butylstannane coupling reagents and bis(tri-tert-butyl phosphine)palladium(0).

Examples 187-194

| Example | Compound Name | NMR | m/z |
|---|---|---|---|
| 187 | 2-(6-amino-5-(1-methyl-1H-pyrazol-4-yl)pyridazin-3-yl)phenol | $^1$H NMR (500 MHz, DMSO-$d_6$) δ 13.80 (s, 1H), 8.39 (s, 1H), 8.18 (s, 1H), 8.14 (s, 1H), 8.00 (dd, J = 1.46, 8.05 Hz, 1H), 7.22-7.29 (m, 1H), 6.89-6.95 (m, 2H), 6.48 (s, 2H), 3.93 (s, 3H) | 268 |
| 188 | 2-(6-amino-5-(1-(1-phenylethyl)-1H-pyrazol-4-yl)pyridazin-3-yl)phenol | $^1$H NMR (400 MHz, DMSO-$d_6$) δ 13.83 (s, 1H), 8.62 (s, 1H), 8.21 (d, J = 11.23 Hz, 2H), 8.01 (d, J = 7.08 Hz, 1H), 7.31-7.40 (m, 4H), 7.22-7.30 (m, 2H), 6.88-6.97 (m, 2H), 6.52 (s, 2H), 5.69 (q, J = 7.08 Hz, 1H), 1.88 (d, J = 6.84 Hz, 3H) | 358 |
| 189 | 2-(6-amino-5-(4-((dimethylamino)methyl)phenyl)pyridazin-3-yl)phenol | | 321 |
| 190 | 2-(6-amino-5-cyclopropylpyridazin-3-yl)phenol | $^1$H NMR (400 MHz, DMSO-$d_6$) δ 13.98 (br. s., 1H), 7.93 (dd, J = 1.59, 8.42 Hz, 1H), 7.63 (s, 1H), 7.12-7.29 (m, 1H), 6.82-6.94 (m, 2H), 6.74 (s, 2H), 1.86 (tt, J = 5.43, 8.24 Hz, 1H), 0.98-1.10 (m, 2H), 0.86-0.95 (m, 2H) | 228 |
| 191 | 2-(6-amino-5-(1-methyl-1H-imidazol-4-yl)pyridazin-3-yl)phenol | | 280 |
| 192 | 2-(6-amino-5-(1-(1-phenylethyl)-1H- | $^1$H NMR (400 MHz, DMSO-$d_6$) δ 13.96 (s, 1H), 8.61 (d, J = 1.22 Hz, 1H), 8.41 (s, 1H), | 358 |

| Example | Compound Name | NMR | m/z |
|---|---|---|---|
| | imidazol-4-yl)pyridazin-3-yl)phenol | 8.15 (d, J = 1.22 Hz, 1H), 7.99 (dd, J = 1.59, 8.42 Hz, 1H), 7.80 (br. s., 2H), 7.28-7.44 (m, 5H), 7.14-7.28 (m, 1H), 6.77-7.02 (m, 2H), 5.68 (q, J = 7.00 Hz, 1H), 1.88 (d, J = 7.08 Hz, 3H) | |
| 193 | 2-(6-amino-5-(1-methyl-1H-pyrazol-5-yl)pyridazin-3-yl)phenol | $^1$H NMR (400 MHz, DMSO-$d_6$) δ 13.31 (s, 1H), 8.13 (s, 1H), 7.91 (dd, J = 1.59, 7.93 Hz, 1H), 7.56-7.67 (m, 1H), 7.25 (ddd, J = 1.71, 7.08, 8.30 Hz, 1H), 6.81-7.00 (m, 2H), 6.59 (s, 2H), 6.56 (d, J = 1.95 Hz, 1H), 3.62-4.02 (m, 3H) | 268 |
| 194 | 2-(4-(3-amino-6-(2-hydroxyphenyl)pyridazin-4-yl)-1H-pyrazol-1-yl)-N,N-dimethylpropanamide | $^1$H NMR (400 MHz, DMSO-$d_6$) δ 13.81 (s, 1 H), 8.55 (s, 1 H), 8.23 (s, 1 H), 8.16 (d, J = 0.7 Hz, 1 H), 8.02 (dd, J = 1.5, 8.3 Hz, 1 H), 7.26 (dt, J = 1.5, 7.7 Hz, 1 H), 7.00-6.82 (m, 2 H), 6.49 (s, 2 H), 5.64 (q, J = 6.9 Hz, 1 H), 3.06 (s, 3 H), 2.85 (s, 3 H), 1.63 (d, J = 6.8 Hz, 3 H) | 353 |

Preparation of Intermediates Used to Prepare the Compounds in Examples 187-194 tert-butyl 2-(4-(4,4,5,5-tetramethyl-1,3,2-dioxaborolan-2-yl)-1H-pyrazol-1-yl)propanoate To 4-(4,4,5,5-tetramethyl-1,3,2-dioxaborolan-2-yl)-1H-pyrazole (2.5 g, 12.88 mmol) dissolved in dimethylformamide (30 mL), cesium carbonate (5.25 g, 16.1 mmol) was added, followed by tert-butyl 2-bromopropanoate (2.83 g, 13.52 mmol), and the reaction mixture was stirred for 5 d. The reaction mixture was partitioned between brine and ethyl acetate. The organic layer was washed twice with brine, dried with sodium sulfate, filtered, and concentrated in vacuo. The crude residue was purified by silica gel chromatography (eluting with hexanes and ethyl acetate) to provide the title compound (2.43 g, 7.54 mmol, 59%). LCMS M/Z (M+H) 323.

1-(1-phenylethyl)-4-(tributylstannyl)-1H-imidazole

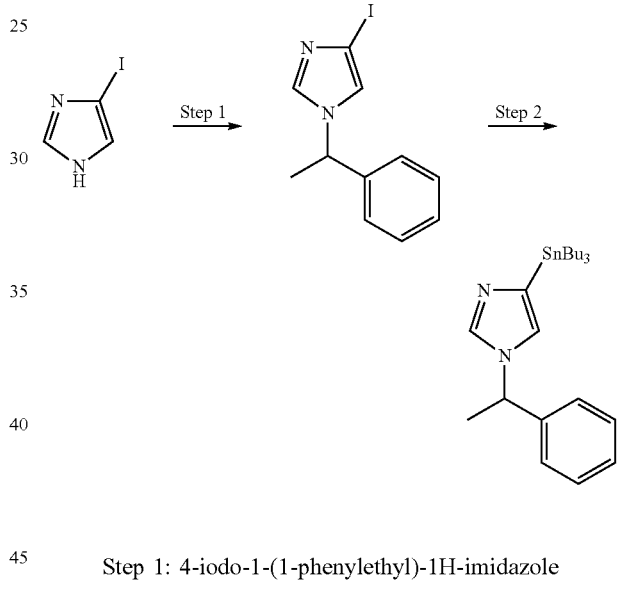

Step 1: 4-iodo-1-(1-phenylethyl)-1H-imidazole

To a round-bottom flask was added 4-iodo-1H-imidazole (0.884 g, 4.557 mmol) and cesium carbonate (3.113 g, 9.554 mmol). The flask was capped, dimethylformamide (20 mL) was added, and the atmosphere was vacuum purged thrice with nitrogen. (1-bromoethyl)benzene (884 mg, 4.777 mmol) was added, and the reaction was heated at 80° C. for 2 h. The reaction mixture was poured into water and extracted with twice with ethyl acetate. The combined organic layers were washed with brine, dried over sodium sulfate, filtered and concentrated in vacuo. The crude residue was purified by silica gel chromatography (eluting with hexanes and ethyl acetate) to provide 4-iodo-1-(1-phenylethyl)-1H-imidazole (0.954 g, 3.2 mmol, 67%), as a clear yellow oil. LCMS M/Z (M+H) 298.8.

Step 2:
1-(1-phenylethyl)-4-(tributylstannyl)-1H-imidazole

Iso-propylmagnesium chloride-lithium chloride 1.3 M in tetrahydrofuran (3.07 mL, 3.99 mmol) was added dropwise to a solution of 4-iodo-1-(1-phenylethyl)-1H-imidazole (954 mg, 3.19 mmol) in tetrahydrofuran (30 mL) at −78° C. After stirring for 2 h, tributylchlorostannane (1.3 g, 3.99 mmol) was added. After stirring for an additional 2 h, the solution was concentrated under reduced pressure to afford the title compound as a crude residue that was used immediately in the next step. LCMS M/Z (M+H) 459.0/461.0/463.0/465.0 (M+H, Sn pattern).

2-(4-(3-Amino-6-(2-hydroxyphenyl)pyridazin-4-yl)-1H-pyrazol-1-yl)-N,N-dimethylpropanamide was Separated into its Individual Enantiomers, Examples 195 and 196

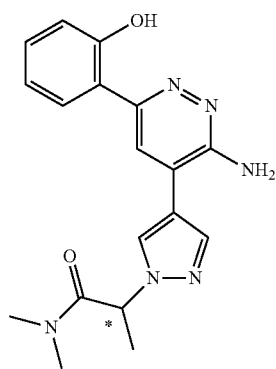 [SMILES: CC(C(=O)N(C)C)n1cc(-c2cc(-c3ccccc3O)nnc2N)cn1]

Separated by SFC chromatography (eluting with carbon dioxide and isopropanol, 0.1% ammonium hydroxide) using a Chiralpak AD column.

Example 195

$^1$H NMR (400 MHz, DMSO-d$_6$) δ 13.82 (s, 1H), 8.56 (d, J=0.8 Hz, 1H), 8.24 (s, 1H), 8.17 (d, J=0.7 Hz, 1H), 8.03 (dd, J=8.4, 1.6 Hz, 1H), 7.27 (ddd, J=8.2, 7.2, 1.6 Hz, 1H), 6.96-6.86 (m, 2H), 6.49 (s, 2H), 5.65 (q, J=7.0 Hz, 1H), 3.07 (s, 3H), 2.87 (s, 3H), 1.65 (d, J=7.0 Hz, 3H). LCMS M/Z (M+H) 353.

Example 196

$^1$H NMR (400 MHz, DMSO-d$_6$) δ 13.82 (s, 1H), 8.56 (d, J=0.8 Hz, 1H), 8.24 (s, 1H), 8.17 (d, J=0.7 Hz, 1H), 8.03 (dd, J=8.4, 1.6 Hz, 1H), 7.27 (ddd, J=8.2, 7.2, 1.6 Hz, 1H), 6.99-6.86 (m, 2H), 6.49 (s, 2H), 5.65 (d, J=7.0 Hz, 1H), 3.07 (s, 3H), 2.87 (s, 3H), 1.65 (d, J=7.0 Hz, 3H). LCMS M/Z (M+H) 353.

Example 197

2-(4-(3-amino-6-(2-hydroxyphenyl)pyridazin-4-yl)-1H-imidazol-1-yl)-N,N-dimethylpropanamide

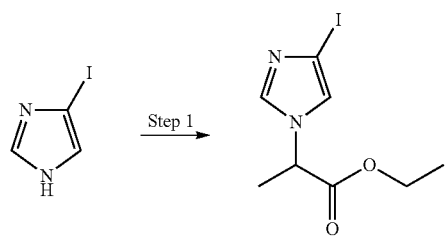

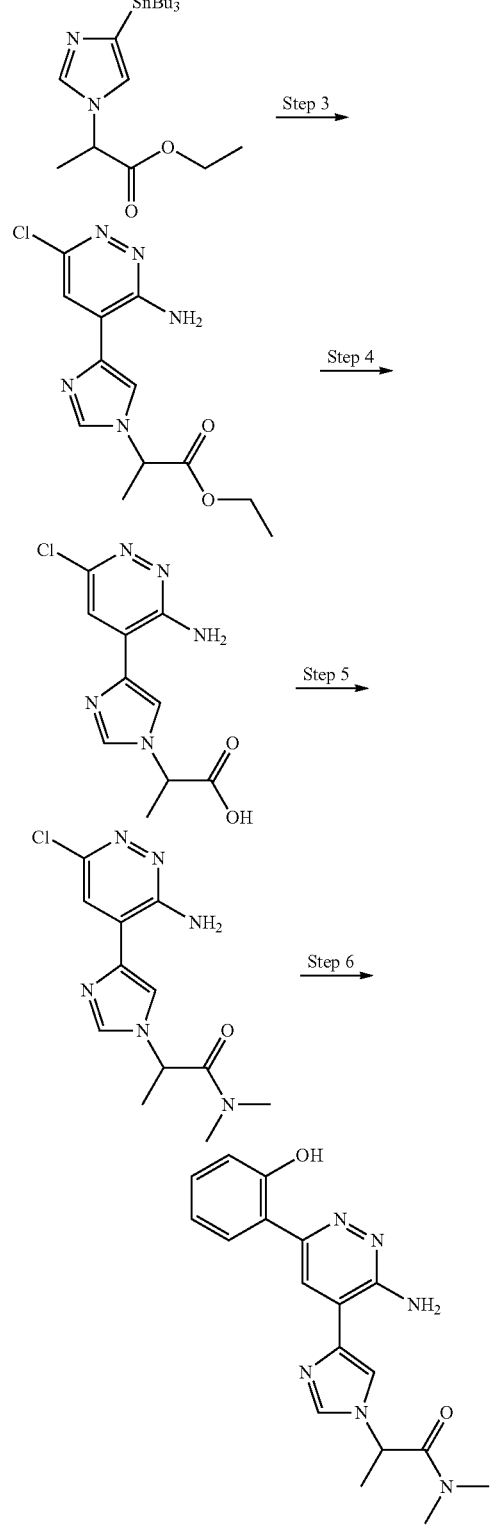

Step 1: (rac)-ethyl 2-(4-iodo-1H-imidazol-1-yl)propanoate

To a round bottom flask was added 4-iodo-1H-imidazole (2.29 g, 11.806 mmol) and dimethylformamide (20 mL). The atmosphere was evacuate and purged thrice with nitrogen. Sodium hydride (0.59 g, 14.757 mmol) was added, and the reaction mixture was stirred at 25° C. for 10 min. Ethyl 2-bromopropanoate (2.201 g, 12.16 mmol) was added, and the reaction was stirred at room temperature overnight. The reaction mixture was poured into water and extracted twice with ethyl acetate (2×125 mL). The combined organic layers were washed with brine, dried over sodium sulfate, filtered and concentrated. The crude residue was purified by silica gel chromatography (eluting with hexanes and ethyl acetate) to provide the title compound as a clear yellow oil (2.829 g, 9.62 mmol, 81%). LCMS M/Z (M+H) 295.

Step 2: Ethyl 2-(4-(tributylstannyl)-1H-imidazol-1-yl)propanoate

Iso-propylmagnesium chloride Lithium chloride complex (1.3 M in THF, 1.2 mL, 1.56 mmol) was added dropwise to a solution of ethyl 2-(4-iodo-1H-imidazol-1-yl)propanoate (2.85 g, 9.7 mmol) in tetrahydrofuran (12 ml) at −78° C. After stirring for 2 h, tributylchlorostannane (3.3 mL, 12.17 mmol) was added. After stirring for an additional 2 h, the solution was concentrated in vacuo. Ethyl 2-(4-(tributylstannyl)-1H-imidazol-1-yl)propanoate was obtained. The crude product was used immediately, without further purification, in the subsequent step. LCMS M/Z (M+H, Sn pattern) 457.0/459.0/461.0.

Step 3: Ethyl 2-(4-(3-amino-6-chloropyridazin-4-yl)-1H-imidazol-1-yl)propanoate 4-bromo-6-chloropyridazin-3-amine (2.0059 g, 9.623 mmol) and crude ethyl 2-(4-(tributylstannyl)-1H-imidazol-1-yl)propanoate (4.4 g, 9.623 mmol) were dissolved in dimethylformamide (20 mL). The reaction mixture was degassed using Nitrogen. Copper(I) iodide (0.1833 g, 0.9623 mmol) and tetrakis(triphenylphosphine)palladium(0) (0.8891 g, 0.7698 mmol) were added to the reaction mixture, and the mixture was stirred 95° C. 18 h. The crude reaction mixture was impregnated on silica and purified by silica gel chromatography (eluting with ethyl acetate and methanol) to provide the title compound (0.457 g, 1.5454 mmol, 16%). LCMS M/Z (M+H, Sn pattern) 296/298.

Step 4: 2-(4-(3-amino-6-chloropyridazin-4-yl)-1H-imidazol-1-yl)propanoic acid ethyl 2-(4-(3-amino-6-chloropyridazin-4-yl)-1H-imidazol-1-yl)propanoate (260 mg, 0.88 mmol) was dissolved in methanol:tetrahydrofuran (1:1 ml). Sodium hydroxide (6 M aq., 0.88 mL, 5.28 mmol) was added, and reaction mixture was stirred for 3 h at 25° C. The solution was neutralized with aqueous HCl (1 M), and partitioned between brine and ethyl acetate. The organic phase was dried with sodium sulfate, filtered, and concentrated in vacuo to yield the title compound (0.2 g, 0.73 mmol, 83%).

Step 5: 2-(4-(3-amino-6-chloropyridazin-4-yl)-1H-imidazol-1-yl)-N,N-dimethylpropanamide 2-(4-(3-amino-6-chloropyridazin-4-yl)-1H-imidazol-1-yl)propanoic acid (96 mg, 0.37 mmol) was dissolved in dimethylformamide, and diisopropylethylamine (0.13 mL, 0.74 mmol) was added. The reaction mixture was cooled to 0° C. for the addition of HATU (170 mg, 0.46 mmol). The reaction mixture stirred 10 min. Dimethylamine (2 M in THF, 0.37 mL, 0.74 mmol) was added, and the reaction mixture was allowed to warm to 25° C. and stirred 1 h. The crude reaction mixture was partitioned between ethyl acetate and sodium bicarbonate (sat. aq.). The organic phase was washed with brine, dried with sodium sulfate, and concentrated in vacuo. The crude residue was purified by silica gel chromatography (eluting with ethyl acetate and methanol). Pure fractions were concentrated in vacuo to yield the title compound (0.027 g, 0.09 mmol, 24%). LCMS M/Z (M+H, Sn pattern) 295/297.

Step 6: 2-(4-(3-amino-6-(2-hydroxyphenyl) pyridazin-4-yl)-1H-imidazol-1-yl)-N,N-dimethylpropanamide 2-(4-(3-amino-6-chloropyridazin-4-yl)-1H-imidazol-1-yl)-N,N-dimethylpropanamide (27 mg, 0.0916 mmol), (2-hydroxyphenyl)boronic acid (0.0171 g, 0.1237 mmol), potassium carbonate (0.0278 g, 0.2015 mmol) and methanesulfonato(2-dicyclohexylphosphino-2',4',6'-tri-i-propyl-1,1'-biphenyl)(2'-amino-1,1'-biphenyl-2-yl)palladium(II) (0.0073 g, 0.0092 mmol) were placed in a sealable tube. The reaction vessel's atmosphere was purged with nitrogen. Dioxane (2 ml) and water (0.7 ml) were added, and the reaction mixture was degassed with nitrogen before being stirred at 95° C. for 16 h. The organic supernatant was isolated and deposited on silica and purified by silica gel chromatography (eluting with ethyl acetate and methanol). The pure fractions were collected and concentrated in vacuo. The residue was lyophilized from acetonitrile and water to yield the title compound (0.005 g, 0.014 mmol, 16%). LCMS M/Z (M+H) 353.

Example 198

2-(6-amino-5-(trans-2-phenylcyclopropyl)pyridazin-3-yl)phenol

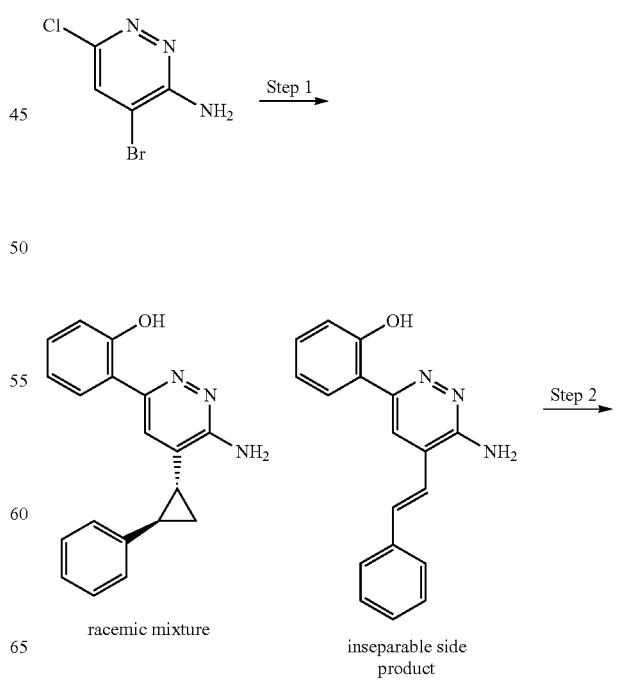

171

-continued

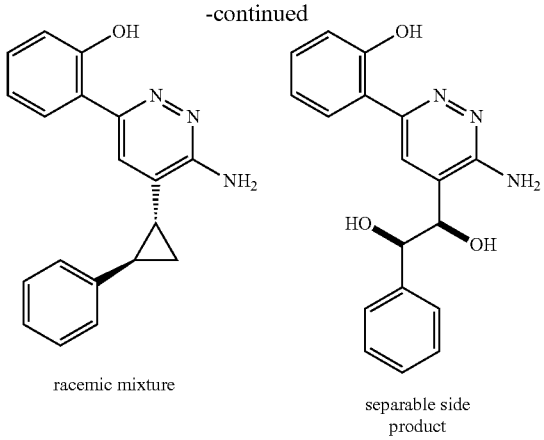

racemic mixture separable side product

Step 1: 2-(6-amino-5-((1R,2R)-2-phenylcyclopropyl)pyridazin-3-yl)phenol 4-bromo-6-chloropyridazin-3-amine (100 mg, 0.480 mmol), 4,4,5,5-tetramethyl-2-(trans-2-phenylcyclopropyl)-1,3-dioxolane (0.177 g, 0.720 mmol) (contaminated with (E)-4,4,5,5-tetramethyl-2-styryl-1,3,2-dioxaborolane), tetrakis(triphenylphosphine)palladium(0) (0.056 g, 0.048 mmol), potassium carbonate (0.1989 g, 1.4391 mmol), 1,4-dioxane (2 mL) and water (0.2 mL) were charged in a vial. The headspace was flushed with nitrogen and the reaction mixture was degassed using 4 cycles of vacuum and nitrogen refilling. The reaction was heated at 100° C. overnight then methanesulfonato(2-dicyclohexylphosphino-2',4',6'-tri-i-propyl-1,1'-biphenyl)(2'-amino-1,1'-biphenyl-2-yl)palladium(II) (0.020 g, 0.024 mmol) and (2-hydroxyphenyl)boronic acid (0.132 g, 0.959 mmol) were added. The headspace was flushed with nitrogen and the reaction was heated to 100° C. for 90 min. After the reaction was cooled to room temperature, the desired product was purified by silica gel chromatography (eluting with hexanes/ethyl acetate) and by reverse phase preparative HPLC (eluting with water/acetonitrile/0.1% trifluoroacetic acid). The stilbene side product could not be separated from the title compound.

Step 2: 2-(6-amino-5-((1R,2R)-2-phenylcyclopropyl)pyridazin-3-yl)phenol

To a solution of (E)-2-(6-amino-5-styrylpyridazin-3-yl)phenol/2-(6-amino-5-((1R,2R)-2-phenylcyclopropyl)pyridazin-3-yl)phenol (inseparable mixture) in methylene chloride/t-butanol (1:3) (4 mL) was added 4-methylmorpholine 4-oxide (0.081 g, 0.691 mmol) then osmium(VIII) oxide (2 drops of 4 w/w % solution in water). The reaction was stirred at room temperature overnight then purified twice by silica gel chromatography (eluting with methylene chloride/methanol). The title compound was obtained as an off-white solid (3.8 mg; 3% yield). LCMS M/Z (M+H) 304.

172

Example 199

2-(6-amino-5-benzylpyridazin-3-yl)phenol

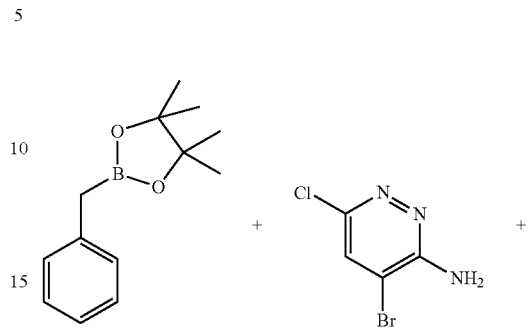

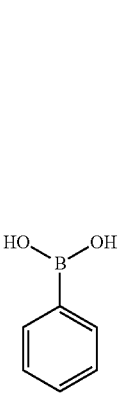

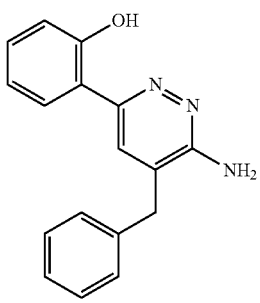

2-benzyl-4,4,5,5-tetramethyl-1,3,2-dioxaborolane (188 mg, 864 μmol), 4-bromo-6-chloropyridazin-3-amine (150 mg, 0.720 mmol), tetrakis(triphenylphosphine)palladium(0) (83.15 mg, 71.96 μmol), potassium carbonate (298 mg, 2.16 mmol), 1,4-dioxane (3 mL) and water (0.2 mL) were charged in a vial. The headspace was flushed with nitrogen and the reaction mixture was degassed using 4 cycles of vacuum and nitrogen refilling. The reaction was heated at 100° C. overnight. Next morning, extra tetrakis(triphenylphosphine)palladium(0) (83.15 mg, 71.96 μmop was added. After 2 d, extra 2-benzyl-4,4,5,5-tetramethyl-1,3,2-dioxaborolane (188.3 mg, 863.5 μmol) was added and the reaction was heated for 4 h, then (2-hydroxyphenyl)boronic acid (0.198 g, 1.44 mmol) and methanesulfonato(2-dicyclohexylphosphino-2',4',6'-tri-i-propyl-1,1'-biphenyl)(2'-amino-1,1'-biphenyl-2-yl)palladium(II) (61 mg, 0.072 mmol) were added. The headspace was flushed with nitrogen and the reaction is heated to 100° C. After 5 h the reaction is cooled to room temperature, filtered and purified by silica gel chromatography (eluting with hexane/ethyl acetate). The residue was purified by reverse phase preparative HPLC to give the title compound as a tan solid (2 mg; 1% yield). LCMS M/Z (M+H) 278.

Example 200

(E)-2-(6-amino-5-(3-phenylprop-1-en-1-yl)pyridazin-3-yl)phenol

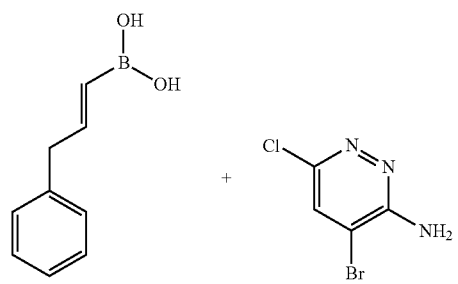

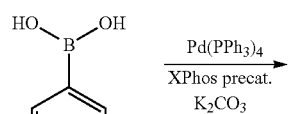 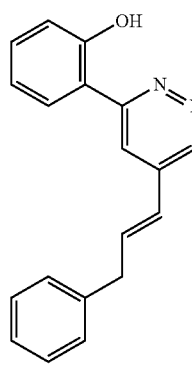

(E)-(3-phenylprop-1-en-1-yl)boronic acid (0.466 g, 2.88 mmol), 4-bromo-6-chloropyridazin-3-amine (400 mg, 1.92 mmol), tetrakis(triphenylphosphine)palladium(0) (0.111 g, 0.096 mmol), potassium carbonate (1.06 g, 7.68 mmol), 1,4-dioxane (3 mL) and water (0.15 mL) were charged in a vial. The headspace was flushed with nitrogen and the reaction mixture was degassed using 3 cycles of vacuum and nitrogen refilling. The reaction was heated at 90° C. After 3 h, methanesulfonato(2-dicyclohexylphosphino-2',4',6'-tri-i-propyl-1,1'-biphenyl)(2'-amino-1,1'-biphenyl-2-yl)palladium(II) (0.081 g, 0.096 mmol) and (2-hydroxyphenyl)boronic acid (0.529 g, 3.84 mmol) were added. The headspace was flushed with nitrogen and the reaction was heated to 90° C. After 2 h the reaction was cooled to room temperature and purified by silica gel chromatography (eluting with methylene chloride/methanol). The title compound was obtain as a tan solid (34 mg; 6% yield). LCMS M/Z (M+H) 304.

Example 201

1-(3-amino-6-(2-hydroxyphenyl)pyridazin-4-yl)-3-phenylpropane-1,2-diol

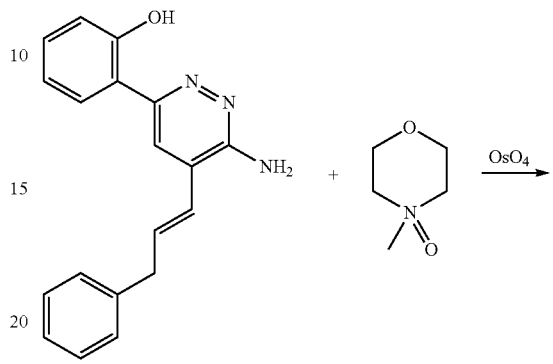

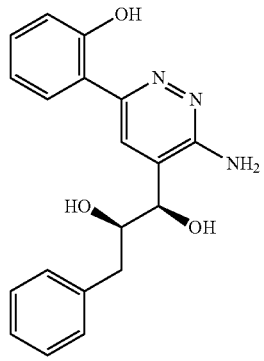

To a solution of (E)-2-(6-amino-5-(3-phenylprop-1-en-1-yl)pyridazin-3-yl)phenol (25 mg, 0.1 mmol) (prepared as in example G02940346) and 4-methylmorpholine 4-oxide (0.02 g, 0.2 mmol) in tetrahydrofuran (5 mL)/water (2 mL) was added osmium(VIII) oxide (5 drops of 4 w/w % solution in water) at room temperature. After 2 h, extra osmium(VIII) oxide (5 drops) was added. After an additional 3 h at room temperature, the reaction was quenched with an aqueous solution of sodium thiosulfate. The desired product was extracted with ethyl acetate (repeated 3 times) and the combined organic layers were dried over sodium sulfate, filtered and concentrated to dryness under vacuum. The reaction was repeated and the two batches were combined before being purified by silica gel chromatography (eluting with hexanes/ethyl acetate). The title compound was obtain as an off-white solid (25 mg; 35% yield). $^1$H NMR (400 MHz, DMSO-$d_6$) δ 13.92 (br. s, 1H), 7.92 (s, 1H), 7.80 (dd, J=1.34, 8.42 Hz, 1H), 7.59-7.67 (m, 3H), 7.52-7.59 (m, 2H), 7.24 (dt, J=1.80, 7.80 Hz, 1H), 6.90 (d, J=7.57 Hz, 2H), 6.48 (br. s, 2H), 5.48 (d, J=4.88 Hz, 1H), 4.96 (d, J=6.59 Hz, 1H), 4.62 (t, J=4.39 Hz, 1H), 3.91-4.00 (m, 1H), 2.70 (dd, J=2.32, 14.77 Hz, 1H), 2.51-2.58 (m, 1H). LCMS M/Z (M+H) 338.

Example 203

2-(6-aminopyridazin-3-yl)phenol

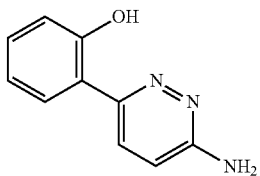

A mixture of 6-chloropyridazin-3-amine (0.15 g, 1.16 mmol), (2-hydroxyphenyl)boronic acid (0.32 g, 2.32 mmol), potassium carbonate (0.32 g, 2.32 mmol) and dichloro 1,1-bis(diphenylphosphino)ferrocene palladium (II) (0.08 g, 0.12 mmol) in 2 mL of acetonitrile and 2 mL of water was heated at 120° C. under microwave for a period of 20 min. The reaction mixture was extracted with ethyl acetate and purified by silica gel chromatography (eluting with ethyl acetate) to yield the title compound (60 mg). $^1$H NMR (400 MHz, DMSO-$d_6$) δ 13.77 (s, 1H), 8.13 (d, J=9.60 Hz, 1H), 7.80 (dd, J=1.30, 7.78 Hz, 1H), 7.25 (ddd, J=1.69, 7.07, 8.37 Hz, 1H), 7.03 (d, J=9.60 Hz, 1H), 6.85-6.94 (m, 2H), 6.74 (s, 2H). LCMS M/Z (M+H) 188.

Example 204

2-(6-(methylamino)pyridazin-3-yl)phenol

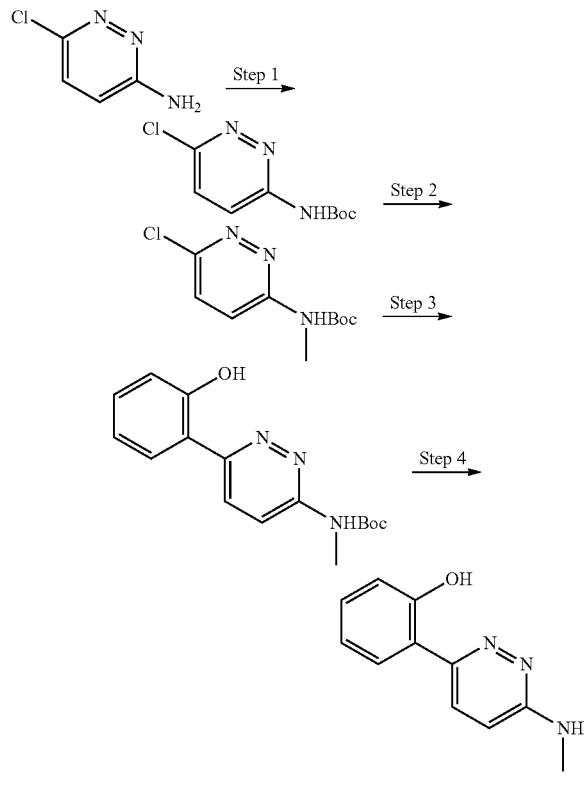

Step 1: tert-butyl (6-chloropyridazin-3-yl)carbamate

To 6-chloropyridazin-3-amine (1.00 g, 7.72 mmol) in 20 mL of 1,4-dioxane was added a catalytic amount of dimethylaminopyridine and di-tert-butyl dicarbonate (2.53 g, 11.58 mmol). The resulting mixture heated at 80° C. for 2 h. Acetonitrile and additional di-tert-butyl dicarbonate were added. After a period of 18 h at 80° C., the reaction mixture was extracted with ethyl acetate and purified by silica gel chromatography (eluting with hexanes/ethyl acetate) to provide the mono- and bis-protected amine. The mixture was dissolved in methanol (20 mL), to which was added potassium carbonate (200 mg). The mixture was stirred at room temperature until no bis-protected material was observed by LCMS. The mixture was partitioned between ethyl acetate and water, and the organic layer was concentrated in vacuo for use crude in the next step.

Step 2: tert-butyl (6-chloropyridazin-3-yl)(methyl)carbamate

To tert-butyl (6-chloropyridazin-3-yl)carbamate (0.15 g, 0.65 mmol) in 3 mL of tetrahydrofuran were added sodium hydride (60% in oil, 0.030 g, 0.78 mmol), followed by iodomethane (0.12 g, 0.85 mmol). After a period of 1 h, the reaction mixture was extracted with ethyl acetate/ammonium chloride (sat., aq.) and purified by silica gel chromatography (eluting with hexanes/ethyl acetate) to provide the title compound (120 mg) as a white solid.

Step 3: tert-butyl (6-(2-hydroxyphenyl)pyridazin-3-yl)(methyl)carbamate

To tert-butyl (6-chloropyridazin-3-yl)(methyl)carbamate (0.06 g, 0.25 mmol) in 1 mL of 1,4-dioxane were added (2-hydroxyphenyl)boronic acid (0.07 g, 0.50 mmol), potassium carbonate (0.07 g, 0.50 mmol), methanesulfonato(2-dicyclohexylphosphino-2',6'-dimethoxy-1,1'-biphenyl)(2'-amino-1,1'-biphenyl-2-yl)palladium(II) (4 mg) and water (50 µL). The mixture was purged with nitrogen and stirred at 90° C. for 1.5 h. The reaction mixture was concentrated in vacuo and purified by silicat gel chromatography (eluting with hexane/ethyl acetate) to provide the title compound (48 mg).

Step 4: 2-(6-(methylamino)pyridazin-3-yl)phenol

To tert-butyl (6-(2-hydroxyphenyl)pyridazin-3-yl)(methyl)carbamate (0.048 g, 0.16 mmol) in methylene chloride was added an excess of trifluoroacetic acid. After a period of 0.5 h, the reaction mixture was concentrated in vacuo, partitioned between ethyl acetate and sodium biocarbonate (sat., aq.), and extracted with ethyl acetate. The organic layers were concentrate in vacuo and purified by silica gel chromatography (eluting with hexanes/ethyl acetate) to yield the title compound (11 mg). $^1$H NMR (400 MHz, DMSO-$d_6$) δ 13.88 (br. s., 1H), 8.10 (d, J=9.63 Hz, 1H), 7.80 (d, J=8.32 Hz, 1H), 7.21-7.27 (m, 1H), 7.15-7.21 (m, 1H), 7.05 (d, J=9.63 Hz, 1H), 6.84-6.95 (m, 2H), 2.91 (d, J=5.04 Hz, 3H). LCMS M/Z (M+H) 202.

Example 205

N-(6-(2-hydroxyphenyl)pyridazin-3-yl)acetamide

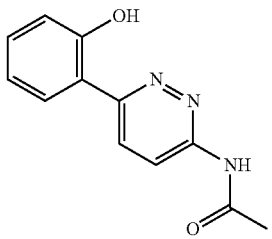 [SMILES: CC(=O)Nc1ccc(-c2ccccc2O)nn1]

Step 1: N-(6-chloropyridazin-3-yl)acetamide

To the 6-chloropyridazin-3-amine (0.20 g, 1.74 mmol) in 2 mL of methylene chloride was added an excess of acetic anhydride, pyridine and a catalytic amount of dimethylaminopyridine. After a period of three d, ethyl acetate was added and the solid was filtered to provide the title compound as a white solid (187 mg). LCMS M/Z (M+H) 172.

Step 2: N-(6-(2-hydroxyphenyl)pyridazin-3-yl)acetamide

A mixture of N-(6-chloropyridazin-3-yl)acetamide (0.15 g, 0.87 mmol), (2-hydroxyphenyl)boronic acid (0.24 g, 1.74 mmol), potassium carbonate (0.24 g, 1.74 mmol) and dichloro 1,1-bis(diphenylphosphino)ferrocene palladium (II) (0.06 g, 0.09 mmol) in 2 mL of acetonitrile and 2 mL of water was heated at 120° C. under microwave for a period of 20 min. The reaction mixture was extracted with ethyl acetate and purified twice by silica gel chromatography (eluting with hexanes/ethyl acetate) to provide the title compound (10 mg). $^1$H NMR (400 MHz, DMSO-$d_6$) δ 12.46 (s, 1H), 11.24 (s, 1H), 8.45 (d, J=3.37 Hz, 2H), 7.91 (dd, J=1.56, 8.04 Hz, 1H), 7.34 (dd, J=1.56, 8.30 Hz, 1H), 6.74-7.08 (m, 2H), 2.18 (s, 3H). LCMS M/Z (M+H) 230.

Example 206

2-(6-amino-5-phenylpyridazin-3-yl)-6-fluorophenol

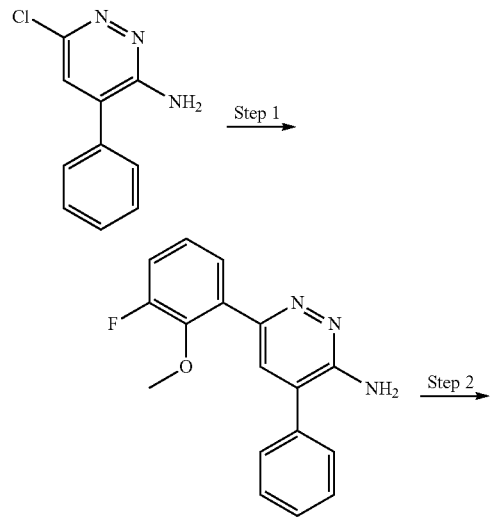

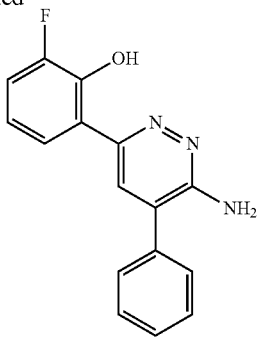

Step 1: 6-(3-fluoro-2-methoxyphenyl)-4-phenylpyridazin-3-amine

A mixture of 6-chloro-4-phenylpyridazin-3-amine (206 mg, 1.0 mmol) (prepared as in example G02858925), (3-fluoro-2-methoxyphenyl)boronic acid (204 mg, 1.2 mmol), cesium carbonate (652 mg, 2.0 mmol) and tetrakis (triphenylphosphine)palladium(0) (115.4 mg, 0.1 mmol) in dioxane/water (14 mL, 6/1) was heated at 110° C. for 12 h. After cooled, the mixture was filtered through a short pad of Celite. The filtrate was extracted with dichloromethane (3×25 mL). The combined organic layers were washed with water (30 mL), dried over sodium sulfate and concentrated under reduced pressure. The residue was purified by silica gel chromatography (eluting with ethyl acetate and petroleum ether) to give the title compound (280 mg, 95% yield) as a light green oil.

Step 2: 2-(6-amino-5-phenylpyridazin-3-yl)-6-fluorophenol

A solution of 6-(3-fluoro-2-methoxyphenyl)-4-phenylpyridazin-3-amine (280 mg, 0.95 mmol) in dichloromethane (25 mL) was added boron tribromide (1 mL) at −78° C. After addition, the mixture was stirred at ambient temperature for 2 h and then quenched by addition of Methanol (5 mL). The solvent was evaporated under reduced pressure and the residue was purified by reverse phase chromatography (eluting with acetonitrile/water/0.1% hydrochloric acid) to give the title compound (45 mg, 16.9% yield) as a yellow solid. $^1$H NMR (400 MHz, CD$_3$OD) δ 8.28 (s, 1H), 7.63-7.61 (m, 5H), 7.53 (d, J=8.0 Hz, 1H) 7.35-7.19 (m, 1H), 7.06-6.88 (m, 1H); LCMS M/Z (M+H) 282.

Example 207

2-(6-amino-5-(2-hydroxypropan-2-yl)pyridazin-3-yl) phenol

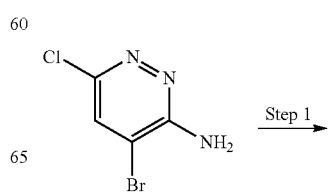

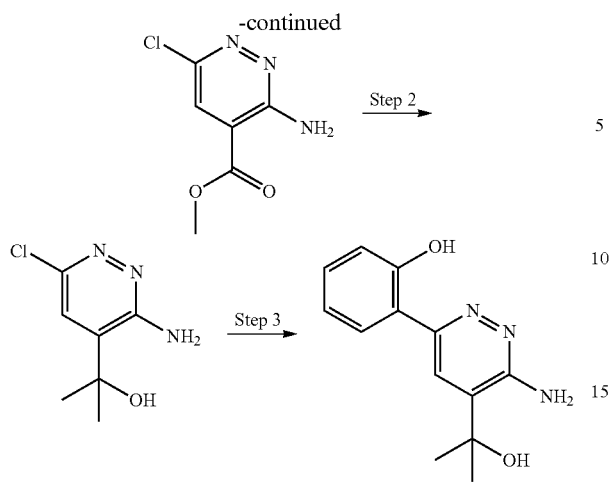

Step 1: methyl 3-amino-6-chloropyridazine-4-carboxylate

To 4-bromo-6-chloropyridazin-3-amine (1.00 g, 4.80 mmol) in 20 mL of methanol were added XanPhos precat G3 (100 mg) and triethylamine (0.97 g, 9.60 mmol). The reaction mixture was evacuated and backfilled with carbon monoxide before being stirred at 70° C. After a period of 18 h, the mixture was concentrated in vacuo with Celite and purified by silica gel chromatography (eluting with hexanes/ethyl acetate) to provide a mixture of the title compound and starting material.

Step 2: 2-(3-amino-6-chloropyridazin-4-yl)propan-2-ol

To methyl 3-amino-6-chloropyridazine-4-carboxylate (0.05 g, 0.27 mmol) in 2 mL of tetrahydrofuran was added at −78° C. a 3 M tetrahydrofuran solution of methylmagnesium chloride (0.27 mL, 0.81 mmol). After a period of 10 min at room temperature, the reaction mixture was portioned between ethyl acetate and saturated ammonium chloride. The resulting mixture was extracted, and the organic layers were purified by silica gel chromatography (eluting with hexanes/ethyl acetate) to provide the title compound (15 mg).

Step 3: 2-(6-amino-5-(2-hydroxypropan-2-yl)pyridazin-3-yl)phenol

To 2-(3-amino-6-chloropyridazin-4-yl)propan-2-ol (0.014 g, 0.05 mmol) in of 1,4-dioxane (1.5 mL) were added (2-hydroxyphenyl)boronic acid (0.01 g, 0.10 mmol), potassium carbonate (0.01 g, 0.10 mmol), methanesulfonato(2-dicyclohexylphosphino-2',6'-dimethoxy-1,1'-biphenyl)(2'-amino-1,1'-biphenyl-2-yl)palladium(II) (10 mg) and water (75 µL). The resulting mixture was purged with nitrogen and stirred at 90° C. 1.5 h. The reaction mixture was concentrated in vacuo and purified by silica gel chromatography (eluting with hexane/ethyl acetate) to provide the title compound. NMR (400 MHz, DMSO-$d_6$) δ 13.61 (s, 1H), 7.86-7.94 (m, 1H), 7.84 (s, 1H), 7.16-7.29 (m, 1H), 6.86-6.96 (m, 1H), 6.78 (s, 2H), 5.84 (s, 1H), 3.47 (s, 1H), 1.57 (s, 6H). LCMS M/Z (M+H) 246.

Example 208

2-(6-amino-5-(benzylsulfonyl)pyridazin-3-yl)phenol

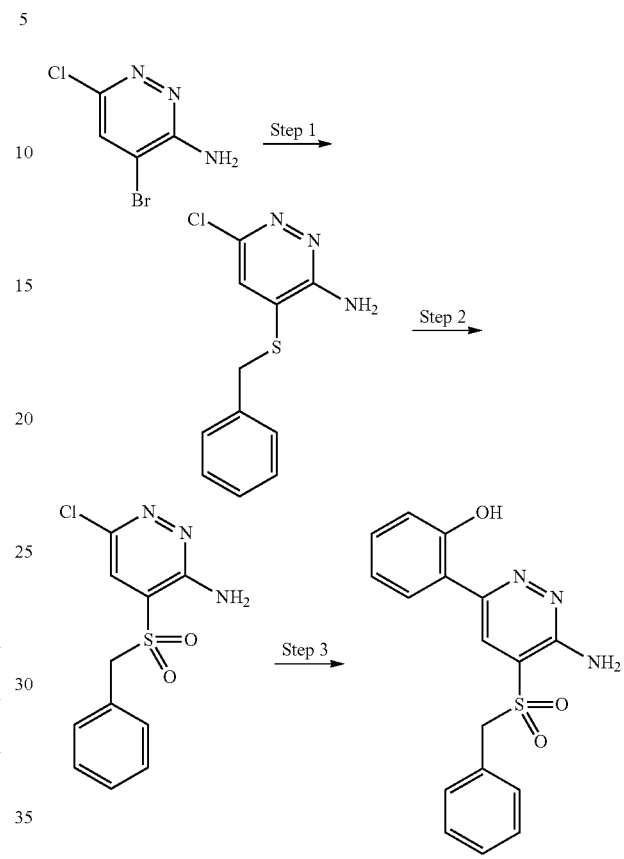

Step 1: 4-(benzylthio)-6-chloropyridazin-3-amine

To phenylmethanethiol (0.29 g, 2.30 mmol) in 5 mL of acetonitrile were added 4-bromo-6-chloropyridazin-3-amine (0.40 g, 1.92 mmol) and potassium carbonate (0.27 g, 1.92 mmol). The resulting mixture was heated at 90° C. After a period of 18 h, the reaction mixture was concentrated in vacuo with Celite and purified by silica gel chromatography (eluting with hexanes/ethyl acetate) to provide the parent compound (220 mg).

Step 2: 4-(benzylsulfonyl)-6-chloropyridazin-3-amine

To 4-(benzylsulfonyl)-6-chloropyridazin-3-amine (0.220 g, 0.87 mmol) in a 1/1 mixture of methylene chloride/methanol was added excess of oxone in water until no starting material remained (as determined by LCMS). The resulting mixture was extracted with ethyl acetate and water, and the organic layers were concentrated in vacuo. Purification by silica gel chromatography (eluting with hexanes/ethyl acetate) provided the title compound (17 mg).

Step 3: 2-(6-amino-5-(benzylsulfonyl)pyridazin-3-yl)phenol

To 4-(benzylsulfonyl)-6-chloropyridazin-3-amine (0.017 g, 0.07 mmol) in 1.5 mL of 1,4-dioxane were (2-hydroxyphenyl)boronic acid (0.02 g, 0.14 mmol), potassium carbonate (0.02 g, 0.14 mmol) methanesulfonato(2-dicyclohexylphosphino-2',6'-dimethoxy-1,1'-biphenyl)(2'-amino-1,1'-biphenyl-2-yl)palladium(II) (5 mg) and water (75 μL). The mixture was purged under nitrogen and stirred at 90° C. After a period of 2 h, the reaction mixture was purified by silica gel chromatography (eluting with hexanes/ethyl acetate) to provide the title compound (20 mg). $^1$H NMR (400 MHz, DMSO-$d_6$) δ 11.19 (s, 1H), 8.08 (s, 1H), 7.63-7.85 (m, 1H), 7.21-7.39 (m, 6H), 7.18 (br. s., 2H), 6.94 (d, J=8.30 Hz, 2H), 4.84 (s, 2H). LCMS M/Z (M+H) 342.

Example 209

2-(6-amino-5-cyclohexylpyridazin-3-yl)phenol

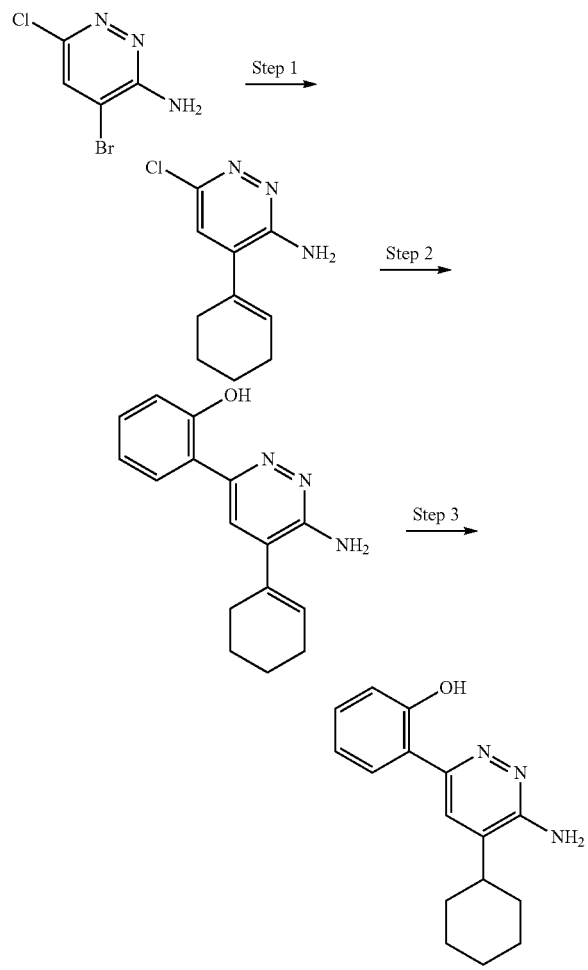

Step 1: 6-chloro-4-(cyclohex-1-en-1-yl)pyridazin-3-amine

A mixture of 4-bromo-6-chloropyridazin-3-amine (500 mg, 2.42 mmol), cyclohex-1-en-1-ylboronic acid (304 mg, 2.42 mmol), tetrakis(triphenylphosphine)palladium(0) (252 mg, 0.22 mmol) and sodium carbonate (513 mg, 4.84 mmol) in dioxane/water (30 mL/5 mL) was heated at 110° C. for 5 h. The mixture was concentrated in vacuo, and the residue was diluted with aqueous hydrochloric acid (1 N, 20 mL) before being washed with ethyl acetate (3×10 mL). The separated aqueous layer was neutralized with sodium carbonate and extracted with methylene chloride (3×20 mL). The combined organic layers were washed with brine, dried over sodium sulfate and concentrated to provide the crude title compound (350 mg, 69% yield) as yellow solid.

Step 2: 2-(6-amino-5-(cyclohex-1-en-1-yl)pyridazin-3-yl)phenol

A mixture of 6-chloro-4-(cyclohex-1-en-1-yl)pyridazin-3-amine (350 mg, 1.67 mmol), (2-hydroxyphenyl)boronic acid (650 mg, 4.74 mmol), [1,1'-Bis(diphenylphosphino)ferrocene]dichloropalladium (125 mg, 0.17 mmol) and potassium carbonate (461 mg, 3.34 mmol) in acetonitrile/water (5 mL/5 mL) was heated at 120° C. for 20 min under microwave conditions. The solvent was evaporated under reduced pressure, and the residue was purified by preparative TLC (50% ethyl acetate in petroleum ether) to give the title compound (100 mg, 22%) as yellow oil.

Step 3: 2-(6-amino-5-cyclohexylpyridazin-3-yl)phenol

A mixture of 2-(6-amino-5-(cyclohex-1-en-1-yl)pyridazin-3-yl)phenol (100.0 mg, 0.37 mmol) and 10% Palladium hydroxide (20 mg) on carbon in Methanol (20 mL) was hydrogenated (15 psi) for 16 h at room temperature. The mixture was filtered through a short pad of Celite and evaporated under reduced pressure. The residue was purified by reverse phase chromatography (eluting with acetonitrile/water/0.1% hydrochloric acid) to give the title compound (45 mg, 45% yield) as a white solid. $^1$H NMR (400 MHz, CD$_3$OD) δ 8.22 (s, 1H), 7.67-7.65 (m, 1H), 7.40-7.31 (m, 1H), 7.01-6.98 (m, 2H), 2.81-2.75 (m, 1H), 2.05-1.87 (m, 4H), 1.85-1.78 (m, 1H), 1.59-1.38 (m, 5H); LCMS M/Z (M+H) 270.

The following compounds were prepared in a similar fashion to Example 209:

Examples 210-214

| Example | Compound Name | NMR | m/z |
|---|---|---|---|
| 210 | 2-(6-amino-5-cyclopentylpyridazin-3-yl)phenol | $^1$H NMR (400 MHz, CD$_3$OD) δ 8.24 (s, 1H), 7.67-7.65 (m, 1H), 7.39-7.35 (m, 1H), 7.01-6.98 (m, 2H), 3.26-3.16 (m, 1H), 2.23-2.13 (m, 2H), 1.88-1.76 (m, 4H), 1.72-1.62 (m, 2H) | 256 |
| 211 | 2-(6-amino-5-(1-methylpiperidin-4-yl)pyridazin-3-yl)phenol | $^1$H NMR (400 MHz, CDCl$_3$) δ 7.72 (s, 1H), 7.59 (d, J = 8.0 Hz, 1H), 7.29 (d, J = 7.2 Hz, 1H), 7.04 (d, J = 8.0 Hz, | 285 |

-continued

| Example | Compound Name | NMR | m/z |
|---|---|---|---|
| | | 1H), 6.91 (t, J = 7.2 Hz, 1H), 5.01 (s, 2H), 3.13-3.10 (m, 2H), 2.42-2.15 (m, 4H), 2.19-2.15 (m, 2H), 2.05 (s, 1H), 1.96-1.87 (m, 4H). | |
| 212 | tert-butyl 3-(3-amino-6-(2-hydroxyphenyl)pyridazin-4-yl)pyrrolidine-1-carboxylate | $^1$H NMR (400 MHz, DMSO-d$_6$) δ 13.71 (d, J = 14.2 Hz, 1 H), 7.95-7.84 (m, 2 H), 7.30-7.19 (m, 1 H), 6.94-6.84 (m, 2 H), 6.75 (s, 2 H), 3.74 (d, J = 4.6 Hz, 1 H), 3.52-3.33 (m, 4 H), 2.31-2.02 (m, 2 H), 1.42 (s, 9 H) | 357 |
| 213 | 2-(6-amino-5-(tetrahydro-2H-pyran-4-yl)pyridazin-3-yl)phenol | $^1$H NMR (400 MHz, DMSO-d$_6$) δ 13.87 (s, 1 H), 7.97 (d, J = 6.8 Hz, 1 H), 7.90 (s, 1 H), 7.32-7.05 (m, 1 H), 6.94-6.80 (m, 2 H), 6.73 (s, 2 H), 3.97 (d, J = 11.0 Hz, 2 H), 3.66-3.38 (m, 2 H), 2.99-2.77 (m, 1 H), 1.85-1.64 (m, 4 H) | 272 |
| 214 | 2-(6-amino-5-(1-benzylpiperidin-3-yl)pyridazin-3-yl)phenol | $^1$H NMR (400 MHz, DMSO-d$_6$) δ 13.81 (s, 1 H), 8.03 (s, 1 H), 7.89-7.83 (m, 1 H), 7.40-7.28 (m, 4 H), 7.28-7.17 (m, 2 H), 6.98-6.82 (m, 2H), 6.65 (s, 2 H), 3.56 (d, J = 12.9 Hz, 1 H), 3.52 (d, J = 12.9 Hz, 1 H), 3.02-2.89 (m, 1 H), 2.82 (d, J = 10.3 Hz, 1 H), 2.76-2.62 (m, 1 H), 2.41 (t, J = 10.0 Hz, 1 H), 2.21 (d, J = 8.5 Hz, 1 H), 1.95-1.76 (m, 1 H), 1.75-1.57 (m, 2 H), 1.58-1.40 (m, 1 H) | 361 |

Example 215

2-(6-amino-5-(pyrrolidin-3-yl)pyridazin-3-yl)phenol Hydrochloride

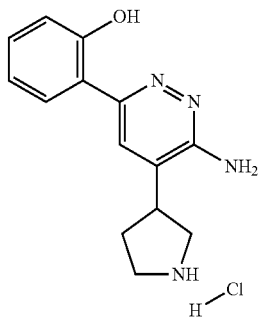

tert-butyl 3-(3-amino-6-(2-hydroxyphenyl)pyridazin-4-yl)pyrrolidine-1-carboxylate (252 mg, 0.71 mmol) (prepared as described for example G02939245) was dissolved in methanol (10 mL). Hydrochloric acid (4 M in dioxane, 1.77 mL, 7.07 mmol) was added, and the reaction was stirred at ambient temperature for 3 h. The reaction was concentrated with benzene twice and then ether. Residual solvent was removed in vacuo to provide the title compound (207 mg, 100%) as a yellow solid. $^1$H NMR (400 MHz, DMSO-d$_6$) δ 9.65 (br. s., 2H), 8.43 (br. s., 2H), 8.21 (s, 1H), 7.64 (dd, J=1.2, 7.8 Hz, 1H), 7.39-7.31 (m, 2H), 7.06 (dd, J=0.7, 8.3 Hz, 1H), 6.99-6.91 (m, 1H), 3.76-3.58 (m, 2H), 3.34 (qd, J=5.9, 11.7 Hz, 2H), 3.28-3.18 (m, 1H), 2.48-2.38 (m, 1H), 1.97 (qd, J=7.9, 13.0 Hz, 1H). LCMS M/Z (M+H) 257.

Example 216

2-(6-amino-5-(1-methylpyrrolidin-3-yl)pyridazin-3-yl)phenol 2,2,2-trifluoroacetate

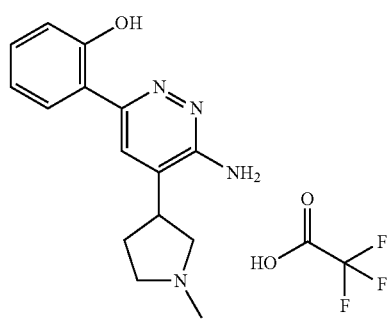 [SMILES: CN1CCC(c2cc(-c3ccccc3O)nnc2N)C1 ; O=C(O)C(F)(F)F]

In a pyrex vial 2-(6-amino-5-(pyrrolidin-3-yl)pyridazin-3-yl)phenol hydrochloride (51.5 mg, 0.18 mmol) (prepared as described for example G02940683) was diluted with formaldehyde (37% wt in water, 0.13 mL, 1.78 mmol) and formic acid (0.5 mL, 13.25 mmol). The solution was heated at 65° C. 12 h. The reaction was then treated with 6 M sodium hydroxide (0.5 mL) at ambient temperature for 12 h. The crude mixture was concentrated and the residue deposited onto silica gel with aid of methylene chloride, then purified by silica gel chromatography (eluting with methylene chloride/methanol/ammonium hydroxide) and reverse phase HPLC (eluting with acetonitrile/water/ammonium hydroxide). The product fractions were pooled and lyophilized to provide 2-(6-amino-5-(1-methylpyrrolidin-3-yl)pyridazin-3-yl)phenol 2,2,2-trifluoroacetate (12 mg, 18%) as a white solid. LCMS M/Z (M+H) 271.

Example 217

2-(6-amino-5-(1-(phenylsulfonyl)pyrrolidin-3-yl)pyridazin-3-yl)phenol

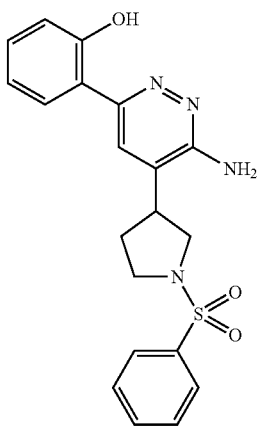 [SMILES: Nc1nnc(-c2ccccc2O)cc1C1CCN(S(=O)(=O)c2ccccc2)C1]

In a 50 mL round bottom flask 2-(6-amino-5-(pyrrolidin-3-yl)pyridazin-3-yl)phenol hydrochloride (75 mg, 0.26 mmol) (prepared as described for example G02940683) was dissolved in dichloromethane (8 mL). Diisopropylethylamine (112 μL, 0.64 mmol) was added, and the solution cooled to 0° C. Benzenesulfonyl chloride (35 μL, 0.27 mmol) was added, and the mixture was stirred at ambient temperature for 1 h. The crude product was concentrated in vacuo with silica gel and purified by silica gel chromatography (eluting with ethyl acetate). The product containing fractions were concentrated then lyophilized to provide 2-(6-amino-5-(1-(phenylsulfonyl)pyrrolidin-3-yl)pyridazin-3-yl)phenol (69 mg, 68%) as a white solid. $^1$H NMR (400 MHz, DMSO-$d_6$) δ 13.66 (br. s., 1H), 7.86-7.76 (m, 3H), 7.72 (s, 1H), 7.66-7.48 (m, 3H), 7.30-7.19 (m, 1H), 6.96-6.84 (m, 2H), 6.71 (s, 2H), 3.68 (dd, J=7.0, 9.9 Hz, 1H), 3.48-3.23 (m, 4H), 2.28-2.15 (m, 1H), 2.04-1.90 (m, 1H). LCMS M/Z (M+H) 397.

Example 218

2-(6-amino-5-(1-benzylpiperidin-4-yl)pyridazin-3-yl)phenol

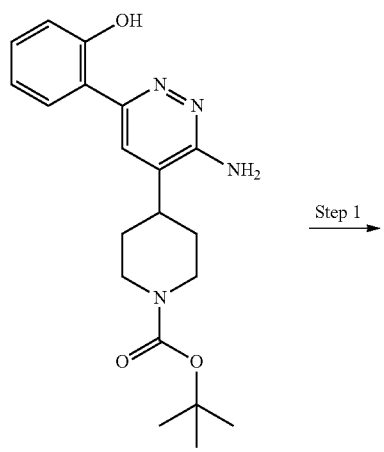

Step 1

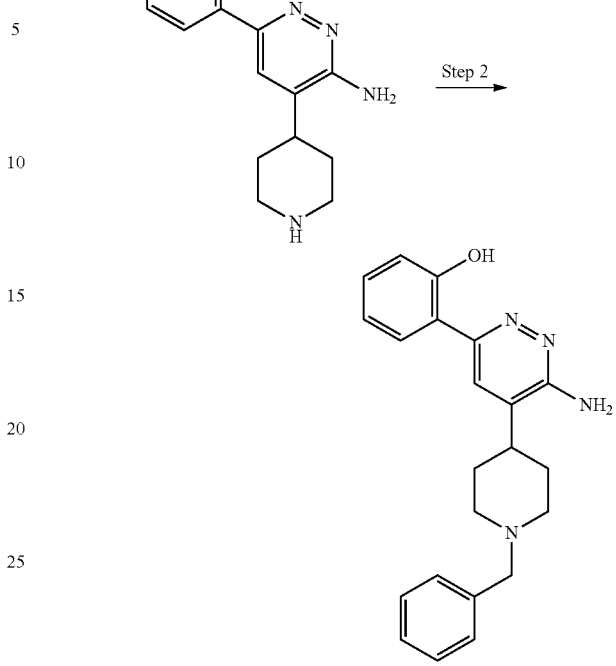

Step 1: 2-(6-amino-5-(piperidin-4-yl)pyridazin-3-yl)phenol Hydrochloride

To a solution of tert-Butyl 4-(3-amino-6-(2-hydroxyphenyl)pyridazin-4-yl)piperidine-1-carboxylate (195 mg, 0.54 mmol) (prepared from tert-butyl 4-(4,4,5,5-tetramethyl-1,3,2-dioxaborolan-2-yl)-3,6-dihydropyridine-1(2H)-carboxylate in a manner similar to that used for example G02925685) in methanol, hydrochloric acid (4 M in Dioxane) (0.16 g, 4.32 mmol) was added, and the reaction mixture was stirred at 25° C. for 4 h. Volatiles were evaporated under reduced pressure, and the solid residue was submitted to high vacuum to afford the title compound (0.1 g, 0.31 mmol). LCMS M/Z (M+H) 271.

Step 2: 2-(6-amino-5-(1-benzylpiperidin-4-yl)pyridazin-3-yl)phenol 2,2,2-trifluoroacetate 2-(6-amino-5-(piperidin-4-yl)pyridazin-3-yl)phenol dihydrochloride (45 mg, 0.16 mmol) was dissolved in tetrahydrofuran, benzaldehyde (0.02 g, 0.16 mmol) was added, and the mixture was stirred 15 min. Sodium cyanoborohydride (0.02 g, 0.32 mmol) was added, and the mixture was stirred 1 h. The reaction mixture was concentrated, re-dissolved in methanol, and purified by preparative reverse phase HPLC (eluting with acetonitrile/water/0.1% trifluoroacetic acid). Pure fractions were pooled, frozen, and lyophilized to yield the title compound as the trifluoroacetic acid salt (0.01 g, 0.03 mmol, 19%). $^1$H NMR (400 MHz, DMSO-$d_6$) δ 9.66 (br. s, 1H), 7.86 (s, 1H), 7.71-7.74 (m, 1H), 7.50-7.58 (m, 5H), 7.28-7.32 (m, 1H), 6.91-6.97 (m, 1H), 4.39 (s, 2H), 3.53-3.57 (m, 1H), 3.28-3.32 (m, 1H), 3.00-3.03 (m, 2H), 2.86-2.88 (m, 1H), 2.07-2.11 (m, 2H), 1.85-1.91 (m, 2H). LCMS M/Z (M+H) 361.

Example 219

2-(6-amino-5-(1-tosylpiperidin-4-yl)pyridazin-3-yl)phenol

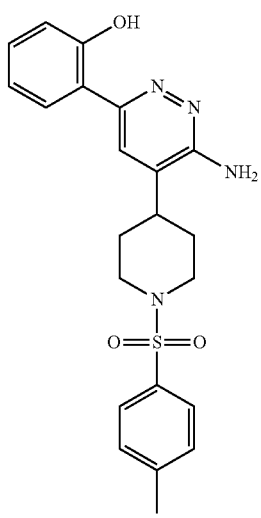 [SMILES: Cc1ccc(S(=O)(=O)N2CCC(c3cc(-c4ccccc4O)nnc3N)CC2)cc1]

To 2-(6-amino-5-(piperidin-4-yl)pyridazin-3-yl)phenol dihydrochloride (49 mg, 0.15 mmol) (prepared as described for Example G02938491) dissolved in tetrahydrofuran (2 mL), was added diisopropylethylamine (0.11 mL, 0.64 mmol), followed by 4-methylbenzene-1-sulfonyl chloride (0.03 g, 0.16 mmol). The reaction mixture was stirred at 60° C. for 30 min. Volatiles were evaporated under reduced pressure. The crude residue was dissolved in methylene chloride and injected on a pre-conditioned silica column (eluting with ethyl acetate and methanol). Pure fractions were pooled and concentrated in vacuo to give a residue that was lyophilized from acetonitrile and water to afford the title compound (0.03 g, 0.06 mmol). $^1$H NMR (400 MHz, DMSO-d$_6$) δ 13.85 (s, 1H), 7.98 (dd, J=1.3, 8.4 Hz, 1H), 7.92 (s, 1H), 7.68 (d, J=8.1 Hz, 2H), 7.50 (d, J=8.3 Hz, 2H), 7.27-7.14 (m, 1H), 6.83-6.95 (m, 2H), 6.63 (s, 2H), 3.78 (d, J=11.2 Hz, 2H), 2.57 (t, J=10.9 Hz, 1H), 2.43 (s, 3H), 2.13-2.36 (m, 2H), 1.74-2.03 (m, 4H). LCMS M/Z (M+H) 425.

Example 220 and 221

Cis- and trans-1-(3-(3-amino-6-(2-hydroxyphenyl)pyridazin-4-yl)-8-azabicyclo[3.2.1]octan-8-yl)ethanone

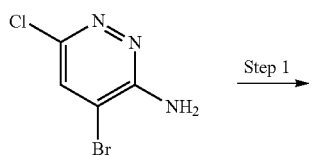

Step 1 →

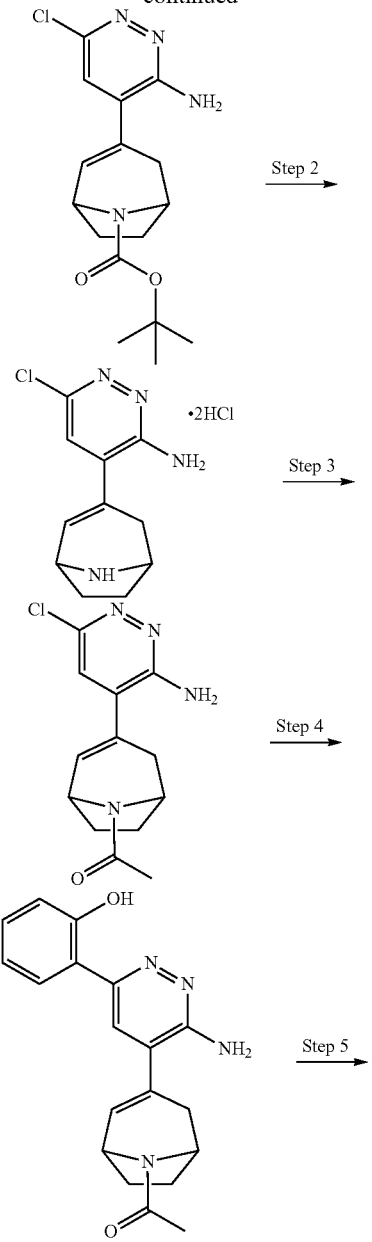

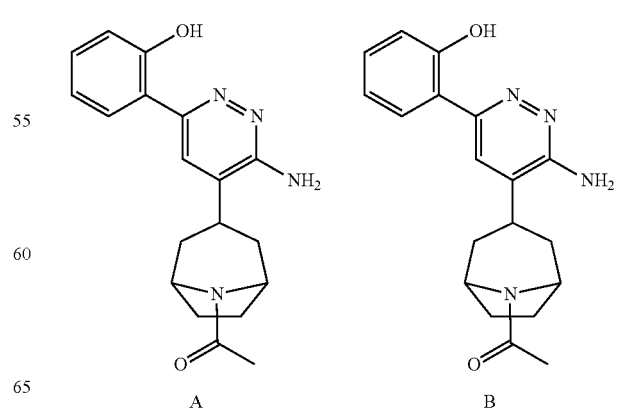

Step 1: tert-butyl 3-(3-amino-6-chloropyridazin-4-yl)-8-azabicyclo[3.2.1]oct-3-ene-8-carboxylate 4-bromo-6-chloropyridazin-3-amine (0.155 g, 0.7436 mmol), tert-butyl 3-(4,4,5,5-tetramethyl-1,3,2-dioxaborolan-2-yl)-8-azabicyclo[3.2.1]oct-3-ene-8-carboxylate (0.245 g, 0.7308 mmol), and potassium carbonate (0.1028 g, 0.7436 mmol) were placed in a sealable tube. The reaction vessel was purged with nitrogen. Dioxane (3 mL) and water (1 mL) added. tetrakis(triphenylphosphine)palladium(0) (0.0859 g, 0.0744 mmol) was added. The reaction mixture was degassed with a nitrogen stream before being sealed and stirred at 95° C. 16 h. The organic supernatant was concentrated under reduced pressure, and the crude residue was purified by silica gel chromatography (eluting with ethyl acetate and methanol). Pure fractions were pooled and concentrated in vacuo to yield the title compound (0.15 g, 0.4453 mmol, 60%). LCMS M/Z (M+H, chloride pattern) 337/339.

Step 2: 4-(8-azabicyclo[3.2.1]oct-3-en-3-yl)-6-chloropyridazin-3-amine Dihydrochloride tert-butyl 3-(3-amino-6-chloropyridazin-4-yl)-8-azabicyclo[3.2.1]oct-3-ene-8-carboxylate (150 mg, 0.45 mmol) was dissolved in methanol, for the addition of hydrochloric acid (4 M in dioxane) (0.9 mL, 3.6 mmol). The reaction was stirred at room temperature for 2 h before being concentrated in vacuo and dried under high vacuum to give the title compound (0.14 g, 0.46 mmol) was obtained. LCMS M/Z (M+H, Cl pattern) 237/239.

Step 3: 1-(3-(3-amino-6-chloropyridazin-4-yl)-8-azabicyclo[3.2.1]oct-3-en-8-yl)ethanone 4-(8-azabicyclo[3.2.1]oct-3-en-3-yl)-6-chloropyridazin-3-amine dihydrochloride (0.14 g, 0.46 mmol) was dissolved in tetrahydrofuran (4.6 mL) for the addition of diisopropylethylamine (0.28 mL, 1.52 mmol), followed by acetic anhydride (0.1 g, 0.99 mmol). The reaction mixture was stirred at 50° C. for 30 min. Volatiles were removed under reduced pressure, and the crude residue was purified by silica gel chromatography (eluting with ethyl acetate and methanol) to afford the title compound (0.09 g, 0.34 mmol, 74%) LCMS M/Z (M+H, Cl pattern) 279/281.

Step 4: 1-(3-(3-amino-6-(2-hydroxyphenyl)pyridazin-4-yl)-8-azabicyclo[3.2.1]oct-3-en-8-yl)ethanone 1-(3-(3-amino-6-chloropyridazin-4-yl)-8-azabicyclo[3.2.1]oct-3-en-8-yl)ethanone (0.09 g, 0.34 mmol), (2-hydroxyphenyl)boronic acid (0.062 g, 0.449 mmol), potassium carbonate (0.099 g, 0.718 mmol) and methanesulfonato(2-dicyclohexylphosphino-2',4',6'-tri-i-propyl-1,1'-biphenyl)(2'-amino-1,1'-biphenyl-2-yl)palladium(II) (0.030 g, 0.0359 mmol) were placed in a sealable tube which was purged with nitrogen. Dioxane (2 ml) and water (0.7 ml) were added. The reaction mixture was degassed with a stream of nitrogen and stirred at 95° C. for 16 h. The organic supernatant was concentrated in vacuo, and the crude residue was purified by silica gel chromatography (eluting with ethyl acetate and methanol) to afford the title compound (0.12 g, 0.34 mmol, 99%). LCMS M/Z (M+H) 357.

Step 5: 1-(3-(3-amino-6-(2-hydroxyphenyl)pyridazin-4-yl)-8-azabicyclo[3.2.1]octan-8-yl)ethanone (2 Isomers)

1-(3-(3-amino-6-(2-hydroxyphenyl)pyridazin-4-yl)-8-azabicyclo[3.2.1]oct-3-en-8-yl)ethanone was dissolved in methanol:ethyl acetate (1 mL:1 mL). Palladium on Charcoal (5% moist added) was added, the reaction vessel was sealed, and the reaction vessel was sealed and put under a hydrogen atmosphere using vacuum/hydrogen cycles. The reaction mixture was stirred for 16 h before the reaction mixture was filtered on celite, concentrated in vacuo, and purified by silic gel chromatography (eluting with ethyl acetate and methanol). First eluting peak: EXAMPLE 220 (0.01 g, 0.04 mmol) (arbitrary assignment of stereochemistry), 11% yield. $^1$H NMR (400 MHz, DMSO-$d_6$) δ 13.79 (br. s., 1H), 7.96 (dd, J=1.22, 8.30 Hz, 1H), 7.91 (s, 1H), 7.17-7.27 (m, 1H), 6.81-6.93 (m, 2H), 6.66 (s, 2H), 4.50-4.60 (m, 1H), 4.22-4.33 (m, 1H), 3.11-3.27 (m, 1H), 2.04-2.08 (m, 1H), 2.02 (s, 3H), 2.00-2.04 (m, 1H), 1.94-2.00 (m, 1H), 1.84-1.93 (m, 1H), 1.56-1.85 (m, 4H) LCMS M/Z (M+H) 339. Second eluting peak: Example 221 (0.02 g, 0.07 mmol) (arbitrary assignment of stereochemistry), 19% yield. $^1$H NMR (400 MHz, DMSO-$d_6$) δ 13.79 (s, 1H), 7.95-8.03 (m, 2H), 7.18-7.28 (m, 1H), 6.84-6.96 (m, 2H), 6.59 (s, 2H), 4.57 (t, J=7.57 Hz, 1H), 4.25 (t, J=7.32 Hz, 1H), 2.68 (s, 1H), 2.38-2.47 (m, 1H), 2.19-2.33 (m, 1H), 2.03 (s, 3H), 1.61-1.99 (m, 5H), 1.45-1.58 (m, 1H). LCMS M/Z (M+H) 339.

Example 222

2-(6-amino-5-(1-tosyl-1,2,3,6-tetrahydropyridin-4-yl)pyridazin-3-yl)phenol

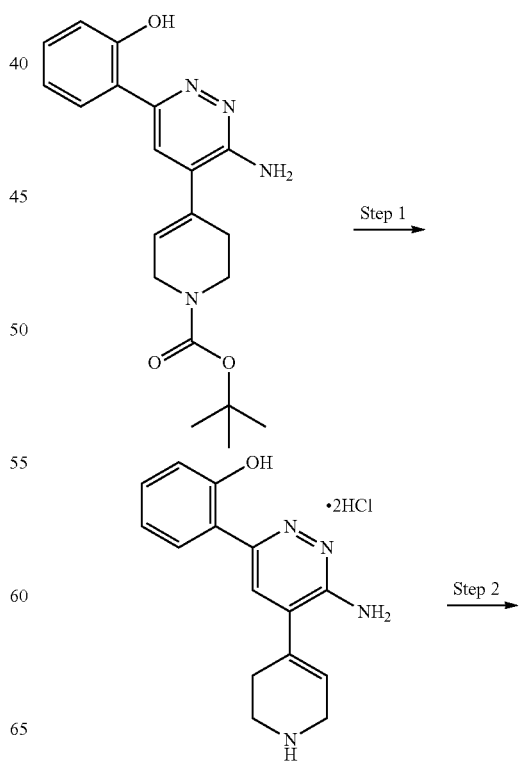

-continued

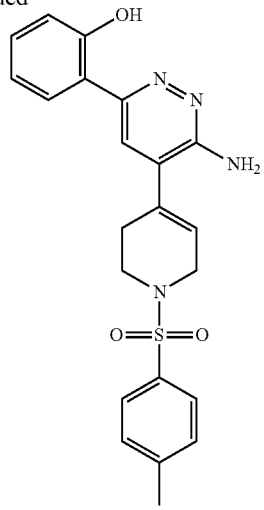

Step 1: 2-(6-amino-5-(1,2,3,6-tetrahydropyridin-4-yl)pyridazin-3-yl)phenol Dihydrochloride tert-Butyl 4-(3-amino-6-(2-hydroxyphenyl)pyridazin-4-yl)-3,6-dihydropyridine-1(2H)-carboxylate (195 mg, 0.54 mmol) (prepared as described in example G02925685 using tert-butyl 4-(4,4,5,5-tetramethyl-1,3,2-dioxaborolan-2-yl)-3,6-dihydropyridine-1(2H)-carboxylate) was dissolved in methanol (4 mL) for the addition of hydrochloric acid (4 M in Dioxane) (1.08 mL, 4.32 mmol). The reaction mixture was stirred for 30 min before being evaporated under reduced pressure. The solid was dried under high vacuum for 2 h to afford the title compound (0.25 g, 0.74 mmol) in quantitative yield. LCMS M/Z (M+H) 269.0

Step 2: 2-(6-amino-5-(1-tosyl-1,2,3,6-tetrahydropyridin-4-yl)pyridazin-3-yl)phenol 2-(6-amino-5-(1,2,3,6-tetrahydropyridin-4-yl)pyridazin-3-yl)phenol dihydrochloride (87 mg, 0.34 mmol) was dissolved in tetrahydrofuran (1.6 mL), and diisopropylethylamine (0.25 mL, 1.36 mmol) was added, followed by 4-methylbenzene-1-sulfonyl chloride (0.06 g, 0.34 mmol). The solution was stirred at 60° C. for 45 min. The crude reaction mixture was deposited on silica and purified by silica gel chromatography (eluting with ethyl acetate and methanol). Pure fractions were concentrated in vacuo. The solid residue was lyophilized from acetonitrile and water to afford the title compound (0.025 g, 0.06 mmol, 18%). $^1$H NMR (400 MHz, DMSO-$d_6$) δ=13.64 (s, 1H), 7.78-7.94 (m, 2H), 7.73 (d, J=8.3 Hz, 2H), 7.49 (d, J=8.3 Hz, 2H), 7.24 (t, J=7.7 Hz, 1H), 6.72-7.03 (m, 2H), 6.51 (s, 2H), 5.94 (br. s., 1H), 3.66 (d, J=2.7 Hz, 2H), 3.26 (t, J=5.5 Hz, 2H), 2.45-2.48 (m, 2H), 2.29-2.46 (s, 3H). LCMS M/Z (M+H) 423.

Example 223

2-(6-amino-5-(1-benzyl-1,2,3,6-tetrahydropyridin-4-yl)pyridazin-3-yl)phenol

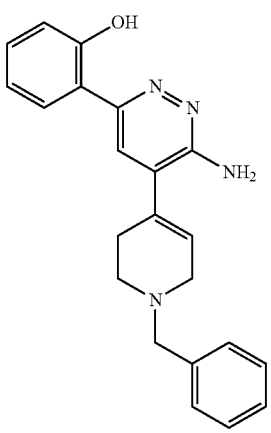 [SMILES: Nc1nnc(-c2ccccc2O)cc1C1=CCN(Cc2ccccc2)CC1]

2-(6-amino-5-(1,2,3,6-tetrahydropyridin-4-yl)pyridazin-3-yl)phenol (86 mg, 0.34 mmol) (prepared as described in example G02938890) was dissolved in tetrahydrofuran (1.5 ml) for the addition of diisopropylethylamine (0.25 mL, 1.36 mmol), followed by (bromomethyl)benzene (0.06 g, 0.34 mmol). The reaction mixture was stirred at 70° C. for 24 h. Volatiles were evaporated, and the crude residue was purified by silica gel chromatography (eluting with methylene chloride, methanol, and ammonium hydroxide). Pure fractions were concentrated in vacuo and lyophilized from acetonitrile and water to obtain the title compound (12 mg, 0.03 mmol, 10%). $^1$H NMR (400 MHz, DMSO-$d_6$) δ 13.74 (s, 1H), 7.77-8.02 (m, 2H), 7.29-7.41 (m, 3H), 7.15-7.29 (m, 2H), 6.79-6.98 (m, 2H), 6.47 (s, 3H), 6.05 (br. s., 1H), 3.62 (s, 2H), 3.11 (d, J=2.9 Hz, 2H), 2.69 (t, J=5.4 Hz, 2H), 2.45 (br. s., 2H). LCMS M/Z (M+H) 359.

Example 224

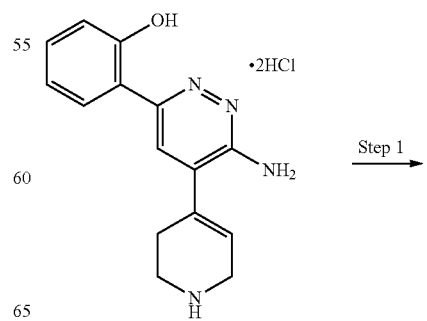

Step 1

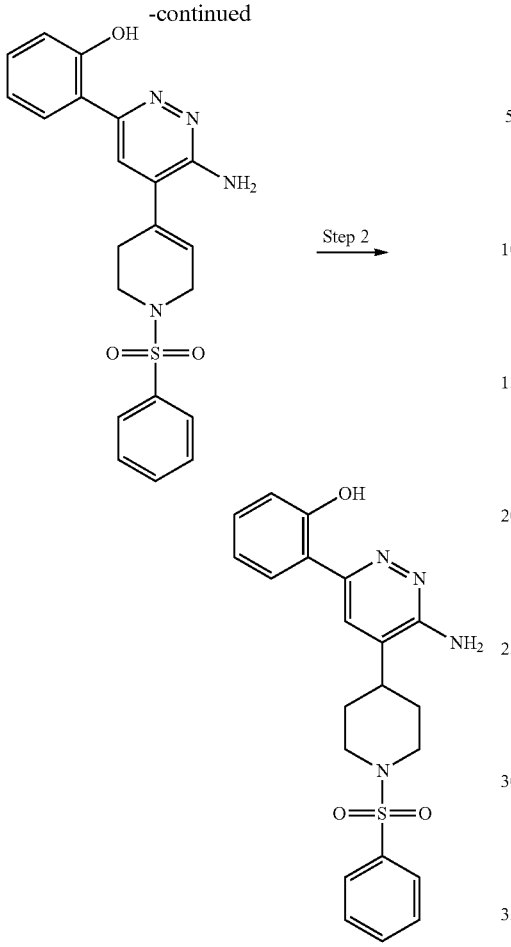

Step 1: 2-(6-amino-5-(1-(phenylsulfonyl)piperidin-4-yl)pyridazin-3-yl)phenol 2-(6-amino-5-(1,2,3,6-tetrahydropyridin-4-yl)pyridazin-3-yl)phenol dihydrochloride (99.5 mg, 0.32 mmol) (prepared according to example G02938890) was dissolved in tetrahydrofuran for the addition of diisopropylethylamine (0.23 mL, 1.32 mmol) and benzenesulfonyl chloride (0.06 g, 0.33 mmol). The reaction mixture was stirred at 60° C. until complete. The reaction was concentrated in vacuo, and the residue was used crude in the subsequent reaction.

Step 2: 2-(6-amino-5-(1-(phenylsulfonyl)piperidin-4-yl)pyridazin-3-yl)phenol The crude residue of 2-(6-amino-5-(1-(phenylsulfonyl)-1,2,3,6-tetrahydropyridin-4-yl)pyridazin-3-yl)phenol was dissolved in tetrahydrofuran:methanol:ethyl acetate (1:1:1), and palladium on charcoal (5%, moist) was added (100 mg). The reaction flask was stoppered with a septum, put under an atmosphere of hydrogen using vacuum/hydrogen cycles (3×), and stirred vigorously under hydrogen atmosphere for 16 h. The mixture was concentrated in vacuo and purified by silica gel chromatography (eluting with hexanes and ethyl acetate) to afford the title compound, which was lyophilized from acetonitrile and water (35 mg, 0.085 mmol, 27%). LCMS M/Z (M+H) 411.

Examples 225 and 226

2-(6-amino-5-((1,4-trans)-4-methylcyclohexyl)pyridazin-3-yl)phenol and Cis-2-(6-amino-5-((1,4-cis-4-methylcyclohexyl)pyridazin-3-yl)phenol

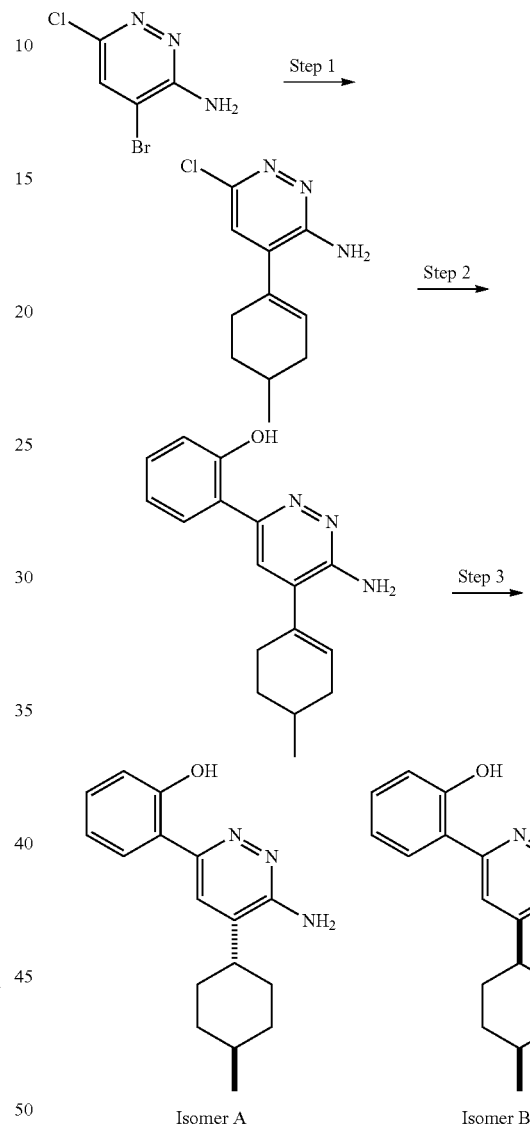

Isomer A        Isomer B

Step 1: 6-chloro-4-(4-methylcyclohex-1-en-1-yl)pyridazin-3-amine 4-bromo-6-chloropyridazin-3-amine (0.3688 g, 1.7692 mmol), 4,4,5,5-tetramethyl-2-(4-methylcyclohex-1-en-1-yl)-1,3,2-dioxaborolane (393 mg, 1.7692 mmol) (prepared from 4-methyl cyclohexanone using procedures found in patents WO 2005092863 and 2011032277), and potassium phosphate (0.7511 g, 3.5384 mmol) were placed in a sealable tube. The reaction vessel's atmosphere was purged with nitrogen. Dioxane (2 mL) and water (0.7 ml) added. The reaction mixture was degassed with a stream of nitrogen. Tetrakis(triphenylphosphine)palladium(0) (200 mg, 0.173 mmol) was added. The reaction mixture was stirred at 95° C.

for 16 h. After cooling down, the organic supernatant was isolated, deposited on silica and purified by silica gel chromatography (eluting with ethyl acetate/methanol). Concentration in vacuo of the pure fractions afforded 6-chloro-4-(4-methylcyclohex-1-en-1-yl)pyridazin-3-amine (0.264 g, 1.1801 mmol, 67% yield). LCMS M/Z (M+H) 224.

Step 4: 2-(6-amino-5-(4-methylcyclohex-1-en-1-yl)pyridazin-3-yl)phenol 1-(4-(3-amino-6-chloropyridazin-4-yl)-2-methylpiperazin-1-yl)ethanone (81 mg, 0.3003 mmol), (2-hydroxyphenyl)boronic acid (0.0497 g, 0.3604 mmol), potassium carbonate (0.0913 g, 0.6607 mmol), and methanesulfonato(2-dicyclohexylphosphino-2',6'-dimethoxy-1,1'-biphenyl)(2'-amino-1,1'-biphenyl-2-yl)palladium(II) (0.0234 g, 0.03 mmol) were placed in a sealable tube. The reaction vessel's atmosphere was purged with nitrogen. Dioxane (2 mL) and water (0.7 ml) were added. The reaction mixture was degassed with a stream of nitrogen. The reaction mixture was heated at 95° C. for 16 h. The reaction mixture was partitioned between ethyl acetate and sodium bicarbonate (aq., sat.). The organic layer was washed with brine, dried with sodium sulfate, filtered, and concentrated to afford the title compound, which was used crude in the subsequent reaction.

Step 5: 2-(6-amino-5-(4-methylcyclohexyl)pyridazin-3-yl)phenol; 2 isomers

The crude residue from previous step (2-(6-amino-5-(4-methylcyclohex-1-en-1-yl)pyridazin-3-yl)phenol) was dissolved in ethyl acetate (2 mL). Palladium hydroxide (20% on charcoal) was added (20 mg). The reaction vessel was evacuated and back filled with hydrogen multiple times. The heterogeneous mixture was stirred for 4 h. The reaction mixture was filtered on celite and the filtrate was concentrated in vacuo. Silica gel chromatography (eluting with ethyl acetate/methanol) afforded the two parent compounds, which were arbitrarily assigned. Early eluting fractions: Arbitrarily assigned as 2-(6-amino-5-((1,4-trans)-4-methylcyclohexyl)pyridazin-3-yl)phenol (12.00 mg, 42.34 µmol, 3.5% yield over 2 steps). $^1$H NMR (400 MHz, DMSO-$d_6$) δ 13.91 (s, 1H), 7.95-7.99 (m, 1H), 7.86 (s, 1H), 7.21 (dt, J=1.95, 7.69 Hz, 1H), 6.87-6.93 (m, 2H), 6.62 (s, 2H), 1.97-1.99 (m, 1H), 1.64-1.85 (m, 4H), 1.38-1.62 (m, 4H), 1.12-1.21 (m, 1H), 0.92 (d, J=6.35 Hz, 3H). LCMS M/Z (M+H) 284. Late eluting fractions: Arbitrarily assigned as 2-(6-amino-5-((1,4-cis)-4-methylcyclohexyl)pyridazin-3-yl)phenol (37.00 mg, 130.5 µmol, 11% yield over 2 steps). $^1$H NMR (400 MHz, DMSO-$d_6$) δ 13.94 (s, 1H), 7.94-7.98 (m, 1H), 7.91 (s, 1H), 7.21-7.25 (dt, J=1.95 Hz, 7.96 Hz, 1H), 6.87-6.93 (m, 2H), 6.61 (s, 2H), 2.52-2.61 (m, 1H), 1.72-1.83 (m, 4H), 1.48-1.59 (m, 4H), 1.06-1.11 (m, 1H), 1.06 (d, J=6.35 Hz, 3H). LCMS M/Z (M+H) 284.

Example 227

1-(4-(3-amino-6-(2-hydroxyphenyl)pyridazin-4-yl)piperidin-1-yl)ethanone

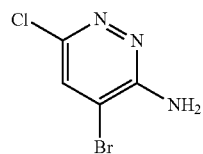

Step 1

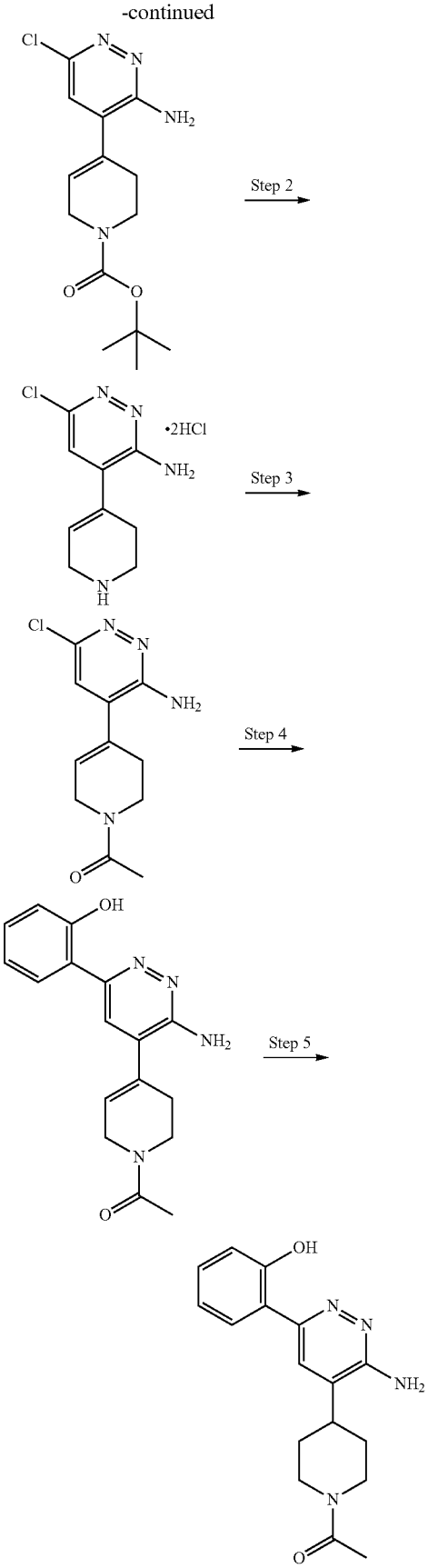

Step 1: tert-butyl 4-(3-amino-6-chloropyridazin-4-yl)-5,6-dihydropyridine-1(2H)-carboxylate 4-bromo-6-chloropyridazin-3-amine (0.5323 g, 2.5536 mmol), tert-butyl 4-(4,4,5,5-tetramethyl-1,3,2-dioxaborolan-2-yl)-5,6-dihydropyridine-1(2H)-carboxylate (0.987 g, 3.192 mmol), and potassium phosphate (1.0841 g, 5.1072 mmol) were placed in a sealable tube and dissolved in dioxane (3 mL) and water (1 mL). The tube was sealed and placed under an atmosphere of nitrogen. Tetrakis(triphenylphosphine)palladium(0) (0.2066 g, 0.1788 mmol) was added, and the reaction mixture was heated at 90° C. for 16 h. The organic supernatant was isolated and concentrate in vacuo to yield a crude residue that was purified by silica gel chromatography (eluting with hexanes and ethyl acetate). Pure fractions were pooled and concentrated in vacuo to afford the title compound (0.45 g, 1.448 mmol, 57%). LCMS M/Z (M+H) 310.9.

Step 2: 6-chloro-4-(1,2,3,6-tetrahydropyridin-4-yl)pyridazin-3-amine Dihydrochloride tert-butyl 4-(3-amino-6-chloropyridazin-4-yl)-5,6-dihydropyridine-1(2H)-carboxylate (450 mg, 1.45 mmol) was dissolved in dioxane (1 ml) and stirred for the addition of hydrochloric acid in dioxane (4 M, 1.45 ml, 5.8 mmol). The mixture was stirred for 12 h. Volatiles were removed under reduced pressure to afford the title compound (0.43 g, 1.51 mmol). LCMS M/Z (M+H) 211/213.

Step 3: 1-(4-(3-amino-6-chloropyridazin-4-yl)-5,6-dihydropyridin-1(2H)-yl)ethanone 6-chloro-4-(1,2,3,6-tetrahydropyridin-4-yl)pyridazin-3-amine dihydrochloride (250 mg, 0.88 mmol) was dissolved in tetrahydrofuran, diisopropylethylamine (0.47 mL, 2.64 mmol) was added, followed by acetic anhydride (0.09 g, 0.88 mmol). The reaction was stirred at room temperature for 30 min. The solvent was removed in vacuo, and the crude residue was purified by silica gel chromatography (eluting with ethyl acetate and methanol) to afford the title compound (0.175 g, 0.69 mmol, 78%). LCMS M/Z (M+H) 253/255

Step 4: 1-(4-(3-amino-6-(2-hydroxyphenyl)pyridazin-4-yl)-5,6-dihydropyridin-1(2H)-yl)ethanone 1-(4-(3-amino-6-chloropyridazin-4-yl)-5,6-dihydropyridin-1(2H)-yl)ethanone (175 mg, 0.6925 mmol), (2-hydroxyphenyl)boronic acid (0.1146 g, 0.831 mmol), potassium carbonate (0.1914 g, 1.385 mmol), and methanesulfonato (2-dicyclohexylphosphino-2',4',6'-tri-i-propyl-1,1'-biphenyl)(2'-amino-1,1'-biphenyl-2-yl)palladium(II) (0.0469 g, 0.0554 mmol) were placed in a sealable tube, which was purged with nitrogen. Dioxane (3 mL) and water (1 mL) added, and the mixture was degassed with nitrogen. The reaction mixture was stirred at 95° C. for 16 h. The organic supernatant was isolated, impregnated on silica, and purified by silica gel chromatography (eluting with ethyl acetate/methanol). Pure fractions were concentrated in vacuo to afford the title compound (0.097 g, 0.3125 mmol, 45%). LCMS M/Z (M+H) 311.

Step 5: 1-(4-(3-amino-6-(2-hydroxyphenyl)pyridazin-4-yl)piperidin-1-yl)ethanone In a 25 mL-round bottom flask equipped with a magnetic stir bar, 1-(4-(3-amino-6-(2-hydroxyphenyl)pyridazin-4-yl)-5,6-dihydropyridin-1(2H)-yl)ethanone (95 mg, 0.32 mmol) was dissolved in 1:1:1 methanol:ethyl acetate: tetrahydrofuran (3 mL). Palladium on charcoal (5%, moist) was added (90 mg), and the reaction vessel was sealed and put under a hydrogen atmosphere using vacuum/hydrogen cycles. The reaction mixture was stirred for 16 h before being filtered over celite and concentrate in vacuo. The crude residue was purified by silic gel chromatography (eluting with ethyl acetate and methanol). Pure fractions were concentrate in vacuo and lyophilized from acetonitrile/water to yield the title compound (0.08 g, 0.26 mmol, 81%). $^1$H NMR (400 MHz, DMSO-$d_6$) δ 13.88 (s, 1H), 7.96 (dd, J=1.34, 7.93 Hz, 1H), 7.91 (s, 1H), 7.18-7.28 (m, 1H), 6.83-6.93 (m, 2H), 6.75 (br. s, 2H), 4.57 (d, J=13.18 Hz, 1H), 3.95 (d, J=13.67 Hz, 1H), 3.08-3.25 (m, 1H), 2.81-2.97 (m, 1H), 2.54-2.70 (m, 1H), 2.04 (s, 3H), 1.76-1.91 (m, 2H), 1.69 (dd, J=3.78, 12.09 Hz, 1H), 1.56 (dd, J=4.15, 12.21 Hz, 1H). LCMS M/Z (M+H) 313.

Example 228

2-(6-amino-5-(1-(methylsulfonyl)piperidin-4-yl)pyridazin-3-yl)phenol

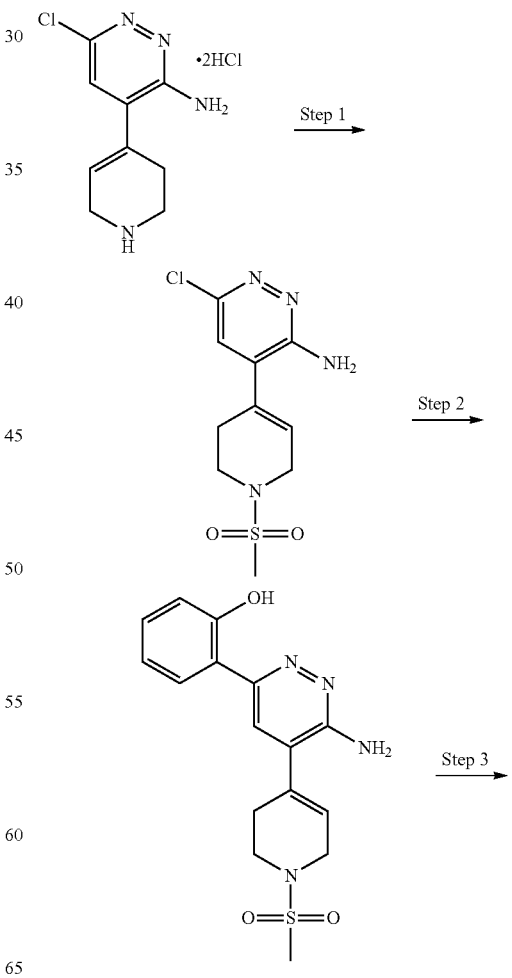

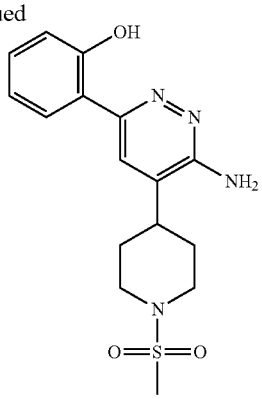

Step 1: 6-chloro-4-(1-(methylsulfonyl)-1,2,3,6-tetrahydropyridin-4-yl)pyridazin-3-amine 2-(6-amino-5-(1,2,3,6-tetrahydropyridin-4-yl)pyridazin-3-yl)phenol dihydrochloride (189 mg, 0.67 mmol) (prepared according to example G02939675) was dissolved in tetrahydrofuran (3 mL) for the addition of diisopropylethylamine (0.48 mL, 1.76 mmol) and methanesulfonyl chloride (50 µL, 0.44 mmol). The mixture was stirred at room temperature for 30 min. The reaction mixture was concentrated in vacuo, and the residue was purified by silica gel chromatography (eluting with ethyl acetate and methanol) to give the title compound (0.089 g, 0.31 mmol, 52%). LCMS M/Z (M+H) 288.9.

Step 2: 2-(6-amino-5-(1-(methylsulfonyl)-1,2,3,6-tetrahydropyridin-4-yl)pyridazin-3-yl)phenol 6-chloro-4-(1-(methylsulfonyl)-1,2,3,6-tetrahydropyridin-4-yl)pyridazin-3-amine (89 mg, 0.3082 mmol), (2-hydroxyphenyl)boronic acid (0.0425 g, 0.3082 mmol), potassium carbonate (0.0426 g, 0.3082 mmol) and methanesulfonato(2-dicyclohexylphosphino-2',4',6'-tri-i-propyl-1,1'-biphenyl)(2'-amino-1,1'-biphenyl-2-yl)palladium(II) (0.026 g, 0.0308 mmol) were placed in a sealable tube and purged with nitrogen. Dioxane (2 ml) and water (0.7 ml) were added, and the vessel was degassed with nitrogen and stirred at 95° C. for 16 h. The organic supernatant was impregnated on silica for purification by silica gel chromatography (eluting with ethyl acetate and methanol) to afford the title compound (0.088 g, 0.254 mmol, 82%). LCMS M/Z (M+H) 346.9.

Step 3: 2-(6-amino-5-(1-(methylsulfonyl)piperidin-4-yl)pyridazin-3-yl)phenol To 2-(6-amino-5-(1-(methylsulfonyl)-1,2,3,6-tetrahydropyridin-4-yl)pyridazin-3-yl)phenol (10 mg, 0.03 mmol) dissolved in 1:1:1 (methanol:ethyl acetate:tetrahydrofuran, 3 mL total), Palladium on charcoal (5% loading, moist) was added. The vessel was put under a hydrogen atmosphere using vacuum/hydrogen cycles and stirred for 16 h. The mixture was filtered over celite, concentrated in vacuo, and purified by silica gel chromatography (eluting with ethyl acetate and methanol) to afford the title compound (5 mg, 33%). $^1$H NMR (400 MHz, DMSO-$d_6$) δ 13.86 (s, 1H), 8.07-7.82 (m, 2H), 7.30-7.11 (m, 1H), 6.97-6.80 (m, 2H), 6.74 (s, 2H), 3.73 (d, J=11.7 Hz, 2H), 2.93 (s, 3H), 2.92-2.80 (m, 2H), 2.78 (t, J=11.7 Hz, 1H), 2.05-1.96 (m, 1H), 1.96-1.87 (m, 1H), 1.90-1.70 (m, 2H). LCMS M/Z (M+H) 349.

Example 229

1-(4-(3-amino-6-(2-hydroxyphenyl)pyridazin-4-yl)piperidin-1-yl)-2-hydroxy-2-methylpropan-1-one

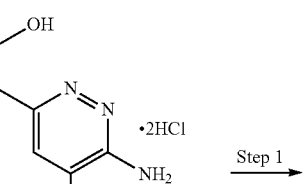
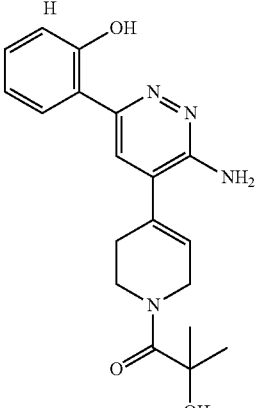
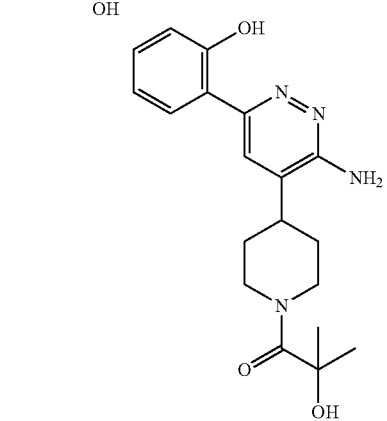

Step 1: 1-(4-(3-amino-6-(2-hydroxyphenyl)pyridazin-4-yl)-5,6-dihydropyridin-1(2H)-yl)-2-hydroxy-2-methylpropan-1-one To 2-(6-amino-5-(1,2,3,6-tetrahydropyridin-4-yl)pyridazin-3-yl)phenol dihydrochloride (0.123 g, 0.35 mmol) (prepared according to example G02939675) was dissolved in dimethylformamide (1.7 mL) was added 2-hydroxy-2-methylpropanoic acid (0.11 g, 1.06 mmol), followed by diisopropylethylamine (0.36 mL, 2.09 mmol). The reaction mixture was cooled to 0° C. and HATU (0.4 g, 1.05 mmol)

was added. The reaction mixture was stirred for 15 min. The reaction mixture was partitioned between ethyl acetate and sodium bicarbonate. The organic layer was isolated, washed with brine, dried with sodium sulfate, filtered, and evaporated under reduced pressure. The crude residue was purified by silica gel chromatography (eluting with ethyl acetate and methanol) to afford the title compound (0.095 g, 0.27 mmol). LCMS M/Z (M+H) 355.

Step 2: 1-(4-(3-amino-6-(2-hydroxyphenyl)pyridazin-4-yl)piperidin-1-yl)-2-hydroxy-2-methyl-propan-1-one 1-(4-(3-amino-6-(2-hydroxyphenyl)pyridazin-4-yl)-5,6-dihydropyridin-1(2H)-yl)-2-hydroxy-2-methylpropan-1-one (95 mg, 0.28 mmol) was dissolved in tetrahydrofuran and methanol for the addition of palladium (5% on charcoal, 55 mg). The reaction vessel was put under an atmosphere of hydrogen using vacuum/hydrogen cycles and stirred for 16 h. The reaction mixture was filtered through celite and the filtrate was concentrated in vacuo for purification by silica gel chromatography (eluting with ethyl acetate and methanol). The pure fractions were pooled and concentrated in vacuo and lyophilized from acetonitrile and water to afford the title compound (0.075 g, 0.21 mmol, 75%). $^1$H-NMR (400 MHz, DMSO-$d_6$) δ 13.85 (s, 1H), 7.99-7.92 (m, 1H), 7.86 (s, 1H), 7.29-7.17 (m, 1H), 6.96-6.84 (m, 2H), 6.74 (s, 2H), 5.36 (s, 1H), 5.15-4.28 (m, 4H), 2.99-2.80 (m, 1H), 1.85 (d, J=12.5 Hz, 2H), 1.76-1.52 (m, 2H), 1.35 (s, 6H). LCMS M/Z (M+H) 357.

Example 230

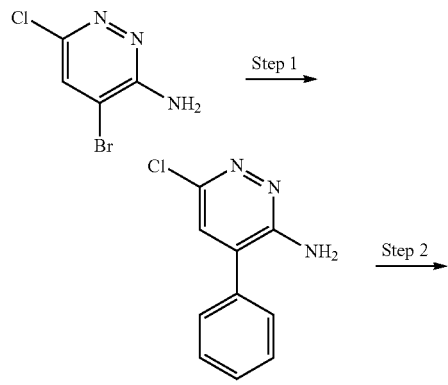

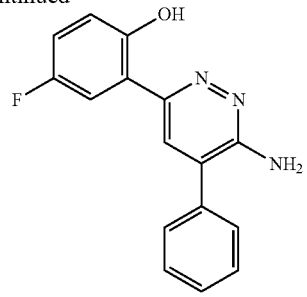

Step 1: 6-chloro-4-phenylpyridazin-3-amine phenylboronic acid (380 mg, 3.1 mmol), 4-bromo-6-chloropyridazin-3-amine (500 mg, 2.4 mmol), tetrakis(triphenylphosphine)palladium(0) (140 mg, 0.12 mmol), potassium carbonate (660 mg, 4.8 mmol), 1,4-dioxane (9.5 mL) and water (0.5 mL) were charged in a disposable reaction tube. The headspace was flushed with nitrogen and the reaction mixture was degassed using 4 cycles of vacuum and nitrogen refilling. The reaction was heated at 100° C. for 5 h, then cooled to room temperature. The crude mixture was purified by silica gel chromatography (eluting with hexanes/ethyl acetate) to obtain the title compound as a beige solid (355 mg; 72% yield). LCMS M/Z (M+H) 206.

Step 2: 2-(6-amino-5-phenylpyridazin-3-yl)-4-fluorophenol 6-chloro-4-phenylpyridazin-3-amine (75 mg, 0.36 mmol), (5-fluoro-2-hydroxyphenyl)boronic acid (0.085 g, 0.55 mmol), potassium carbonate (0.10 g, 0.73 mmol), methanesulfonato(2-dicyclohexylphosphino-2',4',6'-tri-i-propyl-1,1'-biphenyl)(2'-amino-1,1'-biphenyl-2-yl)palladium(II) (0.31 g, 0.36 mmol), 1,4-dioxane (2 mL) and water (0.1 mL) were charged in a vial. The headspace was flushed with nitrogen and the reaction mixture was degassed using 3 cycles of vacuum and nitrogen refilling. The reaction was heated at 90° C. for 3 h, then cooled to room temperature. Silica gel was added and the solvent was removed under vacuum. The desired product was purified by silica gel chromatography (eluting with hexanes/ethyl acetate). The title compound was obtain as a tan solid (67 mg; 65% yield). $^1$H NMR (400 MHz, DMSO-$d_6$) δ 13.39 (s, 1H), 8.07 (s, 1H), 7.87 (dd, J=3.17, 10.50 Hz, 1H), 7.61-7.67 (m, 2H), 7.49-7.60 (m, 3H), 7.09 (dt, J=3.05, 8.48 Hz, 1H), 6.93 (dd, J=5.13, 9.03 Hz, 1H), 6.55 (br. s, 2H). LCMS M/Z (M+H) 282.

The following compounds were prepared in a similar fashion to Example 230:

Examples 231-232

| Example | Compound Name | NMR | m/z |
| --- | --- | --- | --- |
| 231 | 2-(6-amino-5-phenylpyridazin-3-yl)-5-fluorophenol | $^1$H NMR (400 MHz, DMSO-$d_6$) δ 14.24 (s, 1H), 7.98-8.06 (m, 2H), 7.60-7.65 (m, 2H), 7.49-7.59 (m, 3H), 6.73 (s, 2H), 6.47 (br. s, 2H) | 282 |
| 232 | 2-(6-amino-5-phenylpyridazin-3-yl)-4,6-difluorophenol | $^1$H NMR (400 MHz, DMSO-$d_6$) δ 14.06 (s, 1H), 8.11 (s, 1H), 7.79 (td, J = 2.38, 10.38 Hz, 1H), 7.61-7.67 (m, 2H), 7.49-7.60 (m, 3H), 7.29 (ddd, J = 2.93, 8.42, 11.11 Hz, 1H), 6.68 (br. s, 2H) | 300 |

Example 233

2-(6-amino-5-phenylpyridazin-3-yl)-3-fluorophenol

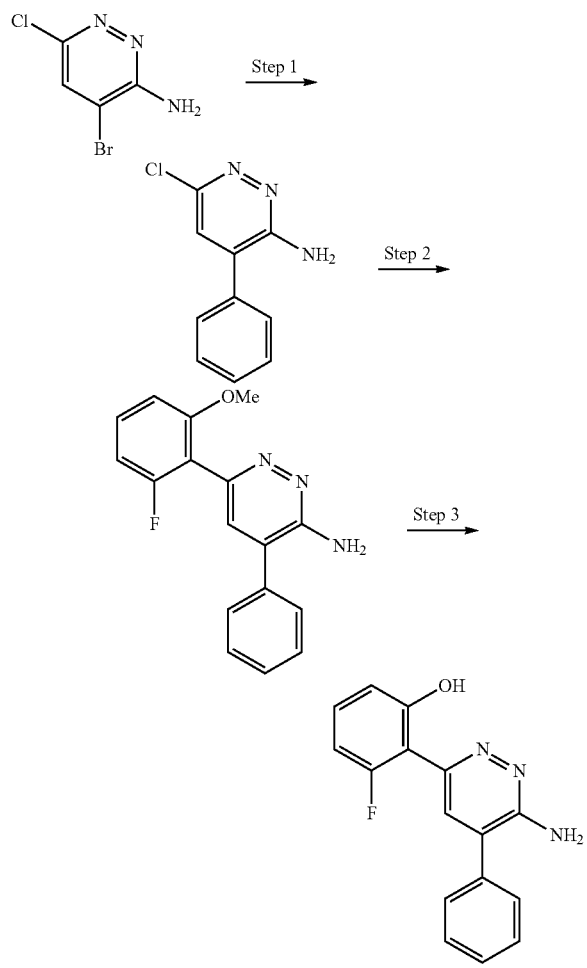

Step 1: 6-chloro-4-phenylpyridazin-3-amine phenylboronic acid (380 mg, 3.1 mmol), 4-bromo-6-chloropyridazin-3-amine (500 mg, 2.4 mmol), tetrakis(triphenylphosphine)-palladium(0) (140 mg, 0.12 mmol), potassium carbonate (660 mg, 4.8 mmol), 1,4-dioxane (9.5 mL) and water (0.5 mL) were charged in a disposable reaction tube. The headspace was flushed with nitrogen and the reaction mixture was degassed using 4 cycles of vacuum and nitrogen refilling. The reaction was heated at 100° C. for 5 h, then cooled to room temperature. The crude mixture was purified by silica gel chromatography (eluting with hexanes/ethyl acetate). The title compound was obtain as a beige solid (355 mg; 72% yield). LCMS M/Z (M+H) 206.

Step 2: 6-(2-fluoro-6-methoxyphenyl)-4-phenylpyridazin-3-amine (2-fluoro-6-methoxyphenyl)boronic acid (0.093 g, 0.55 mmol), 6-chloro-4-phenylpyridazin-3-amine (75 mg, 0.36 mmol), potassium carbonate (0.10 g, 0.73 mmol), methanesulfonato(2-dicyclohexylphosphino-2',4',6'-tri-i-propyl-1,1'-biphenyl)(2'-amino-1,1'-biphenyl-2-yl)palladium(II) (0.015 g, 0.018 mmol), 1,4-dioxane (2 mL) and water (0.1 mL) were charged in a disposable reaction tube. The headspace was flushed with nitrogen and the reaction mixture was degassed using 3 cycles of vacuum and nitrogen refilling. The reaction was heated at 100° C. for 2 h, then cooled to room temperature. The crude mixture was purified by silica gel chromatography (eluting with hexanes/ethyl acetate). The title compound was obtained as a beige solid (105 mg; 97% yield). LCMS M/Z (M+H) 296.

Step 3: 2-(6-amino-5-phenylpyridazin-3-yl)-3-fluorophenol

To a solution of 6-(2-fluoro-6-methoxyphenyl)-4-phenylpyridazin-3-amine (105 mg, 0.356 mmol) in methylene chloride (3.5 mL) at −78° C. was added a solution of boron tribromide (1 M in methylene chloride) (1.8 mL, 1.8 mmol). The reaction was stirred at −78° C. for 30 min then warmed to room temperature. After 3 h at room temperature, the reaction was quenched with water and the desired product was extracted with ethyl acetate (repeated 3 times). The combined organic layers were washed with water, dried with sodium sulfate, filtered and concentrated to dryness under vacuum. The desired product was purified by silica gel chromatography (eluting with hexanes/ethyl acetate). The title compound was obtain as a tan solid (74 mg; 74% yield). $^1$H NMR (400 MHz, DMSO-$d_6$) δ 12.59 (br. s., 1H), 7.41-7.69 (m, 6H), 7.26 (q, J=7.60 Hz, 1H), 6.82 (s, 1H), 6.76 (dd, J=8.55, 11.23 Hz, 1H), 6.49 (br. s., 2H). LCMS M/Z (M+H) 282.

Example 234

3-amino-N-benzyl-6-(2-hydroxyphenyl)pyridazine-4-carboxamide

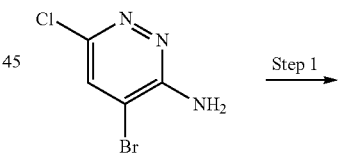

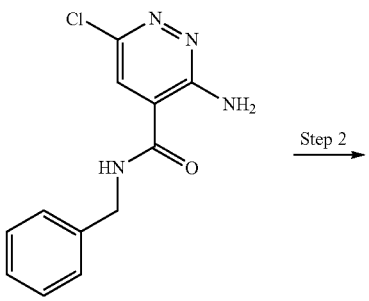

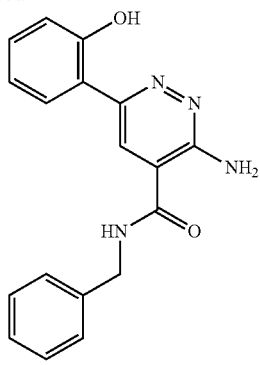

Step 2: 3-amino-N-benzyl-6-chloropyridazine-4-carboxamide phenylmethanamine (0.31 g, 2.9 mmol), 4-bromo-6-chloropyridazin-3-amine (200 mg, 0.96 mmol), tetrakis(triphenylphosphine)palladium(0) (0.12 g, 0.1 mmol), N-ethyl-N-isopropylpropan-2-amine (0.19 g, 1.4 mmol), and dimethylacetamide (4 mL) were charged in a vial. The reaction was heated at 100° C. under a continuous flow of carbon monoxide (bubbling in the reaction mixture) and after 2 h the reaction was cooled to room temperature. The crude mixture was used in the next step. LCMS M/Z (M+H) 263.

Step 2: 3-amino-N-benzyl-6-(2-hydroxyphenyl)pyridazine-4-carboxamide

To the crude mixture of 3-amino-N-benzyl-6-chloropyridazine-4-carboxamide was added (2-hydroxyphenyl)boronic acid (0.158 g, 1.14 mmol), potassium carbonate (0.210 g, 1.52 mmol), methanesulfonato(2-dicyclohexylphosphino-2',4',6'-tri-i-propyl-1,1'-biphenyl)(2'-amino-1,1'-biphenyl-2-yl)palladium(II) (0.032 g, 0.038 mmol), 1,4-dioxane (3 mL) and water (0.15 mL). The headspace was flushed with nitrogen and the reaction mixture was degassed using 3 cycles of vacuum and nitrogen refilling. The reaction was heated at 100° C. for 2 h, then cooled to room temperature. The crude mixture was purified by silica gel chromatography (eluting with hexanes/ethyl acetate). The title compound was obtain as a yellow solid (43 mg; 14% yield). $^1$H NMR (400 MHz, DMSO-d$_6$) δ 13.00 (s, 1H), 9.59 (t, J=5.74 Hz, 1H), 8.45 (s, 1H), 7.88 (dd, J=1.34, 8.18 Hz, 1H), 7.43 (s, 2H), 7.32-7.40 (m, 4H), 7.24-7.31 (m, 2H), 6.92-6.99 (m, 2H), 4.53 (d, J=5.86 Hz, 2H). LCMS M/Z (M+H) 321.

Example 235

3-amino-6-(2-hydroxyphenyl)-N-(trans-2-phenylcyclopropyl)pyridazine-4-carboxamide

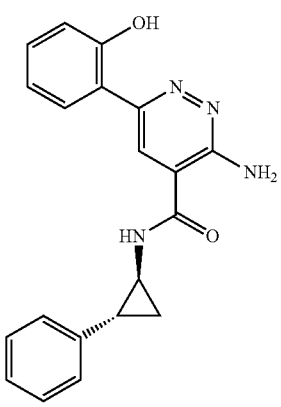 [SMILES: Nc1nnc(-c2ccccc2O)cc1C(=O)N[C@H]1C[C@@H]1c1ccccc1]

4-bromo-6-chloropyridazin-3-amine (300 mg, 1.44 mmol), trans-2-phenylcyclopropanamine (0.767 g, 5.76 mmol), tetrakis(triphenylphosphine)palladium(0) (0.166 g, 0.144 mmol) and dimethylformamide (10 mL) were charged in a disposable reaction tube. The headspace was flushed with nitrogen and the reaction mixture was degassed using 3 cycles of vacuum and nitrogen refilling. The reaction was heated at 85° C. under a continuous flow of carbon monoxide (bubbling in the reaction mixture) and after 90 min the reaction was cooled to room temperature. The headspace was flushed with nitrogen, then (2-hydroxyphenyl)boronic acid (0.397 g, 2.88 mmol), methanesulfonato(2-dicyclohexylphosphino-2',4',6'-tri-i-propyl-1,1'-biphenyl)(2'-amino-1,1'-biphenyl-2-yl)palladium(II) (60 mg) and water (0.3 mL) were added. The reaction mixture was degassed using 3 cycles of vacuum and nitrogen refilling and heated at 100° C. After 3 h, an aqueous solution of ammonium chloride was added and the desired product was extracted with ethyl acetate (repeated three times). The combined organic layers were washed with water, dried with sodium sulfate, filtered and concentrated to dryness under vacuum. The desired product was purified by reverse phase preparative HPLC (eluting with acetonitrile/water/0.1% trifluoroacetic acid) to give the title compound as a light yellow solid (16 mg, 3% yield). $^1$H NMR (400 MHz, DMSO-d$_6$) δ 13.00 (s, 1H), 9.24 (d, J=3.91 Hz, 1H), 8.36 (s, 1H), 7.89 (dd, J=1.59, 7.93 Hz, 1H), 7.36 (br. s, 2H), 7.26-7.32 (m, 3H), 7.16-7.21 (m, 3H), 6.93-6.99 (m, 2H), 3.05 (sxt, J=4.00 Hz, 1H), 2.13-2.21 (m, 1H), 1.34-1.42 (m, 1H), 1.25-1.33 (m, 1H). LCMS M/Z (M+H) 347.

Example 236

(rac)-2-(6-amino-5-(tetrahydrofuran-2-yl)pyridazin-3-yl)phenol

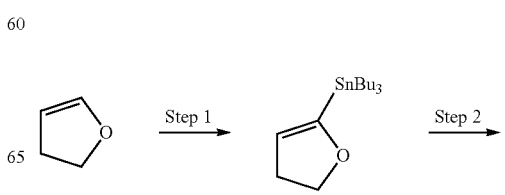

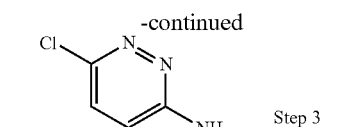

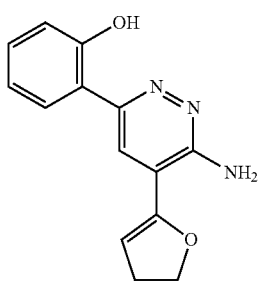

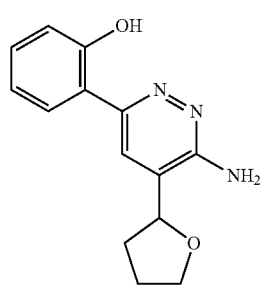

Step 1: tributyl(4,5-dihydrofuran-2-yl)stannane 2,3-dihydrofuran (0.42 g, 5.94 mmol) was dissolved in tetrahydrofuran (30 mL), put under a nitrogen atmosphere, and cooled to −78° C. tert-Butyllithium in pentane (1.7 M, 3.49 mL, 5.94 mmol) was added dropwise under stirring. A color change from colorless to yellow was observed. The reaction mixture was warmed to 0° C., stirred for 1 h at that temperature, and then cooled down to −78° C. Tributylchlorostannane (1.93 g, 5.94 mmol) was added dropwise to the reaction mixture, which was stirred 1 h at −78° C. The reaction mixture was warmed to 0° C., when the volatiles were removed under reduced pressure to afford the title compound as a crude residue that was used immediately in the following step.

Step 2: 6-chloro-4-(4,5-dihydrofuran-2-yl)pyridazin-3-amine 4-bromo-6-chloropyridazin-3-amine (0.46 g, 2.22 mmol) was dissolved in dimethylformamide (10 mL), lithium chloride (0.14 g, 3.36 mmol) was added, followed by tributyl (4,5-dihydrofuran-2-yl)stannane (1.21 g, 3.36 mmol). The reaction mixture was degassed using a stream of nitrogen. Tetrakis(triphenylphosphine)palladium(0) (0.39 g, 0.34 mmol) was added. The flask was sealed and heated to 90° C. overnight. The reaction mixture was partitioned between ethyl acetate and sodium bicarbonate (aq., sat.). The organic phase was isolated, washed with brine, dried with sodium sulfate, filtered, evaporated. Purified by silica gel chromatography (eluting with ethyl acetate and methanol) to afford the title compound (0.36 g, 1.82 mmol). LCMS M/Z (M+H, Cl pattern).

Step 3: 2-(6-amino-5-(4,5-dihydrofuran-2-yl)pyridazin-3-yl)phenol 6-chloro-4-(4,5-dihydrofuran-2-yl)pyridazin-3-amine (367 mg, 1.8571 mmol), (2-hydroxyphenyl)boronic acid (0.3074 g, 2.2285 mmol), potassium carbonate (0.5133 g, 3.7142 mmol), and methanesulfonato(2-dicyclohexylphosphino-2',6'-dimethoxy-1,1'-biphenyl)(2'-amino-1,1'-biphenyl-2-yl)palladium(II) (0.1448 g, 0.1857 mmol) were placed in a sealable tube. The reaction vessel was purged with nitrogen. Dioxane (5 ml) and water (1.2 ml) were added, and the reaction mixture was degassed with nitrogen. The reaction vessel was sealed and stirred at 95° C. 16 h. The reaction mixture was deposited on silica and purified by silica gel chromatography (eluting with ethyl acetate/methanol) to afford the title compound.

Step 4: (rac)-2-(6-amino-5-(tetrahydrofuran-2-yl)pyridazin-3-yl)phenol 2-(6-amino-5-(4,5-dihydrofuran-2-yl)pyridazin-3-yl)phenol was dissolved in methanol:ethyl acetate:tetrahydrofuran (1:1:1), palladium (5% on charcoal) was added (80 mg), and the mixture was put under hydrogen atmosphere using vacuum/hydrogen gas cycles. After stirring 4 h, the mixture was filtered through Celite, concentrated in vacuo, and purified by silica gel chromatography (eluting with ethyl acetate and methanol. Lyophilzation from acetonitrile and water afforded the title compound (0.099 g, 0.3848 mmol). $^1$H NMR (400 MHz, DMSO-$d_6$) δ 13.68 (s, 1H), 7.93 (s, 1H), 7.70-7.89 (m, 1H), 7.07-7.29 (m, 1H), 6.79-6.95 (m, 2H), 6.59 (s, 2H), 4.90 (t, J=6.96 Hz, 1H), 4.15 (dt, J=5.74, 7.63 Hz, 1H), 3.68-4.02 (m, 1H), 2.28-2.48 (m, 1H), 1.78-2.13 (m, 2H), 1.49-1.76 (m, 1H). LCMS M/Z (M+H) 258.

The following compound was prepared in a similar fashion to Example 236.

| Example | Compound Name | NMR | m/z |
|---|---|---|---|
| 237 | 2-(6-amino-5-(tetrahydro-2H-pyran-2-yl)pyridazin-3-yl)phenol | $^1$H NMR (400 MHz, DMSO-$d_6$) δ 13.59 (s, 1H), 7.95 (s, 1H), 7.79 (dd, J = 1.34, 8.42 Hz, 1H), 7.11-7.39 (m, 1H), 6.77-7.00 (m, 2H), 6.63 (s, 2H), 4.34-4.61 (m, 1H), 4.09 (d, J = 11.48 Hz, 1H), 3.58 (dt, J = 3.17, 11.11 Hz, 1H), 1.80-1.97 (m, 2H), 1.51-1.80 (m, 3H), 1.29-1.51 (m, 1H) | 372 |

2-(6-Amino-5-(tetrahydrofuran-2-yl)pyridazin-3-yl)phenol was Separated into its Individual Enantiomers, Examples 238 and 239

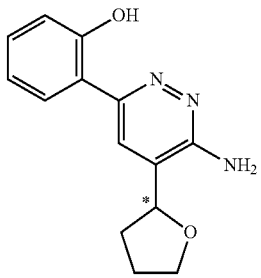

Separated by SFC chromatography (eluting with carbon dioxide and methanol, 0.1% ammonium hydroxide) using a Chiralpak ID column.

Example 238

$^1$H NMR (400 MHz, DMSO-d$_6$) δ 13.67 (s, 1H), 7.93 (d, J=1.0 Hz, 1H), 7.82 (dd, J=8.4, 1.6 Hz, 1H), 7.25 (ddd, J=8.2, 7.3, 1.6 Hz, 1H), 6.58 (s, 2H), 4.90 (ddd, J=7.5, 6.7, 1.0 Hz, 1H), 4.19-4.09 (m, 1H), 3.86 (dt, J=8.1, 7.1 Hz, 1H), 2.48-2.40 (m, 1H), 2.01-1.84 (m, 2H), 1.64 (ddt, J=12.1, 7.8, 6.7 Hz, 1H). LCMS M/Z (M+H) 258.

Example 239

$^1$H NMR (400 MHz, DMSO-d$_6$) δ 13.67 (s, 1H), 7.93 (d, J=1.0 Hz, 1H), 7.82 (dd, J=8.3, 1.6 Hz, 1H), 7.25 (ddd, J=8.2, 7.2, 1.6 Hz, 1H), 7.00-6.85 (m, 2H), 6.58 (s, 2H), 4.96-4.82 (m, 1H), 4.22-4.08 (m, 1H), 3.86 (dt, J=8.1, 7.1 Hz, 1H), 2.06-1.82 (m, 2H), 1.64 (dd, J=12.3, 7.8 Hz, 1H). LCMS M/Z (M+H) 258.

2-(6-Amino-5-(tetrahydro-2H-pyran-2-yl)pyridazin-3-yl)phenol was separated into its individual enantiomers, Example 240 and 241

Enantiomer 1 and enantiomer 2 of 2-(6-amino-5-(tetrahydro-2H-pyran-2-yl)pyridazin-3-yl)phenol

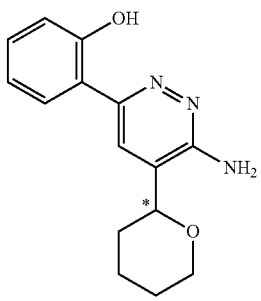 [SMILES: Nc1nnc(-c2ccccc2O)cc1C1CCCCO1]

Separated by SFC chromatography (eluting with carbon dioxide and methanol, 0.1% ammonium hydroxide) using a Chiralpak AD column.

Example 240

$^1$H NMR (400 MHz, DMSO-d$_6$) δ 13.59 (s, 1H), 8.01-7.88 (m, 1H), 7.79 (dd, J=8.4, 1.6 Hz, 1H), 7.31-7.18 (m, 1H), 7.03-6.77 (m, 2H), 6.62 (s, 2H), 4.50-4.39 (m, 1H), 4.10 (dt, J=11.5, 2.0 Hz, 1H), 3.63-3.52 (m, 1H), 1.99-1.82 (m, 2H), 1.82-1.51 (m, 3H), 1.51-1.28 (m, 1H). LCMS M/Z (M+H) 272.

Example 241

$^1$H NMR (400 MHz, DMSO-d$_6$) δ 13.58 (s, 1H), 7.95 (s, 1H), 7.79 (dd, J=8.4, 1.6 Hz, 1H), 7.25 (ddd, J=8.2, 7.3, 1.6 Hz, 1H), 6.98-6.83 (m, 2H), 6.62 (s, 2H), 4.47 (dd, J=11.2, 2.0 Hz, 1H), 4.16-3.95 (m, 1H), 3.59 (td, J=11.4, 3.6 Hz, 1H), 2.03-1.79 (m, 2H), 1.79-1.54 (m, 3H), 1.54-1.29 (m, 1H). LCMS M/Z (M+H) 272.

2-(6-Amino-5-((2S,6R)-2,6-dimethylmorpholino)pyridazin-3-yl)phenol was Separated into its Individual Diastereomers and Enantiomers, Examples 242, 243 and 244

2-(6-amino-5-((2S,6R)-2,6-dimethylmorpholino)pyridazin-3-yl)phenol

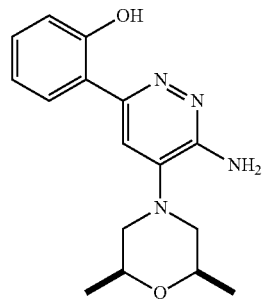 [SMILES: C[C@@H]1CN(c2cc(-c3ccccc3O)nnc2N)C[C@H](C)O1]

Example 242

$^1$H NMR (400 MHz, DMSO-d$_6$) δ 14.17 (s, 1H), 7.92 (dd, J=8.4, 1.6 Hz, 1H), 7.49 (s, 1H), 7.24 (ddd, J=8.2, 7.2, 1.6 Hz, 1H), 6.98-6.72 (m, 2H), 6.24 (s, 2H), 4.21 (td, J=6.2, 3.1 Hz, 2H), 3.30-3.22 (m, 2H), 2.71-2.59 (m, 2H), 1.23 (d, J=6.4 Hz, 6H). LCMS M/Z (M+H) 301.

Enantiomer 1 and enantiomer 2 of 2-(6-amino-5-((trans-2,6)-2,6-dimethylmorpholino)pyridazin-3-yl)phenol

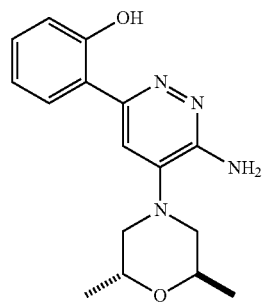 [SMILES: C[C@@H]1CN(c2cc(-c3ccccc3O)nnc2N)C[C@@H](C)O1]

Example 243

$^1$H NMR (400 MHz, DMSO-d6) δ 14.22 (s, 1H), 7.94 (dd, J=8.4, 1.7 Hz, 1H), 7.49 (s, 1H), 7.24 (ddd, J=8.2, 7.2, 1.5

Hz, 1H), 6.98-6.74 (m, 2H), 6.34 (s, 2H), 3.99-3.81 (m, 2H), 3.38 (d, J=12.0 Hz, 2H), 2.38 (dd, J=12.1, 10.1 Hz, 2H), 1.14 (d, J=6.2 Hz, 6H). LCMS M/Z (M+H) 301.

Example 244

$^1$H NMR (400 MHz, DMSO-$d_6$) δ 14.17 (s, 1H), 7.92 (dd, J=8.3, 1.6 Hz, 1H), 7.49 (s, 1H), 7.34-7.17 (m, 1H), 6.98-6.77 (m, 2H), 6.24 (s, 2H), 4.21 (td, J=6.2, 3.2 Hz, 2H), 3.27 (dd, J=12.0, 3.1 Hz, 2H), 2.72-2.61 (m, 2H), 1.23 (d, J=6.4 Hz, 6H). LCMS M/Z (M+H) 301.

Example 245

2-(6-amino-5-(piperidin-3-yloxy)pyridazin-3-yl)phenol

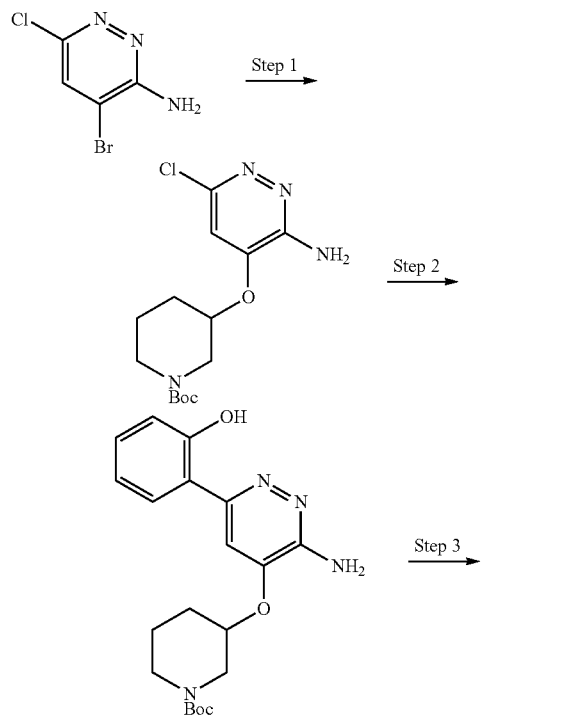

Step 1: tert-butyl 3-((3-amino-6-chloropyridazin-4-yl)oxy)piperidine-1-carboxylate To a solution of tert-butyl 3-hydroxypiperidine-1-carboxylate (1.00 g, 5.0 mmol) in tetrahydrofuran (30 mL) was added sodium hydride (60%, 0.32 g, 8.0 mmol) at 0° C. The mixture was stirred for 30 min before 4-bromo-6-chloropyridazin-3-amine (0.50 mg, 2.4 mmol) was added. The resulting mixture was then heated at 70° C. for 12 h. After cooling, the reaction was quenched by the addition of saturated aqueous ammonium chloride (10 mL) and extracted with ethyl acetate (3×20 mL). The combined organic layers were dried over sodium sulfate and concentrated in vacuo. The residue was purified by Preparative TLC (eluting with ethyl acetate in petroleum ether) to give the title compound (400 mg, 51%) as a pale red solid.

Step 2: tert-butyl 3-((3-amino-6-(2-hydroxyphenyl)pyridazin-4-yl)oxy)piperidine-1-carboxylate A mixture of tert-butyl 3-((3-amino-6-chloropyridazin-4-yl)oxy)piperidine-1-carboxylate (400 mg, 1.21 mmol), (2-hydroxyphenyl)boronic acid (205 mg, 1.50 mmol), [1,1'-Bis(diphenylphosphino)ferrocene]dichloropalladium (58 mg, 0.08 mmol) and potassium carbonate (276 mg, 2.00 mmol) in dioxane/water (10 mL, 1:1) was stirred at 100° C. for 30 min under microwave conditions. After cooling, the mixture was extracted with ethyl acetate (3×20 mL). The combined organic layers were concentrated in vacuo to give the crude title compound (400 mg, 86%) as a brown oil that was used in next step without further purification.

Step 3: 2-(6-amino-5-(piperidin-3-yloxy)pyridazin-3-yl)phenol

To a solution of tert-butyl 3-((3-amino-6-(2-hydroxyphenyl)pyridazin-4-yl)oxy)piperidine-1-carboxylate (400 mg, 1.04 mmol) in ethyl acetate (10 mL) was added hydrochloric acid (4 N in ethyl acetate, 3.5 mL, 14.0 mmol). The mixture was stirred at room temperature for 2 h before being concentrated in vacuo to afford the crude title compound as a hydrochloric acid salt (200 mg, 67%). Part of the crude material (50 mg) was purified by reverse phase chromatography (eluting with acetonitrile/water/ammonium hydroxide) to give the title compound (6 mg, 12% yield) as a white solid. $^1$H NMR (400 MHz, CD$_3$OD) δ 7.80 (d, J=8.0 Hz, 1H), 7.53 (s, 1H), 7.24 (t, J=7.6 Hz, 1H), 6.93-6.90 (m, 2H), 5.06 (s, 1H), 3.36-3.33 (m, 2H), 3.20-3.16 (m, 1H), 3.03-3.00 (m, 1H), 2.15-2.03 (m, 1H), 2.00-1.95 (m, 2H), 1.75-1.72 (m, 1H). LCMS M/Z (M+H) 287.

Example 246

2-(6-amino-5-((1-methylpiperidin-3-yl)oxy)pyridazin-3-yl)phenol

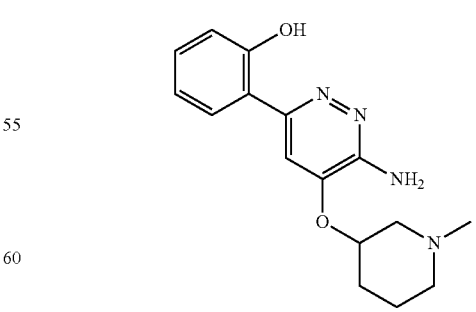

A mixture of 2-(6-amino-5-(piperidin-3-yloxy)pyridazin-3-yl)phenol hydrochloride (55 mg, 0.17 mmol) (prepared as in example G02938763) and formaldehyde (1 mL, 30% in water) in methylene chloride (10 mL) was added sodium cyanoborohydride (33 mg, 0.52 mmol) in one portion. The resulting mixture was stirred at room temperature for 5 h and quenched by addition of saturated aqueous sodium bicarbonate (10 mL). The mixture was extracted with methylene chloride (3×15 mL). The combined organic layers were dried over sodium sulfate and concentrated in vacuo. The residue was purified by reverse phase chromatography (eluting with acetonitrile/water/0.1% ammonium hydroxide) to give the title compound (7 mg, 14% yield) as a white solid. $^1$H NMR (400 MHz, CD$_3$OD) δ 7.82 (d, J=9.2 Hz, 1H), 7.53 (s, 1H), 7.24 (t, J 7.2 Hz, 1H), 6.97-6.89 (m, 2H), 5.16 (s, 1H), 3.36-3.33 (m, 1H), 3.20-3.16 (m, 2H), 2.75-2.65 (m, 4H), 2.09-1.98 (m, 2H), 1.86-1.79 (m, 2H). LCMS M/Z (M+H) 301.

Example 247

1-(3-((3-amino-6-(2-hydroxyphenyl)pyridazin-4-yl)oxy)piperidin-1-yl)ethanone

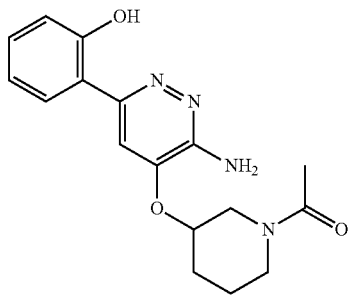 [SMILES: CC(=O)N1CCCC(Oc2cc(-c3ccccc3O)nnc2N)C1]

To a solution of 2-(6-amino-5-(piperidin-3-yloxy)pyridazin-3-yl)phenol hydrochloride (75 mg, 0.23 mmol) (prepared as in example G02938763) and triethylamine (79 mg, 0.79 mmol) in dichloromethane (10 mL) was added acetic anhydride (40 mg, 0.39 mmol). The resulting mixture was stirred at room temperature for 3 h and then concentrated in vacuo. The residue was purified by reverse phase chromatography (eluting with acetonitrile/water/0.1% ammonium hydroxide) to give the title compound (13 mg, 15% yield) as a white solid. $^1$H NMR (400 MHz, CD$_3$OD) δ 7.85 (d, J=8.4 Hz, 1H), 7.62 (d, J=6.8 Hz, 1H), 7.30-7.25 (m, 1H), 6.98-6.93 (m, 2H), 3.93-3.81 (m, 2H), 3.63-3.60 (m, 2H), 3.44-3.38 (m, 1H), 2.18 (s, 3H), 2.07-2.00 (m, 2H), 1.96-1.74 (m, 2H). LCMS M/Z (M+Na) 351.

Example 248

N-(15-(4-(3-amino-6-(2-hydroxyphenyl)pyridazin-4-yl)piperazin-1-yl)-15-oxo-3,6,9,12-tetraoxapentadecyl)-5-((3aS,4S,6aR)-2-oxohexahydro-1H-thieno[3,4-d]imidazol-4-yl)pentanamide 2,2,2trifluoroacetate

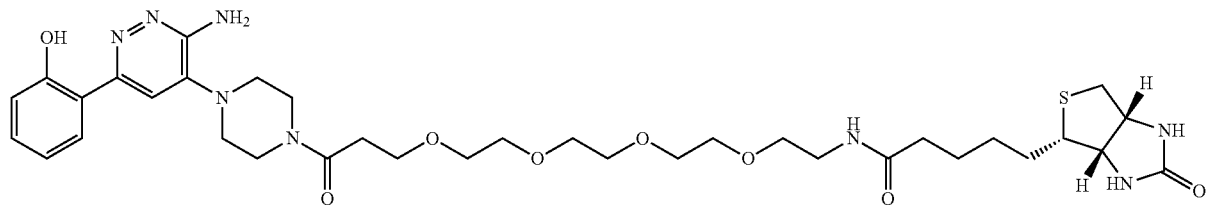 [SMILES: Nc1nnc(-c2ccccc2O)cc1N1CCN(C(=O)CCOCCOCCOCCOCCNC(=O)CCCC[C@@H]2SC[C@@H]3NC(=O)N[C@@H]32)CC1]

A sealable tube was charged with 2-(6-amino-5-(piperazin-1-yl)pyridazin-3-yl)phenol (0.0662 g, 0.2441 mmol) (prepared as described for example G02938881) and 17-oxo-21-((3aS,4S,6aR)-2-oxohexahydro-1H-thieno[3,4-d]imidazol-4-yl)-4,7,10,13-tetraoxa-16-azahenicosan-1-oic acid (100 mg, 0.2034 mmol) in dimethylformamide (4 mL) for the addition of N-isopropyl-N-methylpropan-2-amine (0.0634 mL, 0.4068 mmol). The solution was cooled to 0° C., and 1-((dimethylamino)(dimethyliminio)methyl)-1H-benzo[d][1,2,3]triazole 3-oxide hexafluorophosphate(V) (0.0926 g, 0.2441 mmol) was added. The mixture warmed to room temperature and stirred 18 h. The solution was diluted with water and purified by reverse phase HPLC (eluting with water/acetonitrile/0.1% trifluoroacetic acid). Fractions containing pure product were frozen and lyophilized to afford the title compound (73 mg). LCMS M/Z (M+H) 745.

Example 249

N-(15-(4-(3-amino-6-(2-hydroxyphenyl)pyridazin-4-yl)piperazin-1-yl)-15-oxo-3,6,9,12-tetraoxapentadecyl)-6-carboxamido-X-rhodamine

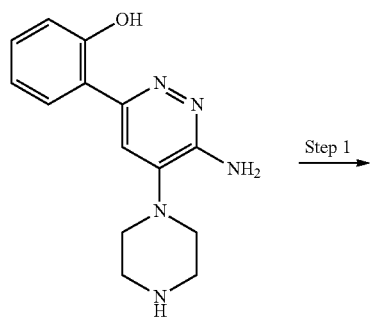

↓ Step 1

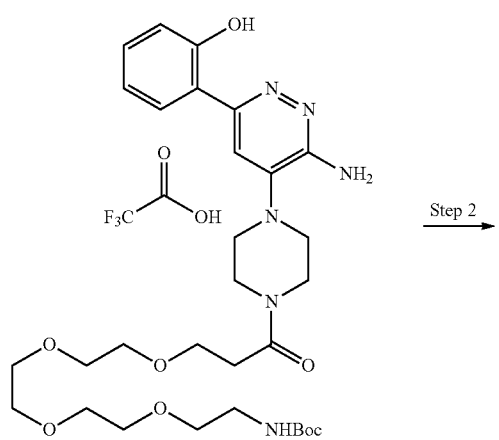

↓ Step 2

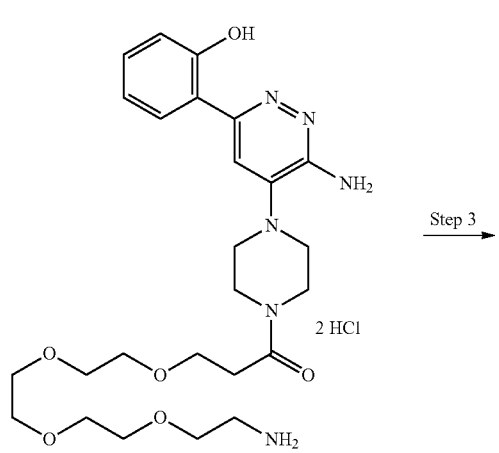

↓ Step 3

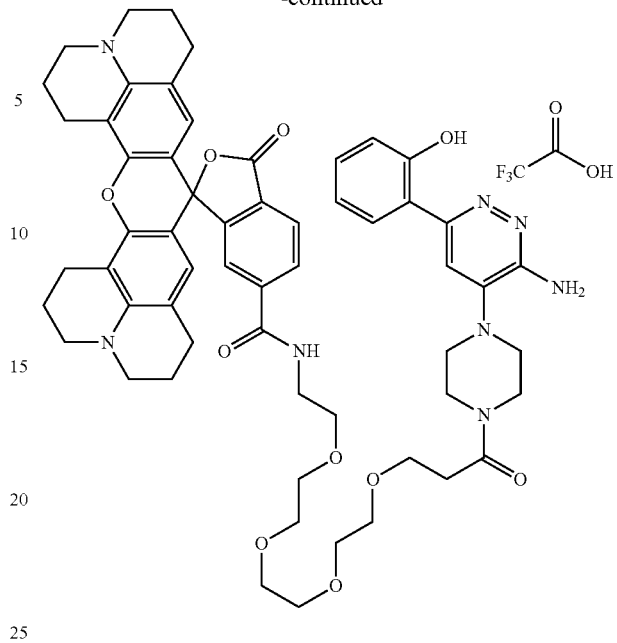

Step 1: tert-butyl (15-(4-(3-amino-6-(2-hydroxyphenyl)pyridazin-4-yl)piperazin-1-yl)-15-oxo-3,6,9,12-tetraoxapentadecyl)carbamate 2,2,2-trifluoroacetate A disposable reaction tube was charged with 2-(6-amino-5-(piperazin-1-yl)pyridazin-3-yl)phenol (68 mg, 0.2488 mmol), 2,2-dimethyl-4-oxo-3,8,11,14,17-pentaoxa-5-aza-icosan-20-oic acid (100 mg, 0.2737 mmol), and a stir bar for the addition of dimethylformamide (2 mL). N-ethyl-N-isopropylpropan-2-amine (0.086 mL, 0.498 mmol) was added, followed by 2-(3H-[1,2,3]triazolo[4,5-b]pyridin-3-yl)-1,1,3,3-tetramethylisouronium hexafluorophosphate(V) (114 mg, 0.299 mmol), and the solution stirred at room temperature 2 h. The reaction mixture was diluted with water and purified by prep-HPLC (eluting with a gradient of water/acetonitrile/0.1% trifluoroacetic acid). Pure fractions were pooled and lyophilized to provide the title compound as an off-white amorphous solid (70 mg). LCMS M/Z (M+H) 619.

Step 2: 1-amino-15-(4-(3-amino-6-(2-hydroxyphenyl)pyridazin-4-yl)piperazin-1-yl)-3,6,9,12-tetraoxa-pentadecan-15-one A disposable tube was charged with tert-butyl (15-(4-(3-amino-6-(2-hydroxyphenyl)pyridazin-4-yl)piperazin-1-yl)-15-oxo-3,6,9,12-tetraoxapentadecyl)carbamate 2,2,2-trifluoroacetate (70 mg, 0.1 mmol) in methanol (3 mL) before the addition of hydrogen chloride in dioxane (4 N, 0.25 mL, 1 mmol). The solution was stirred at room temperature 18 h before the solvent was removed in vacuo. The residue was lyophilized from dioxane to provide the title compound as an amorphous solid (quantitative yield). LCMS M/Z (M+H) 519.

Step 3: N-(15-(4-(3-amino-6-(2-hydroxyphenyl)pyridazin-4-yl)piperazin-1-yl)-15-oxo-3,6,9,12-tetraoxapentadecyl)-6-carboxamido-X-rhodamine A disposable reaction tube was charged with 1-amino-15-(4-(3-amino-6-(2-hydroxyphenyl)pyridazin-4-yl)piperazin- 1-yl)-3,6,9,12-tetraoxapentadecan-15-one dihydrochloride (23 mg 0.0395 mmol), 6-Carboxy-X-Rhodamine, Succinimidyl Ester (5 mg, 0.0079 mmol), and a stir bar for the addition of dimethylformamide (2 mL). N-ethyl-N-isopropylpropan-2-amine (0.014 mL, 0.079 mmol) was added, and the solution stirred at room temperature 72 h before the reaction mixture was diluted with water and purified by prep-HPLC (eluting with a gradient of water/acetonitrile/0.1% trifluoroacetic acid). Pure fractions were pooled and lyophilized to yield the title compound as a deep purple amorphous solid (3 mg). LCMS M/Z (M+2H/2) 518.

Example 250

Biological Assays

The inhibitory activity of representative compounds against BRG1 can be evaluated using known methods or using the following assay protocol.

$IC_{50}$ Measurements for Inhibitors Using BRG1 TR-FRET Binding Assay

His-BRG1 (A1448-S1575; Swiss Prot P51532; mhhhhhhgslvpr\gsAEKLSPNPP NLTKKMKKIVDA-VIKYKDSSSGRQLSEVFIQLPSRKELPEYYELIRK-PVDFKKIKERIRNH KYRSLNDLEKDVMLLC-QNAQTFNLEGSLIYEDSIVLQSVFTSVRQKIEKEDDS EGEES SEQ ID NO:1) was cloned, expressed, and purified to homogeneity. BRG1 binding and inhibition was assessed by monitoring the engagement of a biotinylated small molecule ligand (Example 248) with the target using the TR-FRET assay technology (Perkin-Elmer). Specifically, in a 384 well ProxiPlate, His-BRG1 (4 nM final) was combined with biotinylated-ligand (40 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 20 minutes incubation at room temperature, a mixture Eu-W1024 Anti-6×His antibody ("6×His" disclosed as SEQ ID NO: 4) (Perkin Elmer AD0110) and SureLight™ Streptavidin-Allophycocyanin (SA-APC, Perkin Elmer CR130-100) were added to a final concentrations of 0.2 nM antibody and 50 nM SA-APC, respectively. After sixty minutes equilibration, the plates were read on an Envision instrument and IC50s calculated using a four parameter non-linear curve fit. The compound of Example 248 and the BRG1 TR-FRET Binding Assay described above represent additional embodiments of the invention.

The inhibitory activity of representative compounds against BRM can be evaluated using known methods or using the following assay protocol.

$IC_{50}$ Measurements for Inhibitors Using BRM SM TR-FRET Binding Assay

Histidine epitope tagged BRM (Isoform 2) Bromodomain1377-1486 (S1377-Q1486; Swiss Prot P51531-2; mhhhhhhgslvpr\gsSPNPPKLTKQMNAIIDTVINYKDSS GRQLSEVFIQLPSRKEL PEYYELIRKPVDFKKIKER-IRNHKYRSLGDLEKDVMLLCHNAQTFNLEGSQI-YEDSIVLQ SVFKSARQ SEQ ID NO:2) was cloned, expressed, and purified to homogeneity. BRM-BD binding and inhibition was assessed by monitoring the engagement of a biotinylated small molecule ligand (Example 248) with the target using the TR-FRET assay technology (Perkin-Elmer). Specifically, in a 384 well ProxiPlate, His-BRM-BD (0.3 nM final) was combined with biotinylated-ligand (30 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 20 minutes incubation at room temperature, a mixture Eu-W1024 Anti-6×His antibody ("6×His" disclosed as SEQ ID NO: 4) (Perkin Elmer AD0110) and SureLight™ Streptavidin-Allophycocyanin (SA-APC, Perkin Elmer CR130-100) were added to a final concentrations of 0.2 nM antibody and 50 nM SA-APC, respectively. After sixty minutes equilibration, the plates were read on an Envision instrument and IC50s calculated using a four parameter non-linear curve fit. The compound of Example 248 and the BRM SM TR-FRET Binding Assay described above represent additional embodiments of the invention.

The inhibitory activity of representative compounds against PB1 can be evaluated using known methods or using the following assay protocol.

$IC_{50}$ Measurements for Inhibitors Using Polybromodomain-1 BromoDomain-5 (PB1-BD5) SM TR-FRET Binding Assay Histidine-Flag-PB1-BD5 Bromodomain645-766 (S645-D766; Swiss Prot Q86U86; mhhhhhhasdykddddkgslvpr\gsSGISPKKSKYMTPMQQK LNEVYEAVKNYTDKRGRRLSAI FLRLPSRSELP-DYYLTIKKPMDMEKIRSHMMANKYQDIDSMVED-FVMMFNNACTYNEP ESLIYKDALVLHKVLLE-TRRDLEGD SEQ ID NO:3) was cloned, expressed, and purified to homogeneity. PB1-BD5-BD binding and inhibition was assessed by monitoring the engagement of a biotinylated small molecule ligand (Example 248) with the target using the TR-FRET assay technology (Perkin-Elmer). Specifically, in a 384 well ProxiPlate, His-Flag-PB1-BD5-BD (1 nM final) was combined with biotinylated-ligand (30 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 20 minutes incubation at room temperature, a mixture Eu-W1024 Anti-6×His antibody ("6×His" disclosed as SEQ ID NO: 4) (Perkin Elmer AD0110) and SureLight™ Streptavidin-Allophycocyanin (SA-APC, Perkin Elmer CR130-100) were added to a final concentrations of 0.2 nM antibody and 50 nM SA-APC, respectively. After sixty minutes equilibration, the plates were read on an Envision instrument and IC50s calculated using a four parameter non-linear fit. The compound of Example 248 and the PB1-BD5 SM TR-FRET Binding Assay described above represent additional embodiments of the invention.

Data for representative compounds of formula (I) from the three assays described above is provided in the following table.

| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 1 | 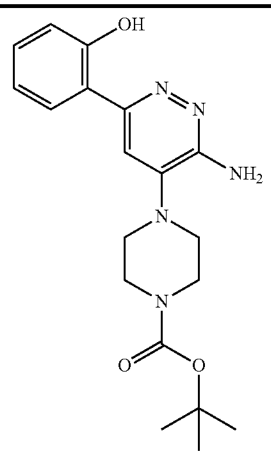 | tert-butyl 4-[3-amino-6-(2-hydroxyphenyl)pyridazin-4-yl]piperazine-1-carboxylate | 0.0214 | | |
| 2 | 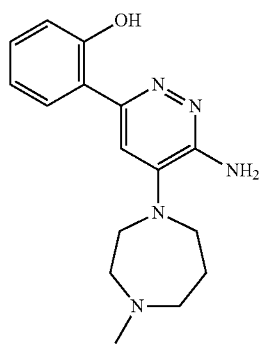 [SMILES: CN1CCCN(c2cc(-c3ccccc3O)nnc2N)CC1] | 2-[6-amino-5-(4-methyl-1,4-diazepan-1-yl)pyridazin-3-yl]phenol | 0.2961 | | |
| 3 | 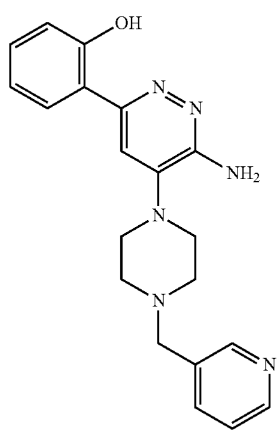 [SMILES: Nc1nnc(-c2ccccc2O)cc1N1CCN(Cc2cccnc2)CC1] | 2-[6-amino-5-[4-(3-pyridylmethyl)piperazin-1-yl]pyridazin-3-yl]phenol | 0.0373 | 0.0607 | 0.0252 |
| 4 | 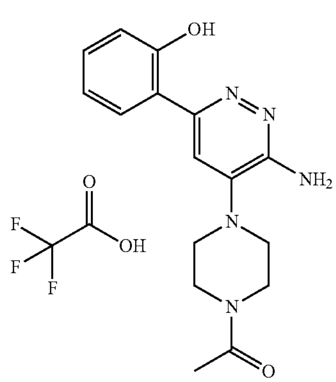 [SMILES: O=C(O)C(F)(F)F ; CC(=O)N1CCN(c2cc(-c3ccccc3O)nnc2N)CC1] | 1-[4-[3-amino-6-(2-hydroxyphenyl)pyridazin-4-yl]piperazin-1-yl]ethanone; 2,2,2-trifluoroacetic acid | 0.0659 | 0.0717 | 0.0246 |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 5 | 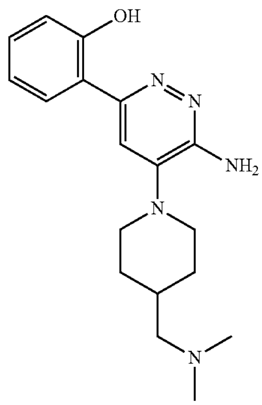 [SMILES: CN(C)CC1CCN(c2cc(-c3ccccc3O)nnc2N)CC1] | 2-[6-amino-5-[4-[(dimethylamino)methyl]-1-piperidyl]pyridazin-3-yl]phenol | 0.0395 | 0.0225 | 0.0164 |
| 6 | | 2-[6-amino-5-[(2S)-2-methyl-1-piperidyl]pyridazin-3-yl]phenol; 2,2,2-trifluoroacetic acid | 0.0846 | | |
| 7 | 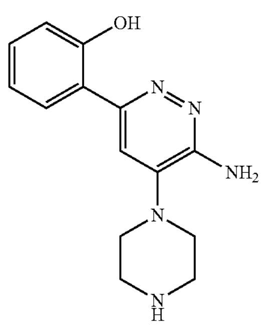 [SMILES: Nc1nnc(-c2ccccc2O)cc1N1CCNCC1] | 2-(6-amino-5-piperazin-1-yl-pyridazin-3-yl)phenol | 0.2137 | | |
| 8 | 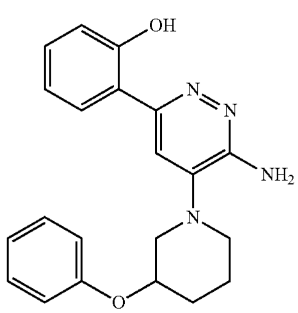 [SMILES: Nc1nnc(-c2ccccc2O)cc1N1CCCC(Oc2ccccc2)C1] | 2-[6-amino-5-(3-phenoxy-1-piperidyl)pyridazin-3-yl]phenol | 0.0498 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 9 | 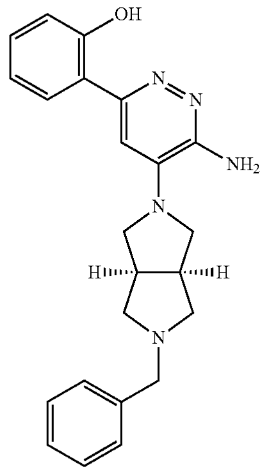 [SMILES: Nc1nnc(-c2ccccc2O)cc1N1C[C@H]2CN(Cc3ccccc3)C[C@H]2C1] | 2-(6-amino-5-((3aR,6aS)-5-benzylhexahydro-pyrrolo[3,4-c]pyrrol-2(1H)-yl)pyridazin-3-yl)phenol | 0.0615 | 0.0476 | 0.0182 |
| 10 | 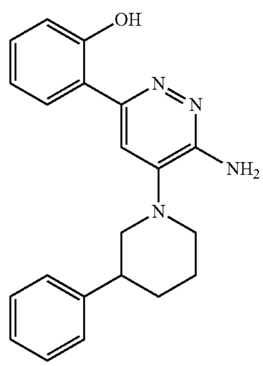 [SMILES: Nc1nnc(-c2ccccc2O)cc1N1CCCC(c2ccccc2)C1] | 2-[6-amino-5-(3-phenyl-1-piperidyl)pyridazin-3-yl]phenol | 0.053 | | |
| 11 | 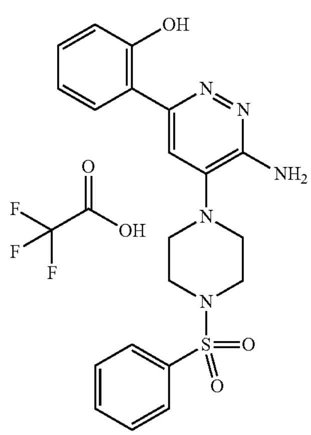 | 2-[6-amino-5-[4-(benzenesulfonyl)piperazin-1-yl]pyridazin-3-yl]phenol; 2,2,2-trifluoroacetic acid | 0.0612 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 12 | 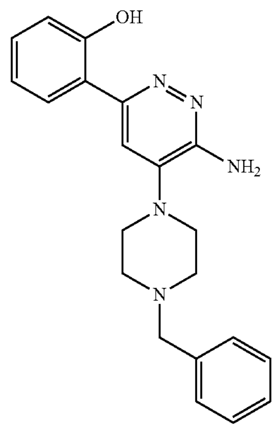 [SMILES: Nc1nnc(-c2ccccc2O)cc1N1CCN(Cc2ccccc2)CC1] | 2-[6-amino-5-(4-benzylpiperazin-1-yl)pyridazin-3-yl]phenol | 0.0612 | | |
| 13 | 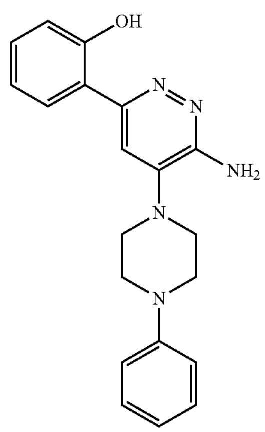 [SMILES: Nc1nnc(-c2ccccc2O)cc1N1CCN(c2ccccc2)CC1] | 2-[6-amino-5-(4-phenylpiperazin-1-yl)pyridazin-3-yl]phenol | 0.0321 | | |
| 14 | 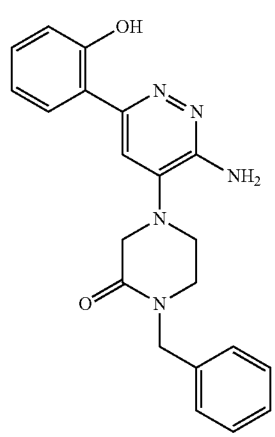 [SMILES: Nc1nnc(-c2ccccc2O)cc1N1CCN(Cc2ccccc2)C(=O)C1] | 4-[3-amino-6-(2-hydroxyphenyl)pyridazin-4-yl]-1-benzyl-piperazin-2-one | 0.0735 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 15 | 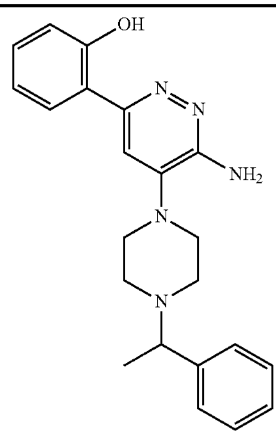 | 2-[6-amino-5-[4-(1-phenylethyl)piperazin-1-yl]pyridazin-3-yl]phenol | 0.0209 | 0.0361 | 0.0245 |
| 16 | 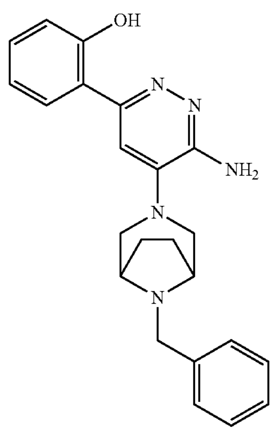 [SMILES: Nc1nnc(-c2ccccc2O)cc1N1CC2CCC(C1)N2Cc1ccccc1] | 2-[6-amino-5-(8-benzyl-3,8-diazabicyclo[3.2.1]octan-3-yl)pyridazin-3-yl]phenol | 0.0563 | 0.079 | 0.0513 |
| 17 | 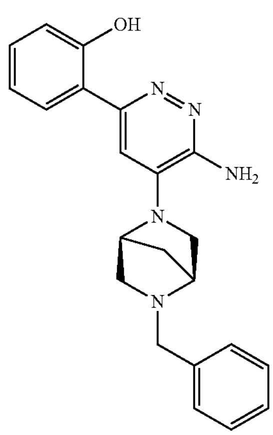 [SMILES: Nc1nnc(-c2ccccc2O)cc1N1C[C@@H]2C[C@H]1CN2Cc1ccccc1] | 2-[6-amino-5-[(1S,4S)-5-benzyl-2,5-diazabicyclo[2.2.1]heptan-2-yl]pyridazin-3-yl]phenol | 0.1471 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 18 | 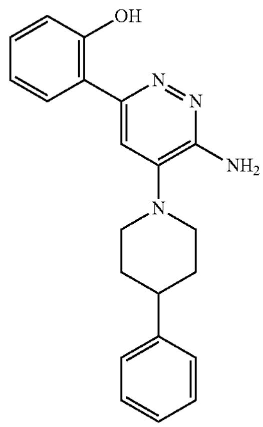 [SMILES: Nc1nnc(-c2ccccc2O)cc1N1CCC(c2ccccc2)CC1] | 2-[6-amino-5-(4-phenyl-1-piperidyl)pyridazin-3-yl]phenol | 0.0967 | | |
| 19 | 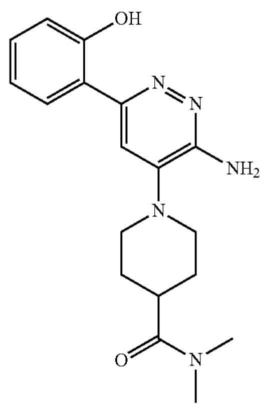 [SMILES: CN(C)C(=O)C1CCN(c2cc(-c3ccccc3O)nnc2N)CC1] | 1-[3-amino-6-(2-hydroxyphenyl)pyridazin-4-yl]-N,N-dimethyl-piperidine-4-carboxamide | 0.0564 | | |
| 20 | 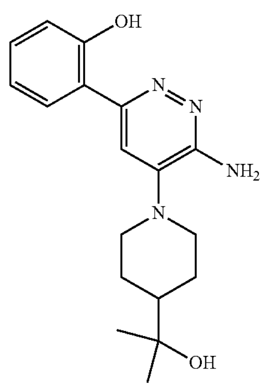 [SMILES: CC(C)(O)C1CCN(c2cc(-c3ccccc3O)nnc2N)CC1] | 2-(6-amino-5-(4-(2-hydroxypropan-2-yl)piperidin-1-yl)pyridazin-3-yl)phenol | 0.0358 | | |
| 21 | 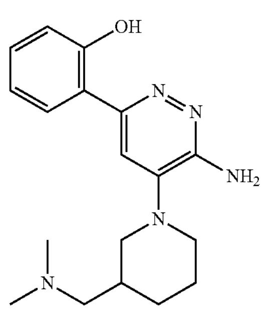 [SMILES: CN(C)CC1CCCN(c2cc(-c3ccccc3O)nnc2N)C1] | 2-[6-amino-5-[3-[(dimethylamino)methyl]-1-piperidyl]pyridazin-3-yl]phenol | 0.1158 | | |

-continued

| Example | Structure | Name | BRG1 HTRF IC$_{50}$ (μM) | BRM_iso 2 HTRF CON (IC50) | PB1-BD5 HTRF CON (IC50) |
|---------|-----------|------|--------------------------|----------------------------|--------------------------|
| 22 | 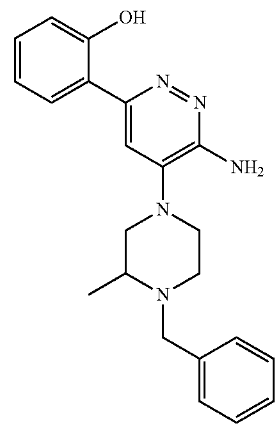 [SMILES: CC1CN(c2cc(-c3ccccc3O)nnc2N)CCN1Cc1ccccc1] | 2-[6-amino-5-(4-benzyl-3-methyl-piperazin-1-yl)pyridazin-3-yl]phenol | 0.0421 | | |
| 23 | 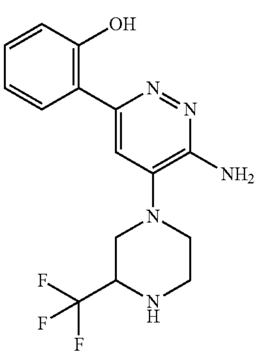 [SMILES: Nc1nnc(-c2ccccc2O)cc1N1CCNC(C(F)(F)F)C1] | 2-[6-amino-5-[3-(trifluoromethyl)piperazin-1-yl]pyridazin-3-yl]phenol | 0.1722 | | |
| 24 | 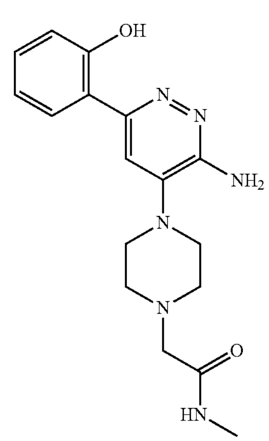 [SMILES: CNC(=O)CN1CCN(c2cc(-c3ccccc3O)nnc2N)CC1] | 2-[4-[3-amino-6-(2-hydroxyphenyl)pyridazin-4-yl]piperazin-1-yl]-N-methyl-acetamide | 0.0746 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 25 | 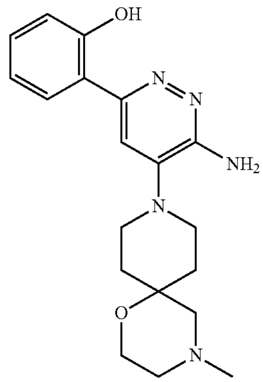 [SMILES: CN1CCOC2(CCN(c3cc(-c4ccccc4O)nnc3N)CC2)C1] | 2-[6-amino-5-(4-methyl-1-oxa-4,9-diazaspiro[5.5]undecan-9-yl)pyridazin-3-yl]phenol | 0.0176 | | |
| 26 | 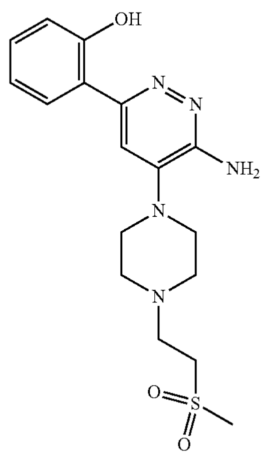 [SMILES: CS(=O)(=O)CCN1CCN(c2cc(-c3ccccc3O)nnc2N)CC1] | 2-[6-amino-5-[4-(2-methylsulfonylethyl)piperazin-1-yl]pyridazin-3-yl]phenol | 0.0978 | | |
| 27 | 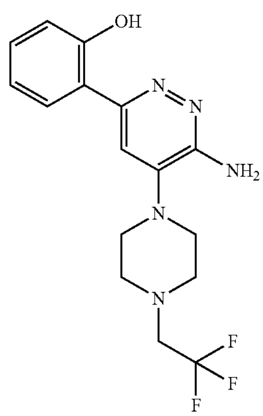 [SMILES: Nc1nnc(-c2ccccc2O)cc1N1CCN(CC(F)(F)F)CC1] | 2-[6-amino-5-[4-(2,2,2-trifluoroethyl)piperazin-1-yl]pyridazin-3-yl]phenol | 0.0755 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 28 | 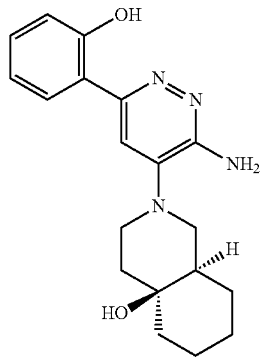 [SMILES: Nc1nnc(-c2ccccc2O)cc1N1CC[C@@]2(O)CCCC[C@@H]2C1] | (4aS,8aR)-2-[3-amino-6-(2-hydroxyphenyl)pyridazin-4-yl]-1,3,4,5,6,7,8,8a-octahydroisoquinolin-4a-ol | 0.0172 | | |
| 29 | 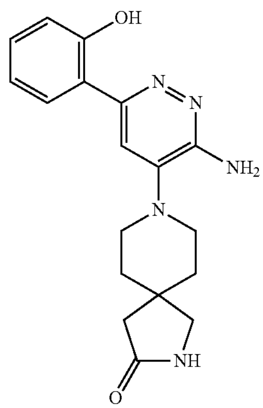 [SMILES: Nc1nnc(-c2ccccc2O)cc1N1CCC2(CC1)CNC(=O)C2] | 8-[3-amino-6-(2-hydroxyphenyl)pyridazin-4-yl]-2,8-diazaspiro[4.5]decan-3-one | 0.0566 | | |
| 30 | 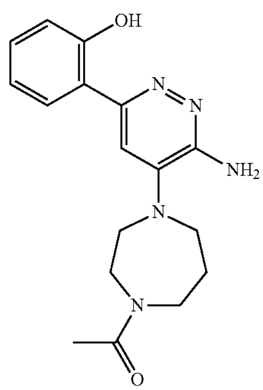 [SMILES: CC(=O)N1CCCN(c2cc(-c3ccccc3O)nnc2N)CC1] | 1-[4-[3-amino-6-(2-hydroxyphenyl)pyridazin-4-yl]-1,4-diazepan-1-yl]ethanone | 0.1116 | | |
| 31 | 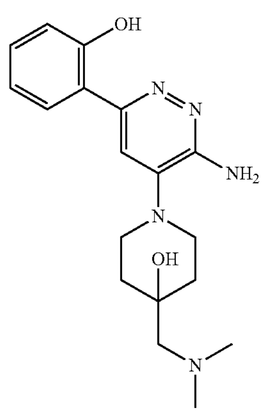 | 1-[3-amino-6-(2-hydroxyphenyl)pyridazin-4-yl]-4-[(dimethylamino)methyl]piperidin-4-ol | 0.0208 | | |

-continued

| Example | Structure | Name | BRG1 HTRF IC₅₀ (μM) | BRM_iso 2 HTRF CON (IC50) | PB1-BD5 HTRF CON (IC50) |
|---|---|---|---|---|---|
| 32 | 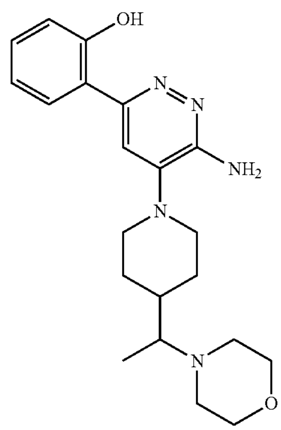 [SMILES: CC(C1CCN(c2cc(-c3ccccc3O)nnc2N)CC1)N1CCOCC1] | 2-[6-amino-5-[4-(1-morpholinoethyl)-1-piperidyl]pyridazin-3-yl]phenol | 0.0309 | | |
| 33 | 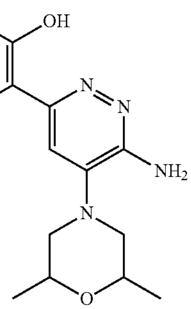 | 2-[6-amino-5-(2,6-dimethylmorpholin-4-yl)pyridazin-3-yl]phenol | 0.0721 | 0.0696 | 0.024 |
| 34 | 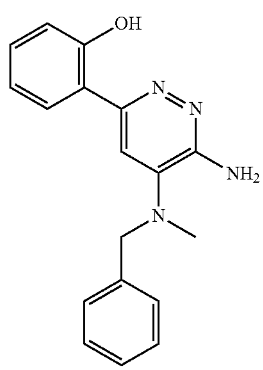 [SMILES: CN(Cc1ccccc1)c1cc(-c2ccccc2O)nnc1N] | 2-[6-amino-5-[benzyl(methyl)amino]pyridazin-3-yl]phenol | 0.072 | | |
| 35 | 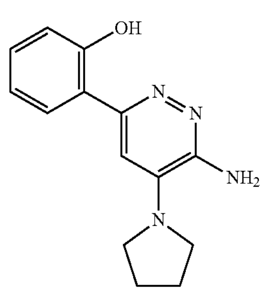 [SMILES: Nc1nnc(-c2ccccc2O)cc1N1CCCC1] | 2-(6-amino-5-pyrrolidin-1-yl-pyridazin-3-yl)phenol | 0.0644 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 36 | 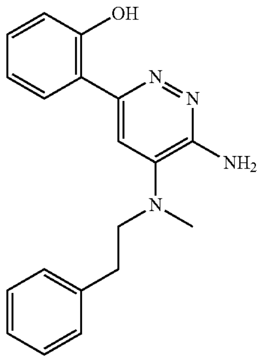 [SMILES: CN(CCc1ccccc1)c1cc(-c2ccccc2O)nnc1N] | 2-[6-amino-5-[methyl(2-phenylethyl)amino]pyridazin-3-yl]phenol | 0.0962 | | |
| 37 | 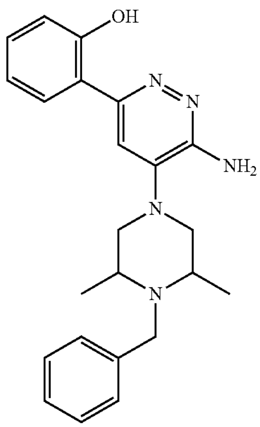 [SMILES: CC1CN(c2cc(-c3ccccc3O)nnc2N)CC(C)N1Cc1ccccc1] | 2-[6-amino-5-(4-benzyl-3,5-dimethyl-piperazin-1-yl)pyridazin-3-yl]phenol | 0.1023 | | |
| 38 | 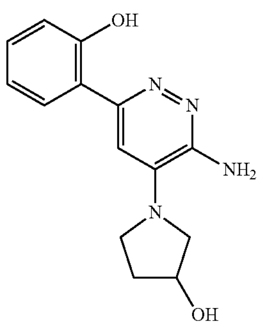 [SMILES: Nc1nnc(-c2ccccc2O)cc1N1CCC(O)C1] | 1-[3-amino-6-(2-hydroxyphenyl)pyridazin-4-yl]pyrrolidin-3-ol | 0.0921 | | |
| 39 | 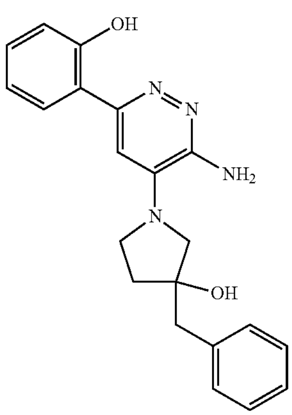 [SMILES: Nc1nnc(-c2ccccc2O)cc1N1CCC(O)(Cc2ccccc2)C1] | 1-[3-amino-6-(2-hydroxyphenyl)pyridazin-4-yl]-3-benzyl-pyrrolidin-3-ol | 0.1127 | | |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 40 | 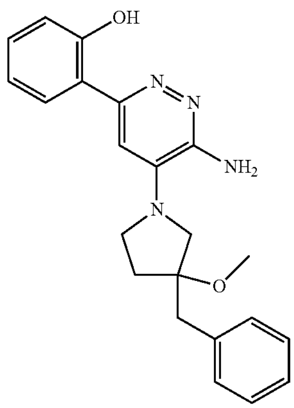 [SMILES: COC1(Cc2ccccc2)CCN(c2cc(-c3ccccc3O)nnc2N)C1] | 2-[6-amino-5-(3-benzyl-3-methoxy-pyrrolidin-1-yl)pyridazin-3-yl]phenol | 0.0794 | | |
| 41 | 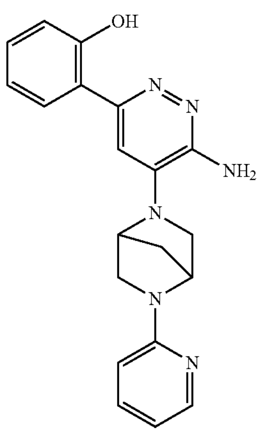 [SMILES: Nc1nnc(-c2ccccc2O)cc1N1CC2CC1CN2c1ccccn1] | 2-[6-amino-5-[5-(2-pyridyl)-2,5-diazabicyclo[2.2.1]heptan-2-yl]pyridazin-3-yl]phenol | 0.0282 | | |
| 42 | 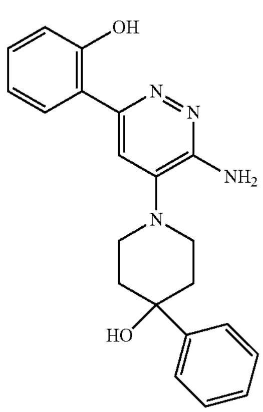 [SMILES: Nc1nnc(-c2ccccc2O)cc1N1CCC(O)(c2ccccc2)CC1] | 1-[3-amino-6-(2-hydroxyphenyl)pyridazin-4-yl]-4-phenyl-piperidin-4-ol | 0.0113 | | |

-continued

| Example | Structure | Name | BRG1 HTRF IC$_{50}$ (μM) | BRM_iso 2 HTRF CON (IC50) | PB1-BD5 HTRF CON (IC50) |
|---------|-----------|------|--------------------------|---------------------------|--------------------------|
| 43 | 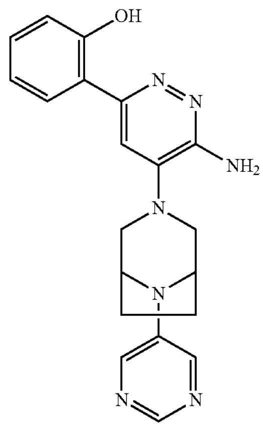 [SMILES: Nc1nnc(-c2ccccc2O)cc1N1CC2CCC(C1)N2c1cncnc1] | 2-[6-amino-5-(8-pyrimidin-5-yl-3,8-diazabicyclo[3.2.1]octan-3-yl)pyridazin-3-yl]phenol | 0.0193 | | |
| 44 | 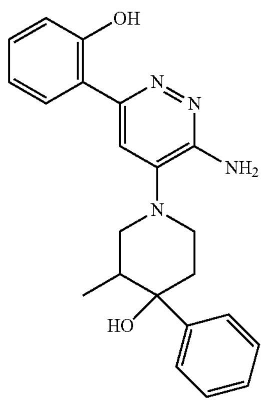 [SMILES: CC1CN(c2cc(-c3ccccc3O)nnc2N)CCC1(O)c1ccccc1] | 1-[3-amino-6-(2-hydroxyphenyl)pyridazin-4-yl]-3-methyl-4-phenyl-piperidin-4-ol | 0.0253 | | |
| 45 | 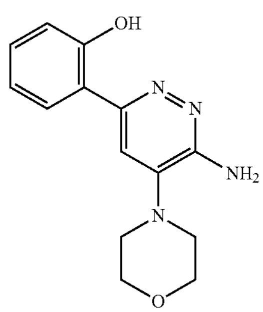 | 2-(6-amino-5-morpholino-pyridazin-3-yl)phenol | 0.1011 | 0.0715 | 0.0209 |
| 46 | 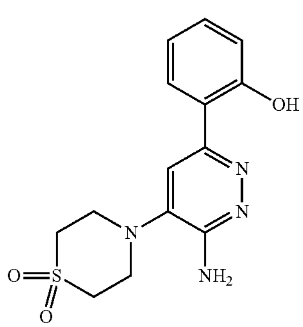 [SMILES: Nc1nnc(-c2ccccc2O)cc1N1CCS(=O)(=O)CC1] | 2-[6-amino-5-(1,1-dioxo-1,4-thiazinan-4-yl)pyridazin-3-yl]phenol | 0.414 | | |

-continued
| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 47 | 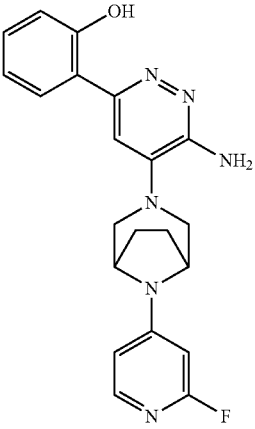 [SMILES: Nc1nnc(-c2ccccc2O)cc1N1CC2CCC(C1)N2c1ccnc(F)c1] | 2-[6-amino-5-[8-(2-fluoro-4-pyridyl)-3,8-3 diazabicyclo[3.2.1]octan-3-yl]pyridazin-3-yl]phenol | 0.0045 | | |
| 48 | 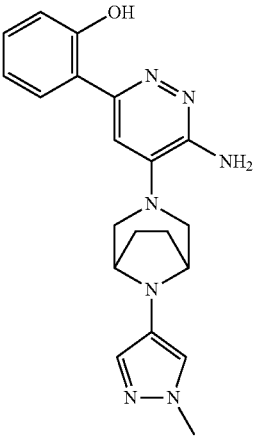 [SMILES: Cn1cc(N2C3CCC2CN(c2cc(-c4ccccc4O)nnc2N)C3)cn1] | 2-[6-amino-5-[8-(1-methylpyrazol-4-yl)-3,8-diazabicyclo[3.2.1]octan-3-yl]pyridazin-3-yl]phenol | 0.0309 | | |
| 49 | 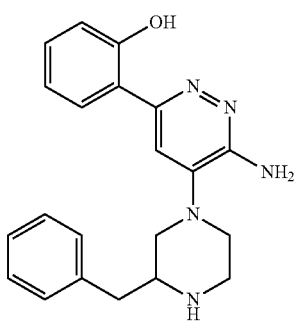 [SMILES: Nc1nnc(-c2ccccc2O)cc1N1CCNC(Cc2ccccc2)C1] | 2-[6-amino-5-(3-benzylpiperazin-1-yl)pyridazin-3-yl]phenol | 0.0848 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 50 | 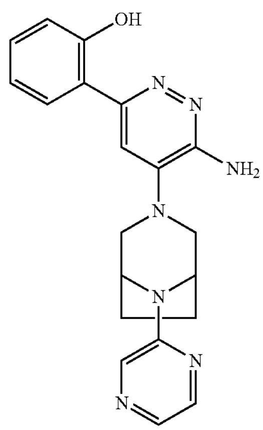 [SMILES: Nc1nnc(-c2ccccc2O)cc1N1CC2CCC(C1)N2c1cnccn1] | 2-[6-amino-5-(8-pyrazin-2-yl-3,8-diazabicyclo[3.2.1]octan-3-yl)pyridazin-3-yl]phenol | 0.0106 | | |
| 51 | 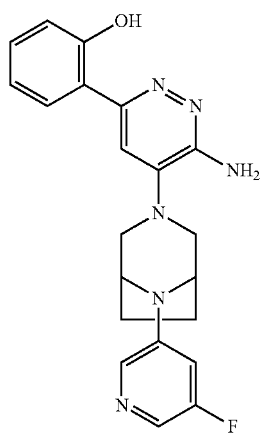 [SMILES: Nc1nnc(-c2ccccc2O)cc1N1CC2CCC(C1)N2c1cncc(F)c1] | 2-[6-amino-5-[8-(5-fluoro-3-pyridyl)-3,8-diazabicyclo[3.2.1]octan-3-yl]pyridazin-3-yl]phenol | 0.0034 | | |
| 52 | 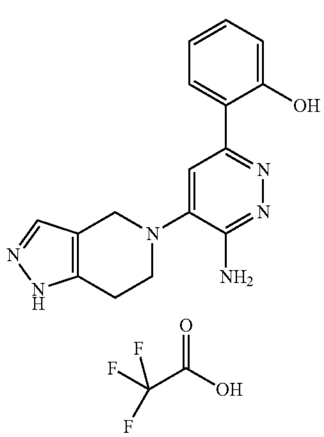 | 2-[6-amino-5-(1,4,6,7-tetrahydropyrazolo[4,3-c]pyridin-5-yl)pyridazin-3-yl]phenol; 2,2,2-trifluoroacetic acid | 0.1282 | | |

-continued
| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 53 | 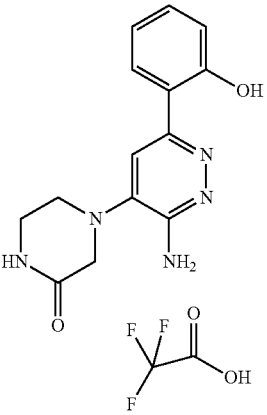 | 4-[3-amino-6-(2-hydroxyphenyl)pyridazin-4-yl]piperazin-2-one; 2,2,2-trifluoroacetic acid | 0.3159 | | |
| 54 | 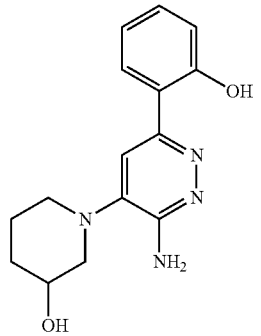 [SMILES: Nc1nnc(-c2ccccc2O)cc1N1CCCC(O)C1] | 1-[3-amino-6-(2-hydroxyphenyl)pyridazin-4-yl]piperidin-3-ol | 0.0952 | | |
| 55 | 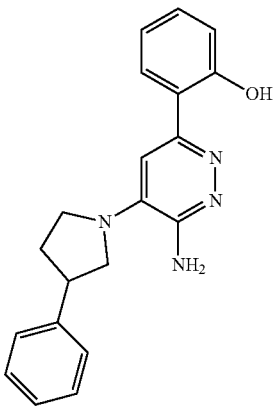 [SMILES: Nc1nnc(-c2ccccc2O)cc1N1CCC(c2ccccc2)C1] | 2-[6-amino-5-(3-phenylpyrrolidin-1-yl)pyridazin-3-yl]phenol | 0.1225 | | |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 56 | 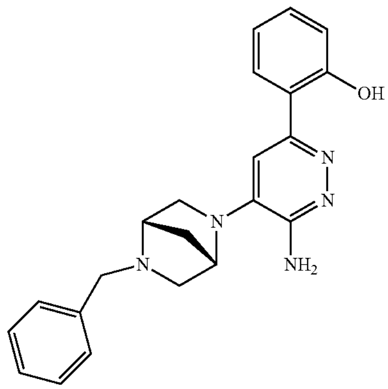 [SMILES: Nc1nnc(-c2ccccc2O)cc1N1C[C@@H]2C[C@H]1CN2Cc1ccccc1] | 2-(6-amino-5-(5-benzyl-2,5-diazabicyclo[2.2.1]heptan-2-yl)pyridazin-3-yl)phenol | 0.1803 | | |
| 57 | 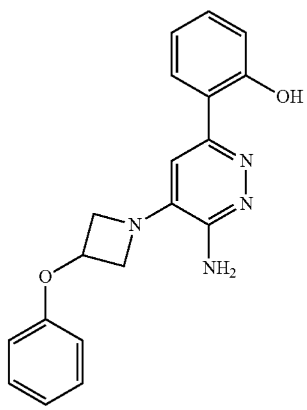 [SMILES: Nc1nnc(-c2ccccc2O)cc1N1CC(Oc2ccccc2)C1] | 2-[6-amino-5-(3-phenoxyazetidin-1-yl)pyridazin-3-yl]phenol | 0.0177 | 0.0356 | 0.0133 |
| 58 | 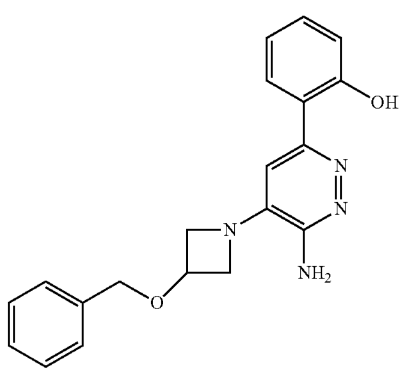 [SMILES: Nc1nnc(-c2ccccc2O)cc1N1CC(OCc2ccccc2)C1] | 2-[6-amino-5-(3-benzyloxyazetidin-1-yl)pyridazin-3-yl]phenol | 0.0252 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 59 | 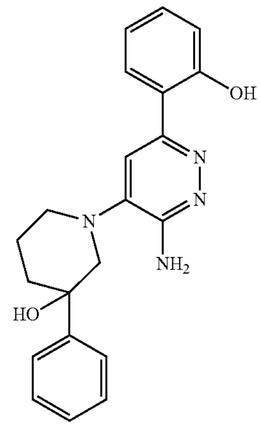 [SMILES: Nc1nnc(-c2ccccc2O)cc1N1CCCC(O)(c2ccccc2)C1] | 1-[3-amino-6-(2-hydroxyphenyl)pyridazin-4-yl]-3-phenyl-piperidin-3-ol | 0.0158 | | |
| 60 | 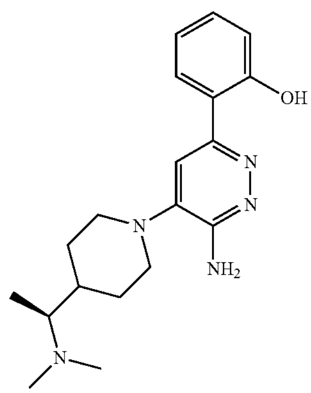 [SMILES: C[C@@H](C1CCN(c2cc(-c3ccccc3O)nnc2N)CC1)N(C)C] | 2-[6-amino-5-[4-[(1S)-1-(dimethylamino)ethyl]-1-piperidyl]pyridazin-3-yl]phenol | 0.0247 | | |
| 61 | 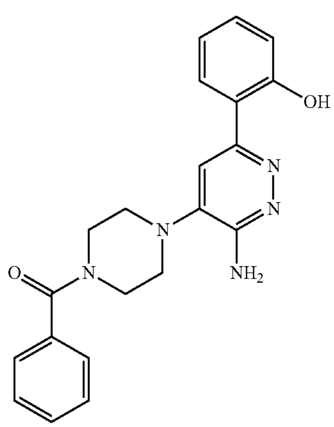 [SMILES: Nc1nnc(-c2ccccc2O)cc1N1CCN(C(=O)c2ccccc2)CC1] | [4-[3-amino-6-(2-hydroxyphenyl)pyridazin-4-yl]piperazin-1-yl]-phenyl-methanone | 0.0348 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 62 | 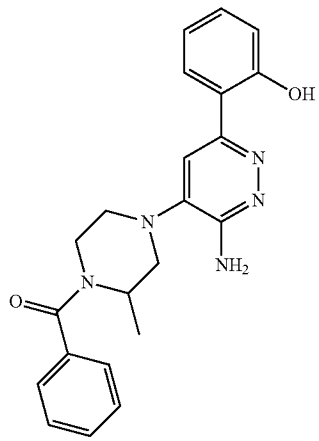 [SMILES: CC1CN(c2cc(-c3ccccc3O)nnc2N)CCN1C(=O)c1ccccc1] | [4-[3-amino-6-(2-hydroxyphenyl)pyridazin-4-yl]-2-methyl-piperazin-1-yl]-phenyl-methanone | 0.0117 | | |
| 63 | 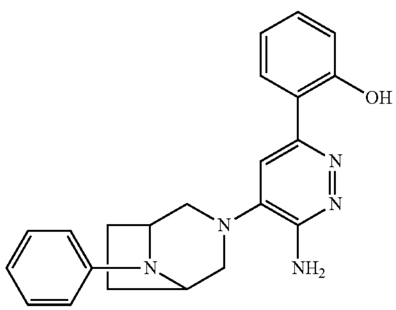 [SMILES: Nc1nnc(-c2ccccc2O)cc1N1CC2CCC(C1)N2c1ccccc1] | 2-[6-amino-5-(8-phenyl-3,8-diazabicyclo[3.2.1]octan-3-yl)pyridazin-3-yl]phenol | 0.0043 | | |
| 64 | 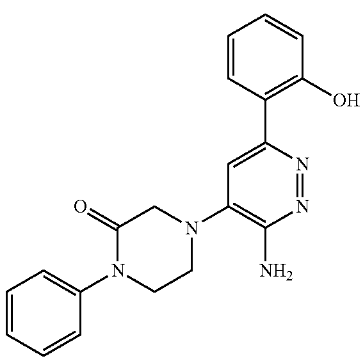 [SMILES: Nc1nnc(-c2ccccc2O)cc1N1CCN(c2ccccc2)C(=O)C1] | 4-[3-amino-6-(2-hydroxyphenyl)pyridazin-4-yl]-1-phenyl-piperazin-2-one | 0.2078 | | |
| 65 | 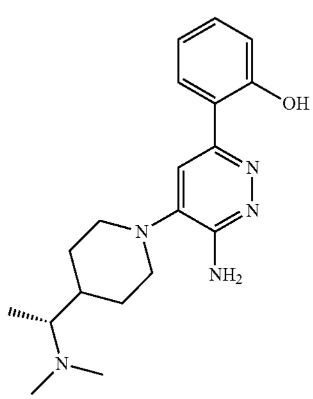 [SMILES: C[C@H](C1CCN(c2cc(-c3ccccc3O)nnc2N)CC1)N(C)C] | 2-[6-amino-5-[4-[(1R)-1-(dimethylamino)ethyl]-1-piperidyl]pyridazin-3-yl]phenol | 0.0276 | | |

-continued
| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 66 | 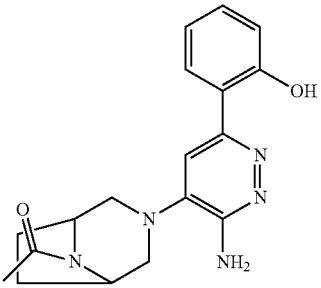 [SMILES: CC(=O)N1C2CCC1CN(c1cc(-c3ccccc3O)nnc1N)C2] | 1-[3-[3-amino-6-(2-hydroxyphenyl)pyridazin-4-yl]-3,8-diazabicyclo[3.2.1]octan-8-yl]ethanone | 0.0713 | | |
| 67 | 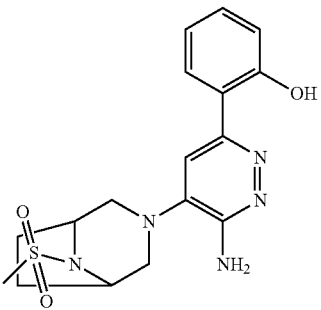 [SMILES: CS(=O)(=O)N1C2CCC1CN(c1cc(-c3ccccc3O)nnc1N)C2] | 2-[6-amino-5-(8-methylsulfonyl-3,8-diazabicyclo[3.2.1]octan-3-yl)pyridazin-3-yl]phenol | 0.0294 | | |
| 68 | 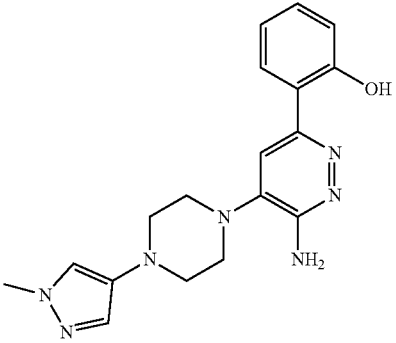 [SMILES: Cn1cc(N2CCN(c3cc(-c4ccccc4O)nnc3N)CC2)cn1] | 2-[6-amino-5-[4-(1-methylpyrazol-4-yl)piperazin-1-yl]pyridazin-3-yl]phenol | 0.0367 | | |
| 69 | 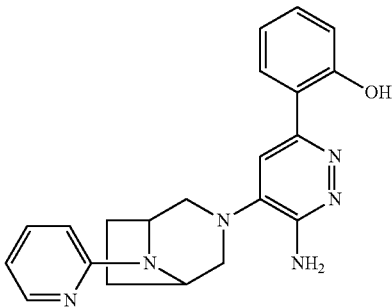 [SMILES: Nc1nnc(-c2ccccc2O)cc1N1CC2CCC(C1)N2c1ccccn1] | 2-[6-amino-5-[8-(2-pyridyl)-3,8-diazabicyclo[3.2.1]octan-3-yl]pyridazin-3-yl]phenol | 0.0039 | | |

-continued

| Example | Structure | Name | BRG1 HTRF IC$_{50}$ (μM) | BRM_iso2 HTRF CON (IC50) | PB1-BD5 HTRF CON (IC50) |
| --- | --- | --- | --- | --- | --- |
| 70 | 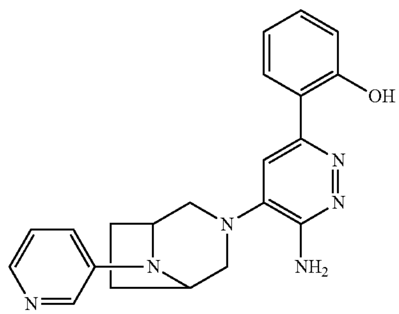 | 2-[6-amino-5-[8-(3-pyridyl)-3,8-diazabicyclo[3.2.1]octan-3-yl]pyridazin-3-yl]phenol | 0.0041 | | |
| 71 | 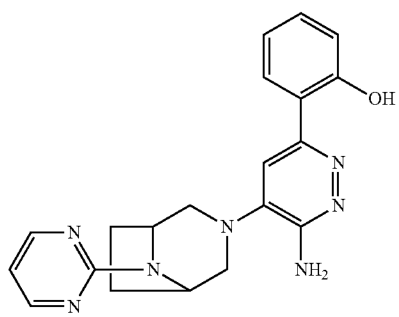 | 2-[6-amino-5-(8-pyrimidin-2-yl-3,8-diazabicyclo[3.2.1]octan-3-yl)pyridazin-3-yl]phenol | 0.005 | | |
| 72 | 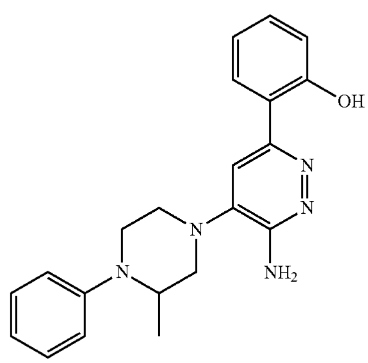 [SMILES: CC1CN(c2cc(-c3ccccc3O)nnc2N)CCN1c1ccccc1] | 2-[6-amino-5-(3-methyl-4-phenyl-piperazin-1-yl)pyridazin-3-yl]phenol | 0.0394 | | |
| 73 | 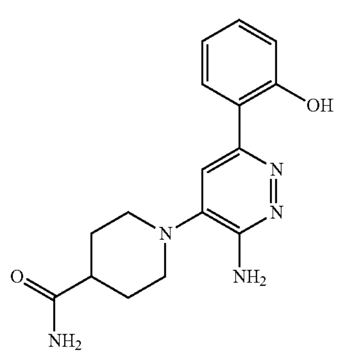 [SMILES: NC(=O)C1CCN(c2cc(-c3ccccc3O)nnc2N)CC1] | 1-[3-amino-6-(2-hydroxyphenyl)pyridazin-4-yl]piperidine-4-carboxamide | 0.0824 | | |

-continued

| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 74 | 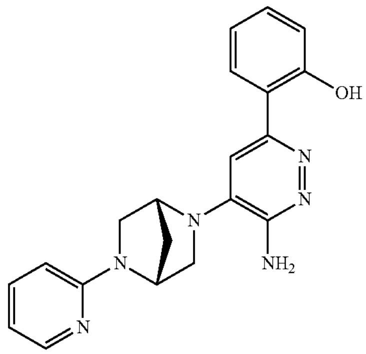 [SMILES: Nc1nnc(-c2ccccc2O)cc1N1C[C@H]2C[C@@H]1CN2c1ccccn1] | 2-[6-amino-5-[(1R,4R)-5-(2-pyridyl)-2,5-diazabicyclo[2.2.1]heptan-2-yl]pyridazin-3-yl]phenol | 0.0106 | | |
| 75 | 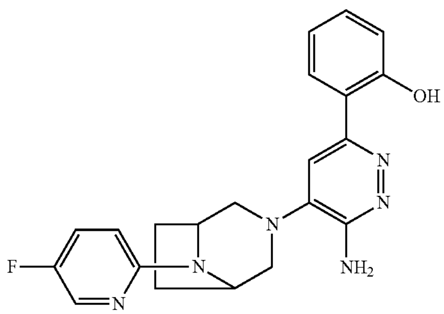 [SMILES: Nc1nnc(-c2ccccc2O)cc1N1CC2CCC(C1)N2c1ccc(F)cn1] | 2-[6-amino-5-[8-(5-fluoro-2-pyridyl)-3,8-diazabicyclo[3.2.1]octan-3-yl]pyridazin-3-yl]phenol | 0.004 | | |
| 76 | 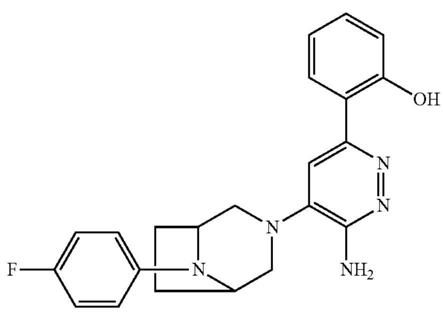 [SMILES: Nc1nnc(-c2ccccc2O)cc1N1CC2CCC(C1)N2c1ccc(F)cc1] | 2-[6-amino-5-[8-(4-fluorophenyl)-3,8-diazabicyclo[3.2.1]octan-3-yl]pyridazin-3-yl]phenol | 0.0067 | | |
| 77 | 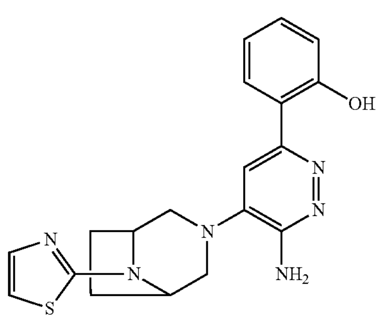 [SMILES: Nc1nnc(-c2ccccc2O)cc1N1CC2CCC(C1)N2c1nccs1] | 2-[6-amino-5-(8-thiazol-2-yl-3,8-diazabicyclo[3.2.1]octan-3-yl)pyridazin-3-yl]phenol | 0.0065 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 78 | 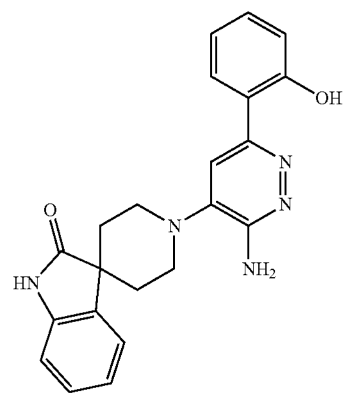 [SMILES: Nc1nnc(-c2ccccc2O)cc1N1CCC2(CC1)C(=O)Nc1ccccc12] | 1'-[3-amino-6-(2-hydroxyphenyl)pyridazin-4-yl]spiro[indoline-3,4'-piperidine]-2-one | 0.0758 | | |
| 79 | 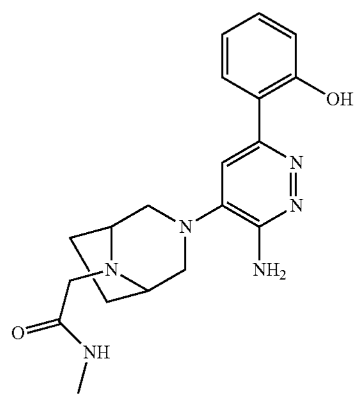 [SMILES: CNC(=O)CN1C2CCC1CN(c1cc(-c3ccccc3O)nnc1N)C2] | 2-[3-[3-amino-6-(2-hydroxyphenyl)pyridazin-4-yl]-3,8-diazabicyclo[3.2.1]octan-8-yl]-N-methyl-acetamide | 0.1386 | | |
| 80 | 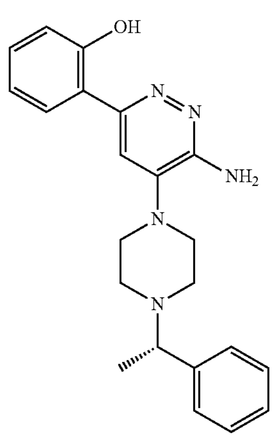 [SMILES: C[C@@H](c1ccccc1)N1CCN(c2cc(-c3ccccc3O)nnc2N)CC1] | 2-[6-amino-5-[4-[(1S)-1-phenylethyl]piperazin-1-yl]pyridazin-3-yl]phenol | 0.0557 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 81 | 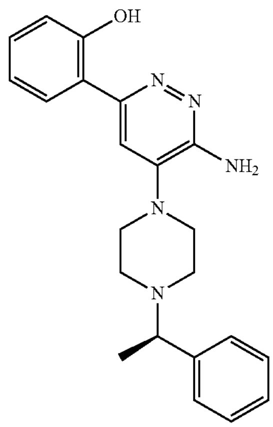 [SMILES: C[C@H](c1ccccc1)N1CCN(c2cc(-c3ccccc3O)nnc2N)CC1] | 2-[6-amino-5-[4-[(1R)-1-phenylethyl]piperazin-1-yl]pyridazin-3-yl]phenol | 0.0191 | | |
| 82 | 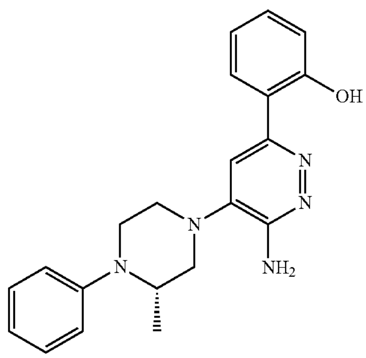 [SMILES: C[C@H]1CN(c2cc(-c3ccccc3O)nnc2N)CCN1c1ccccc1] | 2-[6-amino-5-[(3S)-3-methyl-4-phenyl-piperazin-1-yl]pyridazin-3-yl]phenol | 0.0684 | | |
| 83 | 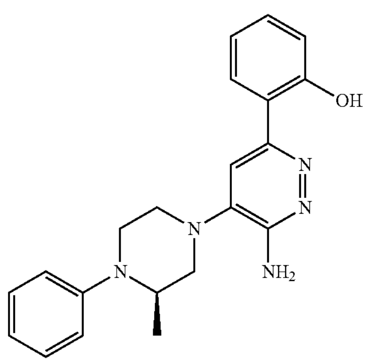 [SMILES: C[C@@H]1CN(c2cc(-c3ccccc3O)nnc2N)CCN1c1ccccc1] | 2-[6-amino-5-[(3R)-3-methyl-4-phenyl-piperazin-1-yl]pyridazin-3-yl]phenol | 0.0276 | | |
| 84 | 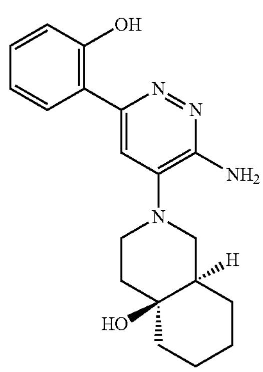 [SMILES: Nc1nnc(-c2ccccc2O)cc1N1CC[C@@]2(O)CCCC[C@@H]2C1] | (4aS,8aR)-2-[3-amino-6-(2-hydroxyphenyl)pyridazin-4-yl]-1,3,4,5,6,7,8,8a-octahydroisoquinolin-4a-ol | 0.0084 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 85 | 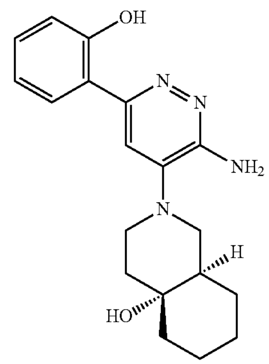 [SMILES: Nc1nnc(-c2ccccc2O)cc1N1CC[C@]2(O)CCCC[C@@H]2C1] | (4aR,8aR)-2-[3-amino-6-(2-hydroxyphenyl)pyridazin-4-yl]-1,3,4,5,6,7,8,8a-octahydroisoquinolin-4a-ol | 0.011 | | |
| 86 | 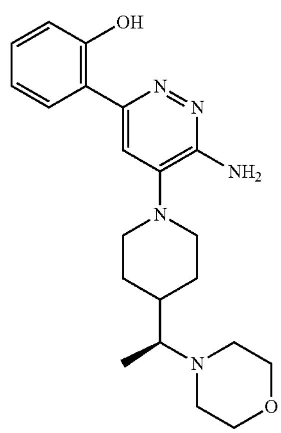 [SMILES: C[C@@H](C1CCN(c2cc(-c3ccccc3O)nnc2N)CC1)N1CCOCC1] | 2-[6-amino-5-[4-[(1S)-1-morpholinoethyl]-1-piperidyl]pyridazin-3-yl]phenol | 0.0302 | | |
| 87 | 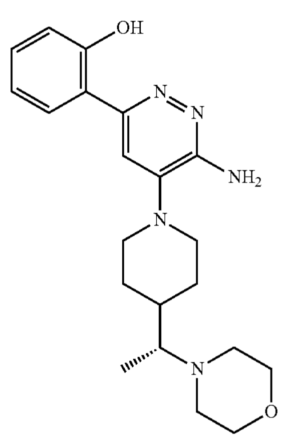 [SMILES: C[C@H](C1CCN(c2cc(-c3ccccc3O)nnc2N)CC1)N1CCOCC1] | 2-[6-amino-5-[4-[(1R)-1-morpholinoethyl]-1-piperidyl]pyridazin-3-yl]phenol | 0.0413 | | |

-continued
| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 88 | 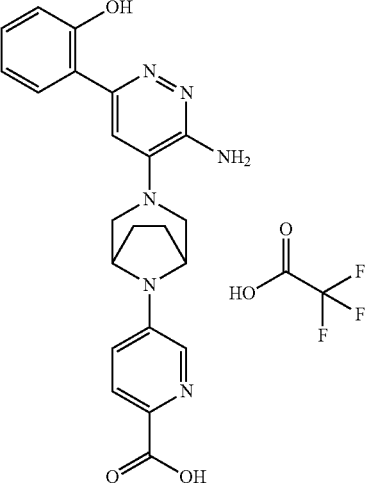 [SMILES: Nc1nnc(-c2ccccc2O)cc1N1CC2CCC(C1)N2c1ccc(C(=O)O)nc1 ; O=C(O)C(F)(F)F] | 5-[3-[3-amino-6-(2-hydroxyphenyl)pyridazin-4-yl]-3,8-diazabicyclo[3.2.1]octan-8-yl]pyridine-2-carboxylic acid; 2,2,2-trifluoroacetic acid | 0.2176 | | |
| 89 | 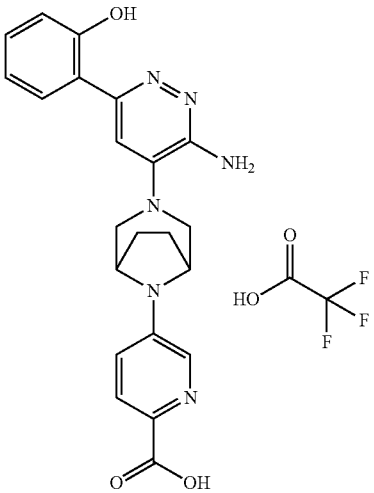 [SMILES: Nc1nnc(-c2ccccc2O)cc1N1CC2CCC(C1)N2c1ccc(C(=O)O)nc1 ; O=C(O)C(F)(F)F] | 5-[3-[3-amino-6-(2-hydroxyphenyl)pyridazin-4-yl]-3,8-diazabicyclo[3.2.1]octan-8-yl]pyridine-2-carboxamide; 2,2,2-trifluoroacetic acid | 0.0517 | | |
| 90 | 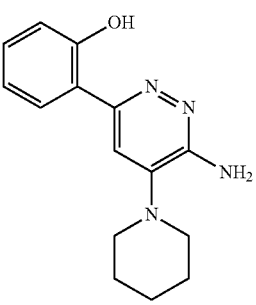 [SMILES: Nc1nnc(-c2ccccc2O)cc1N1CCCCC1] | 2-[6-amino-5-(1-piperidyl)pyridazin-3-yl]phenol | 0.034 | 0.0459 | 0.0139 |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 91 | 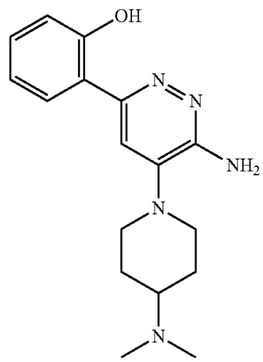 [SMILES: CN(C)C1CCN(c2cc(-c3ccccc3O)nnc2N)CC1] | 2-[6-amino-5-[4-(dimethylamino)-1-piperidyl]pyridazin-3-yl]phenol | 0.0929 | | |
| 92 | 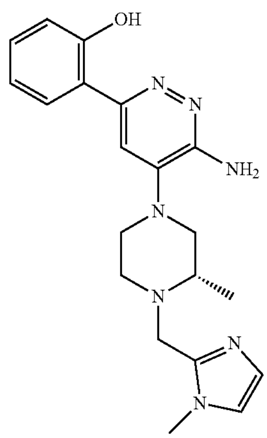 [SMILES: C[C@H]1CN(c2cc(-c3ccccc3O)nnc2N)CCN1Cc1nccn1C] | 2-[6-amino-5-[(3S)-3-methyl-4-[(1-methylimidazol-2-yl)methyl]piperazin-1-yl]pyridazin-3-yl]phenol | 0.0185 | | |
| 93 | 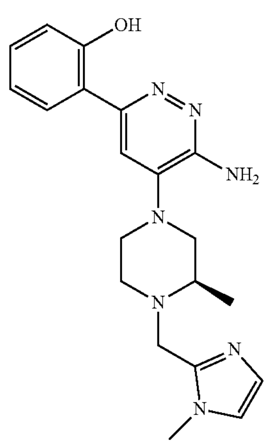 [SMILES: C[C@@H]1CN(c2cc(-c3ccccc3O)nnc2N)CCN1Cc1nccn1C] | (R)-2-(6-amino-5-(3-methyl-4-((1-methyl-1H-imidazol-2-yl)methyl)piperazin-1-yl)pyridazin-3-yl)phenol | 0.0238 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 94 | 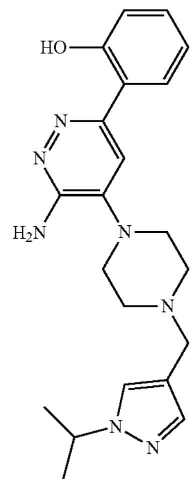 [SMILES: CC(C)n1cc(CN2CCN(c3cc(-c4ccccc4O)nnc3N)CC2)cn1] | 2-[6-amino-5-[4-[(1-isopropylpyrazol-4-yl)methyl]piperazin-1-yl]pyridazin-3-yl]phenol | 0.1221 | | |
| 95 | 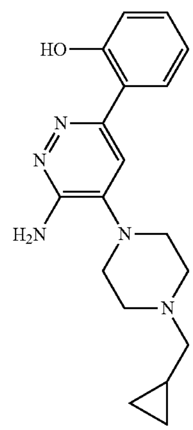 [SMILES: Nc1nnc(-c2ccccc2O)cc1N1CCN(CC2CC2)CC1] | 2-[6-amino-5-[4-(cyclopropylmethyl)piperazin-1-yl]pyridazin-3-yl]phenol | | | |
| 96 | 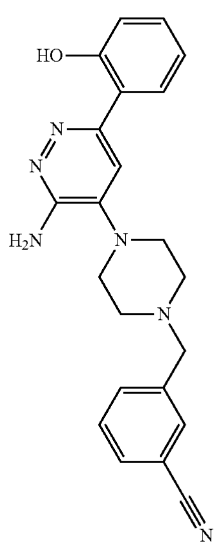 [SMILES: N#Cc1cccc(CN2CCN(c3cc(-c4ccccc4O)nnc3N)CC2)c1] | 3-[[4-[3-amino-6-(2-hydroxyphenyl)pyridazin-4-yl]piperazin-1-yl]methyl]benzonitrile | 0.0569 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 97 | 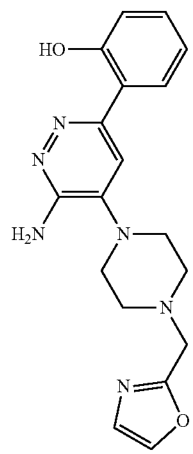 [SMILES: Nc1nnc(-c2ccccc2O)cc1N1CCN(Cc2ncco2)CC1] | 2-[6-amino-5-[4-(oxazol-2-ylmethyl)piperazin-1-yl]pyridazin-3-yl]phenol | 0.0714 | | |
| 98 | 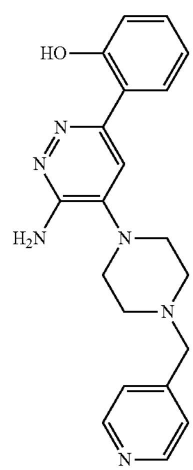 [SMILES: Nc1nnc(-c2ccccc2O)cc1N1CCN(Cc2ccncc2)CC1] | 2-[6-amino-5-[4-(4-pyridylmethyl)piperazin-1-yl]pyridazin-3-yl]phenol | 0.0796 | | |
| 99 | 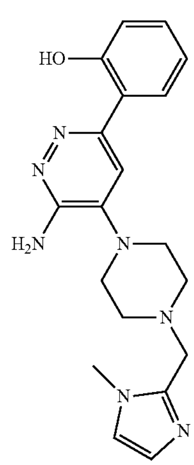 [SMILES: Cn1ccnc1CN1CCN(c2cc(-c3ccccc3O)nnc2N)CC1] | 2-[6-amino-5-[4-[(1-methylimidazol-2-yl)methyl]piperazin-1-yl]pyridazin-3-yl]phenol | 0.0324 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 100 | 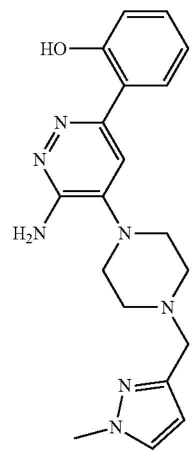 [SMILES: Cn1ccc(CN2CCN(c3cc(-c4ccccc4O)nnc3N)CC2)n1] | 2-[6-amino-5-[4-[(1-methylpyrazol-3-yl)methyl]piperazin-1-yl]pyridazin-3-yl]phenol | 0.038 | | |
| 101 | 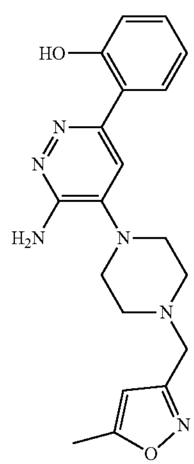 [SMILES: Cc1cc(CN2CCN(c3cc(-c4ccccc4O)nnc3N)CC2)no1] | 2-[6-amino-5-[4-[(5-methylisoxazol-3-yl)methyl]piperazin-1-yl]pyridazin-3-yl]phenol | 0.0653 | | |
| 102 | 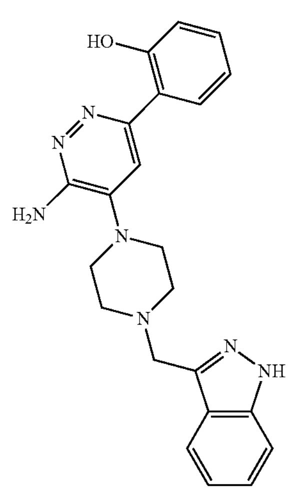 [SMILES: Nc1nnc(-c2ccccc2O)cc1N1CCN(Cc2n[nH]c3ccccc23)CC1] | 2-[6-amino-5-[4-(1H-indazol-3-ylmethyl)piperazin-1-yl]pyridazin-3-yl]phenol | 0.0259 | | |

| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 103 | 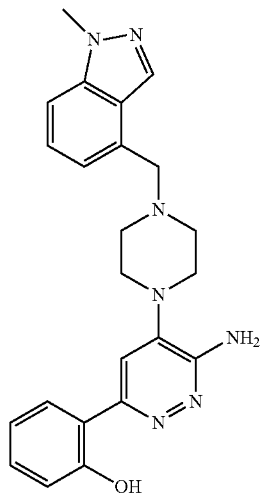 [SMILES: Cn1ncc2c(CN3CCN(c4cc(-c5ccccc5O)nnc4N)CC3)cccc21] | 2-[6-amino-5-[4-[(1-methylindazol-4-yl)methyl]piperazin-1-yl]pyridazin-3-yl]phenol | 0.0289 | | |
| 104 | 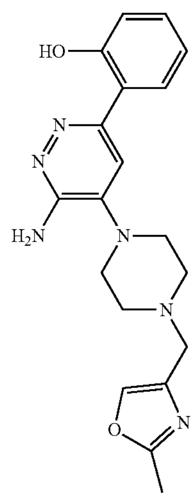 [SMILES: Cc1nc(CN2CCN(c3cc(-c4ccccc4O)nnc3N)CC2)co1] | 2-[6-amino-5-[4-[(2-methyloxazol-4-yl)methyl]piperazin-1-yl]pyridazin-3-yl]phenol | 0.0569 | | |
| 105 | 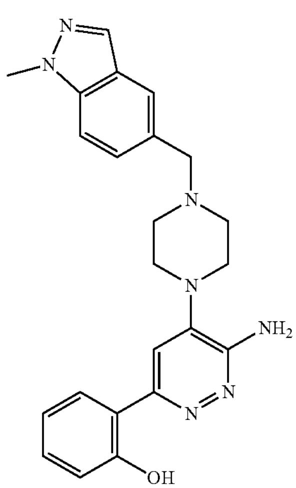 [SMILES: Cn1ncc2cc(CN3CCN(c4cc(-c5ccccc5O)nnc4N)CC3)ccc21] | 2-[6-amino-5-[4-[(1-methylindazol-5-yl)methyl]piperazin-1-yl]pyridazin-3-yl]phenol | 0.0279 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 106 | 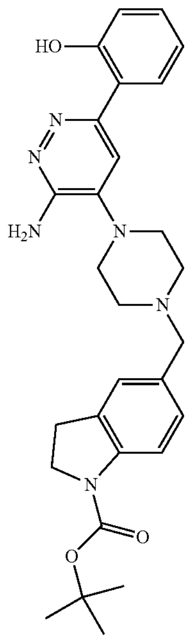 [SMILES: CC(C)(C)OC(=O)N1CCc2cc(CN3CCN(c4cc(-c5ccccc5O)nnc4N)CC3)ccc21] | tert-butyl 5-[[4-[3-amino-6-(2-hydroxyphenyl)pyridazin-4-yl]piperazin-1-yl]methyl]indoline-1-carboxylate | 0.6886 | | |
| 107 | 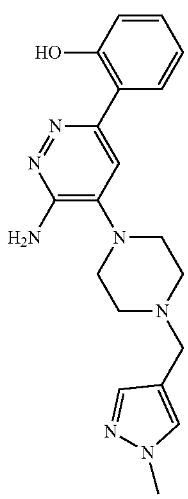 [SMILES: Cn1cc(CN2CCN(c3cc(-c4ccccc4O)nnc3N)CC2)cn1] | 2-[6-amino-5-[4-[(1-methylpyrazol-4-yl)methyl]piperazin-1-yl]pyridazin-3-yl]phenol | 0.0877 | | |
| 108 | 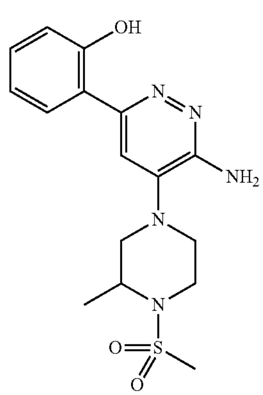 [SMILES: CC1CN(c2cc(-c3ccccc3O)nnc2N)CCN1S(C)(=O)=O] | 2-[6-amino-5-(3-methyl-4-methylsulfonyl-piperazin-1-yl)pyridazin-3-yl]phenol | 0.031 | 0.0358 | 0.0159 |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 109 | 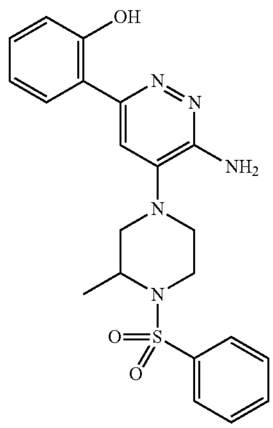 [SMILES: CC1CN(c2cc(-c3ccccc3O)nnc2N)CCN1S(=O)(=O)c1ccccc1] | 2-[6-amino-5-[4-(benzenesulfonyl)-3-methyl-piperazin-1-yl]pyridazin-3-yl]phenol | 0.0176 | | |
| 110 | 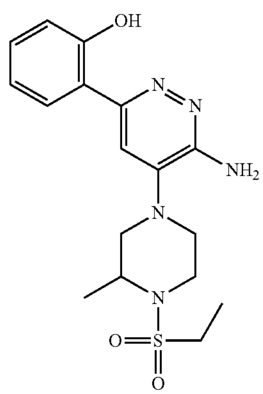 [SMILES: CCS(=O)(=O)N1CCN(c2cc(-c3ccccc3O)nnc2N)CC1C] | 2-[6-amino-5-(4-ethylsulfonyl-3-methyl-piperazin-1-yl)pyridazin-3-yl]phenol | 0.0219 | | |
| 111 | 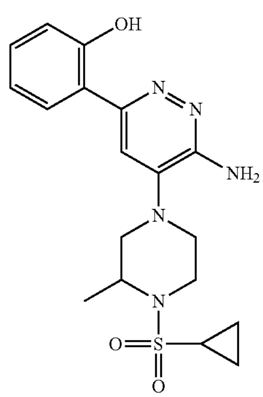 [SMILES: CC1CN(c2cc(-c3ccccc3O)nnc2N)CCN1S(=O)(=O)C1CC1] | 2-[6-amino-5-(4-cyclopropylsulfonyl-3-methyl-piperazin-1-yl)pyridazin-3-yl]phenol | 0.0197 | | |

-continued

| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 112 | 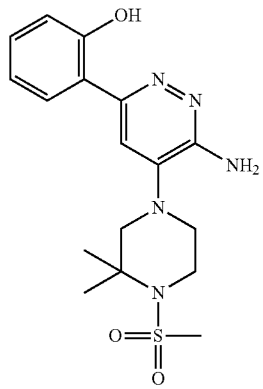 [SMILES: CC1(C)CN(c2cc(-c3ccccc3O)nnc2N)CCN1S(C)(=O)=O] | 2-[6-amino-5-(3,3-dimethyl-4-methylsulfonyl-piperazin-1-yl)pyridazin-3-yl]phenol | 0.0307 | | |
| 113 | 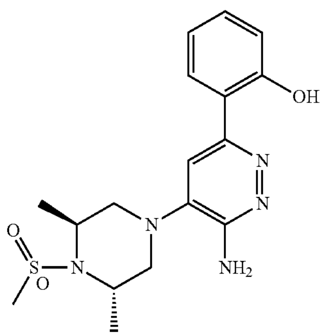 | 2-[6-amino-5-[(3S,5S)-3,5-dimethyl-4-methylsulfonyl-piperazin-1-yl]pyridazin-3-yl]phenol | 0.2633 | | |
| 114 | 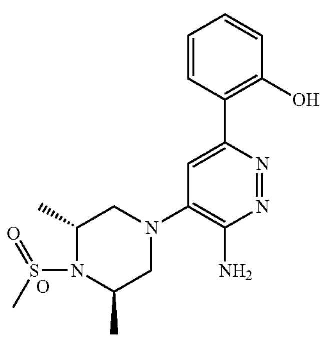 | 2-[6-amino-5-[(3R,5R)-3,5-dimethyl-4-methylsulfonyl-piperazin-1-yl]pyridazin-3-yl]phenol | 0.0515 | | |
| 115 | 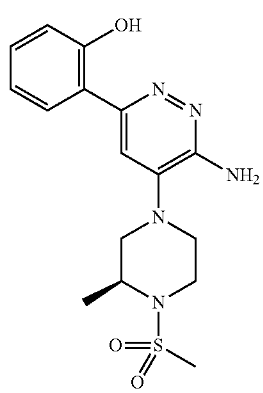 [SMILES: C[C@H]1CN(c2cc(-c3ccccc3O)nnc2N)CCN1S(C)(=O)=O] | 2-[6-amino-5-[(3S)-3-methyl-4-methylsulfonyl-piperazin-1-yl]pyridazin-3-yl]phenol | 0.0636 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 116 | 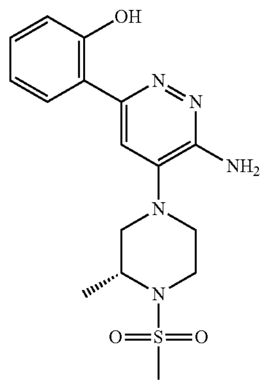 [SMILES: C[C@@H]1CN(c2cc(-c3ccccc3O)nnc2N)CCN1S(C)(=O)=O] | 2-[6-amino-5-[(3R)-3-methyl-4-methylsulfonyl-piperazin-1-yl]pyridazin-3-yl]phenol | 0.037 | | |
| 117 | 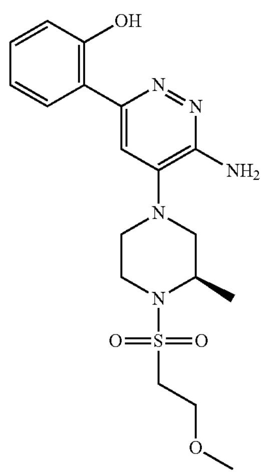 [SMILES: COCCS(=O)(=O)N1CCN(c2cc(-c3ccccc3O)nnc2N)C[C@H]1C] | 2-[6-amino-5-[(3R)-4-(2-methoxyethylsulfonyl)-3-methyl-piperazin-1-yl]pyridazin-3-yl]phenol | 0.0535 | | |
| 118 | 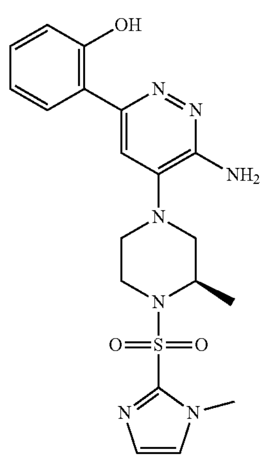 [SMILES: C[C@@H]1CN(c2cc(-c3ccccc3O)nnc2N)CCN1S(=O)(=O)c1nccn1C] | 2-[6-amino-5-[(3R)-3-methyl-4-(1-methylimidazol-2-yl)sulfonyl-piperazin-1-yl]pyridazin-3-yl]phenol | 0.0281 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 119 | 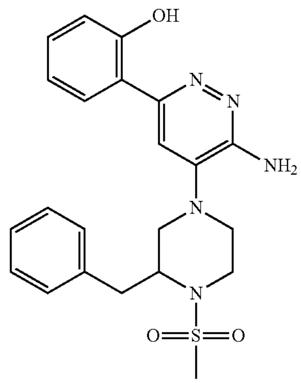 [SMILES: CS(=O)(=O)N1CCN(c2cc(-c3ccccc3O)nnc2N)CC1Cc1ccccc1] | 2-[6-amino-5-(3-benzyl-4-methylsulfonyl-piperazin-1-yl)pyridazin-3-yl]phenol | 0.0385 | 0.0468 | 0.0233 |
| 120 | 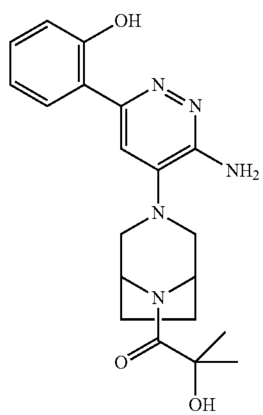 [SMILES: CC(C)(O)C(=O)N1C2CCC1CN(c1cc(-c3ccccc3O)nnc1N)C2] | 1-[3-[3-amino-6-(2-hydroxyphenyl)pyridazin-4-yl]-3,8-diazabicyclo[3.2.1]octan-8-yl]-2-hydroxy-2-methyl-propan-1-one | 0.0444 | | |
| 121 | 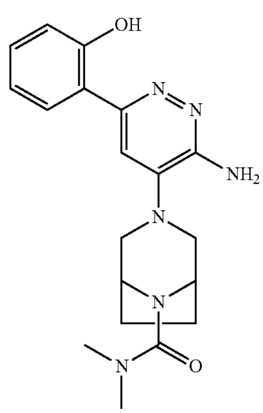 [SMILES: CN(C)C(=O)N1C2CCC1CN(c1cc(-c3ccccc3O)nnc1N)C2] | 3-[3-amino-6-(2-hydroxyphenyl)pyridazin-4-yl]-N,N-dimethyl-3,8-diazabicyclo[3.2.1]octane-8-carboxamide | 0.0225 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 122 | 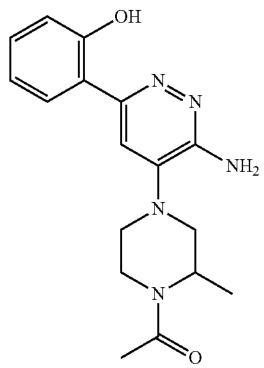 [SMILES: CC(=O)N1CCN(c2cc(-c3ccccc3O)nnc2N)CC1C] | 1-[4-[3-amino-6-(2-hydroxyphenyl)pyridazin-4-yl]-2-methyl-piperazin-1-yl]ethanone | 0.0396 | 0.039 | 0.0163 |
| 123 | 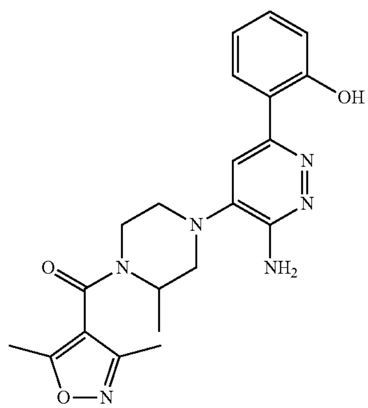 [SMILES: Cc1noc(C)c1C(=O)N1CCN(c2cc(-c3ccccc3O)nnc2N)CC1C] | [4-[3-amino-6-(2-hydroxyphenyl)pyridazin-4-yl]-2-methyl-piperazin-1-yl]-(3,5-dimethylisoxazol-4-yl)methanone | 0.0879 | | |
| 124 | 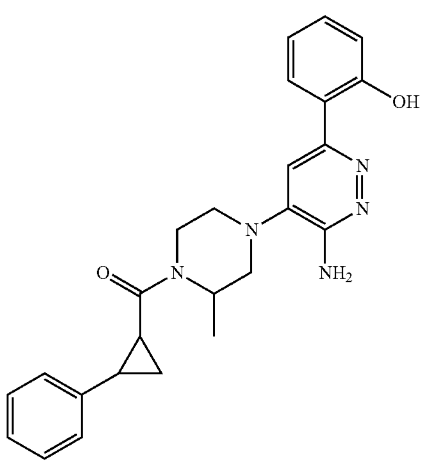 [SMILES: CC1CN(c2cc(-c3ccccc3O)nnc2N)CCN1C(=O)C1CC1c1ccccc1] | [4-[3-amino-6-(2-hydroxyphenyl)pyridazin-4-yl]-2-methyl-piperazin-1-yl]-(2-phenylcyclopropyl)methanone | 0.0258 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 125 | 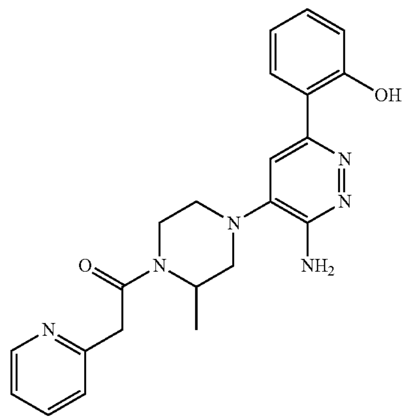 [SMILES: CC1CN(c2cc(-c3ccccc3O)nnc2N)CCN1C(=O)Cc1ccccn1] | 1-[4-[3-amino-6-(2-hydroxyphenyl)pyridazin-4-yl]-2-methyl-piperazin-1-yl]-2-(2-pyridyl)ethanone | 0.0426 | | |
| 126 | 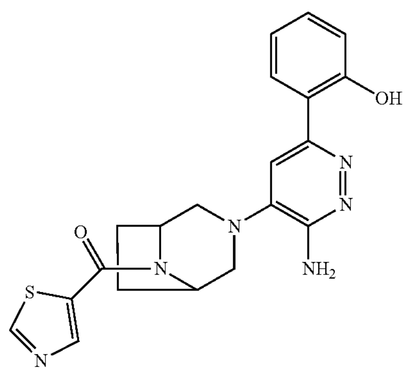 [SMILES: Nc1nnc(-c2ccccc2O)cc1N1CC2CCC(C1)N2C(=O)c1cncs1] | [3-[3-amino-6-(2-hydroxyphenyl)pyridazin-4-yl]-3,8-diazabicyclo[3.2.1]octan-8-yl]-thiazol-5-yl-methanone | 0.0203 | | |
| 127 | 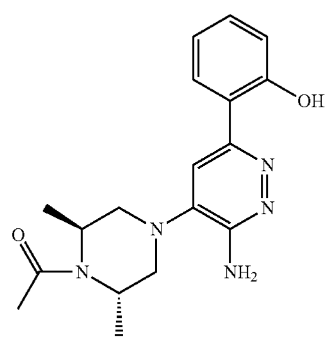 [SMILES: CC(=O)N1[C@@H](C)CN(c2cc(-c3ccccc3O)nnc2N)C[C@@H]1C] | 1-[(2S,6S)-4-[3-amino-6-(2-hydroxyphenyl)pyridazin-4-yl]-2,6-dimethyl-piperazin-1-yl]ethanone | 0.3694 | | |
| 128 | 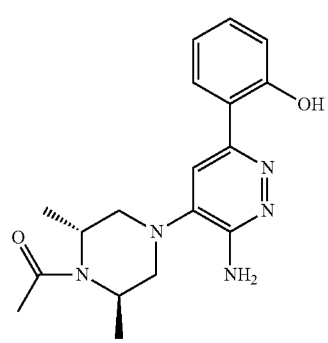 [SMILES: CC(=O)N1[C@H](C)CN(c2cc(-c3ccccc3O)nnc2N)C[C@H]1C] | 1-[(2R,6R)-4-[3-amino-6-(2-hydroxyphenyl)pyridazin-4-yl]-2,6-dimethyl-piperazin-1-yl]ethanone | 0.5046 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 129 | 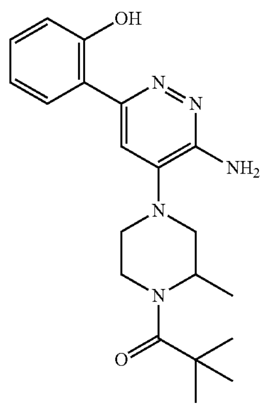 [SMILES: CC1CN(c2cc(-c3ccccc3O)nnc2N)CCN1C(=O)C(C)(C)C] | 1-[4-[3-amino-6-(2-hydroxyphenyl) pyridazin-4-yl]-2-methyl-piperazin-1-yl]-2,2-dimethyl-propan-1-one | 0.0104 | 0.0184 | 0.0068 |
| 130 | 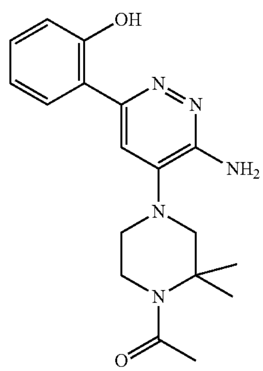 [SMILES: CC(=O)N1CCN(c2cc(-c3ccccc3O)nnc2N)CC1(C)C] | 1-[4-[3-amino-6-(2-hydroxyphenyl) pyridazin-4-yl]-2,2-dimethyl-piperazin-1-yl]ethanone | 0.075 | | |
| 131 | 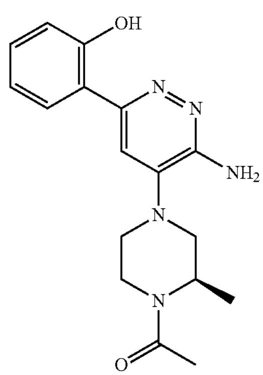 [SMILES: CC(=O)N1CCN(c2cc(-c3ccccc3O)nnc2N)C[C@H]1C] | 1-[(2R)-4-[3-amino-6-(2-hydroxyphenyl) pyridazin-4-yl]-2-methyl-piperazin-1-yl]ethanone | 0.0346 | | |
| 132 | 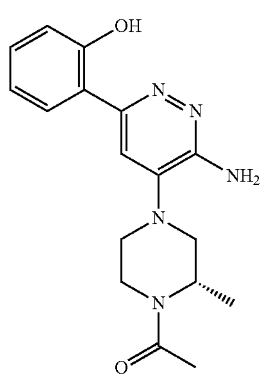 [SMILES: CC(=O)N1CCN(c2cc(-c3ccccc3O)nnc2N)C[C@@H]1C] | 1-[(2S)-4-[3-amino-6-(2-hydroxyphenyl) pyridazin-4-yl]-2-methyl-piperazin-1-yl]ethanone | 0.1186 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 133 | 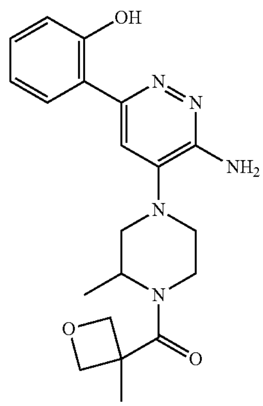 [SMILES: CC1CN(c2cc(-c3ccccc3O)nnc2N)CCN1C(=O)C1(C)COC1] | [4-[3-amino-6-(2-hydroxyphenyl) pyridazin-4-yl]-2-methyl-piperazin-1-yl]-(3-methyloxetan-3-yl)methanone | 0.067 | | |
| 134 | 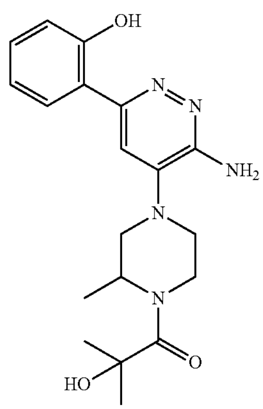 [SMILES: CC1CN(c2cc(-c3ccccc3O)nnc2N)CCN1C(=O)C(C)(C)O] | 1-[4-[3-amino-6-(2-hydroxyphenyl) pyridazin-4-yl]-2-methyl-piperazin-1-yl]-2-hydroxy-2-methyl-propan-1-one | 0.0349 | | |
| 135 | 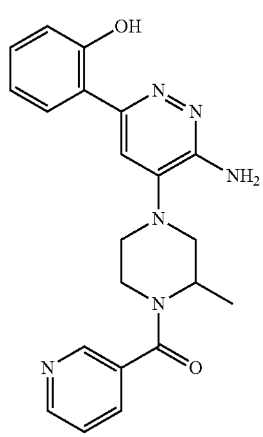 [SMILES: CC1CN(c2cc(-c3ccccc3O)nnc2N)CCN1C(=O)c1cccnc1] | [4-[3-amino-6-(2-hydroxyphenyl) pyridazin-4-yl]-2-methyl-piperazin-1-yl]-(3-pyridyl)methanone | 0.0446 | | |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 136 | 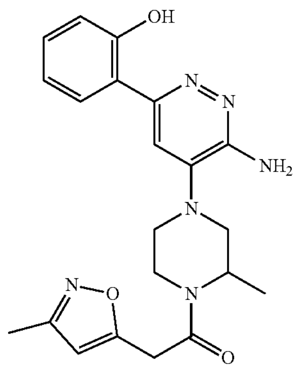 | 1-[4-[3-amino-6-(2-hydroxyphenyl)pyridazin-4-yl]-2-methyl-piperazin-1-yl]-2-(3-methylisoxazol-5-yl)ethanone | 0.0444 | | |
| 137 | 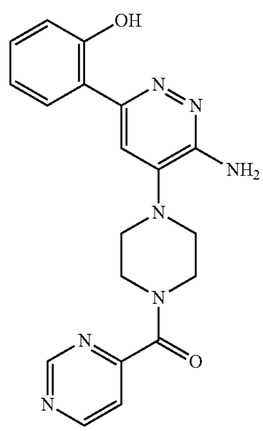 [SMILES: Nc1nnc(-c2ccccc2O)cc1N1CCN(C(=O)c2ccncn2)CC1] | [4-[3-amino-6-(2-hydroxyphenyl)pyridazin-4-yl]-2-methyl-piperazin-1-yl]-pyrimidin-4-yl-methanone | 0.0389 | | |
| 138 | 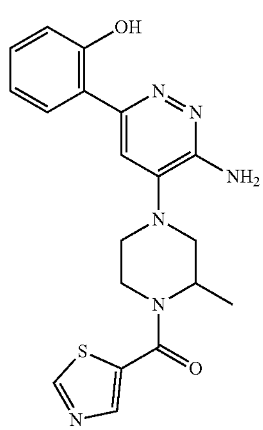 [SMILES: CC1CN(c2cc(-c3ccccc3O)nnc2N)CCN1C(=O)c1cncs1] | [4-[3-amino-6-(2-hydroxyphenyl)pyridazin-4-yl]-2-methyl-piperazin-1-yl]-thiazol-5-yl-methanone | 0.0126 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 139 | 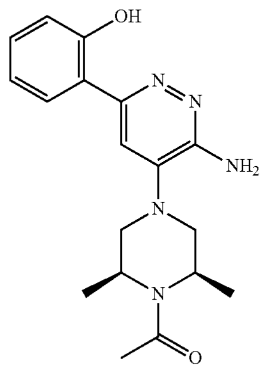 [SMILES: CC(=O)N1[C@H](C)CN(c2cc(-c3ccccc3O)nnc2N)C[C@@H]1C] | 1-[(2S,6R)-4-[3-amino-6-(2-hydroxyphenyl)pyridazin-4-yl]-2,6-dimethyl-piperazin-1-yl]ethanone | 0.1063 | | |
| 140 | 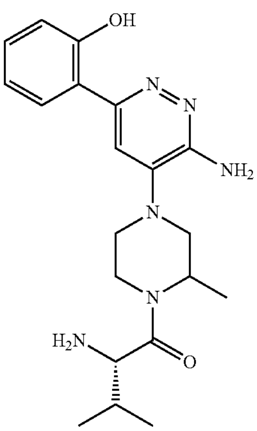 [SMILES: CC(C)[C@H](N)C(=O)N1CCN(c2cc(-c3ccccc3O)nnc2N)CC1C] | (2S)-2-amino-1-(4-(3-amino-6-(2-hydroxyphenyl)pyridazin-4-yl)-2-methylpiperazin-1-yl)-3-methylbutan-1-one | 0.0475 | | |
| 141 | 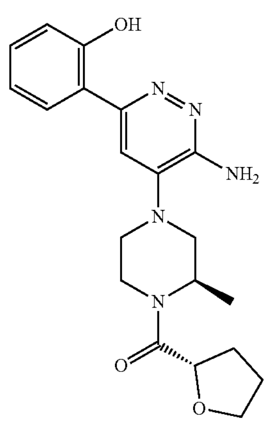 [SMILES: C[C@@H]1CN(c2cc(-c3ccccc3O)nnc2N)CCN1C(=O)[C@@H]1CCCO1] | [(2R)-4-[3-amino-6-(2-hydroxyphenyl)pyridazin-4-yl]-2-methyl-piperazin-1-yl]-[(2S)-tetrahydrofuran-2-yl]methanone | 0.033 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 142 | 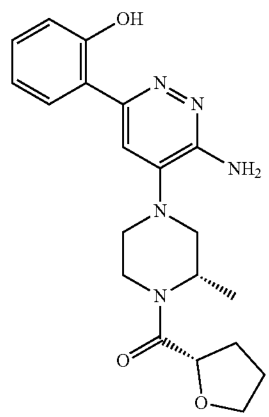 [SMILES: C[C@H]1CN(c2cc(-c3ccccc3O)nnc2N)CCN1C(=O)[C@@H]1CCCO1] | [(2S)-4-[3-amino-6-(2-hydroxyphenyl)pyridazin-4-yl]-2-methyl-piperazin-1-yl]-[(2S)-tetrahydrofuran-2-yl]methanone | 0.0975 | | |
| 143 | 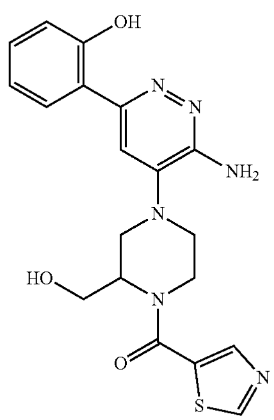 [SMILES: Nc1nnc(-c2ccccc2O)cc1N1CCN(C(=O)c2cncs2)C(CO)C1] | [4-[3-amino-6-(2-hydroxyphenyl)pyridazin-4-yl]-2-(hydroxymethyl)piperazin-1-yl]-thiazol-5-yl-methanone | 0.0206 | | |
| 144 | 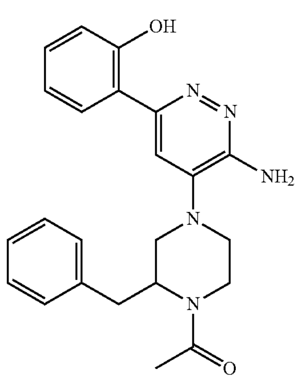 [SMILES: CC(=O)N1CCN(c2cc(-c3ccccc3O)nnc2N)CC1Cc1ccccc1] | 1-[4-[3-amino-6-(2-hydroxyphenyl)pyridazin-4-yl]-2-benzyl-piperazin-1-yl]ethanone | 0.0297 | | |

-continued
| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 145 | 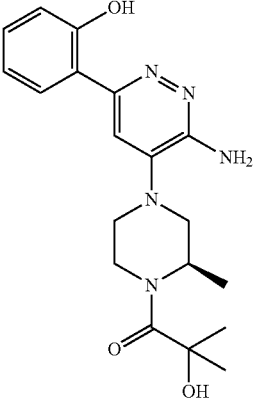 [SMILES: C[C@@H]1CN(c2cc(-c3ccccc3O)nnc2N)CCN1C(=O)C(C)(C)O] | 1-[(2R)-4-[3-amino-6-(2-hydroxyphenyl)pyridazin-4-yl]-2-methyl-piperazin-1-yl]-2-hydroxy-2-methyl-propan-1-one | 0.0642 | | |
| 146 | 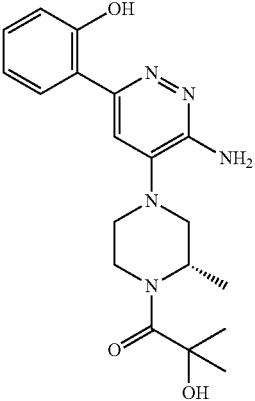 [SMILES: C[C@H]1CN(c2cc(-c3ccccc3O)nnc2N)CCN1C(=O)C(C)(C)O] | 1-[(2S)-4-[3-amino-6-(2-hydroxyphenyl)pyridazin-4-yl]-2-methyl-piperazin-1-yl]-2-hydroxy-2-methyl-propan-1-one | 0.0458 | | |
| 147 | 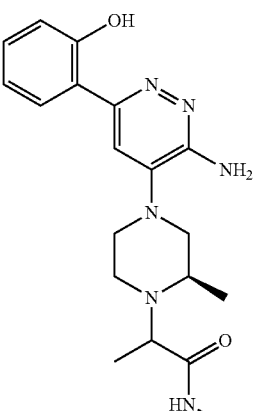 | 2-[(2R)-4-[3-amino-6-(2-hydroxyphenyl)pyridazin-4-yl]-2-methyl-piperazin-1-yl]-N-methyl-propanamide | 0.0268 | | |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 148 | 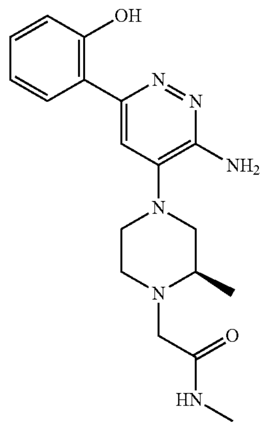 [SMILES: CNC(=O)CN1CCN(c2cc(-c3ccccc3O)nnc2N)C[C@H]1C] | 2-[(2R)-4-[3-amino-6-(2-hydroxyphenyl)pyridazin-4-yl]-2-methyl-piperazin-1-yl]-N-methyl-acetamide | 0.0613 | | |
| 149 | 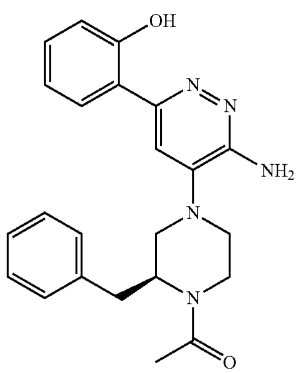 [SMILES: CC(=O)N1CCN(c2cc(-c3ccccc3O)nnc2N)C[C@@H]1Cc1ccccc1] | 1-[(2S)-4-[3-amino-6-(2-hydroxyphenyl)pyridazin-4-yl]-2-benzyl-piperazin-1-yl]ethanone | 0.0869 | | |
| 150 | 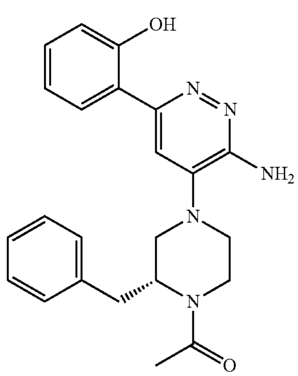 [SMILES: CC(=O)N1CCN(c2cc(-c3ccccc3O)nnc2N)C[C@H]1Cc1ccccc1] | 1-[(2R)-4-[3-amino-6-(2-hydroxyphenyl)pyridazin-4-yl]-2-benzyl-piperazin-1-yl]ethanone | 0.0584 | | |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 151 | 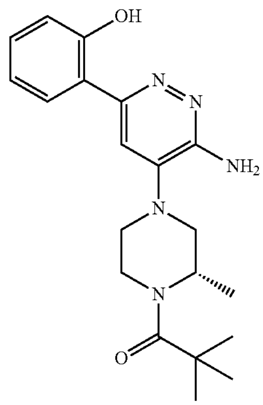 [SMILES: C[C@H]1CN(c2cc(-c3ccccc3O)nnc2N)CCN1C(=O)C(C)(C)C] | 1-[(2S)-4-[3-amino-6-(2-hydroxyphenyl)pyridazin-4-yl]-2-methyl-piperazin-1-yl]-2,2-dimethyl-propan-1-one | | | |
| 152 | 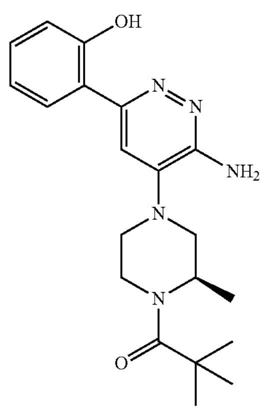 [SMILES: C[C@@H]1CN(c2cc(-c3ccccc3O)nnc2N)CCN1C(=O)C(C)(C)C] | 1-[(2R)-4-[3-amino-6-(2-hydroxyphenyl)pyridazin-4-yl]-2-methyl-piperazin-1-yl]-2,2-dimethyl-propan-1-one | | | |
| 153 | 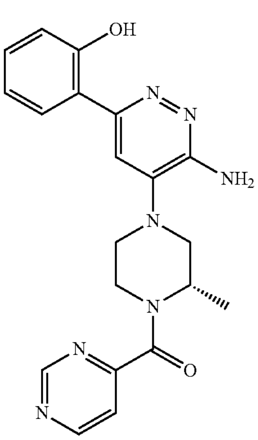 [SMILES: C[C@H]1CN(c2cc(-c3ccccc3O)nnc2N)CCN1C(=O)c1ccncn1] | [(2S)-4-[3-amino-6-(2-hydroxyphenyl)pyridazin-4-yl]-2-methyl-piperazin-1-yl]-pyrimidin-4-yl-methanone | 0.2019 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 154 | 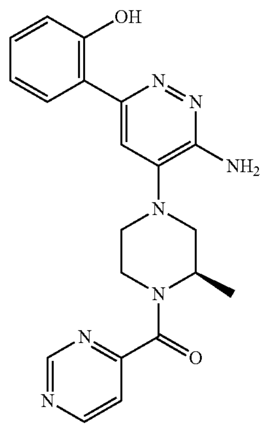 [SMILES: C[C@@H]1CN(c2cc(-c3ccccc3O)nnc2N)CCN1C(=O)c1ccncn1] | [(2R)-4-[3-amino-6-(2-hydroxyphenyl)pyridazin-4-yl]-2-methyl-piperazin-1-yl]-pyrimidin-4-yl-methanone | 0.0496 | | |
| 155 | 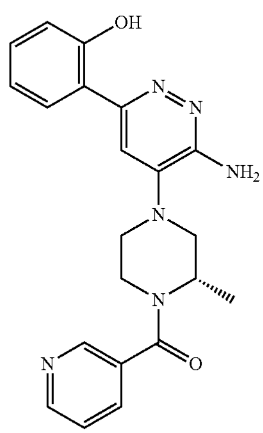 [SMILES: C[C@H]1CN(c2cc(-c3ccccc3O)nnc2N)CCN1C(=O)c1cccnc1] | [(2S)-4-[3-amino-6-(2-hydroxyphenyl)pyridazin-4-yl]-2-methyl-piperazin-1-yl]-(3-pyridyl)methanone | 0.1663 | | |
| 156 | 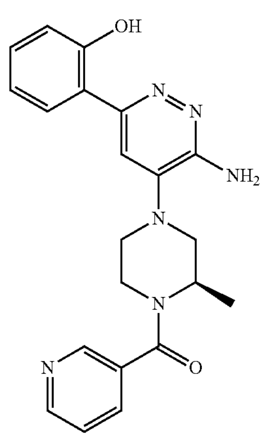 [SMILES: C[C@@H]1CN(c2cc(-c3ccccc3O)nnc2N)CCN1C(=O)c1cccnc1] | [(2R)-4-[3-amino-6-(2-hydroxyphenyl)pyridazin-4-yl]-2-methyl-piperazin-1-yl]-(3-pyridyl)methanone | 0.0435 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 157 | 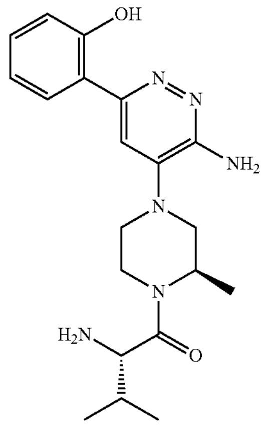 [SMILES: CC(C)[C@H](N)C(=O)N1CCN(c2cc(-c3ccccc3O)nnc2N)C[C@H]1C] | (2S)-2-amino-1-[(2R)-4-[3-amino-6-(2-hydroxyphenyl)pyridazin-4-yl]-2-methyl-piperazin-1-yl]-3-methyl-butan-1-one | 0.0296 | | |
| 158 | 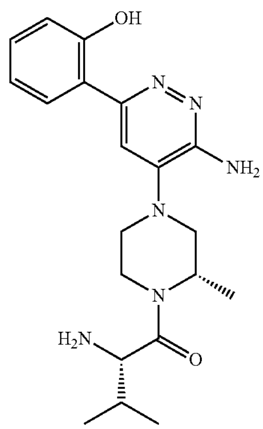 [SMILES: CC(C)[C@H](N)C(=O)N1CCN(c2cc(-c3ccccc3O)nnc2N)C[C@@H]1C] | (2S)-2-amino-1-[(2S)-4-[3-amino-6-(2-hydroxyphenyl)pyridazin-4-yl]-2-methyl-piperazin-1-yl]-3-methyl-butan-1-one | 0.1125 | | |
| 159 | 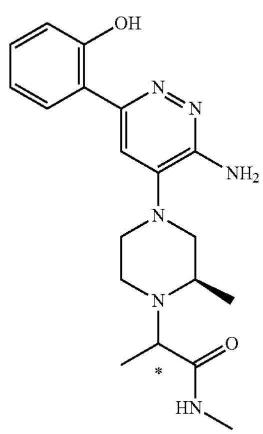 [SMILES: CNC(=O)C(C)N1CCN(c2cc(-c3ccccc3O)nnc2N)C[C@H]1C] | 2-[(2R)-4-[3-amino-6-(2-hydroxyphenyl)pyridazin-4-yl]-2-methyl-piperazin-1-yl]-N-methyl-propanamide | 0.027 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 160 | 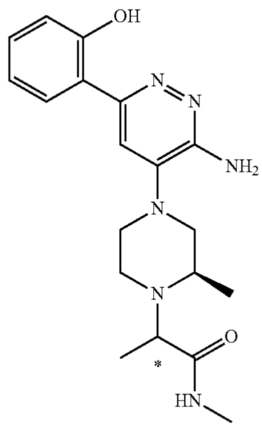 [SMILES: CNC(=O)C(C)N1CCN(c2cc(-c3ccccc3O)nnc2N)C[C@H]1C] | 2-[(2S)-4-[3-amino-6-(2-hydroxyphenyl)pyridazin-4-yl]-2-methyl-piperazin-1-yl]-N-methyl-propanamide | | | |
| 161 | 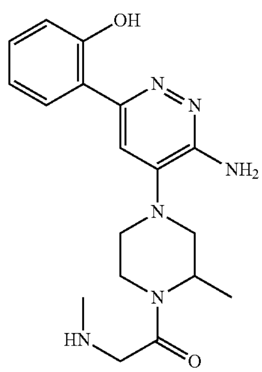 [SMILES: CNCC(=O)N1CCN(c2cc(-c3ccccc3O)nnc2N)CC1C] | 1-[4-[3-amino-6-(2-hydroxyphenyl)pyridazin-4-yl]-2-methyl-piperazin-1-yl]-2-(methylamino)ethanone | 0.046 | | |
| 162 | 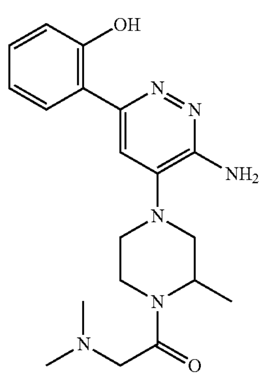 [SMILES: CC1CN(c2cc(-c3ccccc3O)nnc2N)CCN1C(=O)CN(C)C] | 1-[4-[3-amino-6-(2-hydroxyphenyl)pyridazin-4-yl]-2-methyl-piperazin-1-yl]-2-(dimethylamino)ethanone | 0.0586 | | |
| 163 | 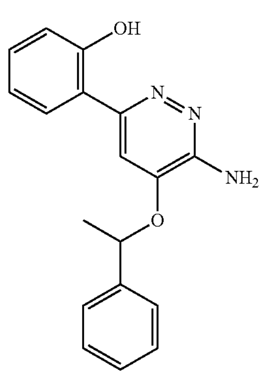 [SMILES: CC(Oc1cc(-c2ccccc2O)nnc1N)c1ccccc1] | 2-[6-amino-5-(1-phenylethoxy)pyridazin-3-yl]phenol | 0.0551 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 164 | 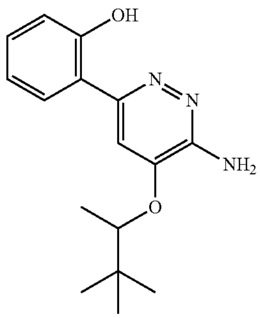 [SMILES: CC(Oc1cc(-c2ccccc2O)nnc1N)C(C)(C)C] | 2-[6-amino-5-(1,2,2-trimethylpropoxy)pyridazin-3-yl]phenol | 0.1432 | | |
| 165 | 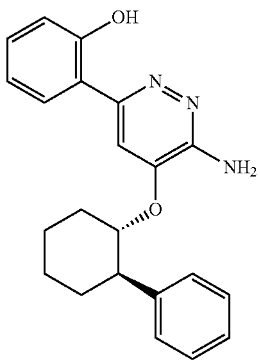 [SMILES: Nc1nnc(-c2ccccc2O)cc1O[C@H]1CCCC[C@@H]1c1ccccc1] | 2-(6-amino-5-(((1,2-trans)-2-phenylcyclohexyl)oxy)pyridazin-3-yl)phenol | 0.9766 | | |
| 166 | 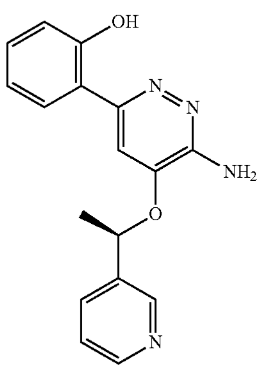 [SMILES: C[C@@H](Oc1cc(-c2ccccc2O)nnc1N)c1cccnc1] | 2-[6-amino-5-[(1R)-1-(3-pyridyl)ethoxy]pyridazin-3-yl]phenol | 0.1315 | | |
| 167 | 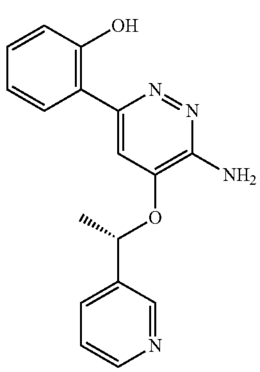 [SMILES: C[C@H](Oc1cc(-c2ccccc2O)nnc1N)c1cccnc1] | 2-[6-amino-5-[(1S)-1-(3-pyridyl)ethoxy]pyridazin-3-yl]phenol | 0.0251 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 168 | 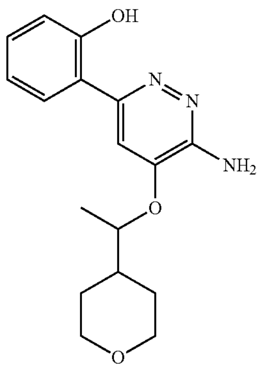 [SMILES: CC(Oc1cc(-c2ccccc2O)nnc1N)C1CCOCC1] | 2-[6-amino-5-(1-tetrahydropyran-4-ylethoxy)pyridazin-3-yl]phenol | 0.1693 | 0.197 | 0.113 |
| 169 | 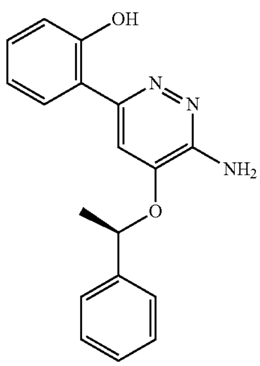 [SMILES: C[C@@H](Oc1cc(-c2ccccc2O)nnc1N)c1ccccc1] | 2-[6-amino-5-[(1R)-1-phenylethoxy]pyridazin-3-yl]phenol | 0.2271 | | |
| 170 | 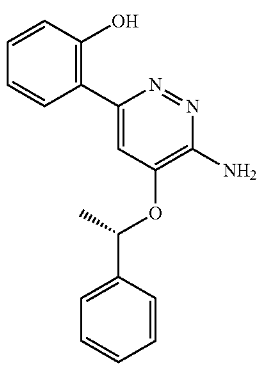 [SMILES: C[C@H](Oc1cc(-c2ccccc2O)nnc1N)c1ccccc1] | 2-[6-amino-5-[(1S)-1-phenylethoxy]pyridazin-3-yl]phenol | 0.0368 | 0.0149 | 0.0096 |
| 171 | 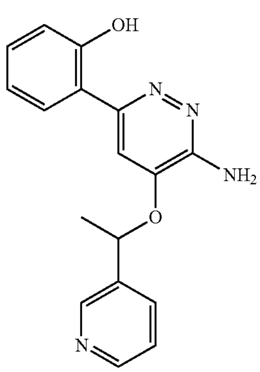 | 2-[6-amino-5-[1-(3-pyridyl)ethoxy]pyridazin-3-yl]phenol | 0.0792 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 172 | 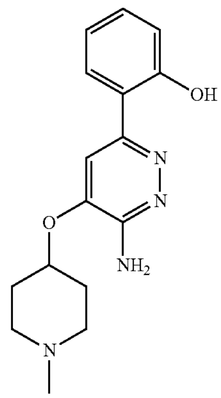 [SMILES: CN1CCC(Oc2cc(-c3ccccc3O)nnc2N)CC1] | 2-[6-amino-5-[(1-methyl-4-piperidyl)oxy]pyridazin-3-yl]phenol | 0.161 | | |
| 173 | 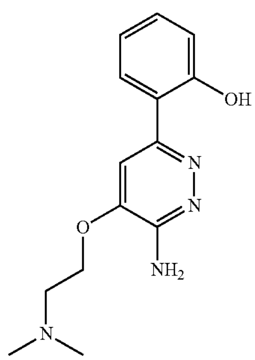 [SMILES: CN(C)CCOc1cc(-c2ccccc2O)nnc1N] | 2-[6-amino-5-[2-(dimethylamino)ethoxy]pyridazin-3-yl]phenol | 0.2631 | 0.276 | 0.257 |
| 174 | 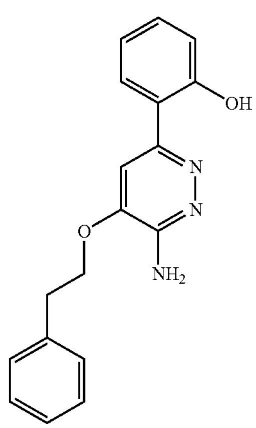 [SMILES: Nc1nnc(-c2ccccc2O)cc1OCCc1ccccc1] | 2-[6-amino-5-(2-phenylethoxy)pyridazin-3-yl]phenol | 0.0148 | 0.019 | 0.0088 |

-continued

| Example | Structure | Name | BRG1 HTRF IC$_{50}$ (μM) | BRM_iso2 HTRF CON (IC50) | PB1-BD5 HTRF CON (IC50) |
|---------|-----------|------|--------------------------|--------------------------|--------------------------|
| 175 | 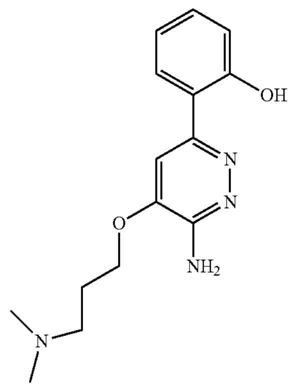 [SMILES: CN(C)CCCOc1cc(-c2ccccc2O)nnc1N] | 2-[6-amino-5-[3-(dimethylamino)propoxy]pyridazin-3-yl]phenol | 0.1167 | | |
| 176 | 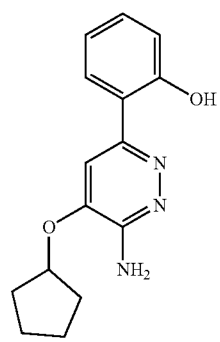 [SMILES: Nc1nnc(-c2ccccc2O)cc1OC1CCCC1] | 2-[6-amino-5-(cyclopentoxy)pyridazin-3-yl]phenol | 0.0371 | | |
| 177 | 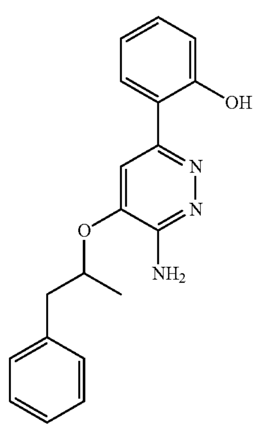 [SMILES: CC(Cc1ccccc1)Oc1cc(-c2ccccc2O)nnc1N] | 2-[6-amino-5-(1-methyl-2-phenyl-ethoxy)pyridazin-3-yl]phenol | 0.1002 | 0.0925 | 0.0292 |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 178 | 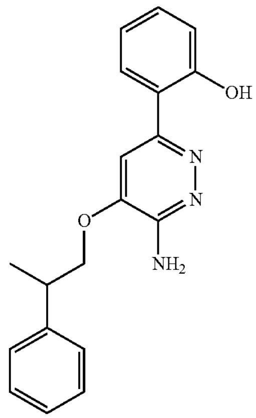 [SMILES: CC(COc1cc(-c2ccccc2O)nnc1N)c1ccccc1] | 2-[6-amino-5-(2-phenylpropoxy)pyridazin-3-yl]phenol | 0.0122 | 0.0072 | 0.0053 |
| 179 | 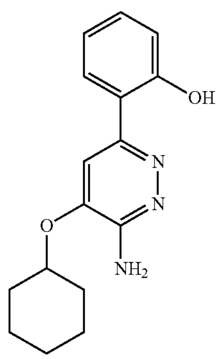 [SMILES: Nc1nnc(-c2ccccc2O)cc1OC1CCCCC1] | 2-[6-amino-5-(cyclohexoxy)pyridazin-3-yl]phenol | 0.0451 | | |
| 180 | 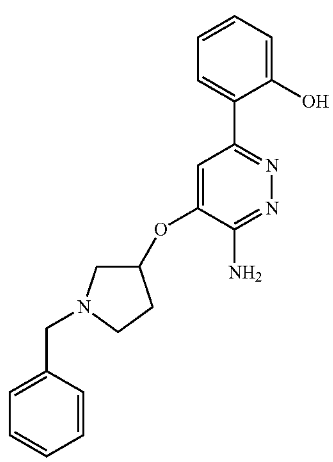 [SMILES: Nc1nnc(-c2ccccc2O)cc1OC1CCN(Cc2ccccc2)C1] | 2-[6-amino-5-(1-benzylpyrrolidin-3-yl)oxy-pyridazin-3-yl]phenol | 0.0432 | 0.0597 | 0.0439 |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 181 | 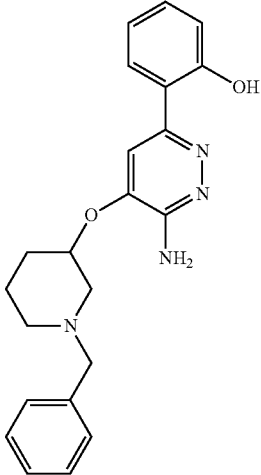 [SMILES: Nc1nnc(-c2ccccc2O)cc1OC1CCCN(Cc2ccccc2)C1] | 2-[6-amino-5-[(1-benzyl-3-piperidyl)oxy]pyridazin-3-yl]phenol | 0.0337 | | |
| 182 | 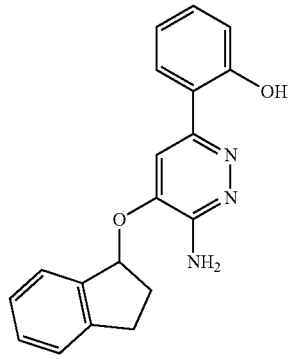 [SMILES: Nc1nnc(-c2ccccc2O)cc1OC1CCc2ccccc21] | 2-(6-amino-5-((2,3-dihydro-1H-inden-1-yl)oxy)pyridazin-3-yl)phenol | 0.6058 | | |
| 183 | 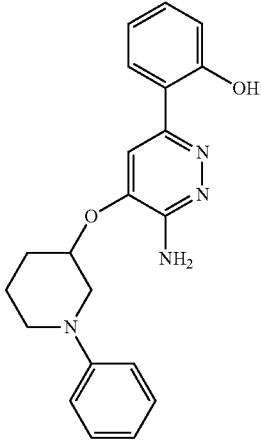 [SMILES: Nc1nnc(-c2ccccc2O)cc1OC1CCCN(c2ccccc2)C1] | 2-[6-amino-5-[(1-phenyl-3-piperidyl)oxy]pyridazin-3-yl]phenol | 0.0172 | | |

-continued
| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 184 | 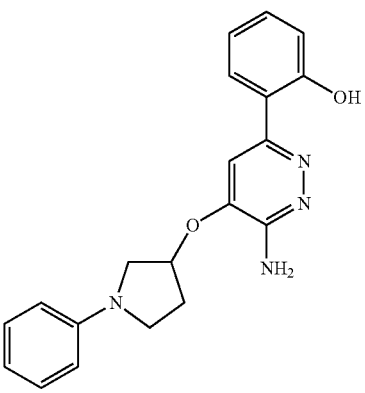 [SMILES: Nc1nnc(-c2ccccc2O)cc1OC1CCN(c2ccccc2)C1] | 2-[6-amino-5-(1-phenylpyrrolidin-3-yl)oxy-pyridazin-3-yl]phenol | 0.1917 | | |
| 185 | 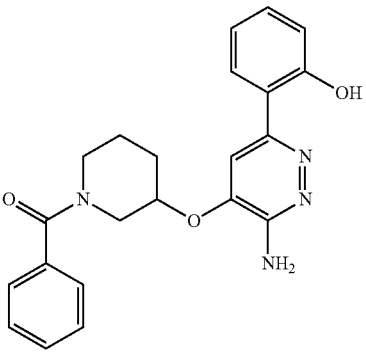 [SMILES: Nc1nnc(-c2ccccc2O)cc1OC1CCCN(C(=O)c2ccccc2)C1] | [3-[3-amino-6-(2-hydroxyphenyl)pyridazin-4-yl]oxy-1-piperidyl]-phenyl-methanone | 0.6409 | | |
| 186 | 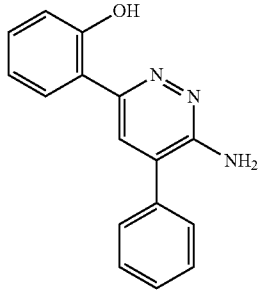 [SMILES: Nc1nnc(-c2ccccc2O)cc1-c1ccccc1] | 2-(6-amino-5-phenyl-pyridazin-3-yl)phenol | 0.0387 | 0.0373 | 0.0089 |
| 187 | 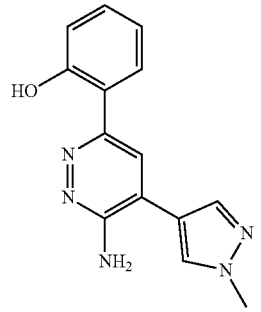 [SMILES: Cn1cc(-c2cc(-c3ccccc3O)nnc2N)cn1] | 2-[6-amino-5-(1-methylpyrazol-4-yl)pyridazin-3-yl]phenol | 0.0128 | 0.010 | 0.0037 |

-continued

| Example | Structure | Name | BRG1 HTRF IC$_{50}$ (μM) | BRM_iso 2 HTRF CON (IC50) | PB1-BD5 HTRF CON (IC50) |
| --- | --- | --- | --- | --- | --- |
| 188 | 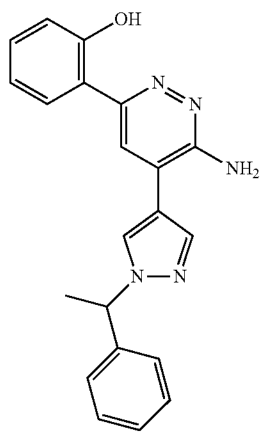 [SMILES: CC(c1ccccc1)n1cc(-c2cc(-c3ccccc3O)nnc2N)cn1] | 2-[6-amino-5-[1-(1-phenylethyl)pyrazol-4-yl]pyridazin-3-yl]phenol | 0.0066 | 0.0057 | 0.0025 |
| 189 | 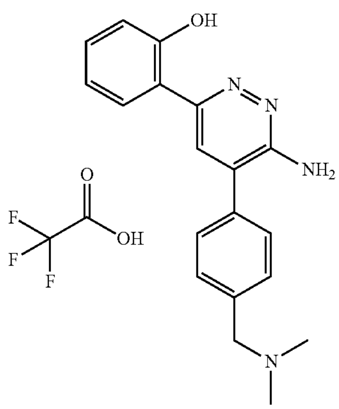 [SMILES: O=C(O)C(F)(F)F ; CN(C)Cc1ccc(-c2cc(-c3ccccc3O)nnc2N)cc1] | 2-[6-amino-5-[4-[(dimethylamino)methyl]phenyl]pyridazin-3-yl]phenol; 2,2,2-trifluoroacetic acid | 0.0222 | 0.0493 | 0.0288 |
| 190 | 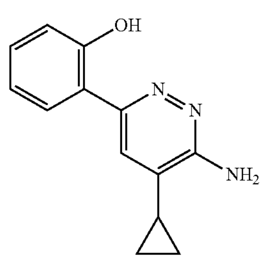 [SMILES: Nc1nnc(-c2ccccc2O)cc1C1CC1] | 2-(6-amino-5-cyclopropyl-pyridazin-3-yl)phenol | 0.0176 | | |
| 191 | 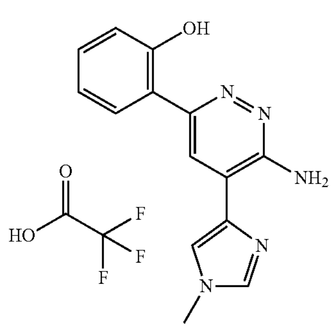 | 2-[6-amino-5-(1-methylimidazol-4-yl)pyridazin-3-yl]phenol; 2,2,2-trifluoroacetic acid | 0.0293 | | |

-continued

| Example | Structure | Name | BRG1 HTRF IC$_{50}$ (μM) | BRM_iso2 HTRF CON (IC50) | PB1-BD5 HTRF CON (IC50) |
| --- | --- | --- | --- | --- | --- |
| 192 | 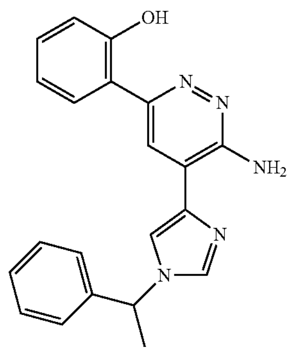 [SMILES: CC(c1ccccc1)n1cnc(-c2cc(-c3ccccc3O)nnc2N)c1] | 2-[6-amino-5-[1-(1-phenylethyl)imidazol-4-yl]pyridazin-3-yl]phenol | 0.0063 | | |
| 193 | 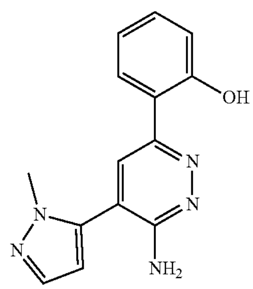 [SMILES: Cn1nccc1-c1cc(-c2ccccc2O)nnc1N] | 2-(6-amino-5-(1-methyl-1H-pyrazol-5-yl)pyridazin-3-yl)phenol | 1.0786 | | |
| 194 | 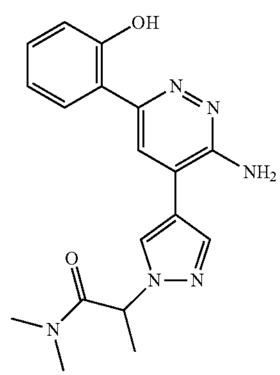 [SMILES: CC(C(=O)N(C)C)n1cc(-c2cc(-c3ccccc3O)nnc2N)cn1] | 2-[4-[3-amino-6-(2-hydroxyphenyl)pyridazin-4-yl]pyrazol-1-yl]-N,N-dimethyl-propanamide | 0.0247 | | |
| 195 | 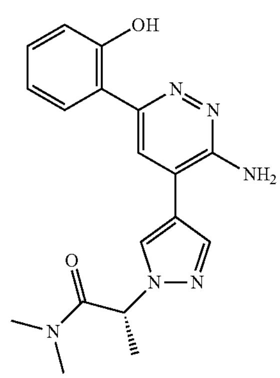 [SMILES: C[C@H](C(=O)N(C)C)n1cc(-c2cc(-c3ccccc3O)nnc2N)cn1] | (2R)-2-[4-[3-amino-6-(2-hydroxyphenyl)pyridazin-4-yl]pyrazol-1-yl]-N,N-dimethyl-propanamide | 0.0217 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 196 | 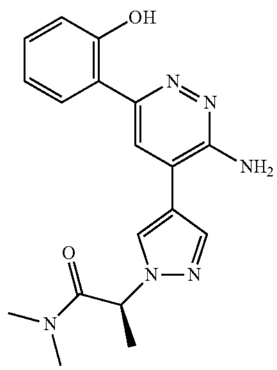 [SMILES: C[C@@H](C(=O)N(C)C)n1cc(-c2cc(-c3ccccc3O)nnc2N)cn1] | (2S)-2-[4-[3-amino-6-(2-hydroxyphenyl)pyridazin-4-yl]pyrazol-1-yl]-N,N-dimethyl-propanamide | 0.0247 | | |
| 197 | 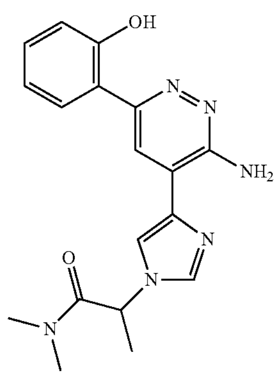 [SMILES: CC(C(=O)N(C)C)n1cnc(-c2cc(-c3ccccc3O)nnc2N)c1] | 2-[4-[3-amino-6-(2-hydroxyphenyl)pyridazin-4-yl]imidazol-1-yl]-N,N-dimethyl-propanamide | 0.0339 | | |
| 198 | 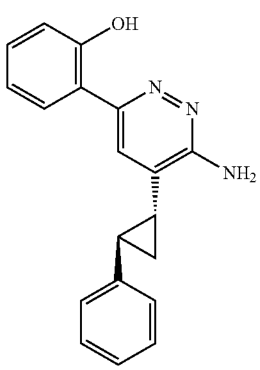 [SMILES: Nc1nnc(-c2ccccc2O)cc1[C@@H]1C[C@H]1c1ccccc1] | 2-[6-amino-5-[(1R,2R)-2-phenylcyclopropyl]pyridazin-3-yl]phenol | 0.0121 | | |
| 199 | 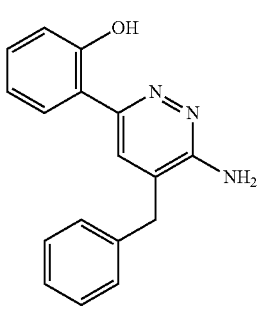 [SMILES: Nc1nnc(-c2ccccc2O)cc1Cc1ccccc1] | 2-(6-amino-5-benzyl-pyridazin-3-yl)phenol | 0.995 | | |

-continued

| Example | Structure | Name | BRG1 HTRF IC$_{50}$ (µM) | BRM_iso 2 HTRF CON (IC50) | PB1-BD5 HTRF CON (IC50) |
|---|---|---|---|---|---|
| 200 | 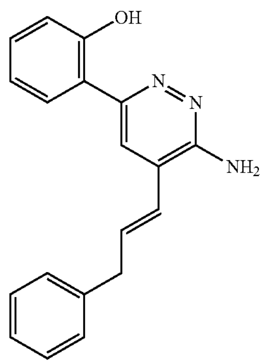 [SMILES: Nc1nnc(-c2ccccc2O)cc1/C=C/Cc1ccccc1] | 2-[6-amino-5-[(E)-3-phenylprop-1-enyl]pyridazin-3-yl]phenol | 0.0316 | | |
| 201 | 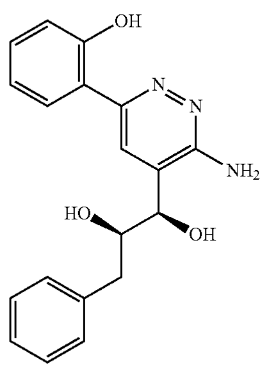 [SMILES: Nc1nnc(-c2ccccc2O)cc1[C@@H](O)[C@H](O)Cc1ccccc1] | (1R,2R)-1-[3-amino-6-(2-hydroxyphenyl)pyridazin-4-yl]-3-phenyl-propane-1,2-diol | 0.3116 | | |
| 203 | 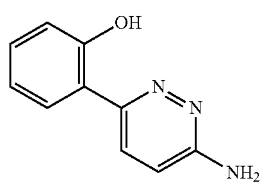 [SMILES: Nc1ccc(-c2ccccc2O)nn1] | 2-(6-aminopyridazin-3-yl)phenol | 0.335 | | |
| 204 | 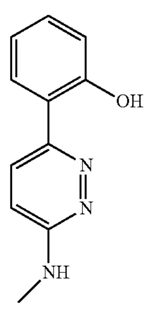 | 2-[6-(methylamino)pyridazin-3-yl]phenol | 0.8935 | 1.04 | 0.349 |
| 205 | 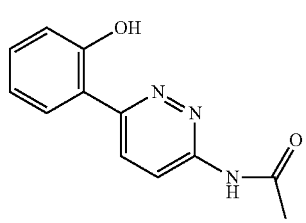 [SMILES: CC(=O)Nc1ccc(-c2ccccc2O)nn1] | N-[6-(2-hydroxyphenyl)pyridazin-3-yl]acetamide | 1.0803 | | |

-continued

| Example | Structure | Name | BRG1 HTRF IC$_{50}$ (µM) | BRM_iso 2 HTRF CON (IC50) | PB1-BD5 HTRF CON (IC50) |
|---|---|---|---|---|---|
| 206 | 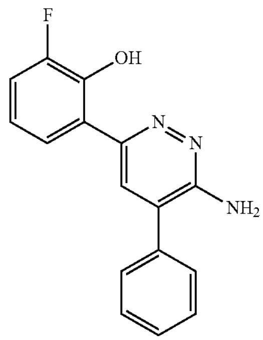 [SMILES: Nc1nnc(-c2cccc(F)c2O)cc1-c1ccccc1] | 2-(6-amino-5-phenyl-pyridazin-3-yl)-6-fluoro-phenol | 0.0982 | 0.32 | 0.0295 |
| 207 | 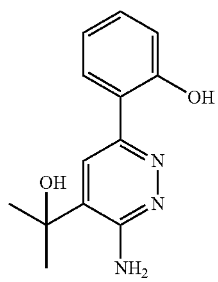 [SMILES: CC(C)(O)c1cc(-c2ccccc2O)nnc1N] | 2-[6-amino-5-(1-hydroxy-1-methyl-ethyl)pyridazin-3-yl]phenol | 0.4488 | | |
| 208 | 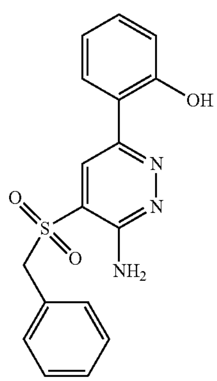 [SMILES: Nc1nnc(-c2ccccc2O)cc1S(=O)(=O)Cc1ccccc1] | 2-(6-amino-5-benzylsulfonyl-pyridazin-3-yl)phenol | 0.995 | | |
| 209 | 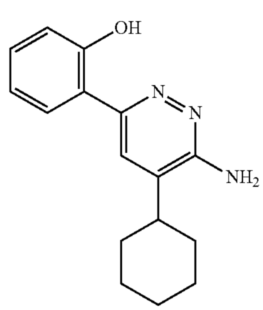 [SMILES: Nc1nnc(-c2ccccc2O)cc1C1CCCCC1] | 2-(6-amino-5-cyclohexyl-pyridazin-3-yl)phenol | 0.0145 | 0.0088 | 0.0052 |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 210 | 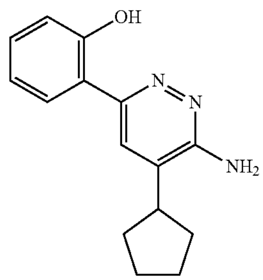 [SMILES: Nc1nnc(-c2ccccc2O)cc1C1CCCC1] | 2-(6-amino-5-cyclopentyl-pyridazin-3-yl)phenol | 0.0239 | 0.025 | 0.0149 |
| 211 | 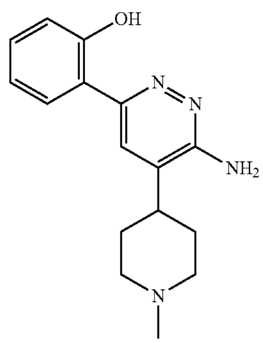 [SMILES: CN1CCC(c2cc(-c3ccccc3O)nnc2N)CC1] | 2-[6-amino-5-(1-methyl-4-piperidyl)pyridazin-3-yl]phenol | 0.183 | | |
| 212 | 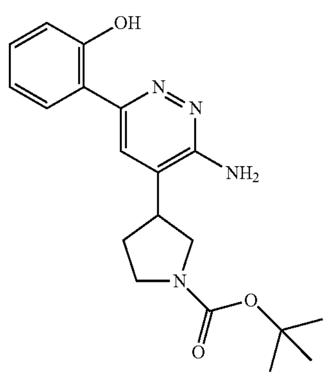 [SMILES: CC(C)(C)OC(=O)N1CCC(c2cc(-c3ccccc3O)nnc2N)C1] | tert-butyl 3-[3-amino-6-(2-hydroxyphenyl)pyridazin-4-yl]pyrrolidine-1-carboxylate | 0.0694 | | |
| 213 | 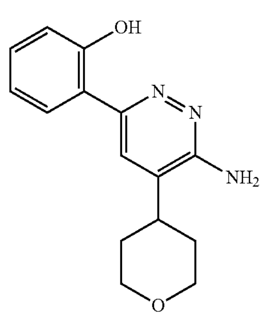 [SMILES: Nc1nnc(-c2ccccc2O)cc1C1CCOCC1] | 2-(6-amino-5-tetrahydropyran-4-yl-pyridazin-3-yl)phenol | 0.0611 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 214 | 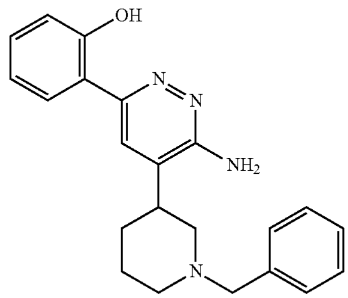 [SMILES: Nc1nnc(-c2ccccc2O)cc1C1CCCN(Cc2ccccc2)C1] | 2-[6-amino-5-(1-benzyl-3-piperidyl)pyridazin-3-yl]phenol | 0.1119 | | |
| 215 | 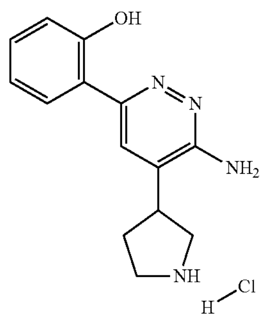 | 2-(6-amino-5-pyrrolidin-3-yl-pyridazin-3-yl)phenol; hydrochloride | 0.7432 | | |
| 216 | 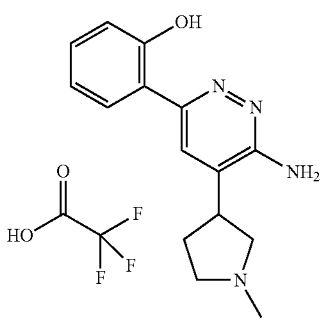 | 2-[6-amino-5-(1-methylpyrrolidin-3-yl)pyridazin-3-yl]phenol; 2,2,2-trifluoroacetic acid | 0.7652 | | |
| 217 | 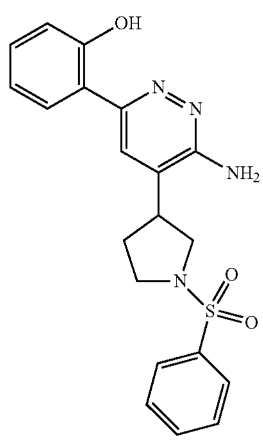 [SMILES: Nc1nnc(-c2ccccc2O)cc1C1CCN(S(=O)(=O)c2ccccc2)C1] | 2-[6-amino-5-[1-(benzenesulfonyl)pyrrolidin-3-yl]pyridazin-3-yl]phenol | 0.4122 | 0.466 | 0.268 |

-continued
| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 218 | 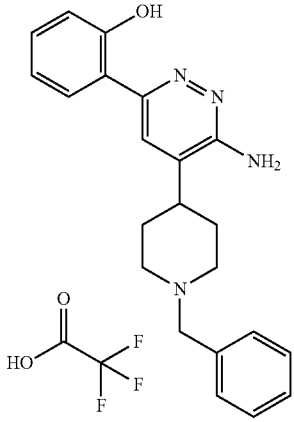 | 2-[6-amino-5-(1-benzyl-4-piperidyl)pyridazin-3-yl]phenol; 2,2,2-trifluoroacetic acid | 0.0553 | 0.0393 | 0.0448 |
| 219 | 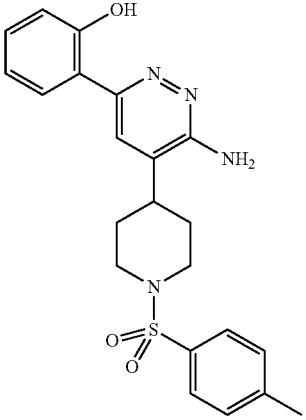 [SMILES: Cc1ccc(S(=O)(=O)N2CCC(c3cc(-c4ccccc4O)nnc3N)CC2)cc1] | 2-[6-amino-5-[1-(p-tolylsulfonyl)-4-piperidyl]pyridazin-3-yl]phenol | 0.3601 | | |
| 220 | 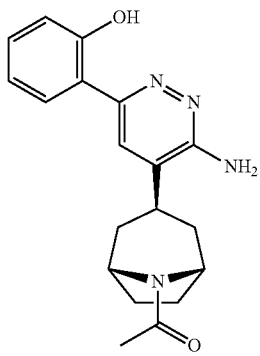 [SMILES: CC(=O)N1[C@@H]2CC[C@H]1C[C@H](c1cc(-c3ccccc3O)nnc1N)C2] | 1-[(1R,5S)-3-[3-amino-6-(2-hydroxyphenyl)pyridazin-4-yl]-8-azabicyclo[3.2.1]octan-8-yl]ethanone | 0.1094 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 221 | 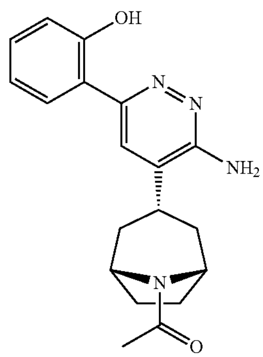 [SMILES: CC(=O)N1[C@@H]2CC[C@H]1C[C@@H](c1cc(-c3ccccc3O)nnc1N)C2] | 1-[(1R,5S)-3-[3-amino-6-(2-hydroxyphenyl)pyridazin-4-yl]-8-azabicyclo[3.2.1]octan-8-yl]ethanone | 0.0898 | | |
| 222 | 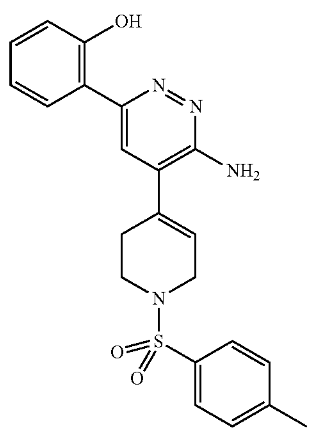 [SMILES: Cc1ccc(S(=O)(=O)N2CC=C(c3cc(-c4ccccc4O)nnc3N)CC2)cc1] | 2-[6-amino-5-[1-(p-tolylsulfonyl)-3,6-dihydro-2H-pyridin-4-yl]pyridazin-3-yl]phenol | 0.0889 | | |
| 223 | 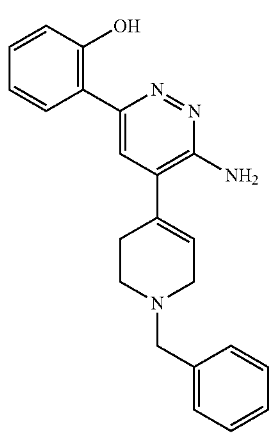 [SMILES: Nc1nnc(-c2ccccc2O)cc1C1=CCN(Cc2ccccc2)CC1] | 2-[6-amino-5-(1-benzyl-3,6-dihydro-2H-pyridin-4-yl)pyridazin-3-yl]phenol | 0.0205 | | |

| Example | Structure | Name | BRG1 HTRF IC$_{50}$ (μM) | BRM_iso2 HTRF CON (IC50) | PB1-BD5 HTRF CON (IC50) |
|---|---|---|---|---|---|
| 224 | 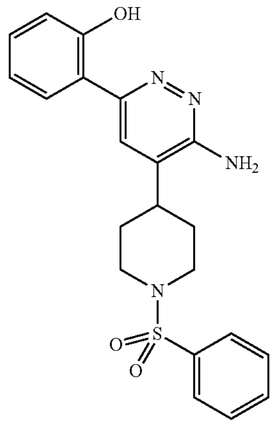 [SMILES: Nc1nnc(-c2ccccc2O)cc1C1CCN(S(=O)(=O)c2ccccc2)CC1] | 2-[6-amino-5-[1-(benzenesulfonyl)-4-piperidyl]pyridazin-3-yl]phenol | 0.0602 | | |
| 225 | 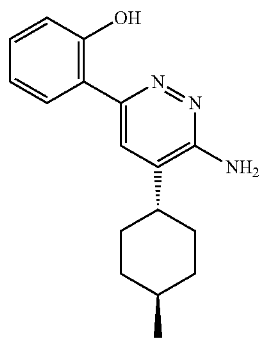 [SMILES: C[C@H]1CC[C@H](c2cc(-c3ccccc3O)nnc2N)CC1] | 2-[6-amino-5-(4-methylcyclohexyl)pyridazin-3-yl]phenol | 0.019 | | |
| 226 | 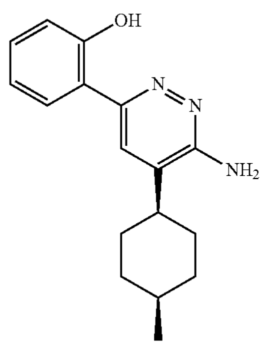 [SMILES: C[C@H]1CC[C@@H](c2cc(-c3ccccc3O)nnc2N)CC1] | 2-[6-amino-5-(4-methylcyclohexyl)pyridazin-3-yl]phenol | 0.0209 | | |
| 227 | 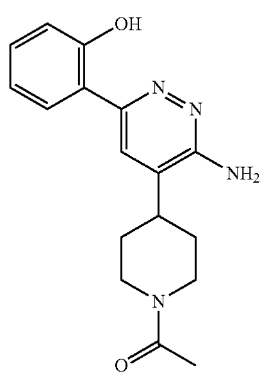 [SMILES: CC(=O)N1CCC(c2cc(-c3ccccc3O)nnc2N)CC1] | 1-[4-[3-amino-6-(2-hydroxyphenyl)pyridazin-4-yl]-1-piperidyl]ethanone | 0.0848 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 228 | 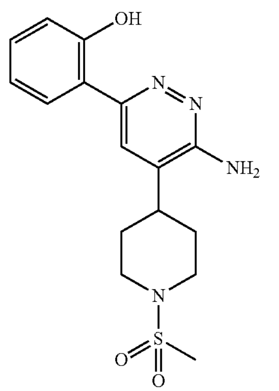 [SMILES: CS(=O)(=O)N1CCC(c2cc(-c3ccccc3O)nnc2N)CC1] | 2-[6-amino-5-(1-methylsulfonyl-4-piperidyl)pyridazin-3-yl]phenol | 0.0537 | | |
| 229 | 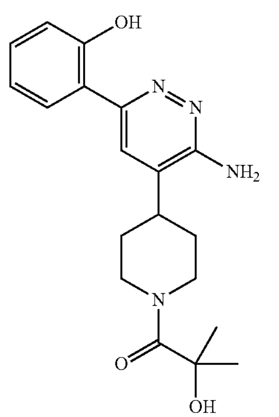 [SMILES: CC(C)(O)C(=O)N1CCC(c2cc(-c3ccccc3O)nnc2N)CC1] | 1-[4-[3-amino-6-(2-hydroxyphenyl)pyridazin-4-yl]-1-piperidyl]-2-hydroxy-2-methyl-propan-1-one | 0.0437 | | |
| 230 | 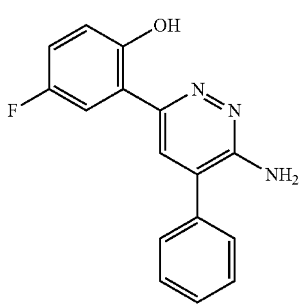 [SMILES: Nc1nnc(-c2cc(F)ccc2O)cc1-c1ccccc1] | 2-(6-amino-5-phenyl-pyridazin-3-yl)-4-fluoro-phenol | 0.0549 | | |
| 231 | 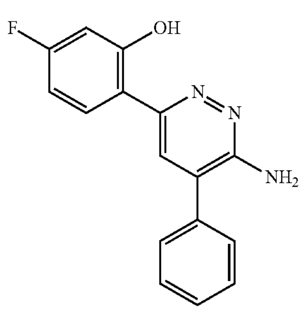 [SMILES: Nc1nnc(-c2ccc(F)cc2O)cc1-c1ccccc1] | 2-(6-amino-5-phenyl-pyridazin-3-yl)-5-fluoro-phenol | 0.995 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 232 | 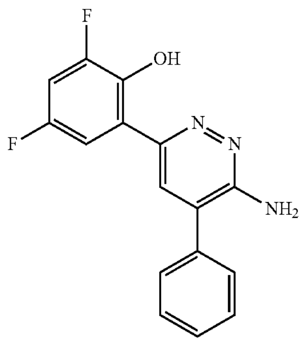 [SMILES: Nc1nnc(-c2cc(F)cc(F)c2O)cc1-c1ccccc1] | 2-(6-amino-5-phenyl-pyridazin-3-yl)-4,6-difluoro-phenol | 0.1762 | | |
| 233 | 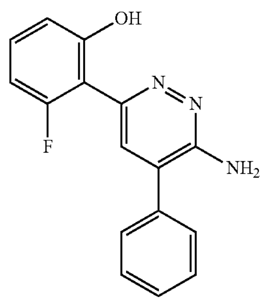 [SMILES: Nc1nnc(-c2c(O)cccc2F)cc1-c1ccccc1] | 2-(6-amino-5-phenyl-pyridazin-3-yl)-3-fluoro-phenol | 0.4348 | | |
| 234 | 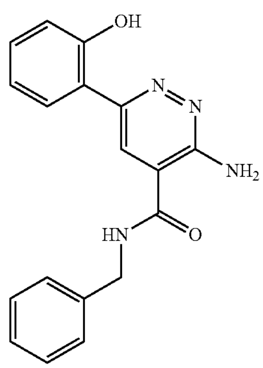 [SMILES: Nc1nnc(-c2ccccc2O)cc1C(=O)NCc1ccccc1] | 3-amino-N-benzyl-6-(2-hydroxyphenyl)pyridazine-4-carboxamide | 0.1023 | | |
| 235 | 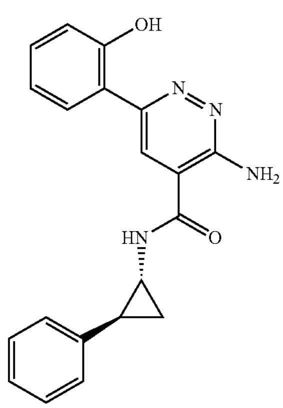 [SMILES: Nc1nnc(-c2ccccc2O)cc1C(=O)N[C@@H]1C[C@H]1c1ccccc1] | 3-amino-6-(2-hydroxyphenyl)-N-(trans-2-phenylcyclopropyl)pyridazine-4-carboxamide | 0.2143 | | |

-continued

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 236 | 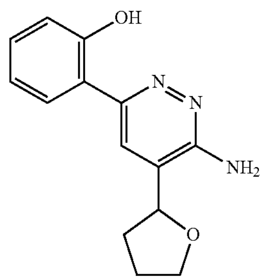 [SMILES: Nc1nnc(-c2ccccc2O)cc1C1CCCO1] | 2-(6-amino-5-tetrahydrofuran-2-yl-pyridazin-3-yl)phenol | 0.0764 | | |
| 237 | 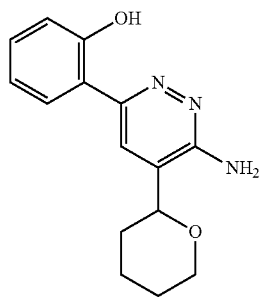 [SMILES: Nc1nnc(-c2ccccc2O)cc1C1CCCCO1] | 2-(6-amino-5-tetrahydropyran-2-yl-pyridazin-3-yl)phenol | 0.0761 | | |
| 238 | 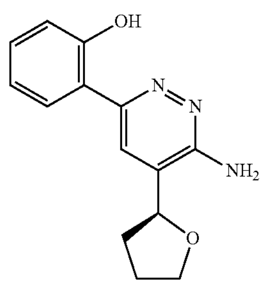 [SMILES: Nc1nnc(-c2ccccc2O)cc1[C@@H]1CCCO1] | 2-[6-amino-5-[(2S)-tetrahydrofuran-2-yl]pyridazin-3-yl]phenol | 0.0405 | | |
| 239 | 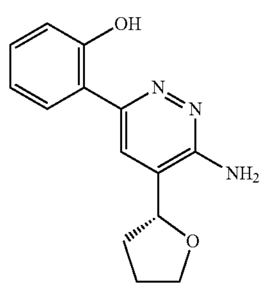 [SMILES: Nc1nnc(-c2ccccc2O)cc1[C@H]1CCCO1] | 2-[6-amino-5-[(2R)-tetrahydrofuran-2-yl]pyridazin-3-yl]phenol | 0.1792 | | |
| 240 | 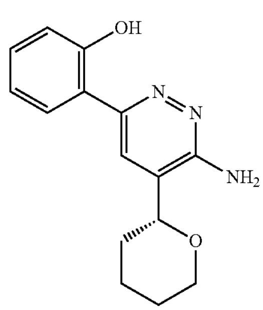 [SMILES: Nc1nnc(-c2ccccc2O)cc1[C@H]1CCCCO1] | 2-[6-amino-5-[(2R)-tetrahydropyran-2-yl]pyridazin-3-yl]phenol | 0.0649 | | |

-continued

| Example | Structure | Name | BRG1 HTRF IC$_{50}$ (µM) | BRM_iso 2 HTRF CON (IC50) | PB1-BD5 HTRF CON (IC50) |
|---|---|---|---|---|---|
| 241 | 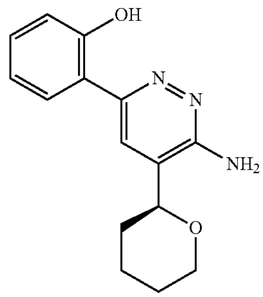 [SMILES: Nc1nnc(-c2ccccc2O)cc1[C@@H]1CCCCO1] | 2-[6-amino-5-[(2S)-tetrahydropyran-2-yl]pyridazin-3-yl]phenol | 0.1189 | | |
| 242 | 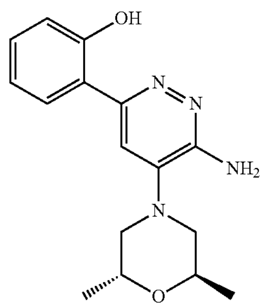 [SMILES: C[C@@H]1CN(c2cc(-c3ccccc3O)nnc2N)C[C@@H](C)O1] | 2-[6-amino-5-[(2R,6R)-2,6-dimethylmorpholin-4-yl]pyridazin-3-yl]phenol | 0.0589 | | |
| 243 | 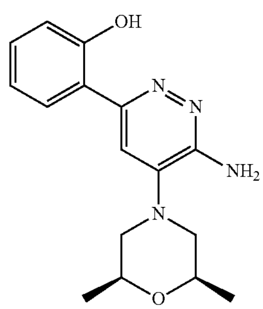 [SMILES: C[C@@H]1CN(c2cc(-c3ccccc3O)nnc2N)C[C@H](C)O1] | 2-[6-amino-5-[(2S,6R)-2,6-dimethylmorpholin-4-yl]pyridazin-3-yl]phenol | 0.0324 | | |
| 244 | 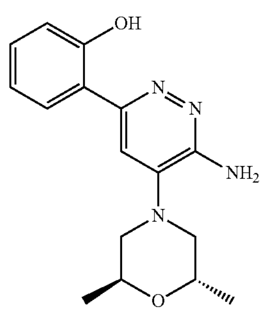 [SMILES: C[C@H]1CN(c2cc(-c3ccccc3O)nnc2N)C[C@H](C)O1] | 2-[6-amino-5-[(2S,6S)-2,6-dimethylmorpholin-4-yl]pyridazin-3-yl]phenol | 0.0379 | | |
| 245 | 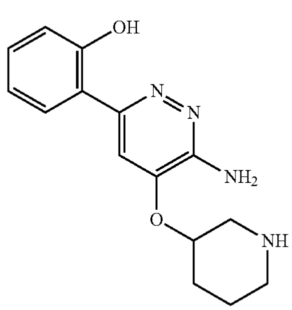 [SMILES: Nc1nnc(-c2ccccc2O)cc1OC1CCCNC1] | 2-[6-amino-5-(3-piperidyloxy)pyridazin-3-yl]phenol | 0.2808 | | |

| Example | Structure | Name | BRG1 HTRF IC$_{50}$ (μM) | BRM_iso 2 HTRF CON (IC50) | PB1-BD5 HTRF CON (IC50) |
|---|---|---|---|---|---|
| 246 | 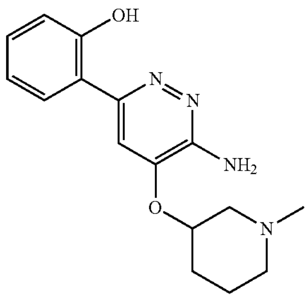 [SMILES: CN1CCCC(Oc2cc(-c3ccccc3O)nnc2N)C1] | 2-[6-amino-5-[(1-methyl-3-piperidyl)oxy]pyridazin-3-yl]phenol | 0.2599 | | |
| 247 | 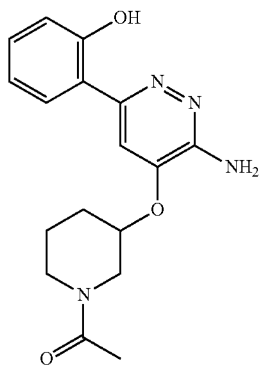 [SMILES: CC(=O)N1CCCC(Oc2cc(-c3ccccc3O)nnc2N)C1] | 1-[3-[3-amino-6-(2-hydroxyphenyl)pyridazin-4-yl]oxy-1-piperidyl]ethanone | 0.137 | | |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

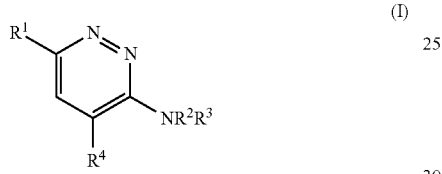

or a salt thereof, wherein:
- $R^1$ is 2-hydroxy phenyl that is optionally substituted with one or more groups independently selected from the group consisting of halo;
- $R^2$ is H;
- $R^3$ is H;
- $R^4$ is selected from the group consisting of, $C_{2-6}$alkenyl, $C_{2-6}$alkynyl, 3-15 membered carbocyclyl, 3-15 membered heterocyclyl —O—$R^b$, —N($R^b$)$_2$, —S(O)$_2R^b$, and —C(O)—N($R^b$)$_2$, wherein each $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;
- each $R^b$ is independently selected from the group consisting of hydrogen, $C_{1-6}$alkyl, $C_{2-6}$alkenyl, $C_{2-6}$alkynyl, 3-15 membered carbocyclyl, and 3-15 membered heterocyclyl, wherein each $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;
- each $R^c$ is independently selected from the group consisting of hydrogen, $C_{1-6}$alkyl, $C_{2-6}$alkenyl, $C_{2-6}$alkynyl, $C_{1-6}$alkoxy, 3-15 membered carbocyclyl, and 3-15 membered heterocyclyl, wherein each $C_{1-6}$alkyl, $C_{2-6}$alkenyl, $C_{2-6}$alkynyl, $C_{1-6}$alkoxy, 3-15 membered carbocyclyl, and 3-15 membered heterocyclyl is optionally substituted with one or more groups independently selected from $R^d$; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;
- each $R^d$ is independently selected from the group consisting of oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, —N($R^e$)—S(O)$_2$—$R^e$, $C_{1-6}$alkyl, $C_{2-6}$alkenyl, $C_{2-6}$alkynyl, 3-15 membered carbocyclyl, and 3-15 membered heterocyclyl, wherein any $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^e$, oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, and —N($R^e$)—S(O)$_2$—$R^e$; and
- each $R^e$ is independently selected from the group consisting of hydrogen, $C_{1-6}$alkyl, $C_{2-6}$alkenyl, $C_{2-6}$alkynyl, carbocyclyl, and carbocyclyl($C_{1-3}$alkyl)-.

2. The compound of claim 1 wherein $R^4$ is a 3-15 membered heterocyclyl that is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$.

3. The compound of claim 1 wherein $R^4$ is selected from the group consisting of:

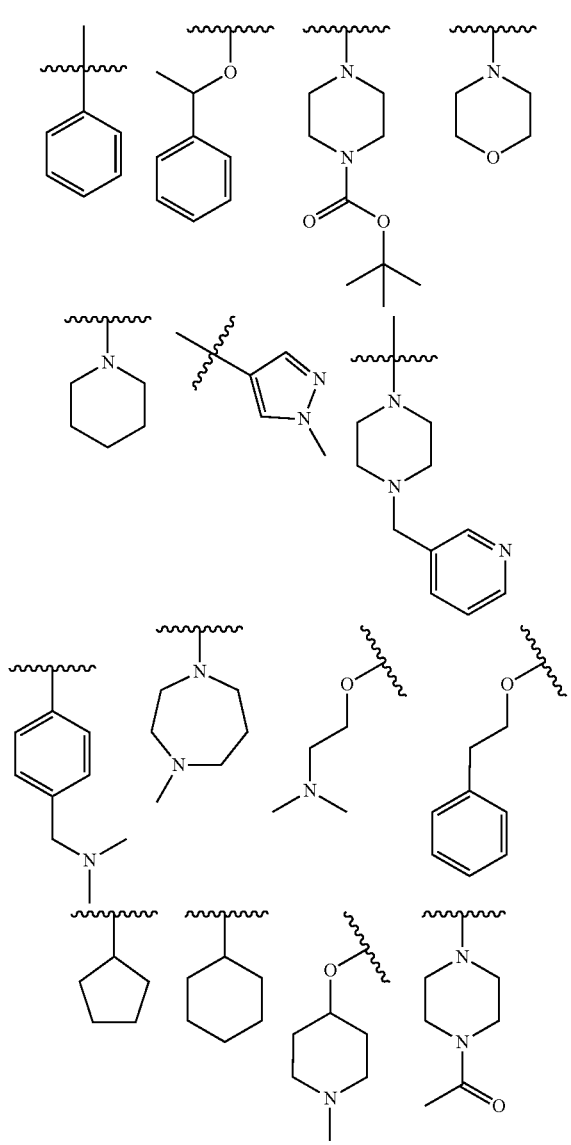
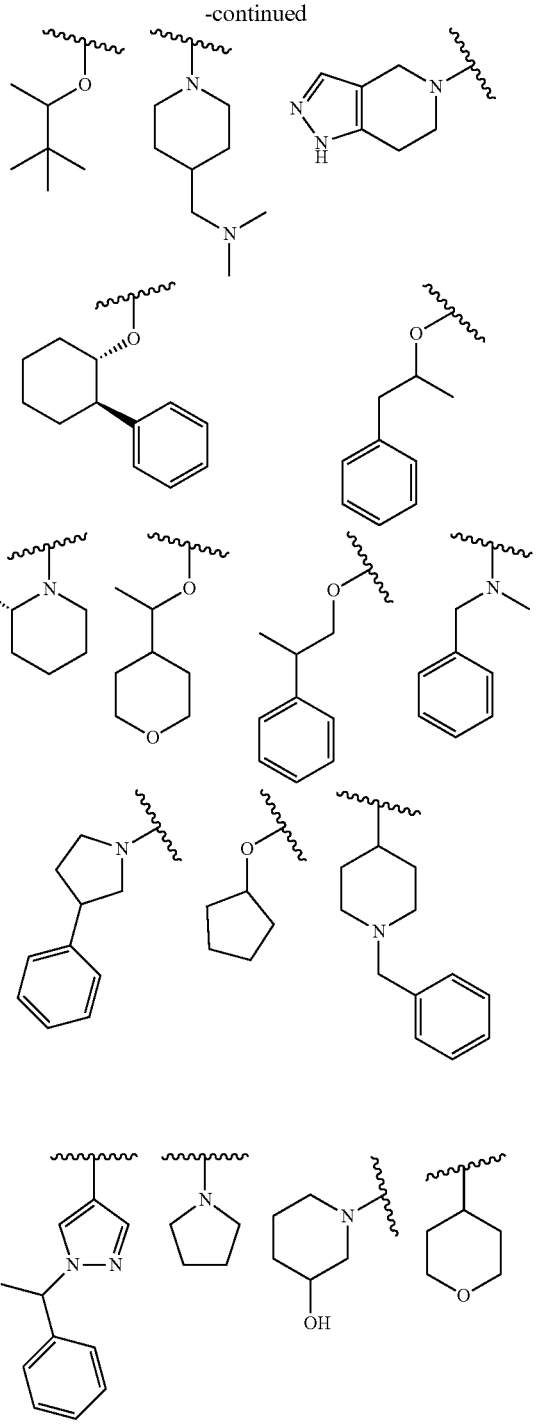
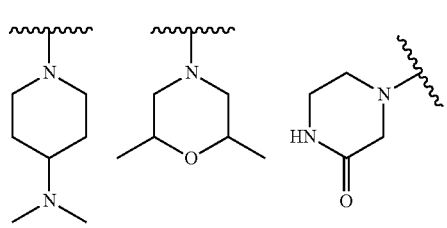
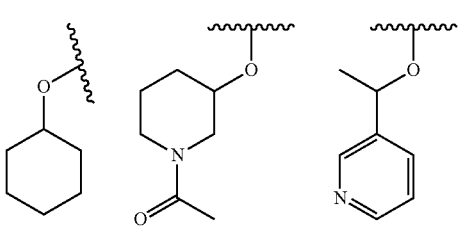

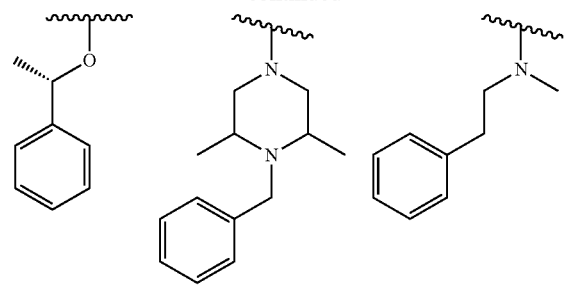
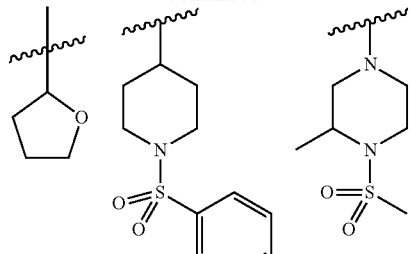
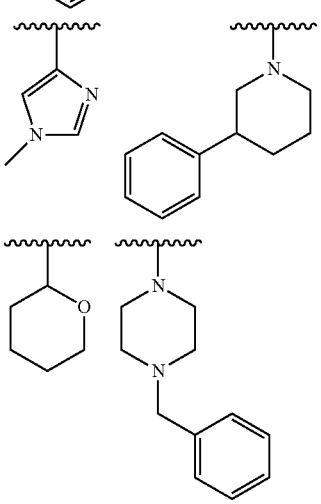
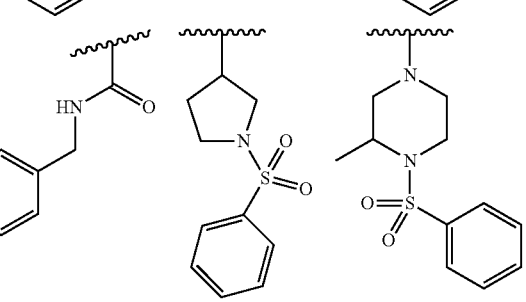
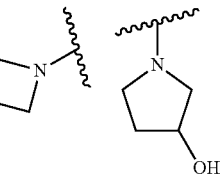
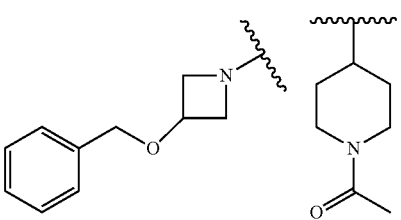

369
-continued
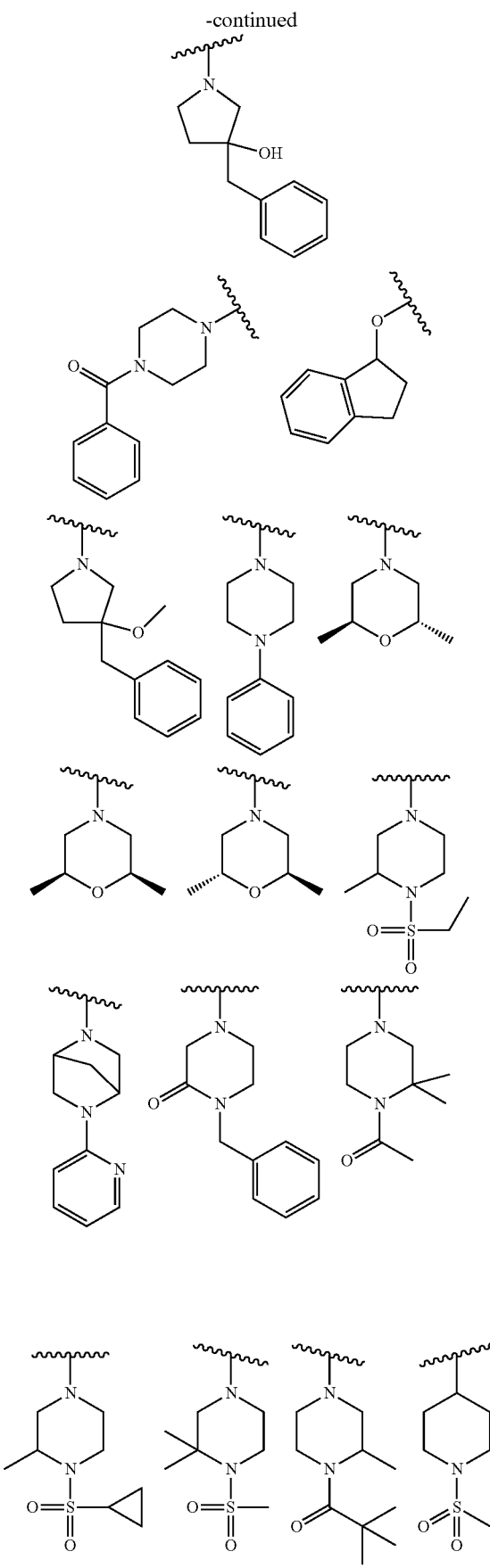
370
-continued
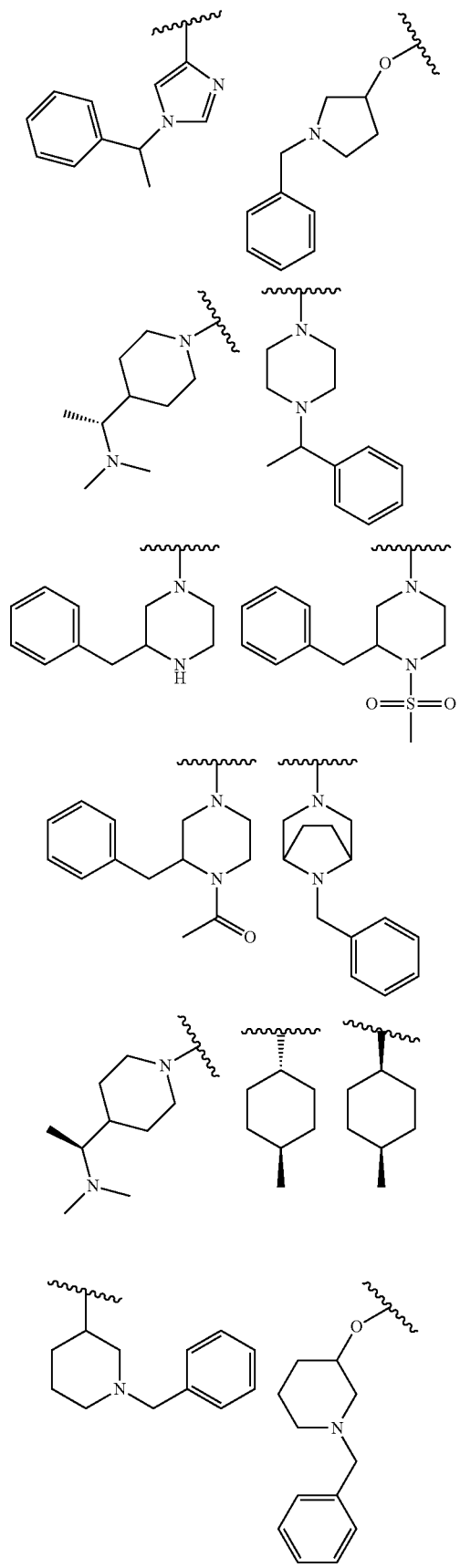

371
-continued
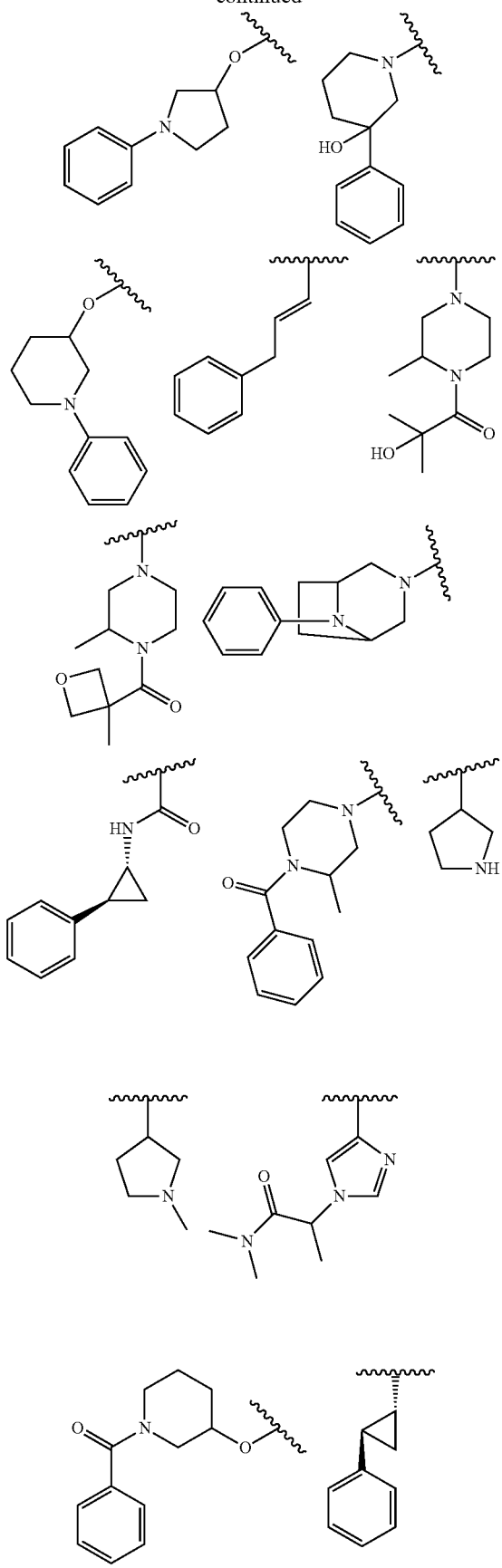
372
-continued
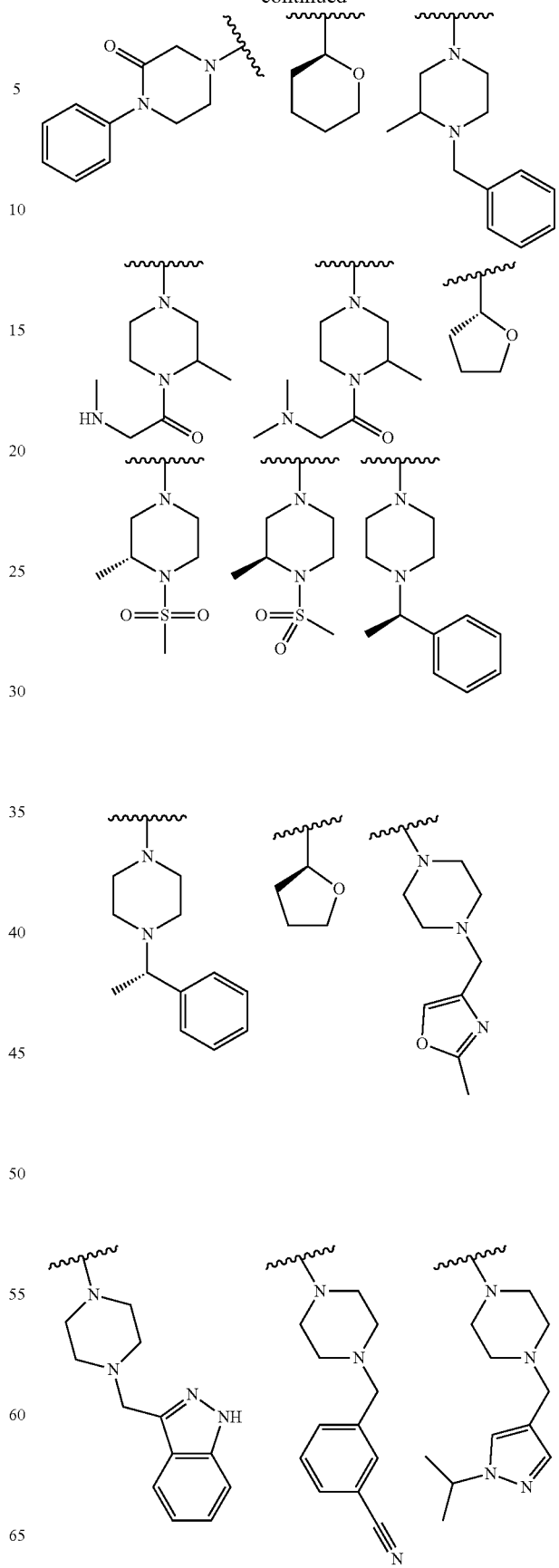

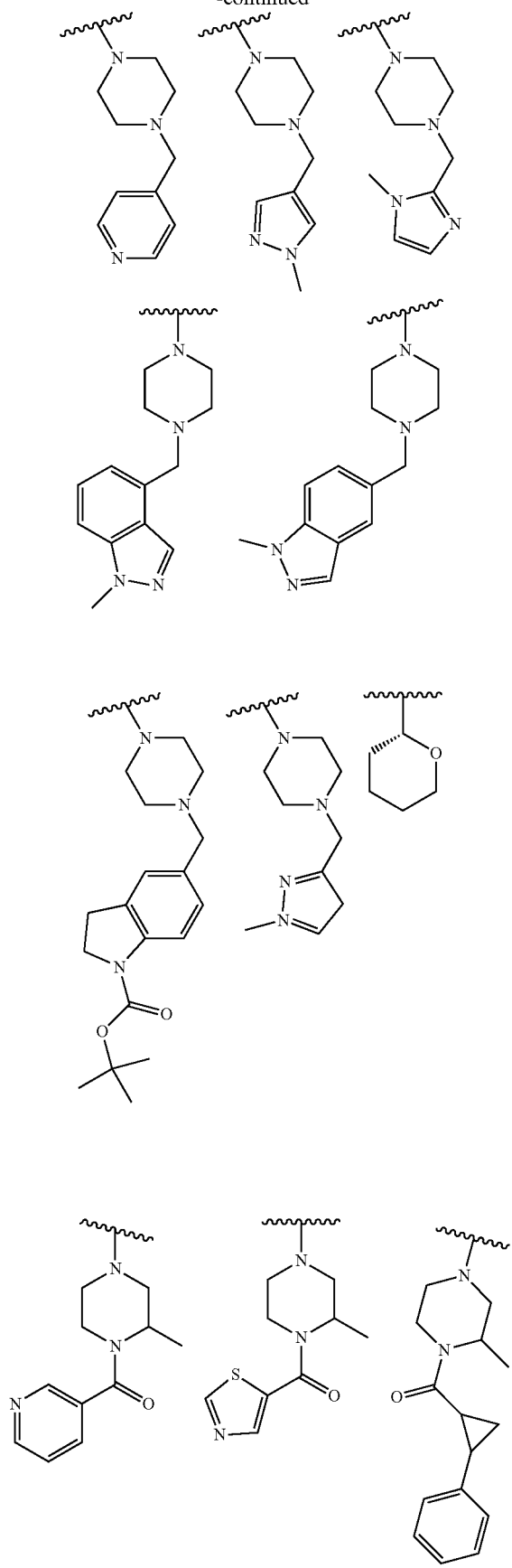
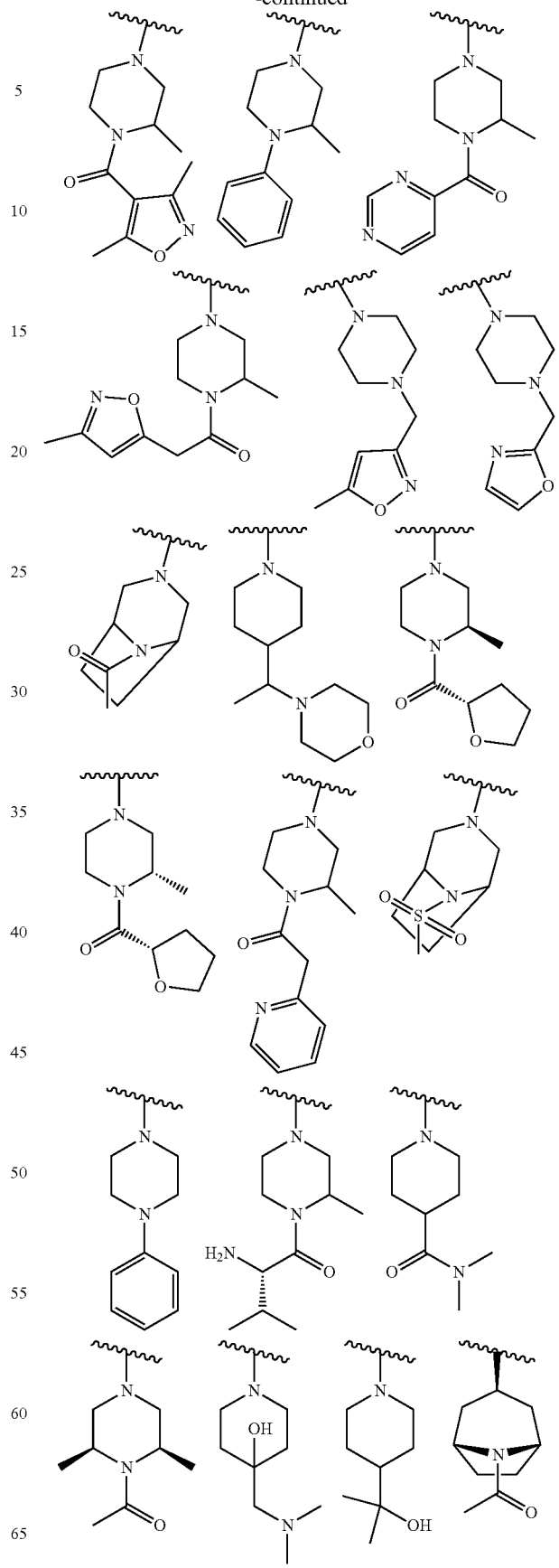

375
-continued
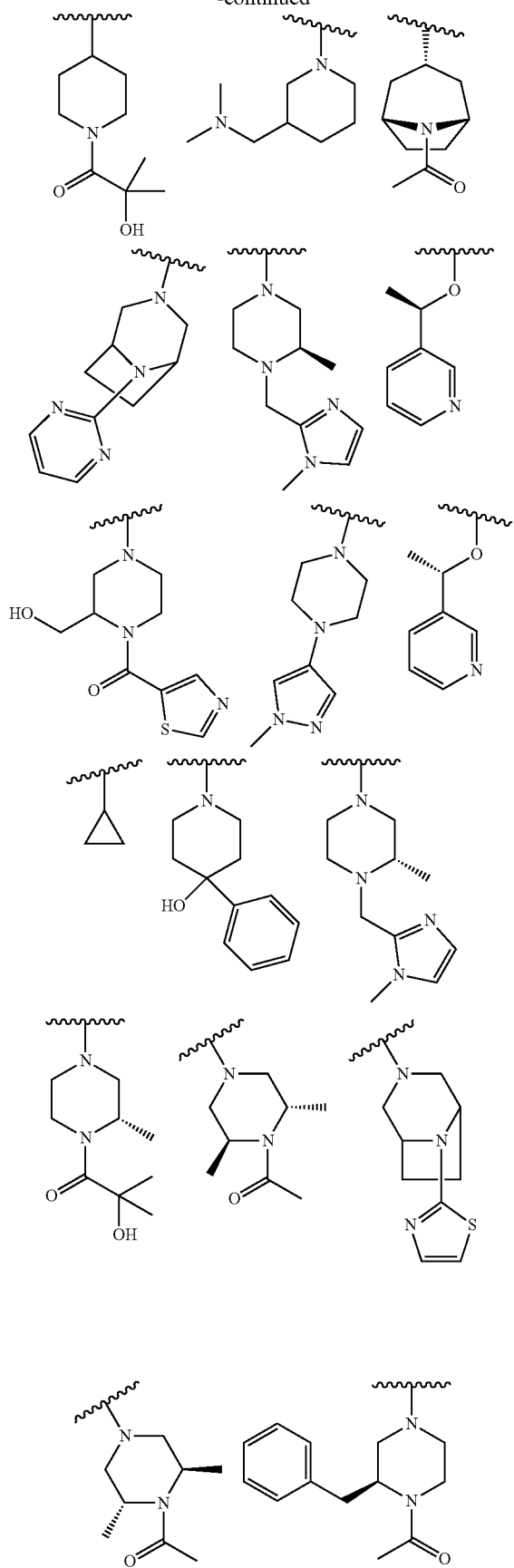
376
-continued
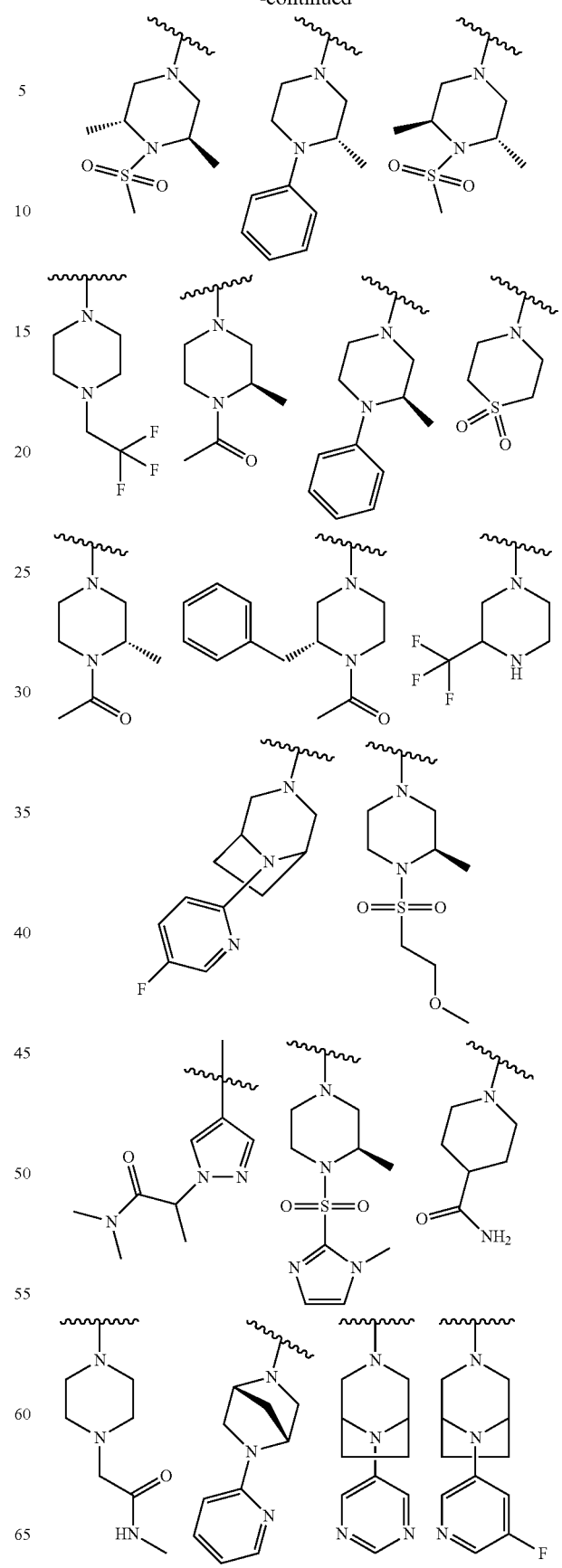

377
-continued
378
-continued
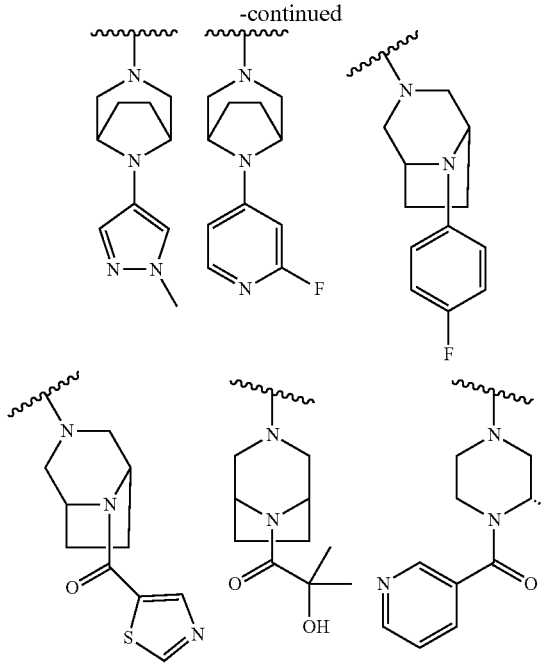
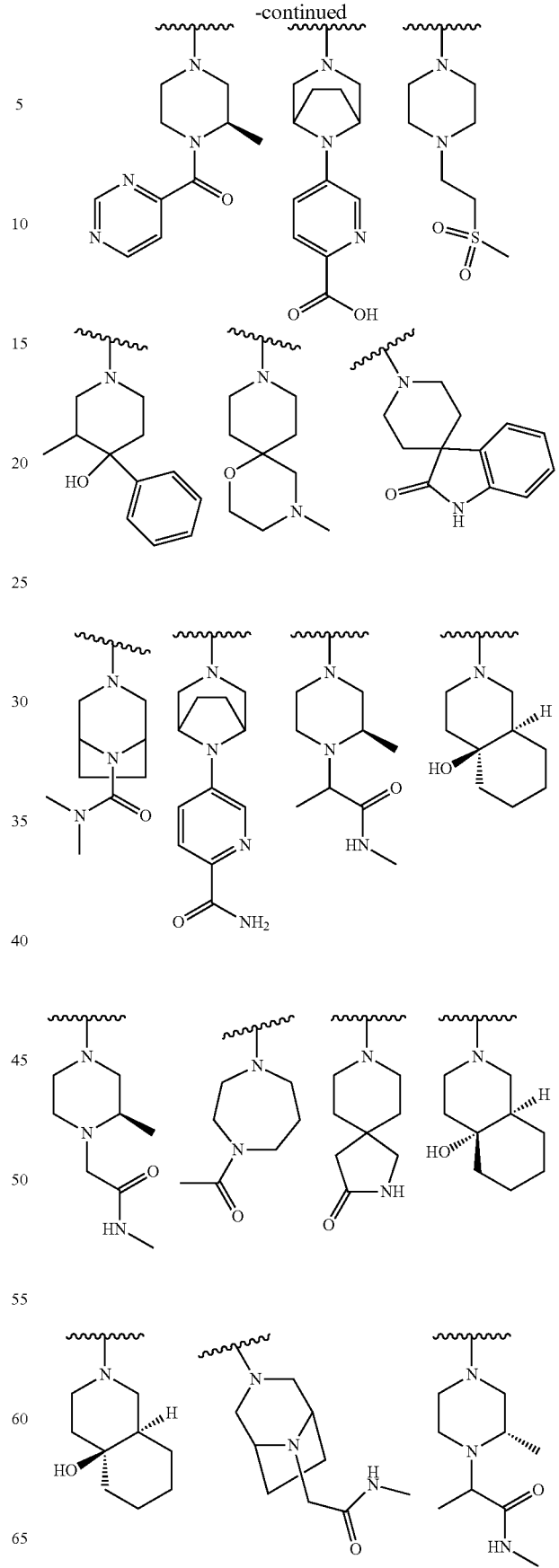

-continued

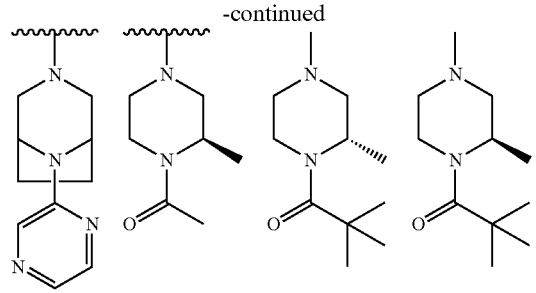

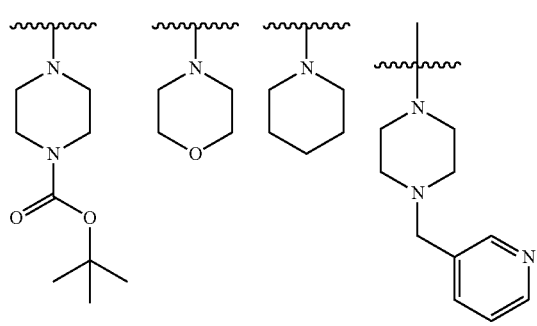

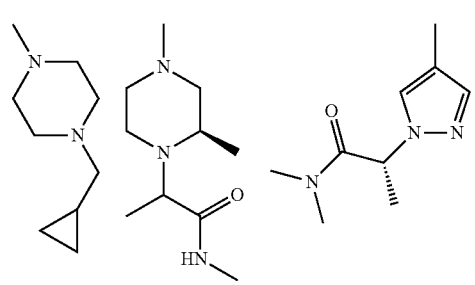

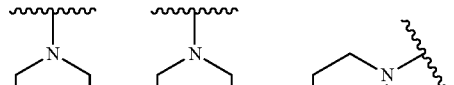

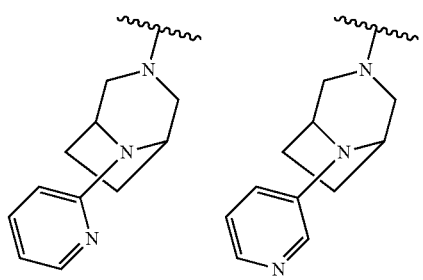

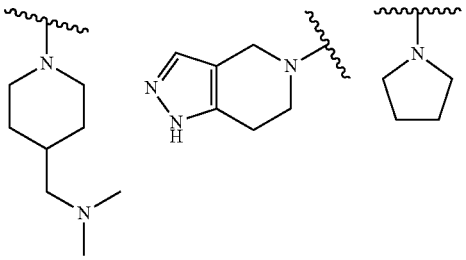

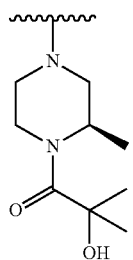

and

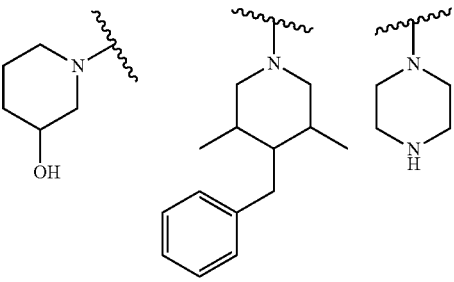

4. The compound of claim 1 wherein $R^4$ is an N-linked 3-15 membered heterocyclyl that is optionally substituted with one or more groups independently selected from the group consisting of $R^c$, oxo, halo, —$NO_2$, —$N(R^c)_2$, —CN, —C(O)—$N(R^c)_2$, —S(O)—$N(R^c)_2$, —S(O)$_2$—$N(R^c)_2$, —S—$R^c$, —O—C(O)—$R^c$, —C(O)—$R^c$, —C(O)—$OR^c$, —S(O)—$R^c$, —S(O)$_2$—$R^c$, —$N(R^c)$—C(O)—$R^c$, —$N(R^c)$—S(O)—$R^c$, —$N(R^c)$—C(O)—$N(R^c)_2$, and —$N(R^c)$—S(O)$_2$—$R^c$.

5. The compound of claim 1 wherein $R^4$ is selected from the group consisting of:

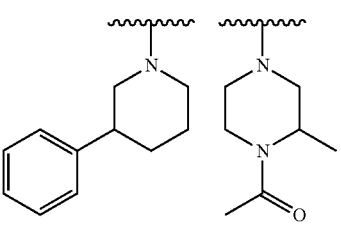

381
-continued
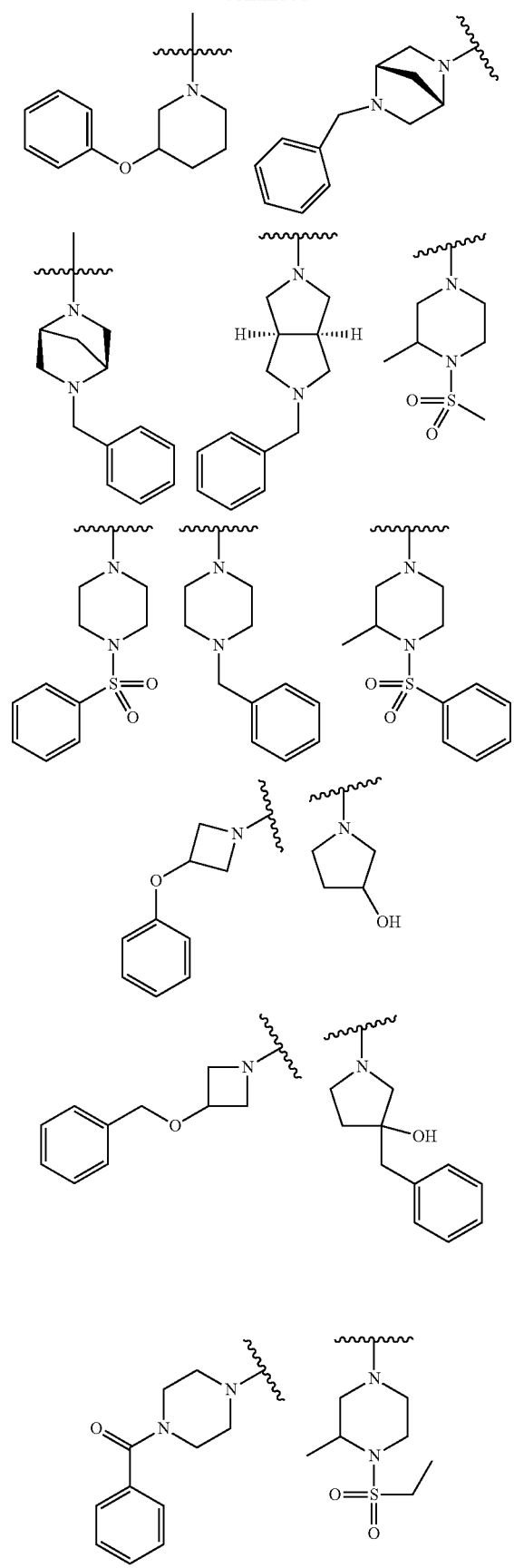
382
-continued
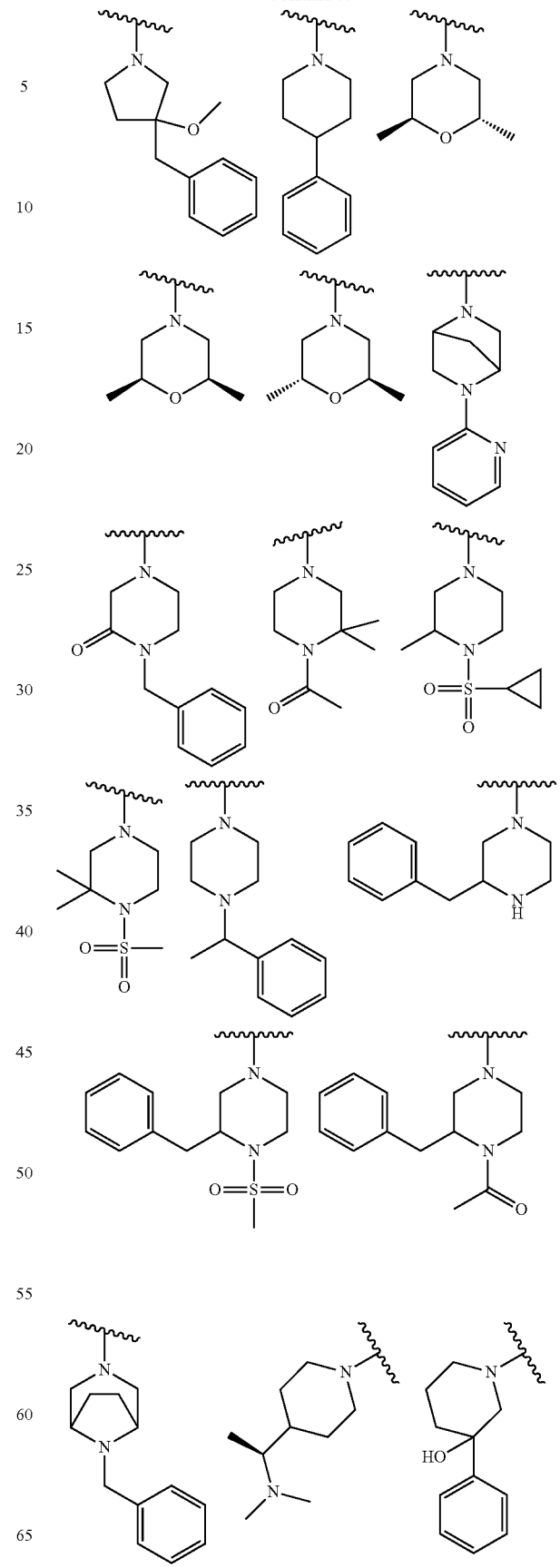

383
-continued
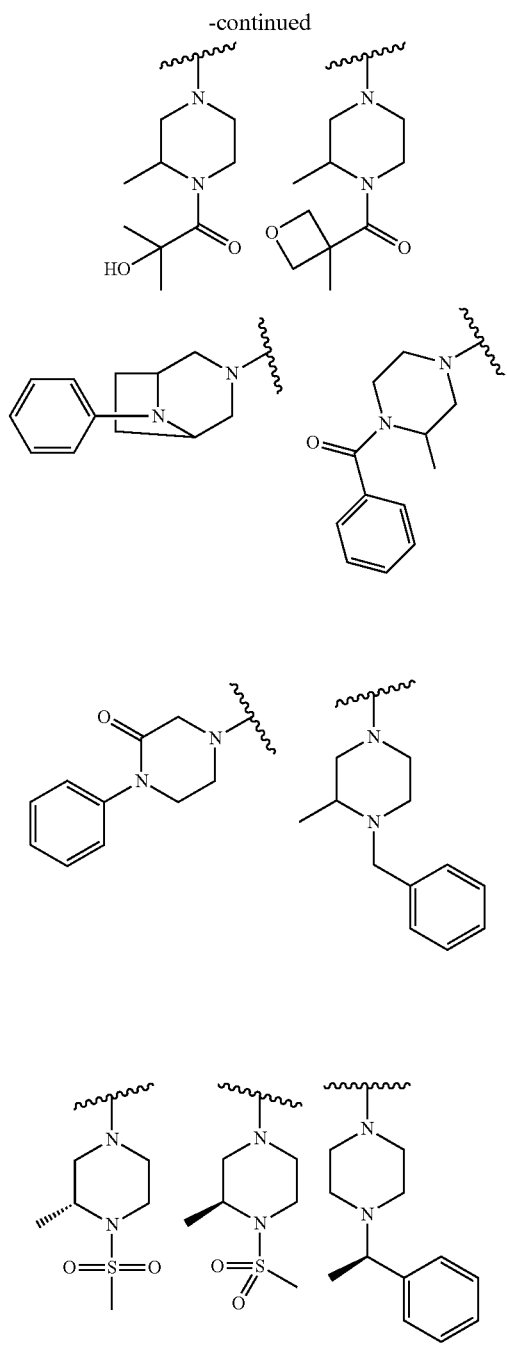
384
-continued
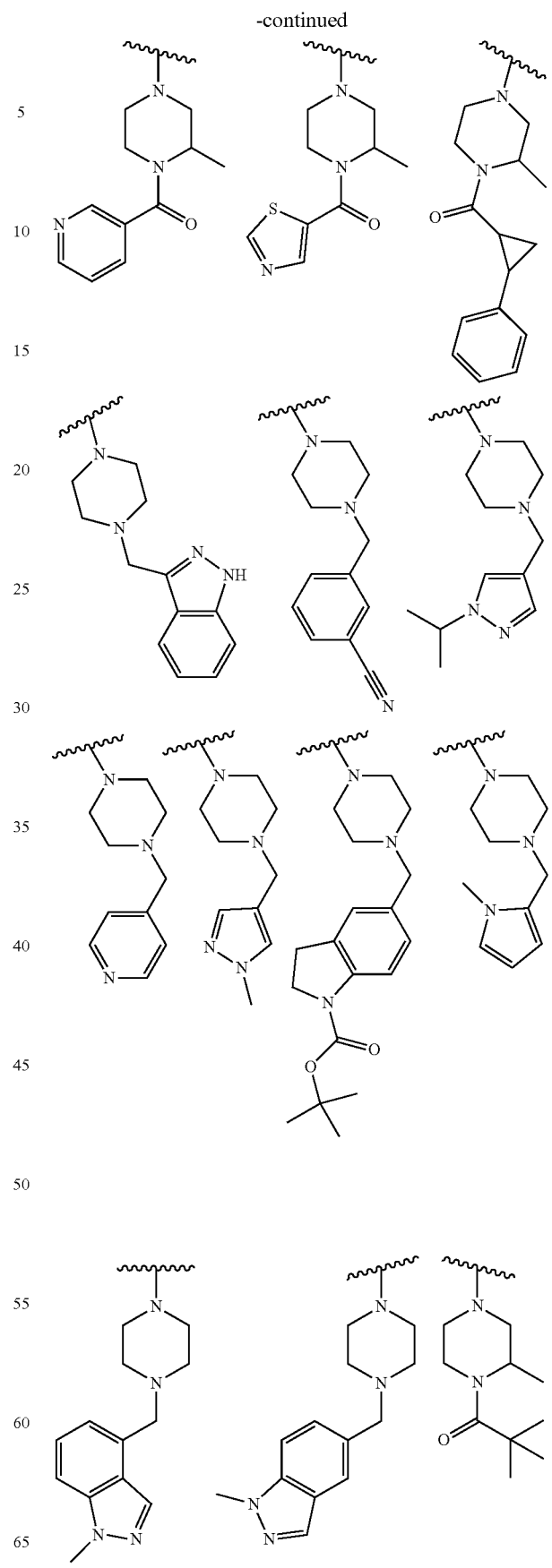

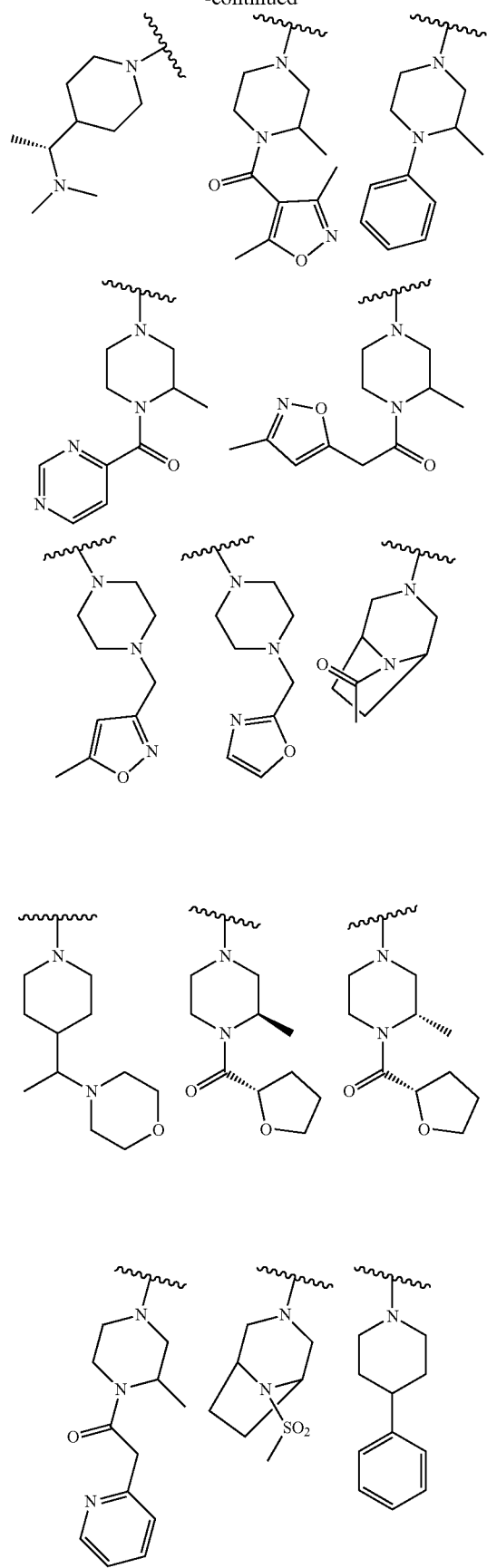
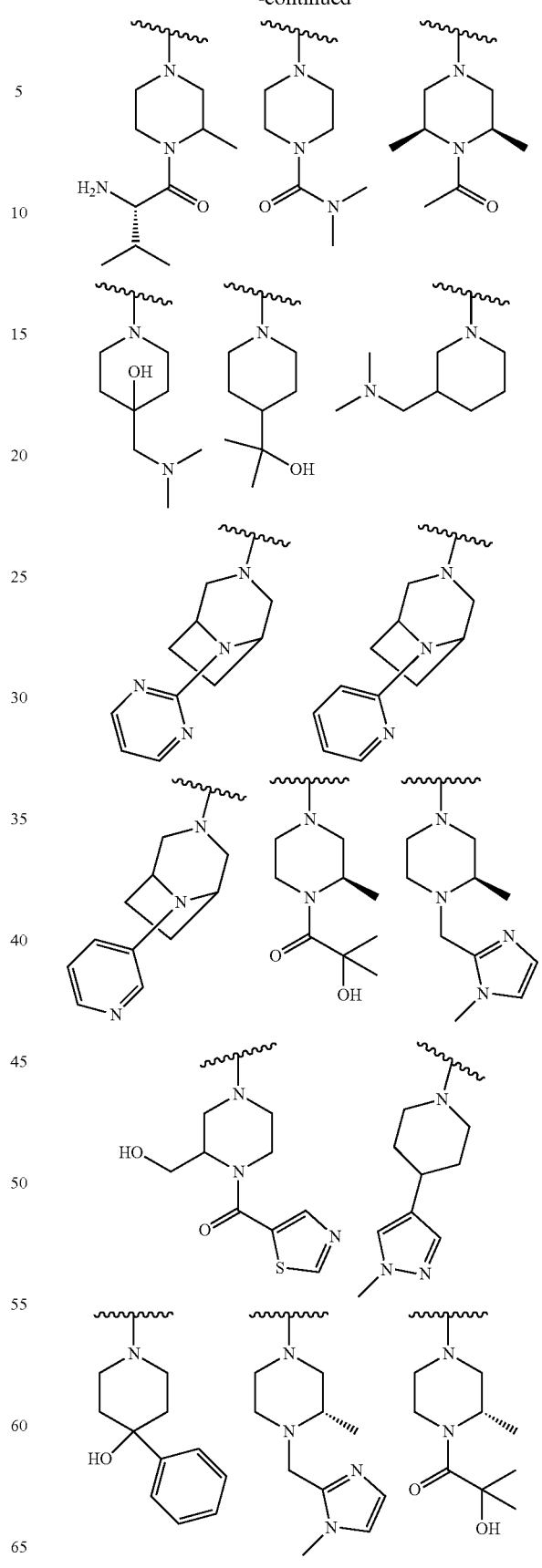

387
-continued
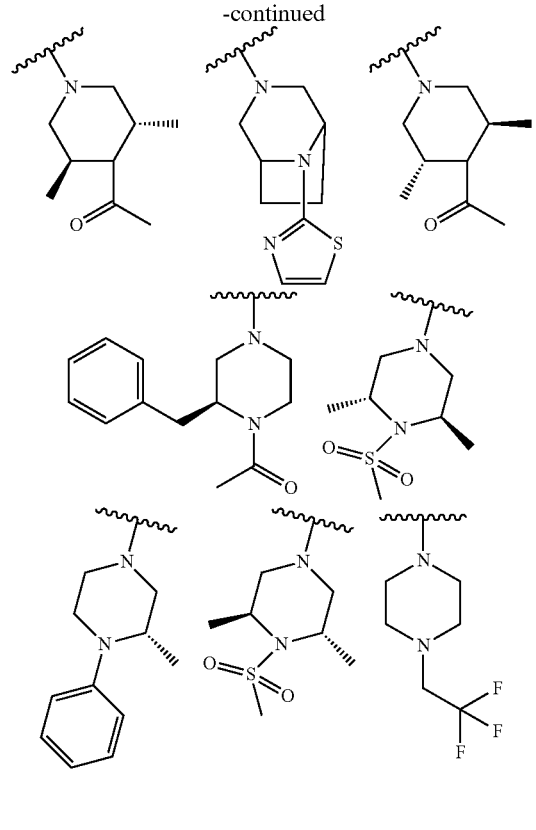
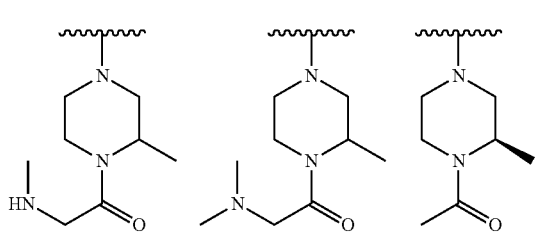
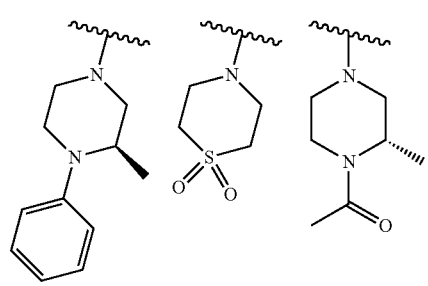
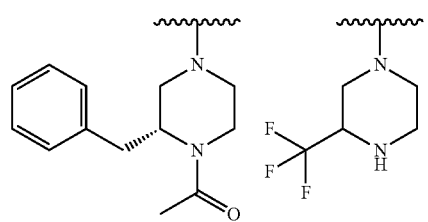
388
-continued
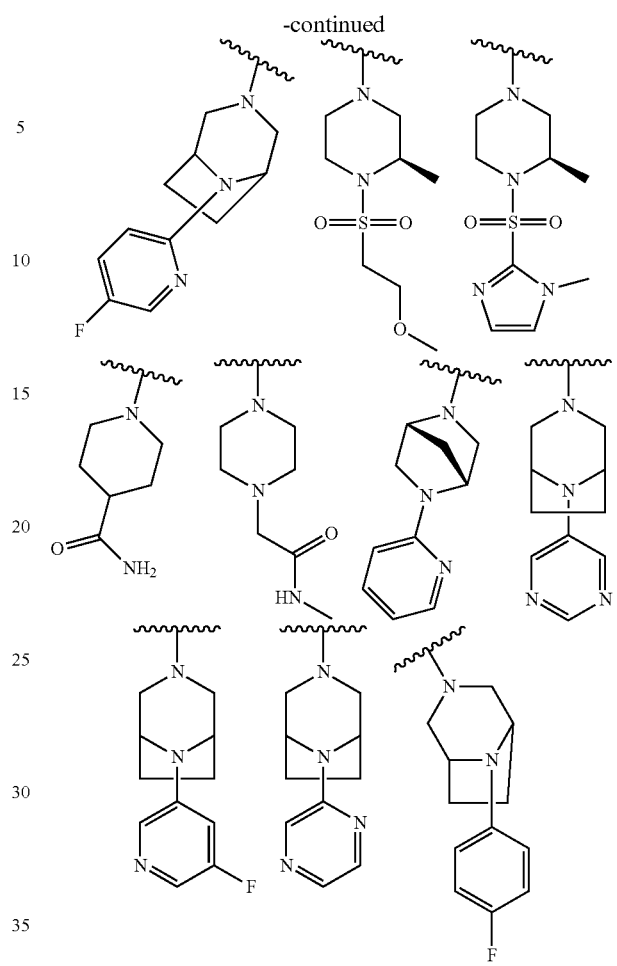
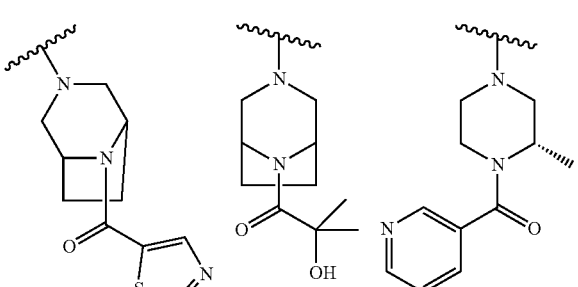
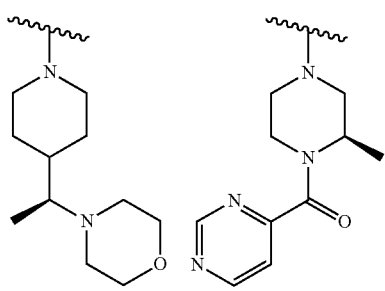

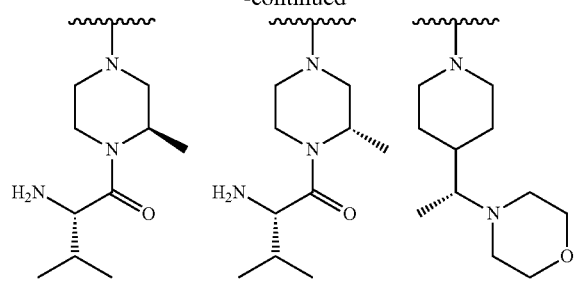
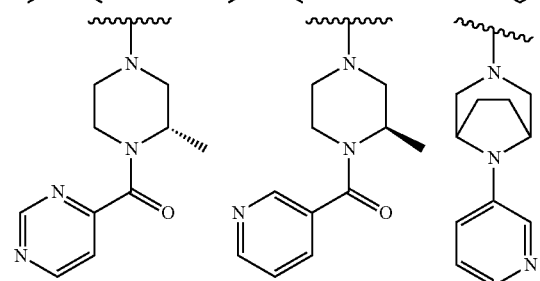
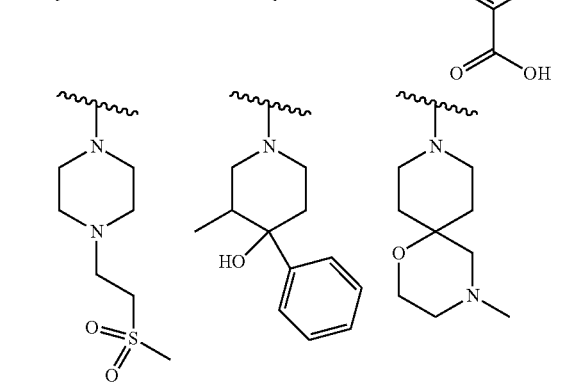
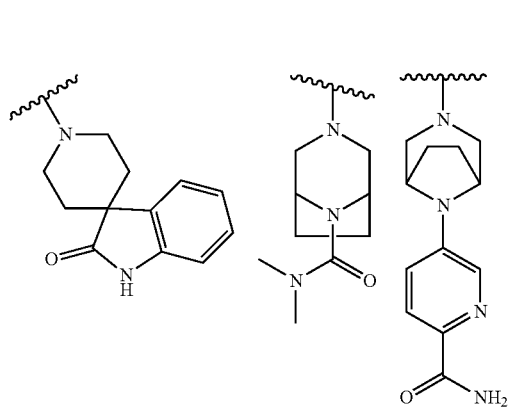
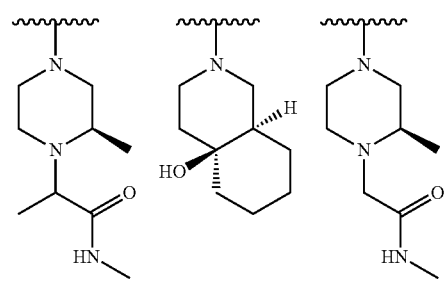
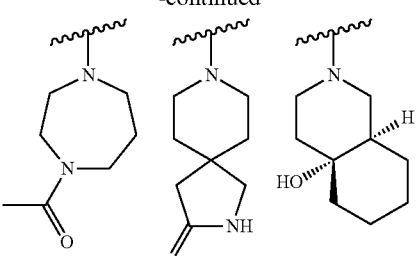
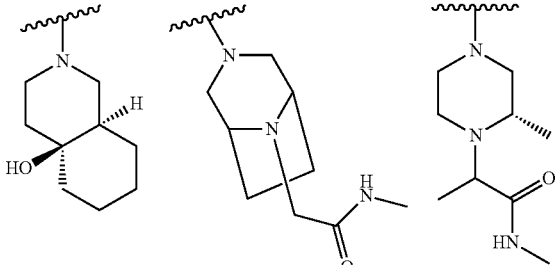
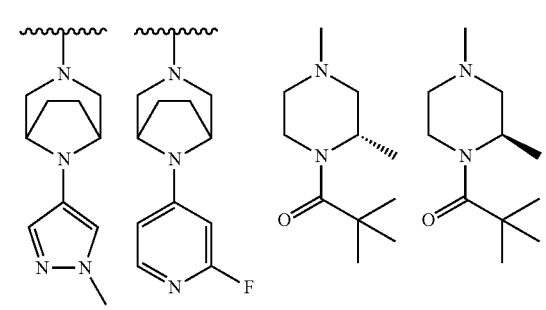
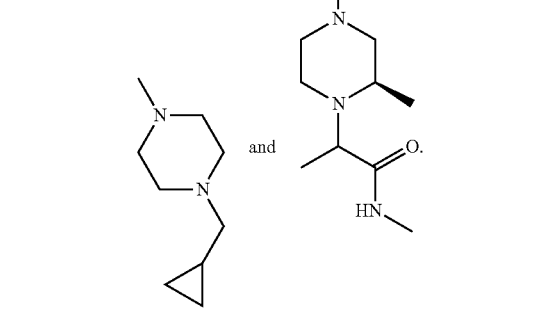
6. The compound of claim 1 wherein $R^4$ is $-O-R^b$.
7. The compound of claim 1 wherein $R^4$ is selected from the group consisting of:
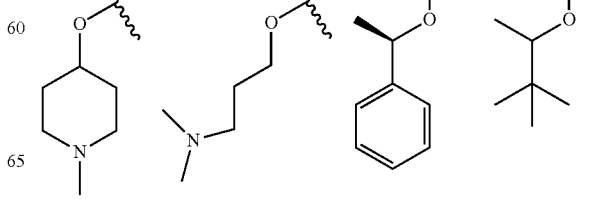

391
-continued

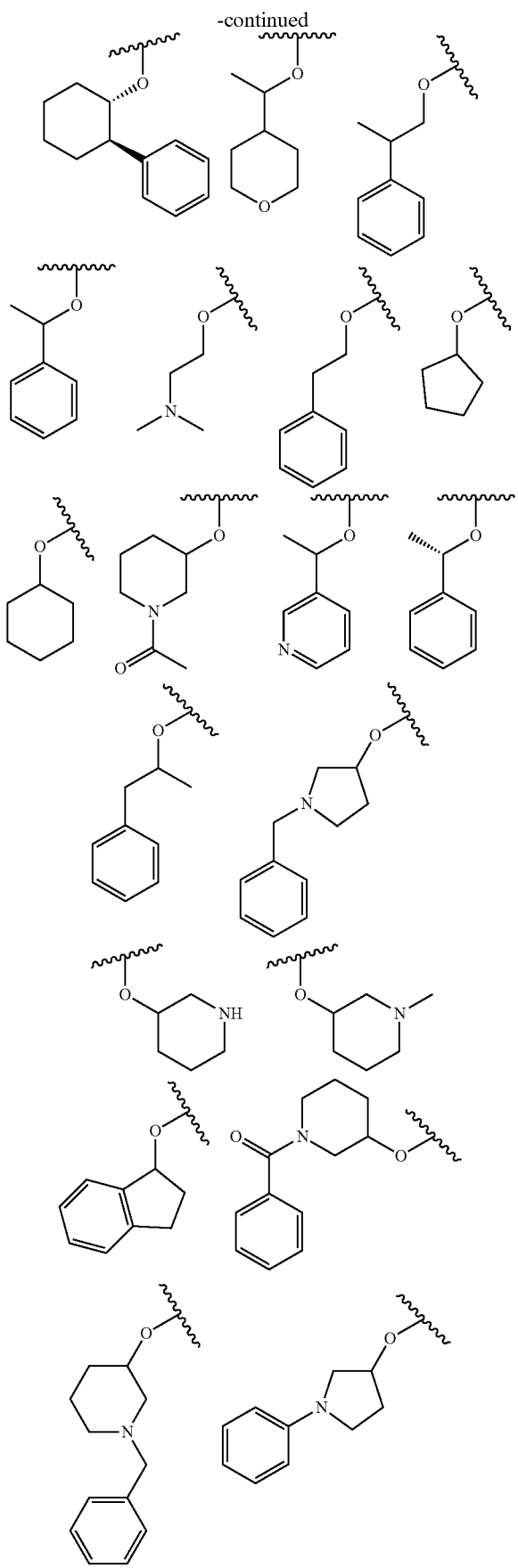

392
-continued

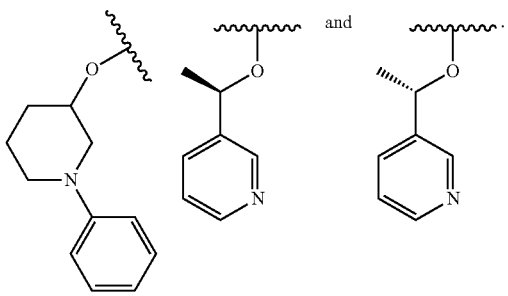

8. The compound of claim 1 wherein $R^4$ is $-N(R^b)_2$.

9. The compound of claim 1 wherein $R^4$ is selected from the group consisting of:

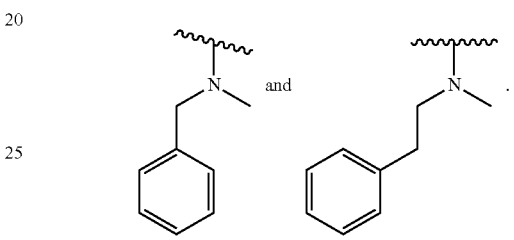

10. The compound of claim 1 wherein $R^4$ is selected from the group consisting of $C_{2-6}$alkenyl, $C_{2-6}$alkynyl, 3-15 membered carbocyclyl, 3-15 membered heterocyclyl, and $-C(O)-N(R^b)_2$, wherein each $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, $-NO_2$, $-N(R^c)_2$, $-CN$, $-C(O)-N(R^c)_2$, $-S(O)-N(R^c)_2$, $-S(O)_2-N(R^c)_2$, $-O-R^c$, $-S-R^c$, $-O-C(O)-R^c$, $-C(O)-R^c$, $-C(O)-OR^c$, $-S(O)-R^c$, $-S(O)_2-R^c$, $-N(R^c)-C(O)-R^c$, $-N(R^c)-S(O)-R^c$, $-N(R^c)-C(O)-N(R^c)_2$, and $-N(R^c)-S(O)_2-R^c$.

11. The compound of claim 1 wherein $R^4$ is selected from the group consisting of:

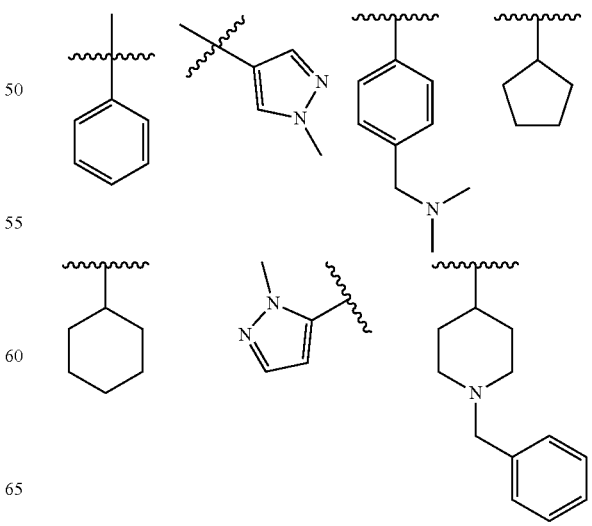

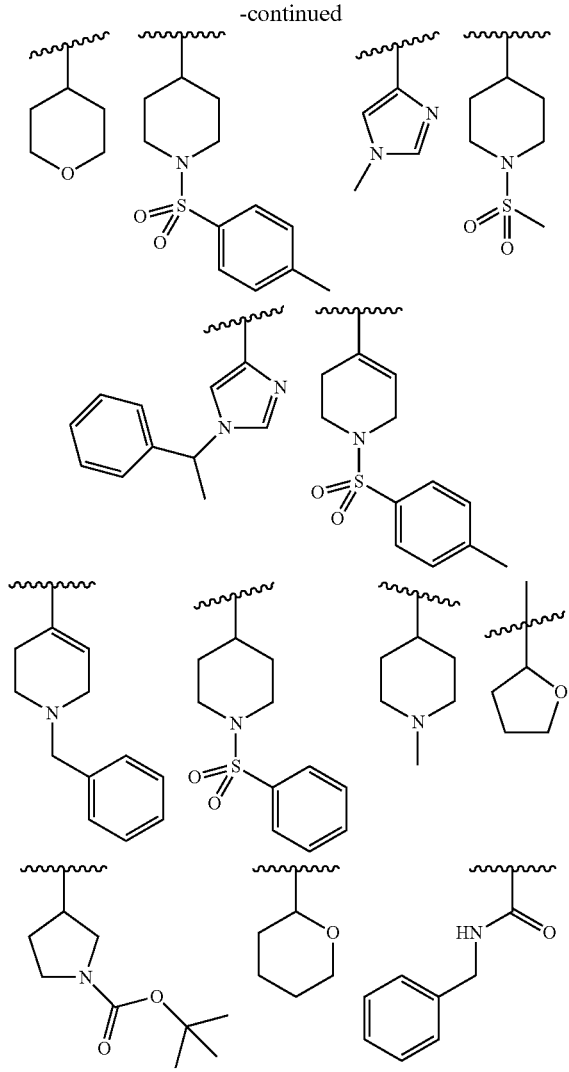
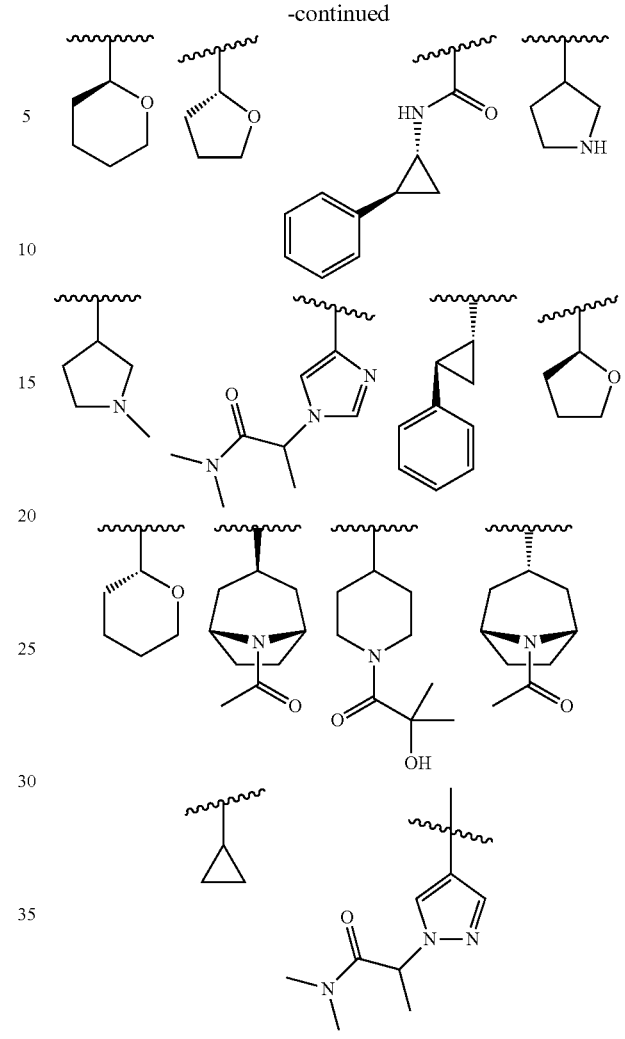
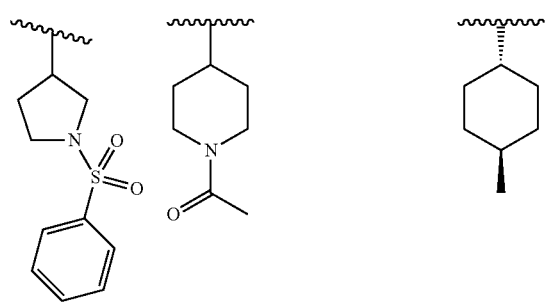
12. The compound of claim 1 wherein $R^4$ is selected from the group consisting of:
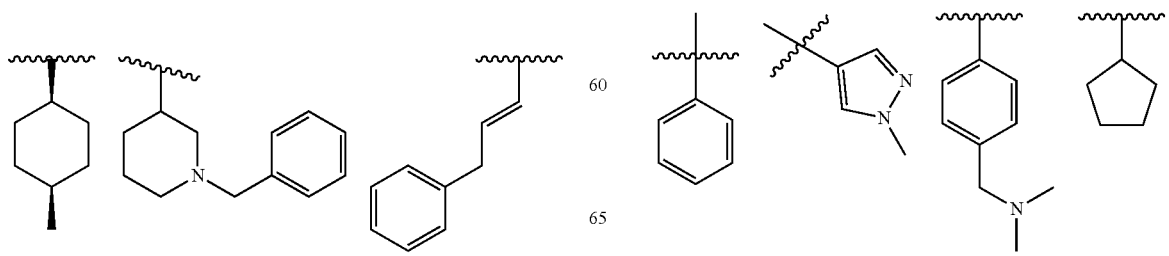

-continued
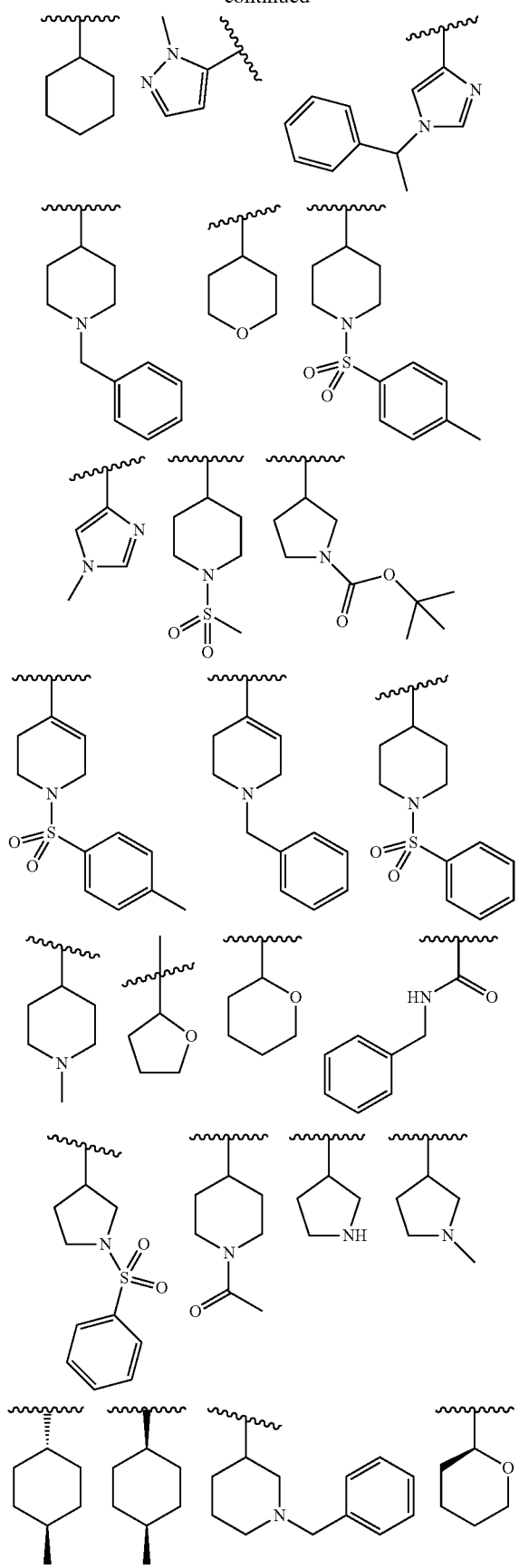
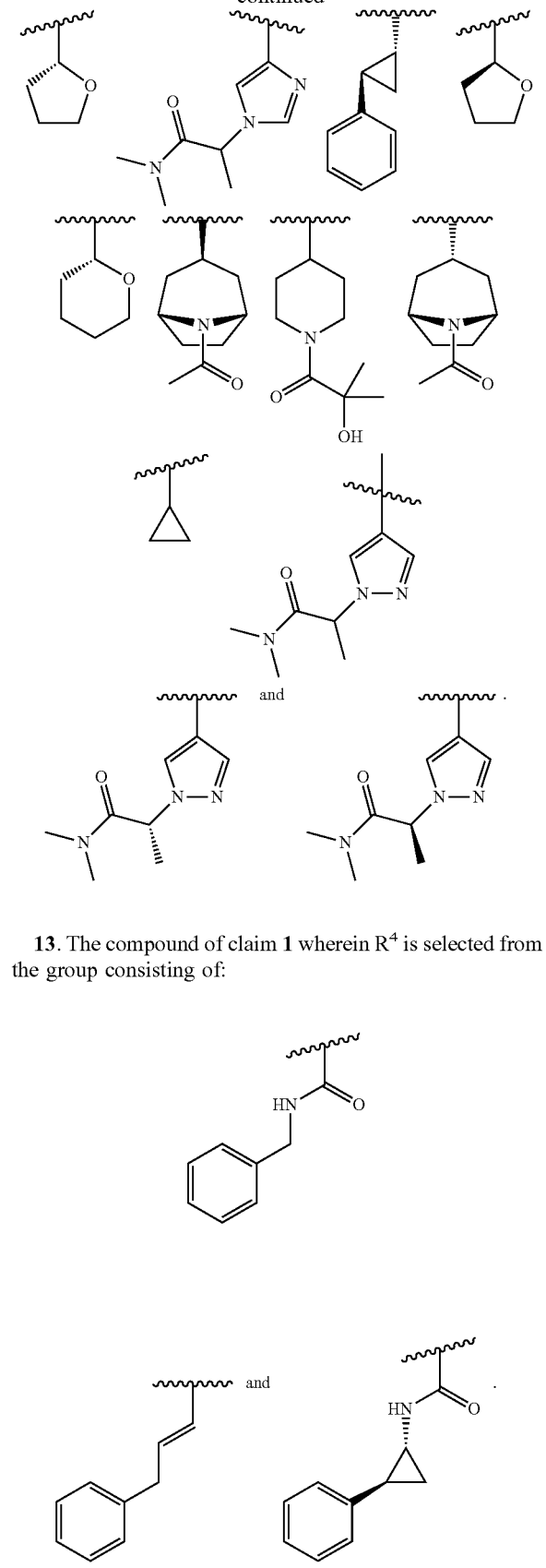
13. The compound of claim 1 wherein $R^4$ is selected from the group consisting of:
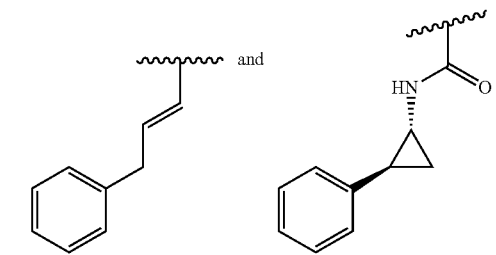

14. A compound of selected from the group consisting of:
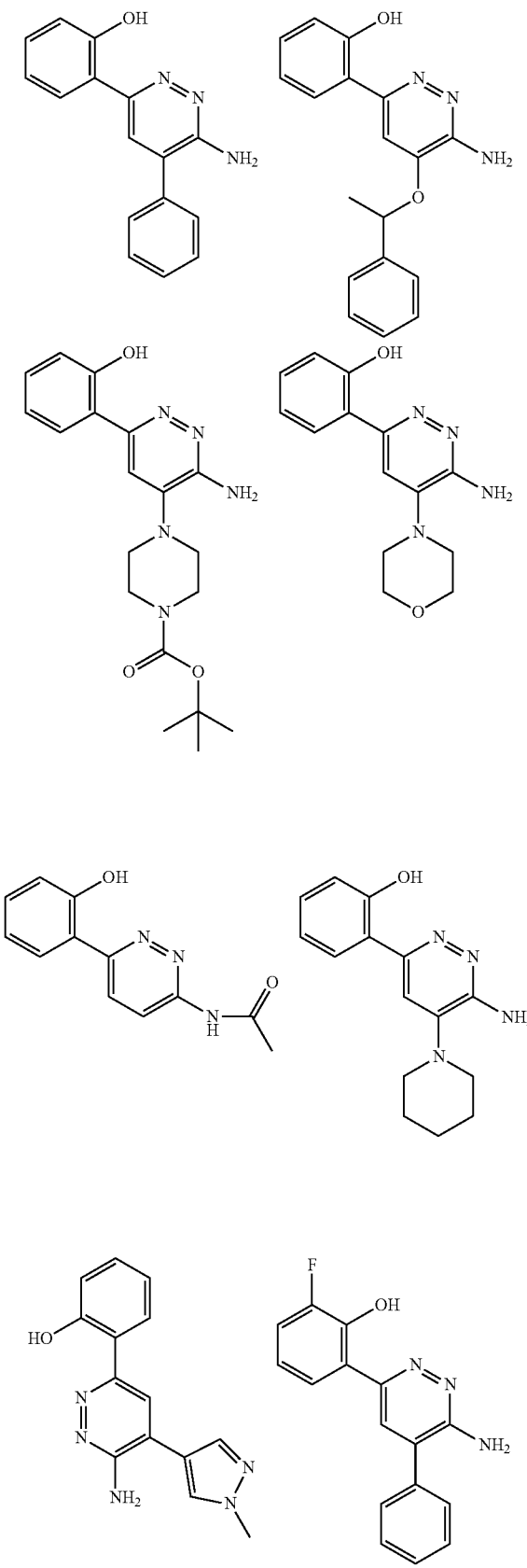
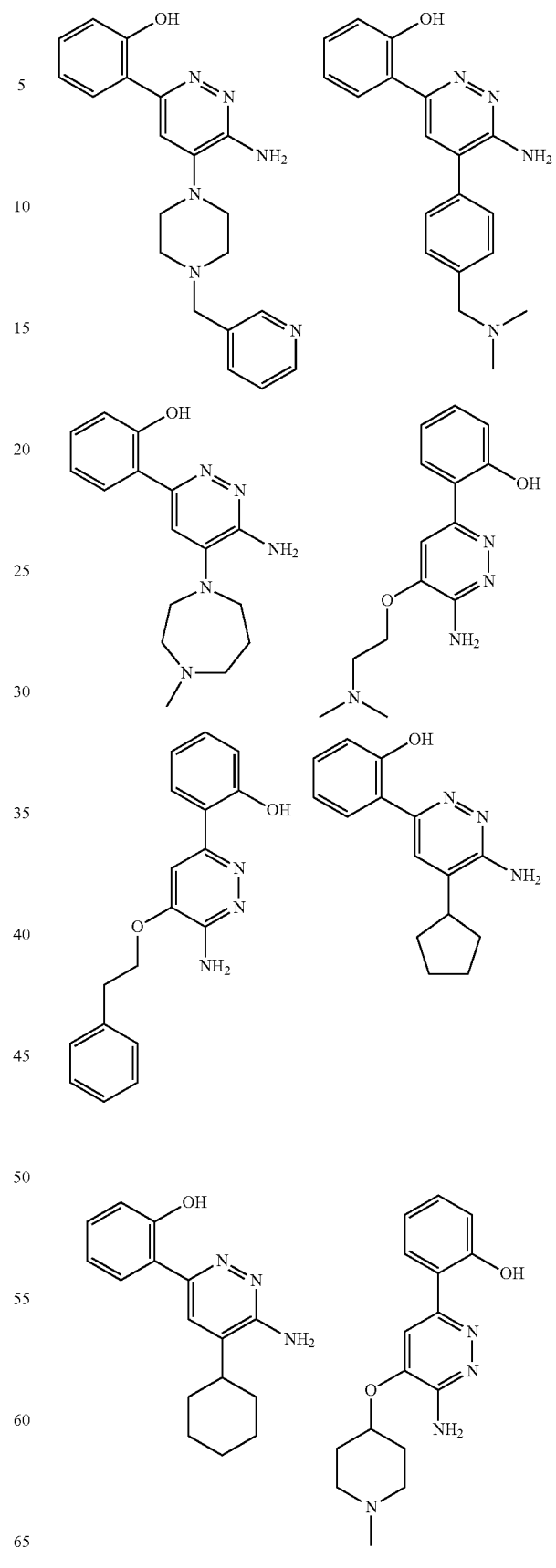

399
-continued
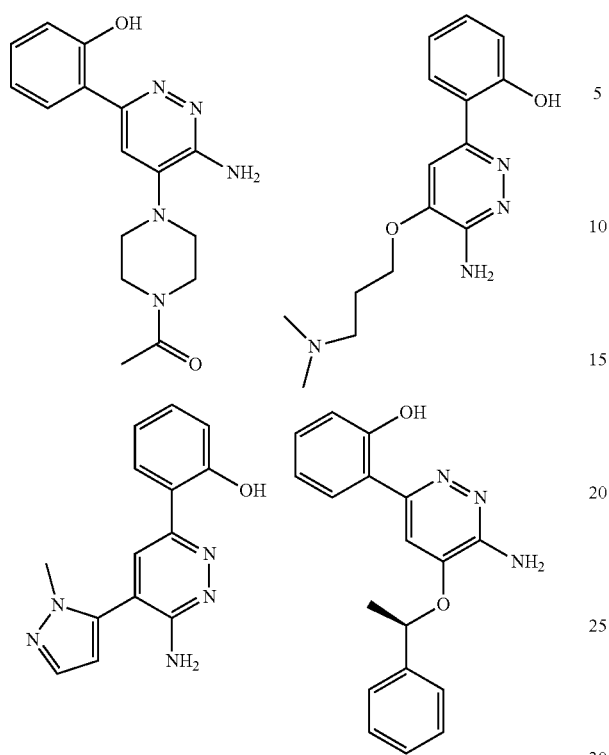
400
-continued
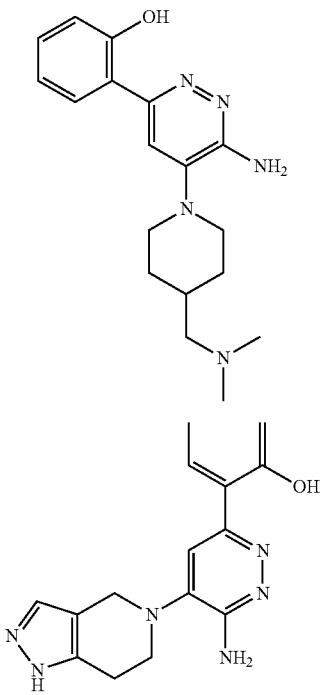
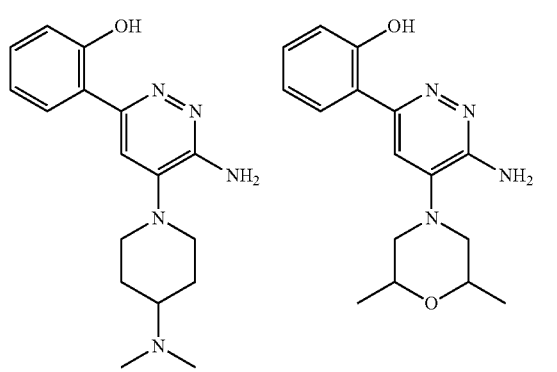
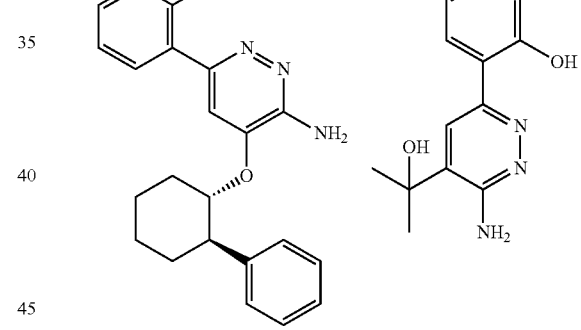
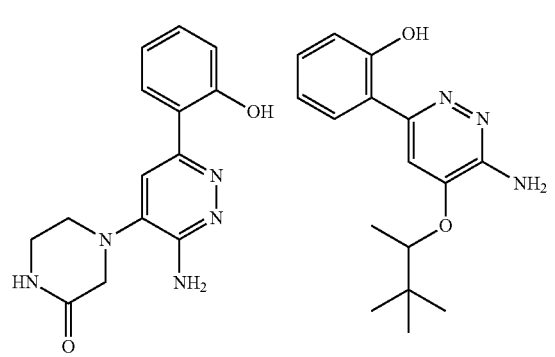
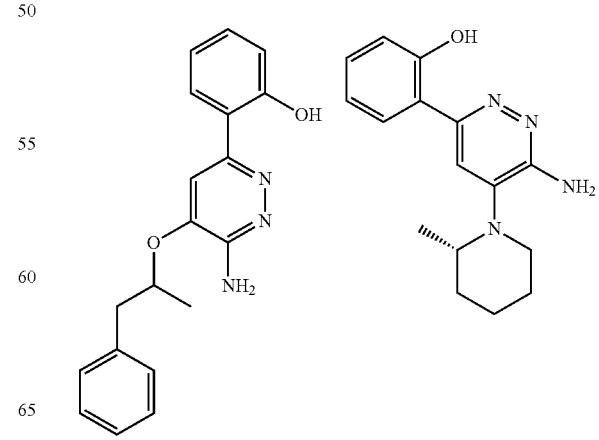

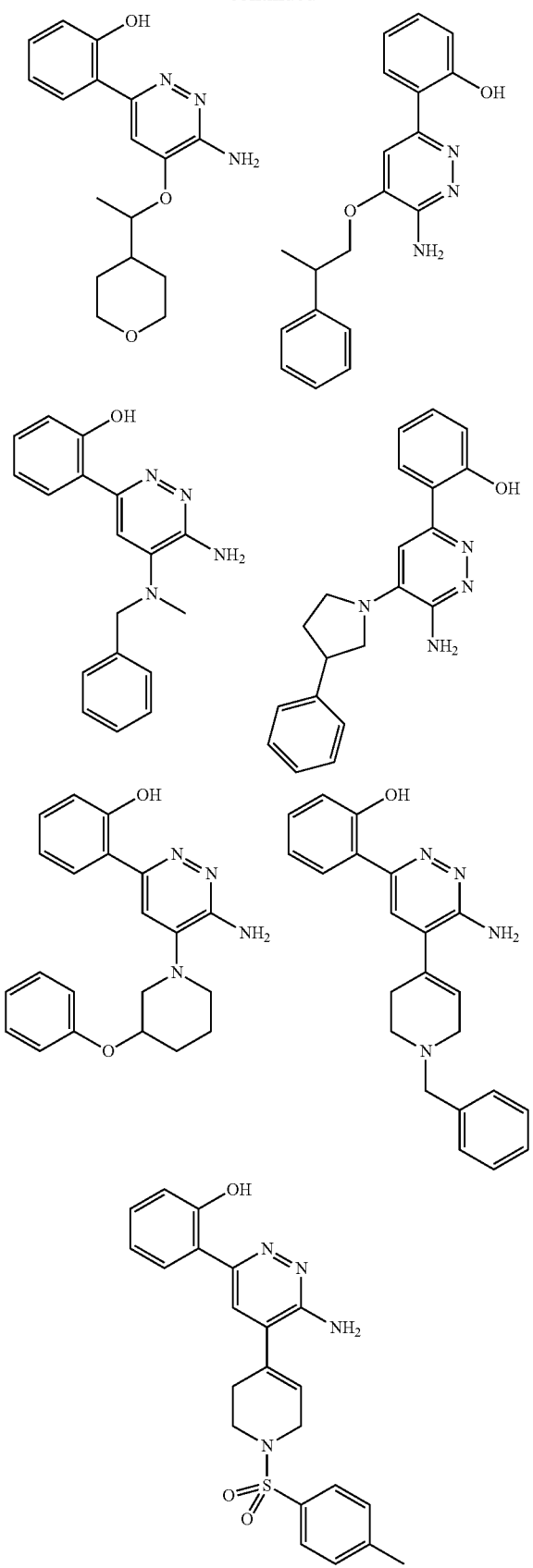
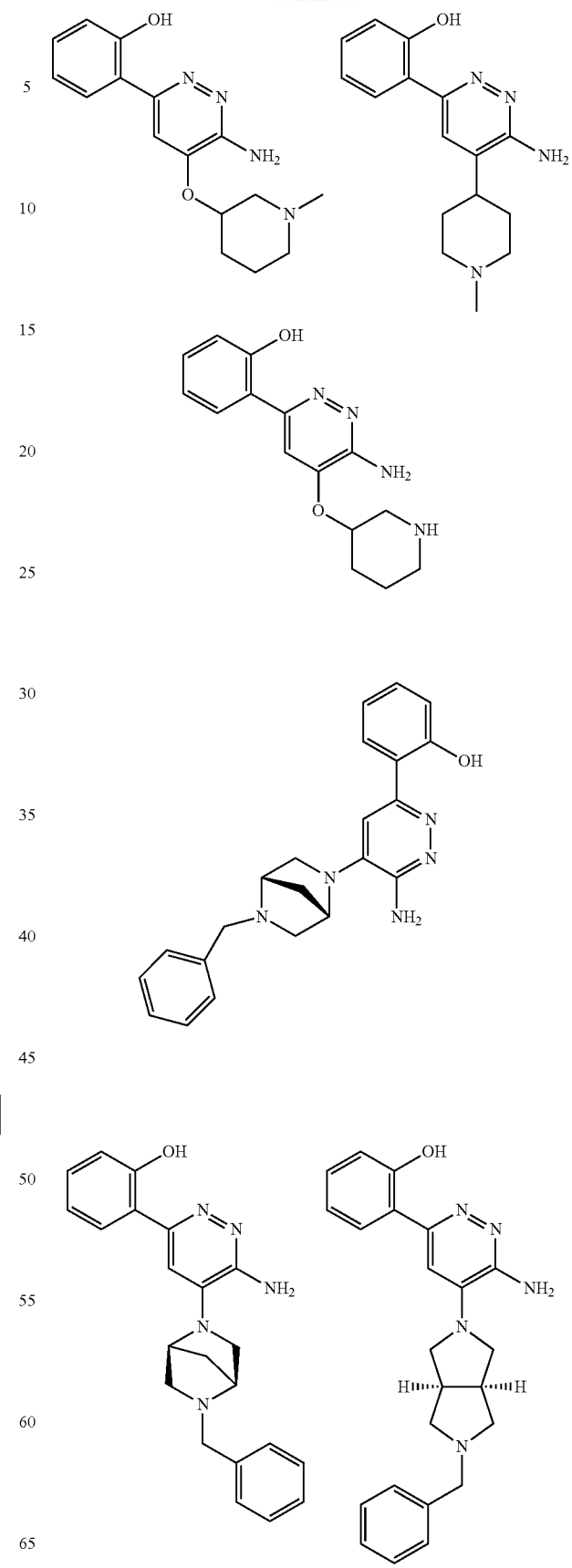

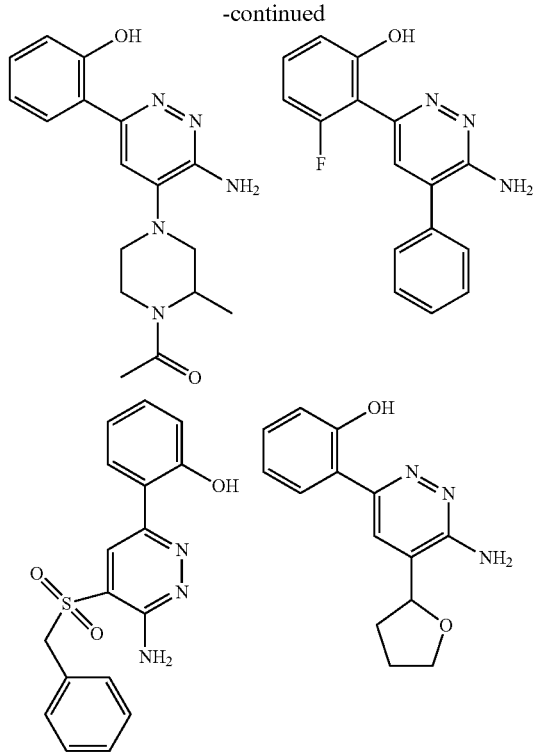
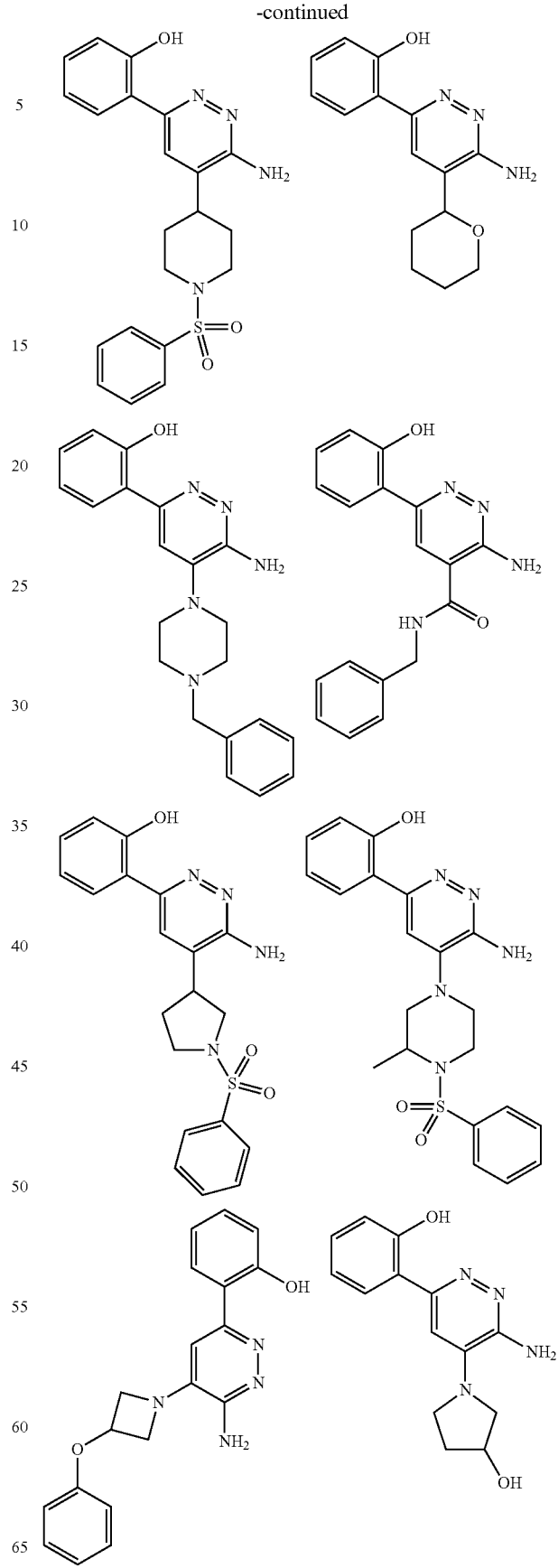

405
-continued
406
-continued
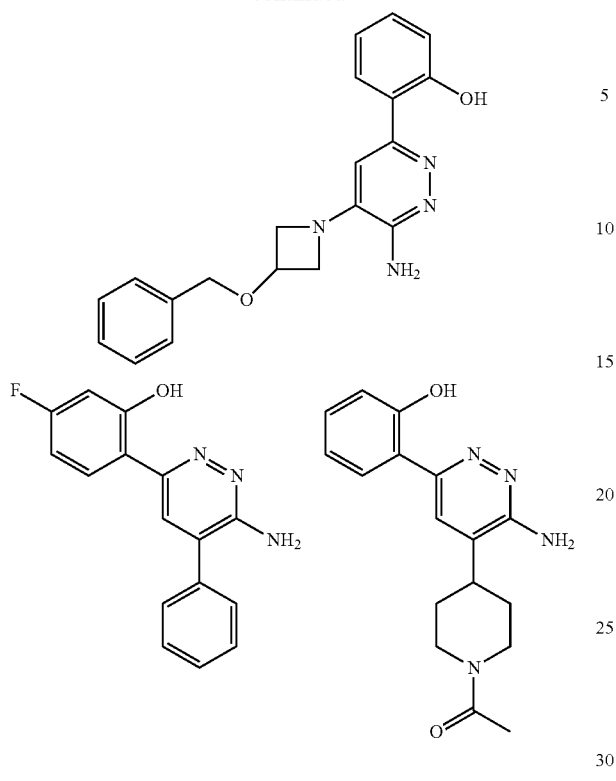
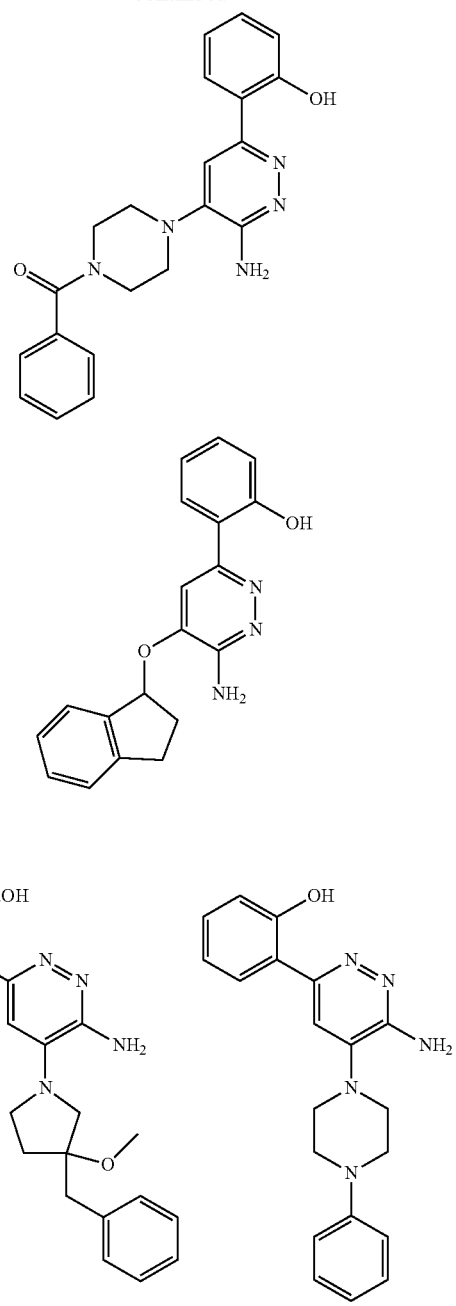
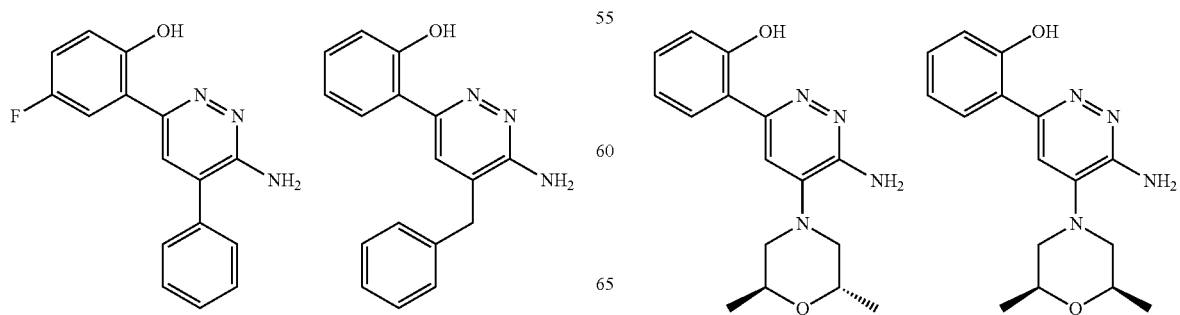

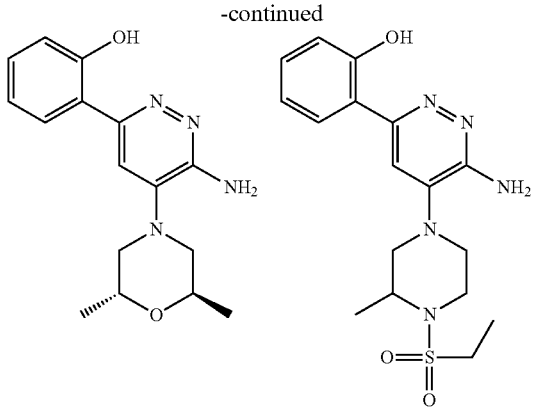
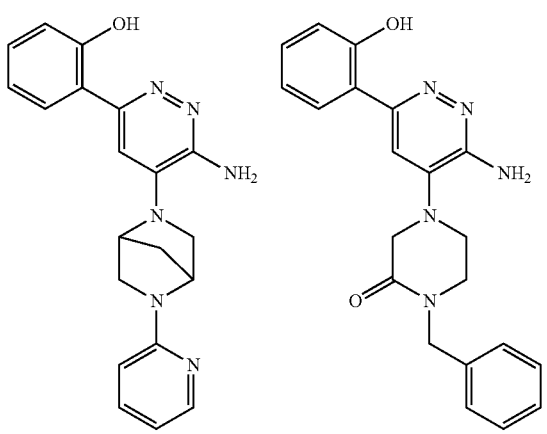
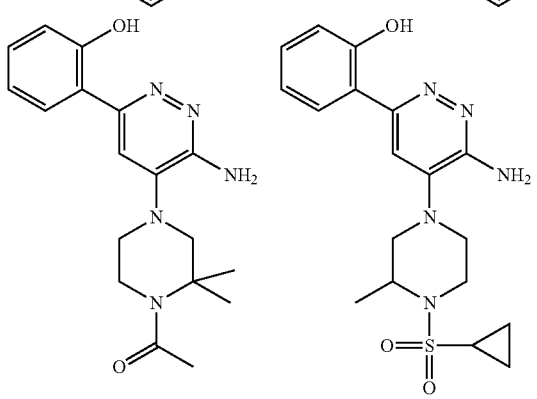
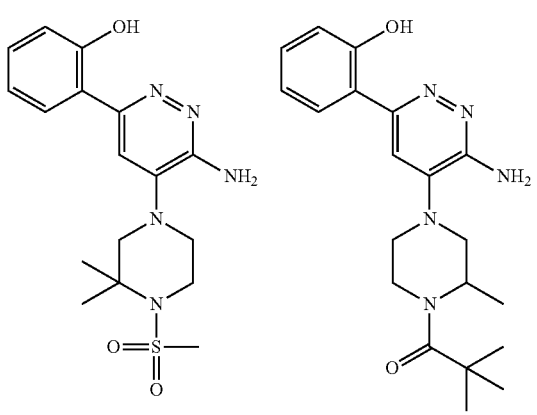
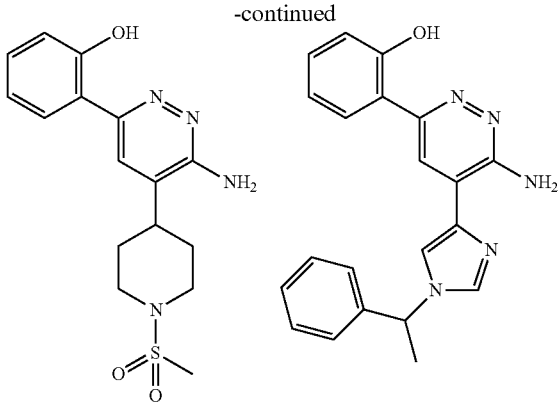
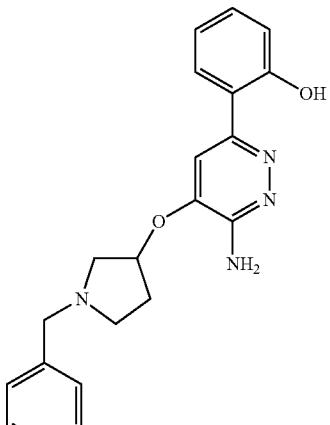
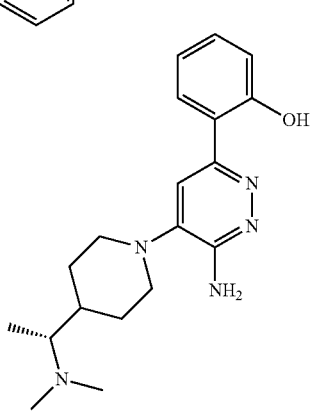
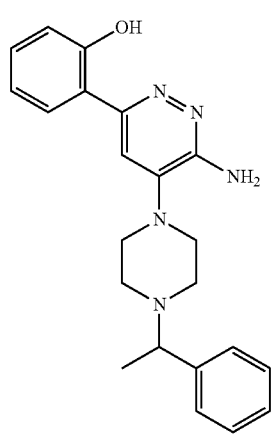

409 -continued
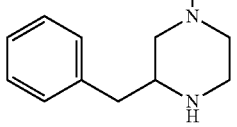
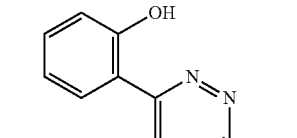
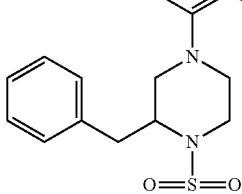
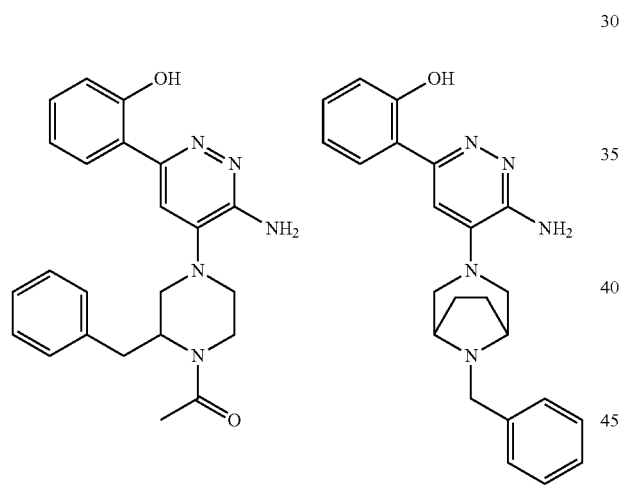
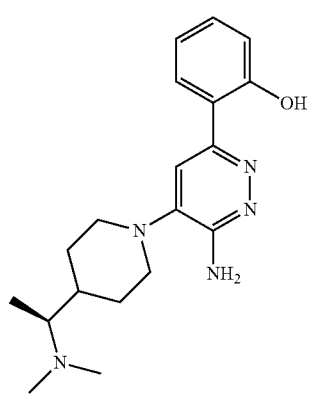
410 -continued
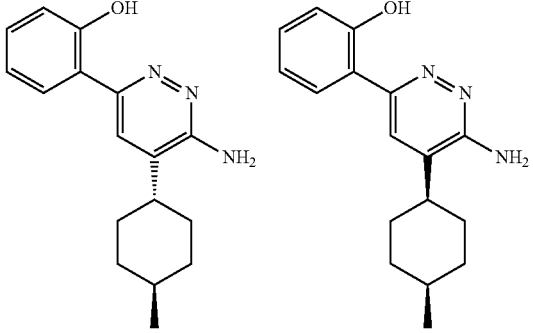
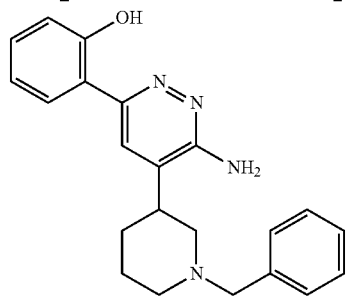
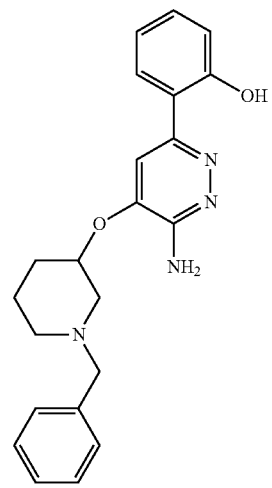
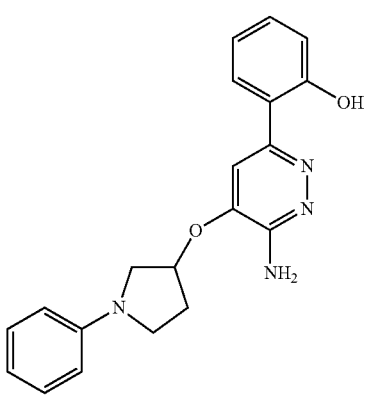

411
-continued
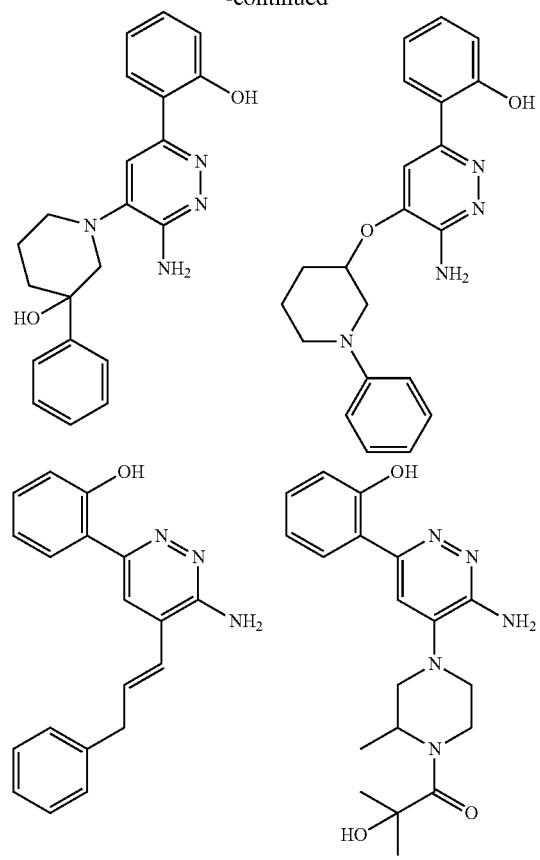
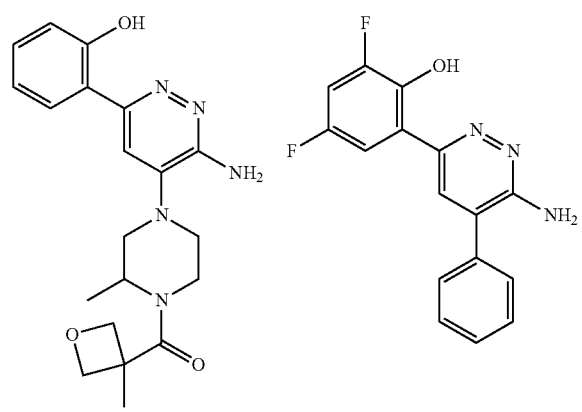
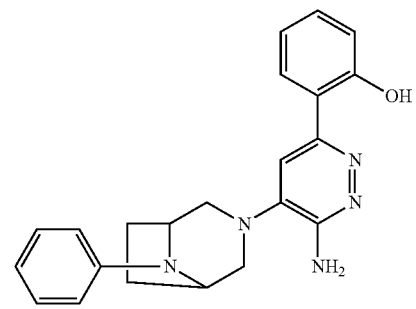
412
-continued
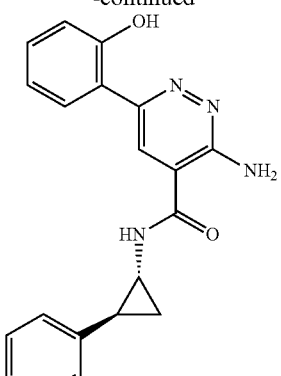
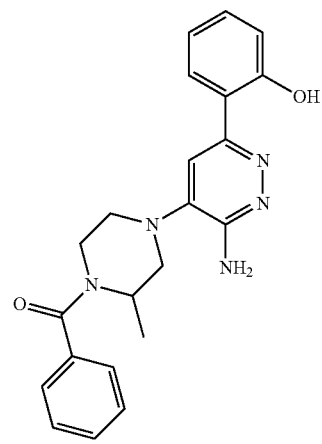
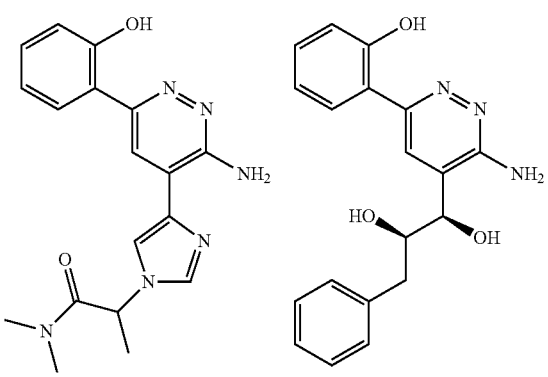

-continued
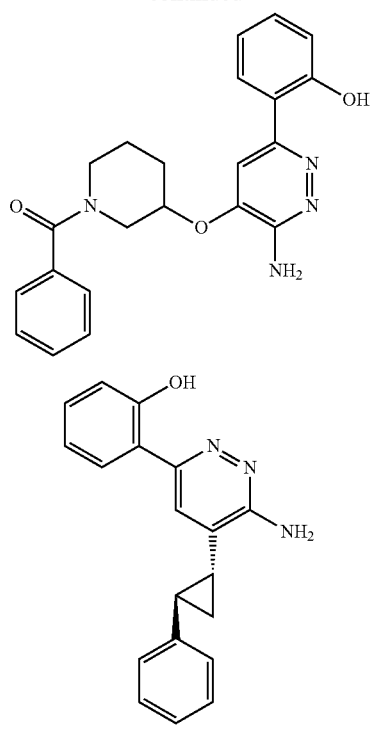
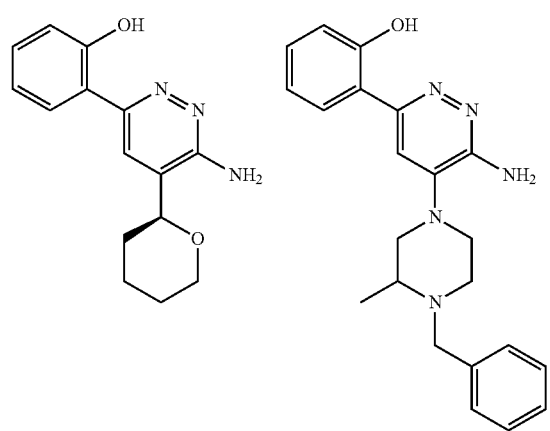
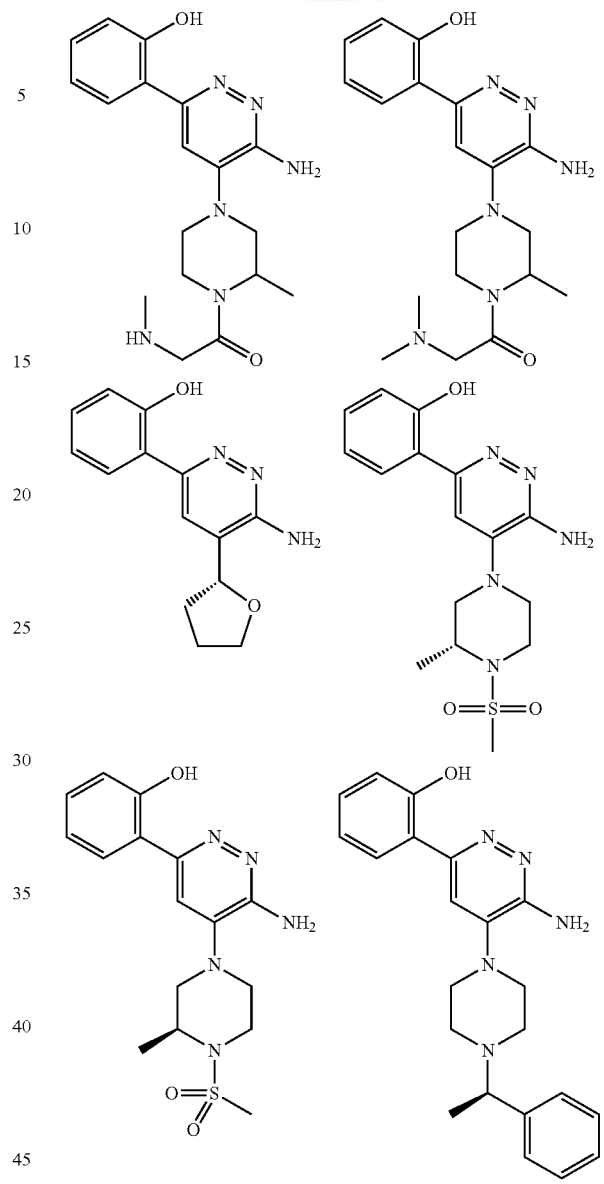

415
-continued
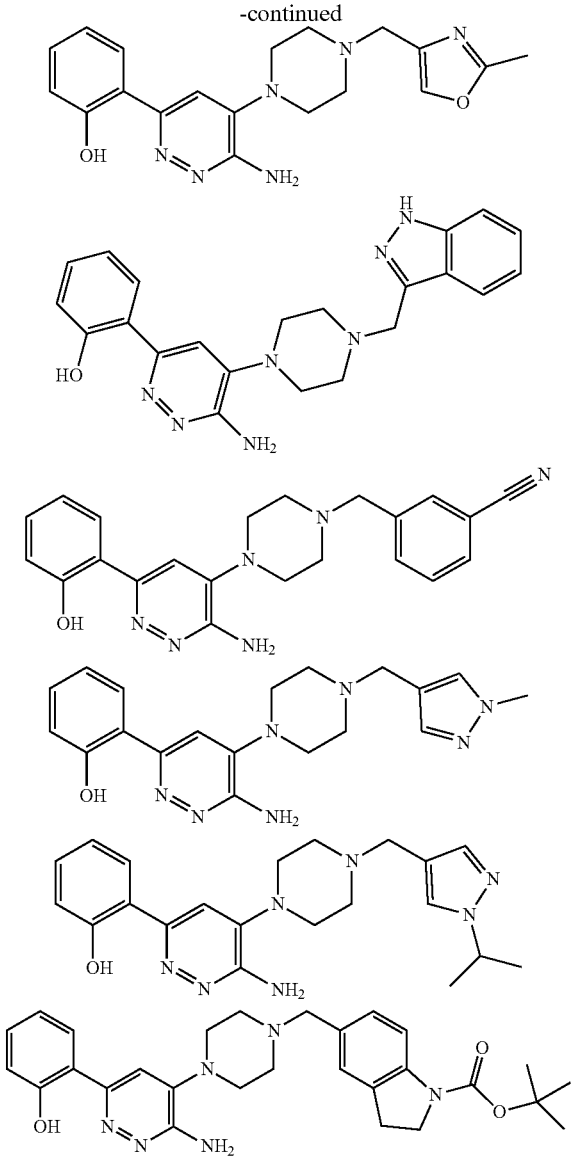
416
-continued
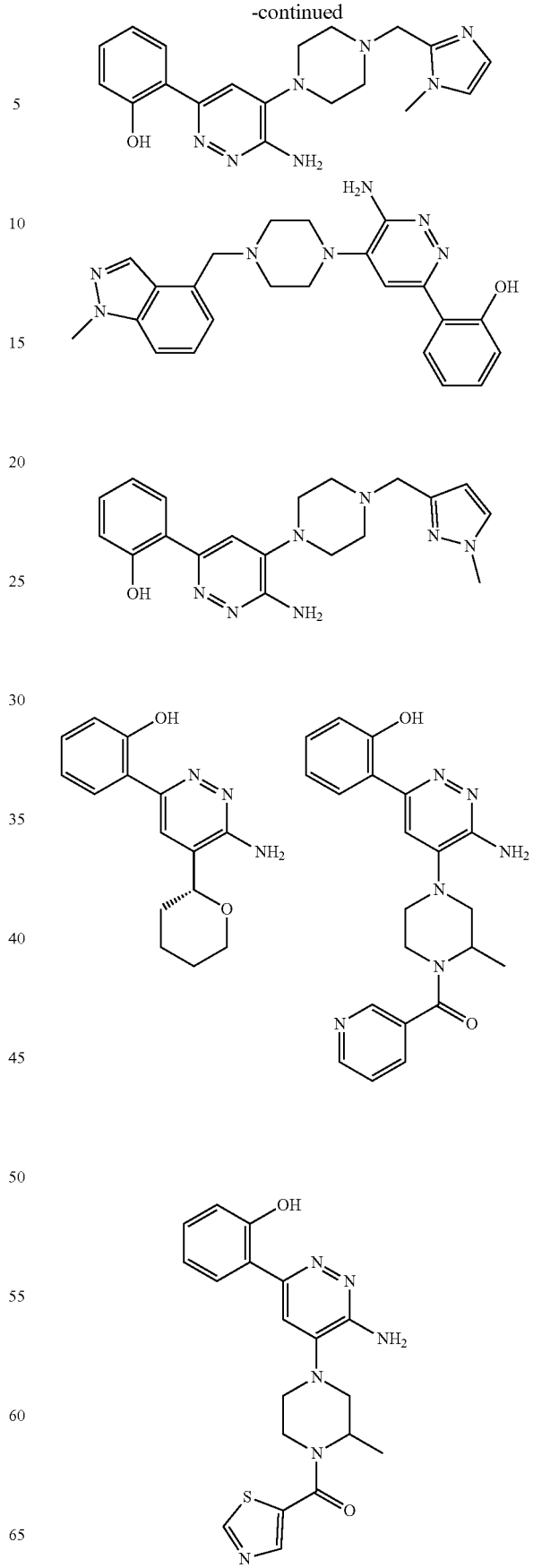

417
-continued
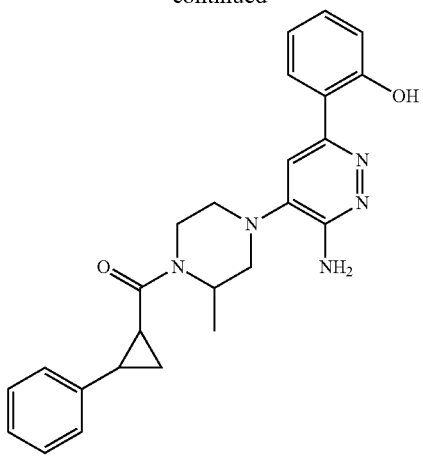
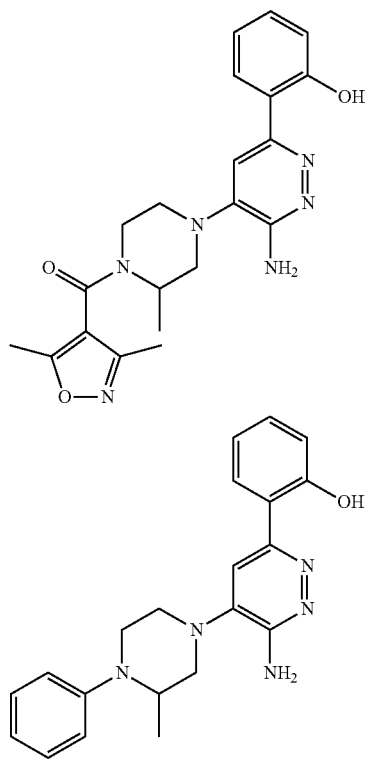
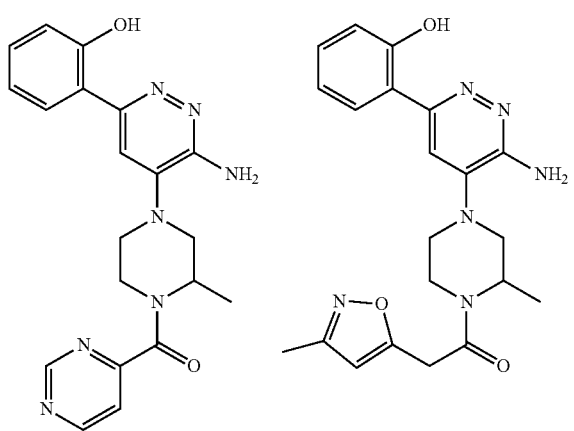
418
-continued
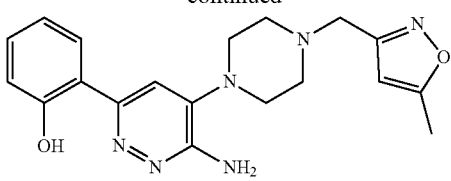
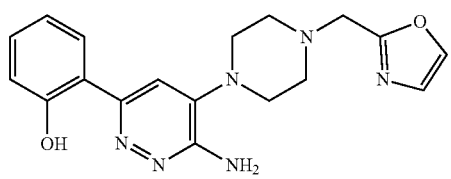
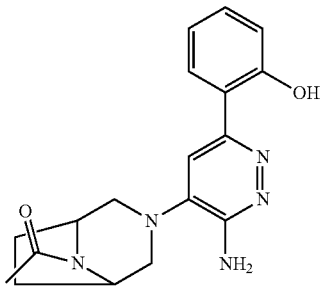
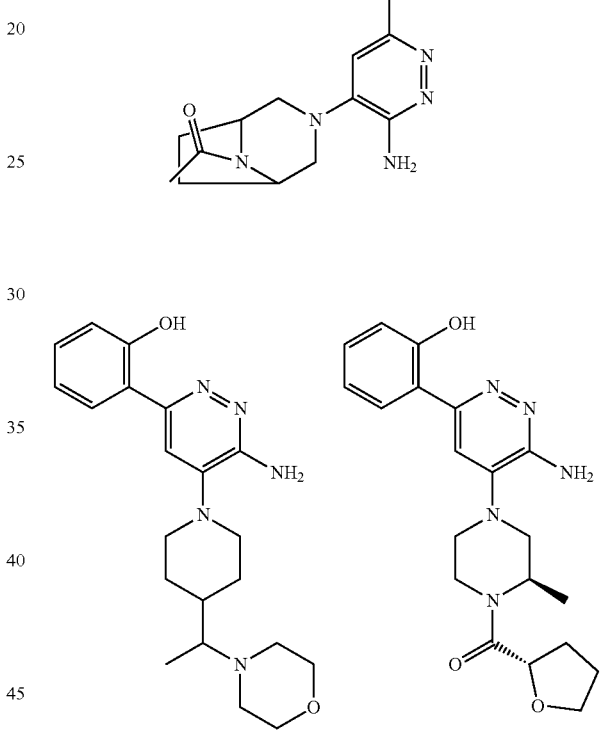
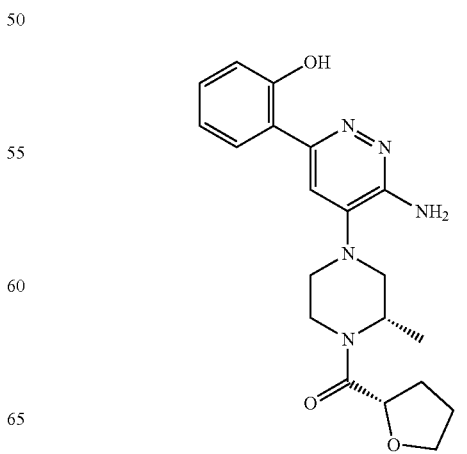

-continued
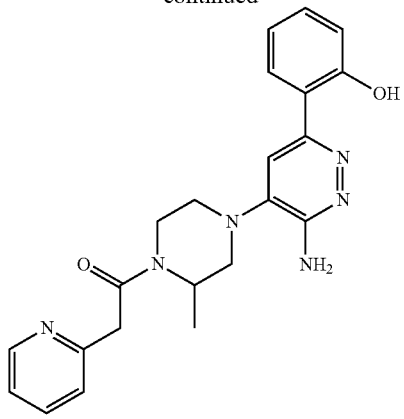
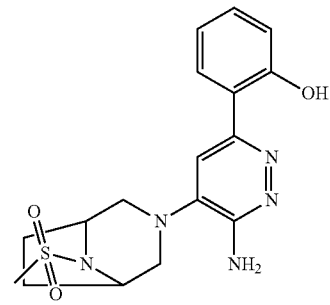
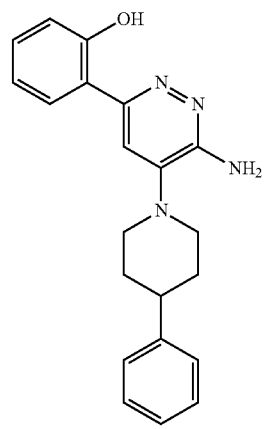
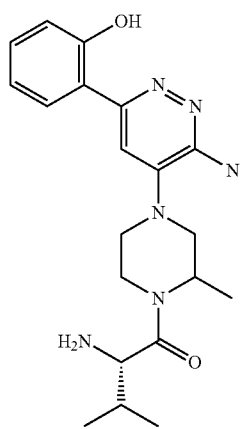
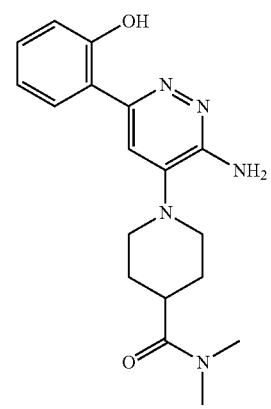
-continued
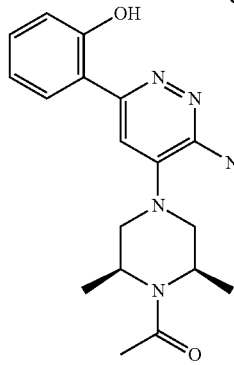
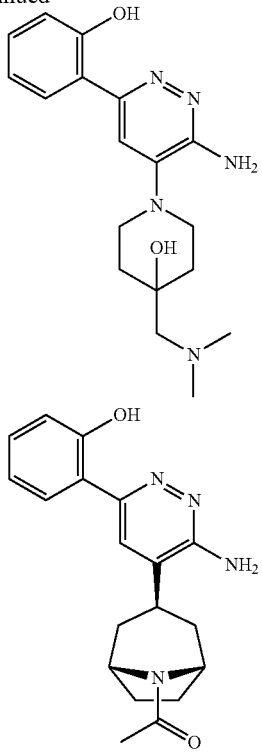
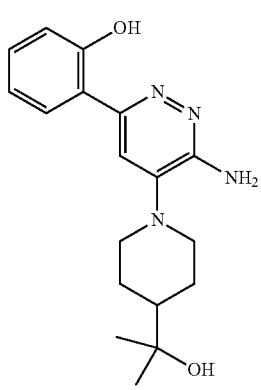
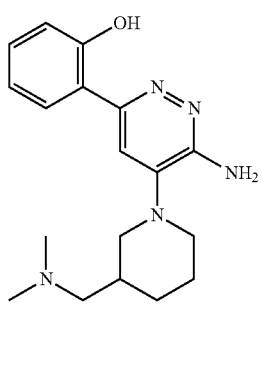
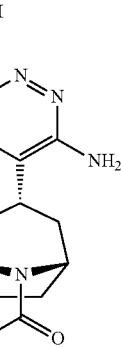

-continued
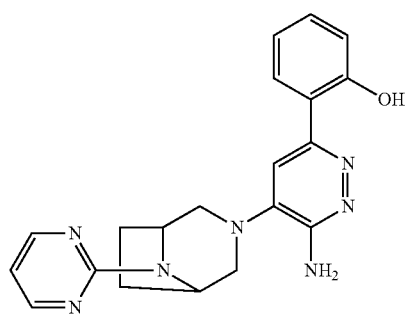
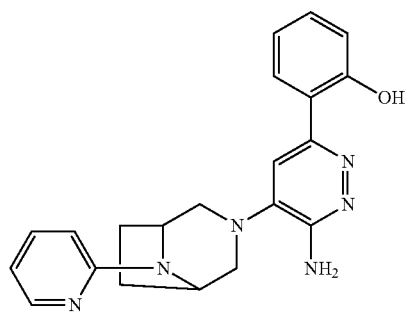
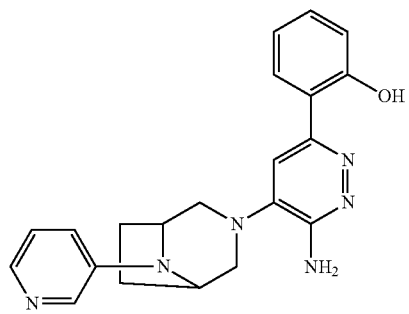
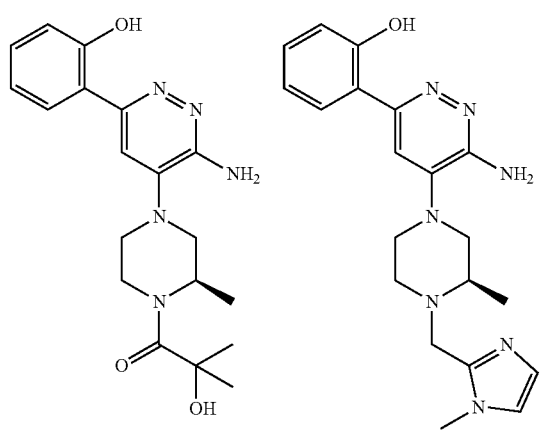
-continued
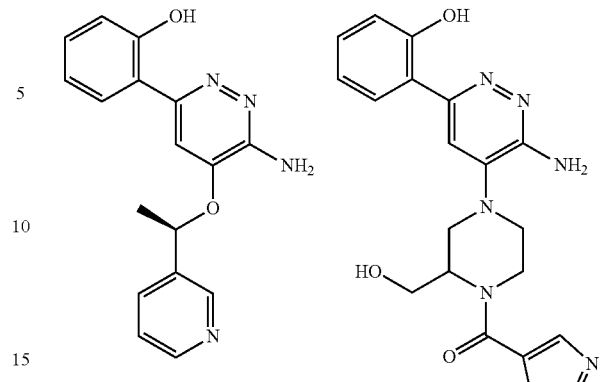
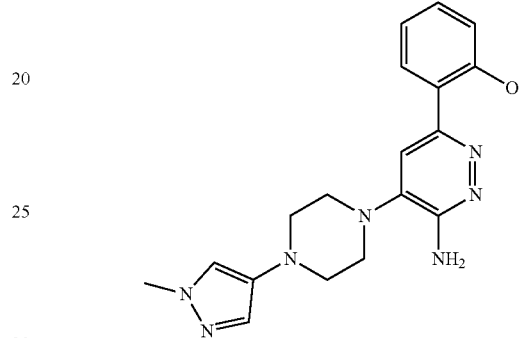
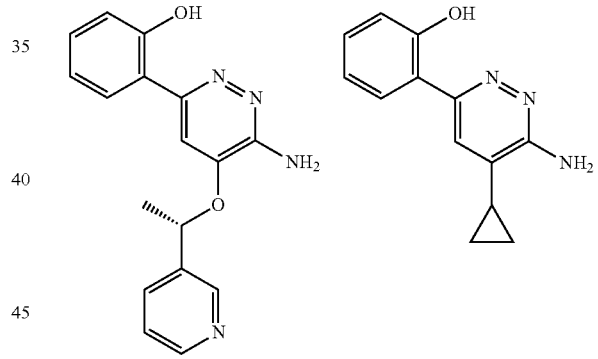
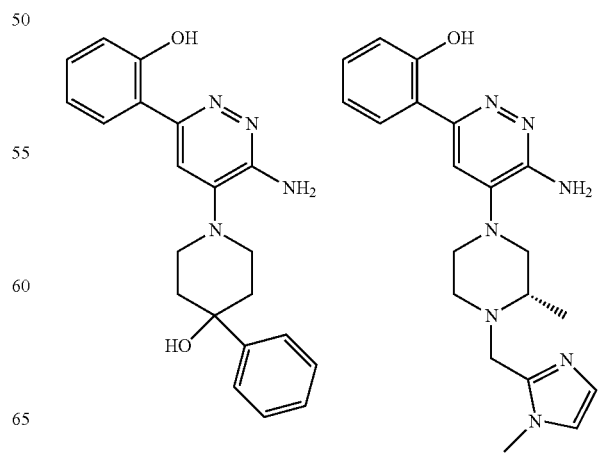

423
-continued
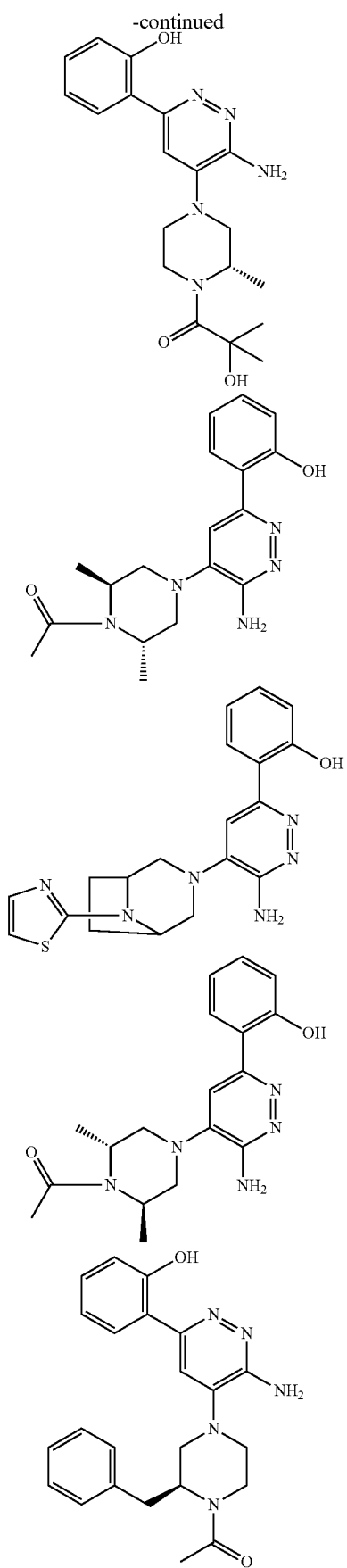
424
-continued
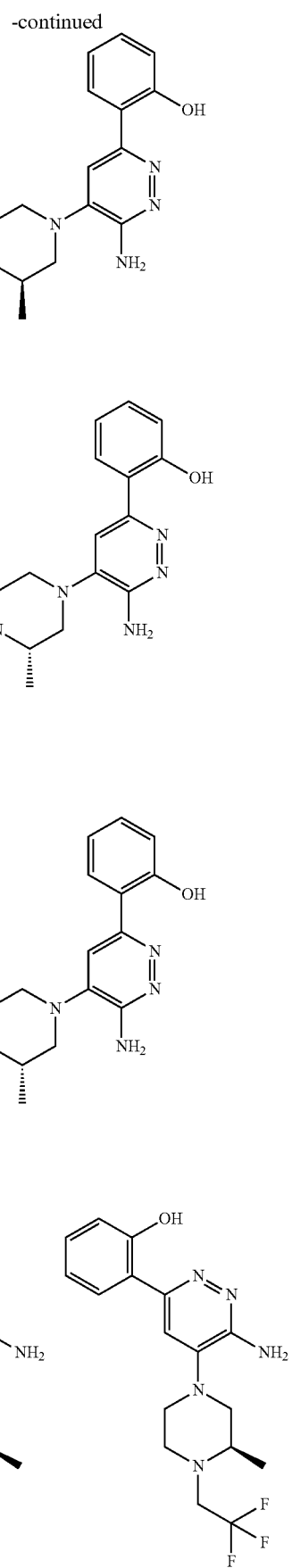

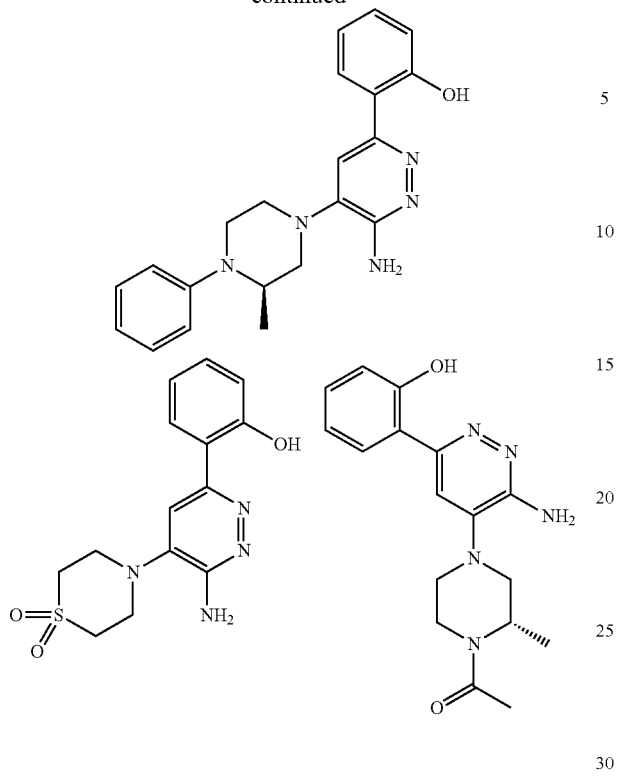
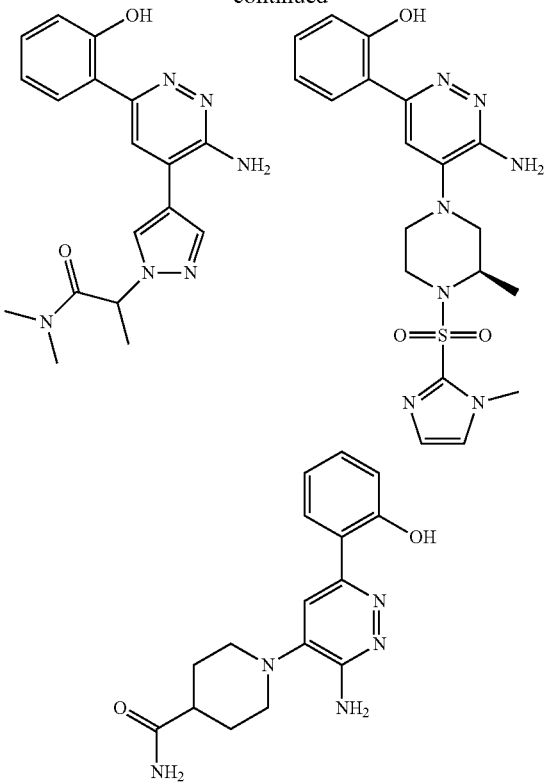
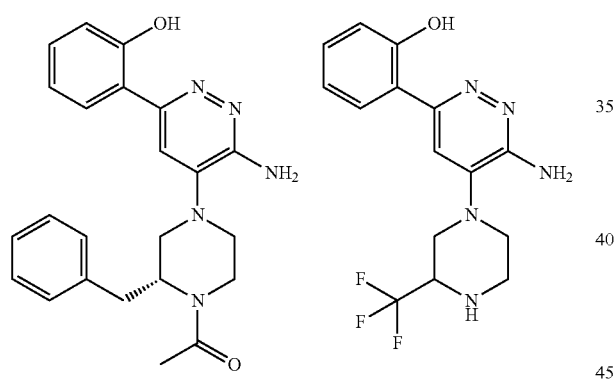
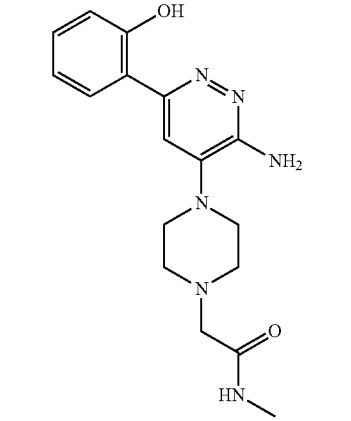
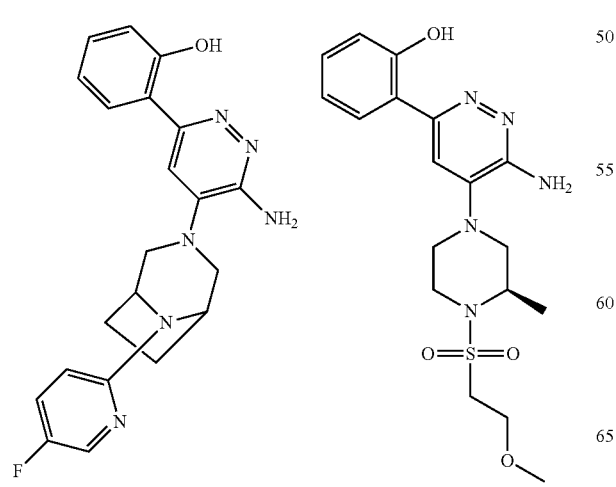
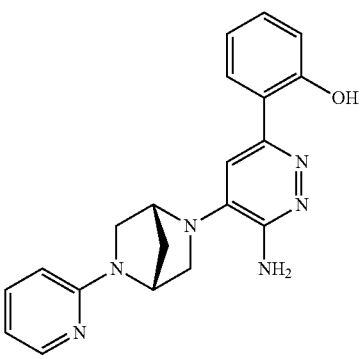

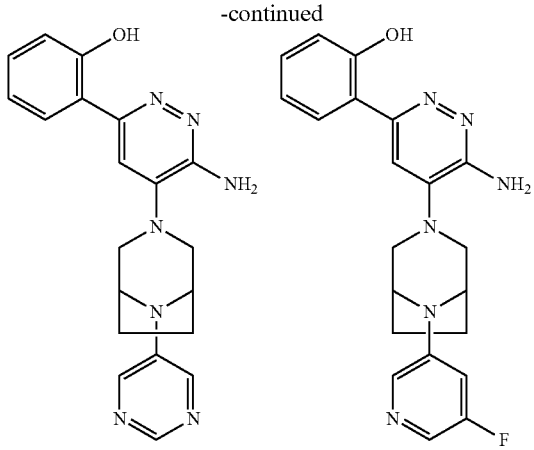
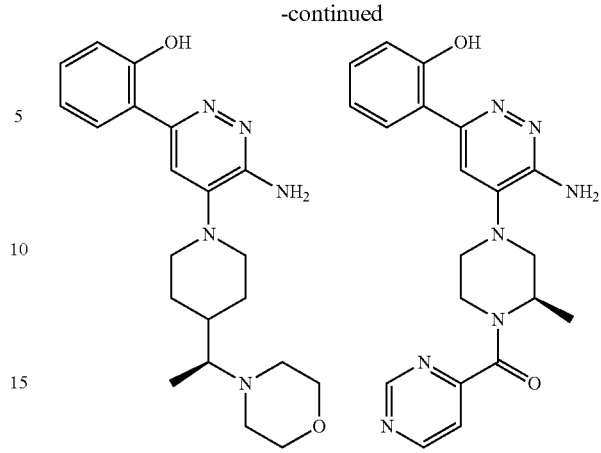

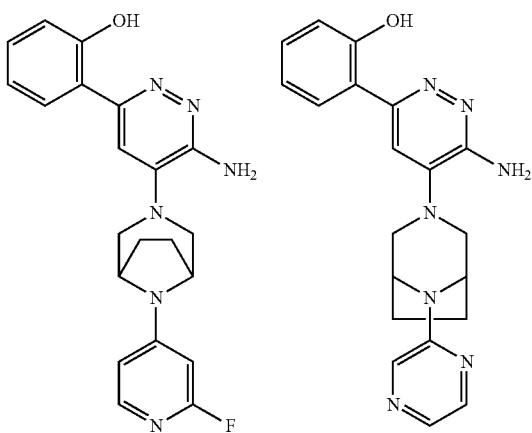
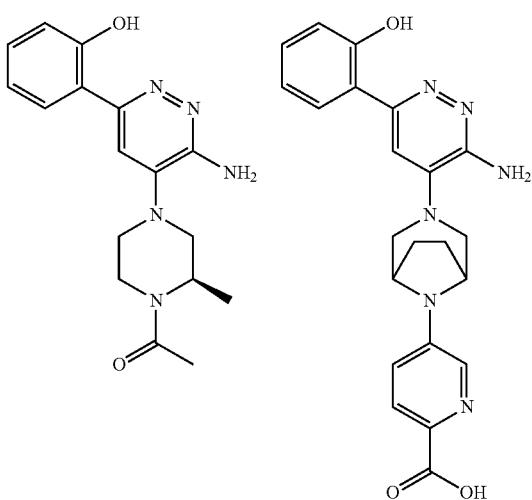
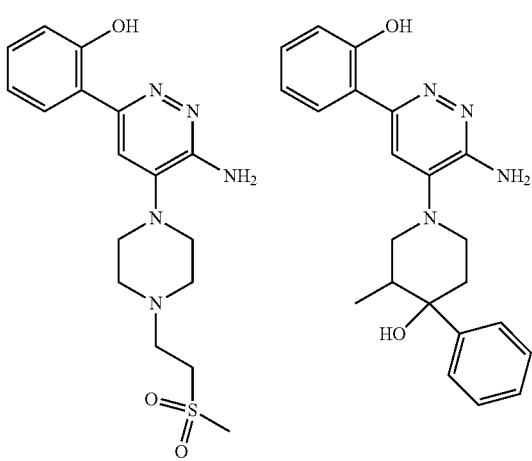
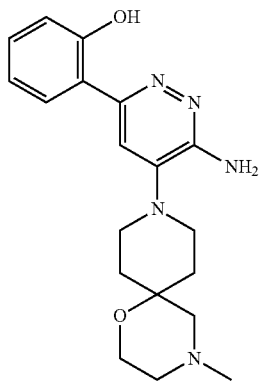
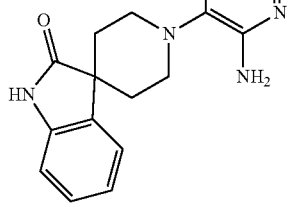
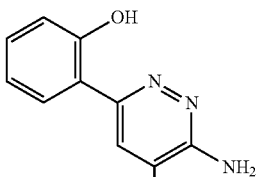
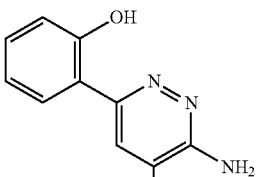
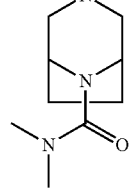
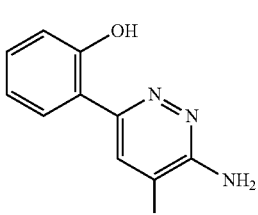
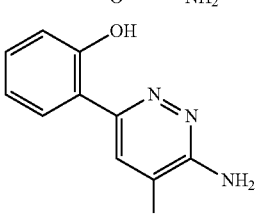
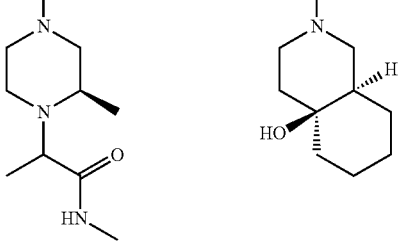

431
-continued
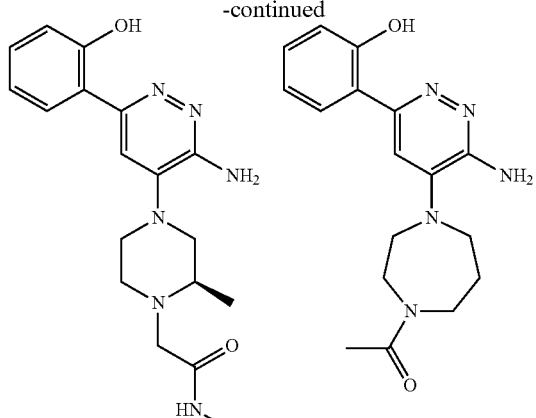
432
-continued
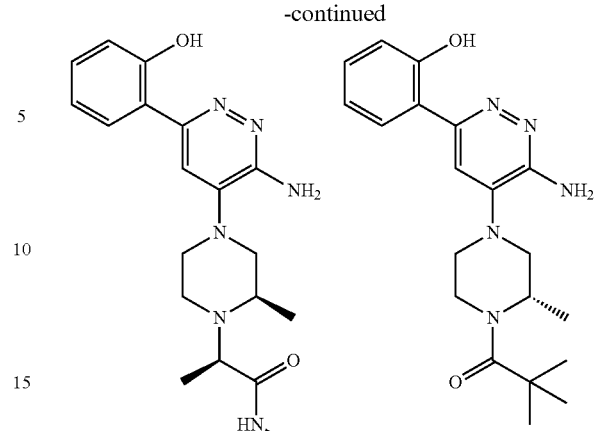
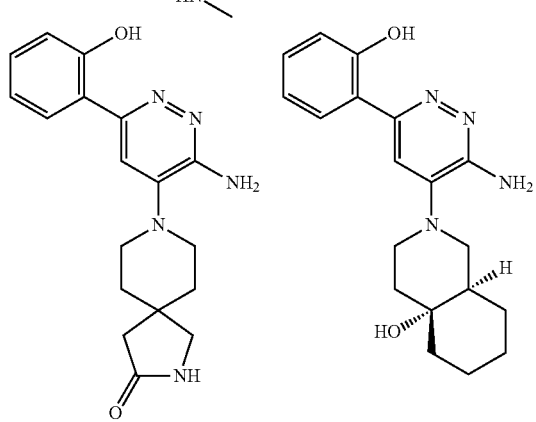
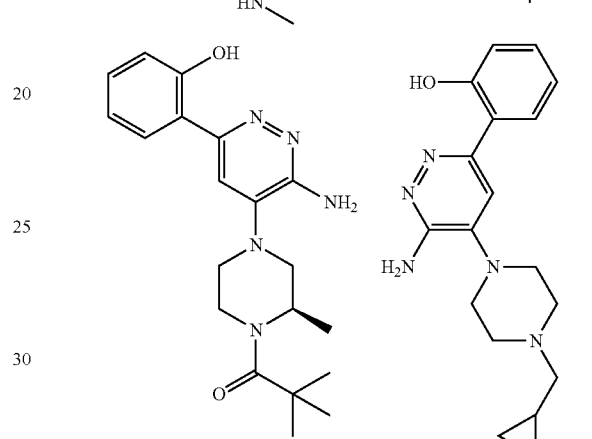
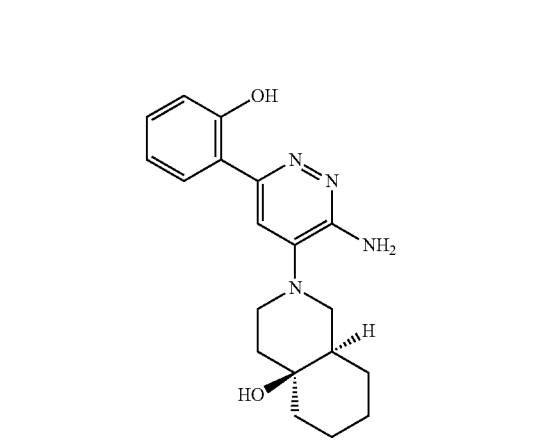
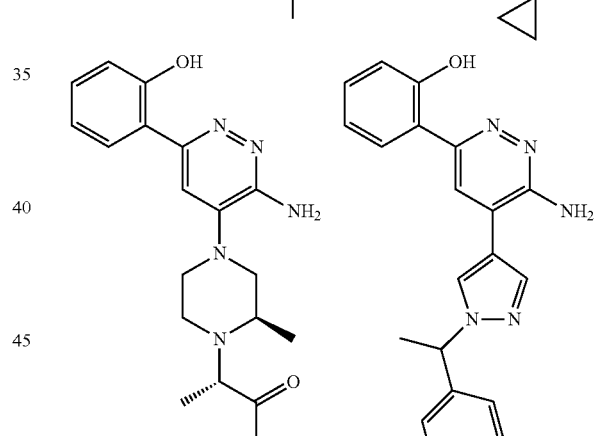
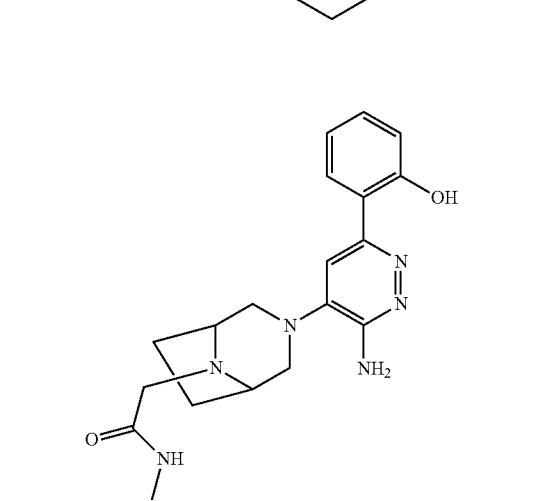
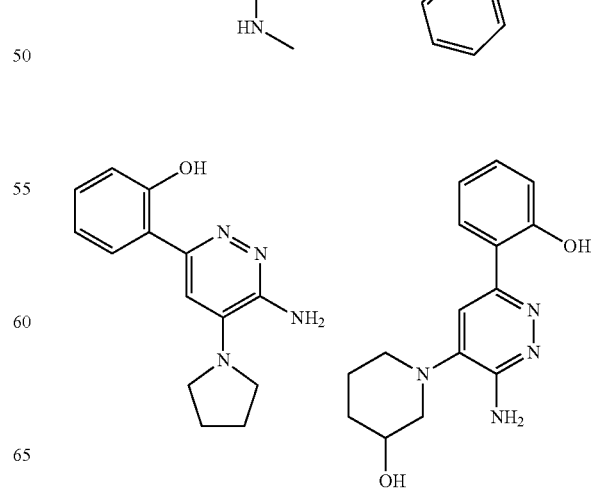

-continued
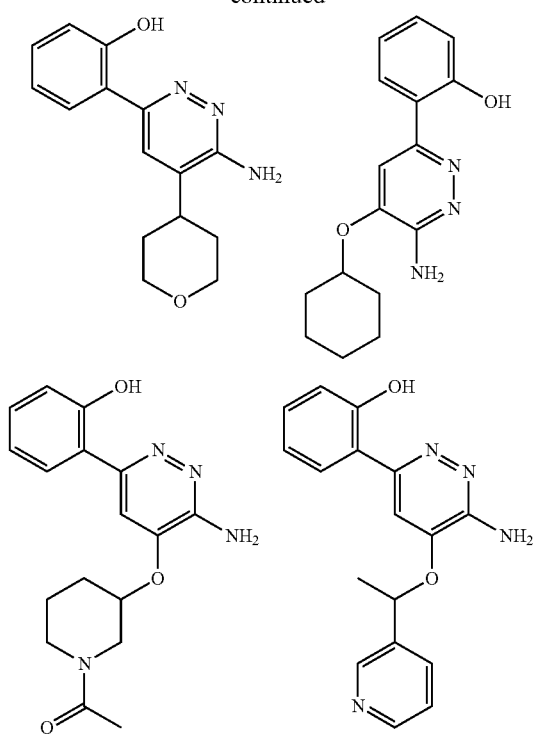
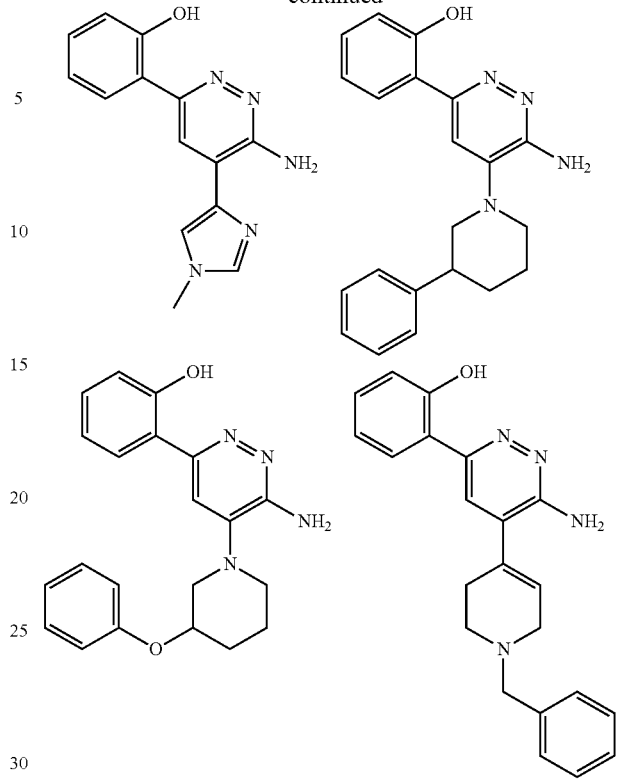
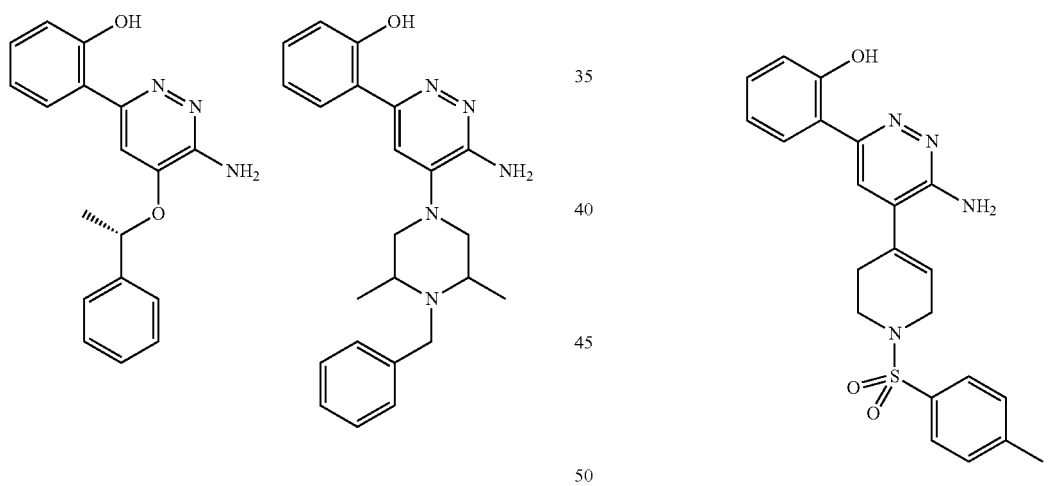
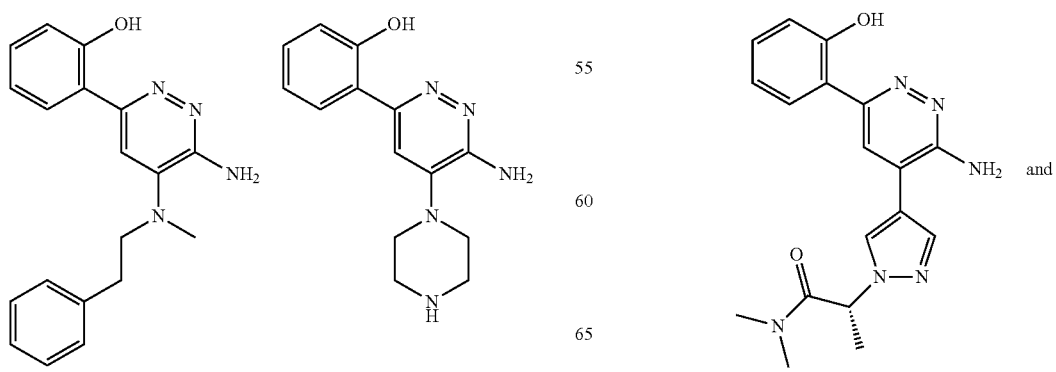

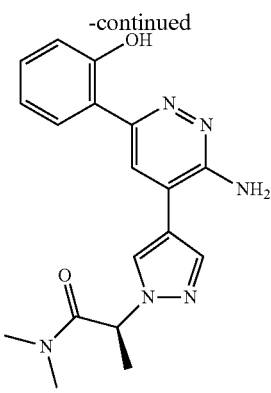

or a salt thereof.

15. The compound:

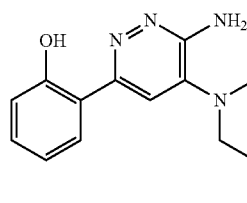

or a salt thereof.

16. A composition comprising a compound of formula (I) as described in claim 1, or a pharmaceutically acceptable salt thereof, and a pharmaceutically acceptable adjuvant, carrier, or vehicle.

17. A compound of formula (I):

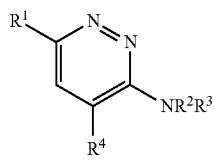

or a salt thereof, wherein:
$R^1$ is phenyl that is substituted with hydroxy and that is optionally substituted with one or more groups independently selected from the group consisting of halo, cyano, trifluoromethyl, trifluoromethoxy, $C_{1-3}$alkyl, and $C_{1-3}$alkoxy;
$R^2$ is H, $C_{1-6}$alkyl, or —C(=O)—$C_{1-6}$alkyl;
$R^3$ is H or $C_{1-6}$alkyl;
$R^4$ is selected from the group consisting of —O—$R^b$, —N($R^b$)$_2$, —S(O)$_2R^b$, —C(O)—N($R^b$)$_2$, $C_{2-6}$alkenyl, $C_{2-6}$alkynyl, 3-15 membered carbocyclyl, and 3-15 membered heterocyclyl, wherein each $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;

each $R^b$ is independently selected from the group consisting of hydrogen, $C_{1-6}$alkyl, $C_{2-6}$alkenyl, $C_{2-6}$alkynyl, 3-15 membered carbocyclyl, and 3-15 membered heterocyclyl, wherein each $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;

each R is independently selected from the group consisting of hydrogen, $C_{1-6}$alkyl, $C_{2-6}$alkenyl, $C_{2-6}$alkynyl, $C_{1-6}$alkoxy, 3-15 membered carbocyclyl, and 3-15 membered heterocyclyl, wherein each $C_{1-6}$alkyl, $C_{2-6}$alkenyl, $C_{2-6}$alkynyl, $C_{1-6}$alkoxy, 3-15 membered carbocyclyl, and 3-15 membered heterocyclyl is optionally substituted with one or more groups independently selected from $R^d$; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^d$ is independently selected from the group consisting of oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, —N($R^e$)—S(O)$_2$—$R^e$, $C_{1-6}$alkyl, $C_{2-6}$alkenyl, $C_{2-6}$alkynyl, 3-15 membered carbocyclyl, and 3-15 membered heterocyclyl, wherein any $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^e$, oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, and —N($R^e$)—S(O)$_2$—$R^e$; and each $R^e$ is independently selected from the group consisting of hydrogen, $C_{1-6}$alkyl, $C_{2-6}$alkenyl, $C_{2-6}$alkynyl, carbocyclyl, and carbocyclyl($C_{1-3}$alkyl)-.

18. A composition comprising a compound of formula (I) as described in claim 17, or a pharmaceutically acceptable salt thereof, and a pharmaceutically acceptable adjuvant, carrier, or vehicle.

19. A composition comprising a compound of formula (I) as described in claim 14, or a pharmaceutically acceptable salt thereof, and a pharmaceutically acceptable adjuvant, carrier, or vehicle.

20. A compound of formula (I):

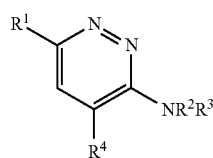

or a salt thereof, wherein:

$R^1$ is 2-hydroxy phenyl that is optionally substituted with one or more groups independently selected from the group consisting of halo;

$R^2$ is H;

$R^3$ is H;

$R^4$ is selected from the group consisting of $C_{1-6}$alkyl, $C_{2-6}$alkenyl, $C_{2-6}$alkynyl, 3-15 membered carbocyclyl, 3-15 membered heterocyclyl —O—$R^b$, —N($R^b$)$_2$, —S(O)$_2R^b$, and —C(O)—N($R^b$)$_2$, wherein each $C_{1-6}$alkyl, $C_{2-6}$alkenyl, $C_{2-6}$alkynyl, 3-15 membered carbocyclyl, and 3-15 membered heterocyclyl of $R^4$ is substituted with one or more groups independently selected from the group consisting of $C_{2-6}$alkenyl, $C_{2-6}$alkynyl, $C_{1-6}$alkoxy, 3-15 membered carbocyclyl, 3-15 membered heterocyclyl, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;

each $R^b$ is independently selected from the group consisting of hydrogen, $C_{1-6}$alkyl, $C_{2-6}$alkenyl, $C_{2-6}$alkynyl, 3-15 membered carbocyclyl, and 3-15 membered heterocyclyl, wherein each $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^c$, oxo, halo, —NO$_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$;

each $R^c$ is independently selected from the group consisting of hydrogen, $C_{1-6}$alkyl, $C_{2-6}$alkenyl, $C_{2-6}$alkynyl, $C_{1-6}$alkoxy, 3-15 membered carbocyclyl, and 3-15 membered heterocyclyl, wherein each $C_{1-6}$alkyl, $C_{2-6}$alkenyl, $C_{2-6}$alkynyl, $C_{1-6}$alkoxy, 3-15 membered carbocyclyl, and 3-15 membered heterocyclyl is optionally substituted with one or more groups independently selected from $R^d$; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^d$ is independently selected from the group consisting of oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, —N($R^e$)—S(O)$_2$—$R^e$, $C_{1-6}$alkyl, $C_{2-6}$alkenyl, $C_{2-6}$alkynyl, 3-15 membered carbocyclyl, and 3-15 membered heterocyclyl, wherein any $C_{1-6}$alkyl, $C_{2-6}$alkenyl, $C_{2-6}$alkynyl, 3-15 membered carbocyclyl, and 3-15 membered heterocyclyl is optionally substituted with one or more groups independently selected from the group consisting of $R^e$, oxo, halo, —NO$_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, and —N($R^e$)—S(O)$_2$—$R^e$; and each $R^e$ is independently selected from the group consisting of hydrogen, $C_{1-6}$alkyl, $C_{2-6}$alkenyl, $C_{2-6}$alkynyl, carbocyclyl, and carbocyclyl($C_{1-3}$alkyl)-.

21. A composition comprising a compound of formula (I) as described in claim 20, or a pharmaceutically acceptable salt thereof, and a pharmaceutically acceptable adjuvant, carrier, or vehicle.

* * * * *

UNITED STATES PATENT AND TRADEMARK OFFICE
CERTIFICATE OF CORRECTION

PATENT NO. : 10,308,614 B2
APPLICATION NO. : 15/686028
DATED : June 4, 2019
INVENTOR(S) : Brian K. Albrecht et al.

Page 1 of 4

It is certified that error appears in the above-identified patent and that said Letters Patent is hereby corrected as shown below:

In the Claims

Column 374, Lines 46-56, Claim 3, please delete the following compound:

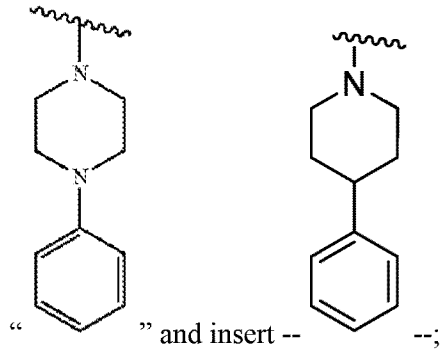

" and insert -- --;

Column 378, Lines 1-11, Claim 3, please delete the following compound:

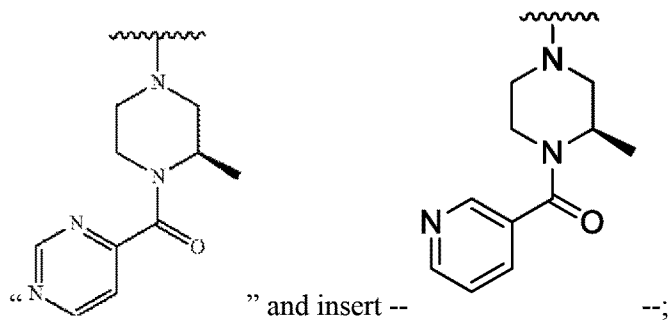

" and insert -- --;

Column 379, Line 61, Claim 4, please delete "-S-R$^c$," and insert -- -O-R$^c$, -S-R$^c$, --;

Signed and Sealed this
First Day of October, 2019

Andrei Iancu
*Director of the United States Patent and Trademark Office*

Column 382, Lines 1-11, Claim 5, please delete the following compound:
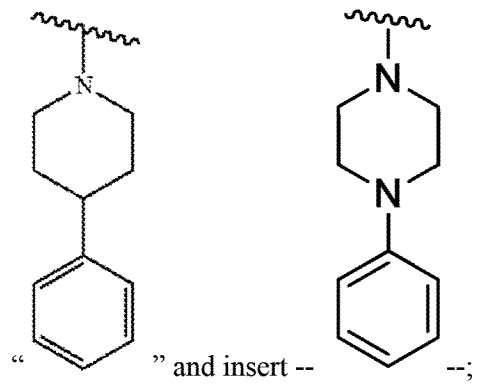
Column 384, Lines 30-40, Claim 5, please delete the compound:
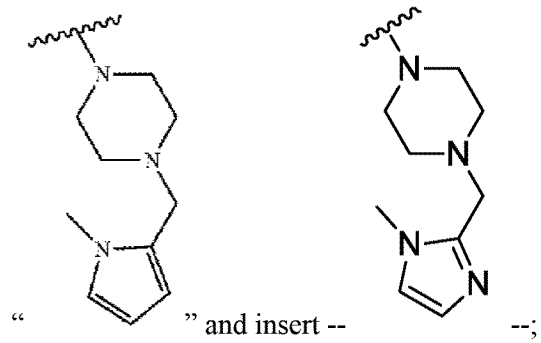
Column 386, Lines 1-12, Claim 5, please delete the following compound:
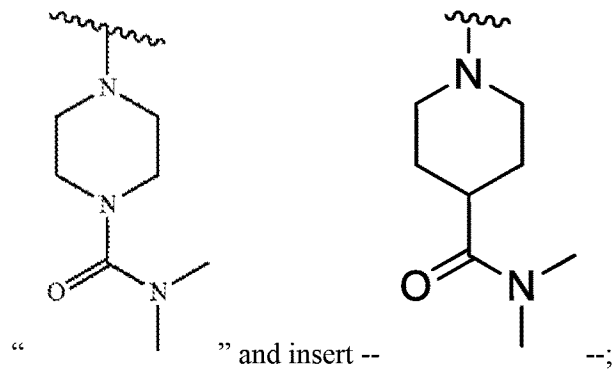

CERTIFICATE OF CORRECTION (continued)
U.S. Pat. No. 10,308,614 B2

Page 3 of 4

Column 386, Lines 45-55, Claim 5, please delete the compound:

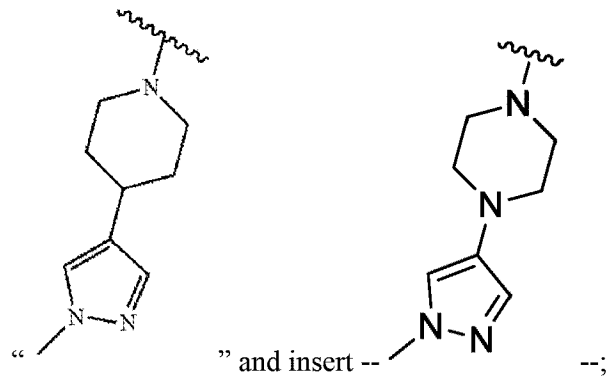

" and insert -- --;

Column 387, Lines 1-9, Claim 5, please delete the following compound:

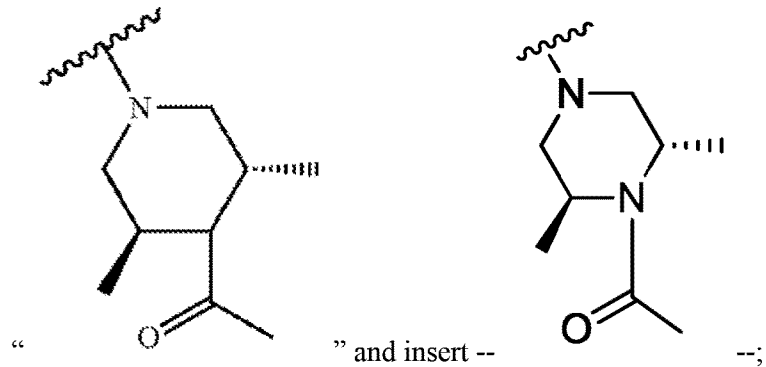

" and insert -- --;

Column 387, Lines 1-9, Claim 5, please delete the following compound:

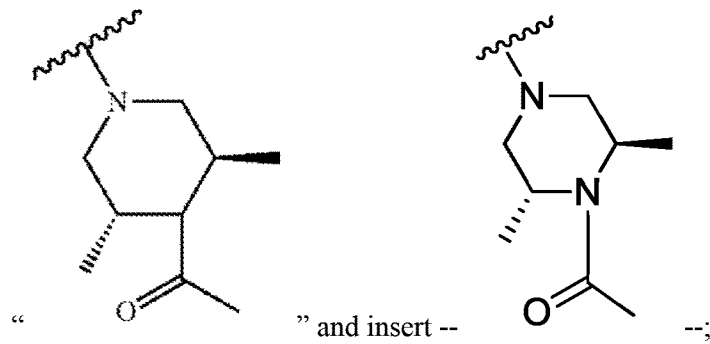

" and insert -- --;

Column 400, Lines 15-27, Claim 14, please delete the following compound:
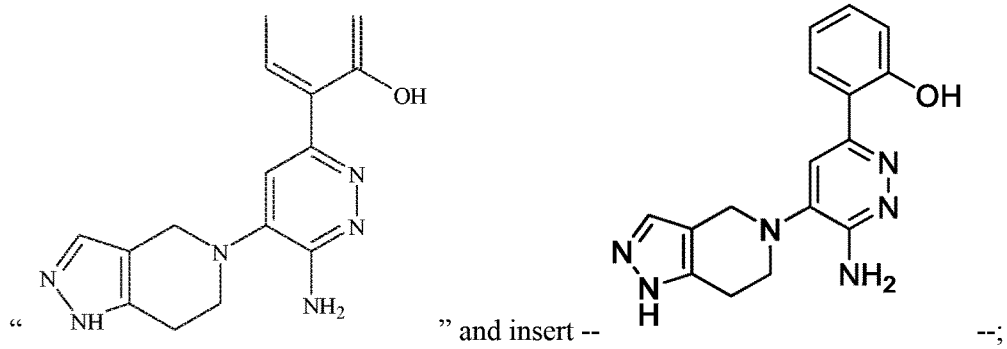 " and insert -- -- ;
Column 424, Lines 51-66, Claim 14, please delete the following compound:
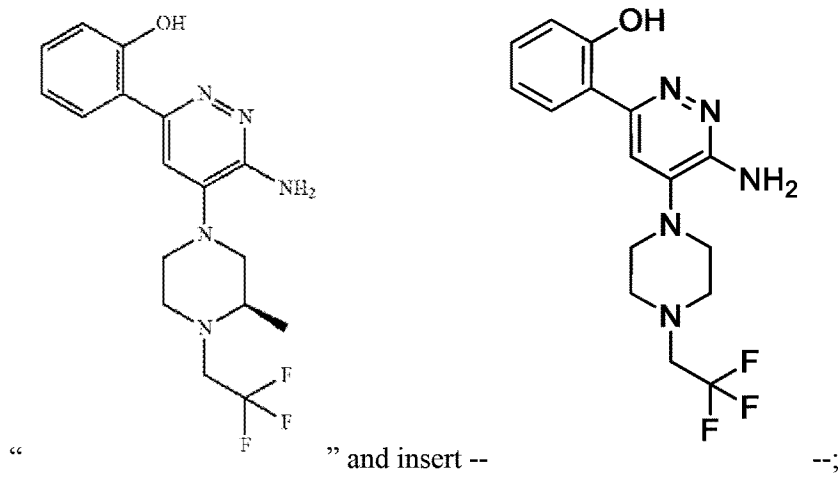 " and insert -- -- ;
Column 436, Line 14, Claim 17, please delete "each R is independently" and insert -- each $R^c$ is independently -- therefor.

```
                        SEQUENCE LISTING

<160> NUMBER OF SEQ ID NOS: 4

<210> SEQ ID NO 1
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met His His His His His Gly Ser Leu Val Pro Arg Gly Ser Ala
1               5                   10                  15

Glu Lys Leu Ser Pro Asn Pro Pro Asn Leu Thr Lys Lys Met Lys Lys
                20                  25                  30

Ile Val Asp Ala Val Ile Lys Tyr Lys Asp Ser Ser Gly Arg Gln
                35                  40                  45

Leu Ser Glu Val Phe Ile Gln Leu Pro Ser Arg Lys Glu Leu Pro Glu
        50                  55                  60

Tyr Tyr Glu Leu Ile Arg Lys Pro Val Asp Phe Lys Lys Ile Lys Glu
65                  70                  75                  80

Arg Ile Arg Asn His Lys Tyr Arg Ser Leu Asn Asp Leu Glu Lys Asp
                85                  90                  95

Val Met Leu Leu Cys Gln Asn Ala Gln Thr Phe Asn Leu Glu Gly Ser
```

```
                100             105             110
Leu Ile Tyr Glu Asp Ser Ile Val Leu Gln Ser Val Phe Thr Ser Val
            115                 120                 125

Arg Gln Lys Ile Glu Lys Glu Asp Ser Glu Gly Glu Glu Ser
            130                 135             140

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His His His His His Gly Ser Leu Val Pro Arg Gly Ser Ser
1               5                   10                  15

Pro Asn Pro Pro Lys Leu Thr Lys Gln Met Asn Ala Ile Ile Asp Thr
                20                  25                  30

Val Ile Asn Tyr Lys Asp Ser Ser Gly Arg Gln Leu Ser Glu Val Phe
            35                  40                  45

Ile Gln Leu Pro Ser Arg Lys Glu Leu Pro Glu Tyr Tyr Glu Leu Ile
    50                  55                  60

Arg Lys Pro Val Asp Phe Lys Lys Ile Lys Glu Arg Ile Arg Asn His
65                  70                  75                  80

Lys Tyr Arg Ser Leu Gly Asp Leu Glu Lys Asp Val Met Leu Leu Cys
                85                  90                  95

His Asn Ala Gln Thr Phe Asn Leu Glu Gly Ser Gln Ile Tyr Glu Asp
            100                 105                 110

Ser Ile Val Leu Gln Ser Val Phe Lys Ser Ala Arg Gln
            115                 120                 125

<210> SEQ ID NO 3
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His His His His His Ala Ser Asp Tyr Lys Asp Asp Asp Asp
1               5                   10                  15

Lys Gly Ser Leu Val Pro Arg Gly Ser Ser Gly Ile Ser Pro Lys Lys
                20                  25                  30

Ser Lys Tyr Met Thr Pro Met Gln Gln Lys Leu Asn Glu Val Tyr Glu
            35                  40                  45

Ala Val Lys Asn Tyr Thr Asp Lys Arg Gly Arg Arg Leu Ser Ala Ile
    50                  55                  60

Phe Leu Arg Leu Pro Ser Arg Ser Glu Leu Pro Asp Tyr Tyr Leu Thr
65                  70                  75                  80

Ile Lys Lys Pro Met Asp Met Glu Lys Ile Arg Ser His Met Met Ala
                85                  90                  95

Asn Lys Tyr Gln Asp Ile Asp Ser Met Val Glu Asp Phe Val Met Met
            100                 105                 110

Phe Asn Asn Ala Cys Thr Tyr Asn Glu Pro Glu Ser Leu Ile Tyr Lys
        115                 120                 125

Asp Ala Leu Val Leu His Lys Val Leu Leu Glu Thr Arg Arg Asp Leu
```

```
                130             135             140
Glu Gly Asp
145

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5
```